US011000560B2

(12) United States Patent
Alemany et al.

(10) Patent No.: US 11,000,560 B2
(45) Date of Patent: May 11, 2021

(54) ONCOLYTIC ADENOVIRUSES WITH MUTATIONS IN IMMUNODOMINANT ADENOVIRUS EPITOPES AND THEIR USE IN CANCER TREATMENT

(71) Applicant: VCN BIOSCIENCES SL, Barcelona (ES)

(72) Inventors: Ramon Alemany, Castelldefels Barcelona (ES); Raul Gil, Bethesda, MD (US); Miriam Bazan, Barcelona (ES)

(73) Assignee: VCN BIOSCIENCES, S.L., Barcelona (ES)

( * ) Notice: Subject to any disclaimer, the term of this patent is extended or adjusted under 35 U.S.C. 154(b) by 0 days.

(21) Appl. No.: 15/571,698

(22) PCT Filed: May 4, 2016

(86) PCT No.: PCT/IB2016/052554
§ 371 (c)(1),
(2) Date: Nov. 3, 2017

(87) PCT Pub. No.: WO2016/178167
PCT Pub. Date: Oct. 11, 2016

(65) Prior Publication Data
US 2018/0153946 A1    Jun. 7, 2018

Related U.S. Application Data

(60) Provisional application No. 62/156,748, filed on May 4, 2015.

(51) Int. Cl.
| | |
|---|---|
| *A61K 35/761* | (2015.01) |
| *C07K 14/075* | (2006.01) |
| *A61P 35/00* | (2006.01) |
| *C07K 14/005* | (2006.01) |
| *A61K 39/00* | (2006.01) |

(52) U.S. Cl.
CPC ............ *A61K 35/761* (2013.01); *A61P 35/00* (2018.01); *C07K 14/005* (2013.01); *C07K 14/075* (2013.01); *A61K 2039/57* (2013.01); *A61K 2039/572* (2013.01); *C12N 2710/10322* (2013.01); *C12N 2710/10332* (2013.01)

(58) Field of Classification Search
None
See application file for complete search history.

(56) References Cited

U.S. PATENT DOCUMENTS

| 4,588,585 A | 5/1986 | Mark et al. |
| 6,127,525 A * | 10/2000 | Crystal ............... C12N 15/86 |
| | | 435/235.1 |
| 6,413,746 B1 | 7/2002 | Field |
| 6,660,501 B2 | 12/2003 | Field |
| 2005/0287122 A1 | 12/2005 | Bartlett et al. |
| 2006/0147420 A1 | 7/2006 | Fueyo et al. |
| 2008/0187954 A1 | 8/2008 | Kallmeier et al. |
| 2009/0142363 A1 * | 6/2009 | Toji ..................... A61K 39/235 |
| | | 424/185.1 |
| 2011/0059135 A1 * | 3/2011 | Kovesdi ................ C12N 15/86 |
| | | 424/233.1 |
| 2012/0148535 A1 | 6/2012 | Carrio et al. |
| 2013/0029358 A1 * | 1/2013 | Valmori ........... G01N 33/56972 |
| | | 435/7.24 |
| 2013/0302313 A1 * | 11/2013 | Yu ......................... C12N 15/87 |
| | | 424/130.1 |
| 2014/0377294 A1 | 12/2014 | Fueyo-Margareto et al. |

FOREIGN PATENT DOCUMENTS

| CN | 102264760 A | 11/2011 |
| CN | 103221423 A | 7/2013 |
| CN | 104271748 A | 1/2015 |
| WO | 95/27071 A2 | 10/1995 |
| WO | 2004009823 A1 | 1/2004 |
| WO | 2005107474 A2 | 11/2005 |
| WO | 2012024351 A2 | 2/2012 |

OTHER PUBLICATIONS

Thacker et al (2009, Expert Rev. Vaccines, vol. 8(6), pp. 761-777). (Year: 2009).*
Leen et al, Identification of Hexon-Specific CD4and CD8 T-Cell Epitopes for Vaccine and Immunotherapy, Journal of Virology, Jan. 2008, p. 546-554.*
E.E. Thacker, et al; Strategies to overcome host immunity to adenovirus vectors in vaccine development; Expert Reviews; 2009; XP009150717; pp. 761-777.
G.J. Tobin, et al; Deceptive imprinting and immune refocusing in vaccine design; Vaccine; 2008; vol. 26; pp. 6189-6199.
K. Tsukuda, et al; An E2F-responsive replication-selective adenovirus targeted to the defective cell cycle in cancer . . . ; Cancer Research; Jun. 2002; vol. 62; pp. 3438-3447.
S. Uebel, et al; Specificity of the proteasome and the TAP transporter; Current Opinion in Immunology; 1999; vol. 11; pp. 203-208.
E. Vacchelli, et al; Trial watch; Peptide vaccines in cancer therapy; OncoImmunology; Dec. 2012; vol. 1; No. 9; pp. 1557-1576.
R. Vanhorssen, et al; TNF-α in cancer treatment: molecular insights, antitumor effects, and clinical utility; The Oncologist; 2006; vol. 11; pp. 397-408.

(Continued)

*Primary Examiner* — Maria Marvich
(74) *Attorney, Agent, or Firm* — Lucas & Mercanti, LLP

(57) ABSTRACT

The present invention relates to oncolytic adenoviruses with functional deletions of immunodominant T-cell epitopes of adenovirus proteins, as well as to methods of using the oncolytic adenoviruses for the treatment of diseases, such as cancer. The oncolytic adenoviruses may also contain one or more heterologous nucleic acid sequences each encoding a tumor antigen or epitope. The oncolytic adenoviruses may also contain other mutations and insertions of DNA sequences used to confer selectivity and antitumor potency. The invention has application in the field of cancer therapy.

9 Claims, 13 Drawing Sheets

Specification includes a Sequence Listing.

(56) References Cited

OTHER PUBLICATIONS

E. Vigne, et al; RGD inclusion in the hexon monomer provides adenovirus type 5-based vectors with a fiber . . . ; Journal of Virology; Jun. 1999; vol. 73; No. 6; pp. 5156-5161.
J. Wan, et al; Software; Open access SVRMHC prediction server for MHC-binding peptides; BMC Bioinformatics; Oct. 2006; vol. 7; 5 pages.
G.P. Wang, et al; A statistical method for comparing viral growth curves; Journal of Virological Methods; 2006; vol. 135; pp. 118-123.
J.W. Yewdell, et al; Immunodominance in TCD8 responses to viruses: cell biology, cellular immunology, and mathematical models; Immunity; Aug. 2004; vol. 21; pp. 149-153.
R. Alba, et al; Identification of coagulation factor (F)X binding sites on the adenovirus serotype 5 hexon: . . . ; Blood, Jul. 2009; vol. 114; No. 5; pp. 965-971; 8 pages.
S.F. Altschul, et al; Local Alignment Statistics; Methods in Enzymology; vol. 266; 1996; pp. 460-480.
S.F. Altschul, et al; Gapped Blast and PSI-Blast: a new generation of protein database search programs; Nucleic Acids Research; 1997; vol. 25; No. 17; pp. 3389-3402.
A. Amin, et al; High-Dose Interleukin-2: Is it still indicated for melanoma and RCC in an era of targeted therapies?; Cancer Network; 2013; pp. 1-14.
R. Arens, et al; Prospects of combinatorial synthetic peptide vaccine-based immunotherapy against cancer; Seminars in Immunology; vol. 25; 2013; pp. 182-190.
Ausubel; Cloning of small RNA molecules; Current Protocols in Molecular Biology; 2003; 18 pages.
D. Bang, et al; His6 tag-assisted chemical protein synthesis; PNAS; 2005; vol. 102; No. 14; pp. 5014-5019.
N. Bayo-Puxan, et al; Replacement of adenovirus type 5 fiber shaft heparan sulfate proteoglycan-binding domain with RGD . . . ; Human Gene Therapy; 2009; vol. 20; pp. 1214-1221.
N.J. Beekman, et al; Abrogation of CTL epitope processing by single amino acid substitution flanking the C-terminal . . . ; The Journal of Immunology; 2000; vol. 164; pp. 1898-1905.
R. Bei, et al; TAA polyepitope DNA-based vaccines: a potential tool for cancer therapy; Journal of Biomedicine and Biotechnology; vol. 2010; 12 pages.
M.P. Bell, et al; A CD8 T-cell epitope variant enhances immune targeting to a recombinant picornavirus vaccine antigen; Viral Immunology; vol. 27; No. 7; 2014; pp. 361-366.
J.R. Bennink, et al; Murine cytotoxic T lymphocyte recognition of individual influenza virus proteins; The Journal of Experimental Medicine; vol. 168; Nov. 1988; pp. 1935-1939.
S.M. Berge, et al; Pharmaceutical salts; Journal of Pharmaceutical Sciences; XP002552191; Jan. 1977; vol. 66; No. 1; 20 pages.
W.E. Biddison, et al; Involvement of H-2L gene products in virus-immune T-cell recognition; The Journal of Experimental Medicine; vol. 148; 1978; pp. 1678-1686.
J.R. Bischoff, et al; An adenovirus mutant that replicates selectively in p53-deficient human tumor cells; Science; vol. 274; Oct. 1996; pp. 373-376.
R.N. Bohnsack; Site-directed mutagenesis using positive antibiotic selection; Methods in Molecular Biology; vol. 57; 1996; In Vitro Mutagenesis Protocols; 12 pages.
I. Bonaccorsi, et al; Novel perspectives on dendritic cell-based immunotherapy of cancer; Immunology Letters; vol. 155; 2013; pp. 6-10.
D.A. Brummell, et al; Probing the combining site of an anti-carbohydrate antibody by saturation-mutagenesis: role of the heavy-chain . . . ; Biochemistry; vol. 32; 1993; pp. 1180-1187.
E.A. Burks, et al; In vitro scanning saturation mutagenesis of an antibody binding pocket; Proc. Natl. Acad. Sci.; vol. 94; Jan. 1997; pp. 412-417.
M. Cascallo, et al; Ras-dependent oncolysis with an adenovirus VAI mutant; Cancer Research; vol. 63; Sep. 2003; pp. 5544-5550.

M. Cascallo, et al; Deletion of VAI and VAII RNA genes in the design of oncolytic adenoviruses; Human Gene Therapy; vol. 17; Sep. 2006; pp. 929-940.
M. Cascallo, et al; Systemic toxicity-efficacy profile of ICOVIR-5, a potent and selective oncolytic adenovirus based on the pRB pathway; Molecular Therapy; vol. 15; No. 9; Sep. 2007; pp. 1607-1615.
P.G. Coulie, et al; Tumour antigens recognized by T lymphocytes: at the core of cancer immunotherapy; Nature—Reviews; Cancer; Perspectives; vol. 14; Feb. 2014; pp. 135-146.
L.K. Curtiss, et al; The relative immunodominance of haptenic determinants on a complex hapten phage conjugate; Immunochemistry; vol. 12; 1975; pp. 949-957.
W.P. Deng, et al; Site-directed mutagenesis of virtually any plasmid by eliminating a unique site; Analytical Biochemistry; vol. 200; 1992; pp. 81-88.
N.G. De Pace; On the disappearance of a huge vegetative cancer of the neck of the uterus without surgery; year 1912; 14 pages.
P.C. Doherty, et al; Enhanced immunological surveillance in mice heterozygous at the H-2 gene complex; Nature; vol. 256; Jul. 1975; pp. 50-52.
P. Donnes, et al; Prediction of MHC class 1 binding peptides, using SVMHC; BMC Bioinformatics; 2002; 3:25; 8 pages.
H. Firat, et al; H-2 class 1 knockout, HLA-A2. 1-transgenic mice: a versatile animal model for preclinical evaluation of . . . ; Eur. J. Immunol.; 1999; vol. 29; pp. 3112-3121.
K.G. Ford, et al; Protein transduction: an alternative to genetic intervention?; Gene Therapy; 2001; vol. 8; pp. 1-4.
J. Fueyo, et al; A mutant oncolytic adenovirus targeting the Rb pathway produces anti-glioma effect in vivo; Oncogene; 2000; vol. 19; pp. 2-12.
F.F. Gonzalez-Galarza, et al; Allele frequency net: a database and online repository for immune gene frequencies in worldwide populations; Nucleic Acids Research; 2011; vol. 39; pp. D913-D919.
F.D. Goodrum, et al; p53 status does not determine outcome of E1B 55-kilodalton mutant adenovirus lytic infection; Journal of Virology; Dec. 1998; pp. 9479-9490.
U. Gowthaman, et al; Evaluation of different generic in silico methods for predicting HLA class 1 binding peptide vaccine candidates using a reverse approach; Amino Acids; 2010; vol. 39; pp. 1333-1342.
F.L. Graham, et al; Manipulation of adenovirus vectors; Methods in Molecular Biology; vol. 7: Gene transfer and expression protocols; 1991; pp. 109-128.
A.R. Hall, et al; p53-dependent cell death/apoptosis is required for a productive adenovirus infection; Nature Medicine; vol. 4; No. 9; Sep. 1998; pp. 1068-1072.
P.L. Hallenbeck, et al; A novel tumor-specific replication-restricted adenoviral vector for gene therapy of hepatocellular carcinoma; Human Gene Therapy; vol. 10; Jul. 1999; pp. 1721-1733.
D. Hanahan, et al; The hallmarks of cancer; Cell; vol. 100; Jan. 2000; pp. 57-70.
C. Heise, et al; An adenovirus E1A mutant that demonstrates potent and selective systemic anti-tumoral efficacy; Nature Medicine; vol. 6; No. 10; Oct. 2000; pp. 1134-1139.
C. Hsieh, et al; A novel targeting modality to enhance adenoviral replication by vitamin D3 in androgen-independent human . . . ; Cancer Research; vol. 62; Jun. 2002; pp. 3084-3092.
H. Jiang, et al; Oncolytic adenovirus: preclinical and clinical studies in patients with human malignant gliomas; Curr Gene Ther.; Oct. 2009; vol. 9; No. 5; pp. 422-427.
L. Johnson, et al; Selectively replicating adenoviruses targeting deregulated E2F activity are potent, systemic antitumor agents; Cancer Cell; May 2002; vol. 1; pp. 325-337.
J.H. Johnston, et al; The immunochemistry of shigella flexneri o-antigens: an analysis of the immuno-dominant sugars . . . ; J. Path. Bact.; vol. 95; 1968; pp. 477-480.
N. Jojic, et al; Learning MHC I-peptide binding; Bioinformatics; vol. 22; No. 14; 2006; pp. e227-e235.
M. Kalos, et al; Adoptive T cell transfer for cancer immunotherapy in the era of synthetic biology; Immunity; vol. 39; Jul. 2013; pp. 49-60.

(56) References Cited

OTHER PUBLICATIONS

S. Karlin, et al; Methods for assessing the statistical significance of molecular sequence features by using . . . ; Proc. Natl. Acad. Sci.; vol. 87; Mar. 1990; pp. 2264-2268.
S. Karlin, et al; Applications and statistics for multiple high-scoring segments in molecular sequences; Proc. Natl. Acad. Sci.; vol. 90; Jun. 1993; pp. 5873-5877.
M. Kim, et al; Diversity and complexity of CD8 T cell responses against a single epitope of adenovirus E1B; Virology; 2002; vol. 295; pp. 238-249.
R.L. Kingston, et al; Structural basis for the attachment of a paramyxoviral polymerase to its template; PNAS; vol. 101; No. 22; Jun. 2004; pp. 8301-8306.
H. Kobayashi, et al; Tryptophan H33 plays an important role in pyrimidine (6-4) pyrimidone photoproduct binding by a . . . ; Protein Engineering; vol. 12; No. 10; 1999; pp. 879-884.
K.P. Kotredes, et al; Interferons as inducers of apoptosis in malignant cells; Journal of Interferon & Cytokine Research; vol. 33; No. 4; 2003; pp. 162-170.
T.A. Kunkel; Rapid and efficient site-specific mutagenesis without phenotypic selection; Proc. Natl. Acad. Sci.; vol. 83; Jan. 1985; pp. 488-492.
T.A. Kunkel; Rapid and efficient site-specific mutagenesis without phenotypic selection; Method in Enzymology; vol. 154; 1987; pp. 367-382.
T. Kurihara, et al; Selectivity of a replication-competent adenovirus for human breast carcinoma cells . . . ; The Journal of Clinical Investigation; vol. 106; No. 6; Sep. 2000; pp. 763-771.
S. Lapenna, et al; Cell cycle kinases as therapeutic targets for cancer; Nature Reviews—Drug Discovery; vol. 8; Jul. 2009; pp. 547-566.
C. Larocca, et al; Viral vector-based therapeutic cancer vaccines; Cancer J; Sep. 2011; vol. 17; No. 5; pp. 359-371.
A.M. Leen, et al; Conserved CTL epitopes on the adenovirus hexon protein expand subgroup cross-reactive and . . . ; Blood; Oct. 2004; vol. 104; No. 8; pp. 2432-2440.
A.M. Leen, et al; Identification of hexon-specific CD4 and CD8 T-cell epitopes for vaccine and immunotherapy; Journal of Virology; Jan. 2008; vol. 82; No. 1; pp. 546-554.
M.K. Lewis, et al; Efficient site directed in vitro mutagenesis using ampicillin selection; Nucleic Acids Research; 1990; vol. 18; No. 12; pp. 3439-3443.
C. Lundegaard, et al; NetMHC-3.0: accurate web accessible predictions of human, mouse and monkey MHC class . . . ; Nucleic Acids Research; 2008; vol. 36; pp. W509-W512.
D.F. Mark, et al; Site-specific mutagenesis of the human fibroblast interferon gene; Proc. Natl. Acad. Sci.; Sep. 1984; vol. 81; pp. 5662-5666.
Q.L. Matthews; Capsid-incorporation of antigens into adenovirus capsid proteins for a vaccine approach; Mol. Pharm.; Feb. 2011; vol. 8; No. 1; 14 pages.
M.H. Moehler, et al; Parvovirus H-1-induced tumor cell death enhances human immune response in vitro via increased . . . ; Human Gene Therapy; Aug. 2005; vol. 16; pp. 996-1005.
L.A. MYC, et al; Cancer vaccines. Any future?; Arch. Immunol. Ther. Exp.; 2011; vol. 59; pp. 249-259.
S.B. Needleman, et al; A general method applicable to the search for similarities in the amino acid sequence . . . ; J. Mol. Biol.; 1970; vol. 48; pp. 443-453.
G.R. Nemerow, et al; Insights into adenovirus host cell interactions from structural studies; Virology; Feb. 2009; vol. 384; No. 2; pp. 380-388.
M. Olive, et al; The adenovirus capsid protein hexon contains a highly conserved human . . . ; Human Gene Therapy; Jul. 2002; vol. 13; pp. 1167-1178.
K. Palucka, et al; Dendritic-cell-based therapeutic cancer vaccines; Immunity; vol. 39; Jul. 2013; pp. 38-48.
D.M. Pardoll; The blockade of immune checkpoints in cancer immunotherapy; Nat Rev Cancer; 2012; vol. 12; No. 4; pp. 252-264.

K.C. Parker, et al; Scheme for ranking potential HLA-A2 binding peptides based on independent binding of . . . ; The Journal of Immunology; 1994; vol. 152; pp. 163-175.
B. Peters, et al; Generating quantitative models describing the sequence specificity of biological processes with the . . . ; BMC Bioinformatics; 2005; vol. 6; 9 pages.
R.J. Prestwich, et al; Oncolytic viruses: a novel form of immunotherapy; Expert Rev Anticancer Ther.; Oct. 2008; vol. 8; No. 10; pp. 1581-1588.
A. Prochiantz; For protein transduction, chemistry can win over biology; Nature Methods; Feb. 2007; vol. 4; No. 2; pp. 119-121.
H.G. Rammensee, et al; SYFPEITHI: database for Mhc ligands and peptide motifs; Immunogenetics; 1999; vol. 50; pp. 213-219.
P.A. Reche, et al; Sequence variability analysis of human class I and class II MHC molecules: functional and . . . ; 2003; 19 pages.
M. Regner, et al; Immunogenicity of two peptide determinants in the cytolytic T-cell response to flavivirus infection: inverse . . . ; Viral Immunology; 2001; vol. 14; No. 2; pp. 135-149.
D.M. Roberts, et al; Hexon-chimaeric adenovirus serotype 5 vectors circumvent pre-existing anti-vector immunity; Nature; Letters; May 2006; vol. 44; XP-002385300; pp. 239-243.
R. Rodriguez, et al; Prostate attenuated replication competent adenovirus (ARCA) CN706: a selective cytotoxic for . . . ; Cancer Research; Jul. 1997; vol. 57; pp. 2559-2563.
J.J. Rojas, et al; A modified E2F-1 promoter improves the efficacy to toxicity ratio of oncolytic adenoviruses; Gene Therapy; 2009; vol. 16; pp. 1441-1451.
J.J. Rojas, et al; Improved systemic antitumor therapy with oncolytic adenoviruses by replacing the fiber shaft . . . ; Gene Therapy; 2012; vol. 19; pp. 453-457.
T. Rothmann, et al; Replication of Onyx-015, a potential anticancer adenovirus, is independent of p53 . . . ; Journal of Virology; Dec. 1998; vol. 72; No. 12; pp. 9470-9478.
P. Rudd, et al; Correlation between interferon sensitivity of reovirus isolates and ability to discriminate between . . . ; Journal of General Virology; 2005; vol. 86; pp. 1489-1497.
E. Ruoslahti, et al; An address system in the vasculature of normal tissues and tumors; Annu. Rev. Immunol.; 2000; vol. 18; pp. 813-827.
W.C. Russell; Adenoviruses: update on structure and function; Journal of General Virology; 2009; vol. 90; pp. 1-20.
O. Schulz, et al; Toll-like receptor 3 promotes cross-priming to virus-infected cells; Nature; Feb. 2005; vol. 433; pp. 887-892.
U. Seifert, et al; Hepatitis C virus mutation affects proteasomal epitope processing; The Journal of Clinical Investigation; Jul. 2004; vol. 114; No. 2; pp. 250-259.
E.E. Sercarz, et al; Dominance and crypticity of T cell antigenic determinants; Annu. Rev. Immunol.; 1993; vol. 11; pp. 729-766.
A. Sette, et al; The relationship between class I binding affinity and immunogenicity of potential cytotoxic . . . ; The Journal of Immunology; 1994; vol. 153; pp. 5586-5592.
A. Shimada; PCR-based site-directed mutagenesis; Methods in Molecular Biology; 1996; vol. 57; pp. 157-165.
R. Schirmbeck, et al; The immunogenicity of adenovirus vectors limits the multispecificity of CD8 T-cell responses to . . . ; Molecular Therapy; Sep. 2008; vol. 16; No. 9; pp. 1609-1616.
J.C.A. Skipper, et al; An HLA-A2-restricted tyrosinase antigen on melanoma cells results from posttranslational modification and . . . ; J. Exp. Med.; Feb. 1996; vol. 183; pp. 527-534.
T.F. Smith, et al; Comparison of biosequences; Advances in Applied Mathematics; 1981; vol. 2; pp. 482-489.
T.E. Sparer, et al; Generation of cytotoxic T lymphocytes against immunorecessive epitopes after multiple immunizations . . . ; Journal of Virology; Mar. 1997; vol. 71; No. 3; pp. 2277-2284.
R.J. Stanton, et al; Re-engineering adenovirus vector systems to enable high-throughput analyses of gene function; BioTechniques; Dec. 2008; vol. 45; pp. 659-668.
K. Suzuki, et al; A conditionally replicative adenovirus with enhanced infectivity shows improved oncolytic potency; Clinical Cancer Research; 2001; vol. 7; pp. 120-126.
M. Takiguchi, et al; Analysis of three HLA-A*3303 binding peptide anchors using an HLA-A*3303 stabilization assay; Tissue Antigens; 2000; vol. 55; pp. 296-302.

(56) References Cited

OTHER PUBLICATIONS

J. Tang, et al; Human CD8 cytotoxic T cell responses to adenovirus capsid proteins; Virology; 2006; vol. 350; pp. 312-322.

S.S. Taremi, et al; Construction, expression, and characterization of a novel fully activated recombinant single-chain . . . ; Protein Science; 1998; vol. 7; pp. 2143-2149.

Zaiss et al., "Considerations in the design of vaccines that induce CD8 T cell mediated immunity", Vaccine, 2010, vol. 28, pp. 7716-7722.

"Antibody Immunogenicity Prediction-Creative Biolabs", https://www.creative-biolabs.com/preciab/antibody-immunogenicity-prediction.htm?gclid=EAlalQobChMluezSIZuu5wIVB_IRCh3HpgS6EAAYASAAEgKIWPD_BwE)., pp. 1-5.

Pichla-Gollon et al., "Structure-Based Identification of a Major Neutralizing Site in an Adenovirus Hexon", Journal of Virology, 2007, vol. 81, No. 4, pp. 1680-1689.

Rawle et al., "Specificity of the Mouse Cytotoxic T Lymphocyte Response to Adenovirus 5", Journal of Immunology, 1991, vol. 146, No. 11, pp. 3977-3984.

Sanchez-Trincado et al.,"Fundamentals and Methods for T- and B-Cell Epitope Prediction", Journal of Immunology Research, 2017, vol. 2017, pp. 1-15.

Ana Lemos De Matos, et al., Oncolytic Viruses and the Immune System: The Dynamic Due, Molecular Therapy Methods & Clinical Development, vol. 17, pp. 349-358, 2020.

Ross M. Kedl, et al., Epitope Dominance, Competition and T Cell Affinity Maturation, Current Opinion in Immunology, vol. 15, pp. 120-127, 2003.

Juan J. Rojas, et al., "Minimal RB-Responsive E1A Promoter Modification to Attain Potency, Selectivity, and Transgene-Arming Capacity in Oncolytic Adenoviruses", Molecular Therapy, vol. 18, No. 11, pp. 1960-1971, 2010.

Alena Gros, et al., Bioselection of a Gain of Function Mutation That Enhances Adenovirus 5 Release and Improves Its Antitumoral Potency, Cancer Res, vol. 68, No. 21, pp. 8928-8937, 2008.

\* cited by examiner

A

B

| Peptide | Origin | Kd (μM) | Functionality of the mutation |
|---|---|---|---|
| Hex512 | wt HAd5 | 4.5 | - |
| L520P | ICOVIR15K-QD | 47.4 | YES |
| Hex917 | wt HAd5 | 3.7 | - |
| V925K | ICOVIR15K-QD | 2150 | YES |

SEQUENCE LISTING

<160> NUMBER OF SEQ ID NOS: 38

<210> SEQ ID NO 1
<211> LENGTH: 36124
<212> TYPE: DNA
<213> ORGANISM: Artificial Sequence
<220> FEATURE:
<223> OTHER INFORMATION: ICOVIR15K (nt1-36124)

<400> SEQUENCE: 1

```
taattaccct gttatcccta catcatcaat aatatacctt attttggatt gaagccaata      60
tgataatgag ggggtggagt ttgtgacgtg gcgcggggcg tgggaacggg gcgggtgacg     120
tagtagtgtg gcggaagtgt gatgttgcaa gtgtggcgga acacatgtaa gcgacggatg     180
tggcaaaagt gacgtttttg gtgtgcgccg gtgtacacag gaagtgacaa ttttcgcgcg     240
gttttaggcg gatgttgtag taaatttggg cgtaaccgag taagatttgg ccattttcgc     300
gggaaaactg aataagagga agtgaaatct gaataatttt gtgttactca tagcgcgtaa     360
tatttgtcta gggccgcggg gactttgacc gtttacgtgg agactcgccc aggtgttttt     420
ctcaggtgtt ttccgcgtac tcggcggctc gtggctcttc gcggcaaaa aggatttggc     480
```

```
gcgtaaaagt ggttcgaagt actcggcggc tcgtggctct ttcgcggcaa aaaggatttg      540
gcgcgtaaaa gtggttcgaa gtacgtcgac cacaaacccc gcccagcgtc ttgtcattgg      600
cgtcgacgct gtacggggtc aaagttggcg ttttattatt atagtcagct gacgtgtagt      660
gtatttatac ccggtgagtt cctcaagagg ccactcttga gtgccagcga gtagagtttt      720
ctcctccgag ccgctccgac accgggactg aaaatgagac atattatctg ccacggaggt      780
gttattaccg aagaaatggc cgccagtctt ttggaccagc tgatcgaaga ggtactggct      840
gataatcttc cacctcctag ccatttttgaa ccacctaccc ttcacgaact gtatgattta      900
gacgtgacgg cccccgaaga tcccaacgag gaggcggttt cgcagatttt tcccgactct      960
gtaatgttgg cggtgcagga agggattgac ttactcactt ttccgccggc gcccggttct     1020
ccggagccgc ctcaccttc ccggcagccc gagcagccgg agcagagagc cttgggtccg     1080
gtttctatgc caaaccttgt accggaggtg atcgatccac ccagtgacga cgaggatgaa     1140
gagggtgagg agtttgtgtt agattatgtg gagcaccccg ggcacggttg caggtcttgt     1200
cattatcacc ggaggaatac gggggaccca gatattatgt gttcgctttg ctatatgagg     1260
acctgtggca tgtttgtcta cagtaagtga aaattatggg cagtgggtga tagagtggtg     1320
ggtttggtgt ggtaattttt ttttttaattt ttacagttttt gtggtttaaa gaattttgta     1380
ttgtgatttt tttaaaaggt cctgtgtctg aacctgagcc tgagcccgag ccagaaccgg     1440
agcctgcaag acctacccgc cgtcctaaaa tggcgcctgc tatcctgaga cgcccgacat     1500
cacctgtgtc cagagaatgc aatagtagta cggatagctg tgactccggt ccttctaaca     1560
cacctcctga gatacacccg gtggtcccgc tgtgccccat taaaccagtt gccgtgagag     1620
ttggtgggcg tcgccaggct gtggaatgta tcgaggactt gcttaacgag cctgggcaac     1680 cttttggactt gagctgtaaa cgccccaggc cataaggtgt aaacctgtga ttgcgtgtgt     1740
ggttaacgcc tttgtttgct gaatgagttg atgtaagttt aataaagggt gagataatgt     1800
ttaacttgca tggcgtgtta aatggggcgg ggcttaaagg gtatataatg cgccgtgggc     1860
taatcttggt tacatctgac ctcatggagg cttgggagtg tttggaagat ttttctgctg     1920
tgcgtaactt gctggaacag agctctaaca gtacctcttg gttttggagg tttctgtggg     1980
gctcatccca ggcaaagtta gtctgcagaa ttaaggagga ttacaagtgg gaatttgaag     2040
agcttttgaa atcctgtggt gagctgtttg attctttgaa tctgggtcac caggcgcttt     2100
tccaagagaa ggtcatcaag actttggatt tttccacacc ggggcgcgct gcggctgctg     2160 ttgcttttttt gagttttata aaggataaat ggagcgaaga aacccatctg agcgggggt     2220 acctgctgga ttttctggcc atgcatctgt ggagagcggt tgtgagacac aagaatcgcc     2280
tgctactgtt gtcttccgtc cgcccggcga taataccgac ggaggagcag cagcagcagc     2340
aggaggaagc caggcggcgg cggcaggagc agagcccatg gaacccgaga gccggcctgg     2400
accctcggga tgaatgttg tacaggtggc tgaactgtat ccagaactga gacgcatttt     2460
gacaattaca gaggatgggc aggggctaaa ggggtaaag agggagcggg gggcttgtga     2520
ggctacagag gaggctagga atctagcttt tagcttaatg accagacacc gtcctgagtg     2580
tattactttt caacagatca aggataattg cgctaatgag cttgatctgc tggcgcagaa     2640
gtattccata gagcagctga ccacttactg gctgcagcca ggggatgatt ttgaggaggc     2700
tattagggta tatgcaaagg tggcacttag gccagattgc aagtacaaga tcagcaaact     2760
tgtaaatatc aggaattgtt gctacatttc tgggaacggg gccgaggtgg agatagatac     2820
ggaggatagg gtggcctta gatgtagcat gataaatatg tggccggggg tgcttggcat     2880
```

```
ggacggggtg gttattatga atgtaaggtt tactggcccc aattttagcg gtacggtttt    2940
cctggccaat accaacctta tcctacacgg tgtaagcttc tatgggttta acaatacctg    3000
tgtggaagcc tggaccgatg taagggttcg gggctgtgcc ttttactgct gctggaaggg    3060
ggtggtgtgt cgccccaaaa gcagggcttc aattaagaaa tgcctctttg aaaggtgtac    3120
cttgggtatc ctgtctgagg gtaactccag ggtgcgccac aatgtggcct ccgactgtgg    3180
ttgcttcatg ctagtgaaaa gcgtggctgt gattaagcat aacatggtat gtggcaactg    3240
cgaggacagg gcctctcaga tgctgacctg ctcggacggc aactgtcacc tgctgaagac    3300
cattcacgta gccagccact ctcgcaaggc ctggccagtg tttgagcata acatactgac    3360
ccgctgttcc ttgcatttgg gtaacaggag ggggtgttc ctaccttacc aatgcaattt    3420
gagtcacact aagatattgc ttgagcccga gagcatgtcc aaggtgaacc tgaacggggt    3480
gtttgacatg accatgaaga tctggaaggt gctgaggtac gatgagaccc gcaccaggtg    3540
cagaccctgc gagtgtggcg gtaaacatat taggaaccag cctgtgatgc tggatgtgac    3600
cgaggagctg aggcccgatc acttggtgct ggcctgcacc cgcgctgagt ttggctctag    3660
cgatgaagat acagattgag gtactgaaat gtgtgggcgt ggcttaaggg tgggaaagaa    3720
tatataaggt gggggtctta tgtagttttg tatctgtttt gcagcagccg ccgccgccat    3780
gagcaccaac tcgtttgatg gaagcattgt gagctcatat ttgacaacgc gcatgccccc    3840
atgggccggg gtgcgtcaga atgtgatggg ctccagcatt gatggtcgcc ccgtcctgcc    3900
cgcaaactct actaccttga cctacgagac cgtgtctgga acgccgttgg agactgcagc    3960
ctccgccgcc gcttcagccg ctgcagccac cgcccgcggg attgtgactg actttgcttt    4020
cctgagcccg cttgcaagca gtgcagcttc ccgttcatcc gcccgcgatg acaagttgac    4080
ggctcttttg gcacaattgg attctttgac ccgggaactt aatgtcgttt ctcagcagct    4140
gttggatctg cgccagcagg tttctgccct gaaggcttcc tcccctccca atgcggttta    4200
aaacataaat aaaaaaccag actctgtttg gatttggatc aagcaagtgt cttgctgtct    4260
ttatttaggg gttttgcgcg cgcggtaggc ccgggaccag cggtctcggt cgttgagggt    4320
cctgtgtatt ttttccagga cgtggtaaag gtgactctgg atgttcagat acatgggcat    4380
aagcccgtct ctggggtgga ggtagcacca ctgcagagct tcatgctgcg gggtggtgtt    4440
gtagatgatc cagtcgtagc aggagcgctg ggcgtggtgc ctaaaaatgt ctttcagtag    4500
caagctgatt gccaggggca ggcccttggt gtaagtgttt acaaagcggt taagctggga    4560
tgggtgcata cgtggggata tgagatgcat cttggactgt attttaggt tggctatgtt    4620 cccagccata tccctccggg gattcatgtt gtgcagaacc accagcacag tgtatccggt    4680
gcacttggga aatttgtcat gtagcttaga aggaaatgcg tggaagaact tggagacgcc    4740
cttgtgacct ccaagatttt ccatgcattc gtccataatg atggcaatgg gcccacgggc    4800
ggcggcctgg gcgaagatat ttctgggatc actaacgtca tagttgtgtt ccaggatgag    4860
atcgtcatag gccattttta caaagcgcgg gcggagggtg ccagactgcg gtataatggt    4920
tccatccggc ccaggggcgt agttaccctc acagatttgc atttcccacg ctttgagttc    4980 agatggggg atcatgtcta cctgcgggc gatgaagaaa acggtttccg gggtagggga    5040
gatcagctgg gaagaaagca ggttcctgag cagctgcgac ttaccgcagc cggtgggccc    5100
gtaaatcaca cctattaccg gctgcaactg gtagttaaga gagctgcagc tgccgtcatc    5160
cctgagcagg ggggccactt cgttaagcat gtccctgact cgcatgtttt ccctgaccaa    5220
```

```
atccgccaga aggcgctcgc cgcccagcga tagcagttct tgcaaggaag caaagttttt    5280
caacggtttg agaccgtccg ccgtaggcat gcttttgagc gtttgaccaa gcagttccag    5340
gcggtcccac agctcggtca cctgctctac ggcatctcga tccagcatat ctcctcgttt    5400
cgcgggttgg ggcggctttc gctgtacggc agtagtcggt gctcgtccag acgggccagg    5460
gtcatgtctt ccacgggcg cagggtcctc gtcagcgtag tctgggtcac ggtgaagggg    5520
tgcgctccgg gctgcgcgct ggccaggtg cgcttgaggc tggtcctgct ggtgctgaag    5580
cgctgccggt cttcgccctg cgcgtcggcc aggtagcatt tgaccatggt gtcatagtcc    5640 agccctccg cggcgtggcc cttgcgcgc agcttgccct tggaggaggc gccgcacgag    5700
gggcagtgca gacttttgag ggcgtagagc ttgggcgcga gaaataccga ttccggggag    5760
taggcatccg cgccgcaggc cccgcagacg gtctcgcatt ccacgagcca ggtgagctct    5820
ggccgttcgg ggtcaaaaac caggtttccc ccatgctttt tgatgcgttt cttacctctg    5880
gtttccatga gccggtgtcc acgctcggtg acgaaaaggc tgtccgtgtc cccgtataca    5940
gacttgagag gcctgtcctc gagcggtgtt ccgcggtcct cctcgtatag aaactcggac    6000
cactctgaga caaaggctcg cgtccaggcc agcacgaagg aggctaagtg ggaggggtag    6060
cggtcgttgt ccactagggg gtccactcgc tccagggtgt gaagacacat gtcgccctct    6120
tcggcatcaa ggaaggtgat tggttttgtag gtgtaggcca cgtgaccggg tgttcctgaa    6180 gggggggctat aaaaggggt gggggcgcgt tcgtcctcac tctcttccgc atcgctgtct    6240
gcgagggcca gctgttgggg tgagtactcc ctctgaaaag cgggcatgac ttctgcgcta    6300
agattgtcag tttccaaaaa cgaggaggat ttgatattca cctggcccgc ggtgatgcct    6360
ttgagggtgg ccgcatccat ctggtcagaa agacaatct ttttgttgtc aagcttggtg    6420
gcaaacgacc cgtagagggc gttggacagc aacttggcga tggagcgcag ggtttggttt    6480
ttgtcgcgat cggcgcgctc cttggccgcg atgtttagct gcacgtattc gcgcgcaacg    6540
caccgccatt cgggaaagac ggtggtgcgc tcgtcgggca ccaggtgcac gcgccaaccg    6600
cggttgtgca gggtgacaag gtcaacgctg gtggctacct ctccgcgtag gcgctcgttg    6660
gtccagcaga ggcggccgcc cttgcgcgag cagaatggcg gtagggggtc tagctgcgtc    6720
tcgtccgggg ggtctgcgtc cacggtaaag accccgggca gcaggcgcgc gtcgaagtag    6780
tctatcttgc atccttgcaa gtctagcgcc tgctgccatg cgcgggcggc aagcgcgcgc    6840
tcgtatgggt tgagtggggg accccatggc atggggtggg tgagcgcgga ggcgtacatg    6900
ccgcaaatgt cgtaaacgta gaggggctct ctgagtattc caagatatgt agggtagcat    6960
cttccaccgc ggatgctggc gcgcacgtaa tcgtatagtt cgtgcgaggg agcgaggagg    7020 tcggaccga ggttgctacg gcgggctgc tctgctcgga agactatctg cctgaagatg    7080
gcatgtgagt tggatgatat ggttggacgc tggaagacgt tgaagctggc gtctgtgaga    7140
cctaccgcgt cacgcacgaa ggaggcgtag gagtcgcgca gcttgttgac cagctcggcg    7200
gtgacctgca cgtctagggc gcagtagtcc agggtttcct tgatgatgtc atacttatcc    7260 tgtcccttt ttttccacag ctcgcggttg aggacaaact cttcgcggtc tttccagtac    7320
tcttggatcg gaaacccgtc ggcctccgaa cggtaagagc ctagcatgta gaactggttg    7380
acggcctggt aggcgcagca tccctttct acgggtagcg cgtatgcctg cgcggccttc    7440
cggagcgagg tgtgggtgag cgcaaaggtg tccctgacca tgactttgag gtactggtat    7500
ttgaagtcag tgtcgtcgca tccgccctgc tcccagcaaa aaagtccgt gcgcttttg    7560 gaacgcggat ttggcagggc gaaggtgaca tcgttgaaga gtatctttcc cgcgcgaggc    7620
```

```
ataaagttgc gtgtgatgcg aagggtccc ggcacctcgg aacgttgtt aattacctgg    7680 gcggcgagca cgatctcgtc aaagccgttg atgttgtggc ccacaatgta aagttccaag    7740
aagcgcggga tgcccttgat ggaaggcaat tttttaagtt cctcgtaggt gagctcttca    7800
ggggagctga gcccgtgctc tgaaagggcc cagtctgcaa gatgagggtt ggaagcgacg    7860
aatgagctcc acaggtcacg ggccattagc atttgcaggt ggtcgcgaaa ggtcctaaac    7920
tggcgaccta tggccatttt ttctggggtg atgcagtaga aggtaagcgg gtcttgttcc    7980
cagcggtccc atccaaggtt cgcggctagg tctcgcgcgg cagtcactag aggctcatct    8040
ccgccgaact tcatgaccag catgaagggc acgagctgct tcccaaaggc ccccatccaa    8100
gtataggtct ctacatcgta ggtgacaaag agacgctcgg tgcgaggatg cgagccgatc    8160
gggaagaact ggatctcccg ccaccaattg gaggagtggc tattgatgtg gtgaaagtag    8220
aagtccctgc gacgggccga acactcgtgc tggctttgt aaaaacgtgc gcagtactgg    8280
cagcggtgca cggctgtac atcctgcacg aggttgacct gacgaccgcg cacaaggaag    8340
cagagtggga atttgagccc ctcgcctggc gggtttggct ggtggtcttc tacttcggct    8400
gcttgtcctt gaccgtctgg ctgctcgagg ggagttacgg tggatcggac caccacgccg    8460
cgcgagccca aagtccagat gtccgcgcgc ggcggtcgga gcttgatgac aacatcgcgc    8520
agatgggagc tgtccatggt ctggagctcc cgcggcgtca ggtcaggcgg gagctcctgc    8580
aggtttacct cgcatagacg ggtcagggcg cgggctagat ccaggtgata cctaatttcc    8640
aggggctggt tggtggcggc gtcgatggct tgcaagaggc cgcatcccg cggcgcgact    8700 acggtaccgc gcggcgggcg gtgggccgcg ggggtgtcct tggatgatgc atctaaaagc    8760
ggtgacgcgg gcgagccccc ggaggtaggg ggggctccgg accgccggg agaggggca    8820 ggggcacgtc ggccgcgcgc gcgggcagga gctggtgctg cgcgcgtagg ttgctggcga    8880
acgcgacgac gcggcggttg atctcctgaa tctggcgcct ctgcgtgaag acgacgggcc    8940
cggtgagctt gaacctgaaa gagagttcga cagaatcaat ttcggtgtcg ttgacggcgg    9000
cctggcgcaa aatctcctgc acgtctcctg agttgtcttg ataggcgatc tcggccatga    9060
actgctcgat ctcttcctcc tggagatctc cgcgtccggc tcgctccacg gtggcggcga    9120
ggtcgttgga aatgcgggcc atgagctgcg agaaggcgtt gaggcctccc tcgttccaga    9180
cgcggctgta gaccacgccc ccttcggcat cgcgggcgcg catgaccacc tgcgcgagat    9240
tgagctccac gtgccgggcg aagacggcgt agtttcgcag gcgctgaaag aggtagttga    9300
gggtggtggc ggtgtgttct gccacgaaga agtacataac ccagcgtcgc aacgtggatt    9360
cgttgatatc ccccaaggcc tcaaggcgct ccatggcctc gtagaagtcc acggcgaagt    9420
tgaaaaactg ggagttgcgc gccgacacgg ttaactcctc ctccagaaga cggatgagct    9480
cggcgacagt gtcgcgcacc tcgcgctcaa aggctacagg ggcctcttct tcttcttcaa    9540
tctcctcttc cataagggcc tcccttctt cttcttctgg cggcggtggg ggaggggga    9600 cacggcggcg acgacggcgc accggaggc ggtcgacaaa gcgctcgatc atctccccgc    9660
ggcgacggcg catggtctcg gtgacggcgc ggccgttctc gcgggggcgc agttggaaga    9720
cgccgcccgt catgtcccgg ttatggggttg gcgggggggct gccatgcggc agggatacgg    9780
cgctaacgat gcatctcaac aattgttgtg taggtactcc gccgccgagg gacctgagcg    9840
agtccgcatc gaccggatcg gaaaacctct cgagaaaggc gtctaaccag tcacagtcgc    9900
aaggtaggct gagcaccgtg gcgggcggca gcggcggcg gtcggggttg tttctggcgg    9960
```

```
aggtgctgct gatgatgtaa ttaaagtagg cggtcttgag acggcggatg gtcgacagaa    10020
gcaccatgtc cttgggtccg gcctgctgaa tgcgcaggcg gtcggccatg ccccaggctt    10080
cgttttgaca tcggcgcagg tctttgtagt agtcttgcat gagcctttct accggcactt    10140
cttcttctcc ttcctcttgt cctgcatctc ttgcatctat cgctgcgcg gcggcggagt     10200 ttggccgtag gtggcgccct cttcctccca tgcgtgtgac cccgaagccc ctcatcggct    10260
gaagcagggc taggtcggcg acaacgcgct cggctaatat ggcctgctgc acctgcgtga    10320
gggtagactg gaagtcatcc atgtccacaa agcggtggta tgcgcccgtg ttgatggtgt    10380
aagtgcagtt ggccataacg gaccagttaa cggtctggtg accggctgc gagagctcgg     10440 tgtacctgag acgcgagtaa gccctcgagt caaatacgta gtcgttgcaa gtccgcacca    10500
ggtactggta tcccaccaaa aagtgcggcg gcggctggcg gtagaggggc cagcgtaggg    10560
tggccggggc tccggggggcg agatcttcca acataaggcg atgatatccg tagatgtacc    10620
tggacatcca ggtgatgccg gcggcggtgg tggaggcgcg cggaaagtcg cggacgcggt    10680
tccagatgtt gcgcagcggc aaaaagtgct ccatggtcgg gacgctctgg ccggtcaggc    10740
gcgcgcaatc gttgacgctc tagaccgtgc aaaaggagag cctgtaagcg ggcactcttc    10800
cgtggtctgg tggataaatt cgcaagggta tcatggcgga cgaccggggt tcgagccccg    10860
tatccggccg tccgccgtga tccatgcggt taccgcccgc gtgtcgaacc caggtgtgcg    10920
acgtcagaca acgggggagt gctcctttg gcttccttcc aggcgcggcg gctgctgcgc     10980
tagctttttt ggccactggc cgcgcgcagc gtaagcggtt aggctggaaa gcgaaagcat    11040
taagtggctc gctccctgta gccggagggt tattttccaa gggttgagtc gcgggacccc    11100
cggttcgagt ctcggaccgg ccggactgcg gcgaacgggg gtttgcctcc ccgtcatgca    11160
agaccccgct tgcaaattcc tccggaaaca gggacgagcc cctttttgc ttttcccaga     11220 tgcatccggt gctgcggcag atgcgccccc ctcctcagca gcggcaagag caagagcagc    11280
ggcagacatg cagggcaccc tcccctcctc ctaccgcgtc aggaggggcg acatccgcgg    11340
ttgacgcggc agcagatggt gattacgaac cccgcggcg ccgggcccgg cactacctgg     11400
acttggagga gggcgagggc ctggcgcgg taggagcgcc ctctcctgag cggcaccccaa     11460 gggtgcagct gaagcgtgat acgcgtgagg cgtacgtgcc gcggcagaac ctgtttcgcg    11520
accgcgaggg agaggagccc gaggagatgc gggatcgaaa gttccacgca gggcgcgagc    11580
tgcggcatgg cctgaatcgc gagcggttgc tgcgcgagga ggactttgag cccgacgcgc    11640
gaaccgggat tagtcccgcg cgcgcacacg tggcggccgc cgacctggta accgcatacg    11700
agcagacggt gaaccaggag attaactttc aaaaaagctt taacaaccac gtgcgtacgc    11760
ttgtggcgcg cgaggaggtg gctataggac tgatgcatct gtgggacttt gtaagcgcgc    11820
tggagcaaaa cccaaatagc aagccgctca tggcgcagct gttccttata gtgcagcaca    11880
gcagggacaa cgaggcattc agggatgcgc tgctaaacat agtagagccc gagggccgct    11940
ggctgctcga tttgataaac atcctgcaga gcatagtggt gcaggagcgc agcttgagcc    12000
tggctgacaa ggtggccgcc atcaactatt ccatgcttag cctgggcaag ttttacgccc    12060
gcaagatata ccatacccct tacgttccca tagacaagga ggtaaagatc gagggggttct    12120 acatgcgcat ggcgctgaag gtgcttacct tgagcgacga cctgggcgtt tatcgcaacg    12180
agcgcatcca caaggccgtg agcgtgagcc ggcggcgcga gctcagcgac cgcgagctga    12240
tgcacagcct gcaagggcc ctggctggca cgggcagcgg cgatagagag gccgagtcct     12300
actttgacgc gggcgctgac ctgcgctggg ccccaagccg acgcgccctg gaggcagctg    12360
```

```
gggccggacc tgggctggcg gtggcacccg cgcgcgctgg caacgtcggc ggcgtggagg   12420
aatatgacga ggacgatgag tacgagccag aggacggcga gtactaagcg gtgatgtttc   12480
tgatcagatg atgcaagacg caacggaccc ggcggtgcgg gcggcgctgc agagccagcc   12540
gtccggcctt aactccacgg acgactggcg ccaggtcatg gaccgcatca tgtcgctgac   12600
tgcgcgcaat cctgacgcgt tccggcagca gccgcaggcc aaccggctct ccgcaattct   12660
ggaagcggtg gtcccggcgc gcgcaaaccc cacgcacgag aaggtgctgg cgatcgtaaa   12720
cgcgctggcc gaaaacaggg ccatccggcc cgacgaggcc ggcctggtct acgacgcgct   12780
gcttcagcgc gtggctcgtt acaacagcgg caacgtgcag accaacctgg accggctggt   12840
gggggatgtg cgcgaggccg tggcgcagcg tgagcgcgcg cagcagcagg caacctggg    12900 ctccatggtt gcactaaacg ccttcctgag tacacagccc gccaacgtgc cgcggggaca   12960
ggaggactac accaactttg tgagcgcact gcggctaatg gtgactgaga caccgcaaag   13020
tgaggtgtac cagtctgggc cagactattt tttccagacc agtagacaag gcctgcagac   13080
cgtaaacctg agccaggctt tcaaaaactt gcaggggctg tgggggggtgc gggctcccac   13140 aggcgaccgc gcgaccgtgt ctagcttgct gacgcccaac tcgcgcctgt tgctgctgct   13200
aatagcgccc ttcacggaca gtggcagcgt gtcccgggac acatacctag gtcacttgct   13260
gacactgtac cgcgaggcca taggtcaggc gcatgtggac gagcatactt tccaggagat   13320
tacaagtgtc agccgcgcgc tggggcagga ggacacgggc agcctggagg caaccctaaa   13380
ctacctgctg accaaccggc ggcagaagat cccctcgttg cacagtttaa acagcgagga   13440
ggagcgcatt ttgcgctacg tgcagcagag cgtgagcctt aacctgatgc gcgacgggt    13500 aacgcccagc gtggcgctgg acatgaccgc gcgcaacatg gaaccgggca tgtatgcctc   13560
aaaccggccg tttatcaacc gcctaatgga ctacttgcat cgcgcggccg ccgtgaaccc   13620
cgagtatttc accaatgcca tcttgaaccc gcactggcta ccgcccctg gtttctacac    13680 cggggggattc gaggtgcccg agggtaacga tggattcctc tgggacgaca tagacgacag   13740
cgtgttttcc ccgcaaccgc agaccctgct agagttgcaa cagcgcgagc aggcagaggc   13800
ggcgctgcga aaggaaagct tccgcaggcc aagcagcttg tccgatctag gcgctgcggc   13860
cccgcggtca gatgctagta gcccatttcc aagcttgata gggtctctta ccagcactcg   13920
caccacccgc ccgcgcctgc tgggcgagga ggagtaccta aacaactcgc tgctgcagcc   13980
gcagcgcgaa aaaaacctgc ctccggcatt tcccaacaac gggatagaga gcctagtgga   14040
caagatgagt agatggaaga cgtacgcgca ggagcacagg gacgtgccag gcccgcgccc   14100
gcccacccgt cgtcaaaggc acgaccgtca gcggggtctg tgtgggagg acgatgactc    14160 ggcagacgac agcagcgtcc tggatttggg agggagtggc aacccgtttg cgcaccttcg   14220
ccccaggctg gggagaatgt tttaaaaaaa aaaaagcat gatgcaaaat aaaaaactca    14280
ccaaggccat ggcaccgagc gttggttttc ttgtattccc cttagtatgc ggcgcgcggc   14340
gatgtatgag gaaggtcctc ctccctccta cgagagtgtg gtgagcgcgg cgccagtggc   14400
ggcggcgctg ggttctccct tcgatgctcc cctggaccg ccgtttgtgc ctccgcggta    14460
cctgcggcct accgggggga gaaacagcat ccgttactct gagttggcac ccctattcga   14520
caccacccgt gtgtacctgg tggacaacaa gtcaacggat gtggcatccc tgaactacca   14580
gaacgaccac agcaactttc tgaccacggt cattcaaaac aatgactaca gcccggggga   14640
ggcaagcaca cagaccatca atcttgacga ccggtcgcac tggggcggcg acctgaaaac   14700
```

```
catcctgcat accaacatgc caaatgtgaa cgagttcatg tttaccaata agtttaaggc    14760
gcgggtgatg gtgtcgcgct tgcctactaa ggacaatcag gtggagctga aatacgagtg    14820
ggtggagttc acgctgcccg agggcaacta ctccgagacc atgaccatag accttatgaa    14880
caacgcgatc gtggagcact acttgaaagt gggcagacag aacggggttc tggaaagcga    14940
catcggggta agtttgaca cccgcaactt cagactgggg tttgaccccg tcactggtct     15000
tgtcatgcct ggggtatata caaacgaagc cttccatcca gacatcattt tgctgccagg    15060
atgcggggtg gacttcaccc acagccgcct gagcaacttg ttgggcatcc gcaagcggca    15120
acccttccag gagggcttta ggatcaccta cgatgatctg gagggtggta acattcccgc    15180
actgttggat gtggacgcct accaggcgag cttgaaagat gacaccgaac agggcggggg    15240
tggcgcaggc ggcagcaaca gcagtggcag cggcgcggaa gagaactcca acgcggcagc    15300
cgcggcaatg cagccggtgg aggacatgaa cgatcatgcc attcgcggcg acacctttgc    15360
cacacgggct gaggagaagc gcgctgaggc cgaagcagcg gccgaagctg ccgccccgc     15420 tgcgcaaccc gaggtcgaga agcctcagaa gaaaccggtg atcaaacccc tgacagagga    15480
cagcaagaaa cgcagttaca acctaataag caatgacagc accttcaccc agtaccgcag    15540
ctggtacctt gcatacaact acggcgaccc tcagaccgga atccgctcat ggaccctgct    15600
ttgcactcct gacgtaacct gcggctcgga gcaggtctac tggtcgttgc cagacatgat    15660
gcaagacccc gtgaccttcc gctccacgcg ccagatcagc aactttccgg tggtgggcgc    15720
cgagctgttg cccgtgcact ccaagagctt ctacaacgac caggccgtct actcccaact    15780
catccgccag tttacctctc tgacccacgt gttcaatcgc tttcccgaga accagatttt    15840
ggcgcgcccg ccagccccca ccatcaccac cgtcagtgaa aacgttcctg ctctcacaga    15900
tcacgggacg ctaccgctgc gcaacagcat cggaggagtc cagcgagtga ccattactga    15960
cgccagacgc cgcacctgcc cctacgttta caaggccctg gcatagtct cgccgcgcgt     16020 cctatcgagc cgcacttttt gagcaagcat gtccatcctt atatcgccca gcaataacac    16080
aggctggggc ctgcgcttcc caagcaagat gtttggcggg gccaagaagc gctccgacca    16140
acacccagtg cgcgtgcgcg ggcactaccg cgcgccctgg ggcgcgcaca aacgcggccg    16200
cactgggcgc accaccgtcg atgacgccat cgacgcggtg gtggaggagg cgcgcaacta    16260
cacgcccacg ccgccaccag tgtccacagt ggacgcggcc attcagaccg tggtgcgcgg    16320
agcccggcgc tatgctaaaa tgaagagacg gcggaggcgc gtagcacgtc gccaccgccg    16380
ccgacccggc actgccgccc aacgcgcggc ggcggccctg cttaaccgcg cacgtcgcac    16440
cggccgacgg gcggccatgc gggccgctcg aaggctggcc gcgggtattg tcactgtgcc    16500
ccccaggtcc aggcgacgag cggccgccgc agcagccgcg gccattagtg ctatgactca    16560
gggtcgcagg ggcaacgtgt attgggtgcg cgactcggtt agcggcctgc gcgtgcccgt    16620
gcgcacccgc cccccgcgca actagattgc aagaaaaaac tacttagact cgtactgttg    16680
tatgtatcca gcggcggcgg cgcgcaacga agctatgtcc aagcgcaaaa tcaaagaaga    16740
gatgctccag gtcatcgcgc cggagatcta tggcccccg aagaaggaag agcaggatta    16800 caagcccga aagctaaagc gggtcaaaaa gaaaagaaa gatgatgatg atgaacttga    16860
cgacgaggtg gaactgctgc acgctaccgc gcccaggcga cgggtacagt ggaaaggtcg    16920
acgcgtaaaa cgtgttttgc gacccggcac caccgtagtc tttacgcccg gtgagcgctc    16980
cacccgcacc tacaagcgcg tgtatgatga ggtgtacggc gacgaggacc tgcttgagca    17040
ggccaacgag cgcctcgggg agtttgccta cggaaagcgg cataaggaca tgctggcgtt    17100
```

```
gccgctggac gagggcaacc caacacctag cctaaagccc gtaacactgc agcaggtgct    17160
gcccgcgctt gcaccgtccg aagaaaagcg cggcctaaag cgcgagtctg gtgacttggc    17220
acccaccgtg cagctgatgg tacccaagcg ccagcgactg aagatgtct tggaaaaaat     17280 gaccgtggaa cctgggctgg agcccgaggt ccgcgtgcgg ccaatcaagc aggtggcgcc    17340
gggactgggc gtgcagaccg tggacgttca gatacccact accagtagca ccagtattgc    17400
caccgccaca gagggcatgg agacacaaac gtccccggtt gcctcagcgg tggcggatgc    17460
cgcggtgcag gcggtcgctg cggccgcgtc caagacctct acggaggtgc aaacggaccc    17520
gtggatgttt cgcgtttcag cccccgcgcg cccgcgccgt tcgaggaagt acggcgccgc    17580
cagcgcgcta ctgcccgaat atgccctaca tccttccatt gcgcctaccc ccggctatcg    17640
tggctacacc taccgcccca gaagacgagc aactacccga cgccgaacca ccactggaac    17700
ccgccgccgc cgtcgccgtc gccagcccgt gctggccccg atttccgtgc gcagggtggc    17760
tcgcgaagga ggcaggaccc tggtgctgcc aacagcgcgc taccacccca gcatcgttta    17820
aaagccggtc tttgtggttc ttgcagatat ggccctcacc tgccgcctcc gtttccggt    17880 gccgggattc cgaggaagaa tgcaccgtag gaggggcatg gccggccacg gcctgacggg    17940
cggcatgcgt cgtgcgcacc accggcggcg gcgcgcgtcg caccgtcgca tgcgcggcgg    18000
tatcctgccc ctccttattc cactgatcgc cgcggcgatt ggcgccgtgc ccggaattgc    18060
atccgtggcc ttgcaggcgc agagacactg attaaaaaca agttgcatgt ggaaaaatca    18120
aaataaaaag tctggactct cacgctcgct tggtcctgta actattttgt agaatggaag    18180
acatcaactt tgcgtctctg gccccgcgac acggctcgcg cccgttcatg ggaaactggc    18240
aagatatcgg caccagcaat atgagcggtg gcgccttcag ctggggctcg ctgtggagcg    18300
gcattaaaaa tttcggttcc accgttaaga actatggcag caaggcctgg aacagcagca    18360
caggccagat gctgagggat aagttgaaag agcaaaattt ccaacaaaag gtggtagatg    18420
gcctggcctc tggcattagc ggggtggtgg acctggccaa ccaggcagtg caaaataaga    18480
ttaacagtaa gcttgatccc cgccctcccg tagaggagcc tccaccggcc gtggagacag    18540
tgtctccaga ggggcgtggc gaaaagcgtc gcgccccga cagggaagaa actctggtga    18600
cgcaaataga cgagcctccc tcgtacgagg aggcactaaa gcaaggcctg cccaccaccc    18660
gtcccatcgc gcccatggct accggagtgc tgggccagca cacaccgta acgctggacc    18720 tgcctccccc cgccgacacc cagcagaaac ctgtgctgcc aggcccgacc gccgttgttg    18780
taacccgtcc tagccgcgcg tccctgcgcc gcgccgccag cggtccgcga tcgttgcggc    18840
ccgtagccag tggcaactgg caaagcacac tgaacagcat cgtgggtctg ggggtgcaat    18900
ccctgaagcg ccgacgatgc ttctgatagc taacgtgtcg tatgtgtgtc atgtatgcgt    18960
ccatgtcgcc gccagaggag ctgctgagcc gccgcgcgcc cgctttccaa gatggctacc    19020
ccttcgatga tgccgcagtg gtcttacatg cacatctcgg gccaggacgc ctcggagtac    19080
ctgagccccg ggctggtgca gtttgcccgc gccaccgaga cgtacttcag cctgaataac    19140
aagtttagaa accccacggt ggcgcctacg cacgacgtga ccacagaccg gtcccagcgt    19200
ttgacgctgc ggttcatccc tgtggaccgt gaggatactg cgtactcgta caaggcgcgg    19260 ttcacccctag ctgtgggtga taacgtgtg ctggacatgg cttccacgta ctttgacatc    19320
cgcggcgtgc tggacagggg ccctacttttt aagccctact ctggcactgc ctacaacgcc    19380
ctggctccca agggtgcccc aaatccttgc gaatgggatg aagctgctac tgctcttgaa    19440
```

```
ataaacctag aagaagagga cgatgacaac gaagacgaag tagacgagca agctgagcag    19500
caaaaaactc acgtatttgg gcaggcgcct tattctggta taaatattac aaaggagggt    19560
attcaaatag gtgtcgaagg tcaaacacct aaatatgccg ataaaacatt tcaacctgaa    19620
cctcaaatag gagaatctca gtggtacgaa acagaaatta atcatgcagc tgggagagtc    19680
ctaaaaaaga ctaccccaat gaaccatgt tacggttcat atgcaaaacc cacaaatgaa     19740
aatggagggc aaggcattct tgtaaagcaa caaaatggaa agctagaaag tcaagtggaa    19800 atgcaattt tctcaactac tgaggcagcc gcaggcaatg gtgataactt gactcctaaa     19860
gtggtattgt acagtgaaga gtagatata gaaaccccag acactcatat ttcttacatg      19920
cccactatta aggaaggtaa ctcacgagaa ctaatgggcc aacaatctat gcccaacagg    19980
cctaattaca ttgcttttag ggacaatttt attggtctaa tgtattacaa cagcacgggt    20040
aatatgggtg ttctggcggg ccaagcatcg cagttgaatg ctgttgtaga tttgcaagac    20100
agaaacacag agcttttcata ccagcttttg cttgattcca ttggtgatag aaccaggtac    20160
ttttctatgt ggaatcaggc tgttgacagc tatgatccag atgttagaat tattgaaaat    20220
catggaactg aagatgaact tccaaattac tgctttccac tgggaggtgt gattaataca    20280
gagactctta ccaaggtaaa acctaaaaca ggtcaggaaa atggatggga aaaagatgct    20340
acagaatttt cagataaaaa tgaaataaga gttggaaata attttgccat ggaaatcaat    20400
ctaaatgcca acctgtggag aaatttcctg tactccaaca tagcgctgta tttgcccgac    20460
aagctaaagt acagtccttc caacgtaaaa atttctgata acccaaacac ctacgactac    20520
atgaacaagc gagtggtggc tcccgggcta gtggactgct acattaacct tggagcacgc    20580
tggtcccttg actatatgga caacgtcaac ccatttaacc accaccgcaa tgctggcctg    20640
cgctaccgct caatgttgct gggcaatggt cgctatgtgc ccttccacat ccaggtgcct    20700
cagaagttct ttgccattaa aaacctcctt ctcctgccgg gctcatacac ctacgagtgg    20760
aacttcagga aggatgttaa catggttctg cagagctccc taggaaatga cctaagggtt    20820
gacggagcca gcattaagtt tgatagcatt tgcctttacg ccaccttctt ccccatggcc    20880
cacaacaccg cctccacgct tgaggccatg cttagaaacg acaccaacga ccagtccttt    20940
aacgactatc tctccgccgc caacatgctc taccctatac ccgccaacgc taccaacgtg    21000
cccatatcca tccctcccg caactgggcg gctttccgcg gctgggcctt cacgcgcctt    21060
aagactaagg aaaccccatc actgggctcg ggctacgacc cttattacac ctactctggc    21120
tctataccct acctagatgg aaccttttac ctcaaccaca cctttaagaa ggtggccatt    21180
acctttgact cttctgtcag ctggcctggc aatgaccgcc tgcttacccc caacgagttt    21240
gaaattaagc gctcagttga cggggagggt tacaacgttg cccagtgtaa catgaccaaa    21300
gactggttcc tggtacaaat gctagctaac tataacattg gctaccaggg cttctatatc    21360
ccagagagct acaaggaccg catgtactcc ttctttagaa acttccagcc catgagccgt    21420
caggtggtgg atgatactaa atacaaggac taccaacagg tgggcatcct acaccaacac    21480
aacaactctg gatttgttgg ctaccttgcc cccaccatgc gcgaaggaca ggcctaccct    21540
gctaacttcc cctatccgct tataggcaag accgcagttg acagcattac ccagaaaaag    21600
tttctttgcg atcgcaccct ttggcgcatc ccattctcca gtaactttat gtccatgggc    21660
gcactcacag acctgggcca aaaccttctc tacgccaact ccgccacgc gctagacatg    21720 acttttgagg tggatcccat ggacgagccc accettctt atgttttgtt tgaagtcttt    21780
gacgtggtcc gtgtgcacca gccgcaccgc ggcgtcatcg aaaccgtgta cctgcgcacg    21840
```

```
cccttctcgg ccggcaacgc cacaacataa agaagcaagc aacatcaaca acagctgccg   21900
ccatgggctc cagtgagcag gaactgaaag ccattgtcaa agatcttggt tgtgggccat   21960
attttttggg cacctatgac aagcgctttc caggctttgt ttctccacac aagctcgcct   22020
gcgccatagt caatacggcc ggtcgcgaga ctggggcgt acactggatg gcctttgcct   22080
ggaacccgca ctcaaaaaca tgctacctct ttgagccctt tggcttttct gaccagcgac   22140
tcaagcaggt ttaccagttt gagtacgagt cactcctgcg ccgtagcgcc attgcttctt   22200
cccccgaccg ctgtataacg ctggaaaagt ccacccaaag cgtacagggg cccaactcgg   22260
ccgcctgtgg actattctgc tgcatgtttc tccacgcctt tgccaactgg ccccaaactc   22320
ccatggatca accccacc atgaaccta ttaccggggt acccaactcc atgctcaaca   22380
gtccccaggt acagcccacc ctgcgtcgca accaggaaca gctctacagc ttcctggagc   22440
gccactcgcc ctacttccgc agccacagtg cgcagattag gagcgccact tcttttttgtc   22500
acttgaaaaa catgtaaaaa taatgtacta gagacacttt caataaaggc aaatgctttt   22560
atttgtacac tctcgggtga ttatttaccc ccacccttgc cgtctgcgcc gtttaaaaat   22620
caaagggggtt ctgccgcgca tcgctatgcg ccactggcag ggacacgttg cgatactggt   22680
gtttagtgct ccacttaaac tcaggcacaa ccatccgcgg cagctcggtg aagttttcac   22740
tccacaggct gcgcaccatc accaacgcgt ttagcaggtc gggcgccgat atcttgaagt   22800
cgcagttggg gcctccgccc tgcgcgcgcg agttgcgata cacagggttg cagcactgga   22860
acactatcag cgccgggtgg tgcacgctgg ccagcacgct cttgtcggag atcagatccg   22920
cgtccaggtc ctccgcgttg ctcagggcga acggagtcaa ctttggtagc tgccttccca   22980
aaaagggcgc gtgcccaggc tttgagttgc actcgcaccg tagtggcatc aaaaggtgac   23040
cgtgcccggt ctgggcgtta ggatacagcg cctgcataaa agccttgatc tgcttaaaag   23100
ccacctgagc ctttgcgcct tcagagaaga acatgccgca agacttgccg gaaaactgat   23160
tggccggaca ggccgcgtcg tgcacgcagc accttgcgtc ggtgttggag atctgcacca   23220
catttcggcc ccaccggttc ttcacgatct tggccttgct agactgctcc ttcagcgcgc   23280
gctgcccgtt ttcgctcgtc acatccattt caatcacgtg ctcctttattt atcataatgc   23340
ttccgtgtag acacttaagc tcgccttcga tctcagcgca gcggtgcagc cacaacgcgc   23400
agcccgtggg ctcgtgatgc ttgtaggtca cctctgcaaa cgactgcagg tacgcctgca   23460
ggaatcgccc catcatcgtc acaaaggtct tgttgctggt gaaggtcagc tgcaacccgc   23520
ggtgctcctc gttcagccag gtcttgcata cggccgccag agcttccact tggtcaggca   23580
gtagtttgaa gttcgccttt agatcgttat ccacgtggta cttgtccatc agcgcgcgcg   23640
cagcctccat gcccttctcc cacgcagaca cgatcggcac actcagcggg ttcatcaccg   23700
taatttcact ttccgcttcg ctgggctctt cctcttcctc ttgcgtccgc ataccacgcg   23760
ccactgggtc gtcttcattc agccgccgca ctgtgcgctt acctcctttg ccatgcttga   23820
ttagcaccgg tgggttgctg aaacccacca tttgtagcgc cacatcttct ctttcttcct   23880
cgctgtccac gattacctct ggtgatggcg ggcgctcggg cttgggagaa gggcgcttct   23940
ttttcttctt gggcgcaatg gccaaatccg ccgccgaggt cgatgccgc gggctgggtg   24000
tgcgcggcac cagcgcgtct tgtgatgagt cttcctcgtc ctcggactcg atacgccgcc   24060
tcatccgctt ttttgggggc gcccggggag gcggcggcga cggggacggg gacgacacgt   24120
cctccatggt tggggacgt cgcgccgcac cgcgtccgcg ctcgggggtg gtttcgcgct   24180
```

-continued

```
gctcctcttc ccgactggcc atttccttct cctataggca gaaaaagatc atggagtcag   24240
tcgagaagaa ggacagccta accgcccct ctgagttcgc caccaccgcc tccaccgatg    24300
ccgccaacgc gcctaccacc ttccccgtcg aggcaccccc gcttgaggag gaggaagtga   24360
ttatcgagca ggacccaggt tttgtaagcg aagacgacga ggaccgctca gtaccaacag   24420
aggataaaaa gcaagaccag gacaacgcag aggcaaacga ggaacaagtc gggcgggggg   24480
acgaaaggca tggcgactac ctagatgtgg gagacgacgt gctgttgaag catctgcagc   24540
gccagtgcgc cattatctgc gacgcgttgc aagagcgcag cgatgtgccc ctcgccatag   24600
cggatgtcag ccttgcctac gaacgccacc tattctcacc gcgcgtaccc cccaaacgcc   24660
aagaaaacgg cacatgcgag cccaacccgc gcctcaactt ctacccgta tttgccgtgc    24720 cagaggtgct tgccacctat cacatctttt tccaaaactg caagatcccc ctatcctgcc   24780
gtgccaaccg cagccgagcg gacaagcagc tggccttgcg gcagggcgct gtcatacctg   24840
atatcgcctc gctcaacgaa gtgccaaaaa tctttgaggg tcttggacgc gacgagaagc   24900
gcgcggcaaa cgctctgcaa caggaaaaca gcgaaaatga aagtcactct ggagtgttgg   24960
tggaactcga gggtgacaac gcgcgcctag ccgtactaaa acgcagcatc gaggtcaccc   25020
actttgccta cccggcactt aacctacccc ccaaggtcat gagcacagtc atgagtgagc   25080
tgatcgtgcg ccgtgcgcag cccctggaga gggatgcaaa tttgcaagaa caaacagagg   25140
agggcctacc cgcagttggc gacgagcagc tagcgcgctg gcttcaaacg cgcgagcctg   25200
ccgacttgga ggagcgacgc aaactaatga tggccgcagt gctcgttacc gtggagcttg   25260
agtgcatgca gcggttcttt gctgacccgg agatgcagcg caagctagag gaaacattgc   25320
actacacctt tcgacagggc tacgtacgcc aggcctgcaa gatctccaac gtggagctct   25380
gcaacctggt ctcctacctt ggaattttgc acgaaaaccg ccttgggcaa aacgtgcttc   25440
attccacgct caagggcgag gcgcgccgcg actacgtccg cgactgcgtt tacttatttc   25500
tatgctacac ctggcagacg gccatgggcg tttggcagca gtgcttggag gagtgcaacc   25560
tcaaggagct gcagaaactg ctaaagcaaa acttgaagga cctatggacg gccttcaacg   25620
agcgctccgt ggccgcgcac ctggcggaca tcatttttccc cgaacgcctg cttaaaaccc   25680
tgcaacaggg tctgccagac ttcaccagtc aaagcatgtt gcagaacttt aggaacttta   25740
tcctagagcg ctcaggaatc ttgcccgcca cctgctgtgc acttcctagc gactttgtgc   25800
ccattaagta ccgcgaatgc cctccgccgc tttggggcca ctgctacctt ctgcagctag   25860
ccaactacct tgcctaccac tctgacataa tggaagacgt gagcggtgac ggtctactgg   25920
agtgtcactg tcgctgcaac ctatgcaccc cgcaccgctc cctggtttgc aattcgcagc   25980
tgcttaacga aagtcaaatt atcggtacct ttgagctgca gggtccctcg cctgacgaaa   26040
agtccgcggc tccggggttg aaactcactc cggggctgtg gacgtcggct taccttcgca   26100
aatttgtacc tgaggactac cacgcccacg agattaggtt ctacgaagac caatcccgcc   26160
cgcctaatgc ggagcttacc gcctgcgtca ttacccaggg ccacattctt ggccaattgc   26220
aagccatcaa caaagcccgc caagagtttc tgctacgaaa gggacggggg tttacttgg    26280 accccagtc cggcgaggag ctcaacccaa tcccccgcc gccgcagccc tatcagcagc     26340
agccgcgggc ccttgcttcc caggatggca cccaaaaaga agctgcagct gccgccgcca   26400 cccacgacg aggaggaata ctgggacagt caggcagagg aggttttgga cgaggaggag    26460
gaggacatga tggaagactg ggagagccta gacgaggaag cttccgaggt cgaagaggtg   26520
tcagacgaaa caccgtcacc ctcggtcgca ttcccctcgc cggcgcccca gaaatcggca   26580
```

-continued

```
accggttcca gcatggctac aacctccgct cctcaggcgc cgccggcact gcccgttcgc   26640
cgacccaacc gtagatggga caccactgga accaggccg  gtaagtccaa gcagccgccg   26700
ccgttagccc aagagcaaca acagcgccaa ggctaccgct catggcgcgg gcacaagaac   26760
gccatagttg cttgcttgca agactgtggg ggcaacatct ccttcgcccg ccgctttctt   26820
ctctaccatc acggcgtggc cttccccgt  aacatcctgc attactaccg tcatctctac   26880
agcccatact gcaccggcgg cagcggcagc aacagcagcg ccacacaga  agcaaaggcg   26940
accggatagc aagactctga caaagcccaa gaaatccaca gcggcggcag cagcaggagg   27000
aggagcgctg cgtctggcgc ccaacgaacc cgtatcgacc cgcgagctta gaaacaggat   27060
ttttcccact ctgtatgcta tatttcaaca gagcaggggc caagaacaag agctgaaaat   27120
aaaaaacagg tctctgcgat ccctcacccg cagctgcctg tatcacaaaa gcgaagatca   27180
gcttcggcgc acgctggaag acgcggaggc tctcttcagt aaatactgcg cgctgactct   27240
taaggactag tttcgcgccc tttctcaaat ttaagcgcga aaactacgtc atctccagcg   27300
gccacacccg gcgccagcac ctgttgtcag cgccattatg agcaaggaaa ttcccacgcc   27360
ctacatgtgg agttaccagc cacaaatggg acttgcggct ggagctgccc aagactactc   27420
aacccgaata aactacatga gcgcgggacc ccacatgata tcccgggtca acggaatacg   27480
cgcccaccga aaccgaattc tcctggaaca ggcggctatt accaccacac ctcgtaataa   27540
ccttaatccc cgtagttggc ccgctgccct ggtgtaccag gaaagtcccg ctcccaccac   27600
tgtggtactt cccagagacg cccaggccga agttcagatg actaactcag ggcgcagct   27660
tgcgggcggc tttcgtcaca gggtgcggtc gcccgggcag ggtataactc acctgacaat   27720
cagagggcga ggtattcagc tcaacgacga gtcggtgagc tcctcgcttg gtctccgtcc   27780
ggacgggaca tttcagatcg gcggcgccgg ccgctcttca ttcacgcctc gtcaggcaat   27840
cctaactctg cagacctcgt cctctgagcc gcgctctgga ggcattggaa ctctgcaatt   27900
tattgaggag tttgtgccat cggtctactt taacccctc  tcgggacctc ccggccacta   27960
tccggatcaa tttattccta actttgacgc ggtaaaggac tcggcggacg gctacgactg   28020
aatgttaagt ggagaggcag agcaactgcg cctgaaacac ctggtccact gtcgccgcca   28080
caagtgcttt gcccgcgact ccggtgagtt ttgctacttt gaattgcccg aggatcatat   28140
cgagggcccg cgcacggcg  tccggcttac cgcccaggga gagcttgccc gtagcctgat   28200
tcgggagttt acccagcgcc ccctgctagt tgagcgggac aggggaccct gtgttctcac   28260
tgtgatttgc aactgtccta accttggatt acatcaagat ctttgttgcc atctctgtgc   28320
tgagtataat aaatacagaa attaaaatat actgggctc  ctatcgccat cctgtaaacg   28380
ccaccgtctt cacccgccca agcaaaccaa ggcgaacctt acctggtact tttaacatct   28440
ctccctctgt gatttacaac agtttcaacc cagacggagt gagtctacga gagaacctct   28500
ccgagctcag ctactccatc agaaaaaaca ccaccctcct tacctgccgg gaacgtacga   28560
gtgcgtcacc ggccgctgca ccacacctac cgcctgaccg taaaccagac ttttccgga   28620
cagacctcaa taactctgtt taccagaaca ggaggtgagc ttagaaaacc cttagggtat   28680
taggccaaag gcgcagctac tgtggggttt atgaacaatt caagcaactc tacgggctat   28740
tctaattcag gtttctctag aatcggggtt gggggttatc tctgtcttgt gattctcttt   28800
attcttatac taacgcttct ctgcctaagg ctcgccgcct gctgtgtgca catttgcatt   28860
tattgtcagc ttttaaacg  ctggggtcgc cacccaagat gattaggtac ataatcctag   28920
```

```
gtttactcac ccttgcgtca gcccacggta ccacccaaaa ggtggatttt aaggagccag   28980
cctgtaatgt tacattcgca gctgaagcta atgagtgcac cactcttata aaatgcacca   29040
cagaacatga aaagctgctt attcgccaca aaaacaaaat tggcaagtat gctgtttatg   29100
ctatttggca gccaggtgac actacagagt ataatgttac agttttccag ggtaaaagtc   29160
ataaaacttt tatgtatact tttccatttt atgaaatgtg cgacattacc atgtacatga   29220
gcaaacagta aagttgtgg cccccacaaa attgtgtgga aaacactggc actttctgct   29280
gcactgctat gctaattaca gtgctcgctt tggtctgtac cctactctat attaaataca   29340
aaagcagacg cagctttatt gaggaaaaga aaatgcctta atttactaag ttacaaagct   29400
aatgtcacca ctaactgctt tactcgctgc ttgcaaaaca aattcaaaaa gttagcatta   29460
taattagaat aggattttaa ccccccggtc atttcctgct caataccatt cccctgaaca   29520
attgactcta tgtgggatat gctccagcgc tacaaccttg aagtcaggct tcctggatgt   29580
cagcatctga ctttggccag cacctgtccc gcggatttgt tccagtccaa ctacagcgac   29640
ccaccctaac agagatgacc aacacaacca acgcggccgc cgctaccgga cttacatcta   29700
ccacaaatac accccaagtt tctgcctttg tcaataactg ggataacttg ggcatgtggt   29760
ggttctccat agcgcttatg tttgtatgcc ttattattat gtggctcatc tgctgcctaa   29820
agcgcaaacg cgcccgacca cccatctata gtcccatcat tgtgctacac ccaaacaatg   29880
atggaatcca tagattggac ggactgaaac acatgttctt ttctcttaca gtatgattaa   29940
atgagacatg attcctcgag tttttatatt actgaccctt gttgcgcttt tttgtgcgtg   30000
ctccacattg gctgcggttt ctcacatcga agtagactgc attccagcct tcacagtcta   30060
tttgctttac ggatttgtca ccctcacgct catctgcagc ctcatcactg tggtcatcgc   30120 cttttatccag tgcattgact gggtctgtgt gcgctttgca tatctcagac accatcccca   30180
gtacagggac aggactatag ctgagcttct tagaattctt taattatgaa atttactgtg   30240
acttttctgc tgattatttg caccctatct gcgttttgtt ccccgacctc caagcctcaa   30300
agacatatat catgcagatt cactcgtata tggaatattc caagttgcta caatgaaaaa   30360
agcgatcttt ccgaagcctg gttatatgca atcatctctg ttatggtgtt ctgcagtacc   30420
atcttagccc tagctatata tccctacctt gacattggct ggaaacgaat agatgccatg   30480
aaccacccaa ctttccccgc gcccgctatg cttccactgc aacaagttgt tgccggcggc   30540
tttgtcccag ccaatcagcc tcgccccact tctcccaccc ccactgaaat cagctacttt   30600
aatctaacag gaggagatga ctgacaccct agatctagaa atggacggaa ttattacaga   30660
gcagcgcctg ctagaaagac gcagggcagc ggccgagcaa cagcgcatga atcaagagct   30720
ccaagacatg gttaacttgc accagtgcaa aaggggtatc ttttgtctgg taaagcaggc   30780
caaagtcacc tacgacagta ataccaccgg acaccgcctt agctacaagt tgccaaccaa   30840
gcgtcagaaa ttggtggtca tggtgggaga aaagcccatt accataactc agcactcggt   30900
agaaaccgaa ggctgcattc actcaccttg tcaaggacct gaggatctct gcacccttat   30960
taagaccctg tgcggtctca agatcttat tcccttaac taataaaaaa aataataaa    31020 gcatcactta cttaaaatca gttagcaaat ttctgtccag tttattcagc agcacctcct   31080
tgccctcctc ccagctctgg tattgcagct tcctcctggc tgcaaacttt ctccacaatc   31140
taaatggaat gtcagtttcc tcctgttcct gtccatccgc acccactatc ttcatgttgt   31200
tgcagatgaa gcgcgcaaga ccgtctgaag atacctttcaa ccccgtgtat ccatatgaca   31260
cggaaaccgg tcctccaact gtgccttttc ttactcctcc cttgtatcc cccaatgggt   31320
```

```
ttcaagagag tccccctggg gtactctctt tgcgcctatc cgaacctcta gttacctcca    31380
atggcatgct tgcgctcaaa atgggcaacg gcctctctct ggacgaggcc ggcaaccttg    31440
cctcccaaaa tgtaaccact gtgagcccac ctctccgagg agacaagtca aacataaacc    31500
tggaaatatc tgcacccctc acagttacct cagaagccct aactgtggct gccgccgcac    31560
ctctaatggt cgcgggcaac acactccacca tgcaatcaca ggccccgcta accgtgcacg    31620
actccaaact tagcattgcc acccaaggac ccctcacagt gtcagaagga agctagccc    31680 tgcaaacatc aggccccctc accaccaccg atagcagtac ccttactatc actgcctcac    31740
cccctctaac tactgccact ggtagcttgg gcattgactt gaaagagccc atttatacac    31800
aaaatggaaa actaggacta aagtacgggg ctcctttgca tgtaacagac gacctaaaca    31860
ctttgaccgt agcaactggt ccaggtgtga ctattaataa tacttccttg caaactaaag    31920
ttactggagc cttgggtttt gattcacaag gcaatatgca acttaatgta gcaggaggac    31980
taaggattga ttctcaaaac agacgcctta tacttgatgt tagttatccg tttgatgctc    32040
aaaaccaact aaatctaaga ctaggacagg gccctctttt tataaactca gcccacaact    32100
tggatattaa ctacaacaaa ggcctttact tgtttacagc ttcaaacaat tccaaaaagc    32160
ttgaggttaa cctaagcact gccaaggggt tgatgtttga cgctacagcc atagccatta    32220
atgcaggaga tgggcttgaa tttggttcac ctaatgcacc aaacacaaat ccctcaaaa    32280 caaaaattgg ccatggccta gaatttgatt caaacaaggc tatggttcct aaactaggaa    32340
ctggccttag ttttgacagc acaggtgcca ttacagtagg aaacaaaaat aatgataagc    32400
taactttgtg gaccacacca gctccatctc ctaactgtag actaaatgca gagaaagatg    32460
ctaaactcac tttggtctta acaaaatgtg gcagtcaaat acttgctaca gtttcagttt    32520
tggctgttaa aggcagtttg gctccaatat ctggaacagt tcaaagtgct catcttatta    32580
taagatttga cgaaaatgga gtgctactaa acaattcctt cctggaccca gaatattgga    32640
actttagaaa tggagatctt actgaaggca cagcctatac aaacgctgtt ggatttatgc    32700
ctaacctatc agcttatcca aaatctcacg gtaaaactgc caaaagtaac attgtcagtc    32760
aagtttactt aaacggagac aaaactaaac ctgtaacact aaccattaca ctaaacggta    32820
cacaggaaac aggagacaca actccatctg catactctat gtcattttca tgggactggt    32880
ctggccacaa ctacattaat gaaatatttg ccacatcctc ttacactttt tcatacattg    32940
cccaagaata aagaatcgtt tgtgttatgt ttcaacgtgt ttattttttca attgcagaaa    33000 atttcaagtc atttttcatt cagtagtata gccccaccac cacatagctt atacagatca    33060
ccgtacctta atcaaactca cagaacccta gtattcaacc tgccacctcc ctcccaacac    33120
acagagtaca cagtccttc tccccggctg gccttaaaaa gcatcatatc atgggtaaca    33180
gacatattct taggtgttat attccacacg gtttcctgtc gagccaaacg ctcatcagtg    33240
atattaataa actccccggg cagctcactt aagttcatgt cgctgtccag ctgctgagcc    33300
acaggctgct gtccaacttg cggttgctta acgggcggcg aaggagaagt ccacgcctac    33360 atggggggtag agtcataatc gtgcatcagg ataggggcggt ggtgctgcag cagcgcgcga    33420
ataaactgct gccgccgccg ctccgtcctg caggaataca acatggcagt ggtctcctca    33480
gcgatgattc gcaccgcccg cagcataagg cgccttgtcc tccgggcaca gcagcgcacc    33540
ctgatctcac ttaaatcagc acagtaactg cagcacagca ccacaatatt gttcaaaatc    33600
ccacagtgca aggcgctgta tccaaagctc atggcgggga ccacagaacc cacgtggcca    33660
```

```
-continued tcataccaca agcgcaggta gattaagtgg cgacccctca taaacacgct ggacataaac    33720
attacctctt ttggcatgtt gtaattcacc acctcccggt accatataaa cctctgatta    33780
aacatggcgc catccaccac catcctaaac cagctggcca aaacctgccc gccggctata    33840
cactgcaggg aaccgggact ggaacaatga cagtggagag cccaggactc gtaaccatgg    33900
atcatcatgc tcgtcatgat atcaatgttg gcacaacaca ggcacacgtg catacacttc    33960
ctcaggatta caagctcctc ccgcgttaga accatatccc agggaacaac ccattcctga    34020
atcagcgtaa atcccacact gcagggaaga cctcgcacgt aactcacgtt gtgcattgtc    34080
aaagtgttac attcgggcag cagcggatga tcctccagta tggtagcgcg ggtttctgtc    34140
tcaaaaggag gtagacgatc cctactgtac ggagtgcgcc gagacaaccg agatcgtgtt    34200
ggtcgtagtg tcatgccaaa tggaacgccg gacgtagtca tatttcctga agcaaaacca    34260
ggtgcgggcg tgacaaacag atctgcgtct ccggtctcgc cgcttagatc gctctgtgta    34320
gtagttgtag tatatccact ctctcaaagc atccaggcgc ccctggctt cgggttctat    34380
gtaaactcct tcatgcgccg ctgccctgat aacatccacc accgcagaat aagccacacc    34440
cagccaacct acacattcgt tctgcgagtc acacacggga ggagcgggaa gagctggaag    34500
aaccatgttt tttttttat tccaaaagat tatccaaaac ctcaaaatga agatctatta    34560
agtgaacgcg ctcccctccg gtggcgtggt caaactctac agccaaagaa cagataatgg    34620
catttgtaag atgttgcaca atggcttcca aaaggcaaac ggccctcacg tccaagtgga    34680
cgtaaaggct aaacccttca gggtgaatct cctctataaa cattccagca ccttcaacca    34740
tgcccaaata attctcatct cgccaccttc tcaatatatc tctaagcaaa tcccgaatat    34800
taagtccggc cattgtaaaa atctgctcca gagcgccctc caccttcagc ctcaagcagc    34860
gaatcatgat tgcaaaaatt caggttcctc acagacctgt ataagattca aaagcggaac    34920
attaacaaaa ataccgcgat cccgtaggtc ccttcgcagg gccagctgaa cataatcgtg    34980
caggtctgca cggaccagcg cggccacttc cccgccagga accatgacaa agaacccac    35040
actgattatg acacgcatac tcggagctat gctaaccagc gtagccccga tgtaagcttg    35100
ttgcatgggc ggcgatataa aatgcaaggt gctgctcaaa aaatcaggca aagcctcgcg    35160
caaaaaagaa agcacatcgt agtcatgctc atgcagataa aggcaggtaa gctccggaac    35220
caccacagaa aaagacacca ttttttctctc aaacatgtct gcgggtttct gcataaacac    35280
aaaataaaat aacaaaaaaa catttaaaca ttagaagcct gtcttacaac aggaaaaaca    35340
acccttataa gcataagacg gactacggcc atgccggcgt gaccgtaaaa aaactggtca    35400
ccgtgattaa aaagcaccac cgacagctcc tcggtcatgt ccggagtcat aatgtaagac    35460
tcggtaaaca catcaggttg attcacatcg gtcagtgcta aaaagcgacc gaaatagccc    35520
gggggaatac ataccccgcag gcgtagagac aacattacag cccccatagg aggtataaca    35580
aaattaatag gagagaaaaa cacataaaca cctgaaaaac cctcctgcct aggcaaaata    35640
gcaccctccc gctccagaac aacatacagc gcttccacag cggcagccat aacagtcagc    35700
cttaccagta aaaagaaaa cctattaaaa aaacaccact cgacacggca ccagctcaat    35760
cagtcacagt gtaaaaaagg gccaagtgca gagcgagtat atataggact aaaaaatgac    35820
gtaacggtta aagtccacaa aaaacaccca gaaaaccgca cgcgaaccta cgcccagaaa    35880
cgaaagccaa aaaacccaca acttcctcaa atcgtcactt ccgttttccc acgttacgtc    35940
acttcccatt ttaagaaaac tacaattccc aacacataca agttactccg ccctaaaacc    36000
tacgtcaccc gccccgttcc cacgcccccgc gccacgtcac aaactccacc ccctcattat    36060
```

```
catattggct tcaatccaaa ataaggtata ttattgatga tgtagggata acagggtaat    36120
taat                                                                 36124

<210> SEQ ID NO 2
<211> LENGTH: 36156
<212> TYPE: DNA
<213> ORGANISM: Artificial Sequence
<220> FEATURE:
<223> OTHER INFORMATION: ICOVIR15K-gp100-tyr

<400> SEQUENCE: 2
catcatcaat aatataccttt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
taaatttggg cgtaaccgag taagatttgg ccatttcgc gggaaaactg aataagagga      300
agtgaaatct gaataatttt gtgttactca tagcgcgtaa tatttgtcta gggccgcggg     360
gactttgacc gtttacgtgg agactcgccc aggtgttttt ctcaggtgtt ttccgcgtac     420
gtcggcggct cgtggctctt tcgcggcaaa aaggatttgg cgcgtaaaag tggttcgagt     480
acgtcggcgg ctcgtggctc tttcgcggca aaaaggattt ggcgcgtaaa agtggttcga     540
agtacgtcga ccacaaaccc cgcccagcgt cttgtcattg gcgtcgacgc tgtacggggt     600
caaagttggc gttttattat tatagtcagc tgacgtgtag tgtatttata cccggtgagt     660
tcctcaagag gccactcttg agtgccagcg agtagagttt tctcctccga gccgctccga     720
caccgggact gaaaatgaga catattatct gccacggagg tgttattacc gaagaaatgg     780
ccgccagtct tttggaccag ctgatcgaag aggtactggc tgataatctt ccacctccta     840
gccattttga accacctacc cttcacgaac tgtatgattt agacgtgacg gccccccgaag    900 atcccaacga ggaggcggtt tcgcagattt ttcccgactc tgtaatgttg gcggtgcagg     960
aagggattga cttactcact tttccgccgg cgccccggttc tccggagccg cctcaccttt    1020
cccggcagcc cgagcagccg gagcagagag ccttgggtcc ggtttctatg ccaaaccttg    1080
taccggaggt gatcgatcca cccagtgacg acgaggatga agagggtgag gagtttgtgt    1140
tagattatgt ggagcacccc gggcacggtt gcaggtcttg tcattatcac cggaggaata    1200
cgggggaccc agatattatg tgttcgcttt gctatatgag gacctgtggc atgtttgtct    1260
acagtaagtg aaaattatgg gcagtgggtg atagagtggt gggtttggtg tggtaatttt    1320 tttttttaatt tttacagttt tgtggtttaa agaattttgt attgtgattt ttttaaaagg    1380
tcctgtgtct gaacctgagc ctgagcccga gccagaaccg gagcctgcaa gacctacccg    1440
ccgtcctaaa atggcgcctg ctatcctgag acgcccgaca tcacctgtgt ccagagaatg    1500
caatagtagt acgatagct gtgactccgg tccttctaac acacctcctg agatacaccc     1560
ggtggtcccg ctgtgcccca ttaaaccagt tgccgtgaga gttggtgggc gtcgccaggc    1620
tgtggaatgt atcgaggact tgcttaacga gcctgggcaa cctttggact tgagctgtaa    1680
acgccccagg ccataaggtg taaacctgtg attgcgtgtg tggttaacgc ctttgtttgc    1740
tgaatgagtt gatgtaagtt taataaaggg tgagataatg tttaacttgc atggcgtgtt    1800
aaatggggcg gggcttaaag ggtatataat gcgccgtggg ctaatcttgg ttacatctga    1860
cctcatggag gcttgggagt gtttggaaga ttttttctgct gtgcgtaact tgctggaaca    1920
```

```
gagctctaac agtacctctt ggttttggag gtttctgtgg ggctcatccc aggcaaagtt    1980
agtctgcaga attaaggagg attacaagtg ggaatttgaa gagcttttga aatcctgtgg    2040
tgagctgttt gattctttga atctgggtca ccaggcgctt ttccaagaga aggtcatcaa    2100
gactttggat ttttccacac cggggcgcgc tgcggctgct gttgcttttt tgagttttat    2160
aaaggataaa tggagcgaag aaacccatct gagcgggggg tacctgctgg attttctggc    2220
catgcatctg tggagagcgg ttgtgagaca caagaatcgc ctgctactgt tgtcttccgt    2280
ccgcccggcg ataataccga cggaggagca gcagcagcag caggaggaag ccaggcggcg    2340
gcggcaggag cagagcccat ggaacccgag agccggcctg gaccctcggg aatgaatgtt    2400
gtacaggtgg ctgaactgta tccagaactg agacgcattt tgacaattac agaggatggg    2460
caggggctaa aggggtaaa  gagggagcgg ggggcttgtg aggctacaga ggaggctagg    2520
aatctagctt ttagcttaat gaccagacac cgtcctgagt gtattacttt tcaacagatc    2580
aaggataatt gcgctaatga gcttgatctg ctggcgcaga agtattccat agagcagctg    2640
accacttact ggctgcagcc aggggatgat tttgaggagg ctattagggt atatgcaaag    2700
gtggcactta ggccagattg caagtacaag atcagcaaac ttgtaaatat caggaattgt    2760
tgctacattt ctgggaacgg ggccgagtg  gagatagata cggaggatag ggtggccttt    2820
agatgtagca tgataaatat gtggccgggg gtgcttggca tggacggggt ggttattatg    2880
aatgtaaggt ttactggccc caatttagc  ggtacggttt tcctggccaa taccaacctt    2940
atcctacacg gtgtaagctt ctatgggttt aacaatacct gtgtggaagc ctggaccgat    3000
gtaagggttc ggggctgtgc cttttactgc tgctggaagg gggtggtgtg tcgccccaaa    3060
agcagggctt caattaagaa atgcctcttt gaaaggtgta ccttgggtat cctgtctgag    3120
ggtaactcca gggtgcgcca caatgtggcc tccgactgtg gttgcttcat gctagtgaaa    3180
agcgtggctg tgattaagca taacatggta tgtggcaact gcgaggacag ggcctctcag    3240
atgctgacct gctcggacgg caactgtcac ctgctgaaga ccattcacgt agccagccac    3300
tctcgcaagg cctggccagt gtttgagcat aacatactga cccgctgttc cttgcatttg    3360
ggtaacagga gggggtgtt  cctaccttac caatgcaatt tgagtcacac taagatattg    3420
cttgagcccg agagcatgtc caaggtgaac ctgaacgggg tgtttgacat gaccatgaag    3480
atctggaagg tgctgaggta cgatgagacc cgcaccaggt gcagaccctg cgagtgtggc    3540
ggtaaacata ttaggaacca gcctgtgatg ctggatgtga ccgaggagct gaggcccgat    3600
cacttggtgc tggcctgcac ccgcgctgag tttggctcta gcgatgaaga tacagattga    3660
ggtactgaaa tgtgtgggcg tggcttaagg gtgggaaaga atatataagg tgggggtctt    3720
atgtagtttt gtatctgttt tgcagcagcc gccgccgcca tgagcaccaa ctcgtttgat    3780
ggaagcattg tgagctcata tttgacaacg cgcatgcccc catgggccgg ggtgcgtcag    3840
aatgtgatgg gctccagcat tgatggtcgc cccgtcctgc ccgcaaactc tactaccttg    3900
acctacgaga ccgtgtctgg aacgccgttg gagactgcag cctccgccgc cgcttcagcc    3960
gctgcagcca ccgccgcgg  gattgtgact gactttgctt tcctgagccc gcttgcaagc    4020
agtgcagctt cccgttcatc cgcccgcgat gacaagttga cggctctttt ggcacaattg    4080
gattctttga cccgggaact taatgtcgtt tctcagcagc tgttggatct cgccagcag    4140 gtttctgccc tgaaggcttc ctcccctccc aatgcggttt aaaacataaa taaaaaacca    4200
gactctgttt ggatttggat caagcaagtg tcttgctgtc tttatttagg ggttttgcgc    4260
gcgcggtagg cccgggacca gcggtctcgg tcgttgaggg tcctgtgtat ttttccagg     4320
```

```
acgtggtaaa ggtgactctg gatgttcaga tacatgggca taagcccgtc tctggggtgg    4380
aggtagcacc actgcagagc ttcatgctgc ggggtggtgt tgtagatgat ccagtcgtag    4440
caggagcgct gggcgtggtg cctaaaaatg tctttcagta gcaagctgat tgccaggggc    4500
aggcccttgg tgtaagtgtt tacaaagcgg ttaagctggg atgggtgcat acgtggggat    4560
atgagatgca tcttggactg tattttagg ttggctatgt tcccagccat atccctccgg     4620
ggattcatgt tgtgcagaac caccagcaca gtgtatccgg tgcacttggg aaatttgtca    4680
tgtagcttag aaggaaatgc gtggaagaac ttggagacgc ccttgtgacc tccaagattt    4740
tccatgcatt cgtccataat gatggcaatg ggcccacggg cggcggcctg ggcgaagata    4800
tttctgggat cactaacgtc atagttgtgt tccaggatga gatcgtcata ggccattttt    4860
acaaagcgcg ggcggagggt gccagactgc ggtataatgg ttccatccgg cccaggggcg    4920
tagttaccct cacagatttg catttcccac gctttgagtt cagatggggg gatcatgtct    4980
acctgcgggc gatgaagaa aacggtttcc ggggtagggg agatcagctg ggaagaaagc     5040
aggttcctga gcagctgcga cttaccgcag ccggtgggcc cgtaaatcac acctattacc    5100
gggtgcaact ggtagttaag agagctgcag ctgccgtcat ccctgagcag ggggccact     5160 tcgttaagca tgtccctgac tcgcatgttt tccctgacca aatccgccag aaggcgctcg    5220
ccgcccagcg atagcagttc ttgcaaggaa gcaaagtttt tcaacggttt gagaccgtcc    5280
gccgtaggca tgcttttgag cgtttgacca agcagttcca ggcggtccca cagctcggtc    5340
acctgctcta cggcatctcg atccagcata tctcctcgtt tcgcgggttg gggcggcttt    5400
cgctgtacgg cagtagtcgg tgctcgtcca gacgggccag ggtcatgtct ttccacgggc    5460
gcagggtcct cgtcagcgta gtctgggtca cggtgaaggg gtgcgctccg ggctgcgcgc    5520
tggccagggt gcgcttgagg ctggtcctgc tggtgctgaa gcgctgccgg tcttcgccct    5580
gcgcgtcggc caggtagcat ttgaccatgg tgtcatagtc cagcccctcc gcggcgtggc    5640
ccttggcgcg cagcttgccc ttggaggagg cgccgcacga ggggcagtgc agacttttga    5700
gggcgtagag cttgggcgcg agaaataccg attccgggga gtaggcatcc cgcccgcagg    5760
ccccgcagac ggtctcgcat tccacgagcc aggtgagctc tggccgttcg gggtcaaaaa    5820 ccaggttttcc cccatgcttt ttgatgcgtt tcttacctct ggtttccatg agccggtgtc    5880
cacgctcggt gacgaaaagg ctgtccgtgt ccccgtatac agacttgaga ggcctgtcct    5940
cgagcggtgt tccgcggtcc tcctcgtata gaaactcgga ccactctgag acaaaggctc    6000
gcgtccaggc cagcacgaag gaggctaagt gggagggta gcggtcgttg tccactaggg     6060
ggtccactcg ctccagggtg tgaagacaca tgtcgccctc ttcggcatca aggaaggtga    6120
ttggtttgta ggtgtaggcc acgtgaccgg tgttcctga aggggggcta taaaggggg     6180 tgggggcgcg ttcgtcctca ctctcttccg catcgctgtc tgcgagggcc agctgttggg    6240
gtgagtactc cctctgaaaa gcgggcatga cttctgcgct aagattgtca gtttccaaaa    6300
acgaggagga tttgatattc acctggcccg cggtgatgcc tttgagggtg gccgcatcca    6360
tctggtcaga aaagacaatc tttttgttgt caagcttggt ggcaaacgac ccgtagaggg    6420
cgttggacag caacttggcg atggagcgca gggtttggtt tttgtcgcga tcggcgcgct    6480
ccttggccgc gatgtttagc tgcacgtatt cgcgcgcaac gcaccgccat tcgggaaaga    6540
cggtggtgcg ctcgtcgggc accaggtgca cgcgccaacc gcggttgtgc agggtgacaa    6600
ggtcaacgct ggtggctacc tctccgcgta ggcgctcgtt ggtccagcag aggcggccgc    6660
```

```
ccttgcgcga gcagaatggc ggtagggggt ctagctgcgt ctcgtccggg gggtctgcgt    6720
ccacggtaaa gacccggc agcaggcgcg cgtcgaagta gtctatcttg catccttgca     6780
agtctagcgc ctgctgccat gcgcgggcgg caagcgcgcg ctcgtatggg ttgagtgggg    6840
gaccccatgg catggggtgg gtgagcgcgg aggcgtacat gccgcaaatg tcgtaaacgt    6900 agagggctc tctgagtatt ccaagatatg tagggtagca tcttccaccg cggatgctgg     6960
cgcgcacgta atcgtatagt tcgtgcgagg gagcgaggag gtcgggaccg aggttgctac    7020
gggcgggctg ctctgctcgg aagactatct gcctgaagat ggcatgtgag ttggatgata    7080
tggttggacg ctgaagacg ttgaagctgg cgtctgtgag acctaccgcg tcacgcacga     7140
aggaggcgta ggagtcgcgc agcttgttga ccagctcggc ggtgacctgc acgtctaggg    7200
cgcagtagtc cagggtttcc ttgatgatgt catacttatc ctgtcccttt tttttccaca    7260
gctcgcggtt gaggacaaac tcttcgcggt ctttccagta ctcttggatc ggaaacccgt    7320
cggcctccga acgtaagag cctagcatgt agaactggtt gacggcctgg taggcgcagc     7380 atccttttc tacgggtagc gcgtatgcct gcgcggcctt ccggagcgag gtgtgggtga     7440
gcgcaaaggt gtccctgacc atgactttga ggtactggta tttgaagtca gtgtcgtcgc    7500
atccgccctg ctcccagagc aaaaagtccg tgcgcttttt ggaacgcgga tttggcaggg    7560
cgaaggtgac atcgttgaag agtatctttc ccgcgcgagg cataaagttg cgtgtgatgc    7620
ggaagggtcc cggcacctcg gaacggttgt taattacctg ggcggcgagc acgatctcgt    7680
caaagccgtt gatgttgtgg cccacaatgt aaagttccaa gaagcgcggg atgcccttga    7740
tggaaggcaa ttttttaagt tcctcgtagg tgagctcttc aggggagctg agcccgtgct    7800
ctgaaagggc ccagtctgca agatgagggt tggaagcgac gaatgagctc cacaggtcac    7860
gggccattag catttgcagg tggtcgcgaa aggtcctaaa ctggcgacct atggccattt    7920
tttctggggt gatgcagtag aaggtaagcg ggtcttgttc ccagcggtcc catccaaggt    7980
tcgcggctag gtctcgcgcg gcagtcacta gaggctcatc tccgccgaac ttcatgacca    8040
gcatgaaggg cacgagctgc ttcccaaagg cccccatcca agtataggtc tctacatcgt    8100
aggtgacaaa gagacgctcg gtgcgaggat gcgagccgat cggaagaac tggatctccc     8160 gccaccaatt ggaggagtgg ctattgatgt ggtgaaagta gaagtccctg cgacgggccg    8220
aacactcgtg ctggcttttg taaaaacgtg cgcagtactg gcagcggtgc acgggctgta    8280
catcctgcac gaggttgacc tgacgaccgc gcacaaggaa gcagagtggg aatttgagcc    8340
cctcgcctgg cgggtttggc tggtggtctt ctacttcggc tgcttgtcct tgaccgtctg    8400
gctgctcgag gggagttacg gtggatcgga ccaccacgcc gcgcgagccc aaagtccaga    8460
tgtccgcgcg cggcggtcgg agcttgatga caacatcgcg cagatgggag ctgtccatgg    8520
tctggagctc ccgcggcgtc aggtcaggcg ggagctcctg caggtttacc tcgcatagac    8580
gggtcagggc gcgggctaga tccaggtgat acctaatttc caggggctgg ttggtggcgg    8640
cgtcgatggc ttgcaagagg ccgcatcccc gcggcgcgac tacggtaccg cgcggcgggc    8700
ggtgggccgc gggggtgtcc ttggatgatg catctaaaag cggtgacgcg ggcgagcccc    8760
cggaggtagg gggggctccg gacccgccgg gagaggggc aggggcacgt cggcgccgcg     8820
cgcgggcagg agctggtgct gcgcgcgtag gttgctggcg aacgcgacga cgcggcggtt    8880
gatctcctga atctggcgcc tctgcgtgaa gacgacgggc ccgtgagct tgagcctgaa     8940 agagagttcg acagaatcaa tttcggtgtc gttgacggcg gcctgcgca aaatctcctg     9000 cacgtctcct gagttgtctt gataggcgat ctcggccatg aactgctcga tctcttcctc    9060
```

| | |
|---|---|
| ctggagatct ccgcgtccgg ctcgctccac ggtggcggcg aggtcgttgg aaatgcgggc | 9120 |
| catgagctgc gagaaggcgt tgaggcctcc ctcgttccag acgcggctgt agaccacgcc | 9180 |
| cccttcggca tcgcgggcgc gcatgaccac ctgcgcgaga ttgagctcca cgtgccgggc | 9240 |
| gaagacggcg tagtttcgca ggcgctgaaa gaggtagttg agggtggtgg cggtgtgttc | 9300 |
| tgccacgaag aagtacataa cccagcgtcg aacgtggat tcgttgatat ccccccaaggc | 9360 |
| ctcaaggcgc tccatggcct cgtagaagtc cacggcgaag ttgaaaaact gggagttgcg | 9420 |
| cgccgacacg gttaactcct cctccagaag acggatgagc tcggcgacag tgtcgcgcac | 9480 |
| ctcgcgctca aaggctacag gggcctcttc ttcttcttca atctcctctt ccataagggc | 9540 |
| ctccccttct tcttcttctg gcggcggtgg gggaggggg acacggcggc gacgacggcg | 9600 |
| caccgggagg cggtcgacaa agcgctcgat catctccccg cggcgacggc gcatggtctc | 9660 |
| ggtgacggcg cggccgttct cgcgggggcg cagttggaag acgccgcccg tcatgtcccg | 9720 |
| gttatgggtt ggcgggggc tgccatgcgg cagggatacg cgctaacga tgcatctcaa | 9780 |
| caattgttgt gtaggtactc cgccgccgag ggacctgagc gagtccgcat cgaccggatc | 9840 |
| ggaaaacctc tcgagaaagg cgtctaacca gtcacagtcg caaggtaggc tgagcaccgt | 9900 |
| ggcgggcggc agcgggcggc ggtcggggtt gtttctggcg gaggtgctgc tgatgatgta | 9960 |
| attaaagtag gcggtcttga gacggcggat ggtcgacaga agcaccatgt ccttgggtcc | 10020 |
| ggcctgctga atgcgcaggc ggtcggccat gccccaggct tcgttttgac atcggcgcag | 10080 |
| gtctttgtag tagtcttgca tgagcctttc taccggcact tcttcttctc cttcctcttg | 10140 |
| tcctgcatct cttgcatcta tcgctgcggc ggcggcggag tttggccgta ggtggcgccc | 10200 |
| tcttcctccc atgcgtgtga ccccgaagcc cctcatcggc tgaagcaggg ctaggtcggc | 10260 |
| gacaacgcgc tcggctaata tggcctgctg cacctgcgtg agggtagact ggaagtcatc | 10320 |
| catgtccaca aagcggtggt atgcgcccgt gttgatggtg taagtgcagt ggccataac | 10380 |
| ggaccagtta acggtctggt gacccggctg cgagagctcg gtgtacctga gacgcgagta | 10440 |
| agccctcgag tcaaatacgt agtcgttgca agtccgcacc aggtactggt atcccaccaa | 10500 |
| aaagtgcggg ggcggctggc ggtagagggg ccagcgtagg gtggccgggg ctccggggc | 10560 |
| gagatcttcc aacataaggc gatgatatcc gtagatgtac ctggacatcc aggtgatgcc | 10620 |
| ggcggcggtg gtggaggcgc gcggaaagtc gcggacgcgg ttccagatgt tgcgcagcgg | 10680 |
| caaaaagtgc tccatggtcg ggacgctctg gccggtcagg cgcgcgcaat cgttgacgct | 10740 |
| ctagaccgtg caaaaggaga gcctgtaagc gggcactctt ccgtggtctg gtggataaat | 10800 |
| tcgcaagggt atcatggcgg acgaccgggg ttcgagcccc gtatccggcc gtccgccgtg | 10860 |
| atccatgcgg ttaccgcccg cgtgtcgaac ccaggtgtgc gacgtcagac aacggggag | 10920 |
| tgctcctttt ggcttccttc caggcgcggc ggctgctgcg ctagcttttt tggccactgg | 10980 |
| ccgcgcgcag cgtaagcggt taggctgaa agcgaaagca ttaagtggct cgctccctgt | 11040 |
| agccggaggg ttatttttcca agggttgagt cgcgggaccc ccggttcgag tctcggaccg | 11100 |
| gccggactgc ggcgaacggg ggtttgcctc cccgtcatgc aagacccgc ttgcaaattc | 11160 |
| ctccggaaac agggacgagc ccctttttg ctttcccag atgcatccgg tgctgcggca | 11220 |
| gatgcgcccc cctcctcagc agcggcaaga gcaagagcag cggcagacat gcagggcacc | 11280 |
| ctccctcct cctaccgcgt caggagggc gacatccgcg gttgacgcgg cagcagatgc | 11340 |
| tgattacgaa ccccgcggc gccggcccg gcactacctg gacttggagg agggcgaggg | 11400 |

-continued

```
cctggcgcgg ctaggagcgc cctctcctga gcggtaccca agggtgcagc tgaagcgtga   11460
tacgcgtgag gcgtacgtgc cgcggcagaa cctgtttcgc gaccgcgagg gagaggagcc   11520
cgaggagatg cgggatcgaa agttccacgc agggcgcgag ctgcggcatg gcctgaatcg   11580
cgagcggttg ctgcgcgagg aggactttga gcccgacgcg cgaaccggga ttagtcccgc   11640
gcgcgcacac gtggcggccg ccgacctggt aaccgcatac gagcagacgg tgaaccagga   11700
gattaacttt caaaaaagct taacaacca cgtgcgtacg cttgtggcgc gcaggaggt    11760 ggctatagga ctgatgcatc tgtgggactt tgtaagcgcg ctggagcaaa cccaaatag   11820 caagccgctc atggcgcagc tgttccttat agtgcagcac agcagggaca acgaggcatt   11880
cagggatgcg ctgctaaaca tagtagagcc cgagggccgc tggctgctcg atttgataaa   11940
catcctgcag agcatagtgg tgcaggagcg cagcttgagc ctggctgaca aggtggccgc   12000
catcaactat tccatgctta gcctgggcaa gttttacgcc cgcaagatat accataccc    12060 ttacgttccc atagacaagg aggtaaagat cgaggggttc tacatgcgca tggcgctgaa   12120
ggtgcttacc ttgagcgacg acctgggcgt ttatcgcaac gagcgcatcc acaaggccgt   12180
gagcgtgagc cggcggcgcg agctcagcga ccgcgagctg atgcacagcc tgcaaagggc   12240
cctggctggc acgggcagcg gcgatagaga ggccgagtcc tactttgacg cgggcgctga   12300
cctgcgctgg gccccaagcc gacgcgccct ggaggcagct ggggccggac ctgggctggc   12360
ggtggcaccc cgcgcgcgctg gcaacgtcgg cggcgtggag gaatatgacg aggacgatga   12420
gtacgagcca gaggacggcg agtactaagc ggtgatgttt ctgatcagat gatgcaagac   12480
gcaacggacc cggcggtgcg ggcggcgctg cagagccagc cgtccggcct taactccacg   12540
gacgactggc gccaggtcat ggaccgcatc atgtcgctga ctgcgcgcaa tcctgacgcg   12600
ttccggcagc agccgcaggc caaccggctc tccgcaattc tggaagcggt ggtcccggcg   12660
cgcgcaaacc ccacgcacga aaggtgctg gcgatcgtaa acgcgctggc cgaaaacagg   12720
gccatccggc ccgacgaggc cggcctggtc tacgacgcgc tgcttcagcg cgtggctcgt   12780
tacaacagcg gcaacgtgca gaccaacctg gaccggctgg tggggatgt gcgcgaggcc   12840 gtggcgcagc gtgagcgcgc gcagcagcag gcaacctgg gctccatggt tgcactaaac   12900
gccttcctga gtacacagcc cgccaacgtg ccgcggggac aggaggacta caccaacttt   12960
gtgagcgcac tgcggctaat ggtgactgag acaccgcaaa gtgaggtgta ccagtctggg   13020
ccagactatt ttttccagac cagtagacaa ggcctgcaga ccgtaaacct gagccaggct   13080
ttcaaaaact tgcaggggct gtgggggtg cgggctccca caggcgaccg cgcgaccgtg   13140
tctagcttgc tgacgcccaa ctcgcgcctg ttgctgctgc taatagcgcc cttcacggac   13200
agtggcagcg tgtcccggga cacataccta ggtcacttgc tgacactgta ccgcgaggcc   13260
ataggtcagg cgcatgtgga cgagcatact ttccaggaga ttacaagtgt cagccgcgcg   13320
ctggggcagg aggacacggg cagcctggag gcaaccctaa actacctgct gaccaaccgg   13380
cggcagaaga tccccctcgtt gcacagtta aacagcgagg aggagcgcat tttgcgctac   13440
gtgcagcaga gcgtgagcct taacctgatg cgcgacgggg taacgcccag cgtggcgctg   13500
gacatgaccg cgcgcaacat ggaaccgggc atgtatgcct caaaccggcc gtttatcaac   13560
cgcctaatgg actacttgca tcgcgcggcc gccgtgaacc ccgagtattt caccaatgcc   13620
atcttgaacc cgcactggct accgccccct ggtttctaca ccgggggatt cgaggtgccc   13680
gagggtaacg atggattcct ctgggacgac atagacgaca gcgtgttttc cccgcaaccg   13740
cagaccctgc tagagttgca acagcgcgag caggcagagg cggcgctgcg aaaggaaagc   13800
```

```
ttccgcaggc caagcagctt gtccgatcta ggcgctgcgg ccccgcggtc agatgctagt    13860
agcccatttc caagcttgat agggtctctt accagcactc gcaccacccg cccgcgcctg    13920
ctgggcgagg aggagtacct aaacaactcg ctgctgcagc cgcagcgcga aaaaaacctg    13980
cctccggcat ttcccaacaa cgggatagag agcctagtgg acaagatgag tagatggaag    14040
acgtacgcgc aggagcacag ggacgtgcca ggcccgcgcc cgcccacccg tcgtcaaagg    14100
cacgaccgtc agcggggtct ggtgtgggag gacgatgact cggcagacga cagcagcgtc    14160
ctggatttgg gagggagtgg caacccgttt gcgcaccttc gccccaggct ggggagaatg    14220
ttttaaaaaa aaaaaagcat gatgcaaaat aaaaaactca ccaaggccat ggcaccgagc    14280
gttggttttc ttgtattccc cttagtatgc ggcgcgcggc gatgtatgag gaaggtcctc    14340
ctccctccta cgagagtgtg gtgagcgcgg cgccagtggc ggcggcgctg ggttctccct    14400
tcgatgctcc cctggacccg ccgtttgtgc ctccgcggta cctgcggcct accgggggga    14460
gaaacagcat ccgttactct gagttggcac ccctattcga caccacccgt gtgtacctgg    14520
tggacaacaa gtcaacggat gtggcatccc tgaactacca gaacgaccac agcaactttc    14580
tgaccacggt cattcaaaac aatgactaca gcccggggga ggcaagcaca cagaccatca    14640
atcttgacga ccggtcgcac tggggcggcg acctgaaaac catcctgcat accaacatgc    14700
caaatgtgaa cgagttcatg tttaccaata agtttaaggc gcgggtgatg gtgtcgcgct    14760
tgcctactaa ggacaatcag gtggagctga aatacgagtg ggtggagttc acgctgcccg    14820
agggcaacta ctccgagacc atgaccatag accttatgaa caacgcgatc gtggagcact    14880
acttgaaagt gggcagacag aacggggttc tggaaagcga catcggggta agtttgaca    14940 cccgcaactt cagactgggg tttgaccccg tcactggtct tgtcatgcct ggggtatata    15000
caaacgaagc cttccatcca gacatcattt tgctgccagg atgcggggtg gacttcaccc    15060
acagccgcct gagcaacttg ttgggcatcc gcaagcggca accttccag gagggctta    15120 ggatcaccta cgatgatctg gagggtggta acattcccgc actgttggat gtggacgcct    15180
accaggcgag cttgaaagat gacaccgaac agggcggggg tggcgcaggc ggcagcaaca    15240
gcagtggcag cggcgcggaa gagaactcca acgcggcagc cgcggcaatg cagccggtgg    15300
aggacatgaa cgatcatgcc attcgcggcg acacctttgc cacacgggct gaggagaagc    15360
gcgctgaggc cgaagcagcg gccgaagctg ccgcccccgc tgcgcaaccc gaggtcgaga    15420
agcctcagaa gaaaccggtg atcaaacccc tgacagagga cagcaagaaa cgcagttaca    15480
acctaataag caatgacagc accttcaccc agtaccgcag ctggtacctt gcatacaact    15540
acggcgaccc tcagaccgga atccgctcat ggaccctgct ttgcactcct gacgtaacct    15600
gcggctcgga gcaggtctac tggtcgttgc cagacatgat gcaagacccc gtgaccttcc    15660
gctccacgcg ccagatcagc aactttccgg tggtgggcgc cgagctgttg cccgtgcact    15720
ccaagagctt ctacaacgac caggccgtct actcccaact catccgccag tttacctctc    15780
tgacccacgt gttcaatcgc tttcccgaga accagatttt ggcgcgcccg ccagccccca    15840
ccatcaccac cgtcagtgaa aacgttcctg ctctcacaga tcacgggacg ctaccgctgc    15900
gcaacagcat cggaggagtc cagcgagtga ccattactga cgccagacgc gcacctgcc    15960 cctacgttta caaggccctg ggcatagtct cgccgcgcgt cctatcgagc cgcacttttt    16020
gagcaagcat gtccatcctt atatcgccca gcaataacac aggctgggc ctgcgcttcc    16080 caagcaagat gtttggcggg gccaagaagc gctccgacca acacccagtg cgcgtgcgcg    16140
```

```
ggcactaccg cgcgccctgg ggcgcgcaca aacgcggccg cactgggcgc accaccgtcg    16200
atgacgccat cgacgcggtg gtggaggagg cgcgcaacta cacgcccacg ccgccaccag    16260
tgtccacagt ggacgcggcc attcagaccg tggtgcgcgg agcccggcgc tatgctaaaa    16320
tgaagagacg gcggaggcgc gtagcacgtc gccaccgccg ccgacccggc actgccgccc    16380
aacgcgcggc ggcggccctg cttaaccgcg cacgtcgcac cggccgacgg gcggccatgc    16440
gggccgctcg aaggctggcc gcgggtattg tcactgtgcc ccccaggtcc aggcgacgag    16500
cggccgccgc agcagccgcg gccattagtg ctatgactca gggtcgcagg ggcaacgtgt    16560
attgggtgcg cgactcggtt agcggcctgc gcgtgcccgt gcgcaccgc ccccgcgca     16620 actagattgc aagaaaaaac tacttagact cgtactgttg tatgtatcca gcggcggcgg    16680
cgcgcaacga agctatgtcc aagcgcaaaa tcaaagaaga gatgctccag gtcatcgcgc    16740
cggagatcta tggccccccg aagaaggaag agcaggatta caagccccga aagctaaagc    16800
gggtcaaaaa gaaaagaaa gatgatgatg atgaacttga cgacgaggtg gaactgctgc     16860
acgctaccgc gcccaggcga cgggtacagt ggaaaggtcg acgcgtaaaa cgtgttttgc    16920
gacccggcac caccgtagtc tttacgcccg gtgagcgctc caccgcacc tacaagcgcg     16980 tgtatgatga ggtgtacggc gacgaggacc tgcttgagca ggccaacgag cgcctcgggg    17040
agtttgccta cggaaagcgg cataaggaca tgctggcgtt ccgctggac gagggcaacc     17100 caacacctag cctaaagccc gtaacactgc agcaggtgct gcccgcgctt gcaccgtccg    17160
aagaaaagcg cggcctaaag cgcgagtctg gtgacttggc acccaccgtg cagctgatgg    17220
tacccaagcg ccagcgactg gaagatgtct tggaaaaaat gaccgtggaa cctgggctgg    17280
agcccgaggt ccgcgtgcgg ccaatcaagc aggtggcgcc gggactgggc gtgcagaccg    17340
tggacgttca gatacccact accagtagca ccagtattgc caccgccaca gagggcatgg    17400
agacacaaac gtccccggtt gcctcagcgg tggcggatgc cgcggtgcag gcggtcgctg    17460
cggccgcgtc caagacctct acggaggtgc aaacggaccc gtggatgttt cgcgtttcag    17520 cccccccggcg cccgcgcggt tcgaggaagt acggcgccgc cagcgcgcta ctgcccgaat    17580
atgccctaca tccttccatt gcgcctaccc ccggctatcg tggctacacc taccgcccca    17640
gaagacgagc aactacccga cgccgaacca ccactggaaa ccgccgccgc cgtcgccgtc    17700
gccagcccgt gctggccccg atttccgtgc gcagggtggc tcgcgaagga ggcaggaccc    17760
tggtgctgcc aacagcgcgc taccaccccca gcatcgttta aaagccggtc tttgtggttc    17820
ttgcagatat ggccctcacc tgccgcctcc gtttcccggt gccgggattc cgaggaagaa    17880
tgcaccgtag gaggggcatg gccggccacg gcctgacggg cggcatgcgt cgtgcgcacc    17940
accggcggcg gcgcgcgtcg caccgtcgca tgcgcggcgg tatcctgccc ctccttattc    18000
cactgatcgc cgcggcgatt ggcgccgtgc ccggaattgc atccgtggcc ttgcaggcgc    18060
agagacactg attaaaaaca agttgcatgt ggaaaaatca aaataaaaag tctgactct     18120 cacgctcgct tggtcctgta actattttgt agaatggaag acatcaactt tgcgtctctg    18180
gccccgcgac acggctcgcg cccgttcatg ggaaactggc aagatatcgg caccagcaat    18240
atgagcggtg gcgccttcag ctggggctcg ctgtggagcg gcattaaaaa tttcggttcc    18300
accgttaaga actatggcag caaggcctgg aacagcagca caggccagat gctgagggat    18360
aagttgaaag agcaaaattt ccaacaaaag gtggtagatg gcctggcctc tggcattagc    18420
ggggtggtgg acctggccaa ccaggcagtg caaaataaga ttaacagtaa gcttgatccc    18480
cgccctcccg tagaggagcc tccaccggcc gtggagacag tgtctccaga ggggcgtggc    18540
```

```
gaaaagcgtc cgcgccccga cagggaagaa actctggtga cgcaaataga cgagcctccc   18600
tcgtacgagg aggcactaaa gcaaggcctg cccaccaccc gtcccatcgc gcccatggct   18660
accggagtgc tgggccagca cacaccegta acgctggacc tgcctccccc cgccgacacc   18720
cagcagaaac ctgtgctgcc aggcccgacc gccgttgttg taacccgtcc tagccgcgcg   18780
tccctgcgcc gcgccgccag cggtccgcga tcgttgcggc ccgtagccag tggcaactgg   18840
caaagcacac tgaacagcat cgtgggtctg ggggtgcaat ccctgaagcg ccgacgatgc   18900
ttctgaatag ctaacgtgtc gtatgtgtgt catgtatgcg tccatgtcgc cgccagagga   18960
gctgctgagc cgccgcgcgc ccgctttcca agatggctac cccttcgatg atgccgcagt   19020
ggtcttacat gcacatctcg ggccaggacg cctcggagta cctgagcccc gggctggtgc   19080
agtttgcccg cgccaccgag acgtacttca gcctgaataa caagtttaga aaccccacgg   19140
tggcgcctac gcacgacgtg accacagacc ggtcccagcg tttgacgctg cggttcatcc   19200
ctgtggaccg tgaggatact gcgtactcgt acaaggcgcg gttcacccta gctgtgggtg   19260
ataaccgtgt gctggacatg gcttccacgt actttgacat ccgcggcgtg ctggacaggg   19320
gccctacttt taagccctac tctggcactg cctacaacgc cctggctccc aagggtgccc   19380
caaatccttg cgaatgggat gaagctgcta ctgctcttga aataaaccta gaagaagagg   19440
acgatgacaa cgaagacgaa gtagacgagc aagctgagca gcaaaaaact cacgtatttg   19500
ggcaggcgcc ttattctggt ataaatatta caaaggaggg tattcaaata ggtgtcgaag   19560
gtcaaacacc taaatatgcc gataaaacat ttcaacctga acctcaaata ggagaatctc   19620
agtggtacga aactgaaatt aatcatgcag ctgggagagt ccttaaaaag actacccaa    19680 tgaaaccatg ttacggttca tatgcaaaac ccacaaatga aaatggaggg caaggcattc   19740
ttgtaaagca acaaaatgga aagctagaaa gtcaagtgga aatgcaattt ttctcaactg   19800
gaagcggttc tcgctacctg gagcctggcc cagtgactgc cgctggttcc ggaagcagat   19860
acatggacgg aacaatgtcc caggttgccg gttctggctc ccctaaagtg gtattgtaca   19920
gtgaagatgt agatatagaa accccagaca ctcatatttc ttacatgccc actattaagg   19980
aaggtaactc acgagaacta atgggccaac aatctatgcc caacaggcct aattacattg   20040
cttttaggga caattttatt ggtctaatgt attacaacag cacgggtaat atgggtgttc   20100
tggcgggcca agcatcgcag ttgaatgctg ttgtagattt gcaagacaga aacacagagc   20160
tttcatacca gcttttgctt gattccattg gtgatagaac caggtacttt tctatgtgga   20220
atcaggctgt tgacagctat gatccagatg ttagaattat tgaaaatcat ggaactgaag   20280
atgaacttcc aaattactgc tttccactgg gaggtgtgat taatacagag actcttacca   20340
aggtaaaacc taaacaggt caggaaaatg gatgggaaaa agatgctaca gaattttcag   20400
ataaaaatga aataagagtt ggaaataatt ttgccatgga aatcaatcta aatgccaacc   20460 tgtgagaaa tttcctgtac tccaacatag cgctgtattt gcccgacaag ctaaagtaca   20520
gtccttccaa cgtaaaaatt tctgataacc caaacaccta cgactacatg aacaagcgag   20580
tggtggctcc cgggttagtg gactgctaca ttaaccttgg agcacgctgg tcccttgact   20640
atatggacaa cgtcaaccca tttaaccacc accgcaatgc tggcctgcgc taccgctcaa   20700
tgttgctggg caatggtcgc tatgtgccct tccacatcca ggtgcctcag aagttctttg   20760
ccattaaaaa cctccttctc ctgccgggct catacaccta cgagtggaac ttcaggaagg   20820
atgttaacat ggtctgcag agctccctag gaaatgacct aagggttgac ggagccagca   20880
```

```
ttaagtttga tagcatttgc ctttacgcca ccttcttccc catggcccac aacaccgcct      20940
ccacgcttga ggccatgctt agaaacgaca ccaacgacca gtcctttaac gactatctct      21000
ccgccgccaa catgctctac cctataccog ccaacgctac caacgtgccc atatccatcc      21060
cctcccgcaa ctgggcggct ttccgcggct gggccttcac gcgccttaag actaaggaaa      21120
ccccatcact gggctcgggc tacgacoctt attacaccta ctctggctct ataccctacc      21180
tagatggaac cttttacctc aaccacacct ttaagaaggt ggccattacc tttgactctt      21240
ctgtcagctg gcctggcaat gaccgcctgc ttaccoccaa cgagtttgaa attaagcgct      21300
cagttgacgg ggagggttac aacgttgccc agtgtaacat gaccaaagac tggttcctgg      21360
tacaaatgct agctaactac aacattggct accagggctt ctatatccca gagagctaca      21420
aggaccgcat gtactccttc tttagaaact tccagcccat gagccgtcag gtggtggatg      21480
atactaaata caaggactac caacaggtgg gcatcctaca ccaacacaac aactctggat      21540
ttgttggcta ccttgccccc accatgcgcg aaggacaggc ctaccctgct aacttcccct      21600
atccgcttat aggcaagacc gcagttgaca gcattaccca gaaaaagttt ctttgcgatc      21660 gcacccttg gcgcatccca ttctccagta actttatgtc catgggcgca ctcacagacc      21720
tgggccaaaa ccttctctac gccaactccg cccacgcgct agacatgact tttgaggtgg      21780
atcccatgga cgagcccacc cttctttatg ttttgtttga agtctttgac gtggtccgtg      21840
tgcaccagcc gcaccgcggc gtcatcgaaa ccgtgtacct gcgcacgccc ttctcggccg      21900
gcaacgccac aacataaaga agcaagcaac atcaacaaca gctgccgcca tgggctccag      21960
tgagcaggaa ctgaaagcca ttgtcaaaga tcttggttgt gggccatatt ttttgggcac      22020
ctatgacaag cgcttttccag gctttgtttc tccacacaag ctcgcctgcg ccatagtcaa      22080
tacggccggt cgcgagactg ggggcgtaca ctggatggcc tttgcctgga ccccgcactc      22140
aaaaacatgc tacctctttg agccctttgg cttttctgac cagcgactca agcaggttta      22200
ccagtttgag tacgagtcac tcctgcgccg tagcgccatt gcttcttccc ccgaccgctg      22260
tataacgctg gaaaagtcca cccaaagcgt acagggccc aactcggccg cctgtggact      22320
attctgctgc atgtttctcc acgcctttgc caactggccc caaactccca tggatcacaa      22380
ccccaccatg aaccttatta ccggggtacc caactccatg ctcaacagtc cccaggtaca      22440
gcccaccctg cgtcgcaacc aggaacagct ctacagcttc ctggagcgcc actcgcccta      22500
cttccgcagc cacagtgcgc agattaggag cgccacttct ttttgtcact tgaaaaacat      22560
gtaaaaataa tgtactagag acactttcaa taaaggcaaa tgcttttatt tgtacactct      22620
cgggtgatta tttacccoca cccttgccgt ctgcgccgtt taaaaatcaa aggggttctg      22680
ccgcgcatcg ctatgcgcca ctggcaggga cacgttgcga tactggtgtt tagtgctcca      22740
cttaaactca ggcacaacca tccgcggcag ctcggtgaag ttttcactcc acaggctgcg      22800
caccatcacc aacgcgttta gcaggtcggg cgccgatatc ttgaagtcgc agttggggcc      22860
tccgccctgc gcgcgcgagt tgcgatacac agggttgcag cactgaaaca ctatcagcgc      22920
cgggtggtgc acgctggcca gcacgctctt gtcggagatc agatccgcgt ccaggtcctc      22980
cgcgttgctc agggcgaacg gagtcaactt tggtagctgc cttcccaaaa agggcgcgtg      23040
cccaggcttt gagttgcact cgcaccgtag tggcatcaaa aggtgaccgt gcccggtctg      23100
ggcgttagga tacagcgcct gcataaaagc cttgatctgc ttaaaagcca cctgagcctt      23160
tgcgccttca gagaagaaca tgccgcaaga cttgccggaa aactgattgg ccggacaggc      23220
cgcgtcgtgc acgcagcacc ttgcgtcggt gttggagatc tgcaccacat tcggccocca      23280
```

```
ccggttcttc acgatcttgg ccttgctaga ctgctccttc agcgcgcgct gcccgttttc   23340
gctcgtcaca tccatttcaa tcacgtgctc cttatttatc ataatgcttc cgtgtagaca   23400
cttaagctcg ccttcgatct cagcgcagcg gtgcagccac aacgcgcagc ccgtgggctc   23460
gtgatgcttg taggtcacct ctgcaaacga ctgcaggtac gcctgcagga atcgcccat    23520 catcgtcaca aaggtcttgt tgctggtgaa ggtcagctgc aacccgcggt gctcctcgtt   23580
cagccaggtc ttgcatacgg ccgccagagc ttccacttgg tcaggcagta gtttgaagtt   23640
cgcctttaga tcgttatcca cgtggtactt gtccatcagc gcgcgcgcag cctccatgcc   23700
cttctcccac gcagacacga tcggcacact cagcgggttc atcaccgtaa tttcactttc   23760
cgcttcgctg ggctcttcct cttcctcttg cgtccgcata ccacgcgcca ctgggtcgtc   23820
ttcattcagc cgccgcactg tgcgcttacc tcctttgcca tgcttgatta gcaccggtgg   23880
gttgctgaaa cccaccattt gtagcgccac atcttctctt tcttcctcgc tgtccacgat   23940
tacctctggt gatggcgggc gctcgggctt gggagaaggg cgcttctttt tcttcttggg   24000
cgcaatggcc aaatccgccg ccgaggtcga tggccgcggg ctgggtgtgc gcggcaccag   24060
cgcgtcttgt gatgagtctt cctcgtcctc ggactcgata cgccgcctca tccgcttttt   24120
tgggggcgcc cggggaggcg gcggcgacgg ggacggggac gacacgtcct ccatggttgg   24180
gggacgtcgc gccgcaccgc gtccgcgctc ggggtggtt tcgcgctgct cctcttcccg    24240
actggccatt tccttctcct ataggcagaa aaagatcatg gagtcagtcg agaagaagga   24300
cagcctaacc gccccctctg agttcgccac accgcctcc accgatgccg ccaacgcgcc     24360
taccaccttc cccgtcgagg cacccccgct tgaggaggag gaagtgatta tcgagcagga   24420
cccaggtttt gtaagcgaag acgacgagga ccgctcagta ccaacagagg ataaaaagca   24480
agaccaggac aacgcagagg caaacgagga acaagtcggg cgggggacg aaaggcatgg     24540 cgactaccta gatgtgggag acgacgtgct gttgaagcat ctgcagcgcc agtgcgccat   24600
tatctgcgac gcgttgcaag agcgcagcga tgtgcccctc gccatagcgg atgtcagcct   24660
tgcctacgaa cgccacctat tctcaccgcg cgtaccccc aaacgccaag aaaacggcac     24720
atgcgagccc aacccgcgcc tcaacttcta ccccgtattt gccgtgccag aggtgcttgc   24780
cacctatcac atcttttcc aaaactgcaa gatacccta tcctgccgtg ccaaccgcag      24840
ccgagcggac aagcagctgg ccttgcggca gggcgctgtc atacctgata tcgcctcgct   24900
caacgaagtg ccaaaaatct ttgagggtct tggacgcgac gagaagcgcg cggcaaacgc   24960
tctgcaacag gaaaacagcg aaaatgaaag tcactctgga gtgttggtgg aactcgaggg   25020
tgacaacgcg cgcctagccg tactaaaacg cagcatcgag gtcacccact tgcctaccc     25080 ggcacttaac ctaccccca aggtcatgag cacagtcatg agtgagctga tcgtgcgccg    25140
tgcgcagccc ctggagaggg atgcaaattt gcaagaacaa acagaggagg cctacccgc     25200 agttggcgac gagcagctag cgcgctggct tcaaacgcgc gagcctgccg acttggagga   25260
gcgacgcaaa ctaatgatgg ccgcagtgct cgttaccgtg gagcttgagt gcatgcagcg   25320
gttctttgct gacccggaga tgcagcgcaa gctagaggaa acattgcact acacctttcg   25380
acagggctac gtacgccagg cctgcaagat ctccaacgtg gagctctgca acctggtctc   25440
ctaccttgga attttgcacg aaaaccgcct tgggcaaaac gtgcttcatt ccacgctcaa   25500
gggcgaggcg cgccgcgact acgtccgcga ctgcgtttac ttatttctat gctacacctg   25560
gcagacggcc atgggcgttt ggcagcagtg cttggaggag tgcaacctca aggagctgca   25620
```

```
gaaactgcta aagcaaaact tgaaggacct atggacggcc ttcaacgagc gctccgtggc   25680
cgcgcacctg gcggacatca ttttccccga acgcctgctt aaaaccctgc aacagggtct   25740
gccagacttc accagtcaaa gcatgttgca gaactttagg aactttatcc tagagcgctc   25800
aggaatcttg cccgccacct gctgtgcact tcctagcgac tttgtgccca ttaagtaccg   25860
cgaatgccct ccgccgcttt ggggccactg ctaccttctg cagctagcca actaccttgc   25920
ctaccactct gacataatgg aagacgtgag cggtgacggt ctactggagt gtcactgtcg   25980
ctgcaaccta tgcaccccgc accgctccct ggtttgcaat cgcagctgc ttaacgaaag     26040 tcaaattatc ggtacctttg agctgcaggg tccctcgcct gacgaaaagt ccgcggctcc   26100
ggggttgaaa ctcactccgg ggctgtggac gtcggcttac cttcgcaaat ttgtacctga   26160
ggactaccac gccccacgaga ttaggttcta cgaagaccaa tcccgcccgc caaatgcgga  26220
gcttaccgcc tgcgtcatta cccagggcca cattcttggc caattgcaag ccatcaacaa   26280
agcccgccaa gagtttctgc tacgaaaggg acgggggtt tacttggacc cccagtccgg    26340
cgaggagctc aacccaatcc ccccgccgcc gcagccctat cagcagcagc cgcgggccct   26400
tgcttcccag gatggcaccc aaaaagaagc tgcagctgcc gccgccaccc acggacgagg   26460
aggaatactg ggacagtcag gcagaggagg ttttggacga ggaggaggag acatgatgg    26520 aagactggga gagcctagac gaggaagctt ccgaggtcga agaggtgtca gacgaaacac   26580
cgtcaccctc ggtcgcattc ccctcgccgg cgccccagaa atcggcaacc ggttccagca   26640
tggctacaac ctccgctcct caggcgccgc cggcactgcc cgttcgccga cccaaccgta   26700
gatgggacac cactggaacc agggccggta agtccaagca gccgccgccg ttagcccaag   26760
agcaacaaca gcgccaaggc taccgctcat ggcgcgggca caagaacgcc atagttgctt   26820
gcttgcaaga ctgtggggc aacatctcct tcgcccgccg ctttcttctc taccatcacg     26880
gcgtggcctt ccccgtaac atcctgcatt actaccgtca tctctacagc ccatactgca   26940
ccggcggcag cggcagcggc agcaacagca gcggccacac agaagcaaag gcgaccggat   27000
agcaagactc tgacaaagcc caagaaatcc acagcggcgg cagcagcagg aggaggagcg   27060
ctgcgtctgg cgcccaacga acccgtatcg acccgcgagc ttagaaacag gattttttccc  27120 actctgtatg ctatatttca acagagcagg ggccaagaac aagagctgaa aataaaaaac   27180
aggtctctgc gatccctcac ccgcagctgc ctgtatcaca aaagcgaaga tcagcttcgg   27240
cgcacgctgg aagacgcgga ggctctcttc agtaaatact gcgcgctgac tcttaaggac   27300
tagtttcgcg ccctttctca aatttaagcg cgaaaactac gtcatctcca gcggccacac   27360
ccggcgccag cacctgtcgt cagcgccatt atgagcaagg aaattcccac gccctacatg   27420
tggagttacc agccacaaat gggacttgcg gctggagctg cccaagacta ctcaacccga   27480
ataaactaca tgagcgcggg accccacatg atatcccggg tcaacggaat ccgcgcccac   27540
cgaaaccgaa ttctcttgga acaggcggct attaccacca cacctcgtaa taaccttaat   27600
ccccgtagtt ggcccgctgc cctggtgtac caggaaagtc ccgctccac cactgtggta   27660 cttcccagag acgcccaggc cgaagttcag atgactaact caggggcgca gcttgcgggc   27720
ggctttcgtc acagggtgcg gtcgcccggg cagggtataa ctcacctgac aatcagaggg   27780
cgaggtattc agctcaacga cgagtcggtg agctcctcgc ttggtctccg tccggacggg   27840
acatttcaga tcggcggcgc cggccgtcct tcattcacgc ctcgtcaggc aatcctaact   27900
ctgcagacct cgtcctctga gccgcgctct ggaggcattg gaactctgca atttattgag   27960
gagtttgtgc catcggtcta ctttaacccc ttctcgggac ctcccggcca ctatccggat   28020
```

```
caatttattc ctaactttga cgcggtaaag gactcggcgg acggctacga ctgaatgtta    28080
agtggagagg cagagcaact gcgcctgaaa cacctggtcc actgtcgccg ccacaagtgc    28140
tttgcccgcg actccggtga gttttgctac tttgaattgc ccgaggatca tatcgagggc    28200
ccggcgcacg gcgtccggct taccgcccag ggagagcttg cccgtagcct gattcggag    28260 tttacccagc gccccctgct agttgagcgg gacagggac cctgtgttct cactgtgatt    28320
tgcaactgtc ctaaccttgg attacatcaa gatctttgtt gccatctctg tgctgagtat    28380
aataaataca gaaattaaaa tatactgggg ctcctatcgc catcctgtaa acgccaccgt    28440
cttcacccgc ccaagcaaac caaggcgaac cttacctggt acttttaaca tctctccctc    28500
tgtgatttac aacagtttca acccagacgg agtgagtcta cgagagaacc tctccgagct    28560
cagctactcc atcagaaaaa acaccacccct ccttacctgc cgggaacgta cgagtgcgtc    28620
accggccgct gcaccacacc taccgcctga ccgtaaacca gactttttcc ggacagacct    28680
caataactct gttaccaga acaggagtg agcttagaaa acccttaggg tattaggcca    28740
aaggcgcagc tactgtgggg tttatgaaca attcaagcaa ctctacgggc tattctaatt    28800
caggtttctc tagaatcggg gttggggtta ttctctgtct tgtgattctc tttattctta    28860
tactaacgct tctctgccta aggctcgccg cctgctgtgt gcacatttgc atttattgtc    28920 agcttttttaa acgctgggt cgccacccaa gatgattagg tacataatcc taggtttact    28980
cacccttgcg tcagcccacg gtaccaccca aaaggtggat tttaaggagc cagcctgtaa    29040
tgttacattc gcagctgaag ctaatgagtg caccactctt ataaaatgca ccacagaaca    29100
tgaaaagctg cttattcgcc acaaaaacaa aattggcaag tatgctgttt atgctatttg    29160
gcagccaggt gacactacag agtataatgt tacagttttc cagggtaaaa gtcataaaac    29220
ttttatgtat acttttccat tttatgaaat gtgcgacatt accatgtaca tgagcaaaca    29280
gtataagttg tggcccccac aaaattgtgt ggaaaacact ggcactttct gctgcactgc    29340
tatgctaatt acagtgctcg cttttggtctg tacccctactc tatattaaat acaaaagcag    29400
acgcagcttt attgaggaaa agaaaatgcc ttaatttact aagttacaaa gctaatgtca    29460
ccactaactg ctttactcgc tgcttgcaaa acaaattcaa aaagttagca ttataattag    29520
aataggattt aaaccccccg gtcatttcct gctcaatacc attccctga acaattgact    29580 ctatgtggga tatgctccag cgctacaacc ttgaagtcag gcttcctgga tgtcagcatc    29640
tgactttggc cagcacctgt cccgcggatt tgttccagtc caactacagc gacccaccct    29700
aacagagatg accaacacaa ccaacgcggc cgccgctacc ggacttacat ctaccacaaa    29760
tacaccccaa gtttctgcct ttgtcaataa ctgggataac ttgggcatgt ggtggttctc    29820
catagcgctt atgtttgtat gccttattat tatgtggctc atctgctgcc taaagcgcaa    29880
acgcgcccga ccacccatct atagtcccat cattgtgcta cacccaaaca atgatggaat    29940
ccatagattg gacggactga acacatgtt cttttctctt acagtatgat taaatgagac    30000
atgattcctc gagttttat attactgacc cttgttgcgc ttttttgtgc gtgctccaca    30060
ttggctgcgg tttctcacat cgaagtagac tgcattccag ccttcacagt ctatttgctt    30120 tacgatttg tcaccctcac gctcatctgc agcctcatca ctgtggtcat cgcctttatc    30180
cagtgcattg actgggtctg tgtgcgcttt gcatatctca gacaccatcc ccagtacagg    30240
gacaggacta tagctgagct tcttagaatt ctttaattat gaatttact gtgactttc    30300 tgctgattat ttgcaccta tctgcgtttt gttccccgac ctccaagcct caaagacata    30360
```

```
tatcatgcag attcactcgt atatggaata ttccaagttg ctacaatgaa aaaagcgatc    30420
tttccgaagc ctggttatat gcaatcatct ctgttatggt gttctgcagt accatcttag    30480
ccctagctat atatccctac cttgacattg gctggaaacg aatagatgcc atgaaccacc    30540
caactttccc cgcgcccgct atgcttccac tgcaacaagt tgttgccggc ggctttgtcc    30600
cagccaatca gcctcgcccc acttctccca ccccactga aatcagctac tttaatctaa     30660
caggaggaga tgactgacac cctagatcta gaaatggacg gaattattac agagcagcgc    30720
ctgctagaaa gacgcagggc agcggccgag caacagcgca tgaatcaaga gctccaagac    30780
atggttaact gcaccagtg caaaagggt atcttttgtc tggtaaagca ggccaaagtc      30840
acctacgaca gtaataccac cggacaccgc cttagctaca agttgccaac caagcgtcag    30900
aaattggtgg tcatggtggg agaaaagccc attaccataa ctcagcactc ggtagaaacc    30960
gaaggctgca ttcactcacc ttgtcaagga cctgaggatc tctgcaccct tattaagacc    31020
ctgtgcggtc tcaaagatct tattcccttt aactaataaa aaaaataat aaagcatcac     31080 ttacttaaaa tcagttagca aatttctgtc cagtttattc agcagcacct ccttgccctc    31140
ctcccagctc tggtattgca gcttcctcct ggctgcaaac tttctccaca atctaaatgg    31200
aatgtcagtt tcctcctgtt cctgtccatc cgcacccact atcttcatgt tgttgcagat    31260
gaagcgcgca agaccgtctg aagataccgt caaccccgtg tatccatatg acacggaaac    31320
cggtcctcca actgtgcctt ttcttactcc tcccctttgta tccccaatg ggtttcaaga    31380 gagtcccct ggggtactct ctttgcgcct atccgaacct ctagttacct ccaatggcat     31440
gcttgcgctc aaaatgggca acggcctctc tctggacgag gccggcaacc ttacctccca    31500
aaatgtaacc actgtgagcc cacctctccg aggagacaag tcaaacataa acctggaaat    31560
atctgcaccc ctcacagtta cctcagaagc cctaactgtg gctgccgccg cacctctaat    31620
ggtcgcgggc aacacactca ccatgcaatc acaggccccg ctaaccgtgc acgactccaa    31680
acttagcatt gccacccaag gacccctcac agtgtcagaa ggaaagctag ccctgcaaac    31740
atcaggcccc ctcaccacca ccgatagcag taccttact atcactgcct caccccctct     31800
aactactgcc actggtagct tgggcattga cttgaaagag cccatttata cacaaaatgg    31860
aaaactagga ctaaagtacg gggctccttt gcatgtaaca gacgacctaa acactttgac    31920
cgtagcaact ggtccaggtg tgactattaa taatacttcc ttgcaaacta agttactgg     31980 agccttgggt tttgattcac aaggcaatat gcaacttaat gtagcaggag gactaaggat    32040
tgattctcaa aacagacgcc ttatacttga tgttagttat ccgtttgatg ctcaaaacca    32100
actaaatcta agactaggac agggccctct ttttataaac tcagcccaca acttggatat    32160
taactacaac aaaggccttt acttgtttac agcttcaaac aattccaaaa agcttgaggt    32220
taacctaagc actgccaagg ggttgatgtt tgacgctaca gccatagcca ttaatgcagg    32280
agatgggctt gaatttggtt cacctaatgc accaaacaca aatcccctca aaacaaaaat    32340
tggccatggc ctagaatttg attcaaacaa ggctatggtt cctaaactag gaactggcct    32400
tagttttgac agcacaggtg ccattacagt aggaaacaaa aataatgata agctaacttt    32460
gtggaccaca ccagctccat ctcctaactg tagactaaat gcagagaaag atgctaaact    32520
cactttggtc ttaacaaaat gtggcagtca aatacttgct acagtttcag ttttggctgt    32580
taaaggcagt ttggctccaa tatctggaac agttcaaagt gctcatctta ttataagatt    32640
tgacgaaaat ggagtgctac taacaattc cttcctggac ccagaatatt ggaactttag    32700
aaatggagat cttactgaag gcacagccta tacaaacgct gttggattta tgcctaacct    32760
```

```
atcagcttat ccaaaatctc acggtaaaac tgccaaaagt aacattgtca gtcaagttta   32820
cttaaacgga gacaaaacta aacctgtaac actaaccatt acactaaacg gtacacagga   32880
aacaggagac acaactccaa gtgcatactc tatgtcattt tcatgggact ggtctggcca   32940
caactacatt aatgaaatat ttgccacatc ctcttacact ttttcataca ttgcccaaga   33000
ataaagaatc gtttgtgtta tgtttcaacg tgtttatttt tcaattgcag aaaatttcaa   33060 gtcattttc attcagtagt atagcccac caccacatag cttatacaga tcaccgtacc   33120
ttaatcaaac tcacagaacc ctagtattca acctgccacc tccctcccaa cacacagagt   33180
acacagtcct ttctccccgg ctggccttaa aaagcatcat atcatgggta acagacatat   33240
tcttaggtgt tatattccac acggtttcct gtcgagccaa acgctcatca gtgatattaa   33300
taaactcccc gggcagctca cttaagttca tgtcgctgtc cagctgctga gccacaggct   33360
gctgtccaac ttgcggttgc ttaacgggcg gcgaaggaga agtccacgcc tacatggggg   33420
tagagtcata atcgtgcatc aggatagggc ggtggtgctg cagcagcgcg cgaataaact   33480
gctgccgccg ccgctccgtc ctgcaggaat acaacatggc agtggtctcc tcagcgatga   33540
ttcgcaccgc ccgcagcata aggcgccttg tcctccgggc acagcagcgc accctgatct   33600
cacttaaatc agcacagtaa ctgcagcaca gcaccacaat attgttcaaa atcccacagt   33660
gcaaggcgct gtatccaaag ctcatggcgg ggaccacaga acccacgtgg ccatcatacc   33720
acaagcgcag gtagattaag tggcgacccc tcataaacac gctggacata acattacct   33780 cttttggcat gttgtaattc accacctccc ggtaccatat aaacctctga ttaaacatgg   33840
cgccatccac caccatccta aaccagctgg ccaaaacctg cccgccggct atacactgca   33900
gggaaccggg actggaacaa tgacagtgga gagcccagga ctcgtaacca tggatcatca   33960
tgctcgtcat gatatcaatg ttggcacaac acaggcacac gtgcatacac ttcctcagga   34020
ttacaagctc ctcccgcgtt agaaccatat cccagggaac aacccattcc tgaatcagcg   34080
taaatcccac actgcaggga agacctcgca cgtaactcac gttgtgcatt gtcaaagtgt   34140
tacattcggg cagcagcgga tgatcctcca gtatggtagc gcgggtttct gtctcaaaag   34200
gaggtagacg atccctactg tacggagtgc gccgagacaa ccgagatcgt gttggtcgta   34260
gtgtcatgcc aaatggaacg ccggacgtag tcatatttcc tgaagcaaaa ccaggtgcgg   34320
gcgtgacaaa cagatctgcg tctccggtct cgccgcttag atcgctctgt gtagtagttg   34380
tagtatatcc actctctcaa agcatccagg cgcccctgg cttcgggttc tatgtaaact   34440
ccttcatgcg ccgctgccct gataacatcc accaccgcag aataagccac acccagccaa   34500
cctacacatt cgttctgcga gtcacacacg ggaggagcgg gaagagctgg aagaaccatg   34560 ttttttttt tattccaaaa gattatccaa aacctcaaaa tgaagatcta ttaagtgaac   34620
gcgctcccct ccggtggcgt ggtcaaactc tacagccaaa gaacagataa tggcatttgt   34680
aagatgttgc acaatggctt ccaaaaggca aacggccctc acgtccaagt ggacgtaaag   34740
gctaaaccct tcagggtgaa tctcctctat aaacattcca gcaccttcaa ccatgcccaa   34800
ataattctca tctcgccacc ttctcaatat atctctaagc aaatcccgaa tattaagtcc   34860
ggccattgta aaaatctgct ccagagcgcc ctccaccttc agcctcaagc agcgaatcat   34920
gattgcaaaa attcaggttc ctcacagacc tgtataagat tcaaaagcgg aacattaaca   34980
aaaataccgc gatcccgtag gtcccttcgc agggccagct gaacataatc gtgcaggtct   35040
gcacggacca gcgcggccac ttccccgcca ggaaccatga caaaagaacc cacactgatt   35100
```

-continued

| | |
|---|---|
| atgacacgca tactcggagc tatgctaacc agcgtagccc cgatgtaagc ttgttgcatg | 35160 |
| ggcggcgata taaatgcaa ggtgctgctc aaaaaatcag gcaaagcctc gcgcaaaaaa | 35220 |
| gaaagcacat cgtagtcatg ctcatgcaga taaaggcagg taagctccgg aaccaccaca | 35280 |
| gaaaaagaca ccattttct ctcaaacatg tctgcgggtt tctgcataaa cacaaaataa | 35340 |
| aataacaaaa aaacatttaa acattagaag cctgtcttac aacaggaaaa acaaccctta | 35400 |
| taagcataag acggactacg gccatgccgg cgtgaccgta aaaaactgg tcaccgtgat | 35460 |
| taaaaagcac caccgacagc tcctcggtca tgtccggagt cataatgtaa gactcggtaa | 35520 |
| acacatcagg ttgattcaca tcggtcagtg ctaaaaagcg accgaaatag cccgggggaa | 35580 |
| tacatacccg caggcgtaga gacaacatta cagcccccat aggaggtata acaaaattaa | 35640 |
| taggagagaa aaacacataa acacctgaaa aaccctcctg cctaggcaaa atagcaccct | 35700 |
| cccgctccag aacaacatac agcgcttcca cagcggcagc cataacagtc agccttacca | 35760 |
| gtaaaaaaga aaacctatta aaaaacacc actcgacacg gcaccagctc aatcagtcac | 35820 |
| agtgtaaaaa agggccaagt gcagagcgag tatatatagg actaaaaaat gacgtaacgg | 35880 |
| ttaaagtcca caaaaacac ccagaaaacc gcacgcgaac ctacgcccag aaacgaaagc | 35940 |
| caaaaaccc acaacttcct caaatcgtca cttccgtttt cccacgttac gtcacttccc | 36000 |
| atttaagaa aactacaatt cccaacacat actagttact ccgccctaaa acctacgtca | 36060 |
| cccgccccgt tccacgcccc gcgccacgt cacaaactcc acccctcat tatcatattg | 36120 |
| gcttcaatcc aaaataaggt atattattga tgatgt | 36156 |

<210> SEQ ID NO 3
<211> LENGTH: 36090
<212> TYPE: DNA
<213> ORGANISM: Artificial Sequence
<220> FEATURE:
<223> OTHER INFORMATION: ICOVIR15K-TD

<400> SEQUENCE: 3

| | |
|---|---|
| catcatcaat aatataccct attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgtac | 420 |
| gtcggcggct cgtggctctt cgcggcaaa aaggatttgg cgcgtaaaag tggttcgagt | 480 |
| acgtcggcgg ctcgtggctc tttgcggca aaaggattt ggcgcgtaaa agtggttcga | 540 |
| agtacgtcga ccacaaaccc cgcccagcgt cttgtcattg gcgtcgacgc tgtacggggt | 600 |
| caaagttggc gttttattat tatagtcagc tgacgtgtag tgtatttata cccggtgagt | 660 |
| tcctcaagag gccactcttg agtgccagcg agtagagttt ctcctccga gccgctccga | 720 |
| caccgggact gaaaatgaga catattatct gccacggagg tgttattacc gaagaaatgg | 780 |
| ccgccagtct tttggaccag ctgatcgaag aggtactggc tgataatctt ccacctccta | 840 |
| gccattttga accacctacc cttcacgaac tgtatgattt agacgtgacg gcccccgaag | 900 |
| atcccaacga ggaggcggtt tcgcagattt ttcccgactc tgtaatgttg gcggtgcagg | 960 |
| aagggattga cttactcact tttccgccgg cgcccggttc tccggagccg cctcaccttt | 1020 |

```
cccggcagcc cgagcagccg gagcagagag ccttgggtcc ggtttctatg ccaaaccttg    1080
taccggaggt gatcgatcca cccagtgacg acgaggatga agagggtgag gagtttgtgt    1140
tagattatgt ggagcacccc gggcacggtt gcaggtcttg tcattatcac cggaggaata    1200
cgggggaccc agatattatg tgttcgcttt gctatatgag gacctgtggc atgtttgtct    1260
acagtaagtg aaaattatgg gcagtgggtg atagagtggt gggtttggtg tggtaatttt    1320 tttttttaatt tttacagttt tgtggtttaa agaattttgt attgtgattt ttttaaaagg    1380
tcctgtgtct gaacctgagc ctgagcccga gccagaaccg gagcctgcaa gacctacccg    1440
ccgtcctaaa atggcgcctg ctatcctgag acgcccgaca tcacctgtgt ccagagaatg    1500
caatagtagt acggatagct gtgactccgg tccttctaac acacctcctg agatacaccc    1560
ggtggtcccg ctgtgcccca ttaaaccagt tgccgtgaga gttggtgggc gtcgccaggc    1620
tgtggaatgt atcgaggact tgcttaacga gcctgggcaa cctttggact tgagctgtaa    1680 acgcccagg ccataaggtg taaacctgtg attgcgtgtg tggttaacgc ctttgtttgc    1740
tgaatgagtt gatgtaagtt taataaaggg tgagataatg tttaacttgc atggcgtgtt    1800
aaatggggcg gggcttaaag ggtatataat gcgccgtggg ctaatcttgg ttacatctga    1860
cctcatggag gcttgggagt gtttggaaga ttttctgct gtgcgtaact tgctggaaca    1920
gagctctaac agtacctctt ggttttggag gtttctgtgg ggctcatccc aggcaaagtt    1980
agtctgcaga attaaggagg attacaagtg ggaatttgaa gagcttttga aatcctgtgg    2040
tgagctgttt gattctttga atctgggtca ccaggcgctt ttccaagaga aggtcatcaa    2100
gactttggat ttttccacac cggggcgcgc tgcggctgct gttgcttttt tgagtttat    2160 aaaggataaa tggagcgaag aaacccatct gagcggggg tacctgctgg attttctggc    2220
catgcatctg tggagagcgg ttgtgagaca caagaatcgc ctgctactgt tgtcttccgt    2280
ccgcccggcg ataataccga cggaggagca gcagcagcag caggaggaag ccaggcggcg    2340
gcggcaggag cagagcccat ggaacccgag agccggcctg gaccctcggg aatgaatgtt    2400
gtacaggtgg ctgaactgta tccagaactg agacgcattt tgacaattac agaggatggg    2460
caggggctaa aggggtaaa gagggagcgg ggggcttgtg aggctacaga ggaggctagg    2520
aatctagctt ttagcttaat gaccagacac cgtcctgagt gtattacttt tcaacagatc    2580
aaggataatt gcgctaatga gcttgatctg ctggcgcaga agtattccat agagcagctg    2640
accacttact ggctgcagcc aggggatgat tttgaggagg ctattagggt atatgcaaag    2700
gtggcactta ggccagattg caagtacaag atcagcaaac ttgtaaatat caggaattgt    2760
tgctacattt ctgggaacgg ggccgaggtg gagatagata cggaggatag ggtggccttt    2820
agatgtagca tgataaatat gtggccgggg gtgcttggca tggacggggt ggttattatg    2880
aatgtaaggt ttactggccc caattttagc ggtacggttt tcctggccaa taccaacctt    2940
atcctacacg tgtaagcttc tatgggttt aacaatacct gtgtgaagc ctggaccgat    3000 gtaagggttc gggctgtgc cttttactgc tgctggaagg gggtggtgtg tcgccccaaa    3060
agcagggctt caattaagaa atgcctcttt gaaaggtgta ccttgggtat cctgtctgag    3120
ggtaactcca gggtgcgcca caatgtgcc tccgactgtg gttgcttcat gctagtgaaa    3180
agcgtggctg tgattaagca taacatggta tgtggcaact gcgaggacag ggcctctcag    3240
atgctgacct gctcggacgg caactgtcac ctgctgaaga ccattcacgt agccagccac    3300
tctcgcaagg cctggccagt gtttgagcat aacatactga cccgctgttc cttgcatttg    3360
```

```
ggtaacagga ggggggtgtt cctaccttac caatgcaatt tgagtcacac taagatattg    3420
cttgagcccg agagcatgtc caaggtgaac ctgaacgggg tgtttgacat gaccatgaag    3480
atctggaagg tgctgaggta cgatgagacc cgcaccaggt gcagaccctg cgagtgtggc    3540
ggtaaacata ttaggaacca gcctgtgatg ctggatgtga ccgaggagct gaggcccgat    3600
cacttggtgc tggcctgcac ccgcgctgag tttggctcta gcgatgaaga tacagattga    3660
ggtactgaaa tgtgtgggcg tggcttaagg gtgggaaaga atatataagg tgggggtctt    3720
atgtagtttt gtatctgttt tgcagcagcc gccgccgcca tgagcaccaa ctcgtttgat    3780
ggaagcattg tgagctcata tttgacaacg cgcatgcccc catgggccgg ggtgcgtcag    3840
aatgtgatgg gctccagcat tgatggtcgc cccgtcctgc ccgcaaactc tactaccttg    3900
acctacgaga ccgtgtctgg aacgccgttg gagactgcag cctccgccgc cgcttcagcc    3960
gctgcagcca ccgcccgcgg gattgtgact gactttgctt tcctgagccc gcttgcaagc    4020
agtgcagctt cccgttcatc cgcccgcgat gacaagttga cggctctttt ggcacaattg    4080
gattctttga cccgggaact taatgtcgtt tctcagcagc tgttggatct gccagcag    4140 gtttctgccc tgaaggcttc ctcccctccc aatgcggttt aaaacataaa taaaaaacca    4200
gactctgttt ggatttggat caagcaagtg tcttgctgtc tttatttagg ggttttgcgc    4260
gcgcggtagg cccgggacca gcggtctcgg tcgttgaggg tcctgtgtat ttttccagg    4320 acgtggtaaa ggtgactctg gatgttcaga tacatgggca taagcccgtc tctggggtgg    4380
aggtagcacc actgcagagc ttcatgctgc ggggtggtgt tgtagatgat ccagtcgtag    4440
caggagcgct gggcgtggtg cctaaaaatg tctttcagta gcaagctgat tgccaggggc    4500
aggcccttgg tgtaagtgtt tacaaagcgg ttaagctggg atgggtgcat acgtggggat    4560
atgagatgca tcttggactg tatttttagg ttggctatgt tcccagccat atccctccgg    4620
ggattcatgt tgtgcagaac caccagcaca gtgtatccgg tgcacttggg aaatttgtca    4680
tgtagcttag aaggaaatgc gtggaagaac ttggagacgc ccttgtgacc tccaagattt    4740
tccatgcatt cgtccataat gatggcaatg ggcccacggg cggcggcctg ggcgaagata    4800
tttctgggat cactaacgtc atagttgtgt tccaggatga gatcgtcata ggccatttt    4860 acaaagcgcg ggcggagggt gccagactgc ggtataatgg ttccatccgg cccaggggcg    4920
tagttaccct cacagatttg catttcccac gctttgagtt cagatggggg gatcatgtct    4980
acctgcgggg cgatgaagaa aacggtttcc ggggtagggg agatcagctg ggaagaaagc    5040
aggttcctga gcagctgcga cttaccgcag ccggtgggcc cgtaaatcac acctattacc    5100
gggtgcaact ggtagttaag agagctgcag ctgccgtcat ccctgagcag gggggccact    5160
tcgttaagca tgtccctgac tcgcatgttt ccctgacca aatccgccag aaggcgctcg    5220
ccgcccagcg atagcagttc ttgcaaggaa gcaaagtttt tcaacggttt gagaccgtcc    5280
gccgtaggca tgcttttgag cgtttgacca agcagttcca gcggtcccca cagctcggtc    5340
acctgctcta cggcatctcg atccagcata tctcctcgtt tcgcgggttg gggcggcttt    5400
cgctgtacgg cagtagtcgg tgctcgtcca gacgggccag ggtcatgtct ttccacgggc    5460
gcagggtcct cgtcagcgta gtctgggtca cggtgaaggg gtgcgctccg ggctgcgcgc    5520
tggccagggt gcgcttgagg ctggtcctgc tggtgctgaa gcgctgccgg tcttcgccct    5580
gcgcgtcggc caggtagcat ttgaccatgg tgtcatagtc cagcccctcc gcggcgtggc    5640
ccttggcgcg cagcttgccc ttggaggagg cgccgcacga ggggcagtgc agactttga    5700 gggcgtagag cttgggcgcg agaaataccg attccgggga gtaggcatcc gcgccgcagg    5760
```

```
ccccgcagac ggtctcgcat tccacgagcc aggtgagctc tggccgttcg gggtcaaaaa   5820
ccaggtttcc cccatgcttt ttgatgcgtt tcttacctct ggtttccatg agccggtgtc   5880
cacgctcggt gacgaaaagg ctgtccgtgt ccccgtatac agacttgaga ggcctgtcct   5940
cgagcggtgt tccgcggtcc tcctcgtata gaaactcgga ccactctgag acaaaggctc   6000
gcgtccaggc cagcacgaag gaggctaagt gggaggggta gcggtcgttg tccactaggg   6060
ggtccactcg ctccagggtg tgaagacaca tgtcgccctc ttcggcatca aggaaggtga   6120
ttggtttgta ggtgtaggcc acgtgaccgg gtgttcctga aggggggcta taaaaggggg   6180
tggggggcgcg ttcgtcctca ctctcttccg catcgctgtc tgcagggggcc agctgttggg   6240
gtgagtactc cctctgaaaa gcgggcatga cttctgcgct aagattgtca gtttccaaaa   6300
acgaggagga tttgatattc acctggcccg cggtgatgcc tttgagggtg gccgcatcca   6360
tctggtcaga aaagacaatc ttttttgttgt caagcttggt ggcaaacgac ccgtagaggg   6420
cgttggacag caacttggcg atggagcgca gggtttggtt tttgtcgcga tcggcgcgct   6480
ccttggccgc gatgtttagc tgcacgtatt cgcgcgcaac gcaccgccat tcgggaaaga   6540
cggtggtgcg ctcgtcgggc accaggtgca cgcgccaacc gcggttgtgc agggtgacaa   6600
ggtcaacgct ggtggctacc tctccgcgta ggcgctcgtt ggtccagcag aggcggccgc   6660
ccttgcgcga gcagaatggc ggtaggggggt ctagctgcgt ctcgtccggg gggtctgcgt   6720
ccacggtaaa gaccccgggc agcaggcgcg cgtcgaagta gtctatcttg catccttgca   6780
agtctagcgc ctgctgccat gcgcgggcgg caagcgcgcg ctcgtatggg ttgagtgggg   6840
gaccccatgg catggggtgg gtgagcgcgg aggcgtacat gccgcaaatg tcgtaaacgt   6900
agaggggctc tctgagtatt ccaagatatg tagggtagca tcttccaccg cggatgctgg   6960
cgcgcacgta atcgtatagt tcgtgcgagg gagcgaggag gtcgggaccg aggttgctac   7020
gggcgggctg ctctgctcgg aagactatct gcctgaagat ggcatgtgag ttggatgata   7080
tggttggacg ctggaagacg ttgaagctgg cgtctgtgag acctaccgcg tcacgcacga   7140
aggaggcgta ggagtcgcgc agcttgttga ccagctcggc ggtgacctgc acgtctaggg   7200
cgcagtagtc cagggttttcc ttgatgatgt catacttatc ctgtcccttt tttttccaca   7260
gctcgcggtt gaggacaaac tcttcgcggt ctttccagta ctcttggatc ggaaacccgt   7320
cggcctccga acggtaagag cctagcatgt agaactggtt gacggcctgg taggcgcagc   7380
atcccttttc tacgggtagc gcgtatgcct gcgcggcctt ccggagcgag gtgtgggtga   7440
gcgcaaaggt gtccctgacc atgactttga ggtactggta tttgaagtca gtgtcgtcgc   7500
atccgccctg ctcccagagc aaaaagtccg tgcgcttttt ggaacgcgga tttggcaggg   7560
cgaaggtgac atcgttgaag agtatctttc ccgcgcgagg cataaagttg cgtgtgatgc   7620
ggaagggtcc cggcacctcg gaacggttgt taattacctg ggcggcgagc acgatctcgt   7680
caaagccgtt gatgttgtgg cccacaatgt aaagttccaa gaagcgcggg atgcccttga   7740
tggaaggcaa tttttttaagt tcctcgtagg tgagctcttc aggggagctg agcccgtgct   7800
ctgaaagggc ccagtctgca agatgaggggt tggaagcgac gaatgagctc cacaggtcac   7860
gggccattag catttgcagg tggtcgcgaa aggtcctaaa ctggcgacct atggccattt   7920
tttctggggt gatgcagtag aaggtaagcg ggtcttgttc ccagcggtcc catccaaggt   7980
tcgcggctag gtctcgcgcg gcagtcacta gaggctcatc tccgccgaac ttcatgacca   8040
gcatgaaggg cacgagctgc ttcccaaagg ccccccatcca agtataggtc tctacatcgt   8100
```

```
aggtgacaaa gagacgctcg gtgcgaggat gcgagccgat cgggaagaac tggatctccc    8160
gccaccaatt ggaggagtgg ctattgatgt ggtgaaagta gaagtccctg cgacgggccg    8220
aacactcgtg ctggcttttg taaaaacgtg cgcagtactg gcagcggtgc acgggctgta    8280
catcctgcac gaggttgacc tgacgaccgc gcacaaggaa gcagagtggg aatttgagcc    8340
cctcgcctgg cgggtttggc tggtggtctt ctacttcggc tgcttgtcct tgaccgtctg    8400
gctgctcgag gggagttacg gtggatcgga ccaccacgcc gcgcgagccc aaagtccaga    8460
tgtccgcgcg cggcggtcgg agcttgatga caacatcgcg cagatgggag ctgtccatgg    8520
tctggagctc ccgcggcgtc aggtcaggcg ggagctcctg caggtttacc tcgcatagac    8580
gggtcagggc gcgggctaga tccaggtgat acctaatttc caggggctgg ttggtggcgg    8640
cgtcgatggc ttgcaagagg ccgcatcccc gcggcgcgac tacggtaccg cgcggcgggc    8700
ggtgggccgc gggggtgtcc ttggatgatg catctaaaag cggtgacgcg ggcgagcccc    8760
cggaggtagg gggggctccg gacccgccgg gagaggggggc aggggcacgt cggcgccgcg    8820
cgcgggcagg agctggtgct gcgcgcgtag gttgctggcg aacgcgacga cgcggcggtt    8880
gatctcctga atctggcgcc tctgcgtgaa gacgacgggc ccggtgagct tgagcctgaa    8940
agagagttcg cacagaatcaa tttcggtgtc gttgacggcg gcctggcgca aaatctcctg    9000
cacgtctcct gagttgtctt gataggcgat ctcggccatg aactgctcga tctcttcctc    9060
ctggagatct ccgcgtccgg ctcgctccac ggtggcggcg aggtcgttgg aaatgcgggc    9120
catgagctgc gagaaggcgt tgaggcctcc ctcgttccag acgcggctgt agaccacgcc    9180
cccttcggca tcgcgggcgc gcatgaccac ctgcgcgaga ttgagctcca cgtgccgggc    9240
gaagacggcg tagtttcgca ggcgctgaaa gaggtagttg agggtggtgg cggtgtgttc    9300
tgccacgaag aagtacataa cccagcgtcg caacgtggat tcgttgatat cccccaaggc    9360
ctcaaggcgc tccatggcct cgtagaagtc cacggcgaag ttgaaaaact gggagttgcg    9420
cgccgacacg gttaactcct cctccagaag acggatgagc tcggcgacag tgtcgcgcac    9480
ctcgcgctca aaggctacag gggcctcttc ttcttcttca atctcctctt ccataagggc    9540 ctcccctttct tcttcttctg gcggcggtgg gggaggggggg acacggcggc gacgacggcg    9600
caccgggagg cggtcgacaa agcgctcgat catctccccg cggcgacggc gcatggtctc    9660
ggtgacggcg cggccgttct cgcggggggcg cagttggaag acgccgcccg tcatgtcccg    9720 gttatggggtt ggcggggggc tgccatgcgg cagggatacg gcgctaacga tgcatctcaa    9780
caattgttgt gtaggtactc cgccgccgag ggacctgagc gagtccgcat cgaccggatc    9840
ggaaaacctc tcgagaaagg cgtctaacca gtcacagtcg caaggtaggc tgagcaccgt    9900
ggcgggcggc agcgggcggc ggtcgggggtt gtttctggcg gaggtgctgc tgatgatgta    9960
attaaagtag gcggtcttga gacggcggat ggtcgacaga agcaccatgt ccttgggtcc    10020
ggcctgctga atgcgcaggc ggtcggccat gccccaggct tcgttttgac atcgcgcag    10080 gtctttgtag tagtcttgca tgagcctttc taccggcact tcttcttctc cttcctcttg    10140
tcctgcatct cttgcatcta tcgctgcggc ggcggcggag tttggccgta ggtggcgccc    10200
tcttcctccc atgcgtgtga ccccgaagcc cctcatcggc tgaagcaggg ctaggtcggc    10260
gacaacgcgc tcggctaata tggcctgctg cacctgcgtg agggtagact ggaagtcatc    10320
catgtccaca aagcggtggt atgcgcccgt gttgatggtg taagtgcagt tggccataac    10380
ggaccagtta acgtctggt gacccggctg cgagagctcg gtgtacctga gacgcgagta    10440
agccctcgag tcaaatacgt agtcgttgca agtccgcacc aggtactggt atcccaccaa    10500
```

```
aaagtgcggc ggcggctggc ggtagagggg ccagcgtagg gtggccgggg ctccggggc    10560
gagatcttcc aacataaggc gatgatatcc gtagatgtac ctggacatcc aggtgatgcc    10620
ggcggcggtg gtggaggcgc gcggaaagtc gcggacgcgg ttccagatgt tgcgcagcgg    10680
caaaaagtgc tccatggtcg ggacgctctg gccggtcagg cgcgcgcaat cgttgacgct    10740
ctagaccgtg caaaaggaga gcctgtaagc gggcactctt ccgtggtctg gtggataaat    10800
tcgcaagggt atcatggcgg acgaccgggg ttcgagcccc gtatccgcc gtccgccgtg     10860
atccatgcgg ttaccgcccg cgtgtcgaac ccaggtgtgc gacgtcagac aacggggag    10920
tgctccttt ggcttccttc caggcgcggc ggctgctgcg ctagcttttt tggccactgg     10980
ccgcgcgcag cgtaagcggt taggctggaa agcgaaagca ttaagtggct cgctccctgt    11040
agccggaggg ttattttcca agggttgagt cgcgggaccc ccggttcgag tctcggaccg    11100
gccggactgc ggcgaacggg ggtttgcctc cccgtcatgc aagacccgc ttgcaaattc    11160
ctccggaaac agggacgagc cccttttttg cttttcccag atgcatccgg tgctgcggca    11220
gatgcgcccc cctcctcagc agcggcaaga gcaagagcag cggcagacat gcagggcacc   11280
ctcccctcct cctaccgcgt caggagggc gacatccgcg gttgacgcgg cagcagatgc    11340
tgattacgaa cccccgcggc gccgggcccg gcactacctg gacttggagg agggcgaggg   11400
cctggcgcgg ctaggagcgc cctctcctga gcggtaccca agggtgcagc tgaagcgtga   11460
tacgcgtgag gcgtacgtgc cgcggcagaa cctgtttcgc gaccgcgagg gagaggagcc   11520
cgaggagatg cgggatcgaa agttccacgc agggcgcgag ctgcggcatg gcctgaatcg   11580
cgagcggttg ctgcgcgagg aggactttga gcccgacgcg cgaaccggga ttagtcccgc   11640
gcgcgcacac gtggcggccg ccgacctggt aaccgcatac gagcagacgg tgaaccagga    11700
gattaactt caaaaaagct ttaacaacca cgtgcgtacg cttgtggcgc gcgaggaggt    11760
ggctatagga ctgatgcatc tgtgggactt tgtaagcgcg ctggagcaaa acccaaatag   11820
caagccgctc atggcgcagc tgttccttat agtgcagcac agcagggaca acgaggcatt   11880
cagggatgcg ctgctaaaca tagtagagcc cgagggccgc tggctgctcg atttgataaa    11940
catcctgcag agcatagtgg tgcaggagcg cagcttgagc ctggctgaca aggtggccgc   12000
catcaactat tccatgctta gcctgggcaa gttttacgcc cgcaagatat accataccc     12060
ttacgttccc atagacaagg aggtaaagat cgaggggttc tacatgcgca tggcgctgaa    12120
ggtgcttacc ttgagcgacg acctgggcgt ttatcgcaac gagcgcatcc acaaggccgt   12180
gagcgtgagc cggcggcgcg agctcagcga ccgcagctg atgcacagcc tgcaaagggc    12240
cctggctggc acgggcagcg gcgatagaga ggccgagtcc tactttgacg cgggcgctga   12300
cctgcgctgg gccccaagcc gacgcgccct ggaggcagct ggggccggac ctgggctggc   12360
ggtggcaccc gcgcgcgctg gcaacgtcgg cggcgtggag gaatatgacg aggacgatga   12420
gtacgagcca gaggacggcg agtactaagc ggtgatgttt ctgatcagat gatgcaagac   12480
gcaacggacc cggcggtgcg ggcggcgctg cagagccagc cgtccggcct taactccacg   12540
gacgactggc gccaggtcat ggaccgcatc atgtcgctga ctgcgcgcaa tcctgacgcg   12600
ttccggcagc agccgcaggc caaccggctc tccgcaattc tggaagcggt ggtcccggcg   12660
cgcgcaaacc ccacgcacga gaaggtgctg gcgatcgtaa acgcgctggc cgaaaacagg    12720
gccatccggc ccgacgaggc cggcctggtc tacgacgcgc tgcttcagcg cgtggctcgt   12780
tacaacagcg gcaacgtgca gaccaacctg gaccggctgg tggggatgt gcgcgaggcc    12840
```

```
gtggcgcagc gtgagcgcgc gcagcagcag ggcaacctgg gctccatggt tgcactaaac   12900
gccttcctga gtacacagcc cgccaacgtg ccgcggggac aggaggacta caccaacttt   12960
gtgagcgcac tgcggctaat ggtgactgag acaccgcaaa gtgaggtgta ccagtctggg   13020
ccagactatt ttttccagac cagtagacaa ggcctgcaga ccgtaaacct gagccaggct   13080
ttcaaaaact tgcaggggct gtgggggggtg cgggctccca caggcgaccg cgcgaccgtg   13140
tctagcttgc tgacgcccaa ctcgcgcctg ttgctgctgc taatagcgcc cttcacggac   13200
agtggcagcg tgtcccggga cacataccta ggtcacttgc tgacactgta ccgcgaggcc   13260
ataggtcagg cgcatgtgga cgagcatact ttccaggaga ttacaagtgt cagccgcgcg   13320
ctggggcagg aggacacggg cagcctggag gcaaccctaa actacctgct gaccaaccgg   13380
cggcagaaga tcccctcgtt gcacagttta acagcgagg aggagcgcat tttgcgctac   13440
gtgcagcaga gcgtgagcct taacctgatg cgcgacgggg taacgcccag cgtggcgctg   13500
gacatgaccg cgcgcaacat ggaaccgggc atgtatgcct caaaccggcc gtttatcaac   13560
cgcctaatgg actacttgca tcgcgcgcc gccgtgaacc ccgagtattt caccaatgcc   13620
atcttgaacc cgcactggct accgcccct ggtttctaca ccgggggatt cgaggtgccc   13680
gagggtaacg atggattcct ctgggacgac atagacgaca gcgtgttttc cccgcaaccg   13740
cagaccctgc tagagttgca acagcgcgag caggcagagg cggcgctgcg aaaggaaagc   13800
ttccgcaggc caagcagctt gtccgatcta ggcgctgcgg ccccgcggtc agatgctagt   13860
agcccatttc caagcttgat agggtctctt accagcactc gcaccacccg cccgcgcctg   13920
ctgggcgagg aggagtacct aaacaactcg ctgctgcagc cgcagcgcga aaaaaacctg   13980
cctccggcat ttcccaacaa cgggatagag agcctagtgg acaagatgag tagatggaag   14040
acgtacgcgc aggagcacag ggacgtgcca ggcccgcgcc cgcccacccg tcgtcaaagg   14100
cacgaccgtc agcggggtct ggtgtgggag gacgatgact cggcagacga cagcagcgtc   14160
ctggatttgg gagggagtgg caacccgttt gcgcaccttc gccccaggct ggggagaatg   14220
ttttaaaaaa aaaaaagcat gatgcaaaat aaaaaactca ccaaggccat ggcaccgagc   14280
gttggttttc ttgtattccc cttagtatgc ggcgcgcggc gatgtatgag gaaggtcctc   14340
ctccctccta cgagagtgtg gtgagcgcgg cgccagtggc ggcggcgctg ggttctccct   14400
tcgatgctcc cctggacccg ccgtttgtgc ctccgcggta cctgcggcct accgggggga   14460
gaaacagcat ccgttactct gagttggcac ccctattcga caccaccgt gtgtacctgg   14520 tggacaacaa gtcaacggat gtggcatccc tgaactacca gaacgaccac agcaactttc   14580
tgaccacggt cattcaaaac aatgactaca gcccggggga ggcaagcaca cagaccatca   14640
atcttgacga ccggtcgcac tggggcgcg acctgaaaac catcctgcat accaacatgc   14700
caaatgtgaa cgagttcatg tttaccaata agtttaaggc gcgggtgatg gtgtcgcgct   14760
tgcctactaa ggacaatcag gtggagctga atacgagtg ggtggagttc acgctgcccg   14820
agggcaacta ctccgagacc atgaccatag accttatgaa caacgcgatc gtggagcact   14880
acttgaaagt gggcagacag aacggggttc tggaaagcga catcggggta agtttgaca   14940 cccgcaactt cagactgggg tttgaccccg tcactggtct tgtcatgcct ggggtatata   15000
caaacgaagc cttccatcca gacatcattt tgctgccagg atgcggggtg gacttcaccc   15060
acagccgcct gagcaacttg ttgggcatcc gcaagcggca acccttccag gagggcttta   15120
ggatcaccta cgatgatctg gagggtggta acattcccgc actgttggat gtggacgcct   15180
accaggcgag cttgaaagat gacaccgaac agggcggggg tggcgcaggc ggcagcaaca   15240
```

```
gcagtggcag cggcgcggaa gagaactcca acgcggcagc cgcggcaatg cagccggtgg   15300
aggacatgaa cgatcatgcc attcgcggcg acacctttgc cacacgggct gaggagaagc   15360
gcgctgaggc cgaagcagcg gccgaagctg ccgcccccgc tgcgcaaccc gaggtcgaga   15420
agcctcagaa gaaaccggtg atcaaacccc tgacagagga cagcaagaaa cgcagttaca   15480
acctaataag caatgacagc accttcaccc agtaccgcag ctggtacctt gcatacaact   15540
acggcgaccc tcagaccgga atccgctcat ggaccctgct ttgcactcct gacgtaacct   15600
gcggctcgga gcaggtctac tggtcgttgc cagacatgat gcaagacccc gtgaccttcc   15660
gctccacgcg ccagatcagc aactttccgg tggtgggcgc cgagctgttg cccgtgcact   15720
ccaagagctt ctacaacgac caggccgtct actcccaact catccgccag tttacctctc   15780
tgacccacgt gttcaatcgc tttcccgaga accagatttt ggcgcgcccg ccagccccca   15840
ccatcaccac cgtcagtgaa aacgttcctg ctctcacaga tcacgggacg ctaccgctgc   15900
gcaacagcat cggaggagtc cagcgagtga ccattactga cgccagacgc cgcacctgcc   15960
cctacgttta caaggccctg gcatagtct cgccgcgcgt cctatcgagc cgcactttt   16020 gagcaagcat gtccatcctt atatcgccca gcaataacac aggctgggc ctgcgcttcc   16080 caagcaagat gtttggcggg gccaagaagc gctccgacca cacccagtg cgcgtgcgcg   16140 ggcactaccg cgcgccctgg ggcgcgcaca aacgcggccg cactgggcgc accaccgtcg   16200
atgacgccat cgacgcggtg gtggaggagg cgcgcaacta cacgcccacg ccgccaccag   16260
tgtccacagt ggacgcggcc attcagaccg tggtgcgcgg agcccggcgc tatgctaaaa   16320
tgaagagacg gcggaggcgc gtagcacgtc gccaccgccg ccgacccggc actgccgccc   16380
aacgcgcggc ggcggccctg cttaaccgcg cacgtcgcac cggccgacgg gcggccatgc   16440
gggccgctcg aaggctggcc gcgggtattg tcactgtgcc ccccaggtcc aggcgacgag   16500
cggccgccgc agcagccgcg gccattagtg ctatgactca gggtcgcagg ggcaacgtgt   16560
attgggtgcg cgactcggtt agcggcctgc gcgtgcccgt gcgcacccgc cccccgcgca   16620
actagattgc aagaaaaaac tacttagact cgtactgttg tatgtatcca gcggcggcgg   16680
cgcgcaacga agctatgtcc aagcgcaaaa tcaaagaaga gatgctccag gtcatcgcgc   16740
cggagatcta tggcccccg aagaaggaag agcaggatta caagcccga aagctaaagc   16800 gggtcaaaaa gaaaaagaaa gatgatgatg atgaacttga cgacgaggtg gaactgctgc   16860
acgctaccgc gcccaggcga cgggtacagt ggaaaggtcg acgcgtaaaa cgtgttttgc   16920
gacccggcac caccgtagtc tttacgcccg gtgagcgctc caccgcacc tacaagcgcg   16980 tgtatgatga ggtgtacggc gacgaggacc tgcttgagca ggccaacgag cgcctcgggg   17040
agtttgccta cggaaagcgg cataaggaca tgctggcgtt ccgctggac gagggcaacc   17100 caacacctag cctaaagccc gtaacactgc agcaggtgct gccgcgcgtt gcaccgtccg   17160
aagaaaagcg cggcctaaag cgcgagtctg gtgacttggc acccaccgtg cagctgatgg   17220
tacccaagcg ccagcgactg gaagatgtct tggaaaaaat gaccgtggaa cctgggctgg   17280
agcccgaggt ccgcgtgcgg ccaatcaagc aggtggcgcc gggactgggc gtgcagaccg   17340
tggacgttca gatacccact accagtagca ccagtattgc caccgccaca gagggcatgg   17400
agacacaaac gtccccggtt gcctcagcgg tggcggatgc cgcggtgcag gcggtcgctg   17460
cggccgcgtc caagacctct acggaggtgc aaacggaccc gtggatgttt cgcgtttcag   17520
ccccccggcg cccgcgcggt tcgaggaagt acggcgccgc cagcgcgcta ctgcccgaat   17580
```

```
atgccctaca tccttccatt gcgcctaccc ccggctatcg tggctacacc taccgcccca   17640
gaagacgagc aactacccga cgccgaacca ccactggaac ccgccgccgc cgtcgccgtc   17700
gccagcccgt gctggccccg atttccgtgc gcagggtggc tcgcgaagga ggcaggaccc   17760
tggtgctgcc aacagcgcgc taccacccca gcatcgttta aaagccggtc tttgtggttc   17820
ttgcagatat ggccctcacc tgccgcctcc gtttcccggt gccgggattc cgaggaagaa   17880
tgcaccgtag gaggggcatg gccggccacg gcctgacggg cggcatgcgt cgtgcgcacc   17940
accggcggcg gcgcgcgtcg caccgtcgca tgcgcggcgg tatcctgccc ctccttattc   18000
cactgatcgc cgcggcgatt ggcgccgtgc ccggaattgc atccgtggcc ttgcaggcgc   18060
agagacactg attaaaaaca agttgcatgt ggaaaaatca aaataaaaag tctggactct   18120
cacgctcgct tggtcctgta actattttgt agaatggaag catcaacttt gcgtctctg   18180 gccccgcgac acggctcgcg cccgttcatg ggaaactggc aagatatcgg caccagcaat   18240
atgagcggtg gcgccttcag ctggggctcg ctgtggagcg gcattaaaaa tttcggttcc   18300
accgttaaga actatggcag caaggcctgg aacagcagca caggcagat gctgagggat   18360 aagttgaaag agcaaaattt ccaacaaaag gtggtagatg gcctggcctc tggcattagc   18420
ggggtggtgg acctggccaa ccaggcagtg caaaataaga ttaacagtaa gcttgatccc   18480
cgccctcccg tagaggagcc tccaccggcc gtggagacag tgtctccaga ggggcgtggc   18540
gaaaagcgtc cgcgccccga cagggaagaa actctggtga cgcaaataga cgagcctccc   18600
tcgtacgagg aggcactaaa gcaaggcctg cccaccaccc gtcccatcgc gcccatggct   18660
accggagtgc tgggccagca cacacccgta acgctggacc tgcctccccc cgccgacacc   18720
cagcagaaac ctgtgctgcc aggcccgacc gccgttgttg taacccgtcc tagccgcgcg   18780
tccctgcgcc gcgccgccag cggtccgcga tcgttgcggc ccgtagccag tggcaactgg   18840
caaagcacac tgaacagcat cgtgggtctg ggggtgcaat ccctgaagcg ccgacgatgc   18900
ttctgaatag ctaacgtgtc gtatgtgtgt catgtatgcg tccatgtcgc cgccagagga   18960
gctgctgagc cgccgcgcgc ccgctttcca agatggctac cccttcgatg atgccgcagt   19020
ggtcttacat gcacatctcg ggccaggacg cctcggagta cctgagcccc gggctggtgc   19080
agtttgcccg cgccaccgag acgtacttca gcctgaataa caagtttaga accccacgg   19140 tggcgcctac gcacgacgtg accacagacc ggtcccagcg tttgacgctg cggttcatcc   19200
ctgtggaccg tgaggatact gcgtactcgt acaaggcgcg gttcaccta gctgtgggtg   19260 ataaccgtgt gctggacatg gcttccacgt actttgacat ccgcggcgtg ctggacaggg   19320
gccctacttt taagccctac tctggcactg cctacaacgc cctggctccc aagggtgccc   19380
caaatccttg cgaatgggat gaagctgcta ctgctcttga aataaaccta gaagaagagg   19440
acgatgacaa cgaagacgaa gtagacgagc aagctgagca gcaaaaaact cacgtatttg   19500
ggcaggcgcc ttattctggt ataaatatta caaggagggg tattcaaata ggtgtcgaag   19560
gtcaaacacc taaatatgcc gataaaacat ttcaacctga acctcaaata ggagaatctc   19620
agtggtacga aactgaaatt aatcatgcag ctgggagagt ccttaaaaag actaccccaa   19680
tgaaaccatg ttacggttca tatgcaaaac ccacaaatga aatggagggg caaggcattc   19740
ttgtaaagca acaaaatgga agctagaaa gtcaagtgga atgcaatttt ttctcaacta   19800
ctgaggcgac cgcaggcaat ggtgataact tgactcctaa agtggtattg tacagtgaag   19860
atgtagatat agaaacccca gacactcata tttcttacat gcccactatt aaggaaggta   19920
actcacgaga actaatgggc caacaatcta tgcccaacag gcctaattac attgctttta   19980
```

```
gggacaattt tattggtcta atgtattaca acagcacggg taatatgggt gttctggcgg    20040
gccaagcatc gcagttgaat gctgttgtag atttgcaaga cagaaacaca gagctttcat    20100
accagctttt gcttgattcc attggtgata gaaccaggta cttttctatg tggaatcagg    20160
ctgttgacag ctatgatcca gatgttagaa ttattgaaaa tcatggaact gaagatgaac    20220
ttccaaatta ctgctttcca ctgggaggtg tgattaatac agagactctt accaaggtaa    20280
aacctaaaac aggtcaggaa aatggatggg aaaaagatgc tacagaattt tcagataaaa    20340
atgaaataag agttggaaat aattttgcca tggaaatcaa tctaaatgcc aacctgtgga    20400
gaaatttcct gtactccaac atagcgctgt atttgcccga caagctaaag tacagtcctt    20460
ccaacgtaaa aatttctgat aacccaaaca cctacgacta catgaacaag cgagtggtgg    20520
ctcccgggtt agtggactgc tacattaacc ttggagcacg ctggtccctt gactatatgg    20580
acaacgtcaa cccatttaac caccaccgca atgctggcct gcgctaccgc tcaatgttgc    20640
tgggcaatgg tcgctatgtg cccttccaca tccaggtgcc tcagaagttc tttgccatta    20700
aaaacctcct tctcctgccg ggctcataca cctacgagtg gaacttcagg aaggatgtta    20760
acatggttct gcagagctcc ctaggaaatg acctaagggt tgacggagcc agcattaagt    20820 tgatagcat ttgcctttac gccaccttct tccccatggc ccacaacacc gcctccacgc    20880
ttgaggccat gctagaaac gacaccaacg accagtcctt taacgactat ctctccgccg    20940
ccaacatgct ctaccctata cccgccaacg ctaccaacgt gcccatatcc atcccctccc    21000
gcaactgggc ggctttccgc ggctgggcct tcacgcgcct taagactaag gaaaccccat    21060
cactgggctc gggctacgac ccttattaca cctactctgg ctctataccc tacctagatg    21120 gaaccttta cctcaaccac accttaaga aggctgccat tacctttgac tcttctgtca    21180
gctggcctgg caatgaccgc ctgcttaccc ccaacgagtt tgaaattaag cgctcagttg    21240
acggggaggg ttacaacgtt gcccagtgta acatgaccaa agactggttc ctggtacaaa    21300
tgctagctaa ctataacatt ggctaccagg gcttctatat cccagagagc tacaaggacc    21360
gcatgtactc cttctttaga aacttccagc ccatgagccg tcaggtggtg gatgatacta    21420
aatacaagga ctaccaacag gtgggcatcc tacaccaaca caacaactct ggatttgttg    21480
gctaccttgc ccccaccatg cgcgaaggac aggcctaccc tgctaacttc ccctatccgc    21540
ttataggcaa gaccgcagtt gacagcatta cccagaaaaa gtttcttgc gatcgcaccc    21600 tttggcgcat cccattctcc agtaacttta tgtccatggg cgcactcaca gacctgggcc    21660
aaaaccttct ctacgccaac tccgcccact ccctagacat gacttttgag gtggatccca    21720
tggacgagcc caccccttctt tatgttttgt ttgaagtctt tgacaaggtc cgtgtgcacc    21780
agccgcaccg cggcgtcatc gaaaccgtgt acctgcgcac gcccttctcg gccggcaacg    21840
ccacaacata aagaagcaag caacatcaac aacagctgcc gccatgggct ccagtgagca    21900
ggaactgaaa gccattgtca agatctctgg ttgtgggcca tattttttgg gcacctatga    21960
caagcgcttt ccaggctttg tttctccaca caagctcgcc tgcgccatag tcaatacggc    22020
cggtcgcgag actgggggcg tacactggat ggcctttgcc tggaaccgc actcaaaaac    22080 atgctacctc tttgagccct ttggcttttc tgaccagcga ctcaagcagg tttaccagtt    22140
tgagtacgag tcactcctgc gccgtagcgc cattgcttct tcccccgacc gctgtataac    22200
gctggaaaag tccacccaaa gcgtacaggg gcccaactcg gccgcctgtg gactattctg    22260
ctgcatgttt ctccacgcct tgccaactg gccccaaact cccatggatc acaacccac    22320
```

```
catgaacctt attaccgggg tacccaactc catgctcaac agtccccagg tacagcccac      22380
cctgcgtcgc aaccaggaac agctctacag cttcctggag cgccactcgc cctacttccg      22440
cagccacagt gcgcagatta ggagcgccac ttcttttgt cacttgaaaa acatgtaaaa       22500
ataatgtact agagacactt tcaataaagg caaatgcttt tatttgtaca ctctcgggtg      22560
attatttacc cccacccttg ccgtctgcgc cgtttaaaaa tcaaggggt tctgccgcgc       22620 atcgctatgc gccactggca gggacacgtt gcgatactgg tgtttagtgc tccacttaaa     22680
ctcaggcaca accatccgcg gcagctcggt gaagttttca ctccacaggc tgcgcaccat      22740
caccaacgcg tttagcaggt cgggcgccga tatcttgaag tcgcagttgg ggcctccgcc      22800
ctgcgcgcgc gagttgcgat acacagggtt gcagcactgg aacactatca gcgccgggtg     22860
gtgcacgctg gccagcacgc tcttgtcgga gatcagatcc gcgtccaggt cctccgcgtt     22920
gctcagggcg aacggagtca actttggtag ctgccttccc aaaaagggcg cgtgcccagg     22980
ctttgagttg cactcgcacc gtagtggcat caaaaggtga ccgtgccgg tctgggcgtt     23040 aggatacagc gcctgcataa aagccttgat ctgcttaaaa gccacctgag cctttgcgcc    23100
ttcagagaag aacatgccgc aagacttgcc ggaaaactga ttggccggac aggccgcgtc    23160
gtgcacgcag caccttgcgt cggtgttgga gatctgcacc acatttcggc cccaccggtt    23220
cttcacgatc ttggccttgc tagactgctc cttcagcgcg cgctgcccgt tttcgctcgt    23280
cacatccatt tcaatcacgt gctccttatt tatcataatg cttccgtgta gacacttaag    23340
ctcgccttcg atctcagcgc agcggtgcag ccacaacgcg cagcccgtgg gctcgtgatg    23400
cttgtaggtc acctctgcaa acgactgcag gtacgcctgc aggaatcgcc ccatcatcgt    23460
cacaaaggtc ttgttgctgg tgaaggtcag ctgcaacccg cggtgctcct cgttcagcca    23520
ggtcttgcat acggccgcca gagcttccac ttggtcaggc agtagtttga agttcgcctt    23580
tagatcgtta tccacgtggt acttgtccat cagcgcgcgc gcagcctcca tgcccttctc    23640
ccacgcagac acgatcggca cactcagcgg gttcatcacc gtaatttcac tttccgcttc    23700
gctgggctct tcctcttcct cttgcgtccg cataccacgc gccactgggt cgtcttcatt    23760
cagccgccgc actgtgcgct tacctccttt gccatgcttg attagcaccg gtgggttgct    23820
gaaacccacc atttgtagcg ccacatcttc tctttcttcc tcgctgtcca cgattacctc    23880
tggtgatggc gggcgctcgg gcttgggaga agggcgcttc tttttcttct tgggcgcaat    23940
ggccaaatcc gccgccgagg tcgatggccg cgggctgggt gtgcgcggca ccagcgcgtc    24000
ttgtgatgag tcttcctcgt cctcggactc gatacgccgc ctcatccgct tttttggggg    24060
cgcccgggga ggcggcggcg acggggacgg ggacgacacg tcctccatgg ttggggggacg   24120 tcgcgccgca ccgcgtccgc gctcgggggt ggtttcgcgc tgctcctctt cccgactggc    24180
catttccttc tcctataggc agaaaaagat catggagtca gtcgagaaga aggacagcct    24240
aaccgccccc tctgagttcg ccaccaccgc ctccaccgat gccgcaacg cgcctaccac     24300 cttccccgtc gaggcacccc cgcttgagga ggaggaagtg attatcgagc aggacccagg    24360
ttttgtaagc gaagacgacg aggaccgctc agtaccaaca gaggataaaa agcaagacca    24420
ggacaacgca gaggcaaacg aggaacaagt cgggcggggg gacgaaaggc atggcgacta    24480
cctagatgtg ggagacgacg tgctgttgaa gcatctgcag cgccagtgcg ccattatctg    24540
cgacgcgttg caagagcgca gcgatgtgcc cctcgccata gcggatgtca gccttgccta    24600
cgaacgccac ctattctcac cgcgcgtacc ccccaaacgc caagaaaacg gcacatgcga    24660
gcccaacccg cgcctcaact tctaccccgt atttgccgtg ccagaggtgc ttgccaccta    24720
```

```
tcacatcttt ttccaaaact gcaagatacc cctatcctgc cgtgccaacc gcagccgagc    24780
ggacaagcag ctggccttgc ggcagggcgc tgtcatacct gatatcgcct cgctcaacga    24840
agtgccaaaa atctttgagg gtcttggacg cgacgagaag cgcgcggcaa acgctctgca    24900
acaggaaaac agcgaaaatg aaagtcactc tggagtgttg gtggaactcg agggtgacaa    24960
cgcgcgccta gccgtactaa aacgcagcat cgaggtcacc cactttgcct acccggcact    25020
taacctaccc cccaaggtca tgagcacagt catgagtgag ctgatcgtgc gccgtgcgca    25080 gccctggag agggatgcaa atttgcaaga acaaacagag gagggcctac ccgcagttgg    25140
cgacgagcag ctagcgcgct ggcttcaaac gcgcgagcct gccgacttgg aggagcgacg    25200
caaactaatg atggccgcag tgctcgttac cgtggagctt gagtgcatgc agcggttctt    25260
tgctgacccg gagatgcagc gcaagctaga ggaaacattg cactacacct tcgacaggg    25320 ctacgtacgc caggcctgca agatctccaa cgtggagctc tgcaacctgg tctcctacct    25380
tggaattttg cacgaaaacc gccttgggca aaacgtgctt cattccacgc tcaagggcga    25440
ggcgcgccgc gactacgtcc gcgactgcgt ttacttattt ctatgctaca cctggcagac    25500
ggccatgggc gtttggcagc agtgcttgga ggagtgcaac ctcaaggagc tgcagaaact    25560
gctaaagcaa aacttgaagg acctatggac ggccttcaac gagcgctccg tggccgcgca    25620
cctggcggac atcatttttcc ccgaacgcct gcttaaaacc ctgcaacagg gtctgccaga    25680
cttcaccagt caaagcatgt tgcagaactt taggaacttt atcctagagc gctcaggaat    25740
cttgcccgcc acctgctgtg cacttcctag cgactttgtg cccattaagt accgcgaatg    25800
ccctccgccg ctttggggcc actgctacct tctgcagcta gccaactacc ttgcctacca    25860
ctctgacata atggaagacg tgagcggtga cggtctactg gagtgtcact gtcgctgcaa    25920
cctatgcacc ccgcaccgct ccctggtttg caattcgcag ctgcttaacg aaagtcaaat    25980
tatcggtacc tttgagctgc agggtccctc gcctgacgaa aagtccgcgg ctccgggg tt    26040 gaaactcact ccggggctgt ggacgtcggc ttaccttcgc aaatttgtac ctgaggacta    26100
ccacgcccac gagattaggt tctacgaaga ccaatcccgc ccgccaaatg cggagcttac    26160
cgcctgcgtc attacccagg gccacattct tggccaattg caagccatca acaaagcccg    26220
ccaagagttt ctgctacgaa agggacgggg ggtttacttg gaccccccagt ccggcgagga    26280 gctcaacccca atccccccgc cgccgcagcc ctatcagcag cagccgcggg cccttgcttc    26340
ccaggatggc acccaaaaag aagctgcagc tgccgccgcc acccacggac gaggaggaat    26400
actgggacag tcaggcagag gaggttttgg acgaggagga ggaggacatg atggaagact    26460
gggagagcct agacgaggaa gcttccgagg tcgaagaggt gtcagacgaa acaccgtcac    26520
cctcggtcgc attcccctcg ccggcgcccc agaaatcggc aaccggttcc agcatggcta    26580
caacctccgc tcctcaggcg ccgccggcac tgcccgttcg ccgacccaac cgtagatggg    26640
acaccactgg aaccagggcc ggtaagtcca agcagccgcc gccgttagcc caagagcaac    26700
aacagcgcca aggctaccgc tcatggcgcg ggcacaagaa cgccatagtt gcttgcttgc    26760
aagactgtgg gggcaacatc tccttcgccc gccgctttct tctctaccat acgcgcgtgg    26820
ccttcccccg taacatcctg cattactacc gtcatctcta cagcccatac tgcaccggcg    26880
gcagcggcag cggcagcaac agcagcggcc acacagaagc aaaggcgacc ggatagcaag    26940
actctgacaa agcccaagaa atccacagcg cggcagcag caggaggagg agcgctgcgt    27000
ctggcgccca acgaacccgt atcgacccgc gagcttagaa acaggatttt tcccactctg    27060
```

```
tatgctatat ttcaacagag caggggccaa gaacaagagc tgaaaataaa aaacaggtct    27120
ctgcgatccc tcacccgcag ctgcctgtat cacaaaagcg aagatcagct tcggcgcacg    27180
ctggaagacg cggaggctct cttcagtaaa tactgcgcgc tgactcttaa ggactagttt    27240
cgcgcccttt ctcaaattta agcgcgaaaa ctacgtcatc tccagcggcc acacccggcg    27300
ccagcacctg tcgtcagcgc cattatgagc aaggaaattc ccacgcccta catgtggagt    27360
taccagccac aaatgggact tgcggctgga gctgcccaag actactcaac ccgaataaac    27420
tacatgagcg cgggacccca catgatatcc cgggtcaacg gaatccgcgc ccaccgaaac    27480
cgaattctct tggaacaggc ggctattacc accacacctc gtaataacct taatccccgt    27540
agttggcccg ctgccctggt gtaccaggaa agtcccgctc ccaccactgt ggtacttccc    27600
agagacgccc aggccgaagt tcagatgact aactcagggg cgcagcttgc gggcggcttt    27660
cgtcacaggg tgcggtcgcc cgggcagggt ataactcacc tgacaatcag agggcgaggt    27720
attcagctca acgacgagtc ggtgagctcc tcgcttggtc tccgtccgga cgggacattt    27780
cagatcggcg gcgccggccg tccttcattc acgcctcgtc aggcaatcct aactctgcag    27840
acctcgtcct ctgagccgcg ctctggaggc attggaactc tgcaatttat tgaggagttt    27900
gtgccatcgg tctactttaa ccccttctcg ggacctcccg gccactatcc ggatcaattt    27960
attcctaact ttgacgcggt aaaggactcg gcggacggct acgactgaat gttaagtgga    28020
gaggcagagc aactgcgcct gaaacacctg gtccactgtc gccgccacaa gtgctttgcc    28080
cgcgactccg gtgagttttg ctactttgaa ttgcccgagg atcatatcga gggcccggcg    28140
cacgcgtcc ggcttaccgc ccagggagag cttgcccgta gcctgattcg ggagtttacc    28200
cagcgccccc tgctagttga gcgggacagg ggaccctgtg ttctcactgt gatttgcaac    28260
tgtcctaacc ttggattaca tcaagatctt tgttgccatc tctgtgctga gtataataaa    28320
tacagaaatt aaaatatact ggggctccta tcgccatcct gtaaacgcca ccgtcttcac    28380
ccgcccaagc aaaccaaggc gaaccttacc tggtactttt aacatctctc cctctgtgat    28440
ttacaacagt ttcaacccag acggagtgag tctacgagag aacctctccg agctcagcta    28500
ctccatcaga aaaaacacca ccctccttac ctgccgggaa cgtacgagtg cgtcaccggc    28560
cgctgcacca cacctaccgc ctgaccgtaa accagacttt ttccggacag acctcaataa    28620
ctctgtttac cagaacagga ggtgagctta gaaaaccctt agggtattag gccaaaggcg    28680
cagctactgt ggggtttatg aacaattcaa gcaactctac gggctattct aattcaggtt    28740
tctctagaat cggggttggg gttattctct gtcttgtgat tctctttatt cttatactaa    28800
cgcttctctg cctaaggctc gccgcctgct gtgtgcacat ttgcatttat tgtcagcttt    28860
ttaaacgctg gggtcgccac ccaagatgat taggtacata atcctaggtt tactcaccct    28920
tgcgtcagcc cacggtacca cccaaaaggt ggatttaag gagccagcct gtaatgttac    28980
attcgcagct gaagctaatg agtgcaccac tcttataaaa tgcaccacag aacatgaaaa    29040
gctgcttatt cgccacaaaa acaaaattgg caagtatgct gtttatgcta tttggcagcc    29100
aggtgacact acagagtata atgttacagt tttccagggt aaaagtcata aaactttat    29160
gtatactttt ccattttatg aaatgtgcga cattaccatg tacatgagca acagtataa    29220
gttgtggccc ccacaaaatt gtgtggaaaa cactggcact ttctgctgca ctgctatgct    29280
aattacagtg ctcgctttgg tctgtaccct actctatatt aaatacaaaa gcagacgcag    29340
ctttattgag gaaagaaaa tgccttaatt tactaagtta caaagctaat gtcaccacta    29400
actgctttac tcgctgcttg caaaacaaat tcaaaaagtt agcattataa ttagaatagg    29460
```

```
atttaaaccc cccggtcatt tcctgctcaa taccattccc ctgaacaatt gactctatgt    29520
gggatatgct ccagcgctac aaccttgaag tcaggcttcc tggatgtcag catctgactt    29580
tggccagcac ctgtcccgcg gatttgttcc agtccaacta cagcgaccca ccctaacaga    29640
gatgaccaac acaaccaacg cggccgccgc taccggactt acatctacca caaatacacc    29700
ccaagtttct gcctttgtca ataactggga taacttgggc atgtggtggt tctccatagc    29760
gcttatgttt gtatgcctta ttattatgtg gctcatctgc tgcctaaagc gcaaacgcgc    29820
ccgaccaccc atctatagtc ccatcattgt gctacaccca aacaatgatg gaatccatag    29880
attggacgga ctgaaacaca tgttcttttc tcttacagta tgattaaatg agacatgatt    29940
cctcgagttt ttatattact gaccttgtt gcgctttttt gtgcgtgctc cacattggct    30000
gcggtttctc acatcgaagt agactgcatt ccagccttca cagtctattt gctttacgga    30060
tttgtcaccc tcacgctcat ctgcagcctc atcactgtgg tcatcgcctt tatccagtgc    30120
attgactggg tctgtgtgcg ctttgcatat ctcagacacc atccccagta cagggacagg    30180
actatagctg agcttcttag aattcttttaa ttatgaaatt tactgtgact tttctgctga    30240
ttatttgcac cctatctgcg tttttgttccc cgacctccaa gcctcaaaga catatatcat    30300
gcagattcac tcgtatatgg aatattccaa gttgctacaa tgaaaaaagc gatctttccg    30360
aagcctggtt atatgcaatc atctctgtta tggtgttctg cagtaccatc ttagccctag    30420
ctatatatcc ctaccttgac attggctgga aacgaataga tgccatgaac cacccaactt    30480
tccccgcgcc cgctatgctt ccactgcaac aagttgttgc cggcggcttt gtcccagcca    30540
atcagcctcg ccccacttct cccacccca ctgaaatcag ctactttaat ctaacaggag    30600
gagatgactg acaccctaga tctagaaatg gacggaatta ttacagagca gcgcctgcta    30660
gaaagacgca gggcagcggc cgagcaacag cgcatgaatc aagagctcca agacatggtt    30720
aacttgcacc agtgcaaaag gggtatcttt tgtctggtaa agcaggccaa agtcacctac    30780
gacagtaata ccaccggaca ccgccttagc tacaagttgc caaccaagcg tcagaaattg    30840
gtggtcatgg tgggagaaaa gcccattacc ataactcagc actcggtaga aaccgaaggc    30900
tgcattcact caccttgtca aggacctgag gatctctgca cccttattaa gaccctgtgc    30960
ggtctcaaag atcttattcc ctttaactaa taaaaaaaaa taataaagca tcacttactt    31020
aaaatcagtt agcaaatttc tgtccagttt attcagcagc acctccttgc cctcctccca    31080
gctctggtat tgcagcttcc tcctggctgc aaactttctc cacaatctaa atggaatgtc    31140
agtttcctcc tgttcctgtc catccgcacc cactatcttc atgttgttgc agatgaagcg    31200
cgcaagaccg tctgaagata ccttcaaccc cgtgtatcca tatgacacgg aaaccggtcc    31260
tccaactgtg cctttttctta ctcctcccctt tgtatccccc aatgggtttc aagagagtcc    31320
ccctggggta ctctctttgc gcctatccga acctctagtt acctccaatg gcatgcttgc    31380
gctcaaaatg ggcaacggcc tctctctgga cgaggccggc aaccttacct cccaaaatgt    31440
aaccactgtg agcccacctc tccgaggaga caagtcaaac ataaacctgg aaatatctgc    31500 accccctcaca gttacctcag aagccctaac tgtggctgcc gccgcacctc taatggtcgc    31560
gggcaacaca ctcaccatgc aatcacaggc cccgctaacc gtgcacgact ccaaacttag    31620
cattgccacc caaggacccc tcacagtgtc agaaggaaag ctagccctgc aaacatcagg    31680 cccccctcacc accaccgata gcagtaccct tactatcact gcctcacccc ctctaactac    31740
tgccactggt agcttgggca ttgacttgaa agagcccatt tatacacaaa atggaaaact    31800
```

```
aggactaaag tacggggctc ctttgcatgt aacagacgac ctaaacactt tgaccgtagc    31860
aactggtcca ggtgtgacta ttaataatac ttccttgcaa actaaagtta ctggagcctt    31920
gggttttgat tcacaaggca atatgcaact taatgtagca ggaggactaa ggattgattc    31980
tcaaaacaga cgccttatac ttgatgttag ttatccgttt gatgctcaaa accaactaaa    32040
tctaagacta ggacagggcc ctcttttat aaactcagcc cacaacttgg atattaacta    32100
caacaaaggc ctttacttgt ttacagcttc aaacaattcc aaaaagcttg aggttaacct    32160
aagcactgcc aaggggttga tgtttgacgc tacagccata gccattaatg caggagatgg    32220
gcttgaattt ggttcaccta atgcaccaaa cacaaatccc ctcaaaacaa aaattggcca    32280
tggcctagaa tttgattcaa acaaggctat ggttcctaaa ctaggaactg gccttagttt    32340
tgacagcaca ggtgccatta cagtaggaaa caaaaataat gataagctaa ctttgtggac    32400
cacaccagct ccatctccta actgtagact aaatgcagag aaagatgcta aactcacttt    32460
ggtcttaaca aaatgtggca gtcaaatact tgctacagtt tcagttttgg ctgttaaagg    32520
cagtttggct ccaatatctg gaacagttca aagtgctcat cttattataa gatttgacga    32580
aaatggagtg ctactaaaca attccttcct ggacccagaa tattggaact ttagaaatgg    32640
agatcttact gaaggcacag cctatacaaa cgctgttgga tttatgccta acctatcagc    32700
ttatccaaaa tctcacggta aaactgccaa aagtaacatt gtcagtcaag tttacttaaa    32760
cggagacaaa actaaacctg taacactaac cattacacta aacggtacac aggaaacagg    32820
agacacaact ccaagtgcat actctatgtc attttcatgg gactggtctg ccacaactat    32880
cattaatgaa atatttgcca catcctctta cactttttca tacattgccc aagaataaag    32940
aatcgtttgt gttatgtttc aacgtgttta ttttcaatt gcagaaaatt tcaagtcatt    33000
tttcattcag tagtatagcc ccaccaccac atagcttata cagatcaccg taccttaatc    33060
aaactcacag aaccctagta ttcaacctgc cacctccctc ccaacacaca gagtacacag    33120 tccttctctcc ccggctggcc ttaaaaagca tcatatcatg ggtaacgac atattcttag    33180 gtgttatatt ccacacggtt tcctgtcgag ccaaacgctc atcagtgata ttaataaact    33240
ccccgggcag ctcacttaag ttcatgtcgc tgtccagctg ctgagccaca ggctgctgtc    33300
caacttgcgg ttgcttaacg ggcggcgaag gagaagtcca cgcctacatg ggggtagagt    33360
cataatcgtg catcaggata gggcggtggt gctgcagcag cgcgcgaata aactgctgcc    33420
gccgccgctc cgtcctgcag gaatacaaca tggcagtggt ctcctcagcg atgattcgca    33480
ccgcccgcag cataaggcgc cttgtcctcc gggcacagca gcgcaccctg atctcactta    33540
aatcagcaca gtaactgcag cacagcacca caatattgtt caaaatccca cagtgcaagg    33600
cgctgtatcc aaagctcatg gcggggacca cagaacccac gtggccatca taccacaagc    33660
gcaggtagat taagtggcga cccctcataa acacgctgga cataaacatt acctcttttg    33720
gcatgttgta attcaccacc tcccggtacc atataaaccct ctgattaaac atggcgccat    33780
ccaccaccat cctaaaccag ctggccaaaa cctgcccgcc ggctatacac tgcagggaac    33840
cgggactgga acaatgacag tggagagccc aggactcgta accatggatc atcatgctcg    33900
tcatgatatc aatgttggca caacacaggc acacgtgcat acacttcctc aggattacaa    33960
gctcctcccg cgttagaacc atatcccagg gaacaaccca ttcctgaatc agcgtaaatc    34020
ccacactgca gggaagacct cgcacgtaac tcacgttgtg cattgtcaaa gtgttacatt    34080
cgggcagcag cggatgatcc tccagtatgg tagcgcgggt ttctgtctca aaaggaggta    34140
gacgatccct actgtacgga gtgcgccgag acaaccgaga tcgtgttggt cgtagtgtca    34200
```

```
tgccaaatgg aacgccggac gtagtcatat ttcctgaagc aaaaccaggt gcgggcgtga   34260
caaacagatc tgcgtctccg gtctcgccgc ttagatcgct ctgtgtagta gttgtagtat   34320
atccactctc tcaaagcatc caggcgcccc ctggcttcgg gttctatgta aactccttca   34380
tgcgccgctg ccctgataac atccaccacc gcagaataag ccacacccag ccaacctaca   34440
cattcgttct gcgagtcaca cacgggagga gcgggaagag ctggaagaac catgttttttt  34500 ttttttattcc aaaagattat ccaaaacctc aaaatgaaga tctattaagt gaacgcgctc  34560
ccctccggtg gcgtggtcaa actctacagc caaagaacag ataatggcat tgtaagatg   34620 ttgcacaatg gcttccaaaa ggcaaacggc cctcacgtcc aagtggacgt aaaggctaaa   34680
cccttcaggg tgaatctcct ctataaacat tccagcacct caaccatgc ccaaataatt   34740 ctcatctcgc caccttctca atatatctct aagcaaatcc gaatattaa gtccggccat   34800 tgtaaaaatc tgctccagag cgccctccac cttcagcctc aagcagcgaa tcatgattgc   34860
aaaaattcag gttcctcaca gacctgtata agattcaaaa gcggaacatt aacaaaaata   34920
ccgcgatccc gtaggtccct tcgcagggcc agctgaacat aatcgtgcag gtctgcacgg   34980
accagcgcgg ccacttcccc gccaggaacc atgacaaaag aacccacact gattatgaca   35040
cgcatactcg gagctatgct aaccagcgta gccccgatgt aagcttgttg catgggcggc   35100
gatataaaat gcaaggtgct gctcaaaaaa tcaggcaaag cctcgcgcaa aaagaaagc   35160 acatcgtagt catgctcatg cagataaagg caggtaagct ccggaaccac cacagaaaaa   35220
gacaccattt ttctctcaaa catgtctgcg ggtttctgca taaacacaaa ataaaataac   35280
aaaaaaacat ttaaacatta gaagcctgtc ttacaacagg aaaaacaacc cttataagca   35340
taagacggac tacggccatg ccggcgtgac cgtaaaaaaa ctggtcaccg tgattaaaaa   35400
gcaccaccga cagctcctcg gtcatgtccg gagtcataat gtaagactcg gtaaacacat   35460
caggttgatt cacatcggtc agtgctaaaa agcgaccgaa atagcccggg ggaatacata   35520
cccgcaggcg tagagacaac attacagccc ccataggagg tataacaaaa ttaataggag   35580
agaaaaacac ataaacacct gaaaaaccct cctgcctagg caaaatagca ccctcccgct   35640
ccagaacaac atacagcgct tccacagcgg cagccataac agtcagcctt accagtaaaa   35700
aagaaaacct attaaaaaaa caccactcga cacggcacca gctcaatcag tcacagtgta   35760
aaaaagggcc aagtgcagag cgagtatata taggactaaa aaatgacgta acggttaaag   35820
tccacaaaaa acacccagaa aaccgcacgc gaacctacgc ccagaaacga aagccaaaaa   35880
acccacaact tcctcaaatc gtcacttccg ttttcccacg ttacgtcact tcccatttta   35940
agaaaactac aattcccaac acatactagt tactccgccc taaaacctac gtcacccgcc   36000
ccgttcccac gccccgcgcc acgtcacaaa ctccaccccc tcattatcat attggcttca   36060
atccaaaata aggtatatta ttgatgatgt                                    36090
```

<210> SEQ ID NO 4
<211> LENGTH: 36156
<212> TYPE: DNA
<213> ORGANISM: Artificial Sequence
<220> FEATURE:
<223> OTHER INFORMATION: ICOVIR15K-TD-gp100-tyr

<400> SEQUENCE: 4

```
catcatcaat aatataccctt attttggatt gaagccaata tgataatgag ggggtggagt     60
ttgtgacgtg gcgcggggcg tgggaacggg gcgggtgacg tagtagtgtg gcggaagtgt    120
```

```
gatgttgcaa gtgtggcgga acacatgtaa gcgacggatg tggcaaaagt gacgttttg      180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgtac    420
gtcggcggct cgtggctctt tcgcggcaaa aaggatttgg cgcgtaaaag tggttcgagt    480
acgtcggcgg ctcgtggctc tttcgcggca aaaggatttt ggcgcgtaaa agtggttcga    540
agtacgtcga ccacaaaccc cgcccagcgt cttgtcattg cgtcgacgc tgtacggggt     600
caaagttggc gttttattat tatagtcagc tgacgtgtag tgtatttata cccggtgagt    660
tcctcaagag gccactcttg agtgccagcg agtagagttt tctcctccga gccgctccga    720
caccgggact gaaaatgaga catattatct gccacggagg tgttattacc gaagaaatgg    780
ccgccagtct tttggaccag ctgatcgaag aggtactggc tgataatctt ccacctccta    840
gccattttga accacctacc cttcacgaac tgtatgattt agacgtgacg gcccccgaag    900
atcccaacga ggaggcggtt tcgcagattt ttcccgactc tgtaatgttg gcggtgcagg    960
aagggattga cttactcact tttccgccgg cgcccggttc tccggagccg cctcacctttt   1020
cccggcagcc cgagcagccg gagcagagag ccttgggtcc ggtttctatg ccaaaccttg    1080
taccggaggt gatcgatcca cccagtgacg acgaggatga agagggtgag gagtttgtgt    1140
tagattatgt ggagcacccc gggcacggtt gcaggtcttg tcattatcac cggaggaata    1200
cgggggaccc agatattatg tgttcgcttt gctatgagg acctgtggc atgtttgtct      1260
acagtaagtg aaaattatgg gcagtgggtg atagagtggt gggtttggtg tggtaatttt    1320
ttttttaatt tttacagttt tgtggtttaa agaattttgt attgtgattt ttttaaaagg    1380
tcctgtgtct gaacctgagc ctgagcccga gccagaaccg gagcctgcaa gacctacccg    1440
ccgtcctaaa atggcgcctg ctatcctgag acgcccgaca tcacctgtgt ccagagaatg    1500
caatagtagt acggatagct gtgactccgg tccttctaac acacctcctg agatacaccc    1560
ggtggtcccg ctgtgcccca ttaaaccagt tgccgtgaga gttggtgggc gtcgccaggc    1620
tgtggaatgt atcgaggact tgcttaacga gcctgggcaa cctttggact tgagctgtaa    1680
acgccccagg ccataaggtg taaacctgtg attgcgtgtg tggttaacgc ctttgtttgc    1740
tgaatgagtt gatgtaagtt taataaaggg tgagataatg tttaacttgc atggcgtgtt    1800
aaatggggcg gggcttaaag ggtatataat gcgccgtggg ctaatcttgg ttacatctga    1860
cctcatggag gcttgggagt gttttggaaga ttttctgct gtgcgtaact tgctggaaca    1920
gagctctaac agtacctctt ggttttggag gtttctgtgg ggctcatccc aggcaaagtt    1980
agtctgcaga attaaggagg attacaagtg ggaatttgaa gagcttttga aatcctgtgg    2040
tgagctgttt gattctttga atctgggtca ccaggcgctt ttccaagaga aggtcatcaa    2100
gactttggat ttttccacac cggggcgcgc tgcggctgct gttgcttttt tgagttttat    2160
aaaggataaa tggagcgaag aaacccatct gagcgggggg tacctgctgg attttctggc    2220
catgcatctg tggagagcgg ttgtgagaca caagaatcgc ctgctactgt tgtcttccgt    2280
ccgcccggcg ataataccga cggaggagca gcagcagcag caggaggaag ccaggcggcg    2340
gcggcaggag cagagcccat ggaacccgag agccggcctg gaccctcggg aatgaatgtt    2400
gtacaggtgg ctgaactgta tccagaactg agacgcattt tgacaattac agaggatggg    2460
caggggctaa aggggtaaa gagggagcgg ggggcttgtg aggctacaga ggaggctagg    2520
```

```
aatctagctt ttagcttaat gaccagacac cgtcctgagt gtattacttt tcaacagatc    2580
aaggataatt gcgctaatga gcttgatctg ctggcgcaga agtattccat agagcagctg    2640
accacttact ggctgcagcc aggggatgat tttgaggagg ctattagggt atatgcaaag    2700
gtggcactta ggccagattg caagtacaag atcagcaaac ttgtaaatat caggaattgt    2760
tgctacattt ctgggaacgg ggccgaggtg gagatagata cggaggatag ggtggccttt    2820
agatgtagca tgataaatat gtggccgggg gtgcttggca tggacggggt ggttattatg    2880
aatgtaaggt ttactggccc caattttagc ggtacggttt cctggccaa taccaacctt     2940 atcctacacg gtgtaagctt ctatgggttt aacaatacct gtgtggaagc ctggaccgat    3000
gtaagggttc ggggctgtgc cttttactgc tgctggaagg gggtggtgtg tcgccccaaa    3060
agcagggctt caattaagaa atgcctcttt gaaaggtgta ccttgggtat cctgtctgag    3120
ggtaactcca gggtgcgcca caatgtggcc tccgactgtg gttgcttcat gctagtgaaa    3180
agcgtggctg tgattaagca taacatggta tgtggcaact cgaggacag ggcctctcag      3240 atgctgacct gctcggacgg caactgtcac ctgctgaaga ccattcacgt agccagccac    3300
tctcgcaagg cctggccagt gtttgagcat aacatactga cccgctgttc cttgcatttg    3360
ggtaacagga gggggtgtt cctaccttac caatgcaatt tgagtcacac taagatattg      3420
cttgagcccg agagcatgtc caaggtaac ctgaacgggg tgtttgacat gaccatgaag      3480
atctggaagg tgctgaggta cgatgagacc cgcaccaggt gcagaccctg cgagtgtggc    3540
ggtaaacata ttaggaacca gcctgtgatg ctggatgtga ccgaggagct gaggcccgat    3600
cacttggtgc tggcctgcac ccgcgctgag tttggctcta gcgatgaaga tacagattga    3660
ggtactgaaa tgtgtgggcg tggcttaagg gtgggaaaga atatataagg tgggggtctt    3720
atgtagtttt gtatctgttt tgcagcagcc gccgccgcca tgagcaccaa ctcgtttgat    3780
ggaagcattg tgagctcata tttgacaacg cgcatgcccc catgggccgg ggtgcgtcag    3840
aatgtgatgg gctccagcat tgatggtcgc cccgtcctgc ccgcaaactc tactaccttg    3900
acctacgaga ccgtgtctgg aacgccgttc gagactgcag cctccgccgc cgcttcagcc    3960
gctgcagcca ccgcccgcgg gattgtgact gactttgctt tcctgagccc gcttgcaagc    4020
agtgcagctt cccgttcatc cgcccgcgat gacaagttga cggctctttt ggcacaattg    4080
gattctttga cccgggaact taatgtcgtt tctcagcagc tgttggatct cgccagcag     4140 gtttctgccc tgaaggcttc ctcccctccc aatgcggttt aaaacataaa taaaaaacca    4200
gactctgttt ggatttggat caagcaagtg tcttgctgtc tttatttagg ggttttgcgc    4260
gcgcggtagg cccgggacca gcggtctcgg tcgttgaggg tcctgtgtat tttttccagg    4320
acgtggtaaa ggtgactctg gatgttcaga tacatgggca taagcccgtc tctggggtgg    4380
aggtagcacc actgcagagc ttcatgctgc ggggtggtgt tgtagatgat ccagtcgtag    4440
caggagcgct gggcgtggtg cctaaaaatg tctttcagta gcaagctgat tgccaggggc    4500
aggcccttgg tgtaagtgtt tacaaagcgg ttaagctggg atgggtgcat acgtggggat    4560
atgagatgca tcttggactg tatttttagg ttggctatgt tcccagccat atccctccgg    4620
ggattcatgt tgtgcagaac caccagcaca gtgtatccgg tgcacttggg aaatttgtca    4680
tgtagcttag aaggaaatgc gtggaagaac ttggagacgc ccttgtgacc tccaagattt    4740
tccatgcatt cgtccataat gatggcaatg ggcccacggg cggcggcctg ggcgaagata    4800
tttctgggat cactaacgtc atagttgtgt tccaggatga gatcgtcata ggccattttt    4860
```

```
acaaagcgcg gcggagggt gccagactgc ggtataatgg ttccatccgg cccagggggcg    4920
tagttaccct cacagatttg catttcccac gctttgagtt cagatggggg gatcatgtct    4980
acctgcgggg cgatgaagaa aacggtttcc ggggtagggg agatcagctg ggaagaaagc    5040
aggttcctga gcagctgcga cttaccgcag ccggtgggcc cgtaaatcac acctattacc    5100
gggtgcaact ggtagttaag agagctgcag ctgccgtcat ccctgagcag ggggccact     5160
tcgttaagca tgtccctgac tcgcatgttt tccctgacca aatccgccag aaggcgctcg    5220
ccgcccagcg atagcagttc ttgcaaggaa gcaaagtttt tcaacggttt gagaccgtcc    5280
gccgtaggca tgcttttgag cgtttgacca agcagttcca gcggtccca cagctcggtc     5340
acctgctcta cggcatctcg atccagcata tctcctcgtt tcgcgggttg gggcggcttt    5400
cgctgtacgg cagtagtcgg tgctcgtcca gacgggccag ggtcatgtct ttccacgggc    5460
gcagggtcct cgtcagcgta gtctgggtca cggtgaaggg gtgcgctccg ggctgcgcgc    5520
tggccagggt gcgcttgagg ctggtcctgc tggtgctgaa gcgctgccgg tcttcgccct    5580
gcgcgtcggc caggtagcat ttgaccatgg tgtcatagtc cagcccctcc gcggcgtggc    5640
ccttggcgcg cagcttgccc ttggaggagg cgccgcacga ggggcagtgc agacttttga    5700
gggcgtagag cttgggcgcg agaaataccg attccgggga gtaggcatcc cgccgcagg    5760
ccccgcagac ggtctcgcat tccacgagcc aggtgagctc tggccgttcg gggtcaaaaa    5820
ccaggttccc cccatgcttt ttgatgcgtt tcttacctct ggtttccatg agccggtgtc    5880
cacgctcggt gacgaaaagg ctgtccgtgt ccccgtatac agacttgaga ggcctgtcct    5940
cgagcggtgt tccgcggtcc tcctcgtata gaaactcgga ccactctgag acaaaggctc    6000
gcgtccaggc cagcacgaag gaggctaagt gggagggta gcggtcgttg tccactaggg     6060
ggtccactcg ctccagggtg tgaagacaca tgtcgccctc ttcggcatca aggaaggtga    6120
ttggtttgta ggtgtaggcc acgtgaccgg gtgttcctga aggggggcta taaaagggg     6180
tgggggcgcg ttcgtcctca ctctcttccg catcgctgtc tgcgagggcc agctgttggg    6240
gtgagtactc cctctgaaaa gcgggcatga cttctgcgct aagattgtca gtttccaaaa    6300
acgaggagga tttgatattc acctggcccg cggtgatgcc tttgagggtg gccgcatcca    6360
tctggtcaga aaagacaatc tttttgttgt caagcttggt ggcaaacgac ccgtagaggg    6420
cgttggacag caacttggcg atggagcgca gggtttggtt tttgtcgcga tcggcgcgct    6480
ccttggccgc gatgtttagc tgcacgtatt cgcgcgcaac gcaccgccat tcgggaaaga    6540
cggtggtgcg ctcgtcgggc accaggtgca cgcgccaacc gcggttgtgc agggtgacaa    6600
ggtcaacgct ggtggctacc tctccgcgta ggcgctcgtt ggtccagcag aggcggccgc    6660
ccttgcgcga gcagaatggc ggtagggggt ctagctgcgt ctcgtccggg gggtctgcgt    6720
ccacggtaaa gaccccgggc agcaggcgcg cgtcgaagta gtctatcttg catccttgca    6780
agtctagcgc ctgctgccat gcgcgggcgg caagcgcgcg ctcgtatggg ttgagtgggg    6840
gaccccatgg catgggtgg gtgagcgcgg aggcgtacat gccgcaaatg tcgtaaacgt     6900
agagggctc tctgagtatt ccaagatatg tagggtagca tcttccaccg cggatgctgg     6960
cgcgcacgta atcgtatagt tcgtgcgagg gagcgaggag gtcgggaccg aggttgctac    7020
gggcgggctg ctctgctcgg aagactatct gcctgaagat ggcatgtgag ttggatgata    7080
tggttggacg ctggaagacg ttgaagctgg cgtctgtgag acctaccgcg tcacgcacga    7140
aggaggcgta ggagtcgcgc agcttgttga ccagctcggc ggtgacctgc acgtctaggg    7200
cgcagtagtc cagggtttcc ttgatgatgt catacttatc ctgtcccttt tttttccaca    7260
```

```
gctcgcggtt gaggacaaac tcttcgcggt cttccagta ctcttggatc ggaaacccgt   7320
cggcctccga acggtaagag cctagcatgt agaactggtt gacggcctgg taggcgcagc   7380
atcccttttc tacgggtagc gcgtatgcct gcgcggcctt ccggagcgag gtgtgggtga   7440
gcgcaaaggt gtccctgacc atgactttga ggtactggta tttgaagtca gtgtcgtcgc   7500
atccgccctg ctcccagagc aaaaagtccg tgcgcttttt ggaacgcgga tttggcaggg   7560
cgaaggtgac atcgttgaag agtatctttc ccgcgcgagg cataaagttg cgtgtgatgc   7620
ggaagggtcc cggcacctcg aacggttgt taattacctg gcggcgagc acgatctcgt    7680
caaagccgtt gatgttgtgg cccacaatgt aaagttccaa gaagcgcggg atgcccttga   7740
tggaaggcaa tttttaagt tcctcgtagg tgagctcttc aggggagctg agcccgtgct   7800
ctgaaagggc ccagtctgca agatgagggt tggaagcgac gaatgagctc cacaggtcac   7860
gggccattag catttgcagg tggtcgcgaa aggtcctaaa ctggcgacct atggccattt   7920
tttctgggt gatgcagtag aaggtaagcg ggtcttgttc ccagcggtcc catccaaggt    7980
tcgcggctag gtctcgcgcg gcagtcacta gaggctcatc tccgccgaac ttcatgacca   8040
gcatgaaggg cacgagctgc ttcccaaagg cccccatcca agtataggtc tctacatcgt   8100
aggtgacaaa gagacgctcg gtgcgaggat gcgagccgat cgggaagaac tggatctccc   8160
gccaccaatt ggaggagtgg ctattgatgt ggtgaaagta gaagtccctg cgacgggccg   8220
aacactcgtg ctggcttttg taaaaacgtg cgcagtactg gcagcggtgc acgggctgta   8280
catcctgcac gaggttgacc tgacgaccgc gcacaaggaa gcagagtggg aatttgagcc   8340
cctcgcctgg cgggtttggc tggtggtctt ctacttcggc tgcttgtcct tgaccgtctg   8400
gctgctcgag gggagttacg gtggatcgga ccaccacgcc gcgcgagccc aaagtccaga   8460
tgtccgcgcg cggcggtcgg agcttgatga caacatcgcg cagatgggag ctgtccatgg   8520
tctggagctc ccgcggcgtc aggtcaggcg ggagctcctg caggtttacc tcgcatagac   8580
gggtcagggc gcgggctaga tccaggtgat acctaatttc caggggctgg ttggtggcgg   8640
cgtcgatggc ttgcaagagg ccgcatcccc gcggcgcgac tacggtaccg cgggcgggc    8700
ggtgggccgg gggggtgtcc ttggatgatg catctaaaag cggtgacgcg ggcgagcccc   8760
cggaggtagg gggggctccg gacccgccgg gagaggggc aggggcacgt cggcgccgcg    8820
cgcgggcagg agctggtgct gcgcgcgtag gttgctggcg aacgcgacga cgcggcggtt   8880
gatctcctga atctggcgcc tctgcgtgaa gacgacgggc ccggtgagct tgagcctgaa   8940
agagagttcg acagaatcaa tttcggtgtc gttgacggcg gcctggcgca aaatctcctg   9000
cacgtctcct gagttgtctt gataggcgat ctcggccatg aactgctcga tctcttcctc   9060
ctggagatct ccgcgtccgg ctcgctccac ggtggcggcg aggtcgttgg aaatgcgggc   9120
catgagctgc gagaaggcgt tgaggcctcc ctcgttccag acgcggctgt agaccacgcc   9180
cccttcggca tcgcgggcgc gcatgaccac ctgcgcgaga ttgagctcca cgtgccggc    9240
gaagacggcg tagtttcgca ggcgctgaaa gaggtagttg agggtggtgg cggtgtgttc   9300
tgccacgaag aagtacataa cccagcgtcg caacgtggat tcgttgatat ccccaaggc    9360
ctcaaggcgc tccatggcct cgtagaagtc cacggcgaag ttgaaaaact gggagttgcg   9420
cgccgacacg gttaactcct cctccagaag acggatgagc tcggcgacag tgtcgcgcac   9480
ctcgcgctca aaggctacag gggcctcttc ttcttcttca atctcctctt ccataagggc   9540
ctccccttct tcttcttctg gcggcggtgg gggaggggg acacgcggc gacgacggcg     9600
```

-continued

```
caccgggagg cggtcgacaa agcgctcgat catctccccg cggcgacggc gcatggtctc    9660
ggtgacggcg cggccgttct cgcggggggcg cagttggaag acgccgcccg tcatgtcccg   9720
gttatgggtt ggcggggggc tgccatgcgg cagggatacg gcgctaacga tgcatctcaa   9780
caattgttgt gtaggtactc cgccgccgag ggacctgagc gagtccgcat cgaccggatc   9840
ggaaaacctc tcgagaaagg cgtctaacca gtcacagtcg caaggtaggc tgagcaccgt   9900
ggcgggcggc agcgggcggc ggtcgggggtt gtttctggcg gaggtgctgc tgatgatgta   9960
attaaagtag gcggtcttga cggcggat ggtcgacaga agcaccatgt ccttgggtcc    10020
ggcctgctga atgcgcaggc ggtcggccat gccccaggct tcgttttgac atcggcgcag   10080
gtctttgtag tagtcttgca tgagccttc taccggcact tcttcttctc cttcctcttg    10140
tcctgcatct cttgcatcta tcgctgcggg ggcggcggag tttggccgta ggtggcgccc   10200
tcttcctccc atgcgtgtga ccccgaagcc cctcatcggc tgaagcaggg ctaggtcggc   10260
gacaacgcgc tcggctaata tggcctgctg cacctgcgtg agggtagact ggaagtcatc   10320
catgtccaca aagcggtggt atgcgcccgt gttgatggtg taagtgcagt tggccataac   10380
ggaccagtta acgtctggt gaccggctg cgagagctcg gtgtacctga gacgcgagta    10440
agccctcgag tcaaatacgt agtcgttgca agtccgcacc aggtactggt atcccaccaa   10500
aaagtgcggc ggcggctggc ggtagagggg ccagcgtagg gtggccgggg ctccggggggc   10560 gagatcttcc aacataaggc gatgatatcc gtagatgtac ctggacatcc aggtgatgcc   10620
ggcggcggtg gtggaggcgc gcggaaagtc gcggacgcgg ttccagatgt tgcgcagcgg   10680
caaaaagtgc tccatggtcg ggacgctctg gccggtcagg cgcgcgcaat cgttgacgct   10740
ctagaccgtg caaaggaga gcctgtaagc gggcactctt ccgtggtctg gtggataaat    10800
tcgcaagggt atcatggcgg acgaccgggg ttcgagcccc gtatccggcc gtccgccgtg   10860
atccatgcgg ttaccgcccg cgtgtcgaac ccaggtgtgc gacgtcagac aacgggggag   10920
tgctcctttt ggcttccttc caggcgcggc ggctgctgcg ctagcttttt tggccactgg   10980
ccgcgcgcag cgtaagcggt taggctggaa agcgaaagca ttaagtggct cgctccctgt   11040
agccggaggg ttattttcca agggttgagt cgcgggaccc ccggttcgag tctcggaccg   11100
gccggactgc ggcgaacggg ggtttgcctc cccgtcatgc aagaccccgc ttgcaaattc   11160
ctccggaaac agggacgagc ccctttttttg cttttcccag atgcatccgg tgctgcggca   11220
gatgcgcccc cctcctcagc agcggcaaga gcaagagcag cggcagacat gcagggcacc   11280
ctcccctcct cctaccgcgt caggaggggc gacatccgcg gttgacgcgg cagcagatgc   11340
tgattacgaa cccccgcggc gccgggcccg gcactacctg gacttggagg agggcgaggg   11400
cctggcgcgg ctaggagcgc cctctcctga gcggtaccca agggtgcagc tgaagcgtga   11460
tacgcgtgag gcgtacgtgc cgcggcagaa cctgtttcgc gaccgcgagg gagaggagcc   11520
cgaggagatg cgggatcgaa agttccacgc agggcgcgag ctgcggcatg gcctgaatcg   11580
cgagcggttg ctgcgcgagg aggactttga gcccgacgcg cgaaccggga ttagtcccgc   11640
gcgcgcacac gtggcggccg ccgacctggt aaccgcatac gagcagacgg tgaaccagga   11700
gattaacttt caaaaaagct ttaacaacca cgtgcgtacg cttgtggcgc gcgaggaggt   11760
ggctatagga ctgatgcatc tgtgggactt tgtaagcgcg ctggagcaaa acccaaatag   11820
caagccgctc atggcgcagc tgttccttat agtgcagcac agcagggaca acgaggcatt   11880
cagggatgcg ctgctaaaca tagtagagcc cgagggccgc tggctgctcg atttgataaa   11940
catcctgcag agcatagtgg tgcaggagcg cagcttgagc ctggctgaca aggtggccgc   12000
```

```
catcaactat tccatgctta gcctgggcaa gttttacgcc cgcaagatat accataccec    12060 ttacgttccc atagacaagg aggtaaagat cgaggggttc tacatgcgca tggcgctgaa    12120
ggtgcttacc ttgagcgacg acctgggcgt ttatcgcaac gagcgcatcc acaaggccgt    12180
gagcgtgagc cggcggcgcg agctcagcga ccgcgagctg atgcacagcc tgcaaagggc    12240
cctggctggc acgggcagcg gcgatagaga ggccgagtcc tactttgacg cgggcgctga    12300
cctgcgctgg gccccaagcc gacgcgccct ggaggcagct ggggccggac ctgggctggc    12360
ggtggcaccc gcgcgcgctg gcaacgtcgg cggcgtggag gaatatgacg aggacgatga    12420
gtacgagcca gaggacggcg agtactaagc ggtgatgttt ctgatcagat gatgcaagac    12480
gcaacggacc cggcggtgcg ggcggcgctg cagagccagc cgtccggcct taactccacg    12540
gacgactggc gccaggtcat ggaccgcatc atgtcgctga ctgcgcgcaa tcctgacgcg    12600
ttccggcagc agccgcaggc caaccggctc tccgcaattc tggaagcggt ggtcccggcg    12660
cgcgcaaacc ccacgcacga aaggtgctg gcgatcgtaa acgcgctggc cgaaaacagg    12720
gccatccggc ccgacgaggc cggcctggtc tacgacgcgc tgcttcagcg cgtggctcgt    12780
tacaacagcg gcaacgtgca gaccaacctg gaccggctgg tggggatgt gcgcgaggcc    12840 gtggcgcagc gtgagcgcgc gcagcagcag ggcaacctgg gctccatggt tgcactaaac    12900
gccttcctga gtacacagcc cgccaacgtg ccgcggggac aggaggacta caccaacttt    12960
gtgagcgcac tgcggctaat ggtgactgag acaccgcaaa gtgaggtgta ccagtctggg    13020
ccagactatt ttttccagac cagtagacaa ggcctgcaga ccgtaaacct gagccaggct    13080
ttcaaaaact tgcaggggct gtgggggtg cgggctccca caggcgaccg cgcgaccgtg    13140
tctagcttgc tgacgcccaa ctcgcgcctg ttgctgctgc taatagcgcc cttcacggac    13200
agtggcagcg tgtcccggga cacataccta ggtcacttgc tgacactgta ccgcgaggcc    13260
ataggtcagg cgcatgtgga cgagcatact ttccaggaga ttacaagtgt cagccgcgcg    13320
ctggggcagg aggacacggg cagcctggag gcaaccctaa actacctgct gaccaaccgg    13380
cggcagaaga tccctcgtt gcacagttta aacagcgagg aggagcgcat tttgcgctac    13440
gtgcagcaga gcgtgagcct taacctgatg cgcgacgggg taacgcccag cgtggcgctg    13500
gacatgaccg cgcgcaacat ggaaccgggc atgtatgcct caaaccggcc gtttatcaac    13560
cgcctaatgg actacttgca tcgcgcggcc gccgtgaacc ccgagtattt caccaatgcc    13620
atcttgaacc cgcactggct accgccccct ggtttctaca ccgggggatt cgaggtgccc    13680
gagggtaacg atggattcct ctgggacgac atagacgaca gcgtgttttc cccgcaaccg    13740
cagaccctgc tagagttgca acagcgcgag caggcagagg cggcgctgcg aaaggaaagc    13800
ttccgcaggc caagcagctt gtccgatcta ggcgctgcgg ccccgcggtc agatgctagt    13860
agcccatttc caagcttgat agggtctctt accagcactc gcaccacccg cccgcgcctg    13920
ctgggcgagg aggagtacct aaacaactcg ctgctgcagc cgcagcgcga aaaaacctg    13980 cctccggcat ttcccaacaa cgggatagag agcctagtgg acaagatgag tagatggaag    14040
acgtacgcgc aggagcacag ggacgtgcca ggcccgcgcc cgcccacccg tcgtcaaagg    14100
cacgaccgtc agcggggtct ggtgtgggag gacgatgact cggcagacga cagcagcgtc    14160
ctggatttgg gagggagtgg caacccgttt gcgcaccttc ccccaggct ggggagaatg    14220 ttttaaaaaa aaaaagcat gatgcaaaat aaaaaactca ccaaggccat ggcaccgagc    14280
gttggttttc ttgtattccc cttagtatgc ggcgcgcggc gatgtatgag gaaggtcctc    14340
```

```
ctccctccta cgagagtgtg gtgagcgcgg cgccagtggc ggcggcgctg ggttctccct   14400
tcgatgctcc cctggacccg ccgtttgtgc ctccgcggta cctgcggcct accgggggga   14460
gaaacagcat ccgttactct gagttggcac ccctattcga caccaccgt gtgtacctgg    14520
tggacaacaa gtcaacggat gtggcatccc tgaactacca gaacgaccac agcaactttc   14580
tgaccacggt cattcaaaac aatgactaca gcccggggga ggcaagcaca cagaccatca   14640
atcttgacga ccggtcgcac tggggcgcg acctgaaaac catcctgcat accaacatgc    14700
caaatgtgaa cgagttcatg tttaccaata agtttaaggc gcgggtgatg gtgtcgcgct   14760
tgcctactaa ggacaatcag gtggagctga aatacgagtg ggtggagttc acgctgcccg   14820
agggcaacta ctccgagacc atgaccatag accttatgaa caacgcgatc gtggagcact   14880
acttgaaagt gggcagacag aacggggttc tggaaagcga catcggggta agtttgaca    14940
cccgcaactt cagactgggg tttgaccccg tcactggtct tgtcatgcct ggggtatata   15000
caaacgaagc cttccatcca gacatcattt tgctgccagg atgcggggtg gacttcaccc   15060
acagccgcct gagcaacttg ttgggcatcc gcaagcggca accttccag gagggcttta    15120
ggatcaccta cgatgatctg gagggtggta acattcccgc actgttggat gtggacgcct   15180
accaggcgag cttgaaagat gacaccgaac agggcggggg tggcgcaggc ggcagcaaca   15240
gcagtggcag cggcgcggaa gagaactcca acgcggcagc cgcggcaatg cagccggtgg   15300
aggacatgaa cgatcatgcc attcgcgcg acacctttgc cacacgggct gaggagaagc    15360
gcgctgaggc cgaagcagcg gccgaagctg ccgcccccgc tgcgcaaccc gaggtcgaga   15420
agcctcagaa gaaaccggtg atcaaacccc tgacagagga cagcaagaaa cgcagttaca   15480
acctaataag caatgacagc accttcaccc agtaccgcag ctggtacctt gcatacaact   15540
acggcgaccc tcagaccgga atccgctcat ggaccctgct ttgcactcct gacgtaacct   15600
gcggctcgga gcaggtctac tggtcgttgc cagacatgat gcaagacccc gtgaccttcc   15660
gctccacgcg ccagatcagc aacttttccg tggtgggcgc cgagctgttg cccgtgcact   15720
ccaagagctt ctacaacgac caggccgtct actcccaact catccgccag tttacctctc   15780
tgacccacgt gttcaatcgc tttcccgaga accagatttt ggcgcgcccg ccagcccca    15840
ccatcaccac cgtcagtgaa aacgttcctg ctctcacaga tcacgggacg ctaccgctgc   15900
gcaacagcat cggaggagtc cagcgagtga ccattactga cgccagacgc cgcacctgcc   15960
cctacgttta caaggccctg gcatagtct cgccgcgcgt cctatcgagc cgcactttt    16020
gagcaagcat gtccatcctt atatcgccca gcaataacac aggctggggc ctgcgcttcc   16080
caagcaagat gttttggcggg gccaagaagc gctccgacca acacccagtg cgcgtgcgcg   16140
ggcactaccg cgcgccctgg ggcgcgcaca aacgcggccg cactgggcgc accaccgtcg   16200
atgacgccat cgacgcggtg gtggaggagg cgcgcaacta cacgcccacg ccgccaccag   16260
tgtccacagt ggacgcggcc attcagaccg tggtgcgcgg agcccggcgc tatgctaaaa   16320
tgaagagacg gcggaggcgc gtagcacgtc gccaccgccg ccgacccggc actgccgccc   16380
aacgcgcggc ggcggcccta cttaaccgcg cacgtcgcac cggccgacgg gcggccatgc   16440
gggccgctcg aaggctggcc gcgggtattg tcactgtgcc ccccaggtcc aggcgacgag   16500
cggccgccgc agcagccgcg gccattagtg ctatgactca gggtcgcagg ggcaacgtgt   16560
attgggtgcg cgactcggtt agcggcctgc gcgtgcccgt gcgcaccgc ccccgcgca    16620
actagattgc aagaaaaaac tacttagact cgtactgttg tatgtatcca gcggcggcgg   16680
cgcgcaacga agctatgtcc aagcgcaaaa tcaaagaaga gatgctccag gtcatcgcgc   16740
```

```
cggagatcta tggcccccg aagaaggaag agcaggatta caagcccga aagctaaagc    16800 gggtcaaaaa gaaaagaaa gatgatgatg atgaacttga cgacgaggtg gaactgctgc    16860
acgctaccgc gcccaggcga cgggtacagt ggaaggtcg acgcgtaaaa cgtgttttgc    16920
gacccggcac caccgtagtc tttacgcccg gtgagcgctc cacccgcacc tacaagcgcg    16980
tgtatgatga ggtgtacggc gacgaggacc tgcttgagca ggccaacgag cgcctcgggg    17040
agtttgccta cggaaagcgg cataaggaca tgctggcgtt gccgctggac gagggcaacc    17100
caacacctag cctaaagccc gtaacactgc agcaggtgct gcccgcgctt gcaccgtccg    17160
aagaaaagcg cggcctaaag cgcgagtctg gtgacttggc acccaccgtg cagctgatgg    17220
tacccaagcg ccagcgactg gaagatgtct tggaaaaaat gaccgtggaa cctgggctgg    17280
agcccgaggt ccgcgtgcgg ccaatcaagc aggtggcgcc gggactgggc gtgcagaccg    17340
tggacgttca gatacccact accagtagca ccagtattgc caccgccaca gagggcatgg    17400
agacacaaac gtccccggtt gcctcagcgg tggcggatgc cgcggtgcag gcggtcgctg    17460
cggccgcgtc caagacctct acggaggtgc aaacggaccc gtggatgttt cgcgtttcag    17520 cccccggcg cccgcgcggt tcgaggaagt acggcgccgc cagcgcgcta ctgcccgaat    17580
atgccctaca tccttccatt gcgcctaccc ccggctatcg tggctacacc taccgcccca    17640
gaagacgagc aactacccga cgccgaacca ccactggaac ccgccgccgc cgtcgccgtc    17700
gccagcccgt gctggccccg atttccgtgc gcagggtggc tcgcgaagga ggcaggaccc    17760
tggtgctgcc aacagcgcgc taccacccca gcatcgttta aaagccggtc tttgtggttc    17820
ttgcagatat ggccctcacc tgccgcctcc gtttcccggt gccgggattc cgaggaagaa    17880
tgcaccgtag gaggggcatg gccggccacg gcctgacggg cggcatgcgt cgtgcgcacc    17940
accggcggcg gcgcgcgtcg caccgtcgca tgcgcggcg tatcctgccc ctccttattc    18000
cactgatcgc cgcggcgatt ggcgccgtgc ccggaattgc atccgtggcc ttgcaggcgc    18060
agagacactg attaaaaaca agttgcatgt ggaaaaatca aaataaaaag tctggactct    18120
cacgctcgct tggtcctgta actattttgt agaatggaag acatcaactt tgcgtctctg    18180
gccccgcgac acggctcgcg cccgttcatg ggaaactggc aagatatcgg caccagcaat    18240
atgagcggtg gcgccttcag ctggggctcg ctgtggagcg gcattaaaaa tttcggttcc    18300
accgttaaga actatggcag caaggcctgg aacagcagca caggccagat gctgagggat    18360
aagttgaaag agcaaaattt ccaacaaaag gtggtagatg gcctggcctc tggcattagc    18420
ggggtggtgg acctggccaa ccaggcagtg caaaataaga ttaacagtaa gcttgatccc    18480
cgccctcccg tagaggagcc tccaccggcc gtggagacag tgtctccaga ggggcgtggc    18540
gaaaagcgtc gcgcccccga cagggaagaa actctggtga cgcaaataga cgagcctccc    18600
tcgtacgagg aggcactaaa gcaaggcctg cccaccaccc gtcccatcgc gcccatggct    18660
accggagtgc tgggccagca cacccgta acgctggacc tgcctccccc cgccgacacc    18720
cagcagaaac ctgtgctgcc aggcccgacc gccgttgttg taacccgtcc tagccgcgcg    18780
tccctgcgcc gcgccgccag cggtccgcga tcgttgcggc ccgtagccag tggcaactgg    18840
caaagcacac tgaacagcat cgtgggtctg ggggtgcaat ccctgaagcg ccgacgatgc    18900
ttctgaatag ctaacgtgtc gtatgtgtgt catgtatgcg tccatgtcgc cgcagagga    18960 gctgctgagc cgccgcgcgc ccgctttcca agatggctac cccttcgatg atgccgcagt    19020
ggtcttacat gcacatctcg ggccaggacg cctcggagta cctgagcccc gggctggtgc    19080
```

```
agtttgcccg cgccaccgag acgtacttca gcctgaataa caagtttaga aaccccacgg  19140
tggcgcctac gcacgacgtg accacagacc ggtcccagcg tttgacgctg cggttcatcc  19200
ctgtggaccg tgaggatact gcgtactcgt acaaggcgcg gttcaccta gctgtgggtg   19260
ataaccgtgt gctggacatg gcttccacgt actttgacat ccgcggcgtg ctggacaggg  19320
gccctacttt taagccctac tctggcactg cctacaacgc cctggctccc aagggtgccc  19380
caaatccttg cgaatgggat gaagctgcta ctgctcttga aataaaccta gaagaagagg  19440
acgatgacaa cgaagacgaa gtagacgagc aagctgagca gcaaaaaact cacgtatttg  19500
ggcaggcgcc ttattctggt ataaatatta caaaggaggg tattcaaata ggtgtcgaag  19560
gtcaaacacc taaatatgcc gataaaacat ttcaacctga acctcaaata ggagaatctc  19620
agtggtacga aactgaaatt aatcatgcag ctgggagagt ccttaaaaag actaccccaa  19680
tgaaaccatg ttacggttca tatgcaaaac ccacaaatga aaatggaggg caaggcattc  19740
ttgtaaagca acaaaatgga aagctagaaa gtcaagtgga aatgcaattt ttctcaactg  19800
gaagcggttc tcgctacctg gagcctggcc cagtgactgc cgctggttcc ggaagcagat  19860
acatggacgg aacaatgtcc caggttgccg gttctggctc ccctaaagtg gtattgtaca  19920
gtgaagatgt agatatagaa accccagaca ctcatatttc ttacatgccc actattaagg  19980
aaggtaactc acgagaacta atgggccaac aatctatgcc caacaggcct aattacattg  20040
cttttaggga caattttatt ggtctaatgt attacaacag cacgggtaat atgggtgttc  20100
tggcgggcca agcatcgcag ttgaatgctg ttgtagattt gcaagacaga aacacagagc  20160
tttcatacca gcttttgctt gattccattg gtgatagaac caggtacttt tctatgtgga  20220
atcaggctgt tgacagctat gatccagatg ttagaattat tgaaaatcat ggaactgaag  20280
atgaacttcc aaattactgc tttccactgg gaggtgtgat taatacagag actcttacca  20340
aggtaaaacc taaaacaggt caggaaaatg gatgggaaaa agatgctaca gaattttcag  20400
ataaaaatga aataagagtt ggaaataatt ttgccatgga aatcaatcta aatgccaacc  20460
tgtggagaaa tttcctgtac tccaacatag cgctgtattt gcccgacaag ctaaagtaca  20520
gtccttccaa cgtaaaaatt tctgataacc caaacaccta cgactacatg aacaagcgag  20580
tggtggctcc cggggttagtg gactgctaca ttaaccttgg agcacgctgg tcccttgact  20640
atatggacaa cgtcaaccca tttaaccacc accgcaatgc tggcctgcgc taccgctcaa  20700
tgttgctggg caatggtcgc tatgtgccct ccacatccca ggtgcctcag aagttctttg  20760
ccattaaaaa cctccttctc ctgccgggct catacaccta cgagtggaac ttcaggaagg  20820
atgttaacat ggttctgcag agctccctag gaaatgacct aagggttgac ggagccagca  20880
ttaagtttga tagcatttgc ctttacgcca ccttcttccc catggcccac aacaccgcct  20940
ccacgcttga ggccatgctt agaaacgaca ccaacgacca gtcctttaac gactatctct  21000
ccgccgccaa catgctctac cctataccccg ccaacgctac caacgtgccc atatccatcc  21060
cctcccgcaa ctgggcggct ttccgcggct gggccttcac gcgccttaag actaaggaaa  21120
ccccatcact gggctcgggc tacgaccctt attcaccta ctctggctct ataccctacc   21180
tagatggaac ctttttacctc aaccacacct ttaagaaggc tgccattacc tttgactctt  21240
ctgtcagctg gcctggcaat gaccgcctgc ttaccccca cgagtttgaa attaagcgct   21300
cagttgacgg ggaggggttac aacgttgccc agtgtaacat gaccaaagac tggttcctgg  21360
tacaaatgct agctaactat aacattggct accaggggctt ctatatcccc agagagctaca  21420
aggaccgcat gtactccttc tttagaaact tccagcccat gagccgtcag gtggtggatg  21480
```

```
atactaaata caaggactac caacaggtgg gcatcctaca ccaacacaac aactctggat   21540
ttgttggcta ccttgccccc accatgcgcg aaggacaggc ctaccctgct aacttcccct   21600
atccgcttat aggcaagacc gcagttgaca gcattaccca gaaaagtttt ctttgcgatc   21660 gcacccttg  gcgcatccca ttctccagta actttatgtc catgggcgca ctcacagacc   21720
tgggccaaaa ccttctctac gccaactccg cccactccct agacatgact tttgaggtgg   21780
atcccatgga cgagcccacc cttctttatg ttttgtttga agtctttgac aaggtccgtg   21840
tgcaccagcc gcaccgcggc gtcatcgaaa ccgtgtacct gcgcacgccc ttctcggccg   21900
gcaacgccac aacataaaga agcaagcaac atcaacaaca gctgccgcca tgggctccag   21960
tgagcaggaa ctgaaagcca ttgtcaaaga tcttggttgt gggccatatt ttttgggcac   22020
ctatgacaag cgcttttccag gctttgtttc tccacacaag ctcgcctgcg ccatagtcaa   22080
tacggccggt cgcgagactg ggggcgtaca ctggatggcc tttgcctgga acccgcactc   22140
aaaaacatgc tacctctttg agccctttgg cttttctgac cagcgactca agcaggttta   22200
ccagtttgag tacgagtcac tcctgcgccg tagcgccatt gcttcttccc ccgaccgctg   22260
tataacgctg gaaaagtcca cccaaagcgt acagggccc  aactcggccg cctgtggact   22320
attctgctgc atgtttctcc acgcctttgc caactggccc caaactccca tggatcacaa   22380
ccccaccatg aaccttatta ccggggtacc caactccatg ctcaacagtc cccaggtaca   22440
gcccaccctg cgtcgcaacc aggaacagct ctacagcttc ctggagcgcc actcgcccta   22500
cttccgcagc cacagtgcgc agattaggag cgccacttct ttttgtcact tgaaaaacat   22560
gtaaaaataa tgtactagag acactttcaa taaaggcaaa tgcttttatt tgtacactct   22620
cgggtgatta tttaccccca cccttgccgt ctgcgccgtt taaaaatcaa aggggttctg   22680
ccgcgcatcg ctatgcgcca ctggcaggga cacgttgcga tactggtgtt tagtgctcca   22740
cttaaactca ggcacaacca tccgcggcag ctcggtgaag ttttcactcc acaggctgcg   22800
caccatcacc aacgcgttta gcaggtcggg cgccgatatc ttgaagtcgc agttggggcc   22860
tccgccctgc gcgcgcgagt tgcgatacac agggttgcag cactggaaca ctatcagcgc   22920
cgggtggtgc acgctggcca gcacgctctt gtcggagatc agatccgcgt ccaggtcctc   22980 gcgttgctc  agggcgaacg gagtcaactt tggtagctgc cttcccaaaa agggcgcgtg   23040
cccaggcttt gagttgcact cgcaccgtag tggcatcaaa aggtgaccgt gcccggtctg   23100
ggcgttagga tacagcgcct gcataaaagc cttgatctgc ttaaaagcca cctgagcctt   23160
tgcgccttca gagaagaaca tgccgcaaga cttgccggaa aactgattgg ccggacaggc   23220
cgcgtcgtgc acgcagcacc ttgcgtcggt gttggagatc tgcaccacat tcggccccca   23280
ccggttcttc acgatcttgg ccttgctaga ctgctccttc agcgcgcgct gcccgttttc   23340
gctcgtcaca tccatttcaa tcacgtgctc cttatttatc ataatgcttc cgtgtagaca   23400
cttaagctcg ccttcgatct cagcgcagcg gtgcagccac aacgcgcagc ccgtgggctc   23460
gtgatgcttg taggtcacct ctgcaaacga ctgcaggtac gcctgcagga atcgccccat   23520
catcgtcaca aaggtcttgt tgctggtgaa ggtcagctgc aacccgcggt gctcctcgtt   23580
cagccaggtc ttgcatacgg ccgccagagc ttccacttgg tcaggcagta gtttgaagtt   23640
cgcctttaga tcgttatcca cgtggtactt gtccatcagc gcgcgcgcag cctccatgcc   23700
cttctcccac gcagacacga tcggcacact cagcgggttc atcaccgtaa tttcactttc   23760
cgcttcgctg ggctcttcct cttcctcttg cgtccgcata ccacgcgcca ctgggtcgtc   23820
```

```
ttcattcagc cgccgcactg tgcgcttacc tcctttgcca tgcttgatta gcaccggtgg    23880
gttgctgaaa cccaccattt gtagcgccac atcttctctt tcttcctcgc tgtccacgat    23940
tacctctggt gatggcgggc gctcgggctt gggagaaggg cgcttctttt tcttcttggg    24000
cgcaatggcc aaatccgccg ccgaggtcga tggccgcggg ctgggtgtgc gcggcaccag    24060
cgcgtcttgt gatgagtctt cctcgtcctc ggactcgata cgccgcctca tccgcttttt    24120
tgggggcgcc cggggaggcg gcggcgacgg ggacggggac gacacgtcct ccatggttgg    24180
gggacgtcgc gccgcaccgc gtccgcgctc gggggtggtt tcgcgctgct cctcttcccg    24240
actggccatt tccttctcct ataggcagaa aaagatcatg gagtcagtcg agaagaagga    24300
cagcctaacc gccccctctg agttcgccac caccgcctcc accgatgccg ccaacgcgcc    24360
taccaccttc cccgtcgagg caccccgct tgaggaggag gaagtgatta tcgagcagga    24420
cccaggtttt gtaagcgaag acgacgagga ccgctcagta ccaacagagg ataaaaagca    24480
agaccaggac aacgcagagg caaacgagga acaagtcggg cggggggacg aaaggcatgg    24540
cgactaccta gatgtgggag acgacgtgct gttgaagcat ctgcagcgcc agtgcgccat    24600
tatctgcgac gcgttgcaag agcgcagcga tgtgcccctc gccatagcgg atgtcagcct    24660
tgcctacgaa cgccacctat tctcaccgcg cgtaccccc aaacgccaag aaaacggcac    24720
atgcgagccc aacccgcgcc tcaacttcta ccccgtattt gccgtgccag aggtgcttgc    24780
cacctatcac atcttttcc aaaactgcaa gatacccta tcctgccgtg ccaaccgcag    24840
ccgagcggac aagcagctgg ccttgcggca gggcgctgtc atacctgata tcgcctcgct    24900
caacgaagtg ccaaaaatct ttgagggtct tggacgcgac gagaagcgcg cggcaaacgc    24960
tctgcaacag gaaaacagcg aaaatgaaag tcactctgga gtgttggtgg aactcgaggg    25020
tgacaacgcg cgcctagccg tactaaaacg cagcatcgag gtcacccact ttgcctaccc    25080
ggcacttaac ctaccccca aggtcatgag cacagtcatg agtgagctga tcgtgcgccg    25140
tgcgcagccc ctggagaggg atgcaaattt gcaagaacaa acagaggagg cctacccgc    25200 agttggcgac gagcagctag cgcgctggct tcaaacgcgc gagcctgccg acttggagga    25260
gcgacgcaaa ctaatgatgg ccgcagtgct cgttaccgtg gagcttgagt gcatgcagcg    25320
gttctttgct gacccggaga tgcagcgcaa gctagaggaa acattgcact acacctttcg    25380
acagggctac gtacgccagg cctgcaagat ctccaacgtg gagctctgca acctggtctc    25440
ctaccttgga atttttgcacg aaaaccgcct tgggcaaaac gtgcttcatt ccacgctcaa    25500
gggcgaggcg cgccgcgact acgtccgcga ctgcgtttac ttatttctat gctacacctg    25560
gcagacggcc atgggcgttt ggcagcagtg cttggaggag tgcaacctca aggagctgca    25620
gaaactgcta aagcaaaact tgaaggacct atggacggcc ttcaacgagc gctccgtggc    25680
cgcgcacctg gcggacatca ttttccccga acgcctgctt aaaaccctgc aacagggtct    25740
gccagacttc accagtcaaa gcatgttgca gaactttagg aactttatcc tagagcgctc    25800
aggaatcttg cccgccacct gctgtgcact tcctagcgac tttgtgccca ttaagtaccg    25860
cgaatgccct ccgccgcttt ggggccactg ctaccttctg cagctagcca actaccttgc    25920
ctaccactct gacataatgg aagacgtgag cggtgacggt ctactggagt gtcactgtcg    25980
ctgcaaccta tgcacccgc accgctccct ggtttgcaat tcgcagctgc ttaacgaaag    26040
tcaaattatc ggtaccttg agctgcaggg tccctcgcct gacgaaaagt ccgcggctcc    26100
ggggttgaaa ctcactccgg ggctgtggac gtcggcttac cttcgcaaat ttgtacctga    26160
ggactaccac gcccacgaga ttaggttcta cgaagaccaa tcccgcccgc caaatgcgga    26220
```

-continued

```
gcttaccgcc tgcgtcatta cccagggcca cattcttggc caattgcaag ccatcaacaa   26280
agcccgccaa gagtttctgc tacgaaaggg acgggggtt tacttggacc cccagtccgg    26340
cgaggagctc aacccaatcc ccccgccgcc gcagccctat cagcagcagc cgcgggccct   26400
tgcttcccag gatggcaccc aaaaagaagc tgcagctgcc gccgccaccc acggacgagg   26460
aggaatactg ggacagtcag gcagaggagg ttttggacga ggaggaggag gacatgatgg   26520
aagactggga gagcctagac gaggaagctt ccgaggtcga agaggtgtca gacgaaacac   26580
cgtcaccctc ggtcgcattc ccctcgccgg cgccccagaa atcggcaacc ggttccagca   26640
tggctacaac ctccgctcct caggcgccgc cggcactgcc cgttcgccga cccaaccgta   26700
gatgggacac cactggaacc agggccggta agtccaagca gccgccgccg ttagcccaag   26760
agcaacaaca gcgccaaggc taccgctcat ggcgcgggca caagaacgcc atagttgctt   26820
gcttgcaaga ctgtggggggc aacatctcct tcgcccgccg ctttcttctc taccatcacg   26880
gcgtggcctt cccccgtaac atcctgcatt actaccgtca tctctacagc ccatactgca   26940
ccggcggcag cggcagcggc agcaacagca gcggccacac agaagcaaag gcgaccggat   27000
agcaagactc tgacaaagcc caagaaatcc acagcggcgg cagcagcagg aggaggagcg   27060
ctgcgtctgg cgcccaacga acccgtatcg acccgcgagc ttagaaacag gatttttccc   27120
actctgtatg ctatatttca acagagcagg ggccaagaac aagagctgaa aataaaaaac   27180
aggtctctgc gatccctcac ccgcagctgc ctgtatcaca aaagcgaaga tcagcttcgg   27240
cgcacgctgg aagacgcgga ggctctcttc agtaaatact gcgcgctgac tcttaaggac   27300
tagtttcgcg cccttttctca aatttaagcg cgaaaactac gtcatctcca gcggccacac   27360
ccggcgccag cacctgtcgt cagcgccatt atgagcaagg aaattcccac gccctacatg   27420
tggagttacc agccacaaat gggacttgcg gctggagctg cccaagacta ctcaacccga   27480
ataaactaca tgagcgcggg accccacatg atatcccggg tcaacggaat ccgcgcccac   27540
cgaaaccgaa ttctcttgga acaggcggct attaccacca cacctcgtaa taaccttaat   27600
ccccgtagtt ggcccgctgc cctggtgtac caggaaagtc ccgctcccac cactgtggta   27660
cttcccagag acgccaggc cgaagttcag atgactaact caggggcgca gcttgcgggc   27720
ggctttcgtc acagggtgcg gtcgcccggg cagggtataa ctcacctgac aatcagaggg   27780
cgaggtattc agctcaacga cgagtcggtg agctcctcgc ttggtctccg tccggacggg   27840
acatttcaga tcggcggcgc cggccgtcct tcattcacgc ctcgtcaggc aatcctaact   27900
ctgcagacct cgtcctctga gccgcgctct ggaggcattg gaactctgca atttattgag   27960
gagtttgtgc catcggtcta ctttaacccc ttctcgggac ctcccggcca ctatccggat   28020
caatttattc ctaactttga cgcggtaaag gactcggcgg acggctacga ctgaatgtta   28080
agtggagagg cagagcaact gcgcctgaaa cacctggtcc actgtcgccg ccacaagtgc   28140
tttgcccgcg actccggtga gttttgctac tttgaattgc ccgaggatca tatcgagggc   28200
ccggcgcacg gcgtccggct taccgcccag ggagagcttg cccgtagcct gattcgggag   28260
tttacccagc gccccctgct agttgagcgg gacagggggac cctgtgttct cactgtgatt   28320
tgcaactgtc ctaaccttgg attacatcaa gatctttgtt gccatctctg tgctgagtat   28380
aataaataca gaaattaaaa tatactgggg ctcctatcgc catcctgtaa acgccaccgt   28440
cttcacccgc ccaagcaaac caaggcgaac cttacctggt acttttaaca tctctcccctc   28500
tgtgatttac aacagtttca acccagacgg agtgagtcta cgagagaacc tctccgagct   28560
```

```
cagctactcc atcagaaaaa acaccaccct ccttacctgc cgggaacgta cgagtgcgtc  28620
accggccgct gcaccacacc taccgcctga ccgtaaacca gacttttccc ggacagacct  28680
caataactct gtttaccaga acaggagtg agcttagaaa acccttaggg tattaggcca  28740
aaggcgcagc tactgtgggg tttatgaaca attcaagcaa ctctacgggc tattctaatt  28800
caggtttctc tagaatcggg gttggggtta ttctctgtct tgtgattctc tttattctta  28860
tactaacgct tctctgccta aggctcgccg cctgctgtgt gcacatttgc atttattgtc  28920 agcttttaa acgctggggt cgccacccaa gatgattagg tacataatcc taggtttact  28980 caccccttgcg tcagcccacg gtaccaccca aaaggtggat tttaaggagc cagcctgtaa  29040
tgttacattc gcagctgaag ctaatgagtg caccactctt ataaaatgca ccacagaaca  29100
tgaaaagctg cttattcgcc acaaaaacaa aattggcaag tatgctgttt atgctatttg  29160
gcagccaggt gacactacag agtataatgt tacagttttc cagggtaaaa gtcataaaac  29220 tttatgtat acttttccat tttatgaaat gtgcgacatt accatgtaca tgagcaaaca  29280
gtataagttg tggcccccac aaaattgtgt ggaaaacact ggcactttct gctgcactgc  29340
tatgctaatt acagtgctcg ctttggtctg taccctactc tatattaaat acaaaagcag  29400
acgcagcttt attgaggaaa agaaaatgcc ttaatttact aagttacaaa gctaatgtca  29460
ccactaactg ctttactcgc tgcttgcaaa acaaattcaa aaagttagca ttataattag  29520
aataggattt aaacccccccg gtcatttcct gctcaatacc attccctga caattgact  29580 ctatgtggga tatgctccag cgctacaacc ttgaagtcag gcttcctgga tgtcagcatc  29640
tgactttggc cagcacctgt cccgcggatt tgttccagtc caactacagc gacccaccct  29700
aacagagatg accaacacaa ccaacgcggc cgccgctacc ggacttacat ctaccacaaa  29760
tacaccccaa gtttctgcct ttgtcaataa ctgggataac ttgggcatgt ggtggttctc  29820
catagcgctt atgtttgtat gccttattat tatgtggctc atctgctgcc taaagcgcaa  29880
acgcgcccga ccaccccatct atagtcccat cattgtgcta cacccaaaca atgatggaat  29940
ccatagattg gacggactga aacacatgtt cttttctctt acagtatgat taaatgagac  30000
atgattcctc gagtttttat attactgacc cttgttgcgc ttttttgtgc gtgctccaca  30060
ttggctgcgg tttctcacat cgaagtagac tgcattccag ccttcacagt ctatttgctt  30120 tacgatttg tcaccctcac gctcatctgc agcctcatca ctgtggtcat cgcctttatc  30180
cagtgcattg actgggtctg tgtgcgcttt gcatatctca gacaccatcc ccagtacagg  30240
gacaggacta tagctgagct tcttagaatt ctttaattat gaatttact gtgacttttc  30300 tgctgattat ttgcacccta tctgcgtttt gttccccgac ctccaagcct caaagacata  30360
tatcatgcag attcactcgt atatggaata ttccaagttg ctacaatgaa aaagcgatc  30420 tttccgaagc ctggttatat gcaatcatct ctgttatggt gttctgcagt accatcttag  30480
ccctagctat atatccctac cttgacattg gctggaaacg aatagatgcc atgaaccacc  30540
caactttccc cgcgcccgct atgcttccac tgcaacaagt tgttgccggc ggctttgtcc  30600
cagccaatca gcctcgcccc acttctccca cccccactga aatcagctac tttaatctaa  30660
caggaggaga tgactgacac cctagatcta gaaatgacg gaattattac agagcagcgc  30720
ctgctagaaa gacgcagggc agcggccgag caacagcgca tgaatcaaga gctccaagac  30780
atggttaact tgcaccagtg caaagggggt atcttttgtc tggtaaagca ggccaaagtc  30840
acctacgaca gtaataccac cggacaccgc cttagctaca agttgccaac caagcgtcag  30900
aaattggtgg tcatggtggg agaaaagccc attaccataa ctcagcactc ggtagaaacc  30960
```

```
gaaggctgca ttcactcacc ttgtcaagga cctgaggatc tctgcaccct tattaagacc    31020
ctgtgcggtc tcaaagatct tattcccttt aactaataaa aaaaataat aaagcatcac    31080 ttacttaaaa tcagttagca aatttctgtc cagtttattc agcagcacct ccttgccctc    31140
ctcccagctc tggtattgca gcttcctcct ggctgcaaac tttctccaca atctaaatgg    31200
aatgtcagtt tcctcctgtt cctgtccatc cgcacccact atcttcatgt tgttgcagat    31260
gaagcgcgca agaccgtctg aagataccct caacccgtg tatccatatg acacggaaac    31320
cggtcctcca actgtgcctt ttcttactcc tcccttgta tcccccaatg ggtttcaaga    31380
gagtccccct ggggtactct ctttgcgcct atccgaacct ctagttacct ccaatgggcat    31440 gcttgcgctc aaaatgggca acggcctctc tctggacgag gccggcaacc ttacctccca    31500
aaatgtaacc actgtgagcc cacctctccg aggagacaag tcaaacataa acctggaaat    31560
atctgcaccc ctcacagtta cctcagaagc cctaactgtg gctgccgccg cacctctaat    31620
ggtcgcgggc aacacactca ccatgcaatc acaggcccg ctaaccgtgc acgactccaa    31680
acttagcatt gccacccaag gacccctcac agtgtcagaa ggaaagctag ccctgcaaac    31740
atcaggcccc ctcaccacca ccgatagcag tacccttact atcactgcct cacccccctct    31800 aactactgcc actggtagct tgggcattga cttgaaagag cccatttata cacaaaatgg    31860
aaaactagga ctaaagtacg gggctccttt gcatgtaaca gacgacctaa acactttgac    31920
cgtagcaact ggtccaggtg tgactattaa taatacttcc ttgcaaacta agttactgg    31980 agccttgggt tttgattcac aaggcaatat gcaacttaat gtagcaggag gactaaggat    32040
tgattctcaa aacagacgcc ttatacttga tgttagttat ccgtttgatg ctcaaaacca    32100
actaaatcta agactaggac agggccctct ttttataaac tcagcccaca acttggatat    32160
taactacaac aaaggccttt acttgtttac agcttcaaac aattccaaaa agcttgaggt    32220
taacctaagc actgccaagg ggttgatgtt tgacgctaca gccatagcca ttaatgcagg    32280
agatgggctt gaatttggtt cacctaatgc accaaacaca aatcccctca aaacaaaaat    32340
tggccatggc ctagaatttg attcaaacaa ggctatggtt cctaaactag gaactggcct    32400 tagtttttgac agcacaggtg ccattacagt aggaaacaaa ataatgata agctaacttt    32460 gtggaccaca ccagctccat ctcctaactg tagactaaat gcagagaaag atgctaaact    32520
cactttggtc ttaacaaaat gtggcagtca atacttgct acagtttcag ttttggctgt    32580
taaaggcagt ttggctccaa tatctggaac agttcaaagt gctcatctta ttataagatt    32640
tgacgaaaat ggagtgctac taaacaattc cttcctggac ccagaatatt ggaacttag    32700 aaatggagat cttactgaag gcacagccta tacaaacgct gttggattta tgcctaacct    32760
atcagcttat ccaaaatctc acggtaaaac tgccaaaagt aacattgtca gtcaagttta    32820
cttaaacgga gacaaaacta aacctgtaac actaaccatt acactaaacg gtacacagga    32880
aacaggagac acaactccaa gtgcatactc tatgtcattt tcatgggact ggtctggcca    32940
caactacatt aatgaaatat tgccacatc ctcttacact ttttcataca ttgcccaaga    33000
ataaagaatc gtttgtgtta tgtttcaacg tgtttatttt tcaattgcag aaaatttcaa    33060 gtcattttc attcagtagt atagcccac cacacatag cttatacaga tcaccgtacc    33120
ttaatcaaac tcacagaacc ctagtattca acctgccacc tccctcccaa cacacagagt    33180
acacagtcct ttctccccgg ctggccttaa aaagcatcat atcatgggta acagacatat    33240
tcttaggtgt tatattccac acggtttcct gtcgagccaa acgctcatca gtgatattaa    33300
```

```
taaactcccc gggcagctca cttaagttca tgtcgctgtc cagctgctga gccacaggct    33360
gctgtccaac ttgcggttgc ttaacgggcg gcgaaggaga agtccacgcc tacatggggg    33420
tagagtcata atcgtgcatc aggatagggc ggtggtgctg cagcagcgcg cgaataaact    33480
gctgccgccg ccgctccgtc ctgcaggaat acaacatggc agtggtctcc tcagcgatga    33540
ttcgcaccgc ccgcagcata aggcgccttg tcctccgggc acagcagcgc accctgatct    33600
cacttaaatc agcacagtaa ctgcagcaca gcaccacaat attgttcaaa atcccacagt    33660
gcaaggcgct gtatccaaag ctcatggcgg ggaccacaga acccacgtgg ccatcatacc    33720
acaagcgcag gtagattaag tggcgacccc tcataaacac gctggacata acattaccct    33780
cttttggcat gttgtaattc accacctccc ggtaccatat aaacctctga ttaaacatgg    33840
cgccatccac caccatccta aaccagctgg ccaaaacctg cccgccggct atacactgca    33900
gggaaccggg actgaacaa tgacagtgga gagcccagga ctcgtaacca tggatcatca    33960
tgctcgtcat gatatcaatg ttggcacaac acaggcacac gtgcatacac ttcctcagga    34020
ttacaagctc ctcccgcgtt agaaccatat cccagggaac aacccattcc tgaatcagcg    34080
taaatcccac actgcaggga agacctcgca cgtaactcac gttgtgcatt gtcaaagtgt    34140
tacattcggg cagcagcgga tgatcctcca gtatggtagc gcgggtttct gtctcaaaag    34200
gaggtagacg atccctactg tacggagtgc gccgagacaa ccgagatcgt gttggtcgta    34260
gtgtcatgcc aaatgaaacg ccggacgtag tcatatttcc tgaagcaaaa ccaggtgcgg    34320
gcgtgacaaa cagatctgcg tctccggtct cgccgcttag atcgctctgt gtagtagttg    34380
tagtatatcc actctctcaa agcatccagg cgcccctgg cttcgggttc tatgtaaact    34440
ccttcatgcg ccgctgccct gataacatcc accaccgcag aataagccac acccagccaa    34500
cctacacatt cgttctgcga gtcacacacg ggaggagcgg gaagagctgg aagaaccatg    34560
tttttttttt tattccaaaa gattatccaa aacctcaaaa tgaagatcta ttaagtgaac    34620
gcgctcccct ccgtggcgt ggtcaaactc tacagccaaa gaacagataa tggcatttgt    34680
aagatgttgc acaatggctt ccaaaaggca aacggccctc acgtccaagt ggacgtaaag    34740
gctaaaccct tcagggtgaa tctcctctat aaacattcca gcaccttcaa ccatgcccaa    34800
ataattctca tctcgccacc ttctcaatat atctctaagc aaatcccgaa tattaagtcc    34860
ggccattgta aaaatctgct ccagagcgcc ctccaccttc agcctcaagc agcgaatcat    34920
gattgcaaaa attcaggttc ctcacagacc tgtataagat tcaaaagcgg aacattaaca    34980
aaaataccgc gatcccgtag gtcccttcgc agggccagct gaacataatc gtgcaggtct    35040
gcacggacca gcgcggccac ttccccgcca ggaaccatga caaaagaacc cacactgatt    35100
atgcacacga tactcggagc tatgctaacc agcgtagccc cgatgtaagc ttgttgcatg    35160
ggcggcgata taaaatgcaa ggtgctgctc aaaaaatcag gcaaagcctc gcgcaaaaaa    35220
gaaagcacat cgtagtcatg ctcatgcaga taaaggcagg taagctccgg aaccaccaca    35280
gaaaaagaca ccattttttct ctcaaacatg tctgcgggtt tctgcataaa cacaaaataa    35340
aataacaaaa aaacatttaa acattagaag cctgtcttac aacagaaaaa acaaccctta    35400
taagcataag acggactacg gccatgccgg cgtgaccgta aaaaactgg tcaccgtgat    35460 taaaaagcac caccgacagc tcctcggtca tgtccggagt cataatgtaa gactcggtaa    35520
acacatcagg ttgattcaca tcggtcagtg ctaaaaagcg accgaaatag cccggggaa    35580 tacatacccg caggcgtaga gacaacatta cagcccccat aggaggtata acaaaattaa    35640
taggagagaa aaacacataa acacctgaaa aaccctcctg cctaggcaaa atagcaccct    35700
```

-continued

| | |
|---|---|
| cccgctccag aacaacatac agcgcttcca cagcggcagc cataacagtc agccttacca | 35760 |
| gtaaaaaaga aaacctatta aaaaaacacc actcgcacg gcaccagctc aatcagtcac | 35820 |
| agtgtaaaaa agggccaagt gcagagcgag tatatatagg actaaaaaat gacgtaacgg | 35880 |
| ttaaagtcca caaaaacac ccagaaaacc gcacgcgaac ctacgccag aaacgaaagc | 35940 |
| caaaaaccc acaacttcct caaatcgtca cttccgtttt cccacgttac gtcacttccc | 36000 |
| attttaagaa aactacaatt cccaacacat actagttact ccgccctaaa acctacgtca | 36060 |
| cccgccccgt tcccacgccc cgcgccacgt cacaaactcc accccctcat tatcatattg | 36120 |
| gcttcaatcc aaaataaggt atattattga tgatgt | 36156 |

<210> SEQ ID NO 5
<211> LENGTH: 36090
<212> TYPE: DNA
<213> ORGANISM: Artificial Sequence
<220> FEATURE:
<223> OTHER INFORMATION: ICOVIR15K-QD

<400> SEQUENCE: 5

| | |
|---|---|
| catcatcaat aatataccct attttggatt gaagccaata tgataatgag ggggtggagt | 60 |
| ttgtgacgtg gcgcggggcg tgggaacggg gcgggtgacg tagtagtgtg gcggaagtgt | 120 |
| gatgttgcaa gtgtggcgga acacatgtaa gcgacggatg tggcaaaagt gacgttttg | 180 |
| gtgtgcgccg gtgtacacag gaagtgacaa ttttcgcgcg gttttaggcg gatgttgtag | 240 |
| taaatttggg cgtaaccgag taagatttgg ccattttcgc gggaaaactg aataagagga | 300 |
| agtgaaatct gaataatttt gtgttactca tagcgcgtaa tatttgtcta gggccgcggg | 360 |
| gactttgacc gtttacgtgg agactcgccc aggtgttttt ctcaggtgtt ttccgcgtac | 420 |
| gtcggcggct cgtggctctt tcgcggcaaa aaggatttgg cgcgtaaaag tggttcgagt | 480 |
| acgtcggcgg ctcgtggctc tttcgcggca aaaaggattt ggcgcgtaaa agtggttcga | 540 |
| agtacgtcga ccacaaaccc cgcccagcgt cttgtcattg gcgtcgacgc tgtacggggt | 600 |
| caaagttggc gttttattat tatagtcagc tgacgtgtag tgtatttata cccggtgagt | 660 |
| tcctcaagag gccactcttg agtgccagcg agtagagttt tctcctccga gccgctccga | 720 |
| caccgggact gaaaatgaga catattatct gccacggagg tgttattacc gaagaaatgg | 780 |
| ccgccagtct tttggaccag ctgatcgaag aggtactggc tgataatctt ccacctccta | 840 |
| gccatttga accacctacc cttcacgaac tgtatgattt agacgtgacg gcccccgaag | 900 |
| atcccaacga ggaggcggtt tcgcagattt ttcccgactc tgtaatgttg gcggtgcagg | 960 |
| aagggattga cttactcact tttccgccgg cgcccggttc tccggagccg cctcaccttt | 1020 |
| cccggcagcc cgagcagccg gagcagagag ccttgggtcc ggtttctatg ccaaaccttg | 1080 |
| taccggaggt gatcgatcca cccagtgacg acgaggatga agagggtgag gagtttgtgt | 1140 |
| tagattatgt ggagcacccc gggcacggtt gcagtcttg tcattatcac cggaggaata | 1200 |
| cggggggaccc agatattatg tgttcgcttt gctatatgag gacctgtggc atgtttgtct | 1260 |
| acagtaagtg aaaattatgg gcagtgggtg atagagtggt gggtttggtg tggtaatttt | 1320 |
| tttttttaatt tttacagttt tgtggtttaa agaattttgt attgtgattt ttttaaaagg | 1380 |
| tcctgtgtct gaacctgagc ctgagcccga gccagaaccg gagcctgcaa gacctacccg | 1440 |
| ccgtcctaaa atggcgcctg ctatcctgag acgcccgaca tcacctgtgt ccagagaatg | 1500 |
| caatagtagt acggatagct gtgactccgg tccttctaac acacctcctg agatacaccc | 1560 |

```
ggtggtcccg ctgtgcccca ttaaaccagt tgccgtgaga gttggtgggc gtcgccaggc   1620
tgtggaatgt atcgaggact tgcttaacga gcctgggcaa cctttggact tgagctgtaa   1680
acgccccagg ccataaggtg taaacctgtg attgcgtgtg tggttaacgc ctttgtttgc   1740
tgaatgagtt gatgtaagtt taataaaggg tgagataatg tttaacttgc atggcgtgtt   1800
aaatggggcg gggcttaaag ggtatataat gcgccgtggg ctaatcttgg ttacatctga   1860
cctcatggag gcttgggagt gttttggaaga ttttctgct gtgcgtaact tgctggaaca   1920
gagctctaac agtacctctt ggttttggag gtttctgtgg ggctcatccc aggcaaagtt   1980
agtctgcaga attaaggagg attacaagtg ggaatttgaa gagcttttga aatcctgtgg   2040
tgagctgttt gattctttga atctgggtca ccaggcgctt ttccaagaga aggtcatcaa   2100
gactttggat ttttccacac cggggcgcgc tgccggctgct gttgcttttt tgagttttat   2160
aaaggataaa tggagcgaag aaacccatct gagcgggggg tacctgctgg attttctggc   2220
catgcatctg tggagagcgg ttgtgagaca caagaatcgc ctgctactgt tgtcttccgt   2280
ccgcccggcg ataataccga cggaggagca gcagcagcag caggaggaag ccaggcggcg   2340
gcggcaggag cagagcccat ggaacccgag agccggcctg gaccctcggg aatgaatgtt   2400
gtacaggtgg ctgaactgta tccagaactg agacgcattt tgacaattac agaggatggg   2460
caggggctaa aggggtaaa gagggagcgg ggggcttgtg aggctacaga ggaggctagg   2520
aatctagctt ttagcttaat gaccagacac cgtcctgagt gtattacttt tcaacagatc   2580
aaggataatt gcgctaatga gcttgatctg ctggcgcaga agtattccat agagcagctg   2640
accacttact ggctgcagcc aggggatgat tttgaggagg ctattagggt atatgcaaag   2700
gtggcactta ggccagattg caagtacaag atcagcaaac ttgtaaatat caggaattgt   2760
tgctacattt ctgggaacgg ggccgagtg gagatagata cggaggatag ggtggccttt   2820
agatgtagca tgataaatat gtggccgggg gtgcttggca tggacggggt ggttattatg   2880
aatgtaaggt ttactggccc caattttagc ggtacggttt tcctggccaa taccaacctt   2940
atcctacacg gtgtaagctt ctatgggttt aacaatacct gtgtggaagc ctggaccgat   3000
gtaagggttc gggctgtgc ctttactgc tgctggaagg gggtggtgtg tcgccccaaa   3060
agcagggctt caattaagaa atgcctcttt gaaaggtgta ccttgggtat cctgtctgag   3120
ggtaactcca gggtgcgcca caatgtggcc tccgactgtg gttgcttcat gctagtgaaa   3180
agcgtggctg tgattaagca taacatggta tgtggcaact gcgaggacag ggcctctcag   3240
atgctgacct gctcggacgg caactgtcac ctgctgaaga ccattcacgt agccagccac   3300
tctcgcaagg cctggccagt gtttgagcat aacatactga cccgctgttc cttgcatttg   3360
ggtaacagga gggggtgtt cctaccttac caatgcaatt tgagtcacac taagatattg   3420
cttgagcccg agagcatgtc caaggtgaac ctgaacgggg tgtttgacat gaccatgaag   3480
atctggaagg tgctgaggta cgatgagacc cgcaccaggt gcagaccctg cgagtgtggc   3540
ggtaaacata ttaggaacca gcctgtgatg ctggatgtga ccgaggagct gaggcccgat   3600
cacttggtgc tggcctgcac ccgcgctgag tttggctcta gcgatgaaga tacagattga   3660
ggtactgaaa tgtgtgggcg tggcttaagg gtggaaaga atatataagg tggggtctt   3720 atgtagtttt gtatctgttt tgcagcagcc gccgccgcca tgagcaccaa ctcgtttgat   3780
ggaagcattg tgagctcata tttgacaacg cgcatgcccc catgggccgg ggtgcgtcag   3840
aatgtgatgg gctccagcat tgatggtcgc cccgtcctgc ccgcaaactc tactaccttg   3900
acctacgaga ccgtgtctgg aacgccgttg gagactgcag cctccgccgc cgcttcagcc   3960
```

```
gctgcagcca ccgcccgcgg gattgtgact gactttgctt tcctgagccc gcttgcaagc    4020
agtgcagctt cccgttcatc cgcccgcgat gacaagttga cggctctttt ggcacaattg    4080
gattctttga cccgggaact taatgtcgtt tctcagcagc tgttggatct gcgccagcag    4140
gtttctgccc tgaaggcttc ctcccctccc aatgcggttt aaaacataaa taaaaaacca    4200
gactctgttt ggatttggat caagcaagtg tcttgctgtc tttatttagg ggttttgcgc    4260
gcgcggtagg cccgggacca gcggtctcgg tcgttgaggg tcctgtgtat tttttccagg    4320
acgtggtaaa ggtgactctg gatgttcaga tacatgggca taagcccgtc tctggggtgg    4380
aggtagcacc actgcagagc ttcatgctgc ggggtggtgt tgtagatgat ccagtcgtag    4440
caggagcgct gggcgtggtg cctaaaaatg tctttcagta gcaagctgat tgccaggggc    4500
aggcccttgg tgtaagtgtt tacaaagcgg ttaagctggg atgggtgcat acgtggggat    4560
atgagatgca tcttggactg tattttaggt tggctatgt tcccagccat atccctccgg     4620
ggattcatgt tgtgcagaac caccagcaca gtgtatccgg tgcacttggg aaatttgtca    4680
tgtagcttag aaggaaatgc gtggaagaac ttggagacgc ccttgtgacc tccaagattt    4740
tccatgcatt cgtccataat gatggcaatg ggcccacggg cggcggcctg ggcgaagata    4800
tttctgggat cactaacgtc atagttgtgt tccaggatga gatcgtcata ggccattttt    4860
acaaagcgcg gcggagggt gccagactgc ggtataatgg ttccatccgg cccaggggcg     4920
tagttaccct cacagatttg catttcccac gctttgagtt cagatggggg gatcatgtct    4980
acctgcgggg cgatgaagaa aacggtttcc ggggtagggg agatcagctg gaagaaagc     5040 aggttcctga gcagctgcga cttaccgcag ccggtgggcc cgtaaatcac acctattacc    5100
gggtgcaact ggtagttaag agagctgcag ctgccgtcat ccctgagcag ggggggccact   5160 tcgttaagca tgtccctgac tcgcatgttt ccctgacca aatccgccag aaggcgctcg     5220
ccgcccagcg atagcagttc ttgcaaggaa gcaaagtttt tcaacggttt gagaccgtcc    5280
gccgtaggca tgcttttgag cgtttgacca agcagttcca ggcggtccca cagctcggtc    5340
acctgctcta cggcatctcg atccagcata tctcctcgtt tcgcggggttg gggcggcttt   5400 cgctgtacgg cagtagtcgg tgctcgtcca gacgggccag ggtcatgtct ttccacgggc    5460
gcagggtcct cgtcagcgta gtctgggtca cggtgaaggg gtgcgctccg ggctgcgcgc    5520
tggccagggt gcgcttgagg ctggtcctgc tggtgctgaa gcgctgccgg tcttcgccct    5580
gcgcgtcggc caggtagcat ttgaccatgg tgtcatagtc cagcccctcc gcggcgtggc    5640
ccttggcgcg cagcttgccc ttggaggagg cgccgcacga ggggcagtgc agactttga    5700 gggcgtagag cttgggcgcg agaaataccg attccgggga gtaggcatcc gcgccgcagg    5760
ccccgcagac ggtctcgcat tccacgagcc aggtgagctc tggccgttcg ggtcaaaaa    5820 ccaggttttcc cccatgcttt ttgatgcgtt tcttacctct ggtttccatg agccggtgtc    5880
cacgctcggt gacgaaaagg ctgtccgtgt ccccgtatac agacttgaga ggcctgtcct    5940
cgagcggtgt tccgcggtcc tcctcgtata gaaactcgga ccactctgag acaaaggctc    6000
gcgtccaggc cagcacgaag gaggctaagt gggagggta gcggtcgttg tccactaggg     6060
ggtccactcg ctccagggtg tgaagacaca tgtcgccctc ttcggcatca aggaaggtga    6120 ttggttttgta ggtgtaggcc acgtgaccgg tgttcctga agggggggcta taaaaggggg    6180 tggggggcgcg ttcgtcctca ctctcttccg catcgctgtc tgcgagggcc agctgttggg    6240
gtgagtactc cctctgaaaa gcgggcatga cttctgcgct aagattgtca gtttccaaaa    6300
```

```
acgaggagga tttgatattc acctggcccg cggtgatgcc tttgagggtg gccgcatcca   6360
tctggtcaga aaagacaatc tttttgttgt caagcttggt ggcaaacgac ccgtagaggg   6420
cgttggacag caacttggcg atggagcgca gggtttggtt tttgtcgcga tcggcgcgct   6480
ccttggccgc gatgtttagc tgcacgtatt cgcgcgcaac gcaccgccat tcgggaaaga   6540
cggtggtgcg ctcgtcgggc accaggtgca cgcgccaacc gcggttgtgc agggtgacaa   6600
ggtcaacgct ggtggctacc tctccgcgta ggcgctcgtt ggtccagcag aggcggccgc   6660
ccttgcgcga gcagaatggc ggtagggggt ctagctgcgt ctcgtccggg gggtctgcgt   6720
ccacggtaaa gaccccgggc agcaggcgcg cgtcgaagta gtctatcttg catccttgca   6780
agtctagcgc ctgctgccat gcgcgggcgg caagcgcgcg ctcgtatggg ttgagtgggg   6840
gaccccatgg catggggtgg gtgagcgcgg aggcgtacat gccgcaaatg tcgtaaacgt   6900 agagggctc tctgagtatt ccaagatatg tagggtagca tcttccaccg cggatgctgg   6960
cgcgcacgta atcgtatagt tcgtgcgagg gagcgaggag gtcgggaccg aggttgctac   7020
gggcgggctg ctctgctcgg aagactatct gcctgaagat ggcatgtgag ttggatgata   7080
tggttggacg ctggaagacg ttgaagctgg cgtctgtgag acctaccgcg tcacgcacga   7140
aggaggcgta ggagtcgcgc agcttgttga ccagctcggc ggtgacctgc acgtctaggg   7200
cgcagtagtc cagggtttcc ttgatgatgt catacttatc ctgtccctt ttttccaca    7260 gctcgcggtt gaggacaaac tcttcgcggt cttttccagta ctcttggatc ggaaacccgt   7320
cggcctccga acggtaagag cctagcatgt agaactggtt gacggcctgg taggcgcagc   7380 atccctttc tacgggtagc gcgtatgcct gcgcggcctt ccggagcgag gtgtgggtga   7440
gcgcaaaggt gtccctgacc atgactttga ggtactggta tttgaagtca gtgtcgtcgc   7500
atccgccctg ctcccagagc aaaaagtccg tgcgcttttt ggaacgcgga tttggcaggg   7560
cgaaggtgac atcgttgaag agtatctttc ccgcgcgagg cataaagttg cgtgtgatgc   7620
ggaagggtcc cggcacctcg gaacggttgt taattacctg ggcggcgagc acgatctcgt   7680
caaagccgtt gatgttgtgg cccacaatgt aaagttccaa gaagcgcggg atgcccttga   7740
tggaaggcaa ttttttaagt tcctcgtagg tgagctcttc aggggagctg agcccgtgct   7800
ctgaaagggc ccagtctgca agatgagggt tggaagcgac gaatgagctc cacaggtcac   7860
gggccattag catttgcagg tggtcgcgaa aggtcctaaa ctggcgacct atggccattt   7920
tttctggggt gatgcagtag aaggtaagcg ggtcttgttc ccagcggtcc catccaaggt   7980
tcgcggctag gtctcgcgcg gcagtcacta gaggctcatc tccgccgaac ttcatgacca   8040
gcatgaaggg cacgagctgc ttcccaaagg cccccatcca agtataggtc tctacatcgt   8100
aggtgacaaa gagacgctcg gtgcgaggat gcgagccgat cgggaagaac tggatctccc   8160
gccaccaatt ggaggagtgg ctattgatgt ggtgaaagta gaagtccctg cgacgggccg   8220
aacactcgtg ctggcttttg taaaaacgtg cgcagtactg gcagcggtgc acgggctgta   8280
catcctgcac gaggttgacc tgacgaccgc gcacaaggaa gcagagtggg aatttgagcc   8340
cctcgcctgg cgggtttggc tggtggtctt tacttcggc tgcttgtcct tgaccgtctg    8400
gctgctcgag gggagttacg gtggatcgga ccaccacgcc gcgcgagccc aaagtccaga   8460
tgtccgcgcg cggcggtcgg agcttgatga caacatcgcg cagatgggag ctgtccatgg   8520
tctggagctc ccgcggcgtc aggtcaggcg ggagctcctg caggtttacc tcgcatagac   8580
gggtcagggc gcgggctaga tccaggtgat acctaatttc caggggctgg ttggtggcgg   8640
cgtcgatggc ttgcaagagg ccgcatcccc gcggcgcgac tacggtaccg cgcggcgggc   8700
```

```
ggtgggccgc gggggtgtcc ttggatgatg catctaaaag cggtgacgcg ggcgagcccc    8760
cggaggtagg gggggctccg gacccgccgg gagaggggc aggggcacgt cggcgccgcg     8820
cgcgggcagg agctggtgct gcgcgcgtag gttgctggcg aacgcgacga cgcggcggtt    8880
gatctcctga atctgcgcc tctgcgtgaa gacgacgggc ccggtgagct tgagcctgaa     8940
agagagttcg acagaatcaa tttcggtgtc gttgacggcg gcctggcgca aaatctcctg    9000
cacgtctcct gagttgtctt gataggcgat ctcggccatg aactgctcga tctcttcctc    9060
ctggagatct ccgcgtccgg ctcgctccac ggtggcggcg aggtcgttgg aaatgcgggc    9120
catgagctgc gagaaggcgt tgaggcctcc ctcgttccag acgcggctgt agaccacgcc    9180
cccttcggca tcgcgggcgc gcatgaccac ctgcgcgaga ttgagctcca cgtgccgggc    9240
gaagacggcg tagtttcgca ggcgctgaaa gaggtagttg agggtggtgg cggtgtgttc    9300
tgccacgaag aagtacataa cccagcgtcg caacgtggat tcgttgatat cccccaaggc    9360
ctcaaggcgc tccatggcct cgtagaagtc cacggcgaag ttgaaaaact gggagttgcg    9420
cgccgacacg gttaactcct cctccagaag acggatgagc tcggcgacag tgtcgcgcac    9480
ctcgcgctca aaggctacag gggcctcttc ttcttcttca atctcctctt ccataagggc    9540
ctccccttct tcttcttctg gcggcggtgg gggagggggg acacggcggc gacgacggcg    9600
caccgggagg cggtcgacaa agcgctcgat catctcccccg cggcgacggc gcatggtctc    9660
ggtgacggcg cggccgttct cgcggggggcg cagttggaag acgccgcccg tcatgtcccg    9720
gttatgggtt ggcgggggc tgccatgcgg cagggatacg gcgctaacga tgcatctcaa    9780
caattgttgt gtaggtactc cgccgccgag ggacctgagc gagtccgcat cgaccggatc    9840
ggaaaacctc tcgagaaagg cgtctaacca gtcacagtcg caaggtaggc tgagcaccgt    9900
ggcgggcggc agcgggcggc ggtcggggtt gtttctggcg gaggtgctgc tgatgatgta    9960
attaaagtag gcggtcttga gacgcggat ggtcgacaga agcaccatgt ccttgggtcc    10020
ggcctgctga atgcgcaggc ggtcggccat gccccaggct tcgttttgac atcggcgcag    10080
gtctttgtag tagtcttgca tgagccttc taccggcact tcttcttctc cttcctcttg    10140
tcctgcatct cttgcatcta tcgctgcggc ggcggcggag tttggccgta ggtggcgccc    10200
tcttcctccc atgcgtgtga ccccgaagcc cctcatcggc tgaagcaggg ctaggtcggc    10260
gacaacgcgc tcggctaata tggcctgctg cacctgcgtg agggtagact ggaagtcatc    10320
catgtccaca aagcggtggt atgcgcccgt gttgatggtg taagtgcagt tggccataac    10380
ggaccagtta acggtctggt gacccggctg cgagagctcg gtgtacctga gacgcgagta    10440
agccctcgag tcaaatacgt agtcgttgca agtccgcacc aggtactggt atcccaccaa    10500
aaagtgcggc ggcggctggc ggtagagggg ccagcgtagg gtggccgggg ctccggggc    10560 gagatcttcc aacataaggc gatgatatcc gtagatgtac ctggacatcc aggtgatgcc    10620
ggcggcggtg gtggaggcgc gcggaaagtc gcggacgcgg ttccagatgt tgcgcagcgg    10680
caaaaagtgc tccatggtcg ggacgctctg gccggtcagg cgcgcgcaat cgttgacgct    10740
ctagaccgtg caaaggaga gcctgtaagc gggcactctt ccgtggtctg gtggataaat    10800
tcgcaagggt atcatggcgg acgaccgggg ttcgagcccc gtatccggcc gtccgccgtg    10860
atccatgcgg ttaccgcccg cgtgtcgaac ccaggtgtgc gacgtcagac aacggggag    10920 tgctcctttt ggcttccttc caggcgcggc ggctgctgcg ctagcttttt tggccactgg    10980
ccgcgcgcag cgtaagcggt taggctggaa agcgaaagca ttaagtggct cgctccctgt    11040
```

```
agccggaggg ttatttttcca agggttgagt cgcgggaccc ccggttcgag tctcggaccg   11100
gccggactgc ggcgaacggg ggtttgcctc cccgtcatgc aagacccgc ttgcaaattc     11160 ctccggaaac agggacgagc cccttttttg cttttcccag atgcatccgg tgctgcggca    11220
gatgcgcccc cctcctcagc agcggcaaga gcaagagcag cggcagacat gcagggcacc    11280
ctcccctcct cctaccgcgt caggagggc gacatccgcg gttgacgcgg cagcagatgg     11340
tgattacgaa ccccccgcggc gccgggcccg gcactacctg gacttggagg agggcgaggg   11400
cctggcgcgg ctaggagcgc cctctcctga gcggtaccca agggtgcagc tgaagcgtga   11460
tacgcgtgag gcgtacgtgc cgcggcagaa cctgtttcgc gaccgcgagg gagaggagcc    11520
cgaggagatg cgggatcgaa agttccacgc agggcgcgag ctgcggcatg gcctgaatcg    11580
cgagcggttg ctgcgcgagg aggactttga gcccgacgcg cgaaccggga ttagtcccgc    11640
gcgcgcacac gtggcggccg ccgacctggt aaccgcatac gagcagacgg tgaaccagga    11700
gattaacttt caaaaaagct ttaacaacca cgtgcgtacg cttgtggcgc gcgaggaggt    11760
ggctatagga ctgatgcatc tgtgggactt tgtaagcgcg ctggagcaaa acccaaatag    11820
caagccgctc atggcgcagc tgttccttat agtgcagcac agcagggaca acgaggcatt    11880
cagggatgcg ctgctaaaca tagtagagcc cgagggccgc tggctgctcg atttgataaa    11940
catcctgcag agcatagtgg tgcaggagcg cagcttgagc ctggctgaca aggtggccgc    12000
catcaactat tccatgctta gcctgggcaa gttttacgcc cgcaagatat accatacccc    12060
ttacgttccc atagacaagg aggtaaagat cgaggggttc tacatgcgca tggcgctgaa    12120
ggtgcttacc ttgagcgacg acctgggcgt ttatcgcaac gagcgcatcc acaaggccgt    12180
gagcgtgagc cggcggcgcg agctcagcga ccgcgagctg atgcacagcc tgcaaagggc    12240
cctggctggg acgggcagcg gcgatagaga ggccgagtcc tactttgacg cgggcgctga    12300
cctgcgctgg gccccaagcc gacgcgccct ggaggcagct ggggccggac ctgggctggc    12360
ggtggcaccc cgcgcgcgctg gcaacgtcgg cggcgtggag gaatatgacg aggacgatga    12420
gtacgagcca gaggacggcg agtactaagc ggtgatgttt ctgatcagat gatgcaagac    12480
gcaacggacc cggcggtgcg ggcggcgctg cagagccagc cgtccggcct taactccacg    12540
gacgactggc gccaggtcat ggaccgcatc atgtcgctga ctgcgcgcaa tcctgacgcg    12600
ttccggcagc agccgcaggc caaccggctc tccgcaattc tggaagcggt ggtcccggcg    12660
cgcgcaaacc ccacgcacga aaggtgctg gcgatcgtaa acgcgctggc cgaaaacagg    12720
gccatccggc ccgacgaggc cggcctggtc tacgacgcgc tgcttcagcg cgtggctcgt    12780
tacaacagcg gcaacgtgca gaccaacctg gaccggctgg tggggatgt gcgcgaggcc    12840 gtggcgcagc gtgagcgcgc gcagcagcag ggcaacctgg gctccatggt tgcactaaac    12900
gccttcctga gtacacagcc cgccaacgtg ccgcggggac aggaggacta caccaacttt    12960
gtgagcgcac tgcggctaat ggtgactgag acaccgcaaa gtgaggtgta ccagtctggg    13020
ccagactatt ttttccagac cagtagacaa ggcctgcaga ccgtaaacct gagccaggct    13080
ttcaaaaact tgcaggggct gtgggggtg cgggctccca caggcgaccg cgcgaccgtg    13140
tctagcttgc tgacgcccaa ctcgcgcctg ttgctgctgc taatagcgcc cttcacggac    13200
agtggcagcg tgtcccggga cacataccta ggtcacttgc tgacactgta ccgcgaggcc    13260
ataggtcagg cgcatgtgga cgagcatact ttccaggaga ttacaagtgt cagccgcgcg    13320
ctggggcagg aggacacggg cagcctggag gcaaccctaa actacctgct gaccaaccgg    13380
cggcagaaga tcccctcgtt gcacagttta aacagcgagg aggagcgcat tttgcgctac    13440
```

```
gtgcagcaga gcgtgagcct taacctgatg cgcgacgggg taacgcccag cgtggcgctg   13500
gacatgaccg cgcgcaacat ggaacgggc atgtatgcct caaaccggcc gtttatcaac   13560
cgcctaatgg actacttgca tcgcgcggcc gccgtgaacc ccgagtattt caccaatgcc   13620
atcttgaacc cgcactggct accgccccct ggtttctaca ccgggggatt cgaggtgccc   13680
gagggtaacg atggattcct ctgggacgac atagacgaca gcgtgttttc cccgcaaccg   13740
cagaccctgc tagagttgca acagcgcgag caggcagagg cggcgctgcg aaaggaaagc   13800
ttccgcaggc caagcagctt gtccgatcta ggcgctgcgg ccccgcggtc agatgctagt   13860
agcccatttc caagcttgat agggtctctt accagcactc gcaccacccg cccgcgcctg   13920
ctgggcgagg aggagtacct aaacaactcg ctgctgcagc cgcagcgcga aaaaaacctg   13980
cctccggcat ttcccaacaa cgggatagag agcctagtgg acaagatgag tagatggaag   14040
acgtacgcgc aggagcacag ggacgtgcca ggcccgcgcc cgcccacccg tcgtcaaagg   14100
cacgaccgtc agcggggtct ggtgtgggag gacgatgact cggcagacga cagcagcgtc   14160
ctggatttgg gagggagtgg caacccgttt gcgcaccttc gccccaggct ggggagaatg   14220
ttttaaaaaa aaaaaagcat gatgcaaaat aaaaaactca ccaaggccat ggcaccgagc   14280
gttggttttc ttgtattccc cttagtatgc ggcgcgcggc gatgtatgag aaggtcctc   14340 ctccctccta cgagagtgtg gtgagcgcgg cgccagtggc ggcggcgctg ggttctccct   14400
tcgatgctcc cctggacccg ccgtttgtgc ctccgcggta cctgcggcct accgggggga   14460
gaaacagcat ccgttactct gagttggcac ccctattcga caccacccgt gtgtacctgg   14520
tggacaacaa gtcaacggat gtggcatccc tgaactacca gaacgaccac agcaactttc   14580
tgaccacggt cattcaaaac aatgactaca gcccggggga ggcaagcaca cagaccatca   14640
atcttgacga ccggtcgcac tggggcggcg acctgaaaac catcctgcat accaacatgc   14700
caaatgtgaa cgagttcatg tttaccaata agtttaaggc gcgggtgatg gtgtcgcgct   14760
tgcctactaa ggacaatcag gtggagctga aatacgagtg ggtggagttc acgctgcccg   14820
agggcaacta ctccgagacc atgaccatag accttatgaa caacgcgatc gtggagcact   14880
acttgaaagt gggcagacag aacgggttc tggaaagcga catcggggta agtttgaca   14940 cccgcaactt cagactgggg tttgaccccg tcactggtct tgtcatgcct ggggtatata   15000
caaacgaagc cttccatcca gacatcattt tgctgccagg atgcggggtg gacttcaccc   15060
acagccgcct gagcaacttg ttgggcatcc gcaagcggca acccttccag gagggcttta   15120
ggatcaccta cgatgatctg gagggtggta acattcccgc actgttggat gtggacgcct   15180
accaggcgag cttgaaagat gacaccgaac agggcggggg tggcgcaggc ggcagcaaca   15240
gcagtggcag cggcgcggaa gagaactcca acgcggcagc cgcggcaatg cagccggtgg   15300
aggacatgaa cgatcatgcc attgcgcgcg acaccttgc cacacgggct gaggagaagc   15360
gcgctgaggc cgaagcagcg gccgaagctg ccgcccccgc tgcgcaaccc gaggtcgaga   15420
agcctcagaa gaaaccggtg atcaaacccc tgacagagga cagcaagaaa cgcagttaca   15480
acctaataag caatgacagc accttcaccc agtaccgcag ctggtacctt gcatacaact   15540
acggcgaccc tcagaccgga atccgctcat ggacctgct ttgcactcct gacgtaacct   15600
gcggctcgga gcaggtctac tggtcgttgc cagacatgat gcaagacccc gtgaccttcc   15660
gctccacgcg ccagatcagc aactttccgg tggtgggcgc cgagctgttg cccgtgcact   15720
ccaagagctt ctacaacgac caggccgtct actcccaact catccgccag tttacctctc   15780
```

```
tgacccacgt gttcaatcgc tttcccgaga accagatttt ggcgcgcccg ccagccccca   15840
ccatcaccac cgtcagtgaa aacgttcctg ctctcacaga tcacgggacg ctaccgctgc   15900
gcaacagcat cggaggagtc cagcgagtga ccattactga cgccagacgc cgcacctgcc   15960
cctacgttta caaggccctg ggcatagtct cgccgcgcgt cctatcgagc cgcactttt   16020 gagcaagcat gtccatcctt atatcgccca gcaataacac aggctggggc ctgcgcttcc   16080
caagcaagat gtttggcggg gccaagaagc gctccgacca acaccagtg cgcgtgcgcg    16140 ggcactaccg cgcgccctgg ggcgcgcaca aacgcggccg cactgggcgc accaccgtcg   16200
atgacgccat cgacgcggtg gtggaggagg cgcgcaacta cacgcccacg ccgccaccag   16260
tgtccacagt ggacgcggcc attcagaccg tggtgcgcgg agcccggcgc tatgctaaaa   16320
tgaagacgcg gcgaggcgc gtagcacgtc gccaccgccg ccgacccggc actgccgccc    16380
aacgcgcggc ggcggccctg cttaaccgcg cacgtcgcac cggccgacgg gcggccatgc   16440
gggccgctcg aaggctggcc gcgggtattg tcactgtgcc ccccaggtcc aggcgacgag   16500
cggccgccgc agcagccgcg gccattagtg ctatgactca gggtcgcagg ggcaacgtgt   16560
attgggtgcg cgactcggtt agcggcctgc gcgtgcccgt gcgcacccgc ccccgcgca   16620 actagattgc aagaaaaaac tacttagact cgtactgttg tatgtatcca gcggcggcgg   16680
cgcgcaacga agctatgtcc aagcgcaaaa tcaaagaaga gatgctccag gtcatcgcgc   16740
cggagatcta tggcccccg aagaaggaag agcaggatta caagcccga aagctaaagc    16800 gggtcaaaaa gaaaaagaaa gatgatgatg atgaacttga cgacgaggtg gaactgctgc   16860
acgctaccgc gcccaggcga cgggtacagt ggaaaggtcg acgcgtaaaa cgtgttttgc   16920
gacccggcac caccgtagtc tttacgcccg gtgagcgctc caccgcacc tacaagcgcg    16980 tgtatgatga ggtgtacggc gacgaggacc tgcttgagca ggccaacgag cgcctcgggg   17040
agtttgccta cggaaagcgg cataaggaca tgctggcgtt gccgctggac gagggcaacc   17100
caacacctag cctaaagccc gtaacactgc agcaggtgct gccgcgcgtt gcaccgtccg    17160
aagaaaagcg cggcctaaag cgcgagtctg gtgacttggc acccaccgtg cagctgatgg   17220
tacccaagcg ccagcgactg gaaagatgtct tggaaaaaat gaccgtggaa cctgggctgg    17280
agcccgaggt ccgcgtgcgg ccaatcaagc aggtggcgcc gggactgggc gtgcagaccg   17340
tggacgttca gatacccact accagtagca ccagtattgc caccgccaca gagggcatgg   17400
agacacaaac gtccccggtt gcctcagcgg tggcggatgc cgcggtgcag gcggtcgctg   17460
cggccgcgtc caagacctct acggaggtgc aaacggaccc gtggatgttt cgcgtttcag   17520 cccccggcg cccgcgcggt tcgaggaagt acggcgccgc cagcgcgcta ctgcccgaat   17580
atgccctaca tccttccatt gcgcctaccc ccggctatcg tggctacacc taccgcccca    17640
gaagacgagc aactacccga cgccgaacca ccactggaac ccgccgccgc cgtcgccgtc    17700
gccagcccgt gctggccccg atttccgtgc gcagggtggc tcgcgaagga ggcaggaccc   17760
tggtgctgcc aacagcgcgc taccacccca gcatcgttta aaagccggtc tttgtggttc   17820
ttgcagatat ggccctcacc tgccgcctcc gttttccggt gccgggattc cgaggaagaa   17880
tgcaccgtag gagggcatg gccggccacg gcctgacggg cggcatgcgt cgtgcgcacc    17940
accggcggcg gcgcgcgtcg caccgtcgca tgcgcggcgg tatcctgccc ctccttattc   18000
cactgatcgc cgcggcgatt ggcgccgtgc ccggaattgc atccgtggcc ttgcaggcgc   18060
agagacactg attaaaaaca agttgcatgt ggaaaaatca aataaaaag tctgaactct     18120 cacgctcgct tggtcctgta actatttgt agaatggaag acatcaactt tgcgtctctg   18180
```

-continued

```
gccccgcgac acggctcgcg cccgttcatg ggaaactggc aagatatcgg caccagcaat   18240
atgagcggtg gcgccttcag ctggggctcg ctgtggagcg gcattaaaaa tttcggttcc   18300
accgttaaga actatggcag caaggcctgg aacagcagca caggccagat gctgagggat   18360
aagttgaaag agcaaaattt ccaacaaaag gtggtagatg gcctggcctc tggcattagc   18420
ggggtggtgg acctggccaa ccaggcagtg caaaataaga ttaacagtaa gcttgatccc   18480
cgccctcccg tagaggagcc tccaccggcc gtggagacag tgtctccaga ggggcgtggc   18540
gaaaagcgtc cgcgccccga cagggaagaa actctggtga cgcaaataga cgagcctccc   18600
tcgtacgagg aggcactaaa gcaaggcctg cccaccaccc gtcccatcgc gcccatggct   18660
accggagtgc tgggccagca cacacccgta acgctggacc tgcctccccc cgccgacacc   18720
cagcagaaac ctgtgctgcc aggcccgacc gccgttgttg taacccgtcc tagccgcgcg   18780
tccctgcgcc gcgccgccag cggtccgcga tcgttgcggc ccgtagccag tggcaactgg   18840
caaagcacac tgaacagcat cgtgggtctg ggggtgcaat ccctgaagcg ccgacgatgc   18900
ttctgaatag ctaacgtgtc gtatgtgtgt catgtatgcg tccatgtcgc cgccagagga   18960
gctgctgagc cgccgcgcgc ccgctttcca agatggctac cccttcgatg atgccgcagt   19020
ggtcttacat gcacatctcg ggccaggacg cctcggagta cctgagcccc gggctggtgc   19080
agtttgcccg cgccaccgag acgtacttca gcctgaataa caagtttaga aaccccacgg   19140
tggcgcctac gcacgacgtg accacagacc ggtcccagcg tttgacgctg cggttcatcc   19200
ctgtggaccg tgaggatact gcgtactcgt acaaggcgcg gttcacccta gctgtgggtg   19260
ataaccgtgt gctggacatg gcttccacgt actttgacat ccgcgcgtg ctggacaggg   19320
gccctacttt taagccctac tctggcactg cctacaacgc cctggctccc aagggtgccc   19380
caaatccttg cgaatgggat gaagctgcta ctgctcttga aataaaccta gaagaagagg   19440
acgatgacaa cgaagacgaa gtagacgagc aagctgagca gcaaaaaact cacgtatttg   19500
ggcaggcgcc ttattctggt ataaatatta caaaggaggg tattcaaata ggtgtcgaag   19560
gtcaaacacc taaatatgcc gataaaacat ttcaacctga acctcaaata ggagaatctc   19620
agtggtacga aactgaaatt aatcatgcag ctgggagagt ccttaaaaag actaccccaa   19680
tgaaaccatg ttacggttca tatgcaaaac ccacaaatga aaatggaggg caaggcattc   19740
ttgtaaagca acaaaatgga aagctagaaa gtcaagtgga aatgcaattt ttctcaacta   19800
ctgaggcgac cgcaggcaat ggtgataact tgactcctaa agtggtattg tacagtgaag   19860
atgtagatat agaaacccca gacactcata tttcttacat gcccactatt aaggaaggta   19920
actcacgaga actaatgggc caacaatcta tgcccaacag gcctaattac attgctttta   19980
gggacaattt tattggtcta atgtattaca acagcacggg taatatgggt gttctggcgg   20040
gccaagcatc gcagttgaat gctgttgtag atttgcaaga cagaaacaca gagctttcat   20100
accagctttt gcttgattcc attggtgata gaaccaggta cttttctatg tggaatcagg   20160
ctgttgacag ctatgatcca gatgttagaa ttattgaaaa tcatggaact gaagatgaac   20220
ttccaaatta ctgctttcca ctgggaggtg tgattaatac agagactctt accaaggtaa   20280
aacctaaaac aggtcaggaa atggatggg aaaaagatgc tacagaattt tcagataaaa   20340
atgaaataag agttggaaat aattttgcca tggaatcaa tctaaatgcc aacctgtgga   20400
gaaatttcct gtactccaac atagcgctgt atttgcccga caagctaaag tacagtcctt   20460
ccaacgtaaa aatttctgat aacccaaaca cctacgacta catgaacaag cgagtggtgg   20520
```

```
ctcccgggtt agtggactgc tacattaacc ccggagcacg ctggtccctt gactatatgg    20580
acaacgtcaa cccatttaac caccaccgca atgctggcct gcgctaccgc tcaatgttgc    20640
tgggcaatgg tcgctatgtg cccttccaca tccaggtgcc tcagaagttc tttgccatta    20700
aaaacctcct tctcctgccg ggctcataca cctacgagtg gaacttcagg aaggatgtta    20760
acatggttct gcagagctcc ctaggaaatg acctaagggt tgacggagcc agcattaagt    20820
ttgatagcat ttgcctttac gccaccttct tccccatggc ccacaacacc gcctccacgc    20880
ttgaggccat gcttagaaac gacaccaacg accagtcctt taacgactat ctctccgccg    20940
ccaacatgct ctaccctata cccgccaacg ctaccaacgt gcccatatcc atccctcc    21000 gcaactgggc ggctttccgc ggctgggcct tcacgcgcct taagactaag gaaaccccat    21060
cactgggctc gggctacgac ccttattaca cctactctgg ctctataccc tacctagatg    21120 gaaccttta cctcaaccac acctttaaga aggctgccat tacctttgac tcttctgtca    21180
gctggcctgg caatgaccgc ctgcttaccc ccaacgagtt tgaaattaag cgctcagttg    21240
acggggaggg ttacaacgtt gcccagtgta acatgaccaa agactggttc ctggtacaaa    21300
tgctagctaa ctataacatt ggctaccagg gcttctatat cccagagagc tacaaggacc    21360
gcatgtactc cttctttaga aacttccagc ccatgagccg tcaggtggtg gatgatacta    21420
aatacaagga ctaccaacag gtgggcatcc taccaacaca caacaactct ggatttgttg    21480
gctaccttgc ccccaccatg cgcgaaggac aggcctaccc tgctaacttc ccctatccgc    21540
ttataggcaa gaccgcagtt gacagcatta cccagaaaaa gtttctttgc gatcgcaccc    21600
tttggcgcat cccattctcc agtaacttta tgtccatggg cgcactcaca gacctgggcc    21660
aaaaccttct ctacgccaac tccgcccact ccctagacat gacttttgag gtggatccca    21720
tggacgagcc caccccttctt tatgttttgt ttgaagtctt tgacaaggtc cgtgtgcacc    21780
agccgcaccg cggcgtcatc gaaaccgtgt acctgcgcac gcccttctcg gccggcaacg    21840
ccacaacata aagaagcaag caacatcaac aacagctgcc gccatgggct ccagtgagca    21900
ggaactgaaa gccattgtca agatcttggg ttgtgggcca tatttttgg gcacctatga    21960 caagcgcttt ccaggctttg tttctccaca caagctcgcc tgcgccatag tcaatacggc    22020
cggtcgcgag actgggggcg tacactggat ggcctttgcc tggaacccgc actcaaaaac    22080
atgctacctc tttgagccct ttggcttttc tgaccagcga ctcaagcagg tttaccagtt    22140
tgagtacgag tcactcctgc gccgtagcgc cattgcttct tcccccgacc gctgtataac    22200
gctggaaaag tccacccaaa gcgtacaggg gcccaactcg gccgcctgtg gactattctg    22260
ctgcatgttt ctccacgcct ttgccaactg gccccaaact cccatggatc acaacccac    22320 catgaacctt attaccgggg tacccaactc catgctcaac agtccccagg tacagcccac    22380
cctgcgtcgc aaccaggaac agctctacag cttcctggag cgccactcgc cctacttccg    22440
cagccacagt gcgcagatta ggagcgccac ttctttttgt cacttgaaaa acatgtaaaa    22500
ataatgtact agagacactt tcaataaagg caaatgcttt tatttgtaca ctctcgggtg    22560
attatttacc cccaccctg ccgtctgcgc cgtttaaaaa tcaagggggt tctgccgcgc    22620
atcgctatgc gccactggca gggacacgtt gcgatactgg tgtttagtgc tccacttaaa    22680
ctcaggcaca accatccgcg gcagctcggt gaagttttca ctccacaggc tgcgcaccat    22740
caccaacgcg tttagcaggt cgggcgccga tatcttgaag tcgcagttgg ggcctccgcc    22800
ctgcgcgcgc gagttgcgat acacagggtt gcagcactgg aacactatca gcgccgggtc    22860
gtgcacgctg gccagcacgc tcttgtcgga gatcagatcc gcgtccaggt cctccgcgtt    22920
```

```
gctcagggcg aacggagtca actttggtag ctgccttccc aaaaagggcg cgtgcccagg   22980
ctttgagttg cactcgcacc gtagtggcat caaaaggtga ccgtgcccgg tctgggcgtt   23040
aggatacagc gcctgcataa aagccttgat ctgcttaaaa gccacctgag cctttgcgcc   23100
ttcagagaag aacatgccgc aagacttgcc ggaaaactga ttggccggac aggccgcgtc   23160
gtgcacgcag caccttgcgt cggtgttgga gatctgcacc acatttcggc cccaccggtt   23220
cttcacgatc ttggccttgc tagactgctc cttcagcgcg cgctgcccgt tttcgctcgt   23280
cacatccatt tcaatcacgt gctccttatt tatcataatg cttccgtgta gacacttaag   23340
ctcgccttcg atctcagcgc agcggtgcag ccacaacgcg cagcccgtgg gctcgtgatg   23400
cttgtaggtc acctctgcaa acgactgcag gtacgcctgc aggaatcgcc ccatcatcgt   23460
cacaaaggtc ttgttgctgg tgaaggtcag ctgcaacccg cggtgctcct cgttcagcca   23520
ggtcttgcat acggccgcca gagcttccac ttggtcaggc agtagtttga agttcgcctt   23580
tagatcgtta tccacgtggt acttgtccat cagcgcgcgc gcagcctcca tgcccttctc   23640
ccacgcagac acgatcggca cactcagcgg gttcatcacc gtaatttcac tttccgcttc   23700
gctgggctct tcctcttcct cttgcgtccg cataccacgc gccactgggt cgtcttcatt   23760
cagccgccgc actgtgcgct tacctccttt gccatgcttg attagcaccg gtgggttgct   23820
gaaacccacc atttgtagcg ccacatcttc tctttcttcc tcgctgtcca cgattacctc   23880
tggtgatggc gggcgctcgg gcttgggaga agggcgcttc ttttttcttct tgggcgcaat   23940
ggccaaatcc gccgccgagg tcgatggccg cgggctgggt gtgcgcggca ccagcgcgtc   24000
ttgtgatgag tcttcctcgt cctcggactc gatacgccgc ctcatccgct tttttggggg   24060
cgcccgggga ggcggcggcg acggggacgg ggacgacacg tcctccatgg ttgggggacg   24120
tcgcgccgca ccgcgtccgc gctcggggt ggtttcgcgc tgctcctctt cccgactggc   24180
catttccttc tcctataggc agaaaaagat catggagtca gtcgagaaga aggacagcct   24240
aaccgccccc tctgagttcg ccaccaccgc ctccaccgat gccgccaacg cgcctaccac   24300
cttcccgtc gaggcacccc cgcttgagga ggaggaagtg attatcgagc aggacccagg   24360
ttttgtaagc gaagacgacg aggaccgctc agtaccaaca gaggataaaa agcaagacca   24420
ggacaacgca gaggcaaacg aggaacaagt cgggcggggg gacgaaaggc atggcgacta   24480
cctagatgtg ggagacgacg tgctgttgaa gcatctgcag cgccagtgcg ccattatctg   24540
cgacgcgttg caagagcgca gcgatgtgcc cctcgccata gcggatgtca gccttgccta   24600
cgaacgccac ctattctcac cgcgcgtacc ccccaaacgc caagaaaacg gcacatgcga   24660
gcccaacccg cgcctcaact tctaccccgt atttgccgtg ccagaggtgc ttgccaccta   24720
tcacatcttt ttccaaaact gcaagatacc cctatcctgc cgtgccaacc gcagccgagc   24780
ggacaagcag ctggccttgc ggcagggcgc tgtcatacct gatatcgcct cgctcaacga   24840
agtgccaaaa atctttgagg gtcttggacg cgacagaag cgcgcggcaa acgtctgtca   24900
acaggaaaac agcgaaaatg aaagtcactc tggagtgttg gtggaactcg agggtgacaa   24960
cgcgcgccta gccgtactaa aacgcagcat cgaggtcacc cactttgcct acccggcact   25020
taacctaccc cccaaggtca tgagcacagt catgagtgag ctgatcgtgc gccgtgcgca   25080
gccctggag agggatgcaa atttgcaaga acaaacagag gagggcctac ccgcagttgg   25140
cgacgagcag ctagcgcgct ggcttcaaac gcgcagcct gccgacttgg aggagcgacg   25200
caaactaatg atggccgcag tgctcgttac cgtggagctt gagtgcatgc agcggttctt   25260
```

```
tgctgacccg gagatgcagc gcaagctaga ggaaacattg cactacacct ttcgacaggg    25320
ctacgtacgc caggcctgca agatctccaa cgtggagctc tgcaacctgg tctcctacct    25380
tggaattttg cacgaaaacc gccttgggca aaacgtgctt cattccacgc tcaagggcga    25440
ggcgcgccgc gactacgtcc gcgactgcgt ttacttattt ctatgctaca cctggcagac    25500
ggccatgggc gtttggcagc agtgcttgga ggagtgcaac ctcaaggagc tgcagaaact    25560
gctaaagcaa aacttgaagg acctatggac ggccttcaac gagcgctccg tggccgcgca    25620
cctggcggac atcattttcc ccgaacgcct gcttaaaacc ctgcaacagg gtctgccaga    25680
cttcaccagt caaagcatgt tgcagaactt taggaacttt atcctagagc gctcaggaat    25740
cttgcccgcc acctgctgtg cacttcctag cgactttgtg cccattaagt accgcgaatg    25800
ccctccgccg ctttgggcc actgctacct tctgcagcta gccaactacc ttgcctacca    25860
ctctgacata atggaagacg tgagcggtga cggtctactg gagtgtcact gtcgctgcaa    25920
cctatgcacc ccgcaccgct ccctggtttg caattcgcag ctgcttaacg aaagtcaaat    25980
tatcggtacc tttgagctgc agggtccctc gcctgacgaa aagtccgcgg ctccggggtt    26040
gaaactcact ccggggctgt ggacgtcggc ttaccttcgc aaatttgtac ctgaggacta    26100
ccacgcccac gagattaggt tctacgaaga ccaatcccgc cgccaaatg cggagcttac    26160 cgcctgcgtc attacccagg ccacattct tggccaattg caagccatca acaaagcccg    26220
ccaagagttt ctgctacgaa agggacgggg ggtttacttg accccagt ccggcgagga    26280 gctcaaccca atcccccgc cgccgcagcc ctatcagcag cagccgcggg cccttgcttc    26340
ccaggatggc acccaaaaag aagctgcagc tgccgccgcc acccacggac gaggaggaat    26400
actgggacag tcaggcagag gaggttttgg acgaggagga ggaggacatg atggaagact    26460
gggagagcct agacgaggaa gcttccgagg tcgaagaggt gtcagacgaa acaccgtcac    26520
cctcggtcgc attccctcg ccggcgcccc agaaatcggc aaccggttcc agcatggcta    26580
caacctccgc tcctcaggcg ccgccggcac tgcccgttcg ccgacccaac cgtagatggg    26640
acaccactgg aaccagggcc ggtaagtcca agcagccgcc gccgttagcc caagagcaac    26700
aacagcgcca aggctaccgc tcatggcgcg ggcacaagaa cgccatagtt gcttgcttgc    26760
aagactgtgg gggcaacatc tccttcgccc gccgcttct tctctaccat cacggcgtgg    26820
ccttcccccg taacatcctg cattactacc gtcatctcta cagcccatac tgcaccggcg    26880
gcagcggcag cggcagcaac agcagcggcc acacagaagc aaaggcgacc ggatagcaag    26940
actctgacaa agcccaagaa atccacacgc gcggcagcag caggaggagg agcgctgcgt    27000
ctggcgccca acgaacccgt atcgacccgc gagcttagaa acaggatttt tcccactctg    27060
tatgctatat ttcaacagag cagggccaa gaacaagagc tgaaaataaa aaacaggtct    27120
ctgcgatccc tcacccgcag ctgcctgtat cacaaaagcg aagatcagct tcggcgcacg    27180
ctggaagacg cggaggctct cttcagtaaa tactgcgcgc tgactcttaa ggactagttt    27240
cgcgcccttt ctcaaattta agcgcgaaaa ctacgtcatc tccagcggcc acacccggcg    27300
ccagcacctg tcgtcagcgc cattatgagc aaggaaattc ccacgcccta catgtggagt    27360
taccagccac aaatgggact tgcggctgga gctgcccaag actactcaac ccgaataaac    27420
tacatgagcg cgggacccca catgatatcc cgggtcaacg aatccgcgc ccaccgaaac    27480 cgaattctct tggaacaggc ggctattacc accacacctc gtaataacct taatcccgt    27540 agttggcccc ctgccctggt gtaccaggaa agtcccgctc ccaccactgt ggtacttccc    27600
agagacgccc aggccgaagt tcagatgact aactcagggg cgcagcttgc gggcggcttt    27660
```

```
cgtcacaggg tgcggtcgcc cgggcagggt ataactcacc tgacaatcag agggcgaggt    27720
attcagctca acgacgagtc ggtgagctcc tcgcttggtc tccgtccgga cgggacattt    27780
cagatcggcg gcgccggccg tccttcattc acgcctcgtc aggcaatcct aactctgcag    27840
acctcgtcct ctgagccgcg ctctggaggc attggaactc tgcaatttat tgaggagttt    27900
gtgccatcgg tctactttaa ccccttctcg ggacctcccg gccactatcc ggatcaattt    27960
attcctaact ttgacgcggt aaaggactcg gcggacggct acgactgaat gttaagtgga    28020
gaggcagagc aactgcgcct gaaacacctg gtccactgtc gccgccacaa gtgctttgcc    28080
cgcgactccg gtgagttttg ctactttgaa ttgcccgagg atcatatcga gggcccggcg    28140
cacggcgtcc ggcttaccgc ccagggagag cttgcccgta gcctgattcg ggagtttacc    28200
cagcgccccc tgctagttga gcgggacagg ggacccgtg ttctcactgt gatttgcaac     28260
tgtcctaacc ttggattaca tcaagatctt tgttgccatc tctgtgctga gtataataaa    28320
tacagaaatt aaaatatact ggggctccta tcgccatcct gtaaacgcca ccgtcttcac    28380
ccgcccaagc aaaccaaggc gaaccttacc tggtactttt aacatctctc cctctgtgat    28440
ttacaacagt ttcaacccag acggagtgag tctacgagag aacctctccg agctcagcta    28500
ctccatcaga aaaaacacca ccctccttac ctgccgggaa cgtacgagtg cgtcaccggc    28560
cgctgcacca cacctaccgc ctgaccgtaa accagacttt ttccggacag acctcaataa    28620
ctctgtttac cagaacagga ggtgagctta gaaaacccett agggtattag gccaaaggcg    28680
cagctactgt ggggtttatg aacaattcaa gcaactctac gggctattct aattcaggtt    28740
tctctagaat cggggttggg gttattctct gtcttgtgat tctctttatt cttatactaa    28800
cgcttctctg cctaaggctc gccgcctgct gtgtgcacat ttgcatttat tgtcagcttt    28860
ttaaacgctg gggtcgccac ccaagatgat taggtacata atcctaggtt tactcaccct    28920
tgcgtcagcc cacggtacca cccaaaaggt ggattttaag gagccagcct gtaatgttac    28980
attcgcagct gaagctaatg agtgcaccac tcttataaaa tgcaccacag aacatgaaaa    29040
gctgcttatt cgccacaaaa acaaaattgg caagtatgct gtttatgcta tttggcagcc    29100
aggtgacact acagagtata atgttacagt tttccagggt aaaagtcata aaacttttat    29160
gtatactttt ccattttatg aaatgtgcga cattaccatg tacatgagca acagtataa    29220 gttgtggccc ccacaaaatt gtgtggaaaa cactggcact ttctgctgca ctgctatgct    29280
aattacagtg ctcgctttgg tctgtaccct actctatatt aaatacaaaa gcagacgcag    29340
ctttattgag gaaaagaaaa tgccttaatt tactaagtta caaagctaat gtcaccacta    29400
actgctttac tcgctgcttg caaaacaaat tcaaaaagtt agcattataa ttagaatagg    29460
atttaaaccc cccggtcatt tcctgctcaa taccattccc ctgaacaatt gactctatgt    29520
gggatatgct ccagcgctac aaccttgaag tcaggcttcc tggatgtcag catctgactt    29580
tggccagcac ctgtcccgcg gatttgttcc agtccaacta cagcgaccca ccctaacaga    29640
gatgaccaac acaaccaacg cggccgccgc taccggactt acatctacca caaatacacc    29700
ccaagtttct gcctttgtca ataactggga taacttgggc atgtggtggt tctccatagc    29760
gcttatgttt gtatgcctta ttattatgtg gctcatctgc tgcctaaagc gcaaacgcgc    29820
ccgaccaccc atctatagtc ccatcattgt gctacaccca aacaatgatg gaatccatag    29880
attggacgga ctgaaacaca tgttctttc tcttacagta tgattaaatg agacatgatt    29940
cctcgagttt ttatattact gaccccttgtt gcgcttttt gtgcgtgctc cacattggct    30000
```

```
gcggtttctc acatcgaagt agactgcatt ccagccttca cagtctattt gctttacgga   30060
tttgtcaccc tcacgctcat ctgcagcctc atcactgtgg tcatcgcctt tatccagtgc   30120
attgactggg tctgtgtgcg cttttgcatat ctcagacacc atccccagta cagggacagg   30180
actatagctg agcttcttag aattctttaa ttatgaaatt tactgtgact tttctgctga   30240
ttatttgcac cctatctgcg ttttgttccc cgacctccaa gcctcaaaga catatatcat   30300
gcagattcac tcgtatatgg aatattccaa gttgctacaa tgaaaaaagc gatctttccg   30360
aagcctggtt atatgcaatc atctctgtta tggtgttctg cagtaccatc ttagccctag   30420
ctatatatcc taccttgac attggctgga aacgaataga tgccatgaac cacccaactt   30480
tccccgcgcc cgctatgctt ccactgcaac aagttgttgc cggcggcttt gtcccagcca   30540
atcagcctcg ccccacttct cccaccccca ctgaaatcag ctactttaat ctaacaggag   30600
gagatgactg acaccctaga tctagaaatg gacggaatta ttacagagca gcgcctgcta   30660
gaaagacgca gggcagcggc cgagcaacag cgcatgaatc aagagctcca agacatggtt   30720
aacttgcacc agtgcaaaag gggtatcttt tgtctggtaa agcaggccaa agtcacctac   30780
gacagtaata ccaccggaca ccgccttagc tacaagttgc caaccaagcg tcagaaattg   30840
gtggtcatgg tgggagaaaa gcccattacc ataactcagc actcggtaga aaccgaaggc   30900
tgcattcact caccttgtca aggacctgag gatctctgca cccttattaa gaccctgtgc   30960
ggtctcaaag atcttattcc ctttaactaa taaaaaaaaa taataaagca tcacttactt   31020
aaaatcagtt agcaaatttc tgtccagttt attcagcagc acctccttgc cctcctccca   31080
gctctggtat tgcagcttcc tcctggctgc aaactttctc cacaatctaa atggaatgtc   31140
agtttcctcc tgttcctgtc catccgcacc cactatcttc atgttgttgc agatgaagcg   31200
cgcaagaccg tctgaagata ccttcaaccc cgtgtatcca tatgacacgg aaaccggtcc   31260
tccaactgtg ccttttctta ctcctcccct tgtatccccc aatgggtttc aagagagtcc   31320
ccctggggta ctctctttgc gcctatccga acctctagtt acctccaatg gcatgcttgc   31380
gctcaaaatg ggcaacggcc tctctctgga cgaggccggc aaccttacct cccaaaatgt   31440
aaccactgtg agcccacctc tccgaggaga caagtcaaac ataaacctgg aaatatctgc   31500
acccctcaca gttacctcag aagccctaac tgtggctgcc gccgcacctc taatggtcgc   31560
gggcaacaca ctcaccatgc aatcacaggc ccgctaacc gtgcacgact ccaaacttag   31620
cattgccacc caaggacccc tcacagtgtc agaaggaaag ctagccctgc aaacatcagg   31680
ccccctcacc accaccgata gcagtaccct tactatcact gcctcacccc ctctaactac   31740
tgccactggt agcttgggca ttgacttgaa agagcccatt tatacacaaa atggaaaact   31800
aggactaaag tacggggctc ctttgcatgt aacagacgac ctaaacactt tgaccgtagc   31860
aactggtcca ggtgtgacta ttaataatac ttccttgcaa actaaagtta ctggagcctt   31920
gggttttgat tcacaaggca atatgcaact taatgtagca ggaggactaa ggattgattc   31980
tcaaaacaga cgcctataac ttgatgttag ttatccgttt gatgctcaaa accaactaaa   32040
tctaagacta ggacagggcc ctctttttat aaactcagcc cacaacttgg atattaacta   32100
caacaaaggc ctttacttgt ttacagcttc aaacaattcc aaaagcttg aggttaacct   32160 aagcactgcc aaggggttga tgtttgacgc tacagccata gccattaatg caggagatgg   32220
gcttgaattt ggttcaccta atgcaccaaa cacaaatccc ctcaaaacaa aaattggcca   32280
tggcctagaa tttgattcaa acaaggctat ggttcctaaa ctaggaactg gccttagttt   32340
tgacagcaca ggtgccatta cagtaggaaa caaaaataat gataagctaa ctttgtggac   32400
```

-continued

```
cacaccagct ccatctccta actgtagact aaatgcagag aaagatgcta aactcacttt    32460
ggtcttaaca aaatgtggca gtcaaatact tgctacagtt tcagttttgg ctgttaaagg    32520
cagtttggct ccaatatctg gaacagttca aagtgctcat cttattataa gatttgacga    32580
aaatggagtg ctactaaaca attccttcct ggacccagaa tattggaact ttagaaatgg    32640
agatcttact gaaggcacag cctatacaaa cgctgttgga tttatgccta acctatcagc    32700
ttatccaaaa tctcacgtta aaactgccaa agtaacatt gtcagtcaag tttacttaaa     32760
cggagacaaa actaaacctg taacactaac cattcacta aacggtacac aggaaacagg     32820
agacacaact ccaagtgcat actctatgtc attttcatgg gactggtctg ccacaacta    32880 cattaatgaa atatttgcca catcctctta cacttttca tacattgccc aagaataaag     32940
aatcgtttgt gttatgtttc aacgtgttta ttttcaatt gcagaaaatt tcaagtcatt    33000
tttcattcag tagtatagcc ccaccaccac atagcttata cagatcaccg taccttaatc    33060
aaactcacag aaccctagta ttcaacctgc cacctccctc ccaacacaca gagtacacag    33120
tcctttctcc ccggctggcc ttaaaaagca tcatatcatg ggtaacagac atattcttag    33180
gtgttatatt ccacacggtt tcctgtcgag ccaaacgctc atcagtgata ttaataaact    33240
ccccgggcag ctcacttaag ttcatgtcgc tgtccagctg ctgagccaca ggctgctgtc    33300
caacttgcgt tgcttaacg ggcggcgaag gagaagtcca cgcctacatg ggggtagagt    33360
cataatcgtg catcaggata gggcggtggt gctgcagcag cgcgcgaata aactgctgcc    33420
gccgccgctc cgtcctgcag gaatacaaca tggcagtggt ctcctcagcg atgattcgca    33480
ccgcccgcag cataaggcgc cttgtcctcc gggcacagca gcgcaccctg atctcactta    33540
aatcagcaca gtaactgcag cacagcacca caatattgtt caaaatccca cagtgcaagg    33600
cgctgtatcc aaagctcatg gcggggacca cagaacccac gtggccatca taccacaagc    33660
gcaggtagat taagtggcga cccctcataa acacgctgga cataaacatt acctcttttg    33720
gcatgttgta attcaccacc tcccggtacc atataaacct ctgattaaac atggcgccat    33780
ccaccaccat cctaaaccag ctggccaaaa cctgcccgcc ggctatacac tgcagggaac    33840
cgggactgga acaatgacag tggagagccc aggactcgta accatggatc atcatgctcg    33900
tcatgatatc aatgttggca caacacaggc acacgtgcat acacttcctc aggattacaa    33960
gctcctcccg cgttagaacc atatcccagg gaacaaccca ttcctgaatc agcgtaaatc    34020
ccacactgca gggaagacct cgcacgtaac tcacgttgtg cattgtcaaa gtgttacatt    34080
cgggcagcag cggatgatcc tccagtatgg tagcgcgggt ttctgtctca aaaggaggta    34140
gacgatccct actgtacgga gtgcgccgag acaaccgaga tcgtgttggt cgtagtgtca    34200
tgccaaatgg aacgccggac gtagtcatat ttcctgaagc aaaaccaggt gcgggcgtga    34260
caaacagatc tgcgtctccg gtctcgccgc ttagatcgct ctgtgtagta gttgtagtat    34320
atccactctc tcaaagcatc caggcgcccc ctggcttcgg gttctatgta aactccttca    34380
tgcgccgctg ccctgataac atccaccacc gcagaataag ccacacccag ccaacctaca    34440
cattcgttct gcgagtcaca cacgggagga gcgggaagag ctggaagaac catgtttttt    34500
tttttattcc aaaagattat ccaaaacctc aaaatgaaga tctattaagt gaacgcgctc    34560
ccctccggtg gcgtggtcaa actctacagc caaagaacag ataatggcat ttgtaagatg    34620
ttgcacaatg gcttccaaaa ggcaaacggc cctcacgtcc aagtggacgt aaaggctaaa    34680
cccttcaggg tgaatctcct ctataaacat tccagcacct tcaaccatgc ccaaataatt    34740
```

```
ctcatctcgc caccttctca atatatctct aagcaaatcc cgaatattaa gtccggccat    34800
tgtaaaaatc tgctccagag cgccctccac cttcagcctc aagcagcgaa tcatgattgc    34860
aaaaattcag gttcctcaca gacctgtata agattcaaaa gcggaacatt aacaaaaata    34920
ccgcgatccc gtaggtccct tcgcagggcc agctgaacat aatcgtgcag gtctgcacgg    34980
accagcgcgg ccacttcccc gccaggaacc atgacaaaag acccacact gattatgaca     35040 cgcatactcg gagctatgct aaccagcgta gccccgatgt aagcttgttg catgggcggc    35100
gatataaaat gcaaggtgct gctcaaaaaa tcaggcaaag cctcgcgcaa aaagaaagc    35160 acatcgtagt catgctcatg cagataaagg caggtaagct ccggaaccac acagaaaaa    35220 gacaccattt ttctctcaaa catgtctgcg ggtttctgca taaacacaaa ataaaataac    35280
aaaaaaacat ttaaacatta gaagcctgtc ttacaacagg aaaaacaacc cttataagca    35340
taagacggac tacggccatg ccggcgtgac cgtaaaaaaa ctggtcaccg tgattaaaaa    35400
gcaccaccga cagctcctcg gtcatgtccg gagtcataat gtaagactcg gtaaacacat    35460
caggttgatt cacatcggtc agtgctaaaa agcgaccgaa atagcccggg ggaatacata    35520
cccgcaggcg tagagacaac attacagccc cataggagg tataacaaaa ttaataggag     35580
agaaaaacac ataaacacct gaaaaaccct cctgcctagg caaaatagca ccctcccgct    35640
ccagaacaac atacagcgct tccacagcgg cagccataac agtcagcctt accagtaaaa    35700
aagaaaacct attaaaaaaa caccactcga cacggcacca gctcaatcag tcacagtgta    35760
aaaaagggcc aagtgcagag cgagtatata taggactaaa aaatgacgta acggttaaag    35820
tccacaaaaa acacccagaa aaccgcacgc gaacctacgc ccagaaacga aagccaaaaa    35880
acccacaact tcctcaaatc gtcacttccg ttttcccacg ttacgtcact tcccatttta    35940
agaaaactac aattcccaac acatactagt tactccgccc taaaacctac gtcacccgcc    36000
ccgttcccac gccccgcgcc acgtcacaaa ctccacccc tcattatcat attggcttca     36060
atccaaaata aggtatatta ttgatgatgt                                     36090

<210> SEQ ID NO 6
<211> LENGTH: 102
<212> TYPE: DNA
<213> ORGANISM: Artificial Sequence
<220> FEATURE:
<223> OTHER INFORMATION: gp100-tyr insertion with linkers

<400> SEQUENCE: 6
ggaagcggtt ctcgctacct ggagcctggc ccagtgactg ccgctggttc cggaagcaga      60
tacatggacg gaacaatgtc ccaggttgcc ggttctggct cc                        102

<210> SEQ ID NO 7
<211> LENGTH: 34
<212> TYPE: PRT
<213> ORGANISM: Artificial Sequence
<220> FEATURE:
<223> OTHER INFORMATION: gp100-tyr insertion with linkers

<400> SEQUENCE: 7

Gly Ser Gly Ser Arg Tyr Leu Glu Pro Gly Pro Val Thr Ala Ala Gly
1               5                   10                  15

Ser Gly Ser Arg Tyr Met Asp Gly Thr Met Ser Gln Val Ala Gly Ser
            20                  25                  30

Gly Ser
```

<210> SEQ ID NO 8
<211> LENGTH: 2859
<212> TYPE: DNA
<213> ORGANISM: Artificial Sequence
<220> FEATURE:
<223> OTHER INFORMATION: wt Hexon

<400> SEQUENCE: 8

| | | | | | |
|---|---|---|---|---|---|
| atggctaccc | cttcgatgat | gccgcagtgg | tcttacatgc | acatctcggg | ccaggacgcc | 60 |
| tcggagtacc | tgagccccgg | gctggtgcag | tttgcccgcg | ccaccgagac | gtacttcagc | 120 |
| ctgaataaca | agtttagaaa | ccccacggtg | gcgcctacgc | acgacgtgac | cacagaccgg | 180 |
| tcccagcgtt | tgacgctgcg | gttcatccct | gtggaccgtg | aggatactgc | gtactcgtac | 240 |
| aaggcgcggt | tcaccctagc | tgtgggtgat | aaccgtgtgc | tggacatggc | ttccacgtac | 300 |
| tttgacatcc | gcgcgtgct | ggacaggggc | cctacttta | agccctactc | tggcactgcc | 360 |
| tacaacgccc | tggctcccaa | gggtgcccca | atccttgcg | aatgggatga | agctgctact | 420 |
| gctcttgaaa | taaacctaga | agaagaggac | gatgacaacg | aagacgaagt | agacgagcaa | 480 |
| gctgagcagc | aaaaaactca | cgtatttggg | caggcgcctt | attctggtat | aaatattaca | 540 |
| aaggagggta | ttcaaatagg | tgtcgaaggt | caaacaccta | aatatgccga | taaacatttt | 600 |
| caacctgaac | ctcaaatagg | agaatctcag | tggtacgaaa | ctgaaattaa | tcatgcagct | 660 |
| gggagagtcc | ttaaaaagac | taccccaatg | aaaccatgtt | acggttcata | tgcaaaaccc | 720 |
| acaaatgaaa | atggagggca | aggcattctt | gtaaagcaac | aaaatggaaa | gctagaaagt | 780 |
| caagtggaaa | tgcaattttt | ctcaactact | gaggcgaccg | caggcaatgg | tgataacttg | 840 |
| actcctaaag | tggtattgta | cagtgaagat | gtagatatag | aaccccaga | cactcatatt | 900 |
| tcttacatgc | ccactattaa | ggaaggtaac | tcacgagaac | taatgggcca | acaatctatg | 960 |
| cccaacaggc | ctaattacat | tgcttttagg | gacaatttta | ttggtctaat | gtattacaac | 1020 |
| agcacgggta | atatgggtgt | tctggcgggc | caagcatcgc | agttgaatgc | tgttgtagat | 1080 |
| ttgcaagaca | gaaacacaga | gctttcatac | cagcttttgc | ttgattccat | tggtgataga | 1140 |
| accaggtact | tttctatgtg | gaatcaggct | gttgacagct | atgatccaga | tgttagaatt | 1200 |
| attgaaaatc | atggaactga | agatgaactt | ccaaattact | gctttccact | gggaggtgtg | 1260 |
| attaatacag | agactcttac | caaggtaaaa | cctaaaacag | gtcaggaaaa | tggatgggaa | 1320 |
| aaagatgcta | cagaattttc | agataaaaat | gaaataagg | ttggaaataa | ttttgccatg | 1380 |
| gaaatcaatc | taaatgccaa | cctgtggaga | aatttcctgt | actccaacat | agcgctgtat | 1440 |
| ttgcccgaca | agctaaagta | cagtccttcc | aacgtaaaaa | tttctgataa | cccaaacacc | 1500 |
| tacgactaca | tgaacaagcg | agtggtggct | cccgggttag | tggactgcta | cattaacctt | 1560 |
| ggagcacgct | ggtccttga | ctatatggac | aacgtcaacc | catttaacca | ccaccgcaat | 1620 |
| gctggcctgc | gctaccgctc | aatgttgctg | ggcaatggtc | gctatgtgcc | cttccacatc | 1680 |
| caggtgcctc | agaagttctt | tgccattaaa | aacctcctc | tcctgccggg | ctcatacacc | 1740 |
| tacgagtgga | acttcaggaa | ggatgttaac | atggttctgc | agagctccct | aggaaatgac | 1800 |
| ctaagggttg | acggagccag | cattaagttt | gatagcattt | gcctttacgc | caccttcttc | 1860 |
| cccatggccc | acaacaccgc | ctccacgctt | gaggccatgc | ttagaaacga | caccaacgac | 1920 |
| cagtcccttta | acgactatct | ctccgccgcc | aacatgctct | accctatacc | gccaacgct | 1980 |
| accaacgtgc | ccatatccat | cccctcccgc | aactgggcgg | cttccgcgg | ctgggccttc | 2040 |
| acgcgcctta | agactaagga | aaccccatca | ctgggctcgg | gctacgaccc | ttattacacc | 2100 |

```
tactctggct ctataccta cctagatgga accttttacc tcaaccacac ctttaagaag    2160
gtggccatta cctttgactc ttctgtcagc tggcctggca atgaccgcct gcttacccc     2220
aacgagtttg aaattaagcg ctcagttgac ggggagggtt acaacgttgc ccagtgtaac    2280
atgaccaaag actggttcct ggtacaaatg ctagctaact acaacattgg ctaccagggc    2340
ttctatatcc cagagagcta caaggaccgc atgtactcct tctttagaaa cttccagccc    2400
atgagccgtc aggtggtgga tgatactaaa tacaaggact accaacaggt gggcatccta    2460
caccaacaca caactctgg  atttgttggc taccttgccc ccaccatgcg cgaaggacag    2520
gcctaccctg ctaacttccc ctatccgctt ataggcaaga ccgcagttga cagcattacc    2580
cagaaaaagt ttctttgcga tcgcaccctt tggcgcatcc cattctccag taactttatg    2640
tccatgggcg cactcacaga cctgggccaa aaccttctct acgccaactc cgcccacgcg    2700
ctagacatga cttttgaggt ggatcccatg gacgagccca cccttcttta tgttttgttt    2760
gaagtctttg acgtggtccg tgtgcaccag ccgcaccgcg gcgtcatcga aaccgtgtac    2820
ctgcgcacgc ccttctcggc cggcaacgcc acaacataa                          2859
```

<210> SEQ ID NO 9
<211> LENGTH: 952
<212> TYPE: PRT
<213> ORGANISM: Artificial Sequence
<220> FEATURE:
<223> OTHER INFORMATION: wt Hexon

<400> SEQUENCE: 9

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Glu Thr Tyr Phe Ser Leu Asn Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ala Leu Ala Pro Lys Gly
        115                 120                 125

Ala Pro Asn Pro Cys Glu Trp Asp Glu Ala Ala Thr Ala Leu Glu Ile
    130                 135                 140

Asn Leu Glu Glu Glu Asp Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
            180                 185                 190

Pro Lys Tyr Ala Asp Lys Thr Phe Gln Pro Glu Pro Gln Ile Gly Glu
        195                 200                 205

Ser Gln Trp Tyr Glu Thr Glu Ile Asn His Ala Ala Gly Arg Val Leu
    210                 215                 220

Lys Lys Thr Thr Pro Met Lys Pro Cys Tyr Gly Ser Tyr Ala Lys Pro

-continued

```
        225                 230                 235                 240
Thr Asn Glu Asn Gly Gly Gln Gly Ile Leu Val Lys Gln Gln Asn Gly
                245                 250                 255

Lys Leu Glu Ser Gln Val Glu Met Gln Phe Ser Thr Thr Glu Ala
                260                 265                 270

Thr Ala Gly Asn Gly Asp Asn Leu Thr Pro Lys Val Leu Tyr Ser
                275                 280                 285

Glu Asp Val Asp Ile Glu Thr Pro Asp Thr His Ile Ser Tyr Met Pro
                290                 295                 300

Thr Ile Lys Glu Gly Asn Ser Arg Glu Leu Met Gly Gln Gln Ser Met
305                 310                 315                 320

Pro Asn Arg Pro Asn Tyr Ile Ala Phe Arg Asp Asn Phe Ile Gly Leu
                325                 330                 335

Met Tyr Tyr Asn Ser Thr Gly Asn Met Gly Val Leu Ala Gly Gln Ala
                340                 345                 350

Ser Gln Leu Asn Ala Val Val Asp Leu Gln Asp Arg Asn Thr Glu Leu
                355                 360                 365

Ser Tyr Gln Leu Leu Leu Asp Ser Ile Gly Asp Arg Thr Arg Tyr Phe
                370                 375                 380

Ser Met Trp Asn Gln Ala Val Asp Ser Tyr Asp Pro Asp Val Arg Ile
385                 390                 395                 400

Ile Glu Asn His Gly Thr Glu Asp Glu Leu Pro Asn Tyr Cys Phe Pro
                405                 410                 415

Leu Gly Gly Val Ile Asn Thr Glu Thr Leu Thr Lys Val Lys Pro Lys
                420                 425                 430

Thr Gly Gln Glu Asn Gly Trp Glu Lys Asp Ala Thr Glu Phe Ser Asp
                435                 440                 445

Lys Asn Glu Ile Arg Val Gly Asn Asn Phe Ala Met Glu Ile Asn Leu
                450                 455                 460

Asn Ala Asn Leu Trp Arg Asn Phe Leu Tyr Ser Asn Ile Ala Leu Tyr
465                 470                 475                 480

Leu Pro Asp Lys Leu Lys Tyr Ser Pro Ser Asn Val Lys Ile Ser Asp
                485                 490                 495

Asn Pro Asn Thr Tyr Asp Tyr Met Asn Lys Arg Val Val Ala Pro Gly
                500                 505                 510

Leu Val Asp Cys Tyr Ile Asn Leu Gly Ala Arg Trp Ser Leu Asp Tyr
                515                 520                 525

Met Asp Asn Val Asn Pro Phe Asn His His Arg Asn Ala Gly Leu Arg
530                 535                 540

Tyr Arg Ser Met Leu Leu Gly Asn Gly Arg Tyr Val Pro Phe His Ile
545                 550                 555                 560

Gln Val Pro Gln Lys Phe Phe Ala Ile Lys Asn Leu Leu Leu Leu Pro
                565                 570                 575

Gly Ser Tyr Thr Tyr Glu Trp Asn Phe Arg Lys Asp Val Asn Met Val
                580                 585                 590

Leu Gln Ser Ser Leu Gly Asn Asp Leu Arg Val Asp Gly Ala Ser Ile
                595                 600                 605

Lys Phe Asp Ser Ile Cys Leu Tyr Ala Thr Phe Phe Pro Met Ala His
                610                 615                 620

Asn Thr Ala Ser Thr Leu Glu Ala Met Leu Arg Asn Asp Thr Asn Asp
625                 630                 635                 640

Gln Ser Phe Asn Asp Tyr Leu Ser Ala Ala Asn Met Leu Tyr Pro Ile
                645                 650                 655
```

```
Pro Ala Asn Ala Thr Asn Val Pro Ile Ser Ile Pro Ser Arg Asn Trp
            660                 665                 670

Ala Ala Phe Arg Gly Trp Ala Phe Thr Arg Leu Lys Thr Lys Glu Thr
        675                 680                 685

Pro Ser Leu Gly Ser Gly Tyr Asp Pro Tyr Tyr Thr Tyr Ser Gly Ser
    690                 695                 700

Ile Pro Tyr Leu Asp Gly Thr Phe Tyr Leu Asn His Thr Phe Lys Lys
705                 710                 715                 720

Val Ala Ile Thr Phe Asp Ser Ser Val Ser Trp Pro Gly Asn Asp Arg
                725                 730                 735

Leu Leu Thr Pro Asn Glu Phe Glu Ile Lys Arg Ser Val Asp Gly Glu
            740                 745                 750

Gly Tyr Asn Val Ala Gln Cys Asn Met Thr Lys Asp Trp Phe Leu Val
        755                 760                 765

Gln Met Leu Ala Asn Tyr Asn Ile Gly Tyr Gln Gly Phe Tyr Ile Pro
    770                 775                 780

Glu Ser Tyr Lys Asp Arg Met Tyr Ser Phe Phe Arg Asn Phe Gln Pro
785                 790                 795                 800

Met Ser Arg Gln Val Val Asp Asp Thr Lys Tyr Lys Asp Tyr Gln Gln
                805                 810                 815

Val Gly Ile Leu His Gln His Asn Asn Ser Gly Phe Val Gly Tyr Leu
            820                 825                 830

Ala Pro Thr Met Arg Glu Gly Gln Ala Tyr Pro Ala Asn Phe Pro Tyr
        835                 840                 845

Pro Leu Ile Gly Lys Thr Ala Val Asp Ser Ile Thr Gln Lys Lys Phe
    850                 855                 860

Leu Cys Asp Arg Thr Leu Trp Arg Ile Pro Phe Ser Ser Asn Phe Met
865                 870                 875                 880

Ser Met Gly Ala Leu Thr Asp Leu Gly Gln Asn Leu Leu Tyr Ala Asn
                885                 890                 895

Ser Ala His Ala Leu Asp Met Thr Phe Glu Val Asp Pro Met Asp Glu
            900                 905                 910

Pro Thr Leu Leu Tyr Val Leu Phe Glu Val Phe Asp Val Val Arg Val
        915                 920                 925

His Gln Pro His Arg Gly Val Ile Glu Thr Val Tyr Leu Arg Thr Pro
    930                 935                 940

Phe Ser Ala Gly Asn Ala Thr Thr
945                 950

<210> SEQ ID NO 10
<211> LENGTH: 27
<212> TYPE: DNA
<213> ORGANISM: Artificial Sequence
<220> FEATURE:
<223> OTHER INFORMATION: Hex713 epitope

<400> SEQUENCE: 10
tacctcaacc acacctttaa gaaggtg                                27

<210> SEQ ID NO 11
<211> LENGTH: 9
<212> TYPE: PRT
<213> ORGANISM: Artificial Sequence
<220> FEATURE:
<223> OTHER INFORMATION: Hex713 epitope

<400> SEQUENCE: 11
```

Tyr Leu Asn His Thr Phe Lys Lys Val
1               5

<210> SEQ ID NO 12
<211> LENGTH: 27
<212> TYPE: DNA
<213> ORGANISM: Artificial Sequence
<220> FEATURE:
<223> OTHER INFORMATION: V721A epitope

<400> SEQUENCE: 12
tacctcaacc acacctttaa gaaggct                                            27

<210> SEQ ID NO 13
<211> LENGTH: 9
<212> TYPE: PRT
<213> ORGANISM: Artificial Sequence
<220> FEATURE:
<223> OTHER INFORMATION: V721A epitope

<400> SEQUENCE: 13

Tyr Leu Asn His Thr Phe Lys Lys Ala
1               5

<210> SEQ ID NO 14
<211> LENGTH: 27
<212> TYPE: DNA
<213> ORGANISM: Artificial Sequence
<220> FEATURE:
<223> OTHER INFORMATION: Hex892 epitope

<400> SEQUENCE: 14
cttctctacg ccaactccgc ccacgcg                                            27

<210> SEQ ID NO 15
<211> LENGTH: 9
<212> TYPE: PRT
<213> ORGANISM: Artificial Sequence
<220> FEATURE:
<223> OTHER INFORMATION: Hex892 epitope

<400> SEQUENCE: 15

Leu Leu Tyr Ala Asn Ser Ala His Ala
1               5

<210> SEQ ID NO 16
<211> LENGTH: 27
<212> TYPE: DNA
<213> ORGANISM: Artificial Sequence
<220> FEATURE:
<223> OTHER INFORMATION: A901S epitope

<400> SEQUENCE: 16
cttctctacg ccaactccgc ccactcc                                            27

<210> SEQ ID NO 17
<211> LENGTH: 9
<212> TYPE: PRT
<213> ORGANISM: Artificial Sequence
<220> FEATURE:
<223> OTHER INFORMATION: A901S epitope

<400> SEQUENCE: 17

Leu Leu Tyr Ala Asn Ser Ala His Ser
1               5

<210> SEQ ID NO 18
<211> LENGTH: 27
<212> TYPE: DNA
<213> ORGANISM: Artificial Sequence
<220> FEATURE:
<223> OTHER INFORMATION: Hex917 epitope

<400> SEQUENCE: 18
tatgttttgt ttgaagtctt tgacgtg                                27

<210> SEQ ID NO 19
<211> LENGTH: 9
<212> TYPE: PRT
<213> ORGANISM: Artificial Sequence
<220> FEATURE:
<223> OTHER INFORMATION: Hex917 epitope

<400> SEQUENCE: 19

Tyr Val Leu Phe Glu Val Phe Asp Val
1               5

<210> SEQ ID NO 20
<211> LENGTH: 27
<212> TYPE: DNA
<213> ORGANISM: Artificial Sequence
<220> FEATURE:
<223> OTHER INFORMATION: V925K epitope

<400> SEQUENCE: 20
tatgttttgt ttgaagtctt tgacaag                                27

<210> SEQ ID NO 21
<211> LENGTH: 9
<212> TYPE: PRT
<213> ORGANISM: Artificial Sequence
<220> FEATURE:
<223> OTHER INFORMATION: V925K epitope

<400> SEQUENCE: 21

Tyr Val Leu Phe Glu Val Phe Asp Lys
1 5

<210> SEQ ID NO 22
<211> LENGTH: 27
<212> TYPE: DNA
<213> ORGANISM: Artificial Sequence
<220> FEATURE:
<223> OTHER INFORMATION: Hex512 epitope

<400> SEQUENCE: 22
gggttagtgg actgctacat taacctt 27

<210> SEQ ID NO 23
<211> LENGTH: 9
<212> TYPE: PRT
<213> ORGANISM: Artificial Sequence
<220> FEATURE:
<223> OTHER INFORMATION: Hex512 epitope

<400> SEQUENCE: 23

Gly Leu Val Asp Cys Tyr Ile Asn Leu
1 5

<210> SEQ ID NO 24
<211> LENGTH: 27
<212> TYPE: DNA

```
<213> ORGANISM: Artificial Sequence
<220> FEATURE:
<223> OTHER INFORMATION: L520P epitope

<400> SEQUENCE: 24
gggttagtgg actgctacat taacccc                                        27

<210> SEQ ID NO 25
<211> LENGTH: 9
<212> TYPE: PRT
<213> ORGANISM: Artificial Sequence
<220> FEATURE:
<223> OTHER INFORMATION: L520P epitope

<400> SEQUENCE: 25

Gly Leu Val Asp Cys Tyr Ile Asn Pro
1               5

<210> SEQ ID NO 26
<211> LENGTH: 4
<212> TYPE: PRT
<213> ORGANISM: Artificial Sequence
<220> FEATURE:
<223> OTHER INFORMATION: heparin sulphate glycosaminoglycan (HSG)-
      binding site

<400> SEQUENCE: 26

Lys Lys Thr Lys
1

<210> SEQ ID NO 27
<211> LENGTH: 4
<212> TYPE: PRT
<213> ORGANISM: Artificial Sequence
<220> FEATURE:
<223> OTHER INFORMATION: integrin-binding motif

<400> SEQUENCE: 27

Arg Gly Asp Lys
1

<210> SEQ ID NO 28
<211> LENGTH: 5
<212> TYPE: PRT
<213> ORGANISM: Artificial Sequence
<220> FEATURE:
<223> OTHER INFORMATION: flexible linker

<400> SEQUENCE: 28

Gly Ser Gly Ser Arg
1               5

<210> SEQ ID NO 29
<211> LENGTH: 6
<212> TYPE: PRT
<213> ORGANISM: Artificial Sequence
<220> FEATURE:
<223> OTHER INFORMATION: flexible linker

<400> SEQUENCE: 29

Ala Gly Ser Gly Ser Arg
1               5

<210> SEQ ID NO 30
<211> LENGTH: 5
<212> TYPE: PRT
<213> ORGANISM: Artificial Sequence
```

```
<220> FEATURE:
<223> OTHER INFORMATION: flexible linker

<400> SEQUENCE: 30

Ala Gly Ser Gly Ser
1               5

<210> SEQ ID NO 31
<211> LENGTH: 9
<212> TYPE: PRT
<213> ORGANISM: Artificial Sequence
<220> FEATURE:
<223> OTHER INFORMATION: gp100-280

<400> SEQUENCE: 31

Tyr Leu Glu Pro Gly Pro Val Thr Ala
1               5

<210> SEQ ID NO 32
<211> LENGTH: 9
<212> TYPE: PRT
<213> ORGANISM: Artificial Sequence
<220> FEATURE:
<223> OTHER INFORMATION: Tyr369(3D)

<400> SEQUENCE: 32

Tyr Met Asp Gly Thr Met Ser Gln Val
1               5

<210> SEQ ID NO 33
<211> LENGTH: 9
<212> TYPE: PRT
<213> ORGANISM: Artificial Sequence
<220> FEATURE:
<223> OTHER INFORMATION: E1A19

<400> SEQUENCE: 33

Leu Leu Asp Gln Leu Ile Glu Glu Val
1               5

<210> SEQ ID NO 34
<211> LENGTH: 9
<212> TYPE: PRT
<213> ORGANISM: Artificial Sequence
<220> FEATURE:
<223> OTHER INFORMATION: Hex63

<400> SEQUENCE: 34

Arg Leu Thr Leu Arg Phe Ile Pro Val
1               5

<210> SEQ ID NO 35
<211> LENGTH: 9
<212> TYPE: PRT
<213> ORGANISM: Artificial Sequence
<220> FEATURE:
<223> OTHER INFORMATION: Hex548

<400> SEQUENCE: 35

Met Leu Leu Gly Asn Gly Arg Tyr Val
1               5

<210> SEQ ID NO 36
<211> LENGTH: 9
<212> TYPE: PRT
<213> ORGANISM: Artificial Sequence
<220> FEATURE:
```

```
<223> OTHER INFORMATION: Hex652

<400> SEQUENCE: 36

Met Leu Tyr Pro Ile Pro Ala Asn Ala
1               5

<210> SEQ ID NO 37
<211> LENGTH: 9
<212> TYPE: PRT
<213> ORGANISM: Artificial Sequence
<220> FEATURE:
<223> OTHER INFORMATION: Hex914

<400> SEQUENCE: 37

Thr Leu Leu Tyr Val Leu Phe Glu Val
1               5

<210> SEQ ID NO 38
<211> LENGTH: 9
<212> TYPE: PRT
<213> ORGANISM: Artificial Sequence
<220> FEATURE:
<223> OTHER INFORMATION: gp100-209

<400> SEQUENCE: 38

Ile Met Asp Gln Val Pro Phe Ser Val
1               5
```

ONCOLYTIC ADENOVIRUSES WITH MUTATIONS IN IMMUNODOMINANT ADENOVIRUS EPITOPES AND THEIR USE IN CANCER TREATMENT

FIELD OF THE INVENTION

The field of this invention generally relates to oncolytic adenoviruses with functional deletions of immunodominant T-cell epitopes of adenovirus proteins, as well as to methods of using the oncolytic adenoviruses for the treatment of diseases, such as cancer.

CROSS REFERENCE TO RELATED APPLICATION

This Application is a 371 of PCT/IB2016/052554 filed on May 4, 2016, which, in turn, claimed the priority of U.S. Patent Application No. 62/156,748 filed on May 4, 2015, both applications are incorporated herein by reference.

BACKGROUND OF THE INVENTION

Current cancer treatment is based mainly on chemotherapy, radiotherapy, and surgery. Despite a high rate of success when the treatment is applied at early stages, most cases of advanced disease are not curable because tumors cannot be excised by surgery or radio and chemotherapy doses that can be administered are limited by toxicity to normal cells. To alleviate this problem, biotechnology strategies that seek higher selectivity and potency have been developed. Among them, gene therapy and virotherapy use viruses with a therapeutic aim against cancer. In gene therapy, the virus is modified to avoid its replication and to function as a vehicle or vector of therapeutic genetic material. Conversely, virotherapy uses viruses that replicate and propagate selectively in tumor cells. In virotherapy, the tumor cell dies by the cytopathic effect caused by the replication of the virus inside the cell rather than by the effect of a therapeutic gene. The preferential replication in a tumor cell is known as oncolysis. In a strict sense, viruses that replicate selectively in tumors are named oncolytic, although in a broader sense the oncolytic word can be applied to any replication-competent virus able to lyse tumor cells, even without selectivity. In this description the oncolytic term is used in both senses.

Immunotherapy is based on the use of the immune system to eliminate a tumor. The main idea of treatment is to stimulate or restore the ability of the immune system to recognize tumor cells and activate effector cells to selectively destroy them. The different immunotherapies are divided into two groups: a) passive, which aims to improve existing anti-tumor immunity; and b) active, which involves directly stimulating a patient's immune system to trigger an anti-tumor immune response. Passive immunotherapies include monoclonal antibodies that block signals suppressing the immune system, such as Ipilimumab (CTLA-4), Nivolumab (PD-1), or MDX-1105 (PD-L1) (Pardoll, D. M., Nat Rev Cancer. 2012 Mar 22; 12(4):252-64). In this group, we also find the transfer of autologous T cells. There are several techniques to confer antitumor capacity, but all involve some degree of ex vivo manipulation of cells. Ex vivo manipulation of cells includes: a) stimulating cells against a tumor antigen and amplifying these cells specifically, and b) introducing tumor-specific receptors by inserting a high affinity T-cell receptor (TCR) transgenic for a tumor-associated antigen or replacing the TCR with a chimeric antigen receptor (CAR) (Kalos, M. and June, C. H., Immunity 2013 Jul. 25; 39(1):49-60). In the case of active therapies, one approach is to reactivate or re-stimulate the immune system of a patient in vivo. For example, use of the immunostimulatory cytokine IL-2 has been used for over a decade to treat melanoma and renal carcinoma (Amin, A. and White, R. L. Jr., Oncology (Williston Park). 2013 July; 27(7):680-91). In addition, TNF-α (van Horssen, R., et al., Oncologist. 2006 April; 11(4):397-408) and IFN type I and II (Kotredes, K. P. and Gamero, A. M., J Interferon Cytokine Res. 2013 April; 33(4):162-70) have been used in cancer treatment. Finally, one of the fields with more development in recent years has been therapeutic vaccines (Myc, L. A., et al., Arch Immunol Ther Exp (Warsz). 2011 August; 59(4): 249-59). A wide range of preparations have been used to immunize, including DNA-based vaccines (Bei, R. and Scardino A., J Biomed Biotechnol. 2010; 2010:102758), peptide-based vaccines (Arens, R., et al., Semin Immunol. 2013 April; 25(2):182-90; Vacchelli, E., et al., Oncoimmunology. 2012 Dec. 1; 1(9):1557-1576), dendritic cell-based vaccines (Bonaccorsi, I., et al., Immunol Lett. 2013 September-October; 155(1-2):6-10; Palucka, K. and Banchereau, J., Immunity. 2013 Jul. 25; 39(1):38-48), and viral vector-based vaccines (Larocca, C. and Schlom, J., Cancer J. 2011 September-October; 17(5):359-71). Despite great efforts made so far, the effectiveness of this type of therapy remains limited. The main obstacles to overcome are tumor immunosuppression and the power and specificity of the induced response.

Cancer virotherapy is older than gene therapy. First reports on cancer cures with viruses date to the beginning of the past century. In 1912, De Pace obtained tumor regressions after the inoculation of rabies virus in cervical carcinomas (De Pace N., Ginecologia 1912; 9:82-89). Since De Pace 1912, many types of viruses have been injected in tumors to treat them. There are viruses that present a natural oncotropism such as autonomous parvovirus, vesicular stomatitis virus, and reovirus. Other viruses can be genetically manipulated to achieve selective replication in tumors. For example, Herpes Simplex virus (HSV) has been rendered oncotropic by deleting the ribonucleotide reductase gene, an enzymatic activity not necessary in cells undergoing active proliferation such as tumor cells. However, adenovirus, due to its low pathogenicity and high efficacy to infect tumor cells, has been the most commonly used virus in virotherapy and gene therapy of cancer.

The use of replicative virus in cancer virotherapy is based on the idea that, as a result of viral replication, the tumor cells are destroyed and released viral progeny infect surrounding cells. After multiple replication rounds, total destruction of the tumor is achieved. In principle, only a few cells are initially infected, but the virus replicative effect generates a chain reaction such that the virus expands throughout the tumor mass. Once the virus reaches and infects normal cells in the periphery, the virus is not able to replicate in them due to its tumor selectivity, and normal tissue does not suffer pathogenic effects.

There are different aspects to consider when choosing a viral species for cancer virotherapy. Adenoviruses are non-enveloped viruses 70-90 nm in diameter with an icosahedral capsid. Their genome is linear, double-stranded DNA varying between 25-45 kilobases in size with inverted terminal repeats (ITRs) at both termini and a terminal protein attached to the 5' ends (Russell, W. C., J Gen Virol 2009 90:1-20). Adenoviruses have a lytic replicative cycle and thus kill cells in which they replicate. In addition, the extensive knowledge of adenovirus biology and the possibility of manipulating adenovirus DNA make it easy to confer selectivity, improve other characteristics such as tumor cell infectivity, and increase the oncolytic potency by several strategies. Also, it is a virus which has a very low mutation rate and very mild pathology in immunocompetent patients. In addition, the replicative capacity of adenovirus is high, which allows it to be produced in highly concentrated amounts ($10^{12}$-$10^{13}$ virus particles (vp)/mL).

The icosahedral capsid is formed by three major proteins, of which the hexon trimers are most abundant (Nemerow, G. R., et al. Virology 2009 384:380-8). Each of the twelve vertices of the capsid also contains a pentameric protein, a penton base that is covalently attached to the fiber. The fiber is a trimeric protein that protrudes from the penton base and is a knobbed rod-like structure. Other viral proteins IIIa, IVa2, VI, VIII, and IX are also associated with the viral capsid. The proteins VII, small peptide mu, and a terminal protein (TP) are associated with DNA. Protein V provides a structural link to the capsid via protein VI.

The hexon protein is the most abundant capsid protein and represents 63% of the total protein mass of the virus. The protein has different well defined structural regions. The V1 and V2 domains form the base of each subunit. These domains adopt a "double barrel" or "double jellyroll" conformation and give the pseudohexagonal homotrimer form, which allows larger assembly of viral shells. These structures are separated by the VC region at the base and loop DE2 in the top half. These regions are highly conserved and thus play an important role in stabilizing V1 and V2. DE1, FG1, and FG2 form the top of the trimer. DE1 and FG1 zones contain highly variable and flexible areas whose structures have not been determined. These areas are called hypervariable regions (HVR). Various modifications in the HVRs can be made without affecting virus assembly (Roberts, D. M., et al., Nature. 2006 May 11; 441(7090):239-43; Alba, R., et al., Blood. 2009 Jul. 30; 114(5):965-71; Matthews, Q. L., Mol Pharm. 2011 Feb. 7; 8(1):3-11).

Human adenoviruses are classified within the family Adenoviridae. Fifty seven serotypes of human adenovirus have been identified and grouped in six differentiated groups, A to G. The human adenovirus type 5 (Ad5), which belongs to group C, consists of an icosahedral protein capsid which contains a double-stranded, linear DNA of 36 kilobases (kb). Adenoviruses are dependent on the cellular machinery to replicate the viral genome. They can infect quiescent cells and induce them into a cell cycle S-phase-like state enabling viral DNA replication. The Ad5 genome has eight overlapping transcriptional units on both DNA strands. The eight units are grouped according to the chronology of the transcripts: immediate early (E1A), early (E1B, E2, E3, E4), intermediate (IX, IVa), and late (L1-L5) genes (Russell, W. C., J Gen Virol 2009 90:1-20). At the ends of the genome are two ITR sequences that are identical to each other and contain the origins of viral DNA replication. A virion packaging signal formed by adenine and thymine rich sequences is present at the left end of the genome.

In adults, Ad5 infection is often asymptomatic and causes colds and conjunctivitis in children. In general terms, Ad5 infects epithelial cells, which in a natural infection are the bronchial epithelial cells. It enters the cell by means of the interaction of the fiber, which extends as an antenna from the twelve vertexes of the capsid, with a cellular protein involved in intercellular adhesion known as Coxsackie-Adenovirus Receptor (CAR). When the virus DNA reaches the nucleus, the transcription of early genes (E1 to E4) begins. The first genes to be expressed are those from the early 1A region (E1A). E1A binds to cellular protein pRb (retinoblastoma protein) to release the transcription factor E2F to activate the transcription of other virus genes such as E2, E3, and E4, and of cellular genes that activate the cell cycle. On the other hand, E1B binds to the transcription factor p53 to activate the cell cycle and to inhibit the apoptosis of the infected cell. E2 encodes proteins for replication of the virus. E3 encodes proteins that inhibit the antiviral immune response. E4 encodes for proteins involved in viral RNA transport. The expression of early genes leads to the replication of the genome and, once replicated, to the activation of the major late promoter. This promoter drives the expression of an mRNA that is processed by differential splicing to give all the RNAs that encode the structural proteins that form the capsid.

There are two important points to consider regarding the design of oncolytic adenoviruses: selectivity and potency. To achieve selectivity towards a tumor cell, three strategies have been used: the deletion of virus functions required for replication in normal cells, but that are dispensable for replication in tumor cells; the substitution of viral promoters with tumor selective promoters, for example driving expression of genes that initiate viral replication under tumor selective promoters; and the modification of the virus capsid proteins implied in the infection of the host cell. With such genetic modifications, a considerable level of selectivity has been obtained, with a replication efficiency in a tumor cell 10000-fold higher than in a normal cell.

Adenoviruses require the machinery of the host cell for replication of their genetic material. Therefore, mutations or deletions in the viral genes involved in the activation of cell replication or inhibition of apoptosis generate conditionally replicating virus. In contrast, tumor cells have both activated cell cycle and inhibited apoptotic pathways, allowing adenoviruses harboring mutations or deletions in the viral genes involved in the activation of cell replication or inhibition of apoptosis to replicate. For example, p53 is activated in an infected cell and its effect is normally blocked by E1b-55K. Given that p53 is mutated in approximately 50% of tumors, the virus dl1520 (ONYX-015) was used as an oncolytic virus (Bischoff, J. R., et al., Science. 1996 Oct. 18; 274 (5286):373-6). This virus has a deletion of 827 bp of the gene E1b-55K. The selectivity mechanism is based on the fact that a normal cell with functional p53 enters apoptosis before allowing the replicative cycle of the virus to be completed. However, tumor cells with non-functional p53 (or other disorders affecting regulation) allow the virus to replicate normally (Hall, A. R., et al., Nat Med. 1998 September; 4(9):1068-72; Rothmann, T., et al., J Virol. 1998 December; 72(12):9470-8; Goodrum, F. D. and Ornelles, D. A., J Virol. 1998 December; 72(12):9479-90).

In another strategy to achieve selectivity, partial deletions of E1A result in restricted replication in normal cells but allow replication in target cells, such as cancer cells. Conditionally replicating viruses featuring a 24 base pair deletion in the CR2 (constant region 2) have been created and shown to be potent and selective in the treatment of glioma and breast cancer xenografts (Fueyo, J., et al., Oncogene 2000 19:2-12; Heise, C., et al., Nat Med 2000 6(10):1139-9). Their cancer specificity results from the inability of dysfunctional E1A to release E2F1 transcription factor, which leads to the requirement of free E2F1. E2F1 is abundant in cancer cells, where the pRb pathway is most often disrupted (Hanahan, D. and Weinberg, R. A., Cell. 2000 Jan. 7; 100(1):57-70).

Another strategy for conferring tumor selectivity is the use of adenoviruses which harbor deletions of adenovirus VA-RNA genes (Cascalló, M., et al., Cancer Res. 2003 Sep. 1; 63(17):5544-50; Cascalló, M., et al., Hum Gene Ther. 2006 September; 17(9):929-40) and which depend on activation of the RAS pathway or truncation of the interferon pathway commonly present in tumor cells.

Another strategy for conferring tumor selectivity is to limit expression of adenovirus genes essential for viral replication using promoters specific for certain types of tumors. Adenoviruses have been generated with various specific promoters, such as the α-fetoprotein promoter (Hallenbeck, P. L., et al., Hum Gene Ther. 1999 Jul. 1; 10(10): 1721-33). This virus selectively replicates in hepatocarcinoma cells overexpressing α-fetoprotein. Similarly, viruses have been constructed which control the expression of E1A using 1) a promoter derived from the human prostate-specific antigen (PSA) gene to achieve selective replication in PSA-expressing prostate cancer cells (Rodriguez, R., et al., Cancer Res. 1997 Jul. 1; 57(13):2559-63), 2) a human osteocalcin (hOC) promoter to achieve selective replication in hOC-expressing prostate cancer cells (Hsieh et al., Cancer Res. 2002 Jun. 1; 62(11):3084-92), and 3) a DF3/MUC1 promoter to achieve selective replication in MUC1-positive breast cancer cells (Kurihara, T., et al., J Clin Invest. 2000 September; 106(6):763-71).

In contrast to promoters specific for certain types of tumors, promoters that respond to the E2F transcription factor, such as the E2F-1 promoter, allow expression of adenovirus genes essential for viral replication in a wide range of tumors (Cascallo, M., et al., Mol Ther. 2007 September; 15(9):1607-15; Johnson, L., et al., Cancer Cell. 2002 May; 1(4):325-37, Rojas, J. J., et al., Gene Ther. 2009 December; 16(12):1441-51, Tsukuda, K., et al., Cancer Res. 2002 Jun. 15; 62(12):3438-47). In normal cells, expression of an essential adenovirus gene from a E2F-1 promoter would be inhibited due to the association of E2F with pRb. In tumor cells, however, there are increased levels of "free" E2F as a consequence of the absence or hyperphosphorylation of pRb, which results in the expression of the essential adenovirus gene from the E2F-1 promoter. For example, the ICOVIR15K adenovirus (SEQ ID NO:1) contains palindromic E2F-binding sites inserted into the endogenous E1A promoter. The insertion of these sites allows selective expression of the E1AΔ24 protein in highly replicative cells, such as cancer cells. In addition, the E1AΔ24 protein of ICOVIR15K harbors a deletion of the pRb-binding site of E1A which renders the mutant adenovirus unable to dissociate pRb from E2F in quiescent normal cells.

An example of a modification of a virus capsid protein to achieve selectivity is the elimination of the heparin sulphate glycosaminoglycan (HSG)-binding site KKTK (SEQ ID NO: 26) of the fiber shaft to reduce hepatic tropism (Bayo-Puxan, N., et al., Hum Gene Ther. 2009 October; 20(10): 1214-21). In the ICOVIR15K adenovirus, this was accomplished by replacing the HSG-binding site KKTK (SEQ ID NO: 26) in the fibre shaft with an integrin-binding motif (RGDK) (SEQ ID NO: 27). This modification in the ICOVIR15K adenovirus improves the tumor/liver transduction ratio with respect to a wild-type virus fiber, enhances the toxicity profile, increases the virus infectivity of cancer cells, and increases the antitumor efficacy in experimental models in vivo (Rojas, J. J., et al., Gene Ther. 2012 April; 19(4):453-7).

With regard to oncolytic potency, several genetic modifications to increase it have been described as well. These modifications affect either the entry of the virus in the cell or the release of virus from the cell. To increase the entry step, the capsid proteins that the virus uses to infect the cell have been modified. For example, the insertion of the RGD peptide (Arginine-Glycine-Asparagine motif) in the fiber allows adenovirus to use integrins to dock in the cell and not only to internalize as it is the case with wild type adenovirus. The use of integrins as cellular receptors of the virus increases the infectivity and the oncolytic potency.

Regarding the modifications that increase the release of virus from the infected cell, these modifications include the deletion of E1b-19K, the overexpression of E3-11.6K (ADP), and localizing E3/19K protein in the plasmatic membrane. E1b-19K is an apoptosis inhibitor homolog to Bcl-2. E1b-19K deletion increases cell death by premature apoptosis of the infected cell. This premature apoptosis often results in a lower total virus production in many infected cell lines; however, it accelerates the fast release of virus and, in turn, the spread of virus in a cell culture. Accordingly the mutants that do not express E1b-19K present a large plaque phenotype compared to the wild type adenovirus in a plaque assay. E3-11.6K (ADP) protein plays a role in the lysis of the infected cell and ADP overexpression increases the release of the virus accumulated inside the nucleus. The phenotype of ADP-overexpressing viruses is also characterized by large plaques and the presence of more viruses in the supernatant of infected cells. ADP overexpression has been achieved by two mechanisms: 1) Eliminating the other E3 genes except ADP, or except ADP and E3-12.5K; and 2) inserting the ADP gene after an strong promoter. Eliminating the other E3 genes except ADP, or except ADP and E3-12.5K, removes other splicing sites in the pre-mRNA driven by the E3 promoter. Without the competition for these splice sites, the processing of the mRNA encoding ADP is favored.

Another strategy used to increase the oncolytic potency of adenovirus is the insertion of a therapeutic gene in the genome of the oncolytic adenovirus to generate an "armed oncolytic adenovirus." In this case, the therapeutic gene would have to mediate the death of non-infected tumor cells by means of the activation of a prodrug with bystander effect (that is to say, that kills the non-infected neighbouring cells), the activation of the immune system against the tumor, the induction of the apoptosis, the inhibition of the angiogenesis, or the elimination of the extracellular matrix, among others. In these cases, the way and the time of expression of the therapeutic gene will be critical in the final result of the therapeutic approach.

Regarding oncolytic viruses armed with a therapeutic gene to activate the immune system against the tumor, virally infected cells are superior at delivery of non-viral antigen (i.e., tumor antigen) for cross-presentation (Schulz, O., et al., Nature. 2005 Feb. 24; 433(7028):887-92), and virally induced cell death would be expected to enhance the availability of tumor-associated antigens for uptake by dendritic cells (DCs) (Moehler, M. H., et al., Hum Gene Ther. 2005 August; 16(8):996-1005) and subsequently enhance stimulation of cytotoxic T-cells. Furthermore, viral infection may alter the balance of cytokine production from the tumor, and subsequently affect the nature of the immune reaction to the tumor, that is, by counteracting the immunosuppressive nature of the tumor microenvironment (Prestwich, R. J., et al., Expert Rev Anticancer Ther. 2008 October; 8(10):1581-8). Most importantly, viruses can be engineered to express highly immunogenic proteins such as granulocyte-macrophage colony-stimulating factor (GM-CSF). When immunogenic proteins are expressed within tumor cells, they are potent stimulators of specific and long-lasting antitumor immunity. Introduction of immunotherapeutic genes into tumor cells and, furthermore, their translation into proteins, leads to the activation of the immune response and to more efficient destruction of tumor cells. The most relevant immune cells in this regard are natural killer cells (NK) and cytotoxic CD8+ T-cells.

The immune response against the oncolytic virus is one of the most important parameters to be considered in developing virotherapies. With respect to the host immune response, two seemingly opposing positions are at play. One being that the immune system is a barrier which eliminates the oncolytic virus before it can destroy all tumor cells. The other being that the virus is a vehicle to induce an antitumor immune response.

The terms "immunodominance" and "immunodominant" were originally used in the 1960s and 1970s to refer to particularly potent humoral immune responses to specific antigenic determinants. (Curtiss, L. K. and Krueger, R. G., Immunochemistry. 1975 December; 12(12):949-57; Johnston et al., J Pathol Bacteriol. 1968 April; 95(2):477-80). Some years later, different authors described that the response to various pathogens in experimental mice was restricted to certain alleles of H-2 depending on the pathogen or that the main response was restricted to one allele specific H-2 (Biddison et al., J. Ex. Med. 1978 Dec. 1; 148(6):1678-86; Doherty P. C. and Zinkernagel R. M., Nature. 1975 Jul. 3; 256(5512):50-2). It was also described that specific H-2 alleles are linked to low responsiveness or non-responsiveness for a given antigenic determinant (Bennink, J. R. and Yewdell, J. W., J Exp Med. 1988 Nov. 1; 168(5):1935-9). As knowledge regarding the peptide nature of antigenic determinants advanced, the existence of immunodominant or subdominant determinants according to the amount of antigen required to induce a detectable immune response was described (Sercarz, E. E., et al., Annu Rev Immunol. 1993; 11:729-66). Epitope immunodominance refers to the phenomenon that is observed after infection with a virus or bacteria, which has multiple antigens and generates hundreds or thousands of peptides that can be presented by between 3 to 6 different alleles (in humans) to MHC class I. However, only a small number of these epitopes are actually presented by certain MHC alleles and are capable of generating a response (Yewdell, J. W. and Del Val, M., Immunity. 2004 August; 21(2):149-53). There are different factors involved in epitope immunodominance, including: immune history, route of infection, abundance of viral proteins and antigen processing, transportation and stability of the peptide/MHC complex, co-expression of multiple alleles of MHC, frequency of precursor T cells in the repertoire of naïve cells, MHC/TCR interaction, memory CTL generation, and generation of regulatory T (Treg) cells. Overall, the most important parameters to define a hierarchy of immunodominance are that an epitope is processed efficiently and to have at least a minimal threshold affinity for anchoring to given MHC allele (Beekman et al., J Immunol. 2000 Feb. 15; 164(4):1898-905; Seifert et al., J Clin Invest. 2004 July; 114(2):250-9; Sette, A., et al., J Immunol. 1994 Dec. 15; 153(12):5586-92; Regner et al., Viral Immunol. 2001; 14(2):135-49). In the absence of these minimal characteristics, an epitope would not differ from the multitude of non-immunogenic peptides produced during the normal process of protein degradation.

In spite of the efforts to date, it is still necessary to find new therapeutic approaches effective in the treatment of cancer.

SUMMARY OF THE INVENTION

The inventors surprisingly found that oncolytic adenoviruses comprising at least one functional deletion of an immunodominant T-cell epitope of an adenovirus protein result in an immune-shift from an anti-adenovirus immune response to an anti-tumoral immune response in a mammal. Thus, the present invention provides novel oncolytic adenoviruses with mutations in immunodominant T-cell epitopes of adenovirus proteins and methods of their use for the treatment of diseases, such as cancer. Polynucleotides comprising nucleic acid sequences encoding the oncolytic adenoviruses are also provided, as are vectors comprising the polynucleotides. Cells comprising the oncolytic adenoviruses and/or polynucleotides of the invention are further provided. Compositions (e.g., pharmaceutical compositions) comprising the novel oncolytic adenoviruses are also provided. In addition, methods of making and using the novel oncolytic adenoviruses are also provided, such as methods of using the novel oncolytic adenoviruses to induce lysis of tumor cells, inhibit tumor growth in a mammal, treat cancer in a mammal, and/or increase the immune response against cancer in a mammal.

Thus, in one aspect, the invention provides an oncolytic adenovirus comprising at least one functional deletion of an immunodominant T-cell epitope of an adenovirus protein. The object of this deletion is to indirectly allow for a stronger immune response against tumor antigens, but not necessarily intended to provide a better infectivity or replication tropism towards tumor cells. In certain embodiments, the immunodominant T-cell epitope is a human lymphocyte antigen (HLA) class I-restricted epitope. In embodiment, the immunodominant T-cell epitope is a human lymphocyte antigen-A2.1 (HLA-A2.1)-restricted epitope. In a certain embodiment, the immunodominant T-cell epitope is a human lymphocyte antigen (HLA) class II-restricted epitope.

In one embodiment, the at least one functional deletion is not associated with substantially reduced cytotoxicity or substantially reduced viral replication in comparison to a parental adenovirus lacking said at least one deletion.

In another embodiment, the at least one functional deletion of an immunodominant T-cell epitope is in an adenovirus protein selected from the group consisting of: E1A, E1B, hexon, penton base, fiber protein, capsid protein IX, DNA polymerase, and single-stranded DNA-binding protein. In a certain embodiment, the at least one functional deletion of an immunodominant T-cell epitope is in the adenovirus hexon protein. In a certain embodiment, the at least one functional deletion of an immunodominant T-cell epitope is in the conserved base region of the adenovirus hexon protein.

In certain embodiments, the at least one functional deletion of an immunodominant T-cell epitope is selected from the group consisting of: Hex512 (GLVDCYINL) (SEQ ID NO: 23), Hex713 (YLNHTFKKV) (SEQ ID NO: 11), Hex892 (LLYANSAHA) (SEQ ID NO: 15), and Hex917 (YVLFEVFDV) (SEQ ID NO: 19). In certain embodiments, the adenovirus comprises at least one mutation selected from the group consisting of: a L520P mutation in the Hex512 epitope, a V721A mutation in the Hex713 epitope, an A900S mutation in the Hex892 epitope, and a V925K mutation in the Hex917 epitope.

In one embodiment, the adenovirus comprises functional deletions of the immunodominant T-cell epitopes Hex512 (GLVDCYINL) (SEQ ID NO: 23) and Hex917 (YVLFEVFDV) (SEQ ID NO: 19). In a certain embodiment, the adenovirus comprises a L520P mutation in the Hex512 epitope and a V925K mutation in the Hex917 epitope.

In one embodiment, the adenovirus comprises functional deletions of the immunodominant T-cell epitopes Hex713

(YLNHTFKKV) (SEQ ID NO: 11), Hex892 (LLYAN-SAHA) (SEQ ID NO: 15), and Hex917 (YVLFEVFDV) (SEQ ID NO: 19). In another embodiment, the adenovirus comprises a V721A mutation in the Hex713 epitope, an A900S mutation in the Hex892 epitope, and a V925K mutation in the Hex917 epitope.

In an embodiment, the adenovirus comprises functional deletions of the immunodominant T-cell epitopes Hex512 (GLVDCYINL) (SEQ ID NO: 23), Hex713 (YLNHTFKKV) (SEQ ID NO: 11), Hex892 (LLYAN-SAHA) (SEQ ID NO: 15), and Hex917 (YVLFEVFDV) (SEQ ID NO: 19). In another embodiment, the adenovirus comprises a L520P mutation in the Hex512 epitope, a V721A mutation in the Hex713 epitope, an A900S mutation in the Hex892 epitope, and a V925K mutation in the Hex917 epitope.

In one embodiment, the adenovirus is a human adenovirus. In certain embodiments, the adenovirus is a human adenovirus selected from the group consisting of: human adenovirus serotypes 1 to 51, and derivatives thereof. In a certain embodiment, the adenovirus is the human adenovirus serotype 5.

In certain embodiments, the oncolytic adenovirus selectively replicates in tumors. In one embodiment, the oncolytic adenovirus selectively replicates in tumors and further comprises a tissue-specific or a tumor-specific promoter to achieve selective replication in tumors. In another embodiment, the tissue-specific promoter or the tumor-specific promoter are promoter sequences to control the expression of one or more genes from the group consisting of E1a, E1b, E2, and E4, to achieve selective replication in tumors. In a certain embodiment, the tissue-specific promoter is selected from the group consisting of the E2F promoter, the telomerase hTERT promoter, the tyrosinase promoter, the prostate-specific antigen promoter, the alpha-fetoprotein promoter, and the COX-2 promoter. In a certain embodiment, the oncolytic adenovirus selectively replicates in tumors and further comprises mutations in one or more genes selected from the group consisting of E1a, E1b, E4, and VA-RNAs to achieve selective replication in tumors.

In certain embodiments, the adenovirus further comprises capsid modifications to increase its infectivity or to target a receptor present in a tumor cell.

In some embodiments, the adenovirus further comprises at least one gene commonly used in the field of cancer gene therapy. In a certain embodiment, the at least one gene commonly used in the field of cancer therapy is a gene selected from the group consisting of: a prodrug-activating gene, a tumor-suppressor gene, and an immunostimulatory gene.

In another embodiment, the oncolytic adenovirus of the invention further comprises one or more heterologous nucleic acid sequences each encoding a tumor antigen or epitope. In a certain embodiment, the one or more heterologous nucleic acid sequences comprise 1 to 5 heterologous nucleic acid sequences each encoding a tumor antigen or epitope. In a certain embodiment, the tumor antigen or epitope is selected from the group consisting of: MAGE-1, MAGE-2, MAGE-3, CEA, Tyrosinase, midkine, BAGE, CASP-8, β-catenin, CA-125, CDK-1, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, MRP-3, Nestin, OLIG2, ART1, ART4, B-cyclin, Gli1, Cav-1, cathepsin B, CD74, E-cadherin, EphA2/Eck, Fra-1/Fosl1, GAGE-1, Ganglioside/GD2, GnT-V, β1,6-N, Ki67, Ku70/80, PROX1, PSCA, SOX10, SOX11, Survivin, UPAR, Mesothelin, and WT-1, or an epitope thereof. In one embodiment, the tumor antigen or epitope is a human tumor antigen or epitope.

In certain embodiments, the heterologous nucleic acid sequence is inserted in the adenovirus gene encoding said adenovirus protein having the at least one deletion of an immunodominant T-cell epitope.

In certain embodiments, the heterologous nucleic acid sequence is inserted in an adenovirus gene encoding an adenovirus protein other than said adenovirus protein having the at least one deletion of an immunodominant T-cell epitope.

In certain embodiments, the heterologous nucleic acid sequence is inserted in an adenovirus gene encoding adenovirus hexon protein. In one embodiment, the heterologous nucleic acid sequence is inserted into a hypervariable region of said adenovirus hexon protein. In another embodiment, the hypervariable region is hypervariable region 5 (HVR5).

In certain embodiments, the tumor antigen or epitope is flanked by flexible linkers. In one embodiment, the flexible linkers comprise an amino acid sequence selected from the group consisting of: GSGSR (SEQ ID NO: 28), AGSGSR (SEQ ID NO: 29), and AGSGS (SEQ ID NO: 30).

In an embodiment, the one or more heterologous nucleic acid sequences encode a gp100 tumor antigen or epitope, or a tyrosinase tumor antigen or epitope. In a certain embodiment, the one or more heterologous nucleic acid sequences comprise (a) a heterologous nucleic acid sequence encoding a gp100 antigen or epitope and (b) a heterologous nucleic acid sequence encoding a tyrosinase antigen or epitope. In a certain embodiment, the gp100 tumor antigen or epitope comprises the amino acid sequence YLEPGPVTA (SEQ ID NO: 31), and the tyrosinase antigen or epitope comprises the amino acid sequence YMDGTMSQV (SEQ ID NO: 32). In a certain embodiment, the heterologous nucleic sequence encoding the gp100 antigen or epitope is inserted into hypervariable region 5 of the adenovirus hexon protein. In a certain embodiment, the heterologous nucleic sequence encoding the tyrosinase tumor antigen or epitope is inserted into hypervariable region 5 of the adenovirus hexon protein. In a certain embodiment, the heterologous nucleic acid sequence encoding a gp100 antigen or epitope and the heterologous nucleic acid sequence encoding a tyrosinase antigen or epitope are both inserted into hypervariable region 5 of the adenovirus hexon protein.

In another embodiment, the invention provides an oncolytic adenovirus comprising the nucleotide sequence of SEQ ID NO: 3 or 4.

In another embodiment, the invention provides an oncolytic adenovirus comprising the nucleotide sequence of SEQ ID NO: 5.

The invention also provides a pharmaceutical composition comprising a pharmacologically effective dosage of an oncolytic adenovirus of the invention and one or more pharmaceutically acceptable carriers or excipients.

The invention also provides a kit comprising the pharmaceutical composition of the present invention and instructions for use. In a certain embodiment, the kit further comprises one or more additional therapeutic agents. In a certain embodiment, the therapeutic agent is a chemotherapeutic agent.

The invention also provides a host cell comprising the oncolytic adenovirus of the present invention.

The invention also provides a method of producing infectious adenovirus particles comprising (a) culturing a host cell of the present invention under conditions that allow said oncolytic adenovirus to propagate and form infectious adenovirus particles and (b) recovering said infectious adenovirus particles.

The invention also provides the use of the oncolytic adenovirus of the present invention in the preparation of a medicament for the treatment or prevention of cancer or a pre-malignant disease leading to cancer in a mammal. In one embodiment, the mammal is a human.

The invention also provides the oncolytic adenovirus of the present invention for use as a medicament. In a certain embodiment, the oncolytic adenovirus of the present invention is for use as a prophylactic and/or therapeutic agent in cancer.

The invention also provides a method of inducing lysis of tumor cells comprising contacting said tumor cells with an effective amount of the oncolytic adenovirus or pharmaceutical composition of the present invention to induce lysis of said tumor cells. The invention also provides a method of inhibiting tumor growth in a mammal comprising administering a therapeutically effective amount of the oncolytic adenovirus or pharmaceutical composition of the present invention to said mammal. In a certain embodiment, the mammal is human.

In an embodiment, the tumor is a tumor selected from the group consisting of: adenocarcinoma, adenoma, astrocytoma, carcinoma, chondroma, chondrosarcoma, cystadenoma, dysgerminoma, erythroid leukemia, fibroma, fibrosarcoma, granulosa cell tumor, hemangioma, hemangiosarcoma, leiomyoma, leiomyosarcoma, Leydig cell tumor, lipoma, liposarcoma, lymphoblastic leukemia, lymphocytic leukemia, lymphoma, malignant histiocytosis, malignant melanoma, mast cell tumor, melanocytoma, meningioma, mesothelioma, multiple myeloma, myeloid leukemia, oligodendroglioma, osteoma, osteosarcoma, plasmacytoma, rhabdomyoma, rhabdomyosarcoma, seminoma, Sertoli cell tumor, soft tissue sarcoma, squamous cell carcinoma, squamous papilloma, synovial cell sarcoma, thymoma, and transitional cell carcinoma.

The invention also provides a method of treating cancer in a mammal comprising administering a therapeutically effective amount of the oncolytic adenovirus or the pharmaceutical composition of the present invention to said mammal. The invention also provides a method for increasing the immune response against cancer in a mammal comprising administering the oncolytic adenovirus or the pharmaceutical composition of the present invention to said mammal in an amount effective to increase the immune response against said one or more tumor antigens or epitopes in said mammal. In a certain embodiment, the mammal is human.

In one embodiment, the cancer is selected from the group consisting of nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, and tonsil cancer.

In one embodiment, the oncolytic adenovirus or pharmaceutical composition is administered intratumorally, intravenously, intravascularly, intrathecally, intratracheally, intramuscularly, subcutaneously, intraperitoneally, intradermally, parenterally, intranasally, percutaneously, ocularly, intracranially, or orally. In one embodiment, approximately $10^4$ to $10^{14}$ viral particles of the adenovirus are administered to said mammal. In a certain embodiment, approximately $10^3$ to $10^{13}$ plaque forming units of the adenovirus are administered to said mammal.

In one embodiment, the method further comprises administering one or more additional therapeutic agents to said mammal. In a certain embodiment, the therapeutic agent is a chemotherapeutic agent.

The invention also provides an isolated polynucleotide comprising a sequence at least 90% identical, at least 95% identical, at least 99% identical, or 100% identical to a sequence selected from the group consisting of SEQ ID NOs: 3, 4, and 5. The invention also provides a vector comprising the isolated polynucleotide of the present invention. The invention also provides a host cell comprising the vector of the present invention.

BRIEF DESCRIPTION OF THE DRAWINGS

FIG. 5A shows the total number of transducing units (TU) per ml produced by each virus at different times post-infection. FIG. 5B shows the number of TU/ml released by each virus at different times post-infection.

FIG. 6A shows the HLA-A2.1 affinity curves for mutated adenoviral epitopes. FIG. 6B shows the HLA-A2.1 affinity curves for tumor epitopes. FIG. 6C shows the Kd values and the functionality for each mutation.

FIG. 8A shows the experimental design to vaccinate HHD transgenic mice with different oncolytic adenovirus including ICOVIR15-TD-gp100-tyr. A single dose of $10^{10}$ viral particles (vp) of inactive virus was given intramuscularly (IM) on day 0, then a boost dose of $10^{10}$ vp at day 14 using an intravenous (IV) injection of active virus. After 21 days, mice were challenged with $10^6$ B16CAR-A2 cells. Tumor growth appearance (FIG. 8B) and growth (FIG. 8C) were monitored over the time until ELISPOT analysis of splenocytes was performed. FIG. 8D shows the survival curves plotted using GraphPad Prism. Final end point was established to be 500 mm$^3$. N=12 tumor injection sites per group and N=6 mice per group.

FIG. 10A shows the HLA-A2.1 affinity curves for mutated Hex512 and Hex917. FIG. 10B shows the Kd values and the functionality of each mutation.

FIG. 11A shows tumor volume. FIG. 11B shows tumor regression. Viruses were injected at $10^{10}$ vp/tumor on day 0. N=7-9 tumors per group.

FIG. 12A is a schematic showing that B16CAR-A2 cells were subcutaneously injected in both flanks of mice and allowed to form tumors. 9 days post-injection, right side tumors were intratumorally injected with ICOVIR15K (N=6), ICOVIR15K-QD (N=5), or PBS (N-4) at $10^{10}$ vp/tumor (day 0). Left side tumors were left untreated for all groups. FIG. 12B shows volume of tumors directly injected. FIG. 12C shows volume of non-injected tumors (contralateral) (N=6-7 tumors per group).

DETAILED DESCRIPTION OF THE INVENTION

Figure 1:
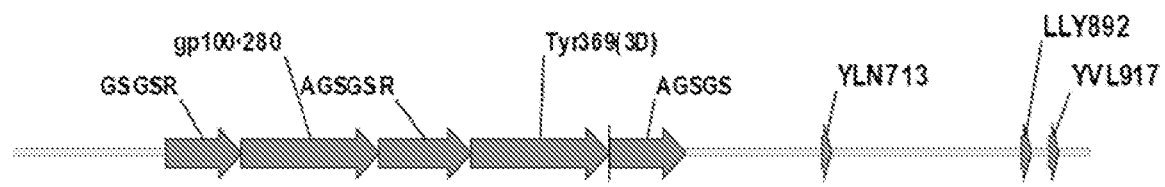
FIG. 1. Schematic representation of the hexon modifications in oncolytic adenovirus ICOVR15K-gp100-tyr (SEQ ID NO: 2).

The present invention provides novel agents, including, but not limited to oncolytic adenoviruses with one or more functional deletions in immunodominant T-cell epitopes of adenovirus proteins. Related polypeptides and polynucleotides, compositions comprising the oncolytic adenoviruses, and methods of making or producing the oncolytic adenoviruses are also provided. Methods of using the novel oncolytic adenoviruses, such as methods of inducing tumor cell lysis, inhibiting tumor growth, treating cancer, and/or increasing the immune response against cancer, are further provided.

I. Definitions

To facilitate an understanding of the present invention, a number of terms and phrases are defined below.

The term "adenovirus" as referred to herein indicates over 52 adenoviral subtypes isolated from humans, and as many from other mammals and birds. See, e.g., Strauss, S. E., "Adenovirus Infections in Humans," in The Adenoviruses, Ginsberg, ed., Plenum Press, New York, N.Y., pp. 451-496 (1984). The term "adenovirus" can be referred to herein with the abbreviation "Ad" followed by a number indicating serotype, e.g., Ad5.

As used herein, the term "oncolytic adenovirus" means an adenovirus that is able to replicate or that it is replication-competent in a tumor cell. They are different from a non-replicating adenovirus because a non-replicating adenovirus is unable to replicate in the target cell. Non-replicating adenoviruses are used in gene therapy as carriers of genes to target cells, since the goal is to express the therapeutic gene within the intact cell and not the lysis of the cell. In contrast, the therapeutic action of oncolytic adenoviruses is based on the ability to replicate and to lyse the target cell, and thereby eliminate the tumor cell. As used herein, oncolytic adenoviruses include both replication-competent adenoviruses able to lyse tumor cells, even without selectivity, and oncolytic adenoviruses that replicate selectively in tumors.

As used herein, the term "replication-competent adenoviral vector" or "replication-competent adenovirus" refers to any adenoviral vector or adenovirus, respectively, that is not deficient in any gene function required for viral replication in specific cells or tissues. The vector or adenovirus is capable of replicating and being packaged, but might replicate selectively or only conditionally in specific cells or tissues.

As used herein, a "tumor-specific oncolytic adenovirus" is an adenovirus that selectively kills cells of a proliferative disorder, e.g., cancer cells. A "tumor-specific oncolytic adenovirus" preferentially inhibits cell proliferation, causes cell lysis, or induces apoptosis (collectively considered killing) in a predetermined cell population with a given phenotype which supports virus replication. Such viruses are unable to or are limited in the ability to inhibit cell proliferation, cause cell lysis, induce apoptosis, or otherwise replicate in cells that do not have the predetermined cell phenotype. Killing of the cancer cells can be detected by any method established in the art, such as determining viable cell count, cytopathic effect, apoptosis of neoplastic cells, synthesis of viral proteins in the cancer cells (e.g., by metabolic labeling, Western analysis of viral proteins, or reverse transcription polymerase chain reaction of viral genes necessary for replication), or reduction in size of a tumor.

As used herein, a "functional deletion of an immunodominant T-cell epitope" refers to any mutation (i.e. insertion, substitution, or deletion) in the coding sequence of an immunodominant T-cell epitope that results in at least about a 10-fold reduction in HLA-A2 binding affinity of the epitope.

The term "epitope" or "antigenic determinant" are used interchangeably herein and refer to that portion of an antigen capable of being recognized by the immune system (e.g. T cells, B cells, and antibodies). When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. The term "immunodominant T-cell epitope" refers to an epitope or antigenic determinant of an antigen that is easily recognized by the immune system and provokes a robust $CD4^+$ or $CD8^+$ T-cell response compared to other epitopes of the same antigen or of other antigens processed simultaneously by the cell.

As used herein, an adenovirus having "substantially reduced cytotoxicity" refers to an adenovirus having about a 2-fold or greater reduction in its $IC_{50}$ value (multiplicity of infection required to achieve 50% cell cytotoxicity) in A549 cells at 5 days post-infection compared to the parental adenovirus.

As used herein, an adenovirus having "substantially reduced viral replication" refers to an adenovirus having a greater than about one log reduction in total viral burst size (amount of virus particles produced by one infected cell) in A549 cells at 60 hours post-infection in comparison to the parental adenovirus.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

As used herein, the term "proliferative disorder" refers to any cellular disorder in which the cells proliferate more rapidly than normal tissue growth. A proliferative disorder includes, but is not limited to, cancer.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, and tonsil cancer.

"Tumor" and "neoplasm" refer to any mass of tissue that results from excessive cell growth or proliferation, either benign (noncancerous) or malignant (cancerous) including pre-cancerous lesions. Examples of tumors include, but are not limited to, adenocarcinoma, adenoma, astrocytoma, carcinoma, chondroma, chondrosarcoma, cystadenoma, dysgerminoma, erythroid leukemia, fibroma, fibrosarcoma, granulosa cell tumor, hemangioma, hemangiosarcoma, leiomyoma, leiomyosarcoma, Leydig cell tumor, lipoma, liposarcoma, lymphoblastic leukemia, lymphocytic leukemia, lymphoma, malignant histiocytosis, malignant melanoma, mast cell tumor, melanocytoma, meningioma, mesothelioma, multiple myeloma, myeloid leukemia, oligodendroglioma, osteoma, osteosarcoma, plasmacytoma, rhabdomyoma, rhabdomyosarcoma, seminoma, Sertoli cell tumor, soft tissue sarcoma, squamous cell carcinoma, squamous papilloma, synovial cell sarcoma, thymoma, and transitional cell carcinoma.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The terms "pharmaceutical formulation" and "pharmaceutical composition" refer to a preparation which is in such form as to permit the biological activity of the active ingredient to be effective, and which contains no additional components which are unacceptably toxic to a subject to which the formulation would be administered. Such formulations and compositions can be sterile.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present application contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present application contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M., et al., J Pharm Sci. 1977 January; 66(1):1-19). Other pharmaceutically acceptable carriers known to those of skill in the art are suitable for compositions of the present application. An "effective amount" of an oncolytic adenovirus or other drug as disclosed herein is an amount sufficient to carry out a specifically stated purpose, such as a therapeutic or prophylactic purpose. An "effective amount" can be determined empirically and in a routine manner, in relation to the stated purpose.

The term "therapeutically effective amount" refers to an amount of an oncolytic adenovirus or other drug effective to "treat" a disease or disorder in a subject or mammal. In the case of cancer, the therapeutically effective amount of the oncolytic adenovirus or drug can reduce the number of cancer cells; reduce the tumor size; inhibit (i.e., slow to some extent and in a certain embodiment, stop) cancer cell infiltration into peripheral organs; inhibit (i.e., slow to some extent and in a certain embodiment, stop) tumor metastasis; inhibit, to some extent, tumor growth; and/or relieve to some extent one or more of the symptoms associated with the cancer. See the definition herein of "treating". To the extent the oncolytic adenovirus or drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

The word "label" when used herein refers to a detectable compound or composition which is conjugated directly or indirectly to a virus particle or a polypeptide so as to generate a "labeled" virus particle or polypeptide. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin, S. and Altschul, S. F., Proc Natl Acad Sci USA. 1990 March; 87(6):2264-2268, as modified in Karlin, S. and Altschul, S. F., Proc Natl Acad Sci USA. 1993 Jun. 15; 90(12):5873-5877, and incorporated into the NBLAST and XBLAST programs (Altschul, S. F., et al., Nucleic Acids Res. 1997 Sep. 1; 25(17):3389-402). In certain embodiments, Gapped BLAST can be used as described in Altschul et al., BLAST-2, WU-BLAST-2 (Altschul, S. F. and Gish, W., Methods Enzymol. 1996; 266: 460-80.), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna. CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second amino acid sequence is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least about 80% identical, at least about 85% identical, at least about 90% identical, and in some embodiments, at least about 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least about 70%, at least about 75%, at least about 80%, at least about 85%, at least about 90%, and in some embodiments at least about 95%, 96%, 97%, 98%, 99% nucleotide or amino acid residue identity, when compared and aligned for maximum correspondence, as measured using a sequence comparison algorithm or by visual inspection. In certain embodiments, identity exists over a region of the sequences that is at least about 10, about 20, about 40-60 residues in length or any integral value there between, or over a longer region than 60-80 residues, at least about 90-100 residues, or the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain embodiments, conservative substitutions in the sequences of the polypeptides and antibodies of the invention do not abrogate the binding of the polypeptide or antibody containing the amino acid sequence, to the antigen(s), i.e., the FOLR1 to which the polypeptide or antibody binds. Methods of identifying nucleotide and amino acid conservative substitutions which do not eliminate antigen binding are well-known in the art (see, e.g., Brummell, D. A., et al., Biochemistry. 1993 Feb. 2; 32(4):1180-7; Kobayashi, H., et al., Protein Eng. 1999 October; 12(10):879-84; and Burks, E. A., et al., Proc Natl Acad Sci USA. 1997 Jan. 21; 94(2):412-7).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, P., Laboratory Techniques in Biochemistry and Molecular Biology—Hybridization with Nucleic Probes. 1993; 24:19-78. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50%> of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30 seconds to 2 minutes, an annealing phase lasting 30 seconds to 2 minutes, and an extension phase of about 72° C. for 1 to 2 minutes. Protocols and guidelines for low and high stringency amplification reactions are provided, e.g., in Innis, M. A., et al., PCR Protocols: A Guide to Methods and Applications, Academic Press, Inc. N.Y. (1990)).

The term "recombinant" when used with reference, e.g., to a cell, or nucleic acid, protein, or virus, or vector, indicates that the cell, nucleic acid, protein, virus, or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled. A recombinant cell, virus, nucleic acid, protein, or vector can include a cell, virus, nucleic acid, protein, or vector that has been modified by the introduction of a heterologous nucleic acid or protein or the alteration of a native nucleic acid or protein. Thus, for example, recombinant cells include cells that express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

As used herein, the term "modification" refers to a change in the sequence of a nucleic acid or polypeptide sequence. For example, amino acid sequence modifications typically fall into one or more of three classes: substitutional, insertional or deletional variants. Insertions include amino and/or carboxyl terminal fusions as well as intrasequence insertions of single or multiple amino acid residues. Deletions are characterized by the removal of one or more amino acid residues from the protein sequence. As used herein, the symbol Δ or delta refers to a deletion. Substitutional modifications are those in which at least one residue has been removed and a different residue inserted in its place. Amino acid substitutions are typically of single residues, but can occur at a number of different locations at once. Substitutions, deletions, insertions or any combination thereof may be combined to arrive at a final construct. These modifications can be prepared by modification of nucleotides in the DNA encoding the protein, thereby producing DNA encoding the modification. Techniques for making insertion, deletion and substitution mutations at predetermined sites in DNA having a known sequence are well known. Modification techniques can involve the use of recombinant DNA technology to manipulate the DNA sequence encoding one or more polypeptide regions. Optionally, modification techniques include, for example, recombination, M13 primer mutagenesis and PCR mutagenesis.

The terms "transfection," "transduction," "transfecting," or "transducing," can be used interchangeably and are defined as a process of introducing a nucleic acid molecule or a protein to a cell. Nucleic acids are introduced to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using an adenoviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford, K. G., et al., Gene Ther. 2001 January; 8(1):1-4 and Prochiantz, A., Nat Methods. 2007 February; 4(2):119-20.

A "control" or "standard control" refers to a sample, measurement, or value that serves as a reference, usually a known reference, for comparison to a test sample, measurement, or value. For example, a test sample can be taken from a patient suspected of having a given disease (e.g. an autoimmune disease, inflammatory autoimmune disease, cancer, infectious disease, immune disease, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage-like synoviocytes, etc.).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Oncolytic Adenoviruses

The present invention provides oncolytic adenoviruses comprising at least one functional deletion of an immunodominant T-cell epitope of an adenovirus protein.

In certain embodiments, the immunodominant T-cell epitope is a human lymphocyte antigen (HLA) class I-restricted epitope. For example, in certain embodiments, the immunodominant T-cell epitope is a human lymphocyte antigen-A2.1 (HLA-A2.1)-restricted epitope. In other embodiments, the immunodominant T-cell epitope is a human lymphocyte antigen (HLA) class II-restricted epitope. Immunodominant epitopes are identified by measuring the potency of an immune response upon immunization of a host (animal) with an antigen. The potency of an immune response against a given epitope refers to the number of lymphocytes that recognize and become activated upon recognition of such epitope. The immunoproteosome of the cells cuts the antigens in small fragments (around 9 amino acids) and such fragments are translocated to the endoplasmic reticulum and loaded into MHC class I or class II molecules to be presented to the T cell receptor on lymphocytes. The efficiency of this processing and presentation pathway depends on the sequence of amino acids and the haplotype of MHC molecules. The presented fragments are defined as epitopes. The immunodominant epitopes are defined as the presented fragments that activate a higher number of lymphocytes of the immunized host. Quantification of the number of activated lymphocytes can be done using different techniques such as ELISPOT or Intracellular Cytokine Staining (ICS), that usually detect the cytokines secreted by activated lymphocytes. The amount of CD8+ or CD4+ that recognize human adenovirus epitopes in humans infected with wild type adenoviruses has been studied to identify the immunodominant epitopes of human adenoviruses. See, e.g., Tang J., et al., Virology 2006 July; 350(2): 312-22; Leen, A. M., et al., Blood 2004 October; 104(8): 2432-40; and Leen, A. M., et al., J Virol. 2008 January; 82(1):546-54.

In some embodiments, the at least one deletion is not associated with substantially reduced cytotoxicity or substantially reduced viral replication in comparison to a parental adenovirus lacking said at least one deletion.

In certain embodiments, the at least one deletion of an immunodominant T-cell epitope is in an adenovirus protein selected from the group consisting of: E1A, E1B, hexon, penton base, fiber protein, capsid protein IX, DNA polymerase, and single-stranded DNA-binding protein. In some embodiments, the at least one deletion of an immunodominant T-cell epitope is in the conserved base region of the adenovirus hexon protein. For example, in certain embodiments, the at least one deletion of an immunodominant T-cell epitope is selected from the group consisting of: Hex512 (GLVDCYINL) (SEQ ID NO: 23), Hex713 (YLNHTFKKV) (SEQ ID NO: 11), Hex892 (LLYANSAHA) (SEQ ID NO: 15), and Hex917 (YVLFEVFDV) (SEQ ID NO: 19). In some embodiments, the adenovirus comprises at least one mutation selected from the group consisting of: a L520P mutation in the Hex512 epitope, a V721A mutation in the Hex713 epitope, an A900S mutation in the Hex892 epitope, and a V925K mutation in the Hex917 epitope. In certain embodiments, the adenovirus comprises deletions of the immunodominant T-cell epitopes Hex512 (GLVDCYINL) (SEQ ID NO: 23) and Hex917 (YVLFEVFDV) (SEQ ID NO: 19). In some embodiments, the adenovirus comprises a L520P mutation in the Hex512 epitope and a V925K mutation in the Hex917 epitope. In certain embodiments, the adenovirus comprises deletions of the immunodominant T-cell epitopes Hex713 (YLNHTFKKV) (SEQ ID NO: 11), Hex892 (LLYANSAHA) (SEQ ID NO: 15), and Hex917 (YVLFEVFDV) (SEQ ID NO: 19). In some embodiments, the adenovirus comprises a V721A mutation in the Hex713 epitope, an A900S mutation in the Hex892 epitope, and a V925K mutation in the Hex917 epitope. In certain embodiments, the adenovirus comprises deletions of the immunodominant T-cell epitopes Hex512 (GLVDCYINL) (SEQ ID NO: 23), Hex713 (YLNHTFKKV) (SEQ ID NO: 11), Hex892 (LLYANSAHA) (SEQ ID NO: 15), and Hex917 (YVLFEVFDV) (SEQ ID NO: 19). In some embodiments, the adenovirus comprises a L520P mutation in the Hex512 epitope, a V721A mutation in the Hex713 epitope, an A900S mutation in the Hex892 epitope, and a V925K mutation in the Hex917 epitope.

In certain embodiments, the adenovirus is a human adenovirus. For example, in certain embodiments, the adenovirus is a human adenovirus selected from the group consisting of: human adenovirus serotypes 1 to 51, and derivatives thereof. In some embodiments, the adenovirus is the human adenovirus serotype 5.

Modifications of oncolytic adenovirus described herein may be made to improve the ability of the oncolytic adenovirus to treat cancer. Such modifications of an oncolytic adenovirus have been described by Jiang, H., et al., Curr Gene Ther. 2009 October; 9(5):422-7, see also U.S. Patent Application No. 20060147420, each of which are incorporated herein by reference. For example, the absence or the presence of low levels of the coxsackievirus and adenovirus receptor (CAR) on several tumor types can limit the efficacy of the oncolytic adenovirus. Various peptide motifs may be added to the fiber knob, for instance an RGD motif (RGD sequences mimic the normal ligands of cell surface integrins), Tat motif, polylysine motif, NGR motif, CTT motif, CNGRL motif, CPRECES motif or a strept-tag motif (Ruoslahti, E. and Rajotte, D., Annu Rev Immunol. 2000; 18:813-27, incorporated herein by reference). A motif can be inserted into the HI loop of the adenovirus fiber protein. Modifying the capsid allows CAR independent target cell infection. This allows higher replication, more efficient infection, and increased lysis of tumor cells (Suzuki et al., Clin Cancer Res. 2001 January; 7(1):120-6, incorporated herein by reference). Peptide sequences that bind specific receptors, such as EGFR or uPR, may also be added. Specific receptors found exclusively or preferentially on the surface of cancer cells may be used as a target for adenoviral binding and infection, such as EGFRvIII.

In certain embodiments, the oncolytic adenovirus selectively replicates in tumors and further comprises mutations in one or more genes selected from the group consisting of E1a, E1b, E4, and VA-RNAs to achieve selective replication in tumors. For example, in some embodiments, the oncolytic adenovirus is modified to include a 24 base pair deletion in the CR2 region of E1A (E1AΔ24).

In certain embodiments, the oncolytic adenovirus selectively replicates in tumors. For example, in some embodiments, the oncolytic adenovirus comprises a tissue-specific or a tumor-specific promoter to achieve selective replication in tumors. In some embodiments, the tissue-specific promoter or the tumor-specific promoter are promoter sequences to control the expression of one or more genes from the group consisting of E1a, E1b, E2, and E4, to achieve selective replication in tumors. In some embodiments, the tissue-specific promoter is selected from the group consisting of the E2F promoter, the telomerase hTERT promoter, the tyrosinase promoter, the prostate-specific antigen promoter, the alphafetoprotein promoter, and the COX-2 promoter. For example, in some embodiments, the oncolytic adenovirus is modified to express an essential adenovirus gene from a E2F-1 promoter. In some embodiments, palindromic E2F-binding sites are inserted into the endogenous E1A promoter of the oncolytic adenovirus to allow selective expression of E1A or E1AΔ24 in highly replicative cells.

In certain embodiments, the adenovirus comprises capsid modifications to increase its infectivity or to target a receptor present in a tumor cell. For example, in some embodiments, the oncolytic adenovirus is further modified to eliminate the heparin sulphate glycosaminoglycan (HSG)-binding site KKTK (SEQ ID NO: 26) of the fiber shaft to reduce hepatic tropism. In some embodiments, the oncolytic adenovirus is further modified to replace the heparin sulphate glycosaminoglycan (HSG)-binding site KKTK (SEQ ID NO: 26) of the fiber shaft with an integrin-binding motif (e.g. RGDK) (SEQ ID NO: 27) to increase the infectivity and oncolytic potency.

In certain embodiments, the adenovirus further comprises at least one gene commonly used in the field of cancer gene therapy. For example, in some embodiments, the at least one gene commonly used in the field of cancer therapy is a gene selected from the group consisting of: a prodrug-activating gene, a tumor-suppressor gene, and an immunostimulatory gene.

In certain embodiments, the oncolytic adenovirus of the invention further comprises one or more heterologous nucleic acid sequences each encoding a tumor antigen or epitope. In some embodiments, the one or more heterologous nucleic acid sequences comprises 1 to 5 heterologous nucleic acid sequences each encoding a tumor antigen or epitope. In some embodiments, the tumor antigens or epitopes include proteins encoded by genes with mutations or rearrangements unique to tumor cells, reactivated embryonic genes, tissue-specific differentiation antigens, and a number of other self-proteins.

In some embodiments, the tumor antigen or epitope is selected from the group consisting of: MAGE-1, MAGE-2, MAGE-3, CEA, Tyrosinase, midkine, BAGE, CASP-8, β-catenin, CA-125, CDK-1, ESO-1, gp75, gp100, MART-1, MUC-1, MUM-1, p53, PAP, PSA, PSMA, ras, trp-1, HER-2, TRP-1, TRP-2, IL13R alpha, IL13R alpha2, AIM-2, AIM-3, NY-ESO-1, C9orf112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, MRP-3, Nestin, OLIG2, ART1, ART4, B-cyclin, Glil, Cav-1, cathepsin B, CD74, E-cadherin, EphA2/Eck, Fra-1/Fosl1, GAGE-1, Ganglioside/GD2, GnT-V, β1,6-N, Ki67, Ku70/80, PROX1, PSCA, SOX10, SOX11, Survivin, UPAR, Mesothelin, and WT-1, or an epitope thereof. In some embodiments, the tumor antigen or epitope is a human tumor antigen or epitope.

In some embodiments, the heterologous nucleic acid sequence is inserted in the adenovirus gene encoding said adenovirus protein having the at least one functional deletion of an immunodominant T-cell epitope. In some embodiments, the heterologous nucleic acid sequence is inserted in an adenovirus gene encoding an adenovirus protein other than said adenovirus protein having the at least one deletion of an immunodominant T-cell epitope. In some embodiments, the heterologous nucleic acid sequence is inserted in an adenovirus gene encoding adenovirus hexon protein. For example, the heterologous nucleic acid sequence can be inserted into a hypervariable region of said adenovirus hexon protein. In a certain embodiment, the hypervariable region is hypervariable region 5 (HVR5). In certain embodiments, the heterologous nucleic acid sequence is inserted into the hexon hypervariable region 1, fiber protein HI loop, or fused to protein IX.

In some embodiments, the tumor antigen or epitope is flanked by flexible linkers. For example, in some embodiments, the flexible linkers comprise an amino acid sequence selected from the group consisting of: GSGSR (SEQ ID NO: 28), AGSGSR (SEQ ID NO: 29), and AGSGS (SEQ ID NO: 30). Preferably, insertion of heterologous nucleic acid sequences is done "in frame."

In certain embodiments, the oncolytic adenovirus of the invention further comprises one or more heterologous nucleic acid sequences encoding a gp100 tumor antigen or epitope, or a tyrosinase tumor antigen or epitope. In some embodiments, the one or more heterologous nucleic acid sequences comprise (a) a heterologous nucleic acid sequence encoding a gp100 antigen or epitope and (b) a heterologous nucleic acid sequence encoding a tyrosinase antigen or epitope. For example, in some embodiments, the gp100 tumor antigen or epitope comprises the amino acid sequence YLEPGPVTA (SEQ ID NO: 31), and the tyrosinase antigen or epitope comprises the amino acid sequence YMDGTMSQV (SEQ ID NO: 32). In some embodiments, the heterologous nucleic sequence encoding the gp100 antigen or epitope is inserted into hypervariable region 5 of the adenovirus hexon protein. In some embodiments, the heterologous nucleic sequence encoding the tyrosinase tumor antigen or epitope is inserted into hypervariable region 5 of the adenovirus hexon protein. In some embodiments, the heterologous nucleic acid sequence encoding a gp100 antigen or epitope and the heterologous nucleic acid sequence encoding a tyrosinase antigen or epitope are both inserted into hypervariable region 5 of the adenovirus hexon protein.

In certain embodiments, the invention provides an oncolytic adenovirus comprising the nucleotide sequence of SEQ ID NO: 3 or 4. In certain embodiments, the invention provides an oncolytic adenovirus comprising the nucleotide sequence of SEQ ID NO: 5.

In certain embodiments, the adenovirus is replication-competent in cells with a mutant Rb pathway. After transfection, adenoviral plaques are isolated from the agarose-overlaid cells and the viral particles are expanded for analysis. For detailed protocols the skilled artisan is referred to Graham, F. L. and Prevec, L., Methods Mol Biol. 1991; 7:109-28 (incorporated herein by reference in its entirety).

Alternative technologies for the generation of adenoviruses or adenovirus vectors include utilization of the bacterial artificial chromosome (BAC) system, in vivo bacterial recombination in a recA+bacterial strain utilizing two plasmids containing complementary adenoviral sequences, and the yeast artificial chromosome (YAC) system (PCT publications 95/27071 and 96/33280, which are incorporated herein by reference).

III. Polynucleotides and Polypeptides

Also provided herein are nucleic acids encoding the oncolytic adenoviruses described above. Optionally, one nucleic acid is provided encoding the oncolytic adenovirus (e.g. a plasmid). Optionally, a plurality of nucleic acids is provided encoding the oncolytic adenovirus (e.g. a plurality of plasmids).

Also provided is a host cell that has been infected with the modified adenovirus described throughout. The host cell can be transformed by the modified adenovirus described above. Optionally, the host cell has been genetically altered as a result of the uptake, incorporation and expression of the genetic material of the modified adenovirus described above. Optionally, the host cell is a mammalian cell, such as a human cell. The adenovirus can be a mammalian adenovirus such as a human adenovirus.

In certain embodiments, the invention encompasses isolated polynucleotides comprising a sequence at least about 90% identical to a sequence selected from the group consisting of SEQ ID NOs: 3, 4, and 5. In some embodiments, the isolated polynucleotides comprise a sequence at least about 95% identical to a sequence selected from the group consisting of SEQ ID NOs: 3, 4, and 5. In some embodiments, the isolated polynucleotides comprise a sequence at least about 99% identical to a sequence selected from the group consisting of SEQ ID NOs: 3, 4, and 5. In some embodiments, the isolated polynucleotides comprise a sequence selected from the group consisting of SEQ ID NOs: 3, 4, and 5. In certain embodiments, the invention encompasses vectors comprising the polynucleotides of the invention. In certain embodiments, the invention encompasses host cells comprising the polynucleotides or vectors of the invention.

Modifications are generated in the nucleic acid of a virus using any number of methods known in the art. For example, site directed mutagenesis can be used to modify a nucleic acid sequence. One of the most common methods of site-directed mutagenesis is oligonucleotide-directed mutagenesis. In oligonucleotide-directed mutagenesis, an oligonucleotide encoding the desired change(s) in sequence is annealed to one strand of the DNA of interest and serves as a primer for initiation of DNA synthesis. In this manner, the oligonucleotide containing the sequence change is incorporated into the newly synthesized strand. See, for example, Kunkel, T. A., Proc Natl Acad Sci USA. 1985 January; 82(2):488-92; Kunkel, T. A., et al., Methods Enzymol. 1987; 154:367-82; Lewis, M. K. and Thompson, D. V., Nucleic Acids Res. 1990 Jun. 25; 18(12):3439-43; Bohnsack, R. N., Methods Mol Biol. 1996; 57:1-12; Deng, W. P. & Nickoloff, J. A., Anal Biochem. 1992 January; 200(1):81-8; and Shimada, A., Methods Mol Biol. 1996; 57:157-65 (each of which are incorporated by reference herein in its entirety). Other methods are routinely used in the art to introduce a modification into a sequence. For example, modified nucleic acids are generated using PCR or chemical synthesis, or polypeptides having the desired change in amino acid sequence can be chemically synthesized. See, for example, Bang, D. and Kent, S. B., Proc Natl Acad Sci USA. 2005 Apr. 5; 102(14):5014-9 and references therein. Selection on a cell type on which virus is not usually grown (e.g., human cells) and/or chemical mutagenesis (see, for example, Rudd, P. and Lemay, G., J Gen Virol. 2005 May; 86(Pt. 5):1489-97) (incorporated herein by reference in its entirety) also can be used to generate modifications in the nucleic acid of a virus.

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Mark, D. F., et al., Proc Natl Acad Sci USA. 1984 September; 81(18):5662-6 and U.S. Pat. No. 4,588,585 (incorporated herein by reference in their entireties)

In some embodiments, a DNA sequence encoding one or more polypeptides of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding one or more polypeptides of interest. Recombinant expression vectors are replicable DNA constructs which have synthetic or cDNA-derived DNA fragments encoding a polypeptide of interest, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from Escherichia coli, including pCR1, pBR322, pMB9 and their derivatives, wider host range plasmids, such as M13 and filamentous single-stranded DNA phages.

Suitable host cells for expression one or more polypeptides of interest include prokaryotes, yeast, insect or higher eukaryotic cells under the control of appropriate promoters. Prokaryotes include gram negative or gram positive organisms, for example E. coli or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

In certain embodiments of the invention, cells infected by the adenovirus or adenoviral vector may be identified in vitro by including a reporter gene in the expression vector. Generally, a selectable reporter is one that confers a property that allows for selection. A positive selectable reporter is one in which the presence of the reporter gene allows for its selection, while a negative selectable reporter is one in which its presence prevents its selection. An example of a positive selectable marker is a drug resistance marker (genes that confer resistance to neomycin, puromycin, hygromycin, DHFR, GPT, zeocin and histidinol). Other types of reporters include screenable reporters such as GFP.

Various assays for determining levels and activities of protein are available, such as amplification/expression methods, immunohistochemistry methods, FISH and shed antigen assays, southern blotting, western blotting, or PCR techniques. Moreover, the protein expression or amplification may be evaluated using in vivo diagnostic assays, e.g. by administering a molecule (such as an antibody) which binds the protein to be detected and is tagged with a detectable label (e.g. a radioactive isotope) and externally scanning the patient for localization of the label. Thus, methods of measuring levels of protein levels in cells are generally known in the art and may be used to assess protein levels and/or activities in connection with the methods and compositions provided herein as applicable. These assays can be used to determine the effect of modifications in the adenovirus polypeptides (e.g. E1A, E1B, hexon, penton base, fiber protein, capsid protein IX, DNA polymerase, and single-stranded DNA-binding protein). For example, these assays can be used to determine if the modifications result in adenoviruses not capable of producing normal levels or fully functional gene products of the polypeptide(s) or to confirm adenoviruses comprising a mutation of all or part of one or more of the adenovirus polypeptides.

IV. Methods of use and Pharmaceutical Compositions

The oncolytic adenoviruses of the invention are useful in a variety of applications including, but not limited to, therapeutic treatment methods, such as the treatment of cancer. In certain embodiments, the oncolytic adenoviruses are useful for inducing tumor cell lysis, inhibiting tumor growth, treating cancer, and/or increasing the immune response against cancer. The methods of use may be in vitro, ex vivo, or in vivo methods.

In one aspect, the oncolytic adenoviruses of the present invention are useful in the preparation of a medicament for the treatment or prevention of cancer or a pre-malignant disease leading to cancer in a mammal. In some embodiments, the mammal is a human.

In one aspect, the oncolytic adenoviruses of the present invention are useful as a medicament. In some embodiments, the oncolytic adenoviruses of the present invention are useful as prophylactic and/or therapeutic agents in cancer.

In one aspect, the invention provides a method of inducing lysis of tumor cells comprising contacting said tumor cells with an effective amount of the oncolytic adenovirus or pharmaceutical composition of the present invention to induce lysis of the tumor cells. In certain embodiments, the method of inducing lysis of tumor cells comprises contacting the tumor cells with the oncolytic adenovirus in vitro. For example, an immortalized cell line or cancer cell line is cultured in a medium to which is added the oncolytic adenovirus to induce lysis of the tumor cells. In some embodiments, tumor cells are isolated from a patient sample such as, for example, a tissue biopsy, pleural effusion, or blood sample and cultured in a medium to which is added an oncolytic adenovirus to induce lysis of the tumor cells. In certain embodiments, the method of inducing lysis of tumor cells comprises contacting the tumor cells with the oncolytic adenovirus in an animal model. For example, oncolytic adenoviruses can be administered to tumor xenografts that have been grown in immunocompromised mice (e.g. NOD/SCID mice) to induce lysis of the tumor cells. In some embodiments, cancer stem cells are isolated from a patient sample such as, for example, a tissue biopsy, pleural effusion, or blood sample and injected into immunocompromised mice that are then administered the oncolytic adenovirus to induce lysis of the tumor cells. In some embodiments, the oncolytic adenovirus is administered at the same time or shortly after introduction of tumorigenic cells into the animal to induce lysis of the tumor cells. In some embodiments, the oncolytic adenovirus is administered as a therapeutic after the tumorigenic cells have grown to a specified size.

In one aspect, the invention provides a method of inhibiting tumor growth in a mammal comprising administering a therapeutically effective amount of the oncolytic adenovirus or pharmaceutical composition of the present invention to said mammal. In some embodiments, the mammal is human. In some embodiments, the mammal has a tumor or has had a tumor removed.

In some embodiments, the tumor is a tumor selected from the group consisting of: adenocarcinoma, adenoma, astrocytoma, carcinoma, chondroma, chondrosarcoma, cystadenoma, dysgerminoma, erythroid leukemia, fibroma, fibrosarcoma, granulosa cell tumor, hemangioma, hemangiosarcoma, leiomyoma, leiomyosarcoma, Leydig cell tumor, lipoma, liposarcoma, lymphoblastic leukemia, lymphocytic leukemia, lymphoma, malignant histiocytosis, malignant melanoma, mast cell tumor, melanocytoma, meningioma, mesothelioma, multiple myeloma, myeloid leukemia, oligodendroglioma, osteoma, osteosarcoma, plasmacytoma, rhabdomyoma, rhabdomyosarcoma, seminoma, Sertoli cell tumor, soft tissue sarcoma, squamous cell carcinoma, squamous papilloma, synovial cell sarcoma, thymoma, and transitional cell carcinoma.

In another aspect, the invention provides a method of treating cancer in a mammal comprising administering a therapeutically effective amount of the oncolytic adenovirus or the pharmaceutical composition of the present invention to said mammal. In another aspect, the invention provides a method for increasing the immune response against cancer in a mammal comprising administering the oncolytic adenovirus or the pharmaceutical composition of the present invention to said mammal in an amount effective to increase the immune response against said one or more tumor antigens or epitopes in said mammal. In some embodiments, the mammal is human. In some embodiments, the mammal has a tumor or has had a tumor removed.

In some embodiments, the cancer is selected from the group consisting of: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, and tonsil cancer.

Adenoviruses according to the invention may be administered locally or systemically. For example, in some embodiments, the oncolytic adenovirus or pharmaceutical composition is administered intratumorally, intravenously, intravascularly, intrathecally, intratracheally, intramuscularly, subcutaneously, intraperitoneally, intradermally, parenterally, intranasally, percutaneously, ocularly, intracranially or orally. Adenoviruses according to the invention may also be administered in a cellular carrier.

An effective amount of the therapeutic or preventive agent is determined based on the intended goal, for example stimulation of an immune response against a tumor. Those of skill in the art are well aware of how to apply gene delivery in vivo and ex vivo situations. For adenoviruses and adenoviral vectors, one generally will prepare a adenovirus or adenoviral vector stock. In some embodiments, adenoviruses according to the invention may be administered in a single administration or multiple administrations. In some embodiments, the virus may be administered at a dosage at least about, at most about, or about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, or $1\times10^{14}$ viral particles, or any value or range there between, to a subject. In some embodiments, the virus may be administered at dosage at least about, at most about, or about $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, or $1\times10^{13}$ plaque forming units (PFU), or any value or range there between, to a subject. The quantity to be administered, both according to number of treatments and dose, depends on the subject to be treated, the state of the subject and the protection desired. Precise amounts of the therapeutic composition also depend on the judgment of the practitioner and are peculiar to each individual.

In some embodiments, the method further comprises administering one or more additional therapeutic agents to said mammal. For example, in some embodiments, the therapeutic agent is a chemotherapeutic agent. Chemotherapeutic agents include, but are not limited to 5-fluorouracil; mitomycin C; methotrexate; hydroxyurea; cyclophosphamide; dacarbazine; mitoxantrone; anthracyclins (epirubicin and doxurubicin); antibodies to receptors, such as herceptin; etoposide; pregnasome; hormone therapies such as tamoxifen and anti-estrogens; interferons; aromatase inhibitors; progestational agents; and LHRH analogs. CDK (Cyclin-dependent kinase) inhibitors are therapeutic agents that inhibit the function of CDKs. Suitable CDK inhibitors for use in the provided methods include, but are not limited to, AG-024322, AT7519, AZD5438, flavopiridol, indisulam, P1446A-05, PD-0332991, and P276-00 (See., e.g., Lapenna, S., et al, Nat Rev Drug Discov. 2009 July; 8(7):547-66, which is incorporated by reference herein in its entirety). The choice of agent and dosage can be determined readily by one of skill in the art based on the given disease being treated. The combined administrations contemplates co-administration, using separate formulations or a single pharmaceutical formulation, and consecutive administration in either order, wherein preferably there is a time period while both (or all) active agents simultaneously exert their biological activities. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

The invention further provides pharmaceutical compositions comprising one or more of the oncolytic adenoviruses described herein. In certain embodiments, the pharmaceutical compositions further comprise a pharmaceutically acceptable carrier or excipient. These pharmaceutical compositions find use in inducing lysis of tumor cells, inhibiting tumor cell growth, treating cancer, and/or increasing the immune response against cancer.

In certain embodiments, formulations are prepared for storage and use by combining a purified antibody or agent of the present invention with a pharmaceutically acceptable vehicle (e.g. carrier, excipient) (Gennaro, A. R., *Remington: The Science and Practice of Pharmacy*, 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery); pulmonary (e.g., by inhalation or insufflation of aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. If needed, various antibacterial an antifungal agents can be used, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain embodiments, sterile injectable solutions are prepared by incorporating compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically or prophylactically effective. For parenteral administration in an aqueous solution, the solution may be suitably buffered if necessary and the liquid diluent first rendered isotonic with sufficient saline or glucose. These particular aqueous solutions are especially suitable for intravascular and intratumoral administration. In this connection, sterile aqueous media, which can be employed will be known to those of skill in the art in light of the present disclosure.

The oncolytic adenoviruses of the invention can be combined in a pharmaceutical combination formulation, or dosing regimen as combination therapy, with an additional therapeutic agent. In one aspect of the invention, the additional therapeutic agent has anti-cancer properties. For example, in some embodiments the additional therapeutic agent is a chemotherapeutic agent. The additional therapeutic agent of the pharmaceutical combination formulation or dosing regimen preferably has complementary activities to the oncolytic adenovirus such that they do not adversely affect each other. Pharmaceutical compositions comprising the oncolytic adenovirus and the additional therapeutic agent are also provided.

For the treatment of the disease, the appropriate dosage of the additional therapeutic agent depends on the type of disease to be treated, the severity and course of the disease, the responsiveness of the disease, previous therapy, patient's clinical history, and so on all at the discretion of the treating physician. The additional therapeutic agent can be administered one time or over a series of treatments lasting from several days to several months, or until a cure is effected or a diminution of the disease state is achieved (e.g. reduction in tumor size). Optimal dosing schedules for the agent can be calculated from measurements of drug accumulation in the body of the patient and will vary depending on the relative potency of an individual agent. The administering physician can easily determine optimum dosages, dosing methodologies and repetition rates. In certain embodiments, the dosage of the agent is from 0.01 µg to 100 mg per kg of body weight, and can be given once or more daily, weekly, monthly or yearly. In certain embodiments, the agent is given once every two weeks or once every three weeks. In certain embodiments, the dosage of the agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

V. Kits Comprising Oncolytic Adenoviruses

The present invention provides kits that comprise the disclosed oncolytic adenoviruses or other agents described herein and that can be used to perform the methods described herein. In certain embodiments, a kit comprises at least one oncolytic adenovirus in one or more containers. In certain embodiments, a kit comprises at least one pharmaceutical composition described herein and instructions for use. One skilled in the art will readily recognize that the disclosed oncolytic adenoviruses or other agents of the present invention can be readily incorporated into one of the established kit formats which are well known in the art.

Further provided are kits comprising an oncolytic adenovirus or pharmaceutical composition of the present invention and one or more additional therapeutic agents. For example, in some embodiments, the kit comprises an oncolytic adenovirus or pharmaceutical composition of the present invention and one or more additional chemotherapeutic agents.

Embodiments of the present disclosure can be further defined by reference to the following non-limiting examples, which describe in detail preparation of certain oncolytic adenoviruses of the present disclosure and methods for using oncolytic adenoviruses of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Examples 1-4 show the immune-shift from anti-adenovirus to anti-tumoral immune responses by deleting adenovirus immunodominant T-cell epitopes. Using ICO15K-TD-gp100-tyr, which is a HAd5 oncolytic adenovirus that includes mutations in three immunodominant T-cell epitopes of hexon and the human tumor epitope gp100-tyr inserted in the hexon, it is demonstrated that mice treated with ICO15K-TD-gp100-tyr have a diminished overall anti-adenovirus immune response and at the same time display a higher immune response against a tyr tumor epitope in comparison to mice treated with ICO15K-gp100-tyr, which is a control virus lacking the three hexon mutations.

Example 5 shows that ICO15K-TD-gp100-tyr induces a more potent antitumoral activity compared to ICO15K-gp100-tyr in animals carrying murine tumors. Specifically, animals injected with ICO15K-TD-gp100-tyr are much more refractory to tumor formation than animals treated with ICO15K-gp100-tyr.

Examples 6-8 show the impact of immune-shift in antitumoral activity in the absence of tumor epitopes. Specifically, a quadruple deletion (QD) ICOVIR15K adenovirus (ICOVIR15K-QD), which lacks a human tumor epitope and has an additional hexon epitope mutation introduced in comparison to ICOVIR15K-TD, induces a more potent antitumoral activity compared to ICO15K in animals carrying murine tumors.

Example 1

Generation of the Oncolytic Adenovirus ICOVIR15K-TD that Contains the Triple Deletion (TD) with the Restricted-Library Method and its Derivative ICO15K-TD-gp100-tyr A search of the immunodominant epitopes restricted by human lymphocyte antigen-A2.1 (HLA-A2.1) of adenovirus 5 in the literature via PubMed was performed. HLA-A2.1 was selected because it is the major histocompatibility complex (MHC) class I that is more prevalent in the Caucasian and Mestizo populations (35-50%) (Gonzalez-Galarza, F. F., et al., Nucleic Acids Res. 2011 January; 39(Database issue):D913-9). Each epitope has two primary anchor sites to HLA-A2.1 in positions 2 and 9 of the peptide and two secondary anchoring sites at positions 1 and 3. The hexon is considered the most immunogenic protein of the human adenovirus 5 and the selection of the following three epitopes was based on the prevalence of human activity in patients infected by adenovirus 5 in different studies (Leen, A. M., et al., Blood. 2004 Oct. 15; 104(8):2432-40; Leen, A. M., et al., J Virol. 2008 January; 82(1):546-54; Olive, M., et al., Hum Gene Ther. 2002 Jul. 1; 13(10):1167-78; Tang, J., et al., Virology. 2006 Jul. 5; 350(2):312-22) and after a set of in silico predictions. With this aim, hexon protein was analyzed using the programs NetMHC, IEDB, BIMAS and Rankpep to predict the epitopes that bind mouse H2-Db epitopes with high affinity (Table 1). These programs were also used to identify human HLA-A2.1 epitopes, in addition to SYFPEITHI and SVRMHC programs (Gowthaman, U., et al., Amino Acids. 2010 November; 39(5):1333-42)(incorporated by reference herein in its entirety). The selected epitopes to be deleted are Hex713 (YLNHTFKKV) (SEQ ID NO: 11), Hex892 (LLYANSAHA) (SEQ ID NO: 15) and Hex917 (YVLFEVFDV) (SEQ ID NO: 19), wherein the number following "Hex" indicates the position of the first amino acid of the epitope in the hexon protein sequence (SEQ ID NO: 9).

TABLE 1

Servers used for MHC type 1-epitope prediction showing the most recent and functional web address and its bibliographical reference

| Server | URL | Reference |
| --- | --- | --- |
| BIMAS | www.bimas.cit.nih.gov/molbio/hla_bind | [Parker et al., 1994] |
| SVMHC | www.sbc.su.se/~pierre/symhc/new.cgi | [Donnes and Elofsson, 2002] |
| RANKPEP | imed.med.umc.es/Tools/rankpep.html | [Reche and Reinherz, 2007] |
| NetMHC 3.4 | www.cbs.dtu.dk/services/NetMHC/ | [Lundegaard et al., 2008] |
| SYFPEITHI | www.syfpeithi.de/bin/MHCServer.dll/EpitopePrediction.htm | [Rammensee et al., 1999] |
| MHCI | Atom.research.microsoft.com/hlabinding/hlabinding.aspx | [Jojic et al., 2006] |
| IEDB SMM | http://tools.immuneepitope.org/mhci | [Peters and Sette, 2005] |
| SVRMHC | svrmhc.biolead.org/index.php | [Wan et al., 2006] |

The plasmid of the oncolytic adenovirus ICOVIR15K (Rojas, J. J., et al., Gene Ther. 2012 April; 19(4):453-7) (incorporated herein by reference in its entirety) was genetically modified by homologous recombination in yeast to delete the selected Hex713, Hex892 and Hex917 epitopes. An initial approach to delete these epitopes was to replace the key amino acids in these epitopes (first amino acid or anchor amino acids in positions 2 and 9 of the epitope). Among several mutants constructed in adenovirus plasmids (Y713C, Y713D, Y713E, L714D, L714G, L714P affecting hex713 epitope; L902D, L902E, L902G, L902K, L902S, L902W affecting Hex892; and Y917D, Y917P, V918D, V918G, V925D, V925G, V925K, V925N, V925P, V925Q, V925S affecting epitope Hex917) only one viable virus was obtained upon transfection of such plasmids in HEK293 cells. The obtained adenovirus had the V925K mutation in epitope Hex 917, in which valine (V) in position 9 of the epitope (corresponding to the 925 amino acid of hexon) was replaced with a lysine (K). Given the difficulty in obtaining viable deletions of the immunodominant epitopes by targeted mutations a different strategy was followed based in creating libraries of mutants. For this, homologous recombination in bacteria was used for introducing subsequent epitope mutations because it is a more efficient compared to recombination in yeast in terms of time used and the number of positive clones (Stanton, R. J., et al., Biotechniques. 2008 December; 45(6):659-62, 664-8). This homologous recombination in bacteria is based on the replacement of positive-negative selection genes inserted in the adenovirus genome by a donor fragment containing the intended genetic mutation (epitope deletion in our case). A restricted-library method was applied to delete the immunodominant epitopes. This system involves using degenerate primers (oligonucleotides) to substitute the coding sequence for any amino acid other than the original amino acid or amino acids, leucine, isoleucine, phenylalanine, methionine, and valine. The original amino acid, as well as leucine, isoleucine, phenylalanine, methionine, and valine, were excluded because these amino acids are capable of binding HLA-A2.1 sites. The degenerate primers are synthesized with certain undefined nucleotides so the synthesized primers correspond to a library of primers. In the degenerate primer, the nucleotides that correspond to the codon of the amino acid to be deleted are synthesized as "NVN", where N can be A,T,C,G and V can A,C,G. Therefore, all amino acids with a codon containing a T in the second position of the codon are not present in the library (Phe, Leu, Ile, Met and Val). These amino acids are non-polar aliphatic hydrophobic commonly found in the anchor residues of epitopes. The degenerated sequence can also be located in the reverse primer as "NBN", where B is T,C or G. A PCR fragment of the hexon was synthesized using the degenerate primers and used as a donor fragment in homologous recombination in bacteria. Applying this restricted library method to delete Hex713 and Hex892 epitopes, mutants with amino acid substitutions of a valine by an alanine (V721A) in Hex713 epitope and an alanine by a serine (A901S) in Hex892 epitope were obtained. This set of mutations together with the previously obtained V925K was designated as "TD" (for triple deletion) and includes the following 3 mutations: (1) V721A mutation in position 9 of Hex713 epitope, which replaces a valine with an alanine; (2) A900S mutation in position 9 of Hex892 epitope, which replaces an alanine with a serine; and (3) V925K mutation in position 9 Hex917 epitope, which replaces a valine (V) with a lysine (K).

Table 2 shows the exact amino acidic sequence of each mutant region compared with its wild-type counterpart, together with the expected affinity for its corresponding HLA allele according to the NetMHC prediction method listed in Table 1. Low IC50 values for this prediction correspond to good binders, whereas mutated versions display high IC50 predicted values.

TABLE 2

Amino acid sequence corresponding to the three mutated epitopes included in TD and its predicted affinity for human HLA-A*02.01 (according to NetMHC simulator)

| Allele | Peptide Length | AA Sequence | IC50 (nM) | Epitope |
|---|---|---|---|---|
| HLA-A*02:01 | 9 | YLNHTFKKV (SEQ ID NO: 11) | 50.24 | Hex713 (wt) |
| HLA-A*02:01 | 9 | YLNHTFKKA (SEQ ID NO: 13) | 618.28 | V721A (in TD) |
| HLA-A*02:01 | 9 | LLYANSAHA (SEQ ID NO: 15) | 63.05 | Hex892 (wt) |
| HLA-A*02:01 | 9 | LLYANSAHS (SEQ ID NO: 17) | 1407.05 | A900S (in TD) |
| HLA-A*02:01 | 9 | YVLFEVFDV (SEQ ID NO: 19) | 18.97 | Hex917 (wt) |
| HLA-A*02:01 | 9 | YVLFEVFDK (SEQ ID NO: 21) | 21734.48 | V925K (in TD) |

Plasmid containing viral genomes were transfected in eukaryotic 293 cells using the calcium phosphate method. Each virus generated was analyzed for its oncolytic capacity using the spectrotiter technique, which measures the number of infectious particles necessary to kill 50% of the cells in tissue culture (IC50). Viruses with mutations V721A, A901S, and V925K did not show any loss in their oncolytic capacity.

To construct ICO15K-TD-gp100-tyr, the hypervariable region 5 (HVR5) of the hexon (HVR5), which corresponds to amino acids 270-281 of hexon, was substituted with melanoma epitopes gp100-280 (gp100) and tyrosinase369 (tyr) as shown in FIG. 1. The gp100 and tyr epitope sequences correspond to YLEPGPVTA (SEQ ID NO: 31) and YMDGTMSQV (SEQ ID NO: 32), respectively. The tyr epitope was modified at the position corresponding to amino acid 372 of the native tyrosinase to introduce a N372D mutation. The N372D mutation in tyr results in a posttranslational modification that makes it easily recognized by the TCRs (Skipper, J. C., et al., J Exp Med. 1996 Feb. 1; 183(2):527-34). The control virus ICO15K-gp100-tyr with epitopes gp100 and tyr was constructed without the triple deletion. The tumor epitopes were flanked by linkers GSGSR (SEQ ID NO: 28), AGSGSR (SEQ ID NO: 29) and AGSGS (SEQ ID NO: 30) as shown in FIG. 1. In order to generate a library of epitope insertions, linkers were inserted between epitopes to have regions of homology that could be used for overlapping PCR products. Linkers were designed to contain Glycine and Serine (GS) amino acids because of their flexibility (Vigne, E., et al., J Virol. 1999 June; 73(6): 5156-61; Taremi, S. S., et al., Protein Sci. 1998 October; 7(10):2143-9; Kingston, R. L., et al., Proc Natl Acad Sci USA. 2004 Jun. 1; 101(22):8301-6). Other than the repetitive GS content in linkers, different codon DNA sequence was used to avoid homologous recombination. In addition, Alanine (A) amino acid was selected for some linkers to provide a good for C-ter cleavage site during proteosome processing by using the proteosome cleavage prediction website NetChop 3.1 Server (http://www.cbs.dtu.dk/services/NetChop/), and Arginine (R) was selected for some linkers to provide a good amino acid for TAP (Transporter associated with antigen processing) binding and its entry into endoplasmic reticulum (Uebel, S. and Tampé, R., Curr Opin Immunol. 1999 April; 11(2):203-8). Both plasmids containing the ICO15K-TD-gp100-tyr and ICO15K-gp100-tyr viral genomes were transfected to 293 cells, amplified in A459, and subsequently purified.

Example 2

Validation of the Viability of the New Constructions In Vitro

Figure 2:
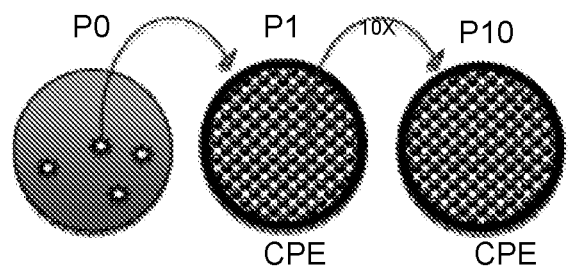
FIG. 2. Schematic representation of ten serial passages (P) of adenovirus showing cytopathic effect (CPE).

Serial Passage of the Viral Stocks in Human Cancer Cells A549 and Time Required to Generate Cytopathic Effect In order to evaluate the stability of the triple deletion, 10 serial passages of each triple deleted virus was analyzed for cytopathic effect (CPE) as shown in FIG. 2. This involved the infection of A549 cell monolayers with ICOVIR15K-TD-gp100-tyr or ICOVIR15K-TD. For wild-type adenovirus, CPE is usually observed 72 h post-infection. This time frame was also observed in all ten passages performed with the triple deleted viruses.

Figure 3:
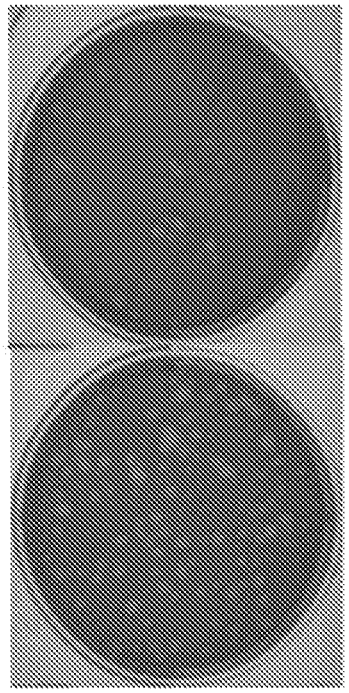
FIG. 3. Plaque-assay of the ICOVIR15K (SEQ ID NO: 1), ICOVIR15K-TD (SEQ ID NO: 3), ICOVIR15K-gp100-tyr (SEQ ID NO: 2), and ICOVIR15K-TD-gp100-tyr (SEQ ID NO: 4) oncolytic viruses.
Figure 3:
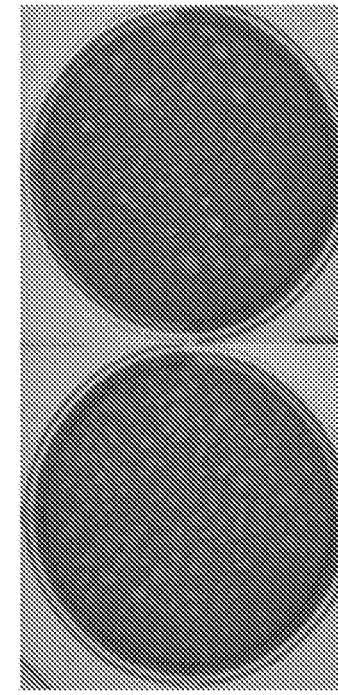
Figure 3:
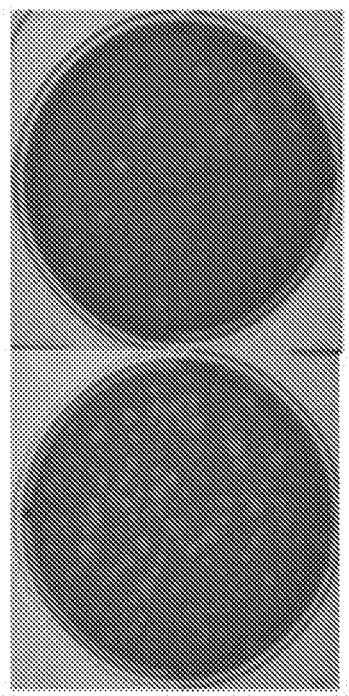
Figure 3:
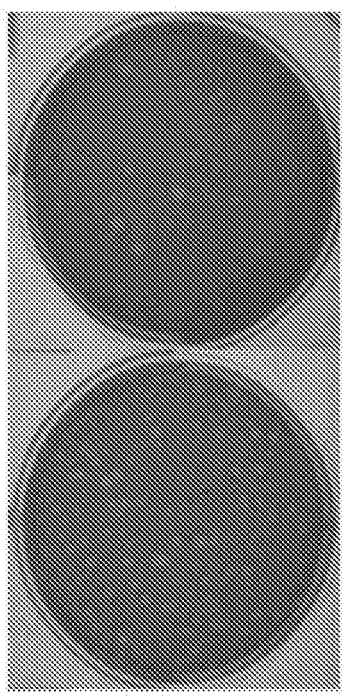

Capability of Generating Plaques and Plaque Size (Wholes in Monolayers) in a Plaque Assay in A549 Cells A549 cell monolayers were infected with a triple deleted virus (ICOVIR15K-TD-gp100-tyr or ICOVIR15K-TD) or a control virus without the triple deletion (ICOVIR15K or ICOVIR15K-gp100-tyr) for 7 days, and viable cells were subsequently stained with the neutral red staining. As shown in FIG. 3, the plaque size of either triple deleted virus does not change compared to either control virus. These findings indicate that the triple deleted viruses continue to behave as the parental virus and do not lose the capability to generate plaques.

In Vitro Cytotoxicity Assay to Determine the IC50 Value in A549 Cells

A549 cells were infected with ICOVIR15K, ICOVIR15K-TD, ICOVIR15K-gp100-tyr, or ICOVIR15K-TD-gp100-tyr at multiplicities of infection (MOIs) ranging from 0.00001 to 200 Transducing Units (TU)/cell, and cell survival was evaluated 5 days post-infection. The IC50 values of each virus with the triple deletion show that these viruses did not lose any oncolytic activity or cytotoxicity when compared to the parental viruses. These findings show that the capsid modifications do not interfere with oncolytic capability of the triple deletion viruses.

Viral Production Assay

Figure 4:
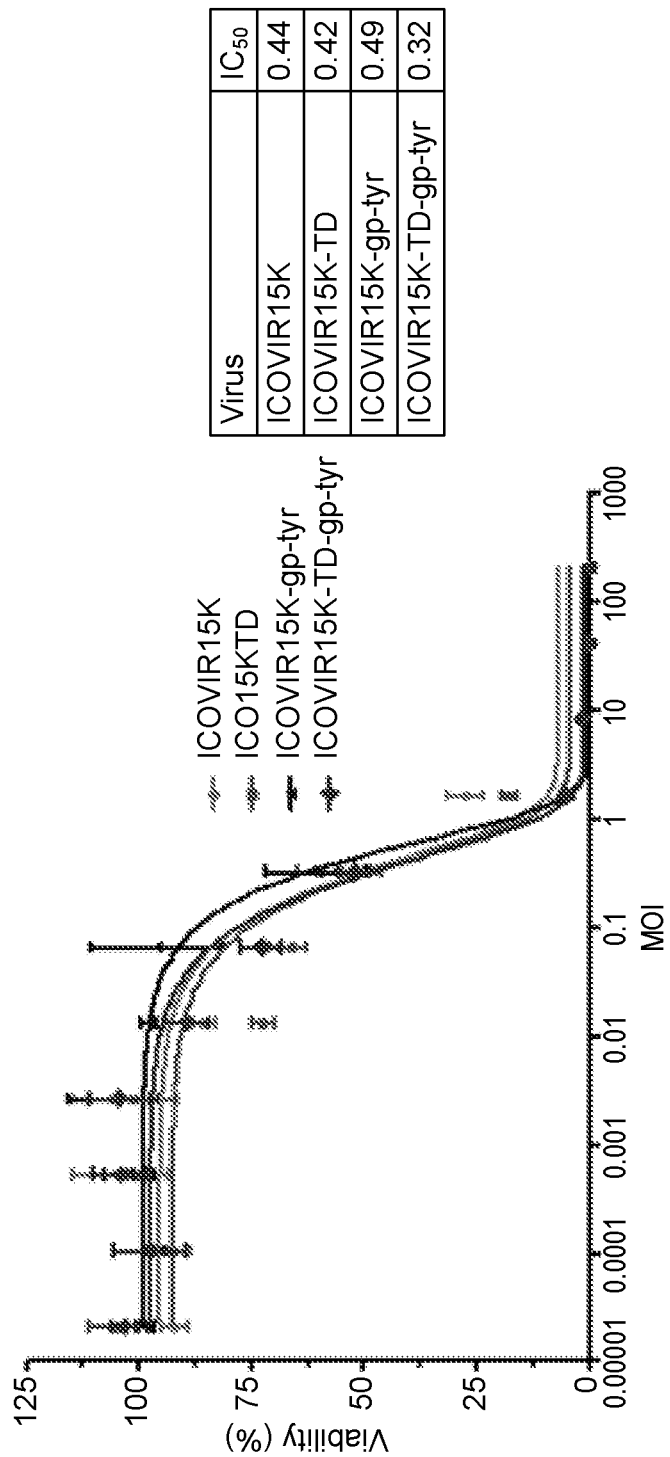
FIG. 4. Cytotoxicity of the ICOVIR15K, ICOVIR15K-TD, ICOVIR15K-gp100-tyr, and ICOVIR15K-TD-gp100-tyr oncolytic viruses and their corresponding $IC_{50}$ values.
Figure 5:
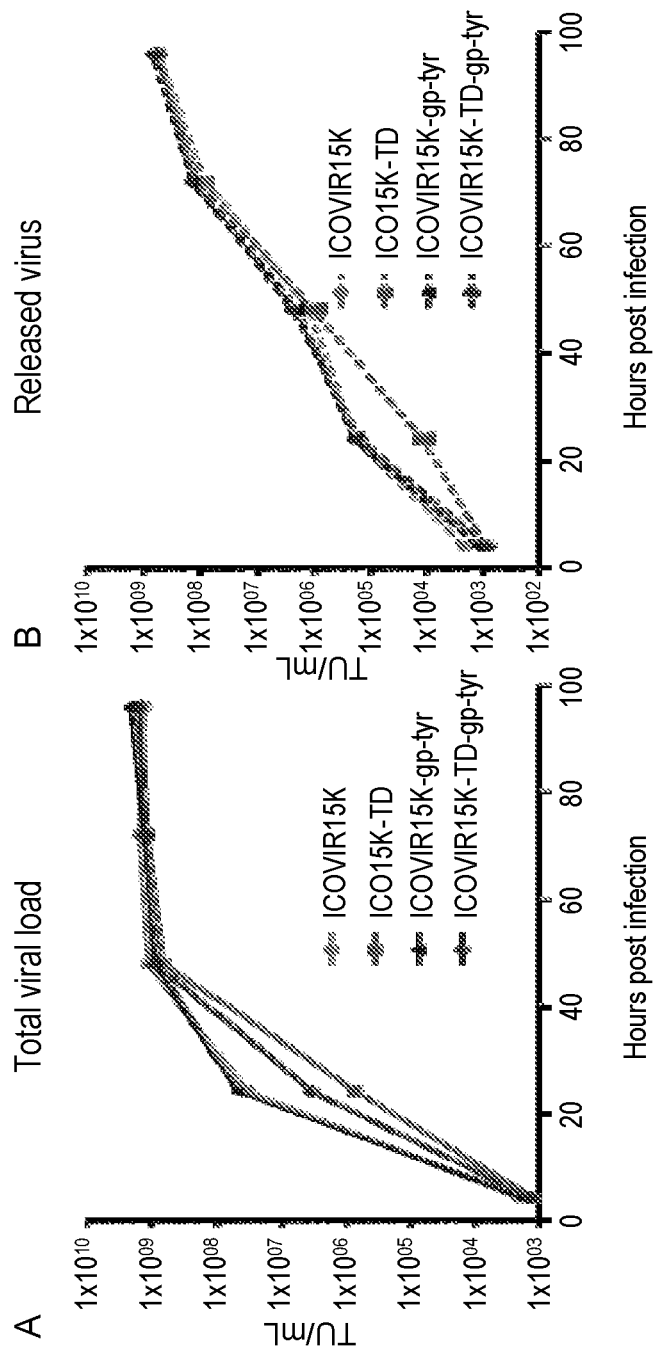
FIG. 5A-B. Viral production assay of the ICOVIR15K, ICOVIR15K-TD, ICOVIR15K-gp100-tyr, and ICOVIR15K-TD-gp100-tyr oncolytic viruses.

A549 cells were infected with ICOVIR15K, ICOVIR15K-TD, ICOVIR15K-gp100-tyr, or ICOVIR15K-TD-gp100-tyr at an MOI of 25 TU/cell for 4 hours and then washed with PBS. The total viral production (solid lines, FIG. 5A) and the released viral production (discontinuous lines, FIG. 5B) were analyzed at 24, 48, 72 and 96 hours post-infection. The parental virus ICOVIR15K was used as a control reference for a good oncolytic virus. The viruses having the triple deletion (ICOVIR15K-TD and ICOVIR15K-TD-gp100-tyr) appeared to have approximately 1 log reduction in total production compared to the ICOVIR15K control virus at 24 h post-infection; however, statistical analysis using the Mann-Whitney U-test to compare the viral production curves (Wang, G. P. and Bushman, F. D., J Virol Methods. 2006 July; 135(1):118-23) demonstrated that there was no difference between the groups. In addition, there was no significant difference between triple deleted viruses and control viruses with respect to the amount of released virus over time. These results show that the triple deletion viruses and control viruses exhibited similar viral production with respect to both total viral production and released viral production. These findings are also supported by the results obtained in the cytotoxicity assay IC50 shown in FIG. 4, in which no differences were observed with the triple deletion viruses in comparison to control viruses lacking genetic modifications in the capsid. The IC50 values were obtained 5 days post-infection, thereby allowing multiple rounds of viral replication for a correct evaluation of oncolytic capability.

Example 3

Binding Affinity to Human HLA-A2.1 of the Mutated Adenoviral Epitopes and Tumor Epitopes Present in ICOVIR15K-TD-gp100-tyr An HLA-A2.1 stabilization assay was used, with minor modifications from Takiguchi et al. (Takiguchi, M., Tissue Antigens. 2000 April; 55(4):296-302) (incorporated by reference herein in its entirety), to evaluate the binding affinity of mutated peptides. Murine cells expressing HLA-A2.1 (RMA-S A2 cells) were incubated for 18 h at 26° C. in order to allow for HLA-A2 surface expression in the absence of any peptide. Peptides were serially diluted 1:3 in a 96-well plate with a U shape bottom, starting with 300 µM up to 0.1 µM in 100 µl volume. 2.5e5 RMA-S A2 cells were added to each well in 100 µl volume. The mixture was incubated for 2 hours at 26° C. and then at 37° C. for 2 hours to allow unbound HLA-A2.1 to be internalized. Cells were spun for 3 minutes at 500 g and washed three times with PBS, FBS 5%, BSA 0.5%. Cells were incubated with 100 µl of the supernatant of hybridoma anti-HLA-A2.1 (PA2.1) and incubated for 30 minutes at 4° C. Cells were washed three times and then incubated with Alexa Fluor® 488 goat anti-mouse IgG (Molecular Probes®) at 1:500 dilution for 30 minutes at 4° C. Cells were washed three times and then analyzed with Gallios flow cytometer (Beckman Coulter). As a negative control, RMA-S A2 cells were incubated with a peptide having no affinity to HLA-A2.1 under the same experimental conditions. The fluorescence index was calculated using the formula: Fluorescein Index=(sample fluorescence−negative control fluorescence)/negative control fluorescence.

Using GraphPad Prism v5, Kd values were analyzed using a non-linear regression. A Kd value was obtained for each peptide that represents the binding constant in equilibrium with half of the maximum possible binding.

Figure 6:
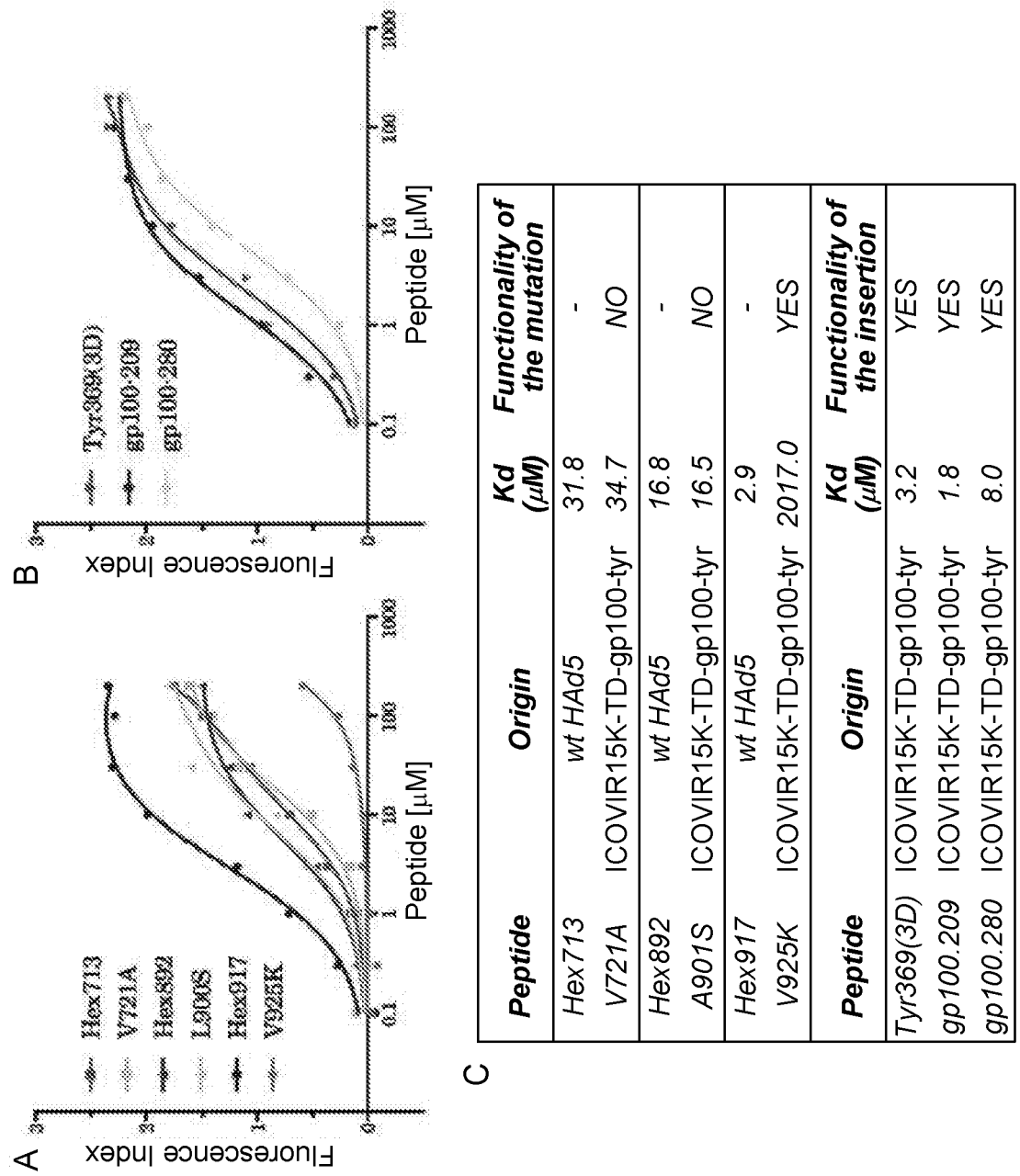
FIG. 6A-C. Binding affinity of mutated epitopes in ICOVIR15K-TD-gp100-tyr compared to wild-type epitopes in HAd5.

Using this assay, the HLA-A2 binding epitopes in the ICOVIR15K-TD-gp100-tyr were analyzed. As shown in FIG. 6A, the mutated versions of the epitopes Hex982 and Hex713 maintained the same level of binding to HLA-A2 compared to their unmodified counterparts. Thus these mutations were considered "non-functional deletions." The mutation V925K in Hex917 epitope significantly reduced the HLA-A2 binding by almost 600 times compared to its unmodified counterpart, as shown in FIG. 6A. Thus this mutation was considered a "functional deletion." Additionally, all tumor epitopes introduced in ICOVIR15K-TD-gp100-tyr bind to human HLA-A2.1 and are functional as shown in FIG. 6B. As summarized in FIG. 6C, ICOVIR15K-TD-gp100-tyr contains a "functional deletion" that results in the loss of an immunodominant adenovirus epitope and functional gp100 and tyr epitopes.

Example 4

In Vivo Analysis of the Immune Response Generated by ICOVIR15K-TD-gp100-tyr

HHD transgenic mice, which are a C57BL/6 mouse strain knocked-out for murine class I MHC H-2 and engineered to express significant quantities of the human class I MHC Ag HLA-A2.1 (also named HHD A2/Kb H-2b-; Firat, H., et al., Eur J Immunol. 1999 October; 29(10):3112-21) were immunized with ICOVIR15K-gp100-tyr or ICOVIR15K-TD-gp100-tyr using an immunization regimen based on a prime with inactivated virus administered intramuscularly on day 0 and further boosted with the active virus intravenously administrated on day 14. On day 28, the immune response against a number of hexon epitopes was analyzed in order to determine which hexon epitopes are more immunogenic and if the triple deleted epitopes failed to generate an immune response.

The immune response against different epitopes at the day 28 time-point was evaluated using the enzyme-linked immunosorbent spot (ELISPOT) assay, which allows visualization of secretory product (i.e. IFNγ) of individual responding cells on a membrane, thereby providing qualitative (type of antigen) and quantitative (number of responding cells) information. To conduct such analysis, mice were sacrificed at day 28, spleens were harvested and splenocytes isolated. Splenocytes of each animal were plated at 2,500,000 cells/well. Phytohaemagglutinin (PHA at 15 ng/mL) plus ionomycin (250 ng/mL) were used as positive control, and media only was used as negative control. Peptides and peptide pools were used at a final concentration of 1 µM. Antigens were incubated with the splenocytes for at least 18 hours at 37° C., 5% $CO_2$. Wells were washed and incubated with the secondary biotinylated anti-IFNγ antibody for 2 hours (Mabtech 3321-6-250), washed, and then incubated for 1 hour with streptavidin-ALP (Sigma E2636-.2ML). Plates were washed with PBS, and spots were developed using the BCIP/NBT solution (Sigma B1911-100ML) until distinct spots emerged (15-30 minutes). The plate was washed with tap water, left to dry overnight, and spots were counted using the AID EliSpot reader classic (ELR071; AID GmbH, Strassberg, Germany). The number of spots was corrected by the content of CD8 lymphocytes in the splenocyte cell population, as CD8 content varied from 0.5% to 3.5%.

In this experiment, the reactivity against a panel of hexon epitopes including those targeted by the triple deletion (Hex713, Hex892 and Hex917) and those predicted to bind with high affinity to HLA-A2.1 according to different in silico methods shown in Table 1 was evaluated. These included the following human HLA-A2.1 restricted adenoviral/tumor epitopes or polypeptides: E1A19 (LLDQLIEEV) (SEQ ID NO: 33); Hex63 (RLTLRFIPV) (SEQ ID NO: 34); Hex512 (GLVDCYINL) (SEQ ID NO: 23); Hex548 (MLLGNGRYV) (SEQ ID NO: 35); Hex652 (MLYPIPANA) (SEQ ID NO: 36); Hex713 (YLNHTFKKV) (SEQ ID NO: 11); Hex892 (LLYANSAHA) (SEQ ID NO: 15); Hex914 (TLLYVLFEV) (SEQ ID NO: 37); Hex917 (YVLFEVFDV) (SEQ ID NO: 19); Tyr369(3D) (YMDGTMSQV) (SEQ ID NO: 32)); gp100-209 (IMDQVPFSV) (SEQ ID NO: 38) and gp100-280 (YLEPGPVTA) (SEQ ID NO: 31)). In addition, a pool of hexon polypeptides (15 amino acid polypeptides overlapping by 9 amino acids of all hexon protein sequence) and naive splenocytes pre-infected with ICOVIR15K-gp100-tyr or ICOVIR15K-TD-gp100-tyr for 24 hours were also included.

Figure 7:
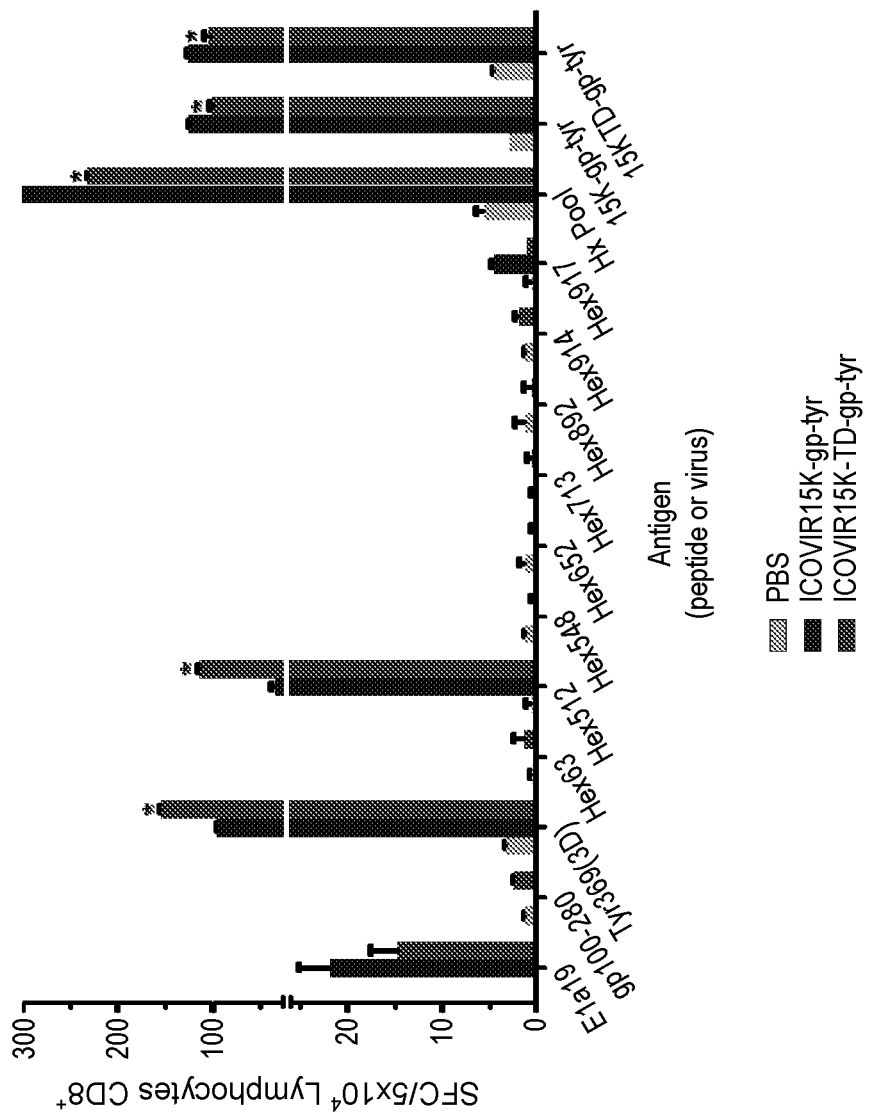
FIG. 7. Immunization of transgenic HLA-A2.1 mice with ICOVIR15K-gp100-tyr with or without the triple deletion. Prime immunization was done with inactive virus given IM and boost was done with intravenous administration of active virus, both at $10^{10}$ vp/mouse. ELISPOT was performed using 2,500,000 splenocytes per well. Hx Pool (hexon pool). Naïve splenocytes were infected with ICOVIR15K-gp100-tyr (15K-gp-tyr) or ICOVIR15K-TD-gp100-tr (15K-TD-pgtyr) for 24h and then added to splenocytes from immunized mice in the ELISPOT assay.

Results are shown in FIG. 7. The panel of hexon epitopes included those targeted by the triple deletion (Hex713, Hex892, and Hex917) and those predicted to bind with high affinity to HLA-A2.1 according to different prediction models. In spite that CD8 T-cell responses against triple deleted hexon epitopes Hex713 and Hex892 were undetectable and small responses were seen against Hex917 when immunizing with ICOVIR15K-gp100-tyr, the triple deleted virus ICOVIR15K-TD-gp100-tyr is not able to mount a response against Hex917 epitope and therefore the amino acid substitution V925K in hexon is functional in vivo. The immune response against other hexon epitopes that were predicted to bind with high affinity to HLA-A2.1, such as Hex63, Hex 512, Hex548, Hex652 and Hex914, was also evaluated. From these predicted epitopes, only the Hex512 was able to induce a high immune response. Interestingly, mice treated with the triple delete virus ICOVIR15K-TD-gp100-tyr gave a higher response against Hex512 than the parental control virus, suggesting that there was a shift in immunodominance to other hexon epitopes when the triple deletion was present.

When a pool of hexon peptides (15 amino acid peptides overlapping by 9 amino acids of all hexon protein sequence) was analyzed in the ELISPOT assay, both ICOVIR15K-gp100-tyr and ICOVIR15K-TD-gp100-tyr viruses generated a high immune response against hexon, but the level of the immune response against hexon generated by the triple deleted virus was significantly lower than the control virus. This important finding shows that, even though a high immune response against individual targeted epitopes in the triple deletion was not detected, the overall anti-hexon immunogenicity is decreased when these three epitopes are deleted (FIG. 7). In addition, to test if the general immunity against all adenovirus proteins was changed due to the triple deletion, we presented the entire set of adenovirus epitopes to splenocytes of immunized animals using naive splenocytes infected with viruses and antigen presenting cells. Naive splenocytes were infected ex vivo with ICOVIR15K-gp100-tyr or ICOVIR15K-TD-gp100-tyr for 24 hours and then added to splenocytes from immunized mice in the ELISPOT assay (FIG. 7). Mice immunized with ICOVIR15K-gp100-tyr responded very well against naive splenocytes infected with ICOVIR15K-gp100-tyr or ICOVIR15K-TD-gp100-tyr. However, mice immunized with the triple deleted virus ICOVIR15K-TD-gp100-tyr responded with less activity to either naive splenocytes infected with ICOVIR15K-gp100-tyr or ICOVIR15K-TD-gp100-tyr. The overall anti-adenovirus immune response was significantly reduced in mice immunized with the triple deleted virus ICOVIR15K-TD-gp100-tyr compared to the non-triple deleted virus ICOVIR15K-gp100-tyr.

In order to evaluate if the modulation the immune response against hexon with the triple deleted epitopes increases the immunogenicity of tumor epitopes presented within the adenovirus capsid, the immune response against the tumor epitope tyrosinase was also analyzed in FIG. 7. Surprisingly, the immune response against tyrosinase increased by 50% when the tumor epitope is displayed in the context of the triple deleted virus ICOVIR15K-TD-gp100-tyr.

Overall, these data shows that the triple deleted virus ICOVIR15K-TD-gp100-tyr was partially able to hide from the immune system, thereby allowing the tyrosinase tumor epitope to be more immunogenic than when it is presented in the control virus ICOVIR15K-gp100-tyr.

Example 5

Impact of Immune-Shift in Antitumoral Activity

As described above, a strong CD8+ immune activity against tyrosinase epitope was detected in mice immunized with ICOVIR15K-TD-gp100-tyr (FIG. 7). The following Example shows that ICO15K-TD-gp100-tyr induces a more potent antitumoral activity compared to ICO15K-gp100-tyr in animals carrying murine tumors. Specifically, animals injected with ICO15K-TD-gp100-tyr are much more refractory to tumor formation than animals treated with ICO15K-gp100-tyr.

HHD transgenic mice were vaccinated with parental oncolytic adenovirus ICOVIR15K, the oncolytic adenovirus with melanoma epitopes displayed in the HVRS (ICOVIR15K-gp100-tyr), and the same oncolytic adenovirus with melanoma epitopes, but bearing the triple deletion (ICOVIR15K-TD-gp100-tyr). Mice were vaccinated as described in the diagram shown in FIG. 8A. Subsequently, mice were challenged 7 days after the last vaccination with $10^6$ B16CAR-A2 murine tumor cells (tyrosinase positive cells) given subcutaneously. B16CAR-A2 cells are derivatives of B16CAR cells previously transduced with a non-replicating retroviral vector MSCV-A2 encoding a cDNA sequence of HLA-A2/Kb in which the HLA-A2/Kb transgene expresses the α1 and α2 domains of the human HLA-A2.1 fused to the murine α3 domain Kb under the control of the CMV promoter.

Figure 8:
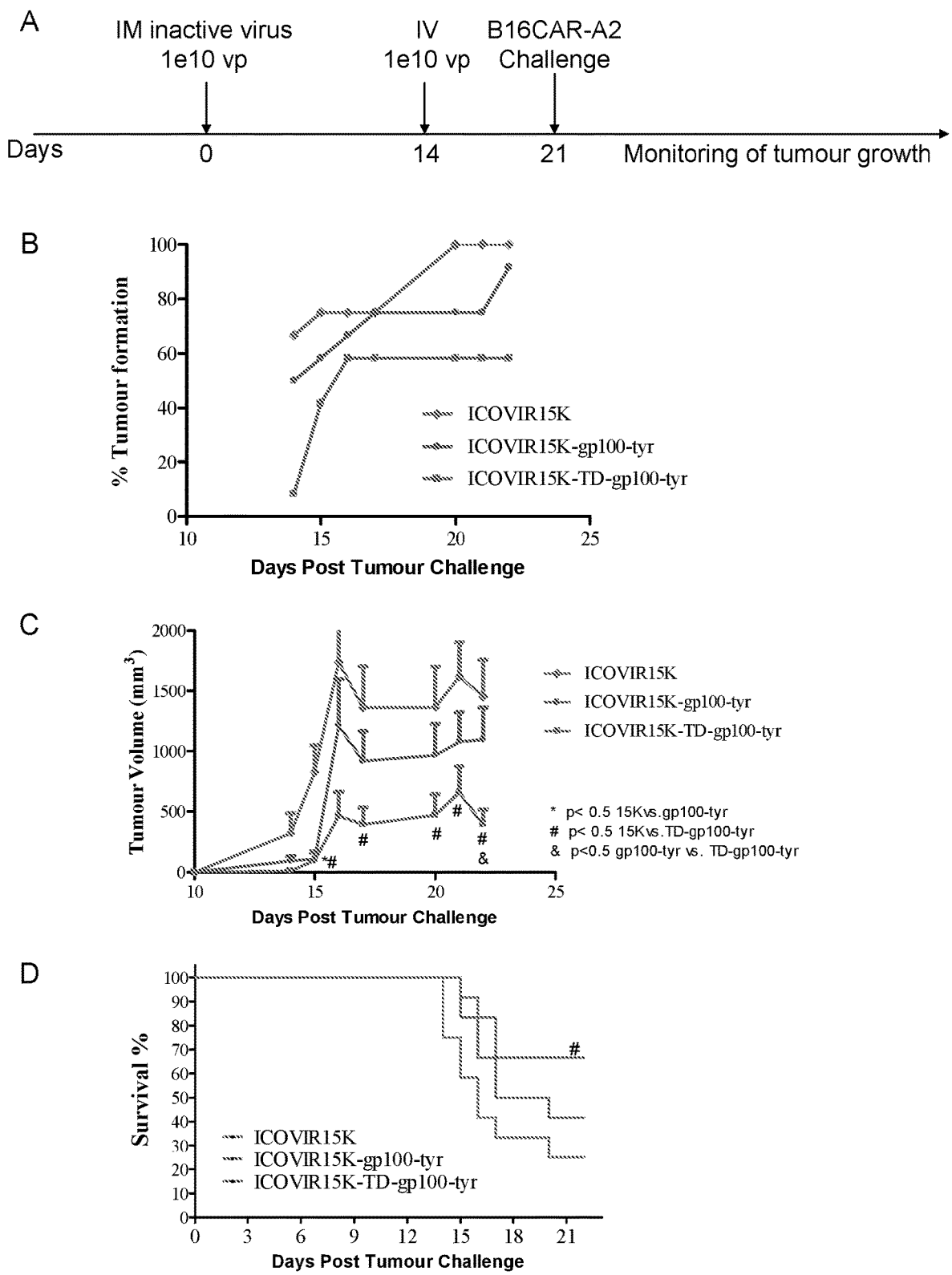
FIG. 8A-D.

Tumor formation was evaluated as in a classical tumor challenge formation assay and tumor growth was also monitored (FIG. 8B). All mice vaccinated with the parental virus ICOVIR15K developed tumors, whereas 90% of the mice vaccinated with ICOVIR15K-gp100-tyr developed tumors, and only 60% of mice developed tumors when vaccinated with ICOVIR15K-TD-gp100-tyr. The only treatment group that demonstrated significant tumor growth inhibition was the one displaying melanoma epitopes and bearing the triple deletion (ICOVIR15K-TD-gp100-tyr).

For further evaluation of the anti-tumor efficacy, tumor size was measured with a digital caliper and was calculated according to the formula V $(mm^3)=\pi/6 \times W \times L \times D$, where W, L, and D are width, length, and depth of the tumor, respectively (FIG. 8C). The two-tailed Student's t test was used to compare by pairs the statistical significance of the differences in the tumor volume between the different treatment groups. Results showed that the vaccination with an oncolytic virus that combines of the triple deletion (TD) with the display of tumor epitopes (gp100/tyr) have significant impact on tumor growth following the injection of B16CAR-A2 cells. Additionally, Kaplan-Meier survival curves were also drawn for each group, for which end-point was established at a tumor volume ≥500 $mm^3$ (FIG. 8D). The animals whose tumor size never reached the threshold were included as right censored information. A log-rank test was used to determine the statistical significance of the differences in time-to-event. Again, the only treatment group that demonstrated significantly enhanced mice survival with respect to untreated group was the one displaying melanoma epitopes and bearing the triple deletion (ICOVIR15K-gp100-tyr)

Overall, these data demonstrate that the deletion of one immunodominant hexon epitope of adenovirus in conjunction with the display of tumor-associated epitopes in adenovirus capsid is able to increase the anti-tumor efficacy of oncolytic adenoviruses.

Example 6

Generation and Characterization of the Oncolytic Adenovirus ICOVIR15K-QD

A new oncolytic adenovirus ICOVIR15K-QD, which maintains the "TD" of ICOVIR15K-TD and incorporates a new mutation in the hexon, was generated using ICOVIR15K-TD as background. Hex512 is an adenoviral epitope which generates one of the highest immune responses in the transgenic HHD murine model as shown in FIG. 7. The method for introducing this new mutation is identical to that followed for the generation of ICOVIR15K-TD, using degenerated primers in order to substitute the coding sequence for Hex512 amino acid for any other except the original. The set of hexon epitopic deletions of this new virus has been called quadruple deletion (Quadruple Deletion, QD). Of note, no tumor antigen has been incorporated in this virus. The following hexon epitopic deletions are included in ICOVIR15K-QD: (1) V721A mutation in position 9 of Hex713 epitope, which replaces a valine with an alanine; (2) A900S mutation in position 9 of Hex892 epitope, which replaces an alanine with a serine; (3) V925K mutation in position 9 of Hex917 epitope, which replaces a valine (V) with a lysine (K); and (4) L520P mutation in position 9 of Hex512 epitope, which replaces a leucine (L) with a proline (P).

Table 3 shows the exact amino acidic sequence of each mutant region compared with its wild-type counterpart.

TABLE 3

Amino acid sequence corresponding to the four mutated epitopes included in QD

| Allele | Peptide Length | AA Sequence | Epitope |
| --- | --- | --- | --- |
| HLA-A*02:01 | 9 | YLNHTFKKV (SEQ ID NO: 11) | Hex713 (wt) |
| HLA-A*02:01 | 9 | YLNHTFKKA (SEQ ID NO: 13) | V721A (in QD) |
| HLA-A*02:01 | 9 | LLYANSAHA (SEQ ID NO: 15) | Hex892 (wt) |
| HLA-A*02:01 | 9 | LLYANSAHS (SEQ ID NO: 17) | A900S (in QD) |
| HLA-A*02:01 | 9 | YVLFEVFDV (SEQ ID NO: 19) | Hex917 (wt) |
| HLA-A*02:01 | 9 | YVLFEVFDK (SEQ ID NO: 21) | V925K (in QD) |
| HLA-A*02:01 | 9 | GLVDCYINL (SEQ ID NO: 23) | Hex512 (wt) |
| HLA-A*02:01 | 9 | GLVDCYINP (SEQ ID NO: 25) | L520P (in QD) |

Figure 9:
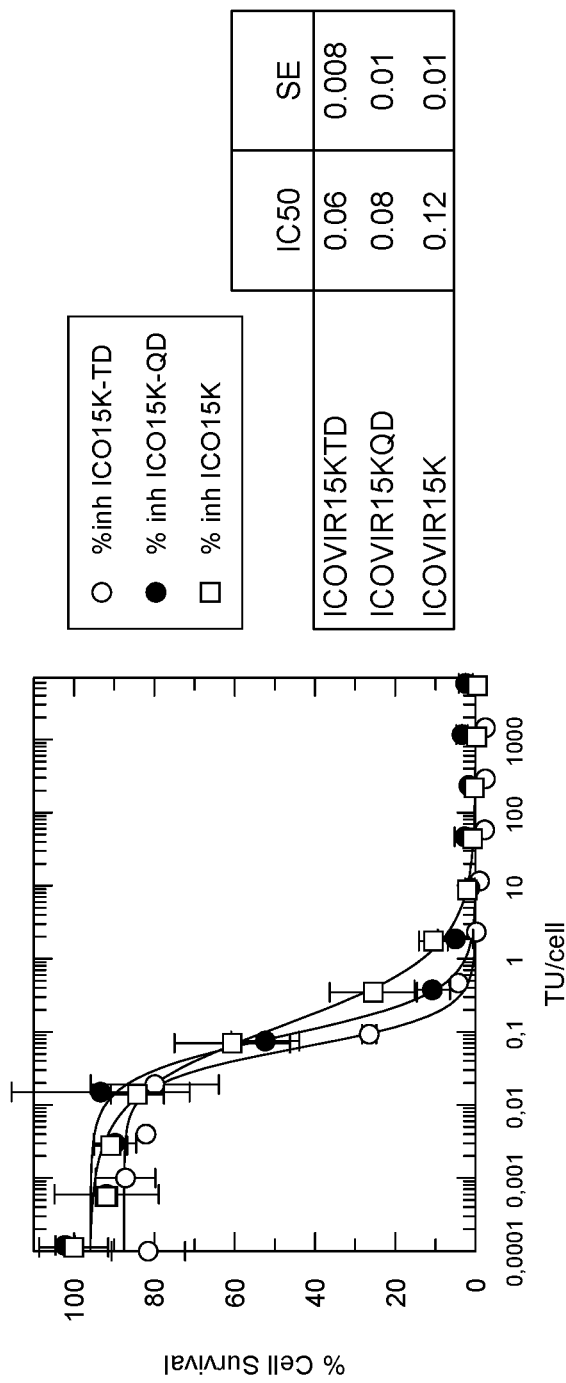
FIG. 9. Cytotoxicity evaluation of oncolytic adenoviruses bearing mutations TD (ICOVIR15K-TD; SEQ ID NO: 3) or QD (ICOVIR15K-QD; SEQ ID NO: 5) compared to parental (ICOVIR15K) in order to determine their IC50 values. A549 cells were infected at different MOIs and cell survival evaluated 6 days post infection with a BCA assay. IC50 values were calculated using GraFit.

All QD deletions in the hexon were confirmed by genome sequencing. Physical and functional characterization of the purified virus ICOVIR15K-QD showed that the functional virus ratio (vp/TU) is within normal standards and showed no loss in oncolytic replication capacity measured by an unaffected IC50 value (FIG. 9).

Figure 10:
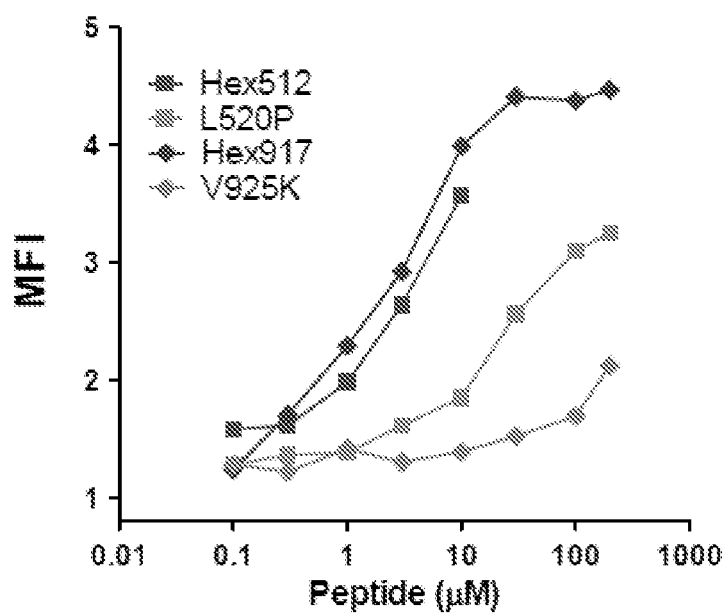
FIG. 10A-B. Peptide binding affinity of mutated epitopes Hex512 and Hex917 in ICOVIR15K-QD compared to wild-type epitopes in HAd5.

The binding affinity of the mutated version Hex512 present in ICOVIR15K-QD was also tested using the previously described HLA-A2.1 stabilization assay. As shown in FIG. 10, the mutation L520P in Hex512 epitope significantly reduced the HLA-A2 binding by more than 10 times and can be considered a functional epitopic deletion.

Example 7

Antitumoral Activity of the Oncolytic Adenovirus ICOVIR15K-QD

Further evaluation of the therapeutic potential of immunoshift by deletion of the immunodominant adenoviral epitopes was conducted with ICOVIR15K-QD, in which no tumor antigen has been inserted. Its antitumoral activity was evaluated in two different mice models: HHD transgenic mice and transgenic C57BL/6 A2/KbH-2+ mice. C57BL/6 A2/KbH-2+ mice are a mouse strain also engineered to express human class I MHC Ag HLA-A2.1 but not knocked-out for murine class I MHC H-2.

Antitumoral Activity of the Oncolytic Adenovirus ICOVIR15K-QD in Transgenic C57BL/6 A2/$K^b$H-2$^+$ Mice $10^6$ B16CAR-A2 cells were subcutaneously injected in both flanks of the transgenic C57BL/6 A2/$K^b$H-2$^+$ mice and allowed to form tumors (n=5 animals/group). At day 8 post-inoculation, tumors were intra-tumorally injected with $10^{10}$ vp of 1) ICOVIR15K oncolytic adenovirus, 2)

Figure 11:
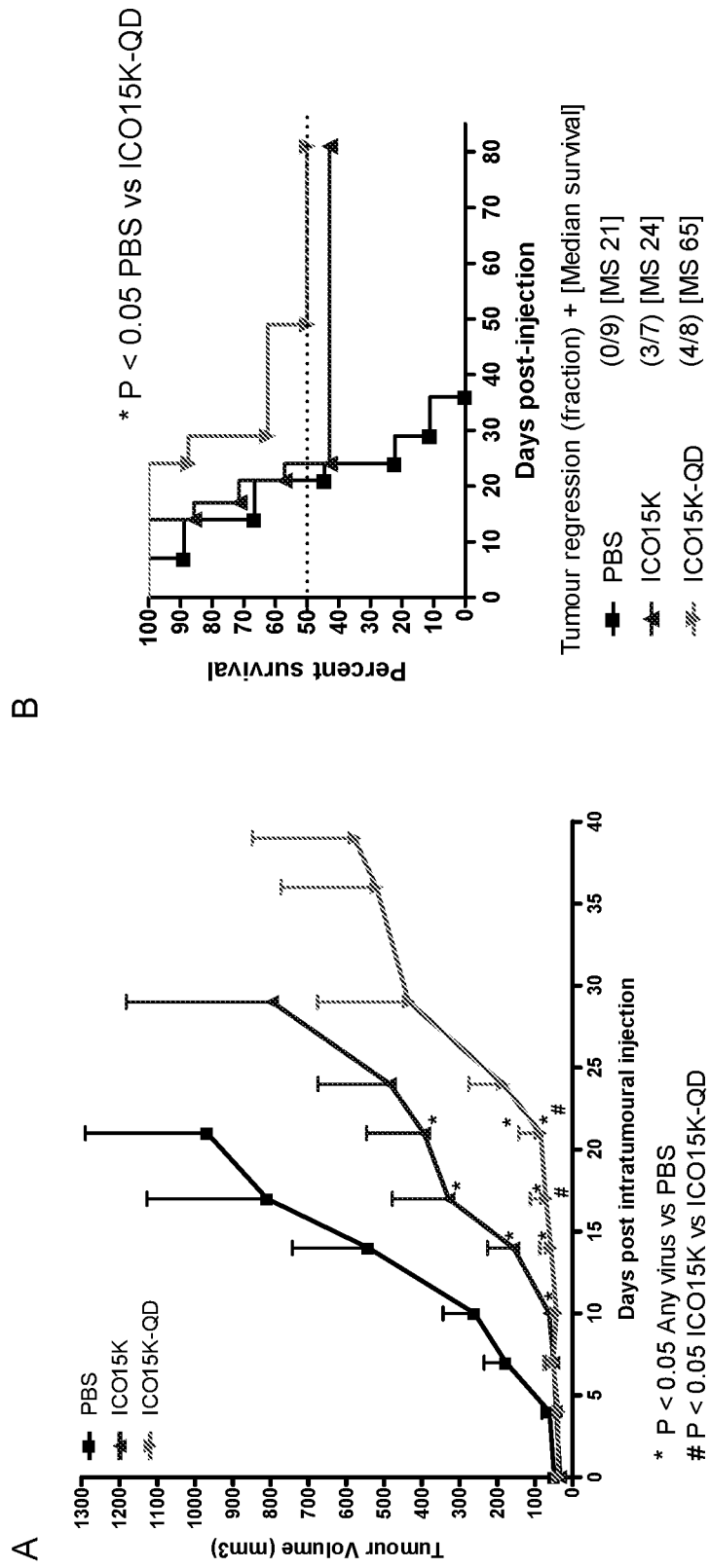
FIG. 11A-B. Comparative anti-tumor efficacy of ICOVIR15K and ICOVIR15K-QD in transgenic C57BL/6 A2/KbH-2+mice. B16CAR-A2 cells were subcutaneously injected in both flanks of mice and allowed to form tumors. Tumors were intratumorally injected with ICOVIR15K, ICOVIR15K-QD, or PBS.

ICOVIR15K-QD, or 3) PBS. Virus stocks were diluted to $5.10^{11}$ vp/ml in PBS and injected twice per tumor with 10 µl volume per injection site using a BD insulin syringe of 0.3 ml, 30 G (Becton Dickinson 324826). Specifically, the first injection was administered to the tumor and sealed with 5 µl of surgical glue (VetBond). After waiting 30 seconds for the first seal to set, the second injection was administered to the same tumor and sealed with VetBond. Tumor size was measured with a digital caliper for up to 81 days and tumor volume was calculated according to the formula V (mm³) =π/6×W×L×D, where W, L and D are width, length and depth of the tumor, respectively. The two-tailed Student's t test was used to compare by pairs the statistical significance of the differences in the tumor volume between the different treatment groups. For Kaplan-Meier survival curves, end-point was established at a tumor volume ≥500 mm³. The animals whose tumor size never reached the threshold were included as right censored information. A log-rank test was used to determine the statistical significance of the differences in time-to-event. Results are shown in FIG. 11.

PBS injected tumors grew rapidly. Tumors injected with ICOVIR15K oncolytic adenovirus significantly delayed tumor growth as a result of tumor cell destruction by intratumoral adenovirus replication. In addition, three of the seven ICOVIR15-injected tumors disappeared. However, in the group injected with ICOVIR15K-QD, the tumor growth was significantly further reduced with respect to ICOVIR15K, with the disappearance of four of the eight injected tumors (FIG. 11A). Median survival of animals treated with ICOVIR15K was set at 24 days (compared to 21 days for the PBS-treated group), whereas the median survival was 65 days for the ICOVIR15K-QD-treated animals (FIG. 11B). These data show that deleting the immunodominant T-cell epitopes of adenovirus (Hex917 and Hex512 mutations) results in enhanced antitumoral activity of oncolytic adenoviruses regardless of the expression of tumor antigen from the virus, which suggests that tumor antigens released from the tumor by the effect of virus replication and cytotoxicity are able to drive an effective antitumor immune response.

Figure 12:
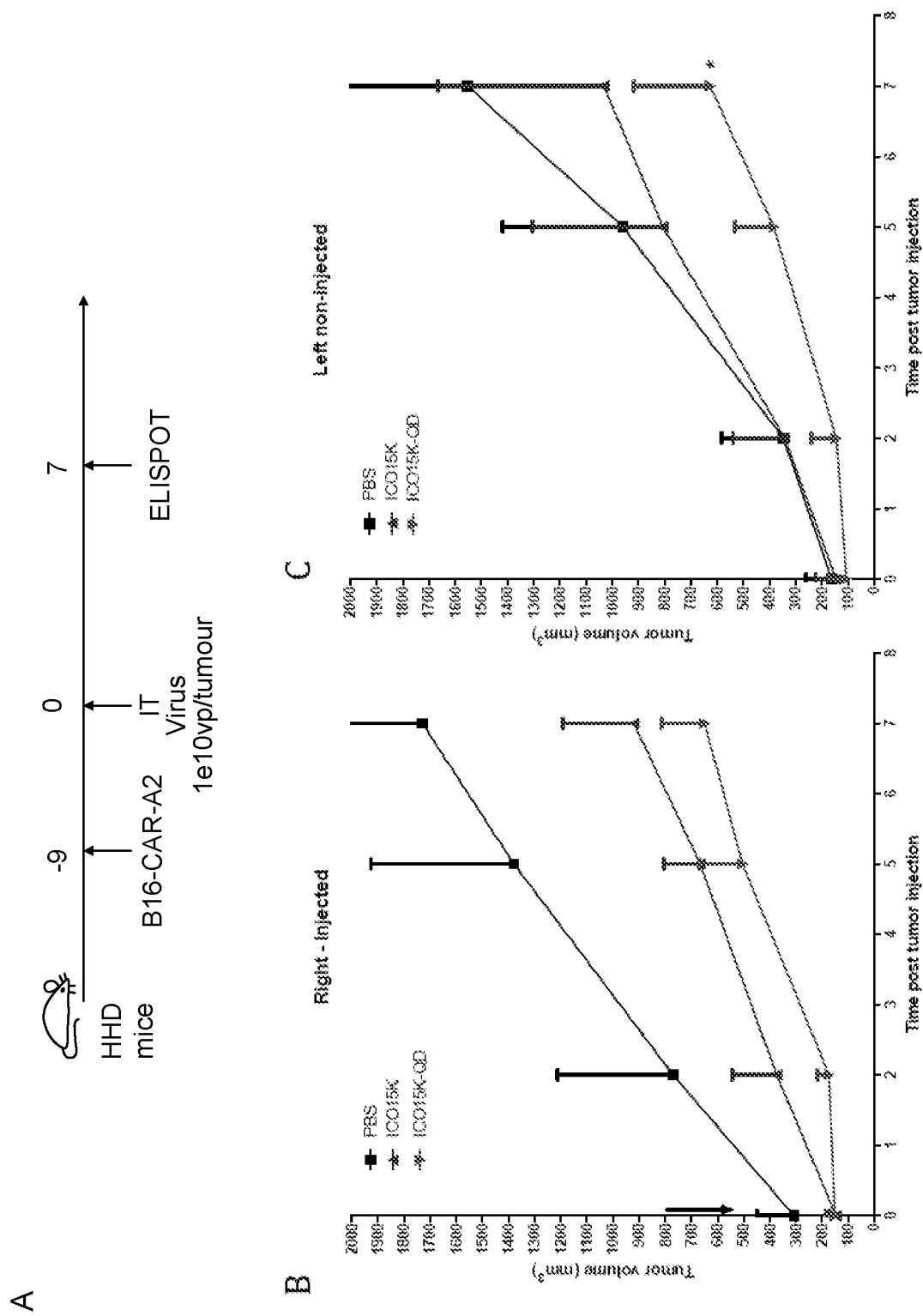
FIG. 12A-C. Comparative anti-tumor efficacy of ICOVIR15K and ICOVIR15K-QD in transgenic HHD transgenic mice.

Antitumoral Activity of the Oncolytic Adenovirus ICOVIR15K-QD in HHD Transgenic Mice 1e6 B16CAR-A2 were subcutaneously injected in both flanks of the transgenic HHD A2/Kb H-2b− mice and allowed to form tumors (n=4 animals per group). Right side tumors were intratumorally injected with $1.10^{10}$ vp of 1) ICOVIR15K oncolytic adenovirus, 2) ICOVIR15K-QD, or 3) PBS. In this experiment, left side tumors were left untreated for all groups to evaluate systemic antitumoral activity. Virus stocks were diluted and administered as previously described. Tumor size was measured for 7 days and its volume calculated according to the formula V (mm³)=π/6×W×L×D. The two-tailed Student's t test was used to compare by pairs the statistical significance of the differences in the tumor volume between the different treatment groups. Results are shown in FIG. 12. Animals were sacrificed 7 days after injection to collect splenocytes for further ELISPOT evaluation as described in Example 8 below.

PBS injected tumors grew rapidly as well as its contralateral non-injected tumors. Tumors injected with ICOVIR15K grew slowly compared to PBS groups, but the growth of ICOVIR15K-QD-treated tumors was further reduced, although not significantly with respect to the other groups during this 7-day period of monitoring (FIG. 12A). Of note, contralateral tumors did not experienced any tumor growth inhibition in the ICOVIR15K-treated group, whereas the growth of contralateral tumors to ICOVIR15K-QD-treated tumors was significantly reduced (FIG. 12B). This evidence strongly supports the generation of a systemic immune response against tumors only for ICOVIR15K-QD-treated animals.

Overall, these data surprisingly demonstrate that the deletion of the immunodominant hexon epitopes in adenovirus capsid increases the anti-tumor efficacy of oncolytic adenoviruses through a systemic mechanism that does not require the display of tumor-associated epitopes from adenovirus.

Example 8

Immune-Shift from Anti-Adenovirus to Anti-Tumoral Immune Responses by Deleting Adenovirus Immunodominant Epitopes in the Absence of Tumor Epitopes The HHD transgenic mice of Example 7, which carry B16CAR-A2 tumors in both flanks and were injected in left-flank tumor with ICOVIR15K, ICOVIR15K-QD or PBS, were also used for an analysis of the immune response generated by the ICOVIR15K-QD virus in vivo. Seven days after being injected as described in Example 7, animals were sacrificed, spleens were harvested, and splenocytes were isolated from the spleen. To evaluate the immune response against different epitopes at this time-point, 2,500,000 splenocytes/well were used to determine immunoreactivity by the enzyme-linked ImmunoSpot (ELISPOT) assay according to protocol described in Example 4.

In this experiment, the reactivity against the following human HLA-A2.1 restricted adenoviral epitopes or polypeptides was evaluated: E1A19 (LLDQLIEEV) (SEQ ID NO: 33); Hex512 (GLVDCYINL) (SEQ ID NO: 23); Hex713 (YLNHTFKKV) (SEQ ID NO: 11); Hex892 (LLY-ANSAHA) (SEQ ID NO: 15); and Hex917 (YVLFEVFDV) (SEQ ID NO: 19). In addition, a pool of hexon peptides (15 amino acid peptides overlapping by 9 amino acids of all hexon protein sequence) was also included. Since the tumor epitopes against which the antitumor response could be mounted are not defined, tumor B16CAR-A2 murine cells that were pre-incubated with IFN-γ to enhance their antigen presenting properties were also included.

Figure 13:
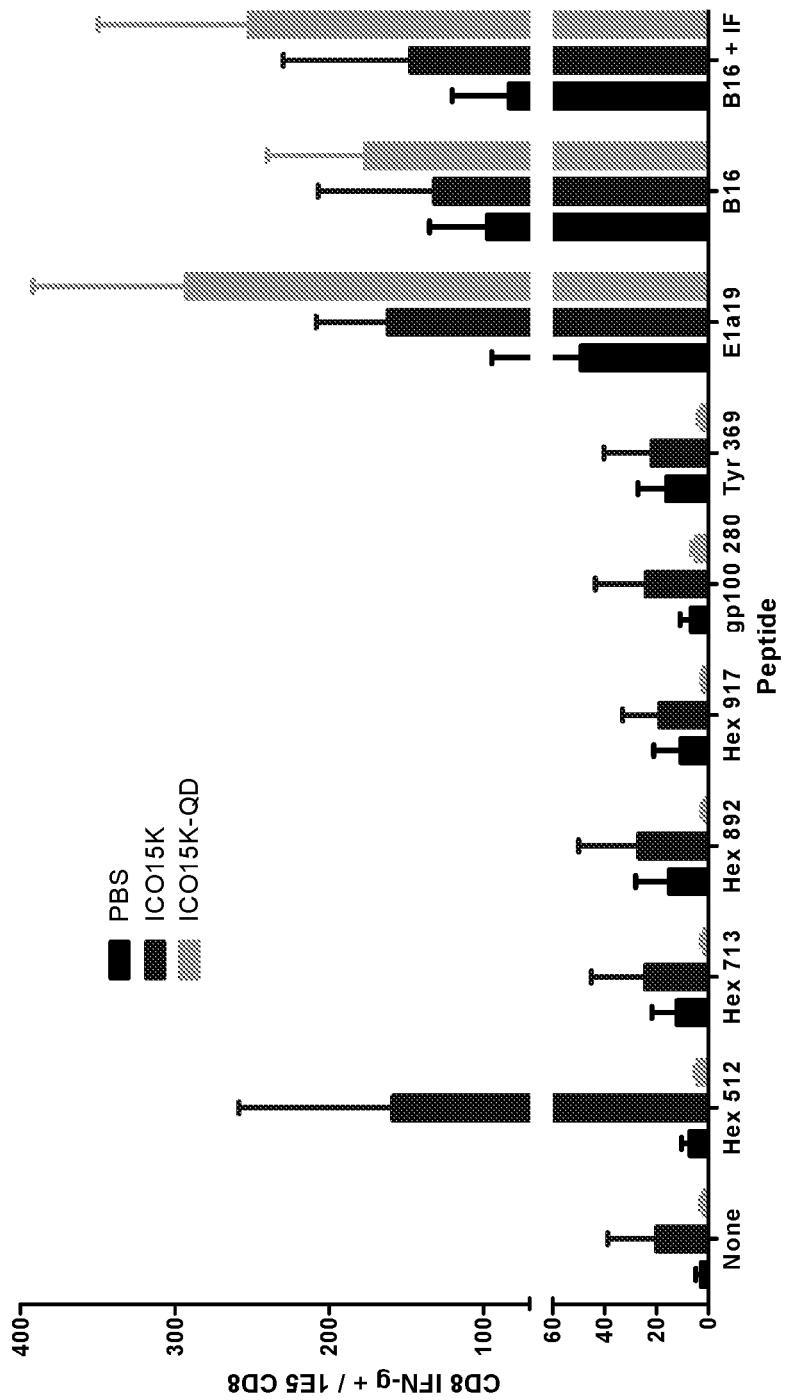
FIG. 13. Immune responses generated after intratumoral administration of $10^{10}$ vp/tumor of ICOVIR15K or ICOVIR15K-QD in transgenic HLA-A2.1 mice carrying B16CAR-A2 tumors. ELISPOT was performed using 2,500, 000 splenocytes per well. B16+IFN refers to reactivity against B16CAR-A2 tumors previously incubated with IFN-γ.

Results from the ELISPOT assay are shown in FIG. 13. In sharp contrast with mice treated with ICOVIR15K, mice intratumorally injected with ICOVIR15K-QD are not able to mount a response against Hex512 and Hex917 epitopes, confirming that the amino acid substitutions L520P and V925K in hexon are functional in vivo.

In addition, when splenocytes of these animals were co-cultured with complete tumor B16CAR-A2 murine cells to test the immunity against these cells, mice treated with ICOVIR15K-QD showed higher immunoreactivity against B16CAR-A2 tumor than mice treated with ICOVIR15K or PBS.

Overall, these data show that the treatment with an oncolytic adenovirus in which the immunodominant adenoviral epitopes have been deleted is able to generate a more potent antitumoral immune response against the tumor compared with a non-modified adenovirus.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

| Sequences |
|---|
| SEQ ID NO: 1 - ICOVIR15K
taattaccctgttatccctacatcatcaataatataccttattttggattgaagccaatatgataatgagggggtggagtttgtgac
gtggcgcggggcgtgggaacggggcgggtgacgtagtagtgtggcggaagtgtgatgttgcaagtgtggcggaacacatgtaagcga
cggatgtggcaaaagtgacgttttggtgtgcgccggtgtacacaggaagtgacaattttcgcgcggttttaggcggatgttgtagt
aaatttgggcgtaaccgagtaagatttggccattttcgcgggaaaactgaataagaggaagtgaaatctgaataattttgtgttact
catagcgcgtaatatttgtctagggccgcggggactttgaccgtttacgtggagactcgcccaggtgtttttctcaggtgttttccg
cgtactcggcggctcgtggctctttcgcggcaaaaggatttggcgcgtaaaagtggttcgaagtactcggcggctcgtggctcttt
cgcggcaaaaggatttggcgcgtaaaagtggttcgaagtacgtcgaccacaaaccccgcccagcgtcttgtcattggcgtcgacgc
tgtacggggtcaaagttggcgttttattattatagtcagctgacgtgtagtgtatttatacccggtgagttcctcaagaggccactc
ttgagtgccagcgagtagagttttctcctccgagccgctccgacaccgggactgaaaatgagacatattatctgccacggaggtgtt
attaccgaagaaatggccgccagtcttttggaccagctgatcgaagaggtactggctgataatcttccacctcctagccattttgaa
ccacctacccttcacgaactgtatgatttagacgtgacggccccgaagatcccaacgaggaggcggtttcgcagattttttcccgac
tctgtaatgttggcggtgcaggaagggattgacttactcacttttccgccggcgcccggttctccggagccgcctcacctttcccgg
cagcccgagcagccggagcagagagccttgggtccggtttctatgccaaaccttgtaccggaggtgatcgatccacccagtgacgac
gaggatgaagagggtgaggagtttgtgttagattatgtggagcaccccgggcacggttgcaggtcttgtcattatcaccggaggaat
acggggacccagatattatgtgttcgctttgctatatgaggacctgtggcatgtttgtctacagtaagtgaaaattatgggcagtg
ggtgatagagtggtgggtttggtgtggtaattttttttttaattttttacagttttgtggtttaaagaattttgtattgtgattttttt
taaaaggtcctgtgtctgaacctgagcctgagcccgagccagaaccggagcctgcaagacctacccgccgtcctaaaatggcgcctg
ctatcctgagacgcccgacatcacctgtgtccagagaatgcaatagtagtacggatagctgtgactccggtccttctaacacacctc
ctgagatacaccggtggtcccgctgtgcccattaaaccagttgccgtgagagttggtgggcgtcgccaggctgtggaatgtatcg
aggacttgcttaacgagcctgggcaacctttggacttgagctgtaaacgccccaggccataaggtgtaaacctgtgattgcgtgtgt
ggttaacgcctttgtttgctgaatgagttgatgtaagtttaataaagggtgagataatgtttaacttgcatggcgtgttaaatgggg
cggggcttaaagggtatataatgcgccgtgggctaatcttggttacatctgacctcatggaggcttgggagtgtttggaagattttt
ctgctgtgcgtaacttgctggaacagagctctaacagtacctcttggttttggaggtttctgtggggctcatcccaggcaaagttag
tctgcagaattaaggaggattacaagtgggaatttgaagagcttttgaaatcctgtggtgagctgtttgattattgaatctgggtca
ccaggcgcttttccaagagaaggtcatcaagactttggattttccacaccggggcgcgctgcggctgctgttgattttttgagtttt
ataaaggataaatggagcgaagaaacccatctgagcgggggggtacctgctggattttctggccatgcatctgtggagagcggttgtg
agacacaagaatcgcctgctactgttgtcttccgtccgcccggcgataataccgacggaggagcagcagcagcagcaggaggaagcc
aggcggcggcgcaggagcagagcccatgaacccgagagccggcctggaccctcgggaatgaatgttgtacaggtggctgaactgt
atccagaactgagacgcattttgacaattacagaggatgggcagggctaaaggggtaaagagggagcgggggcttgtgaggcta
cagaggaggctaggaatctagatttagataatgaccagacaccgtcctgagtgtattacttttcaacagatcaaggataattgcgct
aatgagcttgatctgctggcgcagaagtattccatagagcagctgaccacttactggctgcagccaggggatgattttgaggaggct
attagggtatatgcaaaggtggcacttaggccagattgcaagtacaagatcagcaaacttgtaaatatcaggaattgttgctacatt
tctgggaacggggccgaggtggagatagatacggaggataggggtggcctttagatgtagcatgataaatatgtggccgggggtgctt
ggcatggacggggtggttattatgaatgtaaggtttactggccccaattttagcggtacggttttcctggccaataccaaccttatc
ctacacggtgtaagcttctatgggtttaacaatacctgtgtggaagcctggaccgatgtaagggttcggggctgtgccttttactgc
tgctggaaggggtggtgtgtcgcccaaaagcagggatcaattaagaaatgcctattgaaaggtgtaccttgggtatcctgtctga
gggtaactccagggtgcgccacaatgtggcctccgactgtggttgcttcatgctagtgaaaagcgtggctgtgattaagcataacat
ggtatgtggcaactgcgaggacagggcctctcagatgctgacctgctcggacggcaactgtcacctgctgaagaccattcacgtagc
cagccactctcgcaaggcctggccagtgtttgagcataacatactgacccgctgttccttgcatttgggtaacaggagggggtgtt |

| Sequences |
| --- |
| cctaccttaccaatgcaatttgagtcacactaagatattgcttgagcccgagagcatgtccaaggtgaacctgaacggggtgtttga |
| catgaccatgaagatctggaaggtgctgaggtacgatgagacccgcaccaggtgcagaccctgcgagtgtggcggtaaacatattag |
| gaaccagcctgtgatgctggatgtgaccgaggagctgaggcccgatcacttggtgctggcctgcacccgcgctgagtttggctctag |
| cgatgaagatacagattgaggtactgaaatgtgtgggcgtggcttaagggtgggaagaatatataaggtgggggtcttatgtagtt |
| ttgtatctgttttgcagcagccgccgccgccatgagcaccaactcgtttgatggaagcattgtgagctcatatttgacaacgcgcat |
| gcccccatgggccggggtgcgtcagaatgtgatgggctccagcattgatggtcgcccccgtcctgcccgcaaactctactaccttgac |
| ctacgagaccgtgtctggaacgccgttggagactgcagcctccgccgccgcttcagccgctgcagccaccgcccgcgggattgtgac |
| tgactttgctttcctgagcccgcttgcaagcagtgcagcttcccgttcatccgcccgcgatgacaagttgacggctcttttggcaca |
| attggattcttttgacccgggaacttaatgtcgtttctcagcagctgttggatctgcgccagcaggtttctgccctgaaggcttcctc |
| ccctcccaatgcggttaaaacataaataaaaaaccagactctgtttggatttggatcaagcaagtgtcttgctgtctttatttagg |
| ggttttgcgcgcgcggtaggcccgggaccagcggtctcggtcgttgagggtcctgtgtatttttccaggacgtggtaaaggtgact |
| ctggatgttcagatacatgggcataagcccgtctctggggtggaggtagcaccactgcagagcttcatgctgcggggtggtgttgta |
| gatgatccagtcgtagcaggagcgctgggcgtggtgcctaaaaatgtcttcagtagcaagctgattgccaggggcaggcccttggt |
| gtaagtgtttacaaagcggttaagctgggatgggtgcatacgtggggatatgagatgcatcttggactgtattttaggttggctat |
| gttcccagccatatccctcggggattcatgttgtgcagaaccaccagcacagtgtatccggtgcacttgggaaatttgtcatgtag |
| cttagaaggaaatgcgtggaagaacttggagacgcccttgtgacctccaagattttccatgcattcgtccataatgatggcaatggg |
| cccacgggcggcggcctgggcgaagatatttctgggatcactaacgtcatagttgtgttccaggatgagatcgtcataggccatttt |
| tacaaagcgcgggcggagggtgccagactgcggtataatggttccatccggcccaggggcgtagttaccctcacagatttgcatttc |
| ccacgctttgagttcagatggggggatcatgtctacctgcggggcgatgaagaaaacggtttccggggtaggggagatcagctggga |
| agaaagcaggttcctgagcagctgcgacttaccgcagccggtgggcccgtaaatcacacctattaccggctgcaactggtagttaag |
| agagctgcagctgccgtcatccctgagcagggggccacttcgttaagcatgtccctgactcgcatgttttccctgaccaaatccgc |
| cagaaggcgctcgccgcccagcgatagcagttcttgcaaggaagcaaagttttcaacggtttgagaccgtccgccgtaggcatgct |
| tttgagcgtttgaccaagcagttccaggcggtcccacagctcggtcacctgctctacggcatctcgatccagcatatctcctcgttt |
| cgcgggttggggcggctttcgctgtacggcagtagtcggtgctcgtccagacgggccagggtcatgtcttccacgggcgcagggtc |
| ctcgtcagcgtagtctgggtcacggtgaaggggtgcgctccgggctgcgcgctggccagggtgcgcttgaggctggtcctgctggtg |
| ctgaagcgctgccggtcttcgccctgcgcgtcggccaggtagcatttgaccatggtgtcatagtccagcccctccgcggcgtggccc |
| ttggcgcgcagcttgcccttggaggaggcgccgcacgaggggcagtgcagacttttgagggcgtagagcttgggcgcgagaaatacc |
| gattccggggagtaggcatccgcgccgcaggccccgcagacggtctcgcattccacgagccaggtgagctctggccgttcggggtca |
| aaaaccaggtttcccccatgcttttttgatgcgtttcttacctctggtttccatgagccggtgtccacgctcggtgacgaaaaggctg |
| tccgtgtcccgtatacagacttgagaggcctgtcctcgagcggtgttccgcggtcctcctcgtatagaaactcggaccactctgag |
| acaaaggctcgcgtccaggccagcacgaaggaggctaagtgggaggggtagcggtcgttgtccactagggggtccactcgctccagg |
| gtgtgaagacacatgtcgcccttcggcatcaaggaaggtgattggtttgtaggtgtaggccacgtgaccgggtgttcctgaaggg |
| gggctataaagggggtgggggcgcgttcgtcctcactctcttccgcatcgctgtctgcgagggccagctgttgggtgagtactcc |
| ctctgaaaagcgggcatgacttctgcgctaagattgtcagtttccaaaaacgaggaggatttgatattcacctggcccgcggtgatg |
| cctttgagggtggccgcatccatctggtcagaaaagacaatcttttgttgtcaagcttggtggcaaacgacccgtagagggcgttg |
| gacagcaacttggcgatggagcgcagggtttggtttttgtcgcgatcggcgcgctccttggccgcgatgtttagctgcacgtattcg |
| cgcgcaacgcaccgccattcgggaaagacggtggtgcgctcgtcgggcaccaggtgcacgcgccaaccgcggttgtgcagggtgaca |
| aggtcaacgctggtggctacctctccgcgtaggcgctcgttggtccagcagaggcggccgcccttgcgcgagcagaatggcggtagg |
| gggtctagctgcgtctcgtccggggggtctgcgtccacggtaaagaccccgggcagcaggcgcgcgtcgaagtagtctatcttgcat |

| Sequences |
|---|
| ccttgcaagtctagcgcctgctgccatgcgcgggcggcaagcgcgcgctcgtatgggttgagtgggggaccccatggcatgggtgg |
| gtgagcgcggaggcgtacatgccgcaaatgtcgtaaacgtagaggggctctctgagtattccaagatatgtagggtagcatcttcca |
| ccgcggatgctggcgcgcacgtaatcgtatagttcgtgcgagggagcgaggaggtcgggaccgaggttgctacgggcgggctgctct |
| gctcggaagactatctgcctgaagatggcatgtgagttggatgatatggttggacgctggaagacgttgaagctggcgtctgtgaga |
| cctaccgcgtcacgcacgaaggaggcgtaggagtcgcgcagcttgttgaccagctcggcggtgacctgcacgtctagggcgcagtag |
| tccagggtttccttgatgatgtcatacttatcctgtccttttttttccacagctcgcggttgaggacaaactcttcgcggtctttc |
| cagtactcttggatcggaaacccgtcggcctccgaacggtaagagcctagcatgtagaactggttgacggcctggtaggcgcagcat |
| ccctttctacgggtagcgcgtatgcctgcgcggccttccggagcgaggtgtgggtgagcgcaaaggtgtccctgaccatgactttg |
| aggtactggtatttgaagtcagtgtcgtcgcatccgccctgctcccagagcaaaaagtccgtgcgcttttggaacgcggatttggc |
| agggcgaaggtgacatcgttgaagagtatctttcccgcgcgaggcataaagttgcgtgtgatgcggaagggtcccggcacctcggaa |
| cggttgttaattacctgggcggcgagcacgatctcgtcaaagccgttgatgttgtggcccacaatgtaaagttccaagaagcgcggg |
| atgcccttgatggaaggcaattttttaagttcctcgtaggtgagctcttcaggggagctgagcccgtgctctgaaagggcccagtct |
| gcaagatgagggttggaagcgacgaatgagctccacaggtcacgggccattagcatttgcaggtggtcgcgaaaggtcctaaactgg |
| cgacctatggccattttttctggggtgatgcagtagaaggtaagcgggtcttgttcccagcggtcccatccaaggttcgcggctagg |
| tctcgcgcggcagtcactagaggctcatctccgccgaacttcatgaccagcatgaagggcacgagctgcttcccaaaggcccccatc |
| caagtataggtctctacatcgtaggtgacaaagagacgctcggtgcgaggatgcgagccgatcgggaagaactggatctcccgccac |
| caattggaggagtggctattgatgtggtgaaagtagaagtccctgcgacgggccgaacactcgtgctggcttttgtaaaaacgtgcg |
| cagtactggcagcggtgcacgggctgtacatcctgcacgaggttgacctgacgaccgcgcacaaggaagcagagtgggaatttgagc |
| ccctcgcctggcgggttggctggtggtcttctacttcggctgcttgtccttgaccgtctggctgctcgaggggagttacggtggat |
| cggaccaccacgccgcgcgagcccaaagtccagatgtccgcgcgcggcggtcggagcttgatgacaacatcgcgcagatgggagctg |
| tccatggtctggagctcccgcggcgtcaggtcaggcgggagctcctgcaggtttacctcgcatagacgggtcagggcgcgggctaga |
| tccaggtgatacctaatttccaggggctggttggtggcggcgtcgatggcttgcaagaggccgcatccccgcggcgcgactacggta |
| ccgcgcggcgggcggtgggccgcgggggtgtccttggatgatgcatctaaaagcggtgacgcgggcgagcccccggaggtagggggg |
| gctccggacccgccgggagagggggcaggggcacgtcggcgccgcgcgcgggcaggagctggtgctgcgcgcgtaggttgctggcga |
| acgcgacgacgcggcggttgatctcctgaatctggcgcctctgcgtgaagacgacgggcccggtgagcttgaacctgaaagagagtt |
| cgacagaatcaatttcggtgtcgttgacggcggcctggcgcaaaatctcctgcacgtctcctgagttgtcttgataggcgatctcgg |
| ccatgaactgctcgatctcttcctcctggagatctccgcgtccggctcgctccacggtggcggcgaggtcgttggaaatgcgggcca |
| tgagctgcgagaaggcgttgaggcctccctcgttccagacgcggctgtagaccacgccccttcggcatcgcgggcgcgcatgacca |
| cctgcgcgagattgagctccacgtgccgggcgaagacggcgtagtttcgcaggcgctgaaagaggtagttgagggtggtggcggtgt |
| gttctgccacgaagaagtacataacccagcgtcgcaacgtggattcgttgatatcccccaaggcctcaaggcgctccatggcctcgt |
| agaagtccacggcgaagttgaaaaactgggagttgcgcgccgacacggttaactcctcctccagaagacggatgagctcggcgacag |
| tgtcgcgcacctcgcgctcaaaggctacaggggcctcttcttcttcttcaatctcctcttccataagggcctcccttcttcttcttcttc |
| ctggcggcggtggggagggggacacggcggcgacgacggcgcaccgggaggcggtcgacaaagcgctcgatcatctcccgcggc |
| gacggcgcatggtctcggtgacggcgcggccgttctcgcgggggcgcagttggaagacgccgcccgtcatgtcccggttatgggttg |
| gcgggggctgccatgcggcagggatacgcgctaacgatgcatctcaacaattgttgtgtaggtactccgccgccgagggacctga |
| gcgagtccgcatcgaccggatcggaaaacctctcgagaaaggcgtctaaccagtcacagtcgcaaggtaggctgagcaccgtggcgg |
| gcggcagcgggcggcggtcgggttgtttctggcggaggtgctgctgatgatgtaattaaagtaggcggtcttgagacgcggatgg |
| tcgacagaagcaccatgtccttgggtccggcctgctgaatgcgcaggcggtcggccatgcccaggcttcgttttgacatcggcgca |

-continued

| Sequences |
|---|
| ggtctttgtagtagtcttgcatgagcctttctaccggcacttcttcttctccttcctcttgtcctgcatctcttgcatctatcgctg |
| cggcggcggcggagtttggccgtaggtggcgccctcttcctcccatgcgtgtgaccccgaagcccctcatcggctgaagcagggcta |
| ggtcggcgacaacgcgctcggctaatatggcctgctgcacctgcgtgagggtagactggaagtcatccatgtccacaaagcggtggt |
| atgcgcccgtgttgatggtgtaagtgcagttggccataacggaccagttaacggtctggtgacccggctgcgagagctcggtgtacc |
| tgagacgcgagtaagccctcgagtcaaatacgtagtcgttgcaagtccgcaccaggtactggtatcccaccaaaaagtgcggcggcg |
| gctggcggtagaggggccagcgtagggtggccggggctccggggcgagatcttccaacataaggcgatgatatccgtagatgtacc |
| tggacatccaggtgatgccggcggcggtggtggaggcgcgcggaaagtcgcggacgcggttccagatgttgcgcagcggcaaaaagt |
| gctccatggtcgggacgctctggccggtcaggcgcgcgcaatcgttgacgctctagaccgtgcaaaaggagagcctgtaagcgggca |
| ctcttccgtggtctggtggataaattcgcaagggtatcatggcggacgaccggggttcgagcccgtatccggccgtccgccgtgat |
| ccatgcggttaccgcccgcgtgtcgaacccaggtgtgcgacgtcagacaacggggagtgctccttttggcttccttccaggcgcgg |
| cggctgctgcgctagcttttttggccactggccgcgcgcagcgtaagcggttaggctggaaagcgaaagcattaagtggctcgctcc |
| ctgtagccggagggttattttccaagggttgagtcgcgggaccccggttcgagtctcggaccggccggactgcggcgaacgggggt |
| ttgcctccccgtcatgcaagacccccgcttgcaaattcctccggaaacagggacgagccccttttttgcttttcccagatgcatccgg |
| tgctgcggcagatgcgccccctcctcagcagcggcaagagcaagagcagcggcagacatgcagggcaccctcccctcctcctaccg |
| cgtcaggaggggcgacatccgcggttgacgcggcagcagatggtgattacgaaccccgcggcgccgggccggcactacctggact |
| tggaggagggcgagggcctggcgcggctaggagcgccctctcctgagcggcacccaagggtgcagctgaagcgtgatacgcgtgagg |
| cgtacgtgccgcggcagaacctgtttcgcgaccgcgagggagaggagcccgaggagatgcgggatcgaaagttccacgcagggcgcg |
| agctgcggcatggcctgaatcgcgagcggttgctgcgcgaggaggactttgagcccgacgcgcgaacccgggattagtcccgcgcgcg |
| cacacgtggcggccgccgacctggtaaccgcatacgagcagacggtgaaccaggagattaactttcaaaaaagctttaacaaccacg |
| tgcgtacgcttgtggcgcgcgaggaggtggctataggactgatgcatctgtgggactttgtaagcgcgctggagcaaaacccaaata |
| gcaagccgctcatggcgcagctgttccttatagtgcagcacagcagggacaacgaggcattcagggatgcgctgctaaacatagtag |
| agcccgagggccgctggctgctcgatttgataaacatcctgcagagcatagtggtgcaggagcgcagcttgagcctggctgacaagg |
| tggccgccatcaactattccatgcttagcctgggcaagttttacgcccgcaagatataccatacccttacgttcccatagacaagg |
| aggtaaagatcgaggggttctacatgcgcatggcgctgaaggtgcttaccttgagcgacgacctgggcgtttatcgcaacgagcgca |
| tccacaaggccgtgagcgtgagccggcggcgcgagctcagcgaccgcgagctgatgcacagcctgcaaagggccctggctggcacgg |
| gcagcggcgatagagaggccgagtcctactttgacgcgggcgctgacctgcgctgggcccaagccgacgcgccctggaggcagctg |
| gggccggacctgggctggcggtggcacccgcgcgcgctggcaacgtcggcggcgtggaggaatatgacgaggacgatgagtacgagc |
| cagaggacggcgagtactaagcggtgatgtttctgatcagatgatgcaagacgcaacggacccggcggtgcgggcggcgctgcagag |
| ccagccgtccggccttaactccacggacgactggcgccaggtcatggaccgcatcatgtcgctgactgcgcgcaatcctgacgcgtt |
| ccggcagcagccgcaggccaaccggctctccgcaattctggaagcggtggtcccggcgcgcaaacccacgcacgagaaggtgct |
| ggcgatcgtaaacgcgctggccgaaaacagggccatccgcccgacgaggccggcctggtctacgacgcgctgcttcagcgcgtggc |
| tcgttacaacagcggcaacgtgcagaccaacctggaccggctggtggggatgtgcgcgaggccgtggcgcagcgtgagcgcgcgca |
| gcagcagggcaacctgggctccatggttgcactaaacgccttcctgagtacacagcccgccaacgtgccgcggggacaggaggacta |
| caccaactttgtgagcgcactgcggctaatggtgactgagacaccgcaaagtgaggtgtaccagtctgggccagactatttttttcca |
| gaccagtagacaaggcctgcagaccgtaaacctgagccaggctttcaaaaacttgcaggggctgtggggggtgcgggctcccacagg |
| cgaccgcgcgaccgtgtctagcttgctgacgcccaactcgcgcctgttgctgctgctaatagcgcccttcacggacagtggcagcgt |
| gtcccgggacacatacctaggtcacttgctgacactgtaccgcgaggccataggtcaggcgcatgtggacgagcatactttccagga |
| gattacaagtgtcagccgcgcgctggggcaggaggacacgggcagcctggaggcaacccta aaactacctgctgaccaaccggcggca |
| gaagatcccctcgttgcacagtttaaacagcgaggaggagcgcattttgcgctacgtgcagcagagcgtgagccttaacctgatgcg |

-continued

| Sequences |
|---|
| cgacggggtaacgcccagcgtggcgctggacatgaccgcgcgcaacatggaaccgggcatgtatgcctcaaaccggccgtttatcaa |
| ccgcctaatggactacttgcatcgcgcggccgccgtgaaccccgagtatttcaccaatgccatcttgaacccgcactggctaccgcc |
| ccctggtttctacaccgggggattcgaggtgcccgagggtaacgatggattcctctgggacgacatagacgacagcgtgttttcccc |
| gcaaccgcagaccctgctagagttgcaacagcgcgagcaggcagaggcggcgctgcgaaaggaaagcttccgcaggccaagcagctt |
| gtccgatctaggcgctgcggccccgcggtcagatgctagtagcccatttccaagcttgataggg tctcttaccagcactcgcaccac |
| ccgcccgcgcctgctgggcgaggaggagtacctaaacaactcgctgctgcagccgcagcgcgaaaaaaacctgcctccggcatttcc |
| caacaacgggatagagagcctagtggacaagatgagtagatggaagacgtacgcgcaggagcacagggacgtgccaggcccgcgccc |
| gcccacccgtcgtcaaaggcacgaccgtcagcggggtctggtgtgggaggacgatgactcggcagacgacagcagcgtcctggatt |
| gggagggagtggcaacccgtttgcgcaccttcgcccc aggctggggagaatgttttaaaaaaaaaaaaagcatgatgcaaaataaaa |
| aactcaccaaggccatggcaccgagcgttggttttcttgtattcccc ttagtatgcggcgcgcggcgatgtatgaggaaggtcctcc |
| tccctcctacgagagtgtggtgagcgcggcgccagtggcggcggcgctgggttctcccttcgatgctccc ctggacccgccgtttgt |
| gcctccgcggtacctgcggcctaccggggggagaaacagcatccgttactctgagttggcaccc ctattcgacaccaccc gtgtgta |
| cctggtggacaacaagtcaacggatgtggcatccctgaactaccagaacgaccacagcaactttctgaccacggtcattcaaaacaa |
| tgactacagcccgggggaggcaagcacacagaccatcaatcttgacgaccggtcgcactggggcggcgacctgaaaaccatcctgca |
| taccaacatgccaaatgtgaacgagttcatgtttaccaataagtttaaggcgcgggtgatggtgtcgcgcttgcctactaaggacaa |
| tcaggtggagctgaaatacgagtgggtggagttcacgctgcccgagggcaactactccgagaccatgaccatagaccttatgaacaa |
| cgcgatcgtggagcactacttgaaagtgggcagacagaacggggttctggaaagcgacatcggggtaaagtttgacacccgcaactt |
| cagactggggtttgaccccgtcactggtcttgtcatgcctggggtatatacaaacgaagccttccatccagacatcattttgctgcc |
| aggatgcgggg tggacttcacccacagccgcctgagcaacttgttgggcatccgcaagcggcaacccttccaggagggctttaggat |
| cacctacgatgatctggagggtggtaacattcccgcactgttggatgtggacgcctaccaggcgagcttgaaagatgacaccgaaca |
| gggcgggggtggcgcaggcggcagcaacagcagtggcagcggcgcggaagagaactccaacgcggcagccgcggcaatgcagccggt |
| ggaggacatgaacgatcatgccattcgcggcgacacctttgccacacgggctgaggagaagcgcgctgaggccgaagcagcggccga |
| agctgccgcccccgctgcgcaacccgaggtcgagaagcctcagaagaaaccggtgatcaaacccctgacagaggacagcaagaaacg |
| cagttacaacctaataagcaatgacagcaccttcacccagtaccgcagctggtaccttgcatacaactacggcgaccctcagaccgg |
| aatccgctcatggaccctgctttgcactcctgacgtaacctgcggctcggagcaggtctactggtcgttgccagacatgatgcaaga |
| ccccgtgaccttccgctccacgcgccagatcagcaactttccggtggtgggcgccgagctgttgcccgtgcactccaagagcttcta |
| caacgaccaggccgtctactcccaactcatccgccagtttacctctctgacccacgtgttcaatcgctttccc gagaaccagatttt |
| ggcgcgccgccagcccccaccatcaccaccgtcagtgaaaacgttcctgctctcacagatcacgggacgctaccgctgcgcaacag |
| catcggaggagtccagcgagtgaccattactgacgccagacgccgcacctgcccctacgtttacaaggccctgggcatagtctcgcc |
| gcgcgtcctatcgagccgcacttttt gagcaagcatgtccatccttatatcgcccagcaataacacaggctggggcctgcgcttccc |
| aagcaagatgtttggcggggccaagaagcgctccgaccaacacccagtgcgcgtgcgcgggcactaccgcgcgccctggggcgcgca |
| caaacgcggccgcactgggcgcaccaccgtcgatgacgccatcgacgcggtggtggaggaggcgcgcaactacacgcccacgccgcc |
| accagtgtccacagtggacgcggccattcagaccgtggtgcgcggagcccggcgctatgctaaaatgaagagacggcggaggcgcgt |
| agcacgtcgccaccgccgccgaccccggcactgccgcccaacgcgcggcggcggccctgcttaaccgcgcacgtcgcaccggccgacg |
| ggcggccatgcgggccgctcgaaggctggccgcgggtattgtcactgtgcccccaggtccaggcgacgagcggccgccgcagcagc |
| cgcggccattagtgctatgactcagggtcgcaggggcaacgtgtattgggtgcgcgactcggttagcggcctgcgcgtgccc gtgcg |
| cacccgcccccgcgcaactagattgcaagaaaaaactacttagactcgtactgttgtatgtatccagcggcggcggcgcgcaacga |
| agctatgtccaagcgcaaaatcaaagaagagatgctccaggtcatcgcgccgagatctatggccccccgaagaaggaagagcagga |

| Sequences |
| --- |
| ttacaagccccgaaagctaaagcgggtcaaaaagaaaaagaaagatgatgatgatgaacttgacgacgaggtggaactgctgcacgc |
| taccgcgcccaggcgacgggtacagtggaaaggtcgacgcgtaaaacgtgttttgcgacccggcaccaccgtagtctttacgccgg |
| tgagcgctccacccgcacctacaagcgcgtgtatgatgaggtgtacggcgacgaggacctgcttgagcaggccaacgagcgcctcgg |
| ggagtttgcctacggaaagcggcataaggacatgctggcgttgccgctggacgagggcaacccaacacctagcctaaagcccgtaac |
| actgcagcaggtgctgcccgcgcttgcaccgtccgaagaaaagcgcggcctaaagcgcgagtctggtgacttggcacccaccgtgca |
| gctgatggtacccaagcgccagcgactggaagatgtcttggaaaaaatgaccgtggaacctgggctggagcccgaggtccgcgtgcg |
| gccaatcaagcaggtggcgccgggactgggcgtgcagaccgtggacgttcagatacccactaccagtagcaccagtattgccaccgc |
| cacagagggcatggagacacaaacgtccccggttgcctcagcggtggcggatgccgcggtgcaggcggtcgctgcggccgcgtccaa |
| gacctctacggaggtgcaaacggaccgtggatgtttcgcgtttcagcccccggcgcccgcgccgttcgaggaagtacggcgccgc |
| cagcgcgctactgcccgaatatgccctacatccttccattgcgcctaccccggctatcgtggctacacctaccgccccagaagacg |
| agcaactacccgacgccgaaccaccactggaacccgccgccgccgtcgccgtcgccagcccgtgctggccccgatttccgtgcgcag |
| ggtggctcgcgaaggaggcaggaccctggtgctgccaacagcgcgctaccaccccagcatcgtttaaaagccggtctttgtggttct |
| tgcagatatggccctcacctgccgcctccgtttcccggtgccgggattccgaggaagaatgcaccgtaggaggggcatggccggcca |
| cggcctgacgggcggcatgcgtcgtgcgcaccaccggcggcggcgcgtcgcaccgtcgcatgcgcggcggtatcctgcccctcct |
| tattccactgatcgccgcggcgattggcgccgtgcccggaattgcatccgtggccttgcaggcgcagagacactgattaaaaacaag |
| ttgcatgtggaaaaatcaaaataaaagtctggactctcacgctcgcttggtcctgtaactattttgtagaatggaagacatcaact |
| ttgcgtctctggccccgcgacacggctcgcgcccgttcatgggaaactggcaagatatcggcaccagcaatatgagcggtggcgcct |
| tcagctggggctcgctgtggagcggcattaaaaatttcggttccaccgttaagaactatggcagcaaggcctggaacagcagcacag |
| gccagatgctgagggataagttgaaagagcaaaatttccaacaaaggtggtagatggcctggcctctggcattagcggggtggtgg |
| acctggccaaccaggcagtgcaaaataagattaacagtaagcttgatccccgccctcccgtagaggagcctccaccggccgtggaga |
| cagtgtctccagaggggcgtggcgaaaagcgtccgcgccccgacagggaagaaactctggtgacgcaaatagacgagcctccctcgt |
| acgaggaggcactaaagcaaggcctgccaccacccgtcccatcgcgcccatggctaccggagtgctgggccagcacacacccgtaa |
| cgctggacctgcctcccccgccgacacccagcagaaacctgtgctgccaggcccgaccgccgttgttgtaacccgtcctagccgcg |
| cgtccctgcgccgcgccgcagcggtccgcgatcgttgcggcccgtagccagtggcaactggcaaagcacactgaacagcatcgtgg |
| gtctgggggtgcaatccctgaagcgccgacgatgcttctgatagctaacgtgtcgtatgtgtgtcatgtatgcgtccatgtcgccgc |
| cagaggagctgctgagccgccgcgcgcccgctttccaagatggctaccccttcgatgatgccgcagtggtcttacatgcacatctcg |
| ggccaggacgcctcggagtacctgagccccgggctggtgcagtttgcccgcgccaccgagacgtacttcagcctgaataacaagttt |
| agaaaccccacggtggcgcctacgcacgacgtgaccacagaccggtcccagcgtttgacgctgcggttcatccctgtggaccgtgag |
| gatactgcgtactcgtacaaggcgcggttcaccctagctgtgggtgataaccgtgtgctggacatggcttccacgtactttgacatc |
| cgcggcgtgctggacagggcccctactttttaagccctactctggcactgcctacaacgccctggctcccaagggtgccccaaatcct |
| tgcgaatgggatgaagctgctactgctcttgaaataaacctagaagaagaggacgatgacaacgaagacgaagtagacgagcaagct |
| gagcagcaaaaactcacgtatttgggcaggcgccttattctggtataaatattacaaaggagggtattcaaataggtgtcgaaggt |
| caaacacctaaatatgccgataaaacatttcaacctgaacctcaaataggagaatctcagtggtacgaaacagaaattaatcatgca |
| gctgggagagtcctaaaaaagactaccccaatgaaaccatgttacggttcatatgcaaaacccacaaatgaaaatggagggcaaggc |
| attcttgtaaagcaacaaatggaaagctagaaagtcaagtggaaatgcaattttttctcaactactgaggcagccgcaggcaatggt |
| gataacttgactcctaaagtggtattgtacagtgaagatgtagatatagaaaccccagacactcatatttcttacatgcccactatt |
| aaggaaggtaactcacgagaactaatgggccaacaatctatgcccaacaggcctaattacattgcttttagggacaattttattggt |
| ctaatgtattacaacagcacgggtaatatgggtgttctggcgggccaagcatcgcagttgaatgctgttgtagatttgcaagacaga |
| aacacagagctttcataccagctttttgcttgattccattggtgatagaaccaggtacttttctatgtggaatcaggctgttgacagc |

| Sequences |
|---|
| tatgatccagatgttagaattattgaaaatcatggaactgaagatgaacttccaaattactgctttccactgggaggtgtgattaat |
| acagagactcttaccaaggtaaaacctaaaacaggtcaggaaaatggatgggaaaaagatgctacagaattttcagataaaaatgaa |
| ataagagttggaaataattttgccatggaaatcaatctaaatgccaacctgtggagaaatttcctgtactccaacatagcgctgtat |
| ttgcccgacaagctaaagtacagtccttccaacgtaaaaatttctgataacccaaacacctacgactacatgaacaagcgagtggtg |
| gctcccgggctagtggactgctacattaacctggagcacgctggtcccttgactatatggacaacgtcaacccatttaaccaccac |
| cgcaatgctggcctgcgctaccgctcaatgttgctgggcaatggtcgctatgtgcccttccacatccaggtgcctcagaagttcttt |
| gccattaaaaacctccttctcctgccgggctcatacacctacgagtggaacttcaggaaggatgttaacatggttctgcagagctcc |
| ctaggaaatgacctaagggttgacggagccagcattaagtttgatagcatttgcctttacgccaccttcttcccatggcccacaac |
| accgcctccacgcttgaggccatgcttagaaacgacaccaacgaccagtcctttaacgactatctctccgccgccaacatgctctac |
| cctatacccgccaacgctaccaacgtgcccatatccatccctcccgcaactgggcggctttccgcggctgggccttcacgcgcctt |
| aagactaaggaaacccccatcactgggctcgggctacgaccccttattacacctactctggctctatacccctagatggaaccttt |
| tacctcaaccacacctttaagaaggtggccattacccttgactcttctgtcagctggcctggcaatgaccgcctgcttacccccaac |
| gagtttgaaattaagcgctcagttgacggggagggttacaacgttgcccagtgtaacatgaccaaagactggttcctggtacaaatg |
| ctagctaactataacattggctaccagggcttctatatcccagagagctacaaggaccgcatgtactccttctttagaaacttccag |
| cccatgagccgtcaggtggtggatgatactaaatacaaggactaccaacaggtgggcatcctacaccaacacaacaactctggatt |
| gttggctaccttgcccccaccatgcgcgaaggacaggcctaccctgctaacttcccctatccgcttataggcaagaccgcagttgac |
| agcattacccagaaaaagtttctttgcgatcgcacccttggcgcatcccattctccagtaactttatgtccatgggcgcactcaca |
| gacctgggccaaaaccttctctacgccaactccgcccacgcgctagacatgacttttgaggtggatcccatggacagcccaccctt |
| ctttatgttttgtttgaagtctttgacgtggtccgtgtgcaccagccgcaccgcggcgtcatcgaaaccgtgtacctgcgcacgccc |
| ttctcggccggcaacgccacaacataaagaagcaagcaacatcaacaacagctgccgccatgggctccagtgagcaggaactgaaag |
| ccattgtcaaagatcttggttgtgggccatatttttgggcacctatgacaagcgctttccaggctttgtttctccacacaagctcg |
| cctgcgccatagtcaatacggccggtcgcgagactgggggcgtacactggatggcctttgcctggaaccgcactcaaaaacatgct |
| acctcttttgagccctttggcttttctgaccagcgactcaagcaggtttaccagtttgagtacgagtcactcctgcgccgtagcgcca |
| ttgcttcttcccccgaccgctgtataacgctggaaaagtccacccaaagcgtacaggggcccaactcggccgcctgtggactattct |
| gctgcatgtttctccacgccttttgccaactggcccccaaactcccatggatcacaaccccaccatgaaccttattaccggggtaccca |
| actccatgctcaacagtccccaggtacagcccaccctgcgtcgcaaccaggaacagctctacagcttcctggagcgccactcgccct |
| acttccgcagccacagtgcgcagattaggagcgccacttctttttgtcacttgaaaaacatgtaaaaataatgtactagagacactt |
| tcaataaaggcaaatgcttttatttgtacactctcgggtgattatttaccccaccccttgccgtctgcgccgtttaaaaatcaaagg |
| ggttctgccgcgcatcgctatgcgccactggcagggacacgttgcgatactggtgtttagtgctccacttaaactcaggcacaacca |
| tccgcggcagctcggtgaagttttcactccacaggctgcgcaccatcaccaacgcgtttagcaggtcgggcgccgatatcttgaagt |
| cgcagttggggcctccgccctgcgcgcgcgagttgcgatacacagggttgcagcactggaacactatcagcgccgggtggtgcacgc |
| tggccagcacgctcttgtcggagatcagatccgcgtccaggtcctccgcgttgctcagggcgaacggagtcaactttggtagctgcc |
| ttcccaaaagggcgcgtgcccaggctttgagttgcactcgcaccgtagtggcatcaaaaggtgaccgtgcccggtctgggcgttag |
| gatacagcgcctgcataaaagccttgatctgcttaaaagccacctgagcctttgcgccttcagagaagaacatgccgcaagacttgc |
| cggaaaactgattggccggacaggccgcgtcgtgcacgcagcaccttgcgtcggtgttggagatctgcaccacatttcggccccacc |
| ggttcttcacgatcttggccttgctagactgctccttcagcgcgcgctgcccgttttcgctcgtcacatccatttcaatcacgtgct |
| ccttatttatcataatgcttccgtgtagacacttaagctcgccttcgatctcagcgcagcggtgcagccacaacgcgcagcccgtgg |
| gctcgtgatgcttgtaggtcacctctgcaaacgactgcaggtacgcctgcaggaatcgccccatcatcgtcacaaaggtcttgttgc |

| Sequences |
|---|
| tggtgaaggtcagctgcaacccgcggtgctcctcgttcagccaggtcttgcatacggccgccagagcttccacttggtcaggcagta |
| gtttgaagttcgcctttagatcgttatccacgtggtacttgtccatcagcgcgcgcgcagcctccatgcccttctcccacgcagaca |
| cgatcggcacactcagcgggttcatcaccgtaatttcactttccgcttcgctgggctcttcctcttcctcttgcgtccgcataccac |
| gcgccactgggtcgtcttcattcagccgccgcactgtgcgcttacctcctttgccatgcttgattagcaccggtgggttgctgaaac |
| ccaccatttgtagcgccacatcttctctttcttcctcgctgtccacgattacctctggtgatggcgggcgctcgggcttgggagaag |
| ggcgcttcttttcttcttgggcgcaatggccaaatccgccgccgaggtcgatggccgcgggctgggtgtgcgcggcaccagcgcgt |
| cttgtgatgagtcttcctcgtcctcggactcgatacgccgcctcatccgcttttttgggggcgcccggggaggcggcggcgacgggg |
| acggggacgacacgtcctccatggttggggacgtcgcgccgcaccgcgtccgcgctcggggtggtttcgcgctgctcctcttccc |
| gactggccatttccttctcctataggcagaaaaagatcatggagtcagtcgagaagaaggacagcctaaccgcccctctgagttcg |
| ccaccaccgcctccaccgatgccgccaacgcgcctaccaccttcccgtcgaggcaccccgcttgaggaggaggaagtgattatcg |
| agcaggacccaggttttgtaagcgaagacgacgaggaccgctcagtaccaacagaggataaaaagcaagaccaggacaacgcagagg |
| caaacgaggaacaagtcgggcgggggacgaaaggcatggcgactacctagatgtgggagacgacgtgctgttgaagcatctgcagc |
| gccagtgcgccattatctgcgacgcgttgcaagagcgcagcgatgtgcccctcgccatagcggatgtcagccttgcctacgaacgcc |
| acctattctcaccgcgcgtaccccccaaacgccaagaaaacggcacatgcgagcccaacccgcgcctcaacttctacccgtatttg |
| ccgtgccagaggtgcttgccacctatcacatctttttccaaaactgcaagatacccctatcctgccgtgccaaccgcagccgagcgg |
| acaagcagctggccttgcggcagggcgctgtcatacctgatatcgcctcgctcaacgaagtgccaaaaatctttgagggtcttggac |
| gcgacgagaagcgcgcggcaaacgctctgcaacaggaaaacagcgaaaatgaaagtcactctggagtgttggtggaactcgagggtg |
| acaacgcgcgcctagccgtactaaaacgcagcatcgaggtcacccactttgcctacccggcacttaacctacccccaaggtcatga |
| gcacagtcatgagtgagctgatcgtgcgccgtgcgcagcccctggagagggatgcaaatttgcaagaacaaacagaggagggcctac |
| ccgcagttggcgacgagcagctagcgcgctggcttcaaacgcgcgagcctgccgacttggaggagcgacgcaaactaatgatggccg |
| cagtgctcgttaccgtggagcttgagtgcatgcagcggttctttgctgacccggagatgcagcgcaagctagaggaaacattgcact |
| acacctttcgacagggctacgtacgccaggcctgcaagatctccaacgtggagctctgcaacctggtctcctaccttggaatttgc |
| acgaaaaccgccttgggcaaaacgtgcttcattccacgctcaagggcgaggcgcgccgcgactacgtccgcgactgcgtttacttat |
| ttctatgctacacctggcagacggccatgggcgtttggcagcagtgcttggaggagtgcaacctcaaggagctgcagaaactgctaa |
| agcaaaacttgaaggacctatggacggccttcaacgagcgctccgtggccgcgcacctggcggacatcattttccccgaacgcctgc |
| ttaaaaccctgcaacagggtctgccagacttcaccagtcaaagcatgttgcagaactttaggaactttatcctagagcgctcaggaa |
| tcttgcccgccacctgctgtgcacttcctagcgactttgtgcccattaagtaccgcgaatgccctccgccgctttggggccactgct |
| accttctgcagctagccaactaccttgcctaccactctgacataatggaagacgtgagcggtgacggtctactggagtgtcactgtc |
| gctgcaacctatgcaccccgcaccgctccctggtttgcaattcgcagctgcttaacgaaagtcaaattatcggtacctttgagctgc |
| agggtccctcgcctgacgaaaagtccgcggctccgggggttgaaactcactccggggctgtggacgtcggcttaccttcgcaaatttg |
| tacctgaggactaccacgcccacgagattaggttctacgaagaccaatcccgcccgcctaatgcggagcttaccgcctgcgtcatta |
| cccagggccacattcttggccaattgcaagccatcaacaaagcccgccaagagtttctgctacgaaagggacgggggtttacttgg |
| accccccagtccggcgaggagctcaacccaatcccccgccgcgcagccctatcagcagcagccgcgggcccttgcttcccaggatg |
| gcacccaaaaagaagctgcagctgccgccgccacccacggacgaggaggaatactgggacagtcaggcagaggaggttttggacgag |
| gaggaggaggacatgatggaagactgggagagcctagacgaggaagcttccgaggtcgaagaggtgtcagacgaaacaccgtcaccc |
| tcggtcgcattcccctcgccggcgccccagaaatcggcaaccggttccagcatggctacaacctccgctcctcaggcgccgccggca |
| ctgcccgttcgccgacccaaccgtagatgggacaccactggaaccagggccggtaagtccaagcagccgccgccgttagcccaagag |
| caacaacagcgccaaggctaccgctcatggcgcgggcacaagaacgccatagttgcttgcttgcaagactgtgggggcaacatctcc |
| ttcgcccgccgctttcttctctaccatcacggcgtggccttcccccgtaacatcctgcattactaccgtcatctctacagcccatac |

| Sequences |
|---|
| tgcaccggcggcagcggcagcaacagcagcggccacacagaagcaaaggcgaccggatagcaagactctgacaaagcccaagaaatc |
| cacagcggcggcagcagcaggaggaggagcgctgcgtctggcgcccaacgaacccgtatcgacccgcgagcttagaaacaggatttt |
| tcccactctgtatgctatatttcaacagagcaggggccaagaacaagagctgaaaataaaaaacaggtctctgcgatccctcacccg |
| cagctgcctgtatcacaaaagcgaagatcagcttcggcgcacgctggaagacgcggaggctctcttcagtaaatactgcgcgctgac |
| tcttaaggactagtttcgcgccdttctcaaatttaagcgcgaaaactacgtcatctccagcggccacacccggcgccagcacctgtt |
| gtcagcgccattatgagcaaggaaattcccacgccctacatgtggagttaccagccacaaatgggacttgcggctggagctgcccaa |
| gactactcaacccgaataaactacatgagcgcgggaccccacatgatatcccgggtcaacggaatacgcgcccaccgaaaccgaatt |
| ctcctggaacaggcggctattaccaccacacctcgtaataaccttaatcccgtagttggcccgctgccctggtgtaccaggaaagt |
| cccgctcccaccactgtggtacttcccagagacgcccaggccgaagttcagatgactaactcaggggcgcagcttgcgggcggcttt |
| cgtcacagggtgcggtcgcccgggcagggtataactcacctgacaatcagagggcgaggtattcagctcaacgacgagtcggtgagc |
| tcctcgcttggtctccgtccgacgggacatttcagatcggcggcgccggccgctcttcattcacgcctcgtcaggcaatcctaact |
| ctgcagacctcgtcctctgagccgcgctctggaggcattggaactctgcaatttattgaggagtttgtgccatcggtctactttaac |
| cccttctcgggacctcccggccactatccggatcaatttattcctaactttgacgcggtaaaggactcggcggacggctacgactga |
| atgttaagtggagaggcagagcaactgcgcctgaaacacctggtccactgtcgccgccacaagtgctttgcccgcgactccggtgag |
| ttttgctactttgaattgcccgaggatcatatcgagggcccggcgcacggcgtccggcttaccgcccagggagagcttgcccgtagc |
| ctgattcgggagtttacccagcgccccctgctagttgagcgggacaggggaccctgtgttctcactgtgatttgcaactgtcctaac |
| cttggattacatcaagatctttgttgccatctctgtgctgagtataataaatacagaaattaaaatatactggggctcctatcgcca |
| tcctgtaaacgccaccgtcttcacccgcccaagcaaaccaaggcgaaccttacctggtacttttaacatctctccctctgtgattta |
| caacagtttcaacccagacggagtgagtctacgagagaacctctccgagctcagctactccatcagaaaaaacaccaccctccttac |
| ctgccgggaacgtacgagtgcgtcaccggccgctgcaccacacctaccgcctgaccgtaaaccagacttttttccggacagacctcaa |
| taactctgtttaccagaacaggaggtgagcttagaaaacccttagggtattaggccaaaggcgcagctactgtggggtttatgaaca |
| attcaagcaactctacgggctattctaattcaggtttctctagaatcggggttggggttattctctgtcttgtgattctctttattc |
| ttatactaacgcttctctgcctaaggctcgccgcctgctgtgtgcacatttgcatttattgtcagcttttaaacgctggggtcgcc |
| acccaagatgattaggtacataatcctaggtttactcaccttgcgtcagcccacggtaccacccaaaaggtggattttaaggagcc |
| agcctgtaatgttacattcgcagctgaagctaatgagtgcaccactcttataaaatgcaccacagaacatgaaaagctgcttattcg |
| ccacaaaaacaaaattggcaagtatgctgtttatgctattggcagccaggtgacactacagagtataatgttacagttttccaggg |
| taaaagtcataaaacttttatgtatacttttccatttttatgaaatgtgcgacattaccatgtacatgagcaaacagtataagttgtg |
| gcccccacaaaattgtgtgaaaacactggcactttctgctgcactgctatgctaattacagtgctcgctttggtctgtaccctact |
| ctatattaaatacaaaagcagacgcagctttattgaggaaaagaaaatgccttaatttactaagttacaaagctaatgtcaccacta |
| actgctttactcgctgcttgcaaaacaaattcaaaaagttagcattataattagaataggatttaaaccccccggtcatttcctgct |
| caataccattcccctgaacaattgactctatgtgggatatgctccagcgctacaaccttgaagtcaggcttcctggatgtcagcatc |
| tgactttggccagcacctgtcccgcggatttgttccagtccaactacagcgacccaccctaacagagatgaccaacacaaccaacgc |
| ggccgccgctaccggacttacatctaccacaaatacaccccaagtttctgcctttgtcaataactgggataacttgggcatgtggtg |
| gttctccatagcgcttatgtttgtatgccttattattatgtggctcatctgctgcctaaagcgcaaacgcgcccgaccacccatcta |
| tagtcccatcattgtgctacacccaaacaatgatggaatccatagattggacggactgaaacacatgttcttttctcttacagtatg |
| attaaatgagacatgattcctcgagttttttatattactgacccttgttgcgcttttttgtgcgtgctccacattggctgcggtttct |
| cacatcgaagtagactgcattccagccttcacagtctatttgctttacggatttgtcaccctcacgctcatctgcagcctcatcact |
| gtggtcatcgcctttatccagtgcattgactgggtctgtgtgcgctttgcatatctcagacaccatcccagtacagggacaggact |

| Sequences |
| --- |
| atagctgagcttcttagaattctttaattatgaaatttactgtgacttttctgctgattatttgcaccctatctgcgttttgttccc |
| cgacctccaagcctcaaagacatatatcatgcagattcactcgtatatggaatattccaagttgctacaatgaaaaaagcgatctttt |
| ccgaagcctggttatatgcaatcatctctgttatggtgttctgcagtaccatcttagccctagctatatatcccttaccttgacattg |
| gctggaaacgaatagatgccatgaaccacccaactttccccgcgcccgctatgcttccactgcaacaagttgttgccggcggctttg |
| tcccagccaatcagcctcgccccacttctcccaccccactgaaatcagctactttaatctaacaggaggagatgactgacaccta |
| gatctagaaatggacggaattattacagagcagcgcctgctagaaagacgcagggcagcggccgagcaacagcgcatgaatcaagag |
| ctccaagacatggttaacttgcaccagtgcaaaaggggtatcttttgtctggtaaagcaggccaaagtcacctacgacagtaatacc |
| accggacaccgccttagctacaagttgccaaccaagcgtcagaaattggtggtcatggtgggagaaaagcccattaccataactcag |
| cactcggtagaaaccgaaggctgcattcactcaccttgtcaaggacctgaggatctctgcacccttattaagaccctgtgcggtctc |
| aaagatcttattccdttaactaataaaaaaaaataataaagcatcacttacttaaaatcagttagcaaatttctgtccagtttattc |
| agcagcacctccttgccctcctcccagctctggtattgcagcttcctcctggctgcaaacttctccacaatctaaatggaatgtca |
| gtttcctcctgttcctgtccatccgcacccactatcttcatgttgttgcagatgaagcgcgcaagaccgtctgaagataccttcaac |
| cccgtgtatccatgtgacacggaaaccggtcctccaactgtgccttttcttactcctcccttgtatcccccaatgggtttcaagag |
| agtccccctggggtactctcttgcgcctatccgaacctctagttacctccaatggcatgcttgcgctcaaaatgggcaacggcctc |
| tctctggacgaggccggcaaccttacctcccaaaatgtaaccactgtgagcccacctctccgaggagacaagtcaaacataaacctg |
| gaaatatctgcacccctcacagttacctcagaagccctaactgtggctgccgccgcacctctaatggtcgcgggcaacacactcacc |
| atgcaatcacaggccccgctaaccgtgcacgactccaaacttagcattgccacccaaggacccctcacagtgtcagaaggaaagcta |
| gccctgcaaacatcaggcccccctcaccaccaccgatagcagtaccccttactatcactgcctcaccccctctaactactgccactggt |
| agcttgggcattgacttgaaagagcccatttatacacaaaatggaaaactaggactaaagtacggggctcctttgcatgtaacagac |
| gacctaaacactttgaccgtagcaactggtccaggtgtgactattaataatacttccttgcaaactaaagttactggagccttgggt |
| tttgattcacaaggcaatatgcaacttaatgtagcaggaggactaaggattgattctcaaaacagacgccttatacttgatgttagt |
| tatccgtttgatgctcaaaaccaactaaatctaagactaggacagggccctcttttttataaactcagcccacaacttggatattaac |
| tacaacaaaggcctttacttgtttacagcttcaaacaattccaaaaagcttgaggttaacctaagcactgccaaggggttgatgttt |
| gacgctacagccatagccattaatgcaggagatgggcttgaatttggttcacctaatgcaccaaacacaaatcccctcaaaacaaaa |
| attggccatggcctagaatttgattcaaacaaggctatggttcctaaactaggaactggccttagttttgacagcacaggtgccatt |
| acagtaggaaacaaaataatgataagctaactttgtggaccacaccagctccatctcctaactgtagactaaatgcagagaaagat |
| gctaaactcactttggtcttaacaaaatgtggcagtcaaatacttgctacagtttcagttttggctgttaaaggcagtttggctcca |
| atatctggaacagttcaaagtgctcatcttattataagatttgacgaaaatggagtgctactaaacaattccttcctggacccagaa |
| tattggaactttagaaatggagatcttactgaaggcacagcctatacaaacgctgttggatttatgcctaacctatcagcttatcca |
| aaatctcacggtaaaactgccaaaagtaacattgtcagtcaagtttacttaaacggagacaaaactaaacctgtaacactaaccatt |
| acactaaacggtacacaggaaacaggagacacaactccatctgcatactctatgtcattttcatgggactggtctggccacaactac |
| attaatgaaatatttgccacatcctcttacacttttttcatacattgcccaagaataaagaatcgtttgtgttatgtttcaacgtgtt |
| tattttcaattgcagaaaatttcaagtcattttttcattcagtagtatagccccaccaccacatagcttatacagatcaccgtacct |
| taatcaaactcacagaaccctagtattcaacctgccacctccctcccaacacacagagtacacagtcctttctcccggctggcctt |
| aaaaagcatcatatcatgggtaacagacatattcttaggtgttatattccacacggtttcctgtcgagccaaacgctcatcagtgat |
| attaataaactccccgggcagctcacttaagttcatgtcgctgtccagctgctgagccacaggctgctgtccaacttgcggttgctt |
| aacgggcggcgaaggagaagtccacgcctacatgggggtagagtcataatcgtgcatcaggataggggcggtggtgctgcagcagcgc |
| gcgaataaactgctgccgccgccgctccgtcctgcaggaatacaacatggcagtggtctcctcagcgatgattcgcaccgccgcag |
| cataaggcgccttgtcctccgggcacagcagcgcaccctgatctcacttaaatcagcacagtaactgcagcacagcaccacaatatt |

-continued

Sequences gttcaaaatcccacagtgcaaggcgctgtatccaaagctcatggcggggaccacagaacccacgtggccatcataccacaagcgcag gtagattaagtggcgacccctcataaacacgctggacataaacattacctcttttggcatgttgtaattcaccacctcccggtacca tataaacctctgattaaacatggcgccatccaccaccatcctaaaccagctggccaaaacctgcccgccggctatacactgcaggga accgggactggaacaatgacagtggagagcccaggactcgtaaccatggatcatcatgctcgtcatgatatcaatgttggcacaaca caggcacacgtgcatacacttcctcaggattacaagctcctcccgcgttagaaccatatcccagggacaacccattcctgaatcag cgtaaatcccacactgcagggaagacctcgcacgtaactcacgttgtgcattgtcaaagtgttacattcgggcagcagcggatgatc ctccagtatggtagcgcgggtttctgtctcaaaaggaggtagacgatccctactgtacggagtgcgccgagacaaccgagatcgtgt tggtcgtagtgtcatgccaaatggaacgccggacgtagtcatatttcctgaagcaaaaccaggtgcgggcgtgacaaacagatctgc gtctccggtctcgccgcttagatcgctctgtgtagtagttgtagtatatccactctctcaaagcatccaggcgcccctggcttcgg gttctatgtaaactccttcatgcgccgctgccctgataacatccaccaccgcagaataagccacacccagccaacctacacattcgt tctgcgagtcacacacgggaggagcgggaagagctggaagaaccatgtttttttttttattccaaaagattatccaaaacctcaaaa tgaagatctattaagtgaacgcgctcccctccggtggcgtggtcaaactctacagccaaagaacagataatggcatttgtaagatgt tgcacaatggcttccaaaaggcaaacggccctcacgtccaagtggacgtaaaggctaaacccttcagggtgaatctcctctataaac attccagcaccttcaaccatgcccaaataattctcatctcgccaccttctcaatatatctctaagcaaatcccgaatattaagtccg gccattgtaaaaatctgctccagagcgccctccaccttcagcctcaagcagcgaatcatgattgcaaaaattcaggttcctcacaga cctgtataagattcaaaagcggaacattaacaaaaataccgcgatcccgtaggtcccttcgcagggccagctgaacataatcgtgca ggtctgcacggaccagcgcggccacttccccgccaggaaccatgacaaaagaacccacactgattatgacacgcatactcggagcta tgctaaccagcgtagccccgatgtaagcttgttgcatgggcggcgatataaaatgcaaggtgctgctcaaaaaatcaggcaaagcct cgcgcaaaaagaaagcacatcgtagtcatgctcatgcagataaaggcaggtaagctccggaaccaccacagaaaaagacaccatttt ttctctcaaacatgtctgcgggtttctgcataaacacaaaataaaataacaaaaaaacatttaaacattagaagcctgtcttacaac aggaaaaacaacccttataagcataagacggactacggccatgccggcgtgaccgtaaaaaaactggtcaccgtgattaaaaagcac caccgacagctcctcggtcatgtccggagtcataatgtaagactcggtaaacacatcaggttgattcacatcggtcagtgctaaaaa gcgaccgaaatagcccgggggaatacatacccgcaggcgtagagacaacattacagcccccataggaggtataacaaaattaatagg agagaaaaacacataaacacctgaaaaaccctcctgcctaggcaaaatagcaccctcccgctccagaacaacatacagcgcttccac agcggcagccataacagtcagccttaccagtaaaaaagaaaacctattaaaaaaacaccactcgacacggcaccagctcaatcagtc acagtgtaaaaagggccaagtgcagagcgagtatatataggactaaaaaatgacgtaacggttaaagtccacaaaaaacacccaga aaaccgcacgcgaacctacgcccagaaacgaaagccaaaaaacccacaacttcctcaaatcgtcacttccgttttcccacgttacgt cacttcccatttttaagaaaactacaattcccaacacatacaagttactccgccctaaaacctacgtcacccgccccgttcccacgcc ccgcgccacgtcacaaactccaccccctcattatcatattggcttcaatccaaaataaggtatattattgatgatgtagggataaca gggtaattaat SEQ ID NO: 2 - ICOVIR15K-gp100-tyr
catcatcaataatatacctaattttggattgaagccaatatgataatgagggggtggagtttgtgacgtggcgcggggcgtgggaac ggggcgggtgacgtagtagtgtggcggaagtgtgatgttgcaagtgtggcggaacacatgtaagcgacggatgtggcaaaagtgacg tttttggtgtgcgccggtgtacacaggaagtgacaattttcgcgcggttttaggcggatgttgtagtaaatttgggcgtaaccgagt aagatttggccattttcgcgggaaaactgaataagaggaagtgaaatctgaataattttgtgttactcatagcgcgtaatatttgtc tagggccgcggggactttgaccgtttacgtggagactcgcccaggtgttttttctcaggtgttttccgcgtacgtcggcggctcgtgg ctcttttcgcggcaaaaaggatttggcgcgtaaaagtggttcgagtacgtcggcggctcgtggctctttcgcggcaaaaaggatttgg cgcgtaaaagtggttcgaagtacgtcgaccacaaaccccgcccagcgtcttgtcattggcgtcgacgctgtacggggtcaaagttgg cgttttattattatagtcagctgacgtgtagtgtatttataccggtgagttcctcaagaggccactcttgagtgccagcgagtaga

| Sequences |
|---|
| gttttctcctccgagccgctccgacaccgggactgaaaatgagacatattatctgccacggaggtgttattaccgaagaaatggccg |
| ccagtcttttggaccagctgatcgaagaggtactggctgataatcttccacctcctagccattttgaaccacctaccatcacgaact |
| gtatgatttagacgtgacggccccgaagatcccaacgaggaggcggtttcgcagattttccccgactctgtaatgttggcggtgca |
| ggaagggattgacttactcacttttccgccggcgcccggttctccggagccgcctcacctttcccggcagcccgagcagccggagca |
| gagagccttgggtccggtttctatgccaaaccttgtaccggaggtgatcgatccaccccagtgacgacgaggatgaagagggtgagga |
| gtttgtgttagattatgtggagcaccccgggcacggttgcaggtcttgtcattatcaccggaggaatacgggggacccagatattat |
| gtgttcgctttgctatatgaggacctgtggcatgtttgtctacagtaagtgaaaattatgggcagtgggtgatagagtggtgggttt |
| ggtgtggtaattttttttttaattttttacagttttgtggtttaaagaattttgtattgtgatttttttaaaaggtcctgtgtctgaa |
| cctgagcctgagcccgagccagaaccggagcctgcaagacctacccgccgtcctaaaatggcgcctgctatcctgagacgcccgaca |
| tcacctgtgtccagagaatgcaatagtagtacggatagctgtgactccggtccttctaacacacctcctgagatacacccggtggtc |
| ccgctgtgccccattaaaccagttgccgtgagagttggtgggcgtcgccaggctgtggaatgtatcgaggacttgataacgagcctg |
| ggcaacattggacttgagctgtaaacgccccaggccataaggtgtaaacctgtgattgcgtgtgtggttaacgcctttgtttgctga |
| atgagttgatgtaagtttaataaagggtgagataatgtttaacttgcatggcgtgttaaatggggcggggcttaaagggtatataat |
| gcgccgtgggctaatcttggttacatctgacctcatggaggcttgggagtgtttggaagattttttctgctgtgcgtaacttgctgga |
| acagagctctaacagtacctcttggttttggaggtttctgtggggctcatcccaggcaaagttagtctgcagaattaaggaggatta |
| caagtgggaatttgaagagcttttgaaatcctgtggtgagctgtttgattctttgaatctgggtcaccaggcgcttttccaagagaa |
| ggtcatcaagactttggattttttccacaccggggcgcgctgcggctgctgttgcttttttgagttttataaaggataaatggagcga |
| agaaacccatctgagcgggggggtacctgctggattttctggccatgcatctgtggagagcggttgtgagacacaagaatcgcctgct |
| actgttgtcttccgtccgcccggcgataataccgacggaggagcagcagcagcagcaggaggaagccaggcggcggcggcaggagca |
| gagcccatggaacccgagagccggcctggaccctcgggaatgaatgttgtacaggtggctgaactgtatccagaactgagacgcatt |
| ttgacaattacagaggatgggcaggggctaaaggggggtaaagagggagcggggggcttgtgaggctacagaggaggctaggaatcta |
| gcttttagcttaatgaccagacaccgtcctgagtgtattacttttcaacagatcaaggataattgcgctaatgagcttgatctgctg |
| gcgcagaagtattccatagagcagctgaccacttactggctgcagccaggggatgattttgaggaggctattagggtatatgcaaag |
| gtggcacttaggccagattgcaagtacaagatcagcaaacttgtaaatatcaggaattgttgctacatttctgggaacggggccgag |
| gtggagatagatacggaggataggggtggccttttagatgtagcatgataaatatgtggccggggggtgcttggcatggacggggtggtt |
| attatgaatgtaaggtttactggccccaattttagcggtacggttttcctggccaataccaaccttatcctacacggtgtaagcttc |
| tatgggtttaacaataccgtgtgtggaagcctggaccgatgtaagggttcggggctgtgccttttactgctgctggaaggggggtggtg |
| tgtcgccccaaaagcagggcttcaattaagaaatgcctctttgaaaggtgtaccttgggtatcctgtctgagggtaactccaggtgtg |
| cgccacaatgtggcctccgactgtggttgcttcatgctagtgaaaagcgtggctgtgattaagcataacatggtatgtggcaactgc |
| gaggacagggcctctcagatgctgacctgctcggacggcaactgtcacctgctgaagaccattcacgtagccagccactctcgcaag |
| gcctggccagtgtttgagcataacatactgacccgctgttccttgcatttgggtaacaggaggggggtgttcctaccttaccaatgc |
| aatttgagtcacactaagatattgcttgagcccgagagcatgtccaaggtgaacctgaacgggtgtttgacatgaccatgaagatc |
| tggaaggtgctgaggtacgatgagacccgcaccaggtgcagaccctgcgagtgtggcggtaaacatattaggaaccagcctgtgatg |
| ctggatgtgaccgaggagctgaggcccgatcacttggtgctggcctgcacccgcgctgagtttggctctagcgatgaagatacagat |
| tgaggtactgaaatgtgtgggcgtggcttaaggtgggaaagaatatataaggtgggggtcttatgtagttttgtatctgttttgca |
| gcagccgccgccgccatgagcaccaactcgtttgatggaagcattgtgagctcatatttgacaacgcgcatgcccccatgggccggg |
| gtgcgtcagaatgtgatgggctccagcattgatggtcgcccgtcctgcccgcaaactctactaccttgacctacgagaccgtgtct |
| ggaacgccgttggagactgcagcctccgccgccgcttcagccgctgcagccaccgcccgcgggattgtgactgactttgctttcctg |

| Sequences |
| --- |
| agcccgcttgcaagcagtgcagcttcccgttcatccgcccgcgatgacaagttgacggctcttttggcacaattggattctttgacc |
| cgggaacttaatgtcgtttctcagcagctgttggatctgcgccagcaggtttctgccctgaaggcttcctcccctcccaatgcggtt |
| taaaacataaataaaaaaccagactctgtttggatttggatcaagcaagtgtcttgctgtctttatttaggggttttgcgcgcgcgg |
| taggcccgggaccagcggtctcggtcgttgagggtcctgtgtattttttccaggacgtggtaaaggtgactctggatgttcagatac |
| atgggcataagcccgtctctggggtggaggtagcaccactgcagagcttcatgctgcggggtggtgttgtagatgatccagtcgtag |
| caggagcgctgggcgtggtgcctaaaaatgtctttcagtagcaagctgattgccaggggcaggcccttggtgtaagtgtttacaaag |
| cggttaagctgggatgggtgcatacgtggggatatgagatgcatcttggactgtattttttaggttggctatgttcccagccatatcc |
| ctccggggattcatgttgtgcagaaccaccagcacagtgtatccggtgcacttgggaaatttgtcatgtagcttagaaggaaatgcg |
| tggaagaacttggagacgcccttgtgacctccaagattttccatgcattcgtccataatgatggcaatgggcccacgggcggcggcc |
| tgggcgaagatatttctgggatcactaacgtcatagttgtgttccaggatgagatcgtcataggccattttttacaaagcgcgggcgg |
| agggtgccagactgcggtataatggttccatccggcccaggggcgtagttaccctcacagatttgcatttcccacgctttgagttca |
| gatgggggatcatgtctacctgcggggcgatgaagaaaacggtttccggggtagggagatcagctgggaagaaagcaggttcctg |
| agcagctgcgacttaccgcagccggtgggcccgtaaatcacacctattaccgggtgcaactggtagttaagagagctgcagctgccg |
| tcatccctgagcagggggccacttcgttaagcatgtccctgactcgcatgttttccctgaccaaatccgccagaaggcgctcgccg |
| cccagcgatagcagttcttgcaaggaagcaaagttttttcaacggtttgagaccgtccgccgtaggcatgcttttgagcgtttgacca |
| agcagttccaggcggtcccacagctcggtcacctgctctacggcatctcgatccagcatatctcctcgtttcgcgggttggggcggc |
| tttcgctgtacggcagtagtcggtgctcgtccagacgggccagggtcatgtctttccacgggcgcagggtcctcgtcagcgtagtct |
| gggtcacggtgaaggggtgcgctccgggctgcgcgctggccagggtgcgcttgaggctggtcctgctggtgctgaagcgctgccggt |
| cttcgccctgcgcgtcggccaggtagcatttgaccatggtgtcatagtccagcccctccgcggcgtggccttggcgcgcagcttgc |
| ccttggaggaggcgccgcacgaggggcagtgcagacttttgagggcgtagagcttgggcgcgagaaataccgattccggggagtagg |
| catccgcgccgcaggccccgcagacggtctcgcattccacgagccaggtgagctctggccgttcggggtcaaaaaccaggtttcccc |
| catgctttttgatgcgtttcttacctctggttttccatgagccggtgtccacgctcggtgacgaaaaggctgtccgtgtcccccgtata |
| cagacttgagaggcctgtcctcgagcggtgttccgcggtcctcctcgtatagaaactcggaccactctgagacaaaggctcgcgtcc |
| aggccagcacgaaggaggctaagtgggaggggtagcggtcgttgtccactagggggtccactcgctccaggtgtgaagacacatgt |
| cgccctcttcggcatcaaggaaggtgattggtttgtaggtgtaggccacgtgaccgggtgttcctgaaggggggctataaaaggggg |
| tgggggcgcgttcgtcctcactctcttccgcatcgctgtctgcgagggccagctgttgggtgagtactccctctgaaaagcgggca |
| tgacttctgcgctaagattgtcagtttccaaaaacgaggaggatttgatattcacctggcccgcggtgatgcctttgagggtggccg |
| catccatctggtcagaaaagacaatcttttttgttgtcaagcttggtggcaaacgacccgtagagggcgttggacagcaacttggcga |
| tggagcgcagggtttggttttttgtcgcgatcggcgcgctccttggccgcgatgtttagctgcacgtattcgcgcgcaacgcaccgcc |
| attcgggaagacggtggtgcgctcgtcgggcaccaggtgcacgcgccaaccgcggttgtgcagggtgacaaggtcaacgctggtgg |
| ctacctctccgcgtaggcgctcgttggtccagcagaggcggccgcccttgcgcgagcagaatggcggtaggggtctagctgcgtct |
| cgtccgggggtctgcgtccacggtaaagaccccgggcagcaggcgcgcgtcgaagtagtctatcttgcatccttgcaagtctagcg |
| cctgctgccatgcgcgggcggcaagcgcgcgctcgtatgggttgagtgggggaccccatggcatgggtgggtgagcgcggaggcgt |
| acatgccgcaaatgtcgtaaacgtagaggggctctctgagtattccaagatatgtagggtagcatcttccaccgcggatgctggcgc |
| gcacgtaatcgtatagttcgtgcgaggagcgaggaggtcgggaccgaggttgctacgggcgggctgctctgctcggaagactatct |
| gcctgaagatggcatgtgagttggatgatatggttggacgctggaagacgttgaagctggcgtctgtgagacctaccgcgtcacgca |
| cgaaggaggcgtaggagtcgcgcagcttgttgaccagctcggcggtgacctgcacgtctagggcgcagtagtccagggtttccttga |
| tgatgtcatacttatcctgtccctttttttttccacagctcgcggttgaggacaaactcttcgcggtctttccagtactcttggatcg |
| gaaacccgtcggcctccgaacggtaagagcctagcatgtagaactggttgacggcctggtaggcgcagcatcccttttctacgggta |

-continued

| Sequences |
|---|
| gcgcgtatgcctgcgcggccttccggagcgaggtgtgggtgagcgcaaaggtgtccctgaccatgactttgaggtactggtatttga |
| agtcagtgtcgtcgcatccgccctgctcccagagcaaaaagtccgtgcgcttttggaacgcggatttggcagggcgaaggtgacat |
| cgttgaagagtatctttcccgcgcgaggcataaagttgcgtgtgatgcggaagggtcccggcacctcggaacggttgttaattacct |
| gggcggcgagcacgatctcgtcaaagccgttgatgttgtggcccacaatgtaaagttccaagaagcgcgggatgccttgatggaag |
| gcaattttttaagttcctcgtaggtgagctcttcaggggagctgagcccgtgctctgaaagggcccagtctgcaagatgagggttgg |
| aagcgacgaatgagctccacaggtcacgggccattagcatttgcaggtggtcgcgaaaggtcctaaactggcgacctatggccattt |
| tttctggggtgatgcagtagaaggtaagcgggtcttgttcccagcggtcccatccaaggttcgcggctaggtctcgcgcggcagtca |
| ctagaggctcatctccgccgaacttcatgaccagcatgaagggcacgagctgcttcccaaaggcccccatccaagtataggtctcta |
| catcgtaggtgacaaagagacgctcggtgcgaggatgcgagccgatcgggaagaactggatctcccgccaccaattggaggagtggc |
| tattgatgtggtgaaagtagaagtccctgcgacgggccgaacactcgtgctggcttttgtaaaaacgtgcgcagtactggcagcggt |
| gcacgggctgtacatcctgcacgaggttgacctgacgaccgcgcacaaggaagcagagtgggaatttgagcccctcgcctggcgggt |
| ttggctggtggtcttctacttcggctgcttgtccttgaccgtctggctgctcgaggggagttacggtggatcggaccaccacgccgc |
| gcgagcccaaagtccagatgtccgcgcgcggcggtcggagcttgatgacaacatcgcgcagatgggagctgtccatggtctggagct |
| cccgcggcgtcaggtcaggcgggagctcctgcaggtttacctcgcatagacgggtcagggcgcgggctagatccaggtgatacctaa |
| tttccaggggctggttggtggcggcgtcgatggcttgcaagaggccgcatccccgcggcgcgactacggtaccgcgcggcgggcggt |
| gggccgcgggggtgtccttggatgatgcatctaaaagcggtgacgcgggcgagcccccggaggtagggggggctccggacccgccgg |
| gagaggggcagggcacgtcggcgccgcgcgcgggcaggagctggtgctgcgcgcgtaggttgctggcgaacgcgacgacgcggcg |
| gttgatctcctgaatctggcgcctctgcgtgaagacgacgggcccggtgagcttgagcctgaaagagagttcgacagaatcaatttc |
| ggtgtcgttgacggcggcctggcgcaaaatctcctgcacgtctcctgagttgtcttgataggcgatctcggccatgaactgctcgat |
| ctcttcctcctggagatctccgcgtccggctcgctccacggtggcggcgaggtcgttggaaatgcgggccatgagctgcgagaaggc |
| gttgaggcctccctcgttccagacgcggctgtagaccacgccccttcggcatcgcgggcgcgcatgaccacctgcgcgagattgag |
| ctccacgtgccgggcgaagacggcgtagtttcgcaggcgctgaaagaggtagttgagggtggtggcggtgtgttctgccacgaagaa |
| gtacataacccagcgtcgcaacgtggattcgttgatatccccaaggcctcaaggcgctccatggcctcgtagaagtccacggcgaa |
| gttgaaaaactgggagttgcgcgccgacacggttaactcctcctccagaagacggatgagctcggcgacagtgtcgcgcacctcgcg |
| ctcaaaggctacaggggcctcttcttcttcttcaatctcctcttccataagggcctcccttcttcttcttctggcggcggtgggg |
| agggggacacggcggcgacgacggcgcaccgggaggcggtcgacaaagcgctcgatcatctccccgcggcgacggcgcatggtctc |
| ggtgacggcgcggccgttctcgcgggggcgcagttggaagacgccgcccgtcatgtcccggttatgggttggcgggggctgccatg |
| cggcagggatacggcgctaacgatgcatctcaacaattgttgtgtaggtactccgccgccgagggacctgagcgagtccgcatcgac |
| cggatcggaaaacctctcgagaaaggcgtctaaccagtcacagtcgcaaggtaggctgagcaccgtggcgggcggcagcgggcggcg |
| gtcggggttgtttctggcggaggtgctgctgatgatgtaattaaagtaggcggtcttgagacggcggatggtcgacagaagcaccat |
| gtccttgggtccggcctgctgaatgcgcaggcggtcggccatgccccaggcttcgttttgacatcggcgcaggtctttgtagtagtc |
| ttgcatgagcctttctaccggcacttcttcttctccttcctcttgtcctgcatctcttgcatctatcgctgcggcggcggcggagtt |
| tggccgtaggtggcgccctcttcctcccatgcgtgtgaccccgaagcccctcatcggctgaagcagggctaggtcggcgacaacgcg |
| ctcggctaatatggcctgctgcacctgcgtgagggtagactggaagtcatccatgtccacaaagcggtggtatgcgcccgtgttgat |
| ggtgtaagtgcagttggccataacggaccagttaacggtctggtgacccggctgcgagagctcggtgtacctgagacgcgagtaagc |
| cctcgagtcaaatacgtagtcgttgcaagtccgcaccaggtactggtatcccaccaaaaagtgcggcggcggctggcggtagagggg |
| ccagcgtagggtggccggggctccgggggcgagatcttccaacataaggcgatgatatccgtagatgtacctggacatccaggtgat |
| gccggcggcggtggtggaggcgcgcggaaagtcgcggacgcggttccagatgttgcgcagcggcaaaaagtgctccatggtcgggac |

| Sequences |
| --- |
| gctctggccggtcaggcgcgcgcaatcgttgacgctctagaccgtgcaaaaggagagcctgtaagcgggcactcttccgtggtctgg |
| tggataaattcgcaagggtatcatggcggacgaccggggttcgagccccgtatccggccgtccgccgtgatccatgcggttaccgcc |
| cgcgtgtcgaacccaggtgtgcgacgtcagacaacggggagtgctccttttggcttccttccaggcgcggcggctgctgcgctagc |
| ttttttggccactggccgcgcgcagcgtaagcggttaggctggaaagcgaaagcattaagtggctcgctccctgtagccggagggtt |
| attttccaagggttgagtcgcgggaccccggttcgagtctcggaccggccggactgcggcgaacggggtttgcctccccgtcatg |
| caagacccgcttgcaaattcctccggaaacagggacgagccccttttttgcttttcccagatgcatccggtgctgcggcagatgcg |
| cccccctcctcagcagcggcaagagcaagagcagcggcagacatgcagggcaccctcccctcctcctaccgcgtcaggaggggcgac |
| atccgcggttgacgcggcagcagatggtgattacgaaccccgcggcgccgggcccggcactacctggacttggaggagggcgaggg |
| cctggcgcggctaggagcgccctctcctgagcggtacccaagggtgcagctgaagcgtgatacgcgtgaggcgtacgtgccgcggca |
| gaacctgtttcgcgaccgcgagggagaggagcccgaggagatgcgggatcgaaagttccacgcagggcgcgagctgcggcatggcct |
| gaatcgcgagcggttgctgcgcgaggaggactttgagcccgacgcgcgaaccgggattagtcccgcgcgcgcacacgtggcggccgc |
| cgacctggtaaccgcatacgagcagacggtgaaccaggagattaactttcaaaaaagctttaacaaccacgtgcgtacgcttgtggc |
| gcgcgaggaggtggctataggactgatgcatctgtgggactttgtaagcgcgctggagcaaaacccaaatagcaagccgctcatggc |
| gcagctgttccttatagtgcagcacagcagggacaacgaggcattcagggatgcgctgctaaacatagtagagcccgagggccgctg |
| gctgctcgatttgataaacatcctgcagagcatagtggtgcaggagcgcagcttgagcctggctgacaaggtggccgccatcaacta |
| ttccatgcttagcctgggcaagttttacgcccgcaagatataccatacccttacgttcccatagacaaggaggtaaagatcgaggg |
| gttctacatgcgcatggcgctgaaggtgcttaccttgagcgacgacctgggcgtttatcgcaacgagcgcatccacaaggccgtgag |
| cgtgagccggcggcgcgagctcagcgaccgcgagctgatgcacagcctgcaaagggccctggctggcacgggcagcggcgatagaga |
| ggccgagtcctactttgacgcgggcgctgacctgcgctgggccccaagccgacgcgccctggaggcagctggggccggacctgggct |
| ggcggtggcacccgcgcgcgctggcaacgtcggcggcgtggaggaatatgacgaggacgatgagtacgagccagaggacggcgagta |
| ctaagcggtgatgtttctgatcagatgatgcaagacgcaacggacccggcggtgcgggcggcgctgcagagccagccgtccggcctt |
| aactccacggacgactggcgccaggtcatggaccgcatcatgtcgctgactgcgcgcaatcctgacgcgttccggcagcagccgcag |
| gccaaccggctctccgcaattctggaagcggtggtcccggcgcgcgcaaaccccacgcacgagaaggtgctggcgatcgtaaacgcg |
| ctggccgaaaacagggccatccggcccgacgaggccggcctggtctacgacgcgctgcttcagcgcgtggctcgttacaacagcggc |
| aacgtgcagaccaacctggaccggctggtggggatgtgcgcgaggccgtggcgcagcgtgagcgcgcgcagcagggcaacctg |
| ggctccatggttgcactaaacgccttcctgagtacacagcccgccaacgtgccgcggggacaggaggactacaccaactttgtgagc |
| gcactgcggctaatggtgactgagacaccgcaaagtgaggtgtaccagtctgggccagactattttttccagaccagtagacaaggc |
| ctgcagaccgtaaacctgagccaggctttcaaaaacttgcagggctgtgggggtgcgggctcccacaggcgaccgcgcgaccgtg |
| tctagcttgctgacgcccaactcgcgcctgttgctgctgctaatagcgcccttcacggacagtggcagcgtgtcccgggacacatac |
| ctaggtcacttgctgacactgtaccgcgaggccataggtcaggcgcatgtggacgagcatacttccaggagattacaagtgtcagc |
| cgcgcgctggggcaggaggacacgggcagcctggaggcaaccctaaactacctgctgaccaaccggcggcagaagatcccctcgttg |
| cacagtttaaacagcgaggaggagcgcattttgcgctacgtgcagcagagcgtgagccttaacctgatgcgcgacggggtaacgccc |
| agcgtggcgctggacatgaccgcgcgcaacatggaaccgggcatgtatgcctcaaaccggccgtttatcaaccgcctaatggactac |
| ttgcatcgcgcggccgccgtgaaccccgagtattcaccaatgccatcttgaacccgcactggctaccgcccctggtttctacacc |
| gggggattcgaggtgcccgagggtaacgatggattcctctgggacgacatagacgacagcgtgttttccccgcaaccgcagaccctg |
| ctagagttgcaacagcgcgagcaggcagaggcggcgctgcgaaaggaaagcttccgcaggccaagcagcttgtccgatctaggcgct |
| gcggccccgcgtcagatgctagtagcccatttccaagcttgatagggtctcttaccagcactcgcaccacccgcccgcctgctg |
| ggcgaggaggagtacctaaacaactcgctgctgcagccgcagcgcgaaaaaaacctgcctccggcatttcccaacaacgggatagag |
| agcctagtggacaagatgagtagatggaagacgtacgcgcaggagcacagggacgtgccaggcccgcgcccgcccacccgtcgtcaa |

| Sequences |
|---|
| aggcacgaccgtcagcggggtctggtgtgggaggacgatgactcggcagacgacagcagcgtcctggatttgggagggagtggcaac |
| ccgtttgcgcaccttcgccccaggctggggagaatgttttaaaaaaaaaaaagcatgatgcaaaataaaaaactcaccaaggccatg |
| gcaccgagcgttggttttcttgtattcccccttagtatgcggcgcgcggcgatgtatgaggaaggtcctcctccctcctacgagagtg |
| tggtgagcgcggcgccagtggcggcggcgctgggttctcccttcgatgctccctggacccgccgtttgtgcctccgcggtacctgc |
| ggcctaccggggggagaaacagcatccgttactctgagttggcacccctattcgacaccaccgtgtgtacctggtggacaacaagt |
| caacggatgtggcatccctgaactaccagaacgaccacagcaactttctgaccacggtcattcaaaacaatgactacagcccgggg |
| aggcaagcacacagaccatcaatcttgacgaccgtcgcactggggcggcgacctgaaaaccatcctgcataccaacatgccaaatg |
| tgaacgagttcatgtttaccaataagtttaaggcgcgggtgatggtgtcgcgcttgcctactaaggacaatcaggtggagctgaaat |
| acgagtgggtggagttcacgctgcccgagggcaactactccgagaccatgaccatagaccttatgaacaacgcgatcgtggagcact |
| acttgaaagtgggcagacagaacggggttctggaaagcgacatcggggtaaagtttgacacccgcaacttcagactgggggtttgacc |
| ccgtcactggtcttgtcatgcctggggtatatacaaacgaagccttccatccagacatcattttgctgccaggatgcgggggtggact |
| tcacccacagccgcctgagcaacttgttgggcatccgcaagcggcaaccccttccaggagggctttaggatcacctacgatgatctgg |
| agggtggtaacattcccgcactgttggatgtggacgcctaccaggcgagcttgaaagatgacaccgaacagggcgggggtggcgcag |
| gcggcagcaacagcagtggcagcggcgcggaagagaactccaacgcggcagccgcggcaatgcagccggtggaggacatgaacgatc |
| atgccattcgcggcgacacctttgccacacgggctgaggagaagcgcgctgaggccgaagcagcggccgaagctgccgcccccgctg |
| cgcaacccgaggtcgagaagcctcagaagaaaccggtgatcaaaccctgacagaggacagcaagaaacgcagttacaacctaataa |
| gcaatgacagcaccttcacccagtaccgcagctggtaccttgcatacaactacggcgaccctcagaccggaatccgctcatggaccc |
| tgctttgcactcctgacgtaacctgcggctcggagcaggtctactggtcgttgccagacatgatgcaagacccgtgaccttccgct |
| ccacgcgccagatcagcaactttccggtggtgggcgccgagctgttgcccgtgcactccaagagcttctacaacgaccaggccgtct |
| actcccaactcatccgccagtttacctctctgacccacgtgttcaatcgctttcccgagaaccagatttggcgcgcgccgccagccc |
| ccaccatcaccaccgtcagtgaaaacgttcctgctctcacagatcacgggacgctaccgctgcgcaacagcatcggaggagtccagc |
| gagtgaccattactgacgccagacgccgcacctgcccctacgtttacaaggccctgggcatagtctcgccgcgcgtcctatcgagcc |
| gcactttttgagcaagcatgtccatccttatatcgcccagcaataacacaggctggggcctgcgcttcccaagcaagatgtttggcg |
| gggccaagaagcgctccgaccaacacccagtgcgcgtgcgcgggcactaccgcgcgccctggggcgcgcacaaacgcggccgcactg |
| ggcgcaccaccgtcgatgacgccatcgacgcggtggtggaggaggcgcgcaactacacgcccacgccgccaccagtgtccacagtgg |
| acgcggccattcagaccgtggtgcgcggagcccggcgctatgctaaaatgaagagacggcggaggcgcgtagcacgtcgccaccgcc |
| gccgacccggcactgccgcccaacgcgcggcggcggccctgcttaaccgcgcacgtcgcaccggccgacgggcggccatgcgggccg |
| ctcgaaggctggccgcgggtattgtcactgtgcccccaggtccaggcgacgagcggccgccgcagcagccgcggccattagtgcta |
| tgactcagggtcgcaggggcaacgtgtattgggtgcgcgactcggttagcggcctgcgcgtgcccgtgcgcacccgcccccgcgca |
| actagattgcaagaaaaaactacttagactcgtactgttgtatgtatccagcggcggcggcgcgcaacgaagctatgtccaagcgca |
| aaatcaaagaagagatgctccaggtcatcgcgccggagatctatggccccccgaagaaggaagagcaggattacaagccccgaaagc |
| taaagcgggtcaaaaagaaaaagaaagatgatgatgatgaacttgacgacgaggtggaactgctgcacgctaccgcgcccaggcgac |
| gggtacagtggaaaggtcgacgcgtaaaacgtgttttgcgacccggcaccaccgtagtctttacgcccggtgagcgctccacccgca |
| cctacaagcgcgtgtatgatgaggtgtacggcgacgaggacctgcttgagcaggccaacgagcgcctcggggagtttgcctacggaa |
| agcggcataaggacatgctggcgttgccgctggacgagggcaacccaacacctagcctaaagcccgtaacactgcagcaggtgctgc |
| ccgcgcttgcaccgtccgaagaaaagcgcggcctaaagcgcgagtctggtgacttggcacccaccgtgcagctgatggtacccaagc |
| gccagcgactggaagatgtcttggaaaaaatgaccgtggaacctgggctggagcccgaggtccgcgtgccggccaatcaagcaggtgg |
| cgccgggactgggcgtgcagaccgtggacgttcagataccactaccagtagcaccagtattgccaccgccacagagggcatggaga |

| Sequences |
|---|
| cacaaacgtccccggttgcctcagcggtggcggatgccgcggtgcaggcggtcgctgcggccgcgtccaagacctctacggaggtgc |
| aaacggacccgtggatgtttcgcgtttcagcccccggcgcccgcgcggttcgaggaagtacggcgccgccagcgcgctactgcccg |
| aatatgccctacatccttccattgcgcctaccccggctatcgtggctacacctaccgcccagaagacgagcaactacccgacgcc |
| gaaccaccactggaacccgccgccgccgtcgccgtcgccagcccgtgctggccccgatttccgtgcgcagggtggctcgcgaaggag |
| gcaggacccggtgctgccaacagcgcgctaccaccccagcatcgtttaaaagccggtctttgtggttcttgcagatatggccctca |
| cctgccgcctccgtttccggtgccgggattccgaggaagaatgcaccgtaggaggggcatggccggccacggcctgacgggcggca |
| tgcgtcgtgcgcaccaccggcggcggcgcgcgtcgcaccgtcgcatgcgcggcggtatcctgcccctccttattccactgatcgccg |
| cggcgattggcgccgtgcccggaattgcatccgtggccttgcaggcgcagagacactgattaaaaacaagttgcatgtggaaaaatc |
| aaaataaaaagtctggactctcacgctcgcttggtcctgtaactattttgtagaatggaagacatcaactttgcgtctctggccccg |
| cgacacggctcgcgcccgttcatgggaaactggcaagatatcggcaccagcaatatgagcggtggcgccttcagctggggctcgctg |
| tggagcggcattaaaaatttcggttccaccgttaagaactatggcagcaaggcctggaacagcagcacaggccagatgctgagggat |
| aagttgaaagagcaaaatttccaacaaaggtggtagatggcctggcctctggcattagcggggtggtggacctggccaaccaggca |
| gtgcaaaataagattaacagtaagcttgatccccgccctcccgtagaggagcctccaccggccgtggagacagtgtctccagagggg |
| cgtggcgaaaagcgtccgcgccccgacagggaagaaactctggtgacgcaaatagacgagcctccctcgtacgaggaggcactaaag |
| caaggcctgccaccacccgtcccatcgcgcccatggctaccggagtgctgggccagcacacacccgtaacgctggacctgcctccc |
| cccgccgacacccagcagaaacctgtgctgccaggcccgaccgccgttgttgtaaccgtcctagccgcgcgtccctgcgccgcgcc |
| gccagcggtccgcgatcgttgcggcccgtagccagtggcaactggcaaagcacactgaacagcatcgtgggtctggggtgcaatcc |
| ctgaagcgccgacgatgcttctgaatagctaacgtgtcgtatgtgtgtcatgtatgcgtccatgtcgccgccagaggagctgctgag |
| ccgccgcgcgcccgctttccaagatggctacccttcgatgatgccgcagtggtcttacatgcacatctcgggccaggacgcctcgg |
| agtacctgagccccgggctggtgcagtttgcccgcgccaccgagacgtacttcagcctgaataacaagtttagaaacccacgtgg |
| cgcctacgcacgacgtgaccacagaccggtcccagcgtttgacgctgcggttcatccctgtggaccgtgaggatactgcgtactcgt |
| acaaggcgcggttcaccctagctgtgggtgataaccgtgtgctggacatggcttccacgtactttgacatccgcggcgtgctggaca |
| ggggccctacttttaagccctactctggcactgcctacaacgccctggctcccaagggtgccccaaatccttgcgaatgggatgaag |
| ctgctactgctcttgaaataaacctagaagaagaggacgatgacaacgaagacgaagtagacgagcaagctgagcagcaaaaaactc |
| acgtatttgggcaggcgccttattctggtataaatattacaaaggagggtattcaaataggtgtcgaaggtcaaacacctaaatatg |
| ccgataaaacatttcaacctgaacctcaaataggagaatctcagtggtacgaaactgaaattaatcatgcagctgggagagtcctta |
| aaaagactaccccaatgaaaccatgttacggttcatatgcaaaacccacaaatgaaaatggagggcaaggcattcttgtaaagcaac |
| aaaatgaaagctagaaagtcaagtggaaatgcaattttttctcaactggaagcggttctcgctacctggagcctggcccagtgactg |
| ccgctggttccggaagcagatacatggacggaacaatgtcccaggttgccggttctggctcccctaaagtggtattgtacagtgaag |
| atgtagatatagaaaccccagacactcatatttcttacatgccactattaaggaaggtaactcacgagaactaatgggccaacaat |
| ctatgcccaacaggcctaattacattgcttttagggacaattttattggtctaatgtattacaacagcacgggtaatatgggtgttc |
| tggcgggccaagcatcgcagttgaatgctgttgtagatttgcaagacagaaacacagagctttcataccagcttttgcttgattcca |
| ttggtgatagaaccaggtacttttctatgtggaatcaggctgttgacagctatgatccagatgttagaattattgaaaatcatggaa |
| ctgaagatgaacttccaaattactgctttccactgggaggtgtgattaatacagagactcttaccaaggtaaaacctaaaacaggtc |
| aggaaaatggatgggaaaagatgctacagaattttcagataaaaatgaataagagttggaaataattttgccatggaaatcaatc |
| taaatgccaacctgtggagaaatttcctgtactccaacatagcgctgtatttgcccgacaagctaaagtacagtccttccaacgtaa |
| aaatttctgataacccaaacacctacgactacatgaacaagcgagtggtggctcccgggttagtggactgctacattaaccttggag |
| cacgctggtcccttgactatatggacaacgtcaacccatttaaccaccaccgcaatgctggcctgcgctaccgctcaatgttgctgg |
| gcaatggtcgctatgtgcccttccacatccaggtgcctcagaagttctttgccattaaaaacctccttctcctgccgggctcataca |

-continued

Sequences cctacgagtggaacttcaggaaggatgttaacatggttctgcagagctccctaggaaatgacctaagggttgacggagccagcatta agtttgatagcatttgcctttacgccaccttcttccccatggcccacaacaccgcctccacgcttgaggccatgcttagaaacgaca ccaacgaccagtcctttaacgactatctctccgccgccaacatgctctaccctatacccgccaacgctaccaacgtgcccatatcca tcccctcccgcaactgggcggctttccgcggctgggccttcacgcgccttaagactaaggaaacccatcactgggctcgggctacg acccttattacacctactctggctctatacccttacctagatggaaccttttacctcaaccacaccctttaagaaggtggccattacct ttgactcttctgtcagctggcctggcaatgaccgcctgcttaccccccaacgagtttgaaattaagcgctcagttgacggggagggtt acaacgttgcccagtgtaacatgaccaaagactggttcctggtacaaatgctagctaactacaacattggctaccagggcttctata tcccagagagctacaaggaccgcatgtactccttcctttagaaacttccagcccatgagccgtcaggtggtggatgatactaaataca aggactaccaacaggtgggcatcctacaccaacacaacaactctggatttgttggctaccttgcccccaccatgcgcgaaggacagg cctaccctgctaacttcccctatccgcttataggcaagaccgcagttgacagcattacccagaaaaagtttctttgcgatcgcaccc tttggcgcatcccattctccagtaactttatgtccatgggcgcactcacagacctgggcaaaacctcctctacgccaactccgccc acgcgctagacatgacttttgaggtggatcccatggacgagcccacccttctttatgttttgtttgaagtctttgacgtggtccgtg tgcaccagccgcaccgcggcgtcatcgaaaccgtgtacctgcgcacgcccttctcggccggcaacgccacaacataaagaagcaagc aacatcaacaacagctgccgccatgggctccagtgagcaggaactgaaagccattgtcaaagatcttggttgtgggccatatttttt gggcacctatgacaagcgctttccaggctttgtttctccacacaagctcgcctgcgccatagtcaatacggccggtcgcgagactgg gggcgtacactggatggcctttgcctggaacccgcactcaaaaacatgctacctctttgagccdttggcttttctgaccagcgactc aagcaggtttaccagtttgagtacgagtcactcctgcgccgtagcgccattgcttcttcccccgaccgctgtataacgctggaaaag tccacccaaagcgtacaggggcccaactcggccgcctgtggactattctgctgcatgtttctccacgcctttgccaactggccccaa actcccatggatcacaaccccaccatgaaccttattaccggggtacccaactccatgctcaacagtccccaggtacagcccaccctg cgtcgcaaccaggaacagctctacagcttcctggagcgccactcgccctacttccgcagccacagtgcgcagattaggagcgccact tcttttgtcacttgaaaaacatgtaaaaataatgtactagagacactttcaataaaggcaaatgcttttatttgtacactctcggg tgattatttaccccccacccttgccgtctgcgccgtttaaaaatcaaaggggttctgccgcgcatcgctatgcgccactggcagggac acgttgcgatactggtgtttagtgctccacttaaactcaggcacaaccatccgcggcagctcggtgaagttttcactccacaggctg cgcaccatcaccaacgcgtttagcaggtcgggcgccgatatcttgaagtcgcagttgggccctccgccctgcgcgcgcgagttgcga tacacagggttgcagcactggaacactatcagcgccgggtggtgcacgctggccagcacgctcttgtcggagatcagatccgcgtcc aggtcctccgcgttgctcagggcgaacggagtcaactttggtagctgccttcccaaaagggcgcgtgcccaggctttgagttgcac tcgcaccgtagtggcatcaaaaggtgaccgtgcccggtctgggcgttaggatacagcgcctgcataaaagccttgatctgcttaaaa gccacctgagcctttgcgccttcagagaagaacatgccgcaagacttgccggaaaactgattggccggacaggccgcgtcgtgcacg cagcaccttgcgtcggtgttggagatctgcaccacatttcggccccaccggttcttcacgatcttggccttgctagactgctccttc agcgcgcgctgcccgttttcgctcgtcacatccatttcaatcacgtgctccttatttatcataatgcttccgtgtagacacttaagc tcgccttcgatctcagcgcagcggtgcagccacaacgcgcagcccgtgggctcgtgatgcttgtaggtcacctctgcaaacgactgc aggtacgcctgcaggaatcgcccatcatcgtcacaaaggtcttgttgctggtgaaggtcagctgcaacccgcggtgctcctcgttc agccaggtcttgcatacggccgccagagcttccacttggtcaggcagtagtttgaagttcgcctttagatcgttatccacgtggtac ttgtccatcagcgcgcgcgcagcctccatgcccttctcccacgcagacacgatcggcacactcagcgggttcatcaccgtaatttca ctttccgcttcgctgggctcttcctcttcctcttgcgtccgcataccacgcgccactgggtcgtcttcattcagccgccgcactgtg cgcttacctcctttgccatgcttgattagcaccggtgggttgctgaaacccaccatttgtagcgccacatcttctctttcttcctcg ctgtccacgattacctctggtgatggcgggcgctcggctgggagaagggcgcttcttttcttcttgggcgcaatggccaaatcc gccgccgaggtcgatggccgcgggctgggtgtgcgcggcaccagcgcgtcttgtgatgagtcttcctcgtcctcggactcgatacgc

| Sequences |
|---|
| cgcctcatccgcttttttgggggcgcccggggaggcggcggcgacggggacggggacgacacgtcctccatggttgggggacgtcgc |
| gccgcaccgcgtccgcgctcggggtggtttcgcgctgctcctcttcccgactggccatttccttctcctataggcagaaaagatc |
| atggagtcagtcgagaagaaggacagcctaaccgcccctctgagttcgccaccaccgcctccaccgatgccgccaacgcgcctacc |
| accttccccgtcgaggcaccccgcttgaggaggaggaagtgattatcgagcaggacccaggttttgtaagcgaagacgacgaggac |
| cgctcagtaccaacagaggataaaaagcaagaccaggacaacgcagaggcaaacgaggaacaagtcgggcggggggacgaaaggcat |
| ggcgactacctagatgtgggagacgacgtgctgttgaagcatctgcagcgccagtgcgccattatctgcgacgcgttgcaagagcg |
| agcgatgtgcccctcgccatagcggatgtcagccttgcctacgaacgccacctattctcaccgcgcgtaccccccaaacgccaagaa |
| aacggcacatgcgagcccaacccgcgcctcaacttctaccccgtatttgccgtgccagaggtgcttgccacctatcacatcttttc |
| caaaactgcaagatacccctatcctgccgtgccaaccgcagccgagcggacaagcagctggccttgcggcagggcgctgtcatacct |
| gatatcgcctcgctcaacgaagtgccaaaaatctttgagggtcttggacgcgacgagaagcgcgcggcaaacgctctgcaacaggaa |
| aacagcgaaaatgaaagtcactctggagtgttggtggaactcgagggtgacaacgcgcgcctagccgtactaaaacgcagcatcgag |
| gtcacccactttgcctaccggcacttaacctaccccccaaggtcatgagcacagtcatgagtgagctgatcgtgcgccgtgcgcag |
| cccctggagagggatgcaaatttgcaagaacaaacagaggagggcctacccgcagttggcgacgagcagctagcgcgctggcttcaa |
| acgcgcgagcctgccgacttggaggagcgacgcaaactaatgatggccgcagtgctcgttaccgtggagcttgagtgcatgcagcgg |
| ttctttgctgacccggagatgcagcgcaagctagaggaaacattgcactacacctttcgacagggctacgtacgccaggcctgcaag |
| atctccaacgtggagctctgcaacctggtctcctaccttggaattttgcacgaaaaccgccttgggcaaaacgtgcttcattccacg |
| ctcaagggcgaggcgccgcgcgactacgtccgcgactgcgtttacttatttctatgctacacctggcagacggccatgggcgtttgg |
| cagcagtgcttggaggagtgcaacctcaaggagctgcagaaactgctaaagcaaaacttgaaggacctatggacggccttcaacgag |
| cgctccgtggccgcgcacctggcggacatcattttccccgaacgcctgcttaaaaccctgcaacagggtctgccagacttcaccagt |
| caaagcatgttgcagaactttaggaactttatcctagagcgctcaggaatcttgcccgccacctgctgtgcacttcctagcgactt |
| gtgcccattaagtaccgcgaatgccctccgccgctttggggccactgctaccttctgcagctagccaactaccttgcctaccactct |
| gacataatggaagacgtgagcggtgacggtctactggagtgtcactgtcgctgcaacctatgcacccccgaccgctccctggtttgc |
| aattcgcagctgcttaacgaaagtcaaattatcggtacctttgagctgcagggtccctcgcctgacgaaaagtccgcggctccgggg |
| ttgaaactcactccggggctgtggacgtcggcttaccttcgcaaatttgtacctgaggactaccacgcccacgagattaggttctac |
| gaagaccaatcccgcccgccaaatgcggagcttaccgcctgcgtcattacccagggccacattcttggccaattgcaagccatcaac |
| aaagcccgccaagagtttctgctacgaaagggacgggggggtttacttggaccccagtccggcgaggagctcaacccaatcccccg |
| ccgccgcagccctatcagcagcagccgcgggcccttgcttcccaggatggcacccaaaaagaagctgcagctgccgccgccacccac |
| ggacgaggaggaatactgggacagtcaggcagaggaggttttggacgaggaggaggaggacatgatggaagactgggagagcctaga |
| cgaggaagcttccgaggtcgaagaggtgtcagacgaaacaccgtcaccctcggtcgcattcccctcgccggcgccccagaaatcggc |
| aaccggttccagcatggctacaacctccgctcctcaggcgccgccggcactgcccgttcgccgacccaaccgtagatgggacaccac |
| tggaaccagggccggtaagtccaagcagccgccgccgttagcccaagagcaacaacagcgccaaggctaccgctcatggcgcgggca |
| caagaacgccatagttgcttgcttgcaagactgtgggggcaacatctccttcgcccgccgctttcttctctaccatcacggcgtggc |
| cttcccccgtaacatcctgcattactaccgtcatctctacagcccatactgcaccggcggcagcggcagcggcagcaacagcagcgg |
| ccacacagaagcaaaggcgaccggatagcaagactctgacaaagcccaagaaatccacagcggcggcagcagcaggaggaggagcgc |
| tgcgtctggcgcccaacgaacccgtatcgacccgcgagcttagaaacaggattttttcccactctgtatgctatatttcaacagagca |
| ggggccaagaacaagagctgaaaataaaaaacaggtctctgcgatccctcacccgcagctgcctgtatcacaaaagcgaagatcagc |
| ttcggcgcacgctggaagacgcggaggctctcttcagtaaatactgcgcgctgactcttaaggactagtttcgcgccctttctcaaa |
| tttaagcgcgaaaactacgtcatctccagcggccacaccggcgccagcacctgtcgtcagcgccattatgagcaaggaaattccca |
| cgccctacatgtggagttaccagccacaaatgggacttgcggctggagctgcccaagactactcaacccgaataaactacatgagcg |

| Sequences |
|---|
| cgggaccccacatgatatcccgggtcaacggaatccgcgcccaccgaaaccgaattctcttggaacaggcggctattaccaccacac |
| ctcgtaataaccttaatccccgtagttggcccgctgccctggtgtaccaggaaagtcccgctcccaccactgtggtacttcccagag |
| acgcccaggccgaagttcagatgactaactcaggggcgcagcttgcgggcggctttcgtcacagggtgcggtcgcccgggcaggta |
| taactcacctgacaatcagagggcgaggtattcagctcaacgacgagtcggtgagctcctcgcttggtctccgtccggacgggacat |
| ttcagatcggcggcgccggccgtccttcattcacgcctcgtcaggcaatcctaactctgcagacctcgtcctctgagccgcgctctg |
| gaggcattggaactctgcaatttattgaggagtttgtgccatcggtctactttaaccccttctcgggacctcccggccactatccgg |
| atcaatttattcctaactttgacgcgtaaaggactcggcggacggctacgactgaatgttaagtgggagaggcagagcaactgcgcc |
| tgaaacacctggtccactgtcgccgccacaagtgctttgcccgcgactccggtgagttttgctactttgaattgcccgaggatcata |
| tcgagggcccggcgcacggcgtccggcttaccgcccagggagagcttgcccgtagcctgattcgggagtttacccagcgcccctgc |
| tagttgagcgggacaggggaccctgtgttctcactgtgatttgcaactgtcctaaccttggattacatcaagatctttgttgccatc |
| tctgtgctgagtataataaatacagaaattaaaatatactggggctcctatcgccatcctgtaaacgccaccgtcttcacccgccca |
| agcaaaccaaggcgaaccttacctggtacttttaacatctctccctctgtgatttacaacagtttcaacccagacggagtgagtcta |
| cgagagaacctctccgagctcagctactccatcagaaaaaacaccacccctccttacctgccgggaacgtacgagtgcgtcaccggcc |
| gctgcaccacacctaccgcctgaccgtaaaccagacttttccggacagacctcaataactctgtttaccagaacaggaggtgagct |
| tagaaacccttagggtattaggccaaaggcgcagctactgtggggtttatgaacaattcaagcaactctacgggctattctaattc |
| aggtttctctagaatcggggttggggttattctctgtcttgtgattctcttttattcttatactaacgcttctctgcctaaggctcgc |
| cgcctgctgtgtgcacatttgcatttattgtcagcttttttaaacgctggggtcgccacccaagatgattaggtacataatcctaggt |
| ttactcaccttgcgtcagcccacggtaccacccaaaaggtggattttaaggagccagcctgtaatgttacattcgcagctgaagct |
| aatgagtgcaccactcttataaaatgcaccacagaacatgaaaagctgcttattcgccacaaaaacaaaattggcaagtatgctgtt |
| tatgctatttggcagccaggtgacactacagagtataatgttacagttttccagggtaaaagtcataaaacttttatgtatacttttt |
| ccattttatgaaatgtgcgacattaccatgtacatgagcaaacagtataagttgtggcccccacaaaattgtgtggaaaacactggc |
| actttctgctgcactgctatgctaattacagtgctcgctttggtctgtaccctactctatattaaatacaaaagcagacgcagctttt |
| attgaggaaaagaaaatgccttaatttactaagttacaaagctaatgtcaccactaactgctttactcgctgcttgcaaaacaaatt |
| caaaaagttagcattataattagaataggatttaaaccccccggtcatttcctgctcaataccattccctgaacaattgactctat |
| gtgggatatgctccagcgctacaaccttgaagtcaggcttcctggatgtcagcatctgactttggccagcacctgtcccgcggattt |
| gttccagtccaactacagcgacccaccctaacagagatgaccaacacaaccaacgcggccgcgctaccggacttacatctaccaca |
| aatacaccccaagtttctgcctttgtcaataactgggataacttgggcatgtggtggttctccatagcgcttatgtttgtatgcctt |
| attattatgtggctcatctgctgcctaaaagcgcaaacgcgcccgaccacccatctatagtcccatcattgtgctacacccaaacaat |
| gatggaatccatagattggacggactgaaacacatgttcttttctcttacagtatgattaaatgagacatgattcctcgagttttta |
| tattactgaccttgttgcgctttttttgtgcgtgctccacattgctgcggtttctcacatcgaagtagactgcattccagccttca |
| cagtctatttgctttacggatttgtcaccctcacgctcatctgcagcctcatcactgtggtcatcgcctttatccagtgcattgact |
| gggtctgtgtgcgctttgcatatctcagacaccatcccagtacagggacaggactatagctgagcttcttagaattctttaattat |
| gaaatttactgtgacttttctgctgattatttgcaccctatctgcgttttgttcccgacctccaagcctcaaagacatatatcatg |
| cagattcactcgtatatggaatattccaagttgctacaatgaaaaaagcgatctttccgaagcctggtatatgcaatcatctctgt |
| tatggtgttctgcagtaccatcttagccctagctatatatccctaccttgacattggctggaaacgaatagatgccatgaaccaccc |
| aactttccccgcgcccgctatgcttccactgcaacaagttgttgccggcggctttgtcccagccaatcagcctcgccccacttctcc |
| caccccccactgaaatcagctactttaatctaacaggaggagatgactgacaccctagatctagaaatggacggaattattacagagc |
| agcgcctgctagaaagacgcagggcagcggccgagcaacagcgcatgaatcaagagctccaagacatggttaacttgcaccagtgca |

| Sequences |
|---|
| aaagggg tatcttttgtctggtaaagcaggccaaagtcacctacgacagtaataccaccggacaccgccttagctacaagttgccaa |
| ccaagcgtcagaaattggtggtcatggtgggagaaaagcccattaccataactcagcactcggtagaaaccgaaggctgcattcact |
| caccttgtcaaggacctgaggatctctgcacccttattaagaccctgtgcggtctcaaagatcttattccctttaactaataaaaaa |
| aataataaagcatcacttacttaaaatcagttagcaaatttctgtccagtttattcagcagcacctccttgccctcctcccagctc |
| tggtattgcagcttcctcctggctgcaaactttctccacaatctaaatggaatgtcagtttcctcctgttcctgtccatccgcaccc |
| actatcttcatgttgttgcagatgaagcgcgcaagaccgtctgaagataccttcaaccccgtgtatccatatgacacggaaaccggt |
| cctccaactgtgccttttcttactcctcccttttgtatcccccaatgggtttcaagagagtcccctgggggtactctctttgcgccta |
| tccgaacctctagttacctccaatggcatgcttgcgctcaaaatgggcaacggcctctctctggacgaggccggcaaccttacctcc |
| caaaatgtaaccactgtgagcccacctctccgaggagacaagtcaaacataaacctggaaatatctgcacccctcacagttacctca |
| gaagccctaactgtggctgccgccgcacctctaatggtcgcgggcaacacactcaccatgcaatcacaggccccgctaaccgtgcac |
| gactccaaacttagcattgccacccaaggaccccctcacagtgtcagaaggaaagctagccctgcaaacatcaggcccccctcaccacc |
| accgatagcagtaccccttactatcactgcctcacccccctctaactactgccactggtagcttgggcattgacttgaaagagcccatt |
| tatacacaaaatggaaaactaggactaaagtacggggctcctttgcatgtaacagacgacctaaacactttgaccgtagcaactggt |
| ccaggtgtgactattaataatacttccttgcaaactaaagttactggagccttgggttttgattcacaaggcaatatgcaacttaat |
| gtagcaggaggactaaggattgattctcaaaacagacgccttatacttgatgttagttatccgtttgatgctcaaaaccaactaaat |
| ctaagactaggacagggccctcttttttataaactcagcccacaacttggatattaactacaacaaaggcctttacttgtttacagct |
| tcaaacaattccaaaaagcttgaggttaacctaagcactgccaagggggttgatgtttgacgctacagccatagccattaatgcagga |
| gatgggcttgaatttggttcacctaatgcaccaaacacaaatcccctcaaaacaaaaattggccatggcctagaatttgattcaaac |
| aaggctatggttcctaaactaggaactggccttagttttgacagcacaggtgccattacagtaggaaacaaaaataatgataagcta |
| actttgtggaccacaccagctccatctcctaactgtagactaaatgcagagaaagatgctaaactcactttggtcttaacaaaatgt |
| ggcagtcaaatacttgctacagtttcagttttggctgttaaaggcagtttggctccaatatctggaacagttcaaagtgctcatctt |
| attataagatttgacgaaaatggagtgctactaaacaattccttcctggacccagaatattggaactttagaaatggagatcttact |
| gaaggcacagcctatacaaacgctgttggatttatgcctaacctatcagcttatccaaaatctcacggtaaaactgccaaaagtaac |
| attgtcagtcaagtttacttaaacggagacaaaactaaacctgtaacactaaccattacactaaacggtacacaggaaacaggagac |
| acaactccaagtgcatactctatgtcattttcatgggactggtctggccacaactacattaatgaaatatttgccacatcctcttac |
| acttttcatacattgcccaagaataaagaatcgtttgtgttatgtttcaacgtgtttattttcaattgcagaaaatttcaagtca |
| tttttcattcagtagtatagccccaccaccacatagcttatacagatcaccgtaccttaatcaaactcacagaaccctagtattcaa |
| cctgccacctccctcccaacacacagagtacacagtcctttctccccggctggccttaaaaagcatcatatcatgggtaacagacat |
| attcttaggtgttatattccacacggtttcctgtcgagccaaacgctcatcagtgatattaataaactcccgggcagctcacttaa |
| gttcatgtcgctgtccagctgctgagccacaggctgctgtccaacttgcggttgataacgggcggcgaaggagaagtccacgcctac |
| atgggggtagagtcataatcgtgcatcaggataggcggtggtgctgcagcagcgcgcgaataaactgctgccgccgccgctccgtc |
| ctgcaggaatacaacatggcagtggtctcctcagcgatgattcgcaccgcccgcagcataaggcgccttgtcctccgggcacagcag |
| cgcaccctgatctcacttaaatcagcacagtaactgcagcacagcaccacaatattgttcaaaatcccacagtgcaaggcgctgtat |
| ccaaagctcatggcggggaccacagaacccacgtggccatcataccacaagcgcaggtagattaagtggcgacccctcataaacacg |
| ctggacataaacattacctcttttggcatgttgtaattcaccacctcccggtaccatataaacctctgattaaacatggcgccatcc |
| accaccatcctaaaccagctggccaaaacctgcccgccggctatacactgcagggaaccgggactggaacaatgacagtggagagcc |
| caggactcgtaaccatggatcatcatgctcgtcatgatatcaatgttggcacaacacaggcacacgtgcatacacttcctcaggatt |
| acaagctcctcccgcgttagaaccatatcccagggaacaaccccattcctgaatcagcgtaaatcccacactgcagggaagacctcgc |
| acgtaactcacgttgtgcattgtcaaagtgttacattcgggcagcagcggatgatcctccagtatggtagcgcgggtttctgtctca | aaaggaggtagacgatccctactgtacggagtgcgccgagacaaccgagatcgtgttggtcgtagtgtcatgccaaatggaacgccg gacgtagtcatatttcctgaagcaaaaccaggtgcgggcgtgacaaacagatctgcgtctccggtctcgccgcttagatcgctctgt gtagtagttgtagtatatccactctctcaaagcatccaggcgcccctggcttcgggttctatgtaaactccttcatgcgccgctgc cctgataacatccaccaccgcagaataagccacacccagccaacctacacattcgttctgcgagtcacacacggaggagcgggaag agctggaagaaccatgtttttttttttattccaaaagattatccaaaacctcaaaatgaagatctattaagtgaacgcgctcccctc cggtggcgtggtcaaactctacagccaaagaacagataatggcatttgtaagatgttgcacaatggcttccaaaaggcaaacggccc tcacgtccaagtggacgtaaaggctaaacccttcagggtgaatctcctctataaacattccagccccttcaaccatgcccaaataat tctcatctcgccaccttctcaatatatctctaagcaaatcccgaatattaagtccggccattgtaaaaatctgctccagagcgccct ccaccttcagcctcaagcagcgaatcatgattgcaaaaattcaggttcctcacagacctgtataagattcaaaagcggaacattaac aaaaataccgcgatcccgtaggtccatcgcagggccagctgaacataatcgtgcaggtctgcacggaccagcgcggccacttccccg ccaggaaccatgacaaaagaacccacactgattatgacacgcatactcggagctatgctaaccagcgtagccccgatgtaagcttgt tgcatggcggcgatataaaatgcaaggtgctgctcaaaaaatcaggcaaagcctcgcgcaaaaaagaaagcacatcgtagtcatgc tcatgcagataaaggcaggtaagctccggaaccaccacagaaaaagacaccattttttctctcaaacatgtctgcgggtttctgcata aacacaaaataaaataacaaaaaaacatttaaacattagaagcctgtcttacaacaggaaaaacaacccttataagcataagacgga ctacggccatgccggcgtgaccgtaaaaaaactggtcaccgtgattaaaaagcaccaccgacagctcctcggtcatgtccggagtca taatgtaagactcggtaaacacatcaggttgattcacatcggtcagtgctaaaaagcgaccgaaatagcccgggggaatacataccc gcaggcgtagagacaacattacagcccccataggaggtataacaaaattaataggagagaaaaacacatcaaacacctgaaaaaccct cctgcctaggcaaaatagcaccctcccgctccagaacaacatacagcgcttccacagcggcagccataacagtcagccttaccagta aaaaagaaaacctattaaaaaaacaccactcgacacggcaccagctcaatcagtcacagtgtaaaaaagggccaagtgcagagcgag tatatataggactaaaaaatgacgtaacggttaaagtccacaaaaaacacccagaaaaccgcacgcgaacctacgcccagaaacgaa agccaaaaaacccacaacttcctcaaatcgtcacttccgttttcccacgttacgtcacttcccattttaagaaaactacaattccca acacatactagttactccgccctaaaacctacgtcacccgccccgttcccacgccccgcgccacgtcacaaactccaccccctcatt atcatattggcttcaatccaaaataaggtatattattgatgatgt SEQ ID NO: 3 - ICOVIR15K-TD
catcatcaataatataccttatttggattgaagccaatatgataatgaggggtggagtttgtgacgtggcgcggggcgtgggaac ggggcgggtgacgtagtagtgtggcggaagtgtgatgttgcaagtgtggcggaacacatgtaagcgacggatgtggcaaaagtgacg ttttggtgtgcgccggtgtacacaggaagtgacaattttcgcgcggttttaggcggatgttgtagtaaatttgggcgtaaccgagt aagatttggccattttcgcgggaaaactgaataagaggaagtgaaatctgaataattttgtgttactcatagcgcgtaatatttgtc tagggccgcggggactttgaccgtttacgtggagactcgcccaggtgttttttctcaggtgttttccgcgtacgtcggcggctcgtgg ctctttcgcggcaaaaggatttggcgcgtaaaagtggttcgagtacgtcggcggctcgtggctcttttcgcggcaaaaaggatttgg cgcgtaaaagtggttcgaagtacgtcgaccacaaaccccgcccagcgtcttgtcattggcgtcgacgctgtacggggtcaaagttgg cgttttattattatagtcagctgacgtgtagtgtatttatacccggtgagttcctcaagaggccactcttgagtgccagcgagtaga gttttctcctccgagccgctccgacaccgggactgaaaatgagacatattatctgccacggaggtgttattaccgaagaaatggccg ccagtcttttggaccagctgatcgaagaggtactggctgataatcttccacctcctagccattttgaaccacctaccatcacgaact gtatgatttagacgtgacggccccgaagatcccaacgaggaggcggtttcgcagattttttcccgactctgtaatgttggcggtgca ggaagggattgacttactcacttttccgccggcgcccggttctccggagccgcctcacctttcccggcagcccgagcagccggagca gagagccttgggtccggtttctatgccaaaccttgtaccggaggtgatcgatccacccagtgacgacgaggatgaagagggtgagga gtttgtgttagattatgtggagcacccccgggcacggttgcaggtcttgtcattatcaccggaggaatacgggggacccagatattat gtgttcgctttgctatatgaggacctgtggcatgtttgtctacagtaagtgaaaattatgggcagtgggtgatagagtggtgggttt

```
ggtgtggtaatttttttttttaattttttacagttttgtggtttaaagaattttgtattgtgatttttttaaaaggtcctgtgtctgaa
cctgagcctgagcccgagccagaaccggagcctgcaagacctacccgccgtcctaaaatggcgcctgctatcctgagacgcccgaca
tcacctgtgtccagagaatgcaatagtagtacggatagctgtgactccggtccttctaacacacctcctgagatacaccggtggtc
ccgctgtgccccattaaaccagttgccgtgagagttggtgggcgtcgccaggctgtggaatgtatcgaggacttgcttaacgagcct
gggcaacctttggacttgagctgtaaacgccccaggccataaggtgtaaacctgtgattgcgtgtgtggttaacgcctttgtttgct
gaatgagttgatgtaagtttaataaagggtgagataatgtttaacttgcatggcgtgttaaatggggcgggggcttaaagggtatata
atgcgccgtgggctaatcttggttacatctgacctcatggaggcttgggagtgtttggaagattttttctgctgtgcgtaacttgctg
gaacagagctctaacagtacctcttggttttggagggtttctgtggggctcatcccaggcaaagttagtctgcagaattaaggaggat
tacaagtgggaatttgaagagcttttgaaatcctgtggtgagctgtttgattctttgaatctgggtcaccaggcgcttttccaagag
aaggtcatcaagactttggattttttccacaccggggcgcgctgcggctgctgttgcttttttgagttttataaaggataaatggagc
gaagaaacccatctgagcgggggtacctgctggattttctggccatgcatctgtgggagagcggttgtgagacacaagaatcgcctg
ctactgttgtcttccgtccgcccggcgataataccgacggaggagcagcagcagcagcaggaggaagccaggcggcggcggcaggag
cagagcccatggaacccgagagccggcctggaccctcgggaatgaatgttgtacaggtggctgaactgtatccagaactgagacgca
ttttgacaattacagaggatgggcaggggctaaaggggggtaaagagggagcgggggggcttgtgaggctacagaggaggctaggaatc
tagcttttagcttaatgaccagacaccgtcctgagtgtattacttttcaacagatcaaggataattgcgctaatgagcttgatctgc
tggcgcagaagtattccatagagcagctgaccacttactggctgcagccaggggatgattttgaggaggctattagggtatatgcaa
aggtggcacttaggccagattgcaagtacaagatcagcaaacttgtaaatatcaggaattgttgctacatttctgggaacggggccg
aggtggagatagatacggaggatagggtggcctttagatgtagcatgataaatatgtggccgggggtgcttggcatggacggggtgg
ttattatgaatgtaaggtttactggccccaattttagcggtacggttttcctggccaataccaaccttatcctacacggtgtaagct
tctatgggtttaacaatacctgtgtggaagcctggaccgatgtaagggttcggggctgtgccttttactgctgctggaagggggtgg
tgtgtcgccccaaaagcagggcttcaattaagaaatgcctctcttgaaaggtgtaccttgggtatcctgtctgagggtaactccaggg
tgcgccacaatgtggcctccgactgtggttgcttcatgctagtgaaaagcgtggctgtgattaagcataacatggtatgtggcaact
gcgaggacagggcctctcagatgctgacctgctcggacggcaactgtcacctgctgaagaccattcacgtagccagccactctcgca
aggcctggccagtgtttgagcataacatactgacccgctgttccttgcatttgggtaacaggaggggggtgttcctaccttaccaat
gcaatttgagtcacactaagatattgcttgagcccgagagcatgtccaaggtgaacctgaacggggtgtttgacatgaccatgaaga
tctggaaggtgctgaggtacgatgagacccgcaccaggtgcagaccctgcgagtgtggcggtaaacatattaggaaccagcctgtga
tgctggatgtgaccgaggagctgaggcccgatcacttggtgctggcctgcacccgcgctgagtttggctctagcgatgaagatacag
attgaggtactgaaatgtgtgggcgtggcttaaggtggggaagaatatataaggtgggggtcttatgtagttttgtatctgttttg
cagcagccgccgccgccatgagcaccaactcgtttgatggaagcattgtgagctcatatttgacaacgcgcatgcccccatgggccg
gggtgcgtcagaatgtgatgggctccagcattgatggtcgccccgtcctgcccgcaaactctactaccttgacctacgagaccgtgt
ctggaacgccgttggagactgcagcctccgccgccgcttcagccgctgcagccaccgcccgcgggattgtgactgactttgctttcc
tgagcccgcttgcaagcagtgcagcttcccgttcatccgcccgcgatgacaagttgacggctcttttggcacaattggattcttga
cccgggaacttaatgtcgtttctcagcagctgttggatctgcgccagcaggtttctgccctgaaggcttcctcccctcccaatgcgg
tttaaaacataaataaaaaaaccagactctgtttggatttggatcaagcaagtgtcttgctgtctttatttaggggttttgcgcgcgc
ggtaggcccgggaccagcggtctcggtcgttgagggtcctgtgtattttttccaggacgtggtaaaggtgactctggatgttcgat
acatgggcataagcccgtctctggggtggaggtagcaccactgcagagcttcatgctgcggggtggtgttgtagatgatccagtcgt
agcaggagcgctgggcgtggtgcctaaaaatgtctttcagtagcaagctgattgccaggggcaggcccttggtgtaagtgtttacaa
agcggttaagctgggatgggtgcatacgtggggatatgagatgcatcttggactgtattttaggttggctatgttcccagccatat
```

| Sequences |
| --- |
| ccctccggggattcatgttgtgcagaaccaccagcacagtgtatccggtgcacttgggaaatttgtcatgtagcttagaaggaaatg |
| cgtggaagaacttggagacgcccttgtgacctccaagattttccatgcattcgtccataatgatggcaatgggcccacgggcggcgg |
| cctgggcgaagatatttctgggatcactaacgtcatagttgtgttccaggatgagatcgtcataggccatttttacaaagcgcgggc |
| ggagggtgccagactgcggtataatggttccatccggcccaggggcgtagttaccctcacagatttgcatttcccacgctttgagtt |
| cagatgggggatcatgtctacctgcggggcgatgaagaaaacggtttccggggtaggggagatcagctgggaagaaagcaggttcc |
| tgagcagctgcgacttaccgcagccggtgggcccgtaaatcacacctattaccgggtgcaactggtagttaagagagctgcagctgc |
| cgtcatccctgagcaggggggccacttcgttaagcatgtccctgactcgcatgttttccctgaccaaatccgccagaaggcgctcgc |
| cgcccagcgatagcagttcttgcaaggaagcaaagttttcaacggtttgagaccgtccgccgtaggcatgcttttgagcgtttgac |
| caagcagttccaggcggtcccacagctcggtcacctgctctacggcatctcgatccagcatatctcctcgtttcgcgggttgggcg |
| gctttcgctgtacggcagtagtcggtgctcgtccagacgggccagggtcatgtcttccacgggcgcagggtcctcgtcagcgtagt |
| ctgggtcacggtgaaggggtgcgctccgggctgcgcgctggccagggtgcgcttgaggctggtcctgctggtgctgaagcgctgccg |
| gtcttcgccctgcgcgtcggccaggtagcatttgaccatggtgtcatagtccagcccctccgcggcgtggcccttggcgcgcagctt |
| gcccttggaggaggcgccgcacgaggggcagtgcagacttttgagggcgtagagcttgggcgcgagaaataccgattccggggagta |
| ggcatccgcgccgcaggccccgcagacggtctcgcattccacgagccaggtgagctctggccgttcggggtcaaaaaccaggtttcc |
| cccatgcttttgatgcgtttcttacctctggtttccatgagccggtgtccacgctcggtgacgaaaaggctgtccgtgtccccgta |
| tacagacttgagaggcctgtcctcgagcggtgttccgcggtcctcctcgtatagaaactcggaccactctgagacaaaggctcgcgt |
| ccaggccagcacgaaggaggctaagtgggaggggtagcggtcgttgtccactaggggtccactcgctccagggtgtgaagacacat |
| gtcgccctcttcggcatcaaggaaggtgattggtttgtaggtgtaggccacgtgaccgggtgttcctgaaggggggctataaaaggg |
| ggtgggggcgcgttcgtcctcactctcttccgcatcgctgtctgcgagggccagctgttggggtgagtactccctctgaaaagcggg |
| catgacttctgcgctaagattgtcagtttccaaaaacgaggaggatttgatattcacctggcccgcggtgatgcctttgagggtggc |
| cgcatccatctggtcagaaaagacaatcttttgttgtcaagcttggtggcaaacgacccgtagagggcgttggacagcaacttggc |
| gatggagcgcagggttggttttgtcgcgatcggcgcgctccttggccgcgatgtttagctgcacgtattcgcgcgcaacgcaccg |
| ccattcgggaaagacggtggtgcgctcgtcgggcaccaggtgcacgcgccaaccgcggttgtgcagggtgacaaggtcaacgctggt |
| ggctacctctccgcgtaggcgctcgttggtccagcagaggcggccgcccttgcgcgagcagaatggcggtaggggctctagctgcgt |
| ctcgtccggggggtctgcgtccacggtaaagaccccgggcagcaggcgcgcgtcgaagtagtctatcttgcatccttgcaagtctag |
| cgcctgctgccatgcgcgggcggcaagcgcgcgctcgtatgggttgagtgggggacccccatggcatggggtgggtgagcgcggaggc |
| gtacatgccgcaaatgtcgtaaacgtagaggggctctctgagtattccaagatatgtagggtagcatcttccaccgcggatgctggc |
| gcgcacgtaatcgtatagttcgtgcgagggagcgaggaggtcgggaccgaggttgctacgggcgggctgctctgctcggaagactat |
| ctgcctgaagatggcatgtgagttggatgatatggttggacgctggaagacgttgaagctggcgtctgtgagacctaccgcgtcacg |
| cacgaaggaggcgtaggagtcgcgcagcttgttgaccagctcggcggtgacctgcacgtctagggcgcagtagtccagggtttcctt |
| gatgatgtcatacttatcctgtcccttttttttccacagctcgcggttgaggacaaactcttcgcggtctttccagtactcttggat |
| cggaaacccgtcggcctccgaacggtaagagcctagcatgtagaactggttgacggcctggtaggcgcagcatccctttttctacggg |
| tagcgcgtatgcctgcgcggccttccggagcgaggtgtgggtgagcgcaaaggtgtccctgaccatgactttgaggtactggtattt |
| gaagtcagtgtcgtcgcatccgccctgctcccagagcaaaaagtccgtgcgcttttggaacgcggatttggcagggcgaaggtgac |
| atcgttgaagagtatctttcccgcgcgaggcataaagttgcgtgtgatgcggaagggtcccggcacctcggaacggttgttaattac |
| ctgggcggcgagcacgatctcgtcaaagccgttgatgttgtggcccacaatgtaaagttccaagaagcgcgggatgcccttgatgga |
| aggcaatttttttaagttcctcgtaggtgagctcttcaggggagctgagcccgtgctctgaaagggcccagtctgcaagatgagggtt |
| ggaagcgacgaatgagctccacaggtcacgggccattagcatttgcaggtggtcgcgaaaggtcctaaactggcgacctatggccat |
| ttttctggggtgatgcagtagaaggtaagcgggtcttgttcccagcggtcccatccaaggttcgcggctaggtctcgcgcggcagt |

-continued

Sequences cactagaggctcatctccgccgaacttcatgaccagcatgaagggcacgagctgcttcccaaaggcccccatccaagtataggtctc tacatcgtaggtgacaaagagacgctcggtgcgaggatgcgagccgatcgggaagaactggatctcccgccaccaattggaggagtg gctattgatgtggtgaaagtagaagtccctgcgacgggccgaacactcgtgctggcttttgtaaaaacgtgcgcagtactggcagcg gtgcacgggctgtacatcctgcacgaggttgacctgacgaccgcgcacaaggaagcagagtgggaatttgagcccctcgcctggcgg gtttggctggtggtcttctacttcggctgcttgtccttgaccgtctggctgctcgaggggagttacggtggatcggaccaccacgcc gcgcgagcccaaagtccagatgtccgcgcgcggcggtcggagcttgatgacaacatcgcgcagatgggagctgtccatggtctggag ctcccgcggcgtcaggtcaggcgggagctcctgcaggtttacctcgcatagacgggtcagggcgcgggctagatccaggtgatcct aatttccaggggctggttggtggcggcgtcgatggcttgcaagaggccgcatcccgcggcgcgactacggtaccgcgcggcgggcg gtgggccgcgggggtgtccttggatgatgcatctaaaagcggtgacgcgggcgagccccggaggtagggggggctccggacccgcc gggagaggggcaggggcacgtcggcgccgcgcgggcaggagctggtgctgcgcgcgtaggttgctggcgaacgcgacgacgcgg cggttgatctcctgaatctggcgcctctgcgtgaagacgacgggcccggtgagcttgagcctgaaagagagttcgacagaatcaatt tcggtgtcgttgacggcggcctggcgcaaaatctcctgcacgtctcctgagttgtcttgataggcgatctcggccatgaactgctcg atctcttcctcctggagatctccgcgtccggctcgctccacggtggcggcgaggtcgttggaaatgcgggccatgagctgcgagaag gcgttgaggcctccctcgttccagacgcggctgtagaccacgccccttcggcatcgcgggcgcgcatgaccacctgcgcgagattg agctccacgtgccgggcgaagacggcgtagtttcgcaggcgctgaaagaggtagttgagggtggtggcggtgtgttctgccacgaag aagtacataacccagcgtcgcaacgtggattcgttgatatccccaaggcctcaaggcgctccatggcctcgtagaagtccacggcg aagttgaaaaactgggagttgcgcgccgacacggttaactcctcctccagaagacggatgagctcggcgacagtgtcgcgcacctcg cgctcaaaggctacaggggcctcttcttcttcttcaatctcctcttccataagggcctccccttcttcttcttctggcggcggtggg ggagggggacacggcggcgacgacggcgcaccgggaggcggtcgacaaagcgctcgatcatctccccgcggcgacggcgcatggtc tcggtgacggcgcggccgttctcgcggggcgcagttggaagacgccgcccgtcatgtcccggttatgggttggcggggggctgcca tgcggcagggatacggcgctaacgatgcatctcaacaattgttgtgtaggtactccgccgccgagggacctgagcgagtccgcatcg accggatcggaaaacctctcgagaaaggcgtctaaccagtcacagtcgcaaggtaggctgagcaccgtggcgggcggcagcgggcgg cggtcggggttgtttctggcggaggtgctgctgatgatgtaattaaagtaggcggtcttgagacggcggatggtcgacagaagcacc atgtccttgggtccggcctgctgaatgcgcaggcggtcggccatgccccaggcttcgttttgacatcggcgcaggtctttgtagtag tcttgcatgagcctttctaccggcacttcttcttctccttcctcttgtcctgcatctcttgcatctatcgctgcggcggcggcggag tttggccgtaggtggcgccctcttcctcccatgcgtgtgaccccgaagcccctcatcggctgaagcagggctaggtcggcgacaacg cgctcggctaatatggcctgctgcacctgcgtgagggtagactggaagtcatccatgtccacaaagcggtggtatgcgcccgtgttg atggtgtaagtgcagttggccataacggaccagttaacggtctggtgacccggctgcgagagctcggtgtacctgagacgcgagtaa gccctcgagtcaaatacgtagtcgttgcaagtccgcaccaggtactggtatcccaccaaaaagtgcggcggcggctggcggtagagg ggccagcgtagggtggccggggctccggggcgagatcttccaacataaggcgatgatatccgtagatgtacctggacatccaggtg atgccggcggcggtggtggaggcgcgcggaaagtcgcggacgcggttccagatgttgcgcagcggcaaaaagtgctccatggtcggg acgctctggccggtcaggcgcgcgcaatcgttgacgctctagaccgtgcaaaaggagagcctgtaagcgggcactcttccgtggtct ggtggataaattcgcaagggtatcatggcggacgaccggggttcgagcccgtatccggccgtccgccgtgatccatgcggttaccg cccgcgtgtcgaacccaggtgtgcgacgtcagacaacggggagtgctccttttggcttccttccaggcgcggcggctgctgcgcta gcttttttggccactggccgcgcgcagcgtaagcggttaggctggaaagcgaaagcattaagtggctcgctccctgtagccggaggg ttattttccaagggttgagtcgcgggaccccggttcgagtctcggaccggccggactgcggcgaacgggggtttgcctcccccgtca tgcaagacccccgcttgcaaattcctccggaaacagggacgagccccttttttgcttttcccagatgcatccggtgctgcggcagatg cgccccctcctcagcagcggcaagagcaagagcagcggcagacatgcagggcaccctcccctcctcctaccgcgtcaggagggggcg

| Sequences |
| --- |
| acatccgcggttgacgcggcagcagatggtgattacgaaccccgcggcgcggccggcactacctggacttggaggagggcgag |
| ggcctggcgcggctaggagcgccctctcctgagcggtacccaagggtgcagctgaagcgtgatacgcgtgaggcgtacgtgccgcgg |
| cagaacctgtttcgcgaccgcgagggagaggagcccgaggagatgcgggatcgaaagttccacgcagggcgcgagctgcggcatggc |
| ctgaatcgcgagcggttgctgcgcgaggaggactttgagcccgacgcgcgaaccgggattagtcccgcgcgcgcacacgtggcggcc |
| gccgacctggtaaccgcatacgagcagacggtgaaccaggagattaactttcaaaaaagcttaacaaccacgtgcgtacgcttgtg |
| gcgcgcgaggaggtggctataggactgatgcatctgtgggactttgtaagcgcgctggagcaaaacccaaatagcaagccgctcatg |
| gcgcagctgttccttatagtgcagcacagcagggacaacgaggcattcagggatgcgctgctaaacatagtagagcccgagggccgc |
| tggctgctcgatttgataaacatcctgcagagcatagtggtgcaggagcgcagcttgagcctggctgacaaggtggccgccatcaac |
| tattccatgcttagcctgggcaagttttacgcccgcaagatataccatacccttacgttcccatagacaaggaggtaaagatcgag |
| gggttctacatgcgcatggcgctgaaggtgcttaccttgagcgacgacctgggcgtttatcgcaacgagcgcatccacaaggccgtg |
| agcgtgagccggcggcgcgagctcagcgaccgcgagctgatgcacagcctgcaaagggccctggctggcacgggcagcggcgataga |
| gaggccgagtcctactttgacgcgggcgctgacctgcgctgggccccaagccgacgcgccctggaggcagctggggccggacctggg |
| ctggcggtggcacccgcgcgcgctggcaacgtcggcggcgtggaggaatatgacgaggacgatgagtacgagccagaggacggcgag |
| tactaagcggtgatgtttctgatcagatgatgcaagacgcaacgacccggcggtgcgggcggcgctgcagagccagccgtccggcc |
| ttaactccacggacgactggcgccaggtcatggaccgcatcatgtcgctgactgcgcgcaatcctgacgcgttccggcagcagccgc |
| aggccaaccggctctccgcaattctgaagcggtggtcccggcgcgcgcaaaccccacgcacgagaaggtgctggcgatcgtaaacg |
| cgctggccgaaaacagggccatccggcccgacgaggccggcctggtctacgacgcgctgcttcagcgcgtggctcgttacaacagcg |
| gcaacgtgcagaccaacctggaccggctggtggggatgtgcgcgaggccgtggcgcagcgtgagcgcgcgcagcagcagggcaacc |
| tgggctccatggttgcactaaacgccttcctgagtacacagcccgccaacgtgccgcggggacaggaggactacaccaactttgtga |
| gcgcactgcggctaatggtgactgagacaccgcaaagtgaggtgtaccagtctgggccagactattttttccagaccagtagacaag |
| gcctgcagaccgtaaacctgagccaggcttcaaaaacttgcaggggctgtggggggtgcgggctcccacaggcgaccgcgcgaccg |
| tgtctagcttgctgacgcccaactcgcgcctgttgctgctgctaatagcgcccttcacggacagtggcagcgtgtcccgggacacat |
| acctaggtcacttgctgacactgtaccgcgaggccataggtcaggcgcatgtggacgagcatactttccaggagattacaagtgtca |
| gccgcgcgctggggcaggaggacacgggcagcctggaggcaaccctaaactacctgctgaccaaccggcggcagaagatcccctcgt |
| tgcacagtttaaacagcgaggaggagcgcattttgcgctacgtgcagcagagcgtgagccttaacctgatgcgcgacggggtaacgc |
| ccagcgtggcgctggacatgaccgcgcgcaacatggaaccgggcatgtatgcctcaaaccggccgtttatcaaccgcctaatggact |
| acttgcatcgcgcggccgccgtgaaccccgagtatttcaccaatgccatcttgaacccgcactggctaccgccccctggtttctaca |
| ccggggggattcgaggtgcccgagggtaacgatggattcctctgggacgacatagacgacagcgtgttttcccgcaaccgcagaccc |
| tgctagagttgcaacagcgcgagcaggcagaggcggcgctgcgaaaggaaagcttccgcaggccaagcagcttgtccgatctaggcg |
| ctgcggccccgcggtcagatgctagtagcccattccaagcttgatagggtctcttaccagcactcgcaccaccgcccgcgcctgc |
| tgggcgaggaggagtacctaaacaactcgctgctgcagccgcagcgcgaaaaaaacctgcctccggcatttcccaacaacgggatag |
| agagcctagtggacaagatgagtgatgatggaagacgtacgcgcaggagcacagggacgtgccaggcccgcgcccgcccaccgtcgtc |
| aaaggcacgaccgtcagcggggtctggtgtgggaggacgatgactcggcagacgacagcagcgtcctggatttgggagggagtggca |
| acccgtttgcgcaccttcgccccaggctggggagaatgttttaaaaaaaaaaagcatgatgcaaaataaaaaactcaccaaggcca |
| tggcaccgagcgttggttttcttgtattcccttagtatgcggcgcgcggcgatgtatgaggaaggtcctcctccctcctacgagag |
| tgtggtgagcgcggcgccagtggcggcggcgctgggttctcccttcgatgctcccctggacccgcgtttgtgcctccgcggtacct |
| gcggcctaccgggggagaaacagcatccgttactctgagttggcaccccctattcgacaccaccgtgtgtacctggtggacaacaa |
| gtcaacggatgtggcatccctgaactaccagaacgaccacagcaactttctgaccacggtcattcaaaacaatgactacagcccggg |
| ggaggcaagcacacagaccatcaatcttgacgaccggtcgcactggggcggcgacctgaaaaccatcctgcataccaacatgccaaa |

| Sequences |
| --- |
| tgtgaacgagttcatgtttaccaataagtttaaggcgcgggtgatggtgtcgcgcttgcctactaaggacaatcaggtggagctgaa |
| atacgagtgggtggagttcacgctgcccgagggcaactactccgagaccatgaccatagaccttatgaacaacgcgatcgtggagca |
| ctacttgaaagtgggcagacagaacggggttctggaaagcgacatcggggtaaagtttgacacccgcaacttcagactggggtttga |
| ccccgtcactggtcttgtcatgcctggggtatatacaaacgaagccttccatccagacatcattttgctgccaggatgcggggtgga |
| cttcacccacagccgcctgagcaacttgttgggcatccgcaagcggcaaccttccaggagggctttaggatcacctacgatgatct |
| ggagggtggtaacattcccgcactgttggatgtggacgcctaccaggcgagcttgaaagatgacaccgaacagggcgggggtggcgc |
| aggcggcagcaacagcagtggcagcggcgcggaagagaactccaacgcggcagccgcggcaatgcagccggtggaggacatgaacga |
| tcatgccattcgcggcgacacctttgccacacgggctgaggagaagcgcgctgaggccgaagcagcggccgaagctgccgcccccgc |
| tgcgcaacccgaggtcgagaagcctcagaagaaaccggtgatcaaaccctgacagaggacagcaagaaacgcagttacaacctaat |
| aagcaatgacagcaccttcacccagtaccgcagctggtaccttgcatacaactacggcgaccctcagaccggaatccgctcatggac |
| cctgctttgcactcctgacgtaacctgcggctcggagcaggtctactggtcgttgccagacatgatgcaagaccccgtgaccttccg |
| ctccacgcgccagatcagcaactttccggtggtgggcgccgagctgttgccgtgcactccaagagcttctacaacgaccaggccgt |
| ctactcccaactcatccgccagtttacctctctgacccacgtgttcaatcgctttcccgagaaccagattttggcgcgcccgccagc |
| ccccaccatcaccaccgtcagtgaaaacgttcctgctctcacagatcacgggacgctaccgctgcgcaacagcatcggaggagtcca |
| gcgagtgaccattactgacgccagacgccgcacctgcccctacgtttacaaggccctgggcatagtctcgccgcgcgtcctatcgag |
| ccgcacttttttgagcaagcatgtccatccttatatcgcccagcaataacacaggctggggcctgcgcttcccaagcaagatgtttgg |
| cggggccaagaagcgctccgaccaacacccagtgcgcgtgcgcgggcactaccgcgcgccctggggcgcgcacaaacgcggccgcac |
| tgggcgcaccaccgtcgatgacgccatcgacgcggtggtggaggaggcgcgcaactacacgcccacgccgccaccagtgtccacagt |
| ggacgcggccattcagaccgtggtgcgcggagcccggcgctatgctaaaatgaagagacggcggaggcgcgtagcacgtcgccaccg |
| ccgccgacccggcactgccgcccaacgcgcggcggcggccctgcttaaccgcgcacgtcgcaccggccgacgggcggccatgcgggc |
| cgctcgaaggctggccgcgggtattgtcactgtgcccccaggtccaggcgacgagcggccgccgcagcagccgcggccattagtgc |
| tatgactcagggtcgcaggggcaacgtgtattgggtgcgcgactcggttagcggcctgcgcgtgcccgtgcgcacccgccccccgcg |
| caactagattgcaagaaaaaactacttagactcgtactgttgtatgtatccagcggcggcggcgcgcaacgaagctatgtccaagcg |
| caaaatcaaagaagagatgctccaggtcatcgcgccggagatctatggccccccgaagaaggaagagcaggattacaagccccgaaa |
| gctaaagcgggtcaaaaagaaaaagaaagatgatgatgatgaacttgacgacgaggtggaactgctgcacgctaccgcgcccaggcg |
| acgggtacagtggaaaggtcgacgcgtaaaacgtgttttgcgacccggcaccaccgtagtctttacgcccggtgagcgctccacccg |
| cacctacaagcgcgtgtatgatgaggtgtacggcgacgaggacctgcttgagcaggccaacgagcgcctcggggagtttgcctacgg |
| aaagcggcataaggacatgctggcgttgccgctggacgagggcaacccaacacctagcctaaagcccgtaacactgcagcaggtgct |
| gcccgcgcttgcaccgtccgaagaaaagcgcggcctaaagcgcgagtctggtgacttggcacccaccgtgcagctgatggtacccaa |
| gcgccagcgactggaagatgtcttggaaaaaatgaccgtggaacctgggctggagcccgaggtccgcgtgcggccaatcaagcaggt |
| ggcgccgggactgggcgtgcagaccgtggacgttcagataccctaccagtagcaccagtattgccaccgccacagagggcatgga |
| gacacaaacgtcccggttgcctcagcggtggcggatgccgcggtgcaggcggtcgctgcggccgcgtccaagacctctacggaggt |
| gcaaacggaccctggatgtttcgcgtttcagcccccggcgcccgcgcggttcgaggaagtacggcgccgccagcgcgctactgcc |
| cgaatatgccctacatccttccattgcgcctaccccggctatcgtggctacacctaccgcccagaagacgagcaactacccgacg |
| ccgaaccaccactggaacccgcgccgccgtcgccgtcgccagcccgtgctggccccgatttccgtgcgcagggtggctcgcgaagg |
| aggcaggaccctggtgctgccaacagcgcgctaccaccccagcatcgtttaaaagccggtctttgtggttcttgcagatatggccct |
| cacctgccgcctccgtttcccggtgccgggattccgaggaagaatgcaccgtaggaggggcatgccggccacggcctgacgggcgg |
| catgcgtcgtgcgcaccaccggcggcggcgcgcgtcgcaccgtcgcatgcgcggcggtatcctgccctccttattccactgatcgc |

| Sequences |
| --- |
| cgcggcgattggcgccgtgcccggaattgcatccgtggccttgcaggcgcagagacactgattaaaaacaagttgcatgtggaaaaa |
| tcaaaataaaaagtctggactctcacgctcgcttggtcctgtaactattttgtagaatggaagacatcaactttgcgtctctggccc |
| cgcgacacggctcgcgcccgttcatgggaaactggcaagatatcggcaccagcaatatgagcggtggcgccttcagctgggctcgc |
| tgtggagcggcattaaaaatttcggttccaccgttaagaactatggcagcaaggcctggaacagcagcacaggccagatgctgaggg |
| ataagttgaaagagcaaaatttccaacaaaggtggtagatggcctggcctctggcattagcggggtggtggacctggccaaccagg |
| cagtgcaaataagattaacagtaagcttgatccccgccctcccgtagaggagcctccaccggccgtggagacagtgtctccagagg |
| ggcgtggcgaaaagcgtccgcgccccgacagggaagaaactctggtgacgcaaatagacgagcctccctcgtacgaggaggcactaa |
| agcaaggcctgcccaccacccgtcccatcgcgcccatggctaccggagtgctgggccagcacacacccgtaacgctggacctgcctc |
| cccccgccgacacccagcagaaacctgtgctgccaggcccgaccgccgttgttgtaaccgtcctagccgcgcgtccctgcgccgcg |
| ccgccagcggtccgcgatcgttgcggcccgtagccagtggcaactggcaaagcacactgaacagcatcgtgggtctgggggtgcaat |
| ccctgaagcgccgacgatgcttctgaatagctaacgtgtcgtatgtgtgtcatgtatgcgtccatgtcgccgccagaggagctgctg |
| agccgccgcgcgcccgctttccaagatggctaccccttcgatgatgccgcagtggtcttacatgcacatctcgggccaggacgcctc |
| ggagtacctgagccccgggctggtgcagtttgcccgcgccaccgagacgtacttcagcctgaataacaagtttagaaaccccacggt |
| ggcgcctacgcacgacgtgaccacagaccggtcccagcgtttgacgctgcggttcatccctgtggaccgtgaggatactgcgtactc |
| gtacaaggcgcggttcaccctagctgtgggtgataaccgtgtgctggacatggcttccacgtactttgacatccgcggcgtgctgga |
| caggggccctacttttaagccctactctggcactgcctacaacgccctggctcccaagggtgccccaaatccttgcgaatgggatga |
| agctgctactgctcttgaaataaacctagaagaagaggacgatgacaacgaagacgaagtagacgagcaagctgagcagcaaaaaac |
| tcacgtatttgggcaggcgccttattctggtataaatattacaaaggagggtattcaaataggtgtcgaaggtcaaacacctaaata |
| tgccgataaaacatttcaacctgaacctcaaataggagaatctcagtggtacgaaactgaaattaatcatgcagctgggagagtcct |
| taaaaagactaccccaatgaaaccatgttacggttcatatgcaaaacccacaaatgaaatggagggcaaggcattcttgtaaagca |
| acaaaatggaaagctagaaagtcaagtggaaatgcaattttttctcaactactgaggcgaccgcaggcaatggtgataacttgactcc |
| taaagtggtattgtacagtgaagatgtagatatagaaaccccagacactcatatttcttacatgcccactattaaggaaggtaactc |
| acgagaactaatgggccaacaatctatgcccaacaggcctaattacattgcttttagggacaattttattggtctaatgtattacaa |
| cagcacgggtaatatgggtgttctggcgggccaagcatcgcagttgaatgctgttgtagatttgcaagacagaaacacagagctttc |
| ataccagcttttgcttgattccattggtgatagaaccaggtacttttctatgtggaatcaggctgttgacagctatgatccagatgt |
| tagaattattgaaaatcatggaactgaagatgaacttccaaattactgctttccactgggaggtgtgattaatacagagactcttac |
| caaggtaaaacctaaaacaggtcaggaaaatggatgggaaaaagatgctacagaattttcagataaaaatgaaataagagttggaaa |
| taattttgccatggaaatcaatctaaatgccaacctgtggagaaattcctgtactccaacatagcgctgtatttgcccgacaagct |
| aaagtacagtccttccaacgtaaaaatttctgataacccaaacacctacgactacatgaacaagcgagtggtggctcccgggttagt |
| ggactgctacattaaccttggagcacgctggtcccttgactatatggacaacgtcaacccatttaaccaccaccgcaatgctggcct |
| gcgctaccgctcaatgttgctgggcaatggtcgctatgtgcccttccacatccaggtgcctcagaagttctttgccattaaaaacct |
| ccttctcctgccgggctcatacacctacgagtggaacttcaggaaggatgttaacatggttctgcagagctccctaggaaatgacct |
| aagggttgacggagccagcattaagtttgatagcatttgcctttacgccaccttcttccccatggcccacaacaccgcctccacgct |
| tgaggccatgcttagaaacgacaccaacgaccagtcctttaacgactatctctccgccgcaacatgctctaccctataccccgccaa |
| cgctaccaacgtgcccatatccatcccctcccgcaactgggcggcttccgcggctgggccttcacgcgccttaagactaaggaaac |
| cccatcactgggctcgggctacgacccttattacacctactctggctctataccctacctagatggaaccttttacctcaaccacac |
| ctttaagaaggctgccattacctttgactcttctgtcagctggcctggcaatgaccgcctgcttaccccaacgagtttgaaattaa |
| gcgctcagttgacggggaggttacaacgttgcccagtgtaacatgaccaaagactggttcctggtacaaatgctagctaactataa |
| cattggctaccagggcttctatatcccagagagctacaaggaccgcatgtactccttcttagaaacttccagcccatgagccgtca |

-continued

| Sequences |
|---|
| ggtggtggatgatactaaatacaaggactaccaacaggtgggcatcctacaccaacacaacaactctggatttgttggctaccttgc |
| ccccaccatgcgcgaaggacaggcctaccctgctaacttcccctatccgcttataggcaagaccgcagttgacagcattacccagaa |
| aaagtttctttgcgatcgcacccttt ggcgcatcccattctccagtaactttatgtccatgggcgcactcacagacctgggccaaaa |
| ccttctctacgccaactccgcccactccctagacatgacttttgaggtggatccatggacgagcccacccttctttatgttttgtt |
| tgaagtctttgacaaggtccgtgtgcaccagccgcaccgcggcgtcatcgaaaccgtgtacctgcgcacgccttctcggccggcaa |
| cgccacaacataaagaagcaagcaacatcaacaacagctgccgccatgggctccagtgagcaggaactgaaagccattgtcaaagat |
| cttggttgtgggccatatttttgggcacctatgacaagcgcttccaggctttgtttctccacacaagctcgcctgcgccatagtc |
| aatacggccggtcgcgagactgggggcgtacactggatggcctttgcctggaacccgcactcaaaaacatgctacctctttgagccc |
| tttggcttttctgaccagcgactcaagcaggtttaccagtttgagtacgagtcactcctgcgccgtagcgccattgcttcttccccc |
| gaccgctgtataacgctggaaaagtccaccaaagcgtacaggggcccaactcggccgcctgtggactattctgctgcatgtttctc |
| cacgcctttgccaactggccccaaactcccatggatcacaacccaccatgaacttattaccggggtacccaactccatgctcaac |
| agtccccaggtacagcccaccctgcgtcgcaaccaggaacagctctacagcttcctggagcgccactcgccctacttccgcagccac |
| agtgcgcagattaggagcgccacttcttttttgtcacttgaaaaacatgtaaaaataatgtactagagacactttcaataaaggcaaa |
| tgcttttatttgtacactctcggggtgattatttaccccaccctttgccgtctgcgccgtttaaaaatcaaaggggttctgccgcgca |
| tcgctatgcgccactggcagggacacgttgcgatactggtgtttagtgctccacttaaactcaggcacaaccatccgcggcagctcg |
| gtgaagttttcactccacaggctgcgcaccatcaccaacgcgtttagcaggtcgggcgccgatatcttgaagtcgcagttggggcct |
| ccgccctgcgcgcgcgagttgcgatacacagggttgcagcactggaacactatcagcgccgggtggtgcacgctggccagcacgctc |
| ttgtcggagatcagatccgcgtccaggtcctccgcgttgctcagggcgaacggagtcaactttggtagctgccttcccaaaaagggc |
| gcgtgcccaggctttgagttgcactcgcaccgtagtggcatcaaaaggtgaccgtgcccggtctgggcgttaggatacagcgcctgc |
| ataaaagccttgatctgcttaaaagccacctgagcctttgcgccttcagagaagaacatgccgcaagacttgccggaaaactgattg |
| gccggacaggccgcgtcgtgcacgcagcacccttgcgtcggtgttggagatctgcaccacatttcggcccaccggttcttcacgatc |
| ttggccttgctagactgctccttcagcgcgcgctgcccgttttcgctcgtcacatccatttcaatcacgtgctccttattatcata |
| atgcttccgtgtagacacttaagctcgccttcgatctcagcgcagcggtgcagccacaacgcgcagcccgtgggctcgtgatgcttg |
| taggtcacctctgcaaacgactgcaggtacgcctgcaggaatcgcccatcatcgtcacaaaggtcttgttgctggtgaaggtcagc |
| tgcaacccgcggtgctcctcgttcagccaggtcttgcatacggccgccagagcttccacttggtcaggcagtagtttgaagttcgcc |
| tttagatcgttatccacgtggtacttgtccatcagcgcgcgcgcagcctccatgccttctcccacgcagacacgatcggcacactc |
| agcgggttcatcaccgtaatttcactttccgcttcgctgggctcttcctcttcctcttgcgtccgcataccacgcgccactgggtcg |
| tcttcattcagccgccgcactgtgcgcttacctccttttgccatgcttgattagcaccggtgggttgctgaaacccaccattttgtagc |
| gccacatcttctctttcttcctcgctgtccacgattacctctggtgatggcgggcgctcgggcttgggagaagggcgcttctttttc |
| ttcttgggcgcaatggccaaatccgccgccgaggtcgatggccgcgggctgggtgtgcgcggcaccagcgcgtcttgtgatgagtct |
| tcctcgtcctcggactcgatacgccgcctcatccgcttttttggggcgcccggggaggcggcggcgacggggacggggacgacacg |
| tcctccatggttgggggacgtcgccgcaccgcgtccgcgctcgggggtggtttcgcgctgctcctcttcccgactggccatttcc |
| ttctcctataggcagaaaaagatcatggagtcagtcgagaagaaggacagcctaaccgcccctctgagttcgccaccaccgcctcc |
| accgatgccgccaacgcgcctaccaccttccccgtcgaggcaccccgcttgaggaggaggaagtgattatcgagcaggacccaggt |
| tttgtaagcgaagacgacgaggaccgctcagtaccaacgaggataaaaagcaagaccaggacaacgcagaggcaaacgaggaacaa |
| gtcgggcgggggacgaaaggcatggcgactacctagatgtgggagacgacgtgctgttgaagcatctgcagcgccagtgcgccatt |
| atctgcgacgcgttgcaagagcgcagcgatgtgccctcgccatagcggatgtcagccttgcctacgaacgccacctattctcaccg |
| cgcgtaccccccaaacgccaagaaaacggcacatgcgagcccaacccgcgcctcaacttctaccccgtatttgccgtgccagaggtg |

-continued

| Sequences |
|---|
| cttgccacctatcacatcttttt ccaaaactgcaagatacccctatcctgccgtgccaaccgcagccgagcggacaagcagctggcc |
| ttgcggcagggcgctgtcatacctgatatcgcctcgctcaacgaagtgccaaaaatctttgagggtcttggacgcgacgagaagcgc |
| gcggcaaacgctctgcaacaggaaaacagcgaaaatgaaagtcactctggagtgttggtggaactcgagggtgacaacgcgcgccta |
| gccgtactaaaacgcagcatcgaggtcacccactttgcctacccggcacttaacctacccccaaggtcatgagcacagtcatgagt |
| gagctgatcgtgcgccgtgcgcagcccctggagagggatgcaaatttgcaagaacaaacagaggagggcctacccgcagttggcgac |
| gagcagctagcgcgctggcttcaaacgcgcgagcctgccgacttggaggagcgacgcaaactaatgatggccgcagtgctcgttacc |
| gtggagcttgagtgcatgcagcggttctttgctgacccggagatgcagcgcaagctagaggaaacattgcactacacctttcgacag |
| ggctacgtacgccaggcctgcaagatctccaacgtggagctctgcaacctggtctcctaccttggaattttgcacgaaaaccgcctt |
| gggcaaaacgtgcttcattccacgctcaagggcgaggcgcgccgcgactacgtccgcgactgcgtttacttattctatgctacacc |
| tggcagacgccatgggcgtttggcagcagtgcttggaggagtgcaacctcaaggagctgcagaaactgctaaagcaaaacttgaag |
| gacctatggacggccttcaacgagcgctccgtggccgcgcacctggcggacatcattttccccgaacgcctgcttaaaaccctgcaa |
| cagggtctgccagacttcaccagtcaaagcatgttgcagaactttaggaactttatcctagagcgctcaggaatcttgcccgccacc |
| tgctgtgcacttcctagcgactttgtgcccattaagtaccgcgaatgccctccgccgctttggggccactgctaccttctgcagcta |
| gccaactaccttgcctaccactctgacataatggaagacgtgagcggtgacggtctactggagtgtcactgtcgctgcaacctatgc |
| accccgcaccgctccctggtttgcaattcgcagctgcttaacgaaagtcaaattatcggtacctttgagctgcagggtccctcgcct |
| gacgaaaagtccgcggctccggggttgaaactcactccggggctgtggacgtcggcttaccttcgcaaatttgtacctgaggactac |
| cacgcccacgagattaggttctacgaagaccaatcccgcccgccaaatgcggagcttaccgcctgcgtcattacccagggccacatt |
| cttggccaattgcaagccatcaacaaagcccgccaagagtttctgctacgaaagggacgggggtttacttggaccccagtccggc |
| gaggagctcaacccaatccccccgccgccgcagccctatcagcagcagccgcgggcccttgcttcccaggatggcacccaaaagaa |
| gctgcagctgccgccgccacccacggacgaggaggaatactgggacagtcaggcagaggaggttttggacgaggaggaggaggacat |
| gatggaagactgggagagcctagacgaggaagcttccgaggtcgaagaggtgtcagacgaaacaccgtcaccctcggtcgcattccc |
| ctcgccggcgccccagaaatcggcaaccggttccagcatggctacaacctccgctcctcaggcgccgccggcactgcccgttcgccg |
| acccaaccgtagatgggacaccactggaaccagggccggtaagtccaagcagccgccgccgttagcccaagagcaacaacagcgcca |
| aggctaccgctcatggcgcggggcacaagaacgccatagttgcttgcttgcaagactgtggggcaacatctccttcgcccgccgctt |
| tcttctctaccatcacggcgtggccttcccccgtaacatcctgcattactaccgtcatctctacagcccatactgcaccggcggcag |
| cggcagcggcagcaacagcagcggccacacagaagcaaaggcgaccggatagcaagactctgacaaagcccaagaaatccacagcgg |
| cggcagcagcaggaggaggagcgctgcgtctggcgcccaacgaacccgtatcgaccgcgagcttagaaacaggattttttcccactc |
| tgtatgctatatttcaacagagcaggggccaagaacaagagctgaaaataaaaaacaggtctctgcgatccctcacccgcagctgcc |
| tgtatcacaaaagcgaagatcagcttcggcgcacgctggaagacgcggaggctctcttcagtaaatactgcgcgctgactcttaagg |
| actagtttcgcgccctttctcaaatttaagcgcgaaaactacgtcatctccagcggccacacccggcgccagcacctgtcgtcagcg |
| ccattatgagcaaggaaattcccacgccctacatgtggagttaccagccacaaatgggacttgcggctggagctgcccaagactact |
| caacccgaataaactacatgagcgcgggaccccacatgatatcccgggtcaacgaatccgcgcccaccgaaaccgaattctcttgg |
| aacaggcggctattaccaccacacctcgtaataaccttaatcccgtagttggcccgctgccctggtgtaccaggaaagtcccgctc |
| ccaccactgtggtacttcccagagacgcccaggccgaagttcagatgactaactcaggggcgcagcttgcgggcggctttcgtcaca |
| gggtgcggtcgcccgggcagggtataactcacctgacaatcagagggcgaggtattcagctcaacgacgagtcggtgagctcctcgc |
| ttggtctccgtccggacgggacatttcagatcggcggcgccggccgtccttcattcacgcctcgtcaggcaatcctaactctgcaga |
| cctcgtcctctgagccgcgctctggaggcattggaactctgcaatttattgaggagtttgtgccatcggtctactttaaccccttct |
| cgggacctcccggccactatccggatcaatttattcctaactttgacgcggtaaaggactcggcggacggctacgactgaatgttaa |
| gtggagaggcagagcaactgcgcctgaaacacctggtccactgtcgccgccacaagtgctttgcccgcgactccggtgagttttgct |

-continued

| Sequences |
|---|
| actttgaattgcccgaggatcatatcgagggcccggcgcacggcgtccggcttaccgcccagggagagcttgcccgtagcctgattc |
| gggagtttacccagcgcccctgctagttgagcgggacaggggaccctgtgttctcactgtgatttgcaactgtcctaaccttggat |
| tacatcaagatctttgttgccatctctgtgctgagtataataaatacagaaattaaaatatactggggctcctatcgccatcctgta |
| aacgccaccgtcttcacccgcccaagcaaaccaaggcgaaccttacctggtacttttaacatctctccctctgtgatttacaacagt |
| ttcaacccagacggagtgagtctacgagagaacctctccgagctcagctactccatcagaaaaaacaccaccctccttacctgccgg |
| gaacgtacgagtgcgtcaccggccgctgcaccacacctaccgcctgaccgtaaaccagacttttccggacagacctcaataactct |
| gtttaccagaacaggaggtgagcttagaaaacccttagggtattaggccaaaggcgcagctactgtgggtttatgaacaattcaag |
| caactctacgggctattctaattcaggtttctctagaatcggggttggggttattctctgtcttgtgattctctttattcttatact |
| aacgcttctctgcctaaggctcgccgcctgctgtgtgcacatttgcatttattgtcagcttttaaacgctggggtcgccacccaag |
| atgattaggtacataatcctaggtttactcacccttgcgtcagcccacggtaccacccaaaaggtggattttaaggagccagcctgt |
| aatgttacattcgcagctgaagctaatgagtgcaccactcttataaaatgcaccacagaacatgaaaagctgcttattcgccacaaa |
| aacaaaattggcaagtatgctgtttatgctatttggcagccaggtgacactacagagtataatgttacagttttccagggtaaagt |
| cataaaacttttatgtactttttccattttatgaaatgtgcgacattaccatgtacatgagcaaacagtataagttgtggcccccca |
| caaaattgtgtggaaaacactggcactttctgctgcactgctatgctaattacagtgctcgctttggtctgtaccctactctatatt |
| aaatacaaaagcagacgcagctttattgaggaaaagaaaatgccttaatttactaagttacaaagctaatgtcaccactaactgctt |
| tactcgctgcttgcaaaacaaattcaaaaagttagcattataattagaataggatttaaaccccccggtcatttcctgctcaatacc |
| attcccctgaacaattgactctatgtgggatatgctccagcgctacaaccttgaagtcaggcttcctggatgtcagcatctgactt |
| ggccagcacctgtcccgcggatttgttccagtccaactacagcgacccaccctaacagagatgaccaacacaaccaacgcggccgcc |
| gctaccggacttacatctaccacaaatacaccccaagtttctgcctttgtcaataactgggataacttgggcatgtggtggttctcc |
| atagcgcttatgtttgtatgccttattattatgtggctcatctgctgcctaaagcgcaaacgcgcccgaccacccatctatagtccc |
| atcattgtgctacacccaaacaatgatggaatccatagattggacggactgaaacacatgttcttttctcttacagtatgattaaat |
| gagacatgattcctcgagttttatattactgaccctgttgcgcttttttgtgcgtgctccacattggctgcggtttctcacatcg |
| aagtagactgcattccagccttcacagtctatttgctttacggatttgtcaccctcacgctcatctgcagcctcatcactgtggtca |
| tcgcctttatccagtgcattgactgggtctgtgtgcgctttgcatatctcagacaccatcccagtacagggacaggactatagctg |
| agcttcttagaattctttaattatgaaatttactgtgacttttctgctgattatttgcaccctatctgcgttttgttccccgacctc |
| caagcctcaaagacatatatcatgcagattcactcgtatatggaatattccaagttgctacaatgaaaaagcgatctttccgaagc |
| ctggttatatgcaatcatctctgttatggtgttctgcagtaccatcttagccctagctatatatccctaccttgacattggctggaa |
| acgaatagatgccatgaaccacccaactttccccgcgcccgctatgcttccactgcaacaagttgttgccggcggctttgtcccagc |
| caatcagcctcgccccacttctcccacccccactgaaatcagctactttaatctaacaggaggagatgactgacaccctagatctag |
| aaatggacggaattattacagagcagcgcctgctagaaagacgcagggcagcggccgagcaacagcgcatgaatcaagagctccaag |
| acatggttaacttgcaccagtgcaaaagggggtatctttgtctggtaaagcaggccaaagtcacctacgacagtaataccaccggac |
| accgcctagctacaagttgccaaccaagcgtcagaaattggtggtcatggtgggagaaaagcccattaccataactcagcactcgg |
| tagaaaccgaaggctgcattcactcaccttgtcaaggacctgaggatctctgcacccttattaagaccctgtgcggtctcaaagatc |
| ttattccctttaactaataaaaaaaataataaagcatcacttacttaaaatcagttagcaaatttctgtccagtttattcagcagc |
| acctccttgccctcctcccagctctggtattgcagcttcctcctggctgcaaactttctccacaatctaaatggaatgtcagtttcc |
| tcctgttcctgtccatccgcacccactatcttcatgttgttgcagatgaagcgcgcaagaccgtctgaagataccttcaaccccgtg |
| tatccatatgacacggaaaccggtcctccaactgtgccttttcttactcctccctttgtatccccaatgggtttcaagagagtccc |
| cctggggtactctctttgcgcctatccgaacctctagttacctccaatggcatgcttgcgctcaaaatgggcaacggcctctctctg |

| Sequences |
| --- |
| gacgaggccggcaaccttacctcccaaaatgtaaccactgtgagcccacctctccgaggagacaagtcaaacataaacctggaaata |
| tctgcacccctcacagttacctcagaagccctaactgtggctgccgccgcacctctaatggtcgcgggcaacacactcaccatgcaa |
| tcacaggccccgctaaccgtgcacgactccaaacttagcattgccacccaaggacccctcacagtgtcagaaggaaagctagccctg |
| caaacatcaggccccctcaccaccaccgatagcagtaccttactatcactgcctcaccccctctaactactgccactggtagcttg |
| ggcattgacttgaaagagcccatttatacacaaaatggaaaactaggactaaagtacggggctcctttgcatgtaacagacgaccta |
| aacactttgaccgtagcaactggtccaggtgtgactattaataatacttccttgcaaactaaagttactggagccttgggttttgat |
| tcacaaggcaatatgcaacttaatgtagcaggaggactaaggattgattctcaaaacagacgccttatacttgatgttagttatccg |
| tttgatgctcaaaaccaactaaatctaagactaggacagggccctcttttataaactcagcccacaacttggatattaactacaac |
| aaaggcctttacttgtttacagcttcaaacaattccaaaaagcttgaggttaacctaagcactgccaaggggttgatgtttgacgct |
| acagccatagccattaatgcaggagatgggcttgaatttggttcacctaatgcaccaaacacaaatcccctcaaaacaaaaattggc |
| catggcctagaatttgattcaaacaaggctatggttcctaaactaggaactggccttagttttgacagcacaggtgccattacagta |
| ggaaacaaaaataatgataagctaactttgtggaccacaccagctccatctcctaactgtagactaaatgcagagaaagatgctaaa |
| ctcactttggtcttaacaaaatgtggcagtcaaatacttgctacagtttcagttttggctgttaaaggcagtttggctccaatatct |
| ggaacagttcaaagtgctcatcttattataagatttgacgaaaatggagtgctactaaacaattccttcctggacccagaatattgg |
| aactttagaaatggagatcttactgaaggcacagcctatacaaacgctgttggatttatgcctaacctatcagcttatccaaaatct |
| cacggtaaaactgccaaaagtaacattgtcagtcaagtttacttaaacggagacaaaactaaacctgtaacactaaccattacacta |
| aacggtacacaggaaacaggagacacaactccaagtgcatactctatgtcattttcatgggactggtctggccacaactacattaat |
| gaaatatttgccacatcctatacacttttttcatacattgcccaagaataaaagaatcgtttgtgttatgtttcaacgtgttttttt |
| caattgcagaaaatttcaagtcattttttcattcagtagtatagcccaccaccacatagcttatacagatcaccgtaccttaatcaa |
| actcacagaaccctagtattcaacctgccacctccctcccaacacacagagtacacagtcctttctccccggctggccttaaaaagc |
| atcatatcatgggtaacagacatattcttaggtgttatattccacacggtttcctgtcgagccaaacgctcatcagtgatattaata |
| aactccccgggcagctcacttaagttcatgtcgctgtccagctgctgagccacaggctgctgtccaacttgcggttgcttaacgggc |
| ggcgaaggagaagtccacgcctacatgggggtagagtcataatcgtgcatcaggatagggcggtggtgctgcagcagcgcgcgaata |
| aactgctgccgccgccgctccgtcctgcaggaatacaacatggcagtggtctcctcagcgatgattcgcaccgcccgcagcataagg |
| cgccttgtcctccgggcacagcagcgcaccctgatctcacttaaatcagcacagtaactgcagcacagcaccacaatattgttcaaa |
| atcccacagtgcaaggcgctgtatccaaagctcatggcggggaccacagaacccacgtggccatcataccacaagcgcaggtagatt |
| aagtggcgacccctcataaacacgctggacataaacattacctatttggcatgttgtaattcaccacctcccggtaccatataaacc |
| tctgattaaacatggcgccatccaccaccatcctaaaccagctggccaaaacctgcccgccggctatacactgcagggaaccgggac |
| tggaacaatgacagtggagagcccaggactcgtaaccatggatcatcatgctcgtcatgatatcaatgttggcacaacacaggcaca |
| cgtgcatacacttcctcaggattacaagctcctcccgcgttagaaccatatcccaggaacaacccattcctgaatcagcgtaaatc |
| ccacactgcagggaagacctcgcacgtaactcacgttgtgcattgtcaaagtgttacattcgggcagcagcggatgatcctccagta |
| tggtagcgcgggtttctgtctcaaaaggaggtagacgatccctactgtacggagtgcgccgagacaaccgagatcgtgttggtcgta |
| gtgtcatgccaaatggaacgccggacgtagtcatatttcctgaagcaaaaccaggtgcgggcgtgacaaacagatctgcgtctccgg |
| tctcgccgcttagatcgctctgtgtagtagttgtagtatatccactctctcaaagcatccaggcgcccctggcttcgggttctatg |
| taaactccttcatgcgccgctgccctgataacatccaccaccgcagaataagccacacccagccaacctacacattcgttctgcgag |
| tcacacgggaggagcgggaagagctggaagaaccatgtttttttttttattccaaaagattatccaaaacctcaaaatgaagatc |
| tattaagtgaacgcgctcccctccggtggcgtggtcaaactctacagccaaagaacagataatggcatttgtaagatgttgcacaat |
| ggcttccaaaaggcaaacggccctcacgtccaagtggacgtaaaggctaaacccttcagggtgaatctcctctataaacattccagc |
| accttcaaccatgcccaaataattctcatctcgccaccttctcaatatatctctaagcaaatcccgaatattaagtccggccattgt |

| Sequences |
|---|
| aaaaatctgctccagagcgccctccaccttcagcctcaagcagcgaatcatgattgcaaaaattcaggttcctcacagacctgtata |
| agattcaaaagcggaacattaacaaaaataccgcgatcccgtaggtccatcgcagggccagctgaacataatcgtgcaggtctgcac |
| ggaccagcgcggccacttccccgccaggaaccatgacaaaagaacccacactgattatgacacgcatactcggagctatgctaacca |
| gcgtagccccgatgtaagcttgttgcatgggcggcgatataaaatgcaaggtgctgctcaaaaaatcaggcaaagcctcgcgcaaaa |
| aagaaagcacatcgtagtcatgctcatgcagataaaggcaggtaagctccggaaccaccacagaaaaagacaccatttttctctcaa |
| acatgtctgcgggtttctgcataaacacaaaataaaataacaaaaaaacatttaaacattagaagcctgtcttacaacaggaaaaac |
| aaccctataagcataagacggactacggccatgccggcgtgaccgtaaaaaaactggtcaccgtgattaaaaagcaccaccgacag |
| ctcctcggtcatgtccggagtcataatgtaagactcggtaaacacatcaggttgattcacatcggtcagtgctaaaaagcgaccgaa |
| atagcccggggaatacatacccgcaggcgtagagacaacattacagcccccataggaggtataacaaaattaataggagagaaaaa |
| cacataaacacctgaaaaccctcctgcctaggcaaaatagcaccctcccgctccagaacaacatacagcgcttccacagcggcagc |
| cataacagtcagccttaccagtaaaaaagaaaacctattaaaaaaacaccactcgacacggcaccagctcaatcagtcacagtgtaa |
| aaaagggccaagtgcagagcgagtatatataggactaaaaaatgacgtaacggttaaagtccacaaaaaacacccagaaaaccgcac |
| gcgaacctacgcccagaaacgaaagccaaaaaacccacaacttcctcaaatcgtcacttccgttttcccacgttacgtcacttccca |
| ttttaagaaaactacaattcccaacacatactagttactccgccctaaaacctacgtcacccgcccgttcccacgcccgcgccac |
| gtcacaaactccaccccctcattatcatattggcttcaatccaaaataaggtatattattgatgatgt |

SEQ

-continued

Sequences ttacaagtgggaatttgaagagcttttgaaatcctgtggtgagctgtttgattctttgaatctgggtcaccaggcgcttttccaaga gaaggtcatcaagactttggattttttccacaccggggcgcgctgcggctgctgttgcttttttgagttttataaaggataaatggag cgaagaaacccatctgagcgggggggtacctgctgcctgattttctggccatgcatctgtggagagcggttgtgagacacaagaatcgcct gctactgttgtcttccgtccgcccggcgataataccgacggaggagcagcagcagcagcaggaggaagccaggcggcggcggcagga gcagagcccatggaacccgagagccggcctggaccctcgggaatgaatgttgtacaggtggctgaactgtatccagaactgagacgc attttgacaattacagaggatgggcaggggctaaaggggtaaagagggagcggggggcttgtgaggctacagaggaggctaggaat ctagcttttagcttaatgaccagacaccgtcctgagtgtattacttttcaacagatcaaggataattgcgctaatgagcttgatctg ctggcgcagaagtattccatagagcagctgaccacttactggctgcagccaggggatgattttgaggaggctattagggtatatgca aaggtggcacttaggccagattgcaagtacaagatcagcaaacttgtaaatatcaggaattgttgctacatttctgggaacggggcc gaggtggagatagatacggaggatagggtggcctttagatgtagcatgataaatatgtggccgggggtgcttggcatggacggggtg gttattatgaatgtaaggtttactggccccaattttagcggtacggttttcctggccaataccaaccttatcctacacggtgtaagc ttctatgggtttaacaatacctgtgtggaagcctggaccgatgtaagggttcggggctgtgccttttactgctgctggaaggggtg gtgtgtcgccccaaaagcagggcttcaattaagaaatgcctctttgaaaggtgtaccttgggtatcctgtctgagggtaactccagg gtgcgccacaatgtggcctccgactgtggttgcttcatgctagtgaaaagcgtggctgtgattaagcataacatggtatgtggcaac tgcgaggacagggcctctcagatgctgacctgctcggacggcaactgtcacctgctgaagaccattcacgtagccagccactctcgc aaggcctggccagtgtttgagcataacatactgacccgctgttccttgcatttgggtaacaggagggggtgttcctaccttaccaa tgcaatttgagtcacactaagatattgcttgagcccgagagcatgtccaaggtgaacctgaacggggtgtttgacatgaccatgaag atctggaaggtgctgaggtacgatgagacccgcaccaggtgcagaccctgcgagtgtggcggtaaacatattaggaaccagcctgtg atgctggatgtgaccgaggagctgaggcccgatcacttggtgctggcctgcaccgcgctgagtttggctctagcgatgaagataca gattgaggtactgaaatgtgtgggcgtggcttaagggtgggaaagaatatataaggtgggggtcttatgtagttttgtatctgtttt gcagcagccgccgccgccatgagcaccaactcgtttgatggaagcattgtgagctcatatttgacaacgcgcatgcccccatgggcc ggggtgcgtcagaatgtgatgggctccagcattgatggtcgccccgtcctgcccgcaaactctactaccttgacctacgagaccgtg tctggaacgccgttggagactgcagcctccgccgccgcttcagccgctgcagccaccgcccgcgggattgtgactgactttgctttc ctgagcccgcttgcaagcagtgcagcttcccgttcatccgcccgcgatgacaagttgacggctcttttggcacaattggattctttg acccgggaacttaatgtcgtttctcagcagctgttggatctgcgccagcaggtttctgccctgaaggcttcctcccctcccaatgcg gtttaaaacataaataaaaaaccagactctgtttggatttggatcaagcaagtgtcttgctgtctttatttaggggttttgcgcgcg cggtaggcccgggaccagcggtctcggtcgttgagggtcctgtgtatttttccaggacgtggtaaaggtgactctggatgttcaga tacatgggcataagcccgtctctggggtggaggtagcaccactgcagagcttcatgctgcgggtggtgttgtagatgatccagtcg tagcaggagcgctgggcgtggtgcctaaaaatgtctttcagtagcaagctgattgccaggggcaggcccttggtgtaagtgtttaca aagcggttaagctgggatgggtgcatacgtggggatatgagatgcatcttggactgtattttaggttggctatgttcccagccata tccctccggggattcatgttgtgcagaaccaccagcacagtgtatccggtgcacttgggaaatttgtcatgtagcttagaaggaaat gcgtggaagaacttggagacgcccttgtgacctccaagattttccatgcattcgtccataatgatggcaatgggcccacgggcggcg gcctgggcgaagatatttctgggatcactaacgtcatagttgtgttccaggatgagatcgtcataggccattttttacaaagcgcggg cggagggtgccagactgcggtataatggttccatccggcccaggggcgtagttaccctcacagatttgcatttcccacgctttgagt tcagatgggggggatcatgtctacctgcggggcgatgaagaaaacggtttccggggtagggagatcagctgggaagaaagcaggttc ctgagcagctgcgacttaccgcagccggtgggcccgtaaatcacacctattaccgggtgcaactggtagttaagagagctgcagctg ccgtcatccctgagcagggggggccacttcgttaagcatgtccctgactcgcatgttttccctgaccaaatccgccagaaggcgctcg ccgcccagcgatagcagttcttgcaaggaagcaaagttttttcaacggtttgagaccgtccgccgtaggcatgcttttgagcgtttga

| Sequences |
|---|
| ccaagcagttccaggcggtcccacagctcggtcacctgctctacggcatctcgatccagcatatctcctcgtttcgcgggttggggc |
| ggctttcgctgtacggcagtagtcggtgctcgtccagacgggccagggtcatgtctttccacgggcgcagggtcctcgtcagcgtag |
| tctgggtcacggtgaaggggtgcgctccgggctgcgcgctggccagggtgcgcttgaggctggtcctgctggtgctgaagcgctgcc |
| ggtcttcgccctgcgcgtcggccaggtagcatttgaccatggtgtcatagtccagcccctccgcggcgtggcccttggcgcgcagct |
| tgcccttggaggaggcgccgcacgaggggcagtcagacttttgagggcgtagagcttgggcgcgagaaataccgattccggggagt |
| aggcatccgcgccgcaggccccgcagacggtctcgcattccacgagccaggtgagctctggccgttcggggtcaaaaaccaggtttc |
| ccccatgcttttgatgcgtttcttacctctggtttccatgagccggtgtccacgctcggtgacgaaaaggctgtccgtgtcccgt |
| atacagacttgagaggcctgtcctcgagcggtgttccgcggtcctcctcgtatagaaactcggaccactctgagacaaaggctcgcg |
| tccaggccagcacgaaggaggctaagtgggaggggtagcggtcgttgtccactaggggggccactcgctccagggtgtgaagacaca |
| tgtcgccctcttcggcatcaaggaaggtgattggtttgtaggtgtaggccacgtgaccgggtgttcctgaagggggctataaagg |
| gggtgggggcgcgttcgtcctcactctcttccgcatcgctgtctgcgagggccagctgttgggtgagtactccctctgaaaagcgg |
| gcatgacttctgcgctaagattgtcagtttccaaaaacgaggaggatttgatattcacctggcccgcggtgatgcctttgagggtgg |
| ccgcatccatctggtcagaaaagacaatcttttgttgtcaagcttggtggcaaacgacccgtagagggcgttggacagcaacttgg |
| cgatggagcgcagggttggttttgtcgcgatcggcgcgctccttggccgcgatgtttagctgcacgtattcgcgcgcaacgcacc |
| gccattcggaaagacggtggtgcgctcgtcgggcaccaggtgcacgcgccaaccgcggttgtgcagggtgacaaggtcaacgctgg |
| tggctacctctccgcgtaggcgctcgttggtccagcagaggcggccgcccttgcgcgagcagaatggcggtagggggtctagctgcg |
| tctcgtccgggggtctgcgtccacggtaaagaccccgggcagcaggcgcgcgtcgaagtagtctatcttgcatccttgcaagtcta |
| gcgcctgctgccatgcgcgggcggcaagcgcgcgctcgtatgggttgagtgggggaccccatggcatgggtgggtgagcgcggagg |
| cgtacatgccgcaaatgtcgtaaacgtagaggggctctctgagtattccaagatatgtagggtagcatcttccaccgcggatgctgg |
| cgcgcacgtaatcgtatagttcgtgcgagggagcgaggaggtcgggaccgaggttgctacgggcgggctgctctgctcggaagacta |
| tctgcctgaagatggcatgtgagttggatgatatggttggacgctggaagacgttgaagctggcgtctgtgagacctaccgcgtcac |
| gcacgaaggaggcgtaggagtcgcgcagcttgttgaccagctcggcggtgacctgcacgtctagggcgcagtagtccagggtttcct |
| tgatgatgtcatacttatcctgtccctttttttccacagctcgcggttgaggacaaactcttcgcggtctttccagtactcttgga |
| tcggaaacccgtcggcctccgaacggtaagagcctagcatgtagaactggttgacggcctggtaggcgcagcatcccttttctacgg |
| gtagcgcgtatgcctgcgcggccttccggagcgaggtgtgggtgagcgcaaaggtgtccctgaccatgactttgaggtactggtatt |
| tgaagtcagtgtcgtcgcatccgccctgctcccagagcaaaaagtccgtgcgcttttggaacgcggatttggcagggcgaaggtga |
| catcgttgaagagtatctttcccgcgcgaggcataaagttgcgtgtgatgcggaagggtcccggcacctcggaacggttgttaatta |
| cctgggcggcgagcacgatctcgtcaaagccgttgatgttgtggcccacaatgtaaagttccaagaagcgcgggatgcccttgatgg |
| aaggcaattttttaagttcctcgtaggtgagctcttcaggggagctgagcccgtgctctgaaagggcccagtctgcaagatgagggt |
| tggaagcgacgaatgagctccacaggtcacgggccattagcatttgcaggtggtcgcgaaaggtcctaaactggcgacctatggcca |
| ttttttctggggtgatgcagtagaaggtaagcgggtcttgttcccagcggtcccatccaaggttcgcggctaggtctcgcgcggcag |
| tcactagaggctcatctccgccgaacttcatgaccagcatgaagggcacgagctgcttcccaaaggcccccatccaagtataggtct |
| ctacatcgtaggtgacaaagagacgctcggtgcgaggatgcgagccgatcgggaagaactggatctcccgccaccaattggaggagt |
| ggctattgatgtggtgaaagtagaagtccctgcgacgggccgaacactcgtgctggcttttgtaaaaacgtgcgcagtactggcagc |
| ggtgcacgggctgtacatcctgcacgaggttgacctgacgaccgcgcacaaggaagcagagtgggaatttgagcccctcgcctggcg |
| ggtttggctggtggtcttctacttcggctgcttgtccttgaccgtctggctgctcgagggagttacggtggatcggaccaccacgc |
| cgcgcgagcccaaagtccagatgtccgcgcgcggcggtcggagcttgatgacaacatcgcgcagatgggagctgtccatggtctgga |
| gctcccgcggcgtcaggtcaggcgggagctcctgcaggtttacctcgcatagacgggtcagggcgcgggctagtccaggtgatacc |
| taatttccaggggctggttggtggcggcgtcgatggcttgcaagaggccgcatccccgcggcgcgactacggtaccgcgcggcggc |

| Sequences |
|---|
| ggtgggccgcggggdtgtccttggatgatgcatctaaaagcggtgacgcgggcgagccccggaggtagggggggctccggacccgc |
| cgggagaggggcaggggcacgtcggcgccgcgcgcgggcaggagctggtgctgcgcgcgtaggttgctggcgaacgcgacgacgcg |
| gcggttgatctcctgaatctggcgcctctgcgtgaagacgacgggcccggtgagcttgagcctgaaagagagttcgacagaatcaat |
| ttcggtgtcgttgacggcggcctggcgcaaaatcctgcacgtctcctgagttgtcttgataggcgatctcggccatgaactgctc |
| gatctcttcctcctggagatctccgcgtccggctcgctccacggtggcggcgaggtcgttggaaatgcgggccatgagctgcgagaa |
| ggcgttgaggcctccctcgttccagacgcggctgtagaccacgccccttcggcatcgcgggcgcgcatgaccacctgcgcgagatt |
| gagctccacgtgccgggcgaagacggcgtagtttcgcaggcgctgaaagaggtagttgagggtggtggcggtgtgttctgccacgaa |
| gaagtacataacccagcgtcgcaacgtggattcgttgatatccccaaggcctcaaggcgctccatggcctcgtagaagtccacggc |
| gaagttgaaaaactgggagttgcgcgccgacacggttaactcctcctccagaagacggatgagctcggcgacagtgtcgcgcacctc |
| gcgctcaaaggctacaggggcctcttcttcttcttcaatctcctcttccataagggcctccccttcttcttcttctggcggcggtgg |
| gggaggggggacacggcggcgacgacggcgcaccgggaggcggtcgacaaagcgctcgatcatctccccgcggcgacggcgcatggt |
| ctcggtgacggcgcggccgttctcgcggggggcgcagttggaagacgccgcccgtcatgtcccggttatgggttggcggggggctgcc |
| atgcggcagggatacgcgctaacgatgcatctcaacaattgttgtgtaggtactccgccgccgagggacctgagcgagtccgcatc |
| gaccggatcggaaaacctctcgagaaaggcgtctaaccagtcacagtcgcaaggtaggctgagcaccgtggcgggcggcagcgggcg |
| gcggtcgggttgtttctggcggaggtgctgctgatgatgtaattaaagtaggcggtcttgagacggcggatggtcgacagaagcac |
| catgtccttgggtccggcctgctgaatgcgcaggcggtcggccatgccccaggcttcgttttgacatcggcgcaggtctttgtagta |
| gtcttgcatgagccttttctaccggcacttcttcttctccttcctcttgtcctgcatctcttgcatctatcgctgcggcggcggcgga |
| gtttggccgtaggtggcgccctcttcctcccatgcgtgtgaccccgaagcccctcatcggctgaagcagggctaggtcggcgacaac |
| gcgctcggctaatatgcctgctgcacctgcgtgagggtagactggaagtcatccatgtccacaaagcggtggtatgcgcccgtgtt |
| gatggtgtaagtgcagttggccataacggaccagttaacggtctggtgacccggctgcgagagctcggtgtacctgagacgcgagta |
| agccctcgagtcaaatacgtagtcgttgcaagtccgcaccaggtactggtatcccaccaaaaagtgcggcggcggctggcggtagag |
| gggccagcgtagggtggccggggctccgggggcgagatcttccaacataaggcgatgatatccgtagatgtacctggacatccaggt |
| gatgccggcggcggtggtggaggcgcgcgaaagtcgcggacgcggttccagatgttgcgcagcggcaaaaagtgctccatggtcgg |
| gacgctctggccggtcaggcgcgcgcaatcgttgacgctctagaccgtgcaaaaggagagcctgtaagcgggcactcttccgtggtc |
| tggtggataaattcgcaagggtatcatggcggacgaccggggttcgagccccgtatccggccgtccgccgtgatccatgcggttacc |
| gcccgcgtgtcgaacccaggtgtgcgacgtcagacaacggggagtgctccttttggcttccttccaggcgcggcggctgctgcgct |
| agcttttttggccactggccgcgcgcagcgtaagcggttaggctggaaagcgaaagcattaagtggctcgctccctgtagccggagg |
| gttattttccaagggttgagtcgcgggaccccggttcgagtctcggaccggccggactgcggcgaacggggtttgcctccccgtc |
| atgcaagacccgcttgcaaattcctccggaaacagggacgagccccttttttgcttttcccagatgcatccggtgctgcggcagat |
| gcgcccctcctcagcagcggcaagagcaagagcagcggcagacatgcagggcaccctcccctcctcctaccgcgtcaggaggggc |
| gacatccgcggttgacgcggcagcagatggtgattacgaaccccgcggcgccgggcccggcactacctggacttggaggagggcga |
| gggcctggcgcggctaggagcgccctctcctgagcggtacccaagggtgcagctgaagcgtgatacgcgtgaggcgtacgtgccgcg |
| gcagaacctgtttcgcgaccgcgagggagaggagcccgaggagatgcgggatcgaaagttccacgcagggcgcgagctgcggcatgg |
| cctgaatcgcgagcggttgctgcgcgaggaggactttgagcccgacgcgcgaaccgggattagtcccgcgcgcgcacacgtggcggc |
| cgccgacctggtaaccgcatacgagcagacggtgaaccaggagattaactttcaaaaaagctttaacaaccacgtgcgtacgcttgt |
| ggcgcgcgaggaggtggctataggactgatgcatctgtgggactttgtaagcgcgctggagcaaaacccaaatagcaagccgctcat |
| ggcgcagctgttccttatagtgcagcacagcagggacaacgaggcattcagggatgcgctgctaaacatagtagagcccgagggcca |
| ctggctgctcgatttgataaacatcctgcagagcatagtggtgcaggagcgcagcttgagcctggctgacaaggtggccgccatcaa |

| Sequences |
| --- |
| ctattccatgcttagcctgggcaagttttacgcccgcaagatataccatacccct tacgttcccatagacaaggaggtaaagatcga |
| ggggttctacatgcgcatggcgctgaaggtgcttaccttgagcgacgacctgggcgtttatcgcaacgagcgcatccacaaggccgt |
| gagcgtgagccggcggcgcgagctcagcgaccgcgagctgatgcacagcctgcaaagggccctggctggcacgggcagcggcgatag |
| agaggccgagtcctactttgacgcgggcgctgacctgcgctgggccccaagccgacgcgcccggaggcagctggggccggacctgg |
| gctggcggtggcacccgcgcgcgctggcaacgtcggcggcgtggaggaatatgacgaggacgatgagtacgagccagaggacggcga |
| gtactaagcggtgatgtttctgatcagatgatgcaagacgcaacggacccggcggtgcgggcggcgctgcagagccagccgtccggc |
| cttaactccacggacgactggcgccaggtcatggaccgcatcatgtcgctgactgcgcgcaatcctgacgcgttccggcagcagccg |
| caggccaaccggctctccgcaattctggaagcggtggtcccggcgcgcgcaaacccacgcacgagaaggtgctggcgatcgtaaac |
| gcgctggccgaaaacagggccatccggcccgacgaggccggcctggtctacgacgcgctgcttcagcgcgtggctcgttacaacagc |
| ggcaacgtgcagaccaacctggaccggctggtgggggatgtgcgcgaggccgtggcgcagcgtgagcgcgcgcagcagcagggcaac |
| ctgggctccatggttgcactaaacgccttcctgagtacacagcccgccaacgtgccgcggggacaggaggactacaccaactttgtg |
| agcgcactgcgcgctaatggtgactgagacaccgcaaagtgaggtgtaccagtctgggccagactatttttccagaccagtagacaa |
| ggcctgcagaccgtaaacctgagccaggcttt caaaaact tgcaggggct gt gggggg t gcgggct cccacaggcgaccgcgcgacc |
| gtgtctagcttgctgacgcccaactcgcgcctgttgctgctgctaatagcgcccttcacggacagtggcagcgtgtcccgggacaca |
| tacctaggtcacttgctgacactgtaccgcgaggccataggtcaggcgcatgtggacgagcatacttt ccaggagattacaagt gtc |
| agccgcgcgctggggcaggaggacacgggcagcctggaggcaacccta aa ctacctgctgaccaaccggcggcagaagatcccctcg |
| ttgcacagtttaaacagcgaggaggagcgcatttt gcgctacgtgcagcagagcgtgagccttaacctgat gcgcgacggggtaacg |
| cccagcgtggcgctggacatgaccgcgcgcaacatggaacc gggcatgt atgcctcaaaccggccgtttatcaaccgcctaatggac |
| tacttgcatcgcgcggccgccgtgaaccccgagtatttcaccaatgccatcttgaacccgcactggctaccgcccctggtttctac |
| accggggattcgaggtgcccgagggtaacgatggattcctctgggacgacatagacgacagcgtgttttccccgcaaccgcagacc |
| ctgctagagttgcaacagcgcgagcaggcagaggcggcgctgcgaaaggaaagcttccgcaggccaagcagcttgtccgatctaggc |
| gctgcggccccgcggtcagatgctagtagcccatttccaagcttgatagggtctcttaccagcactcgcaccacccgcccgcgcctg |
| ctgggcgaggaggagtacctaaacaactcgctgctgcagccgcagcgcgaaaaaaacctgcctccggcatttcccaacaacgggata |
| gagagcctagtggacaagatgagtagatggaagacgtacgcgcaggagcacagggacgtgccaggcccgcgcccgcccacccgtcgt |
| caaaggcacgaccgtcagcggggtctggtgtgggaggacgatgactcggcagacgacagcagcgtcctggatttgggagggagtggc |
| aacccgtttgcgcaccttcgcccaggctggggagaatgttttaaaaaaaaaaagcatgatgcaaaataaaaaactcaccaaggcc |
| atggcaccgagcgttggttttcttgtattccccttagtatgcggcgcgcggcgatgtatgaggaaggtcctcctccctcctacgaga |
| gtgtggtgagcgcggcgccagtggcggcggcgctgggttctcccttcgatgctccctggacccgccgtttgtgcctccgcggtacc |
| tgcggcctaccgggggagaaacagcatccgttactctgagttggcaccccta ttcgacaccaccc gtgtgtacctggtggacaaca |
| agtcaacggatgtggcatccctgaactaccagaacgaccacagcaactttctgaccacggtcattcaaaacaatgactacagcccgg |
| gggaggcaagcacacagaccatcaatcttgacgaccggtcgcactggggcggcgacctgaaaaccatcctgcataccaacatgccaa |
| atgtgaacgagttcatgtttaccaataagtttaaggcgcgggtgatggtgtcgcgcttgcctactaaggacaatcaggtggagctga |
| aatacgagtgggtggagttcacgctgcccgagggcaactactccgagaccatgaccatagaccttatgaacaacgcgatcgtggagc |
| actacttgaaagtgggcagacagaacgggggttctggaaagcgacatcggggtaaagtttgacacccgcaacttcagactggggtttg |
| accccgtcactggtcttgtcatgcctggggtatatacaaacgaagccttccatccagacatcattttgctgccaggatgcgggtgg |
| acttcacccacagccgcctgagcaacttgttgggcatccgcaagcggcaaccctt ccaggagggctttaggatcacctacgatgatc |
| tggagggtggtaacattcccgcactgttggatgtggacgcctaccaggcgagcttgaaagatgacaccgaacagggcgggggtggcg |
| caggcggcagcaacagcagtggcagcggcgcggaagagaactccaacgcggcagccgcggcaatgcagccggtggaggacatgaacg |
| atcatgccattcgcggcgacacctttgccacacgggctgaggagaagcgcgctgaggccgaagcagcggccgaagctgccgcccccg |

-continued

| Sequences |
|---|
| ctgcgcaacccgaggtcgagaagcctcagaagaaaccggtgatcaaaccctgacagaggacagcaagaaacgcagttacaacctaa |
| taagcaatgacagcaccttcacccagtaccgcagctggtaccttgcatacaactacggcgaccctcagaccggaatccgctcatgga |
| ccctgctttgcactcctgacgtaacctgcggctcggagcaggtctactggtcgttgccagacatgatgcaagaccccgtgaccttcc |
| gctccacgcgccagatcagcaactttccggtggtgggcgccgagctgttgcccgtgcactccaagagcttctacaacgaccaggccg |
| tctactcccaactcatccgccagtttacctctctgacccacgtgttcaatcgctttcccgagaaccagattttggcgcgcccgccag |
| cccccaccatcaccaccgtcagtgaaaacgttcctgctctcacagatcacgggacgctaccgctgcgcaacagcatcggaggagtcc |
| agcgagtgaccattactgacgccagacgccgcacctgccctacgtttacaaggccctgggcatagtctcgccgcgcgtcctatcga |
| gccgcacttttgagcaagcatgtccatccttatatcgcccagcaataacacaggctggggcctgcgcttcccaagcaagatgtttg |
| gcggggccaagaagcgctccgaccaacacccagtgcgcgtgcgcgggcactaccgcgcgccctgggcgcgcacaaacgcggccgca |
| ctgggcgcaccaccgtcgatgacgccatcgacgcggtggtggaggaggcgcgcaactacacgcccacgccgccaccagtgtccacag |
| tggacgcggccattcagaccgtggtgcgcggagcccggcgctatgctaaaatgaagagacggcggaggcgcgtagcacgtcgccacc |
| gccgccgacccggcactgccgcccaacgcgcggcggcggccctgcttaaccgcgcacgtcgcaccggccgacgggcggccatgcggg |
| ccgctcgaaggctggccgcgggtattgtcactgtgccccccaggtccaggcgacgagcggccgccgcagcagccgcggccattagtg |
| ctatgactcagggtcgcaggggcaacgtgtattgggtgcgcgactcggttagcggcctgcgcgtgcccgtgcgcacccgccccccgc |
| gcaactagattgcaagaaaaaactacttagactcgtactgttgtatgtatccagcggcggcggcgcgcaacgaagctatgtccaagc |
| gcaaaatcaaagaagagatgctccaggtcatcgcgccggagatctatggcccccccgaagaaggaagagcaggattacaagccccgaa |
| agctaaagcgggtcaaaaagaaaaagaaagatgatgatgatgaacttgacgacgaggtggaactgctgcacgctaccgcgcccaggc |
| gacgggtacagtggaaaggtcgacgcgtaaaacgtgttttgcgacccggcaccaccgtagtctttacgcccggtgagcgctccaccc |
| gcacctacaagcgcgtgtatgatgaggtgtacgcgacgaggacctgcttgagcaggccaacgagcgcctcggggagtttgcctacg |
| gaaagcggcataaggacatgctggcgttgccgctggacgagggcaacccaacacctagcctaaagcccgtaacactgcagcaggtgc |
| tgcccgcgcttgcaccgtccgaagaaaagcgcggcctaaagcgcgagtctggtgacttggcaccaccgtgcagctgatggtaccca |
| agcgccagcgactggaagatgtcttggaaaaaatgaccgtggaacctgggctggagcccgaggtccgcgtgcggccaatcaagcagg |
| tggcgccgggactgggcgtgcagaccgtggacgttcagatacccactaccagtagcaccagtattgccaccgccacagagggcatgg |
| agacacaaacgtccccggttgcctcagcggtggcggatgccgcggtgcaggcggtcgctgcggccgcgtccaagacctctacggagg |
| tgcaaacggacccgtggatgtttcgcgtttcagcccccggcgcccgcgcggttcgaggaagtacggcgccgccagcgcgctactgc |
| ccgaatatgccctacatccttccattgcgcctaccccgctatcgtggctacacctaccgcccagaagacgagcaactacccgac |
| gccgaaccaccactggaacccgccgccgccgtcgccgtcgccagcccgtgctggccccgatttccgtgcgcagggtggctcgcgaag |
| gaggcaggaccctggtgctgccaacagcgcgctaccaccccagcatcgtttaaaagccggtctttgtggttcttgcagatatggccc |
| tcacctgccgcctccgtttcccggtgccgggattccgaggaagaatgcaccgtaggaggggcatggccggccacggcctgacgggcg |
| gcatgcgtcgtgcgcaccaccggcggcggcgcgtcgcaccgtcgcatgcgcggcggtatcctgcccctccttattccactgatcg |
| ccgcggcgattggcgccgtgcccggaattgcatccgtggccttgcaggcgcagagacactgattaaaaacaagttgcatgtggaaaa |
| atcaaaataaaaagtctggactctcacgctcgcttggtcctgtaactattttgtagaatggaagacatcaactttgcgtctctggcc |
| ccgcgacacggctcgcgcccgttcatgggaaactggcaagatatcggcaccagcaatatgagcggtggcgccttcagctggggctcg |
| ctgtggagcggcattaaaaatttcggttccaccgttaagaactatggcagcaaggcctggaacagcagcacaggccagatgctgagg |
| gataagttgaaagagcaaaatttccaacaaaaggtggtagatggcctggcctctggcattagcggggtggtggacctggccaaccag |
| gcagtgcaaaataagattaacagtaagcttgatcccgccctcccgtagaggagcctccaccggccgtggagacagtgtctccagag |
| gggcgtggcgaaaagcgtccgcgcccgacagggaagaaactctggtgacgcaaatagacgagcctccctcgtacgaggaggcacta |
| aagcaaggcctgcccaccacccgtcccatcgcgcccatggctaccggagtgctgggccagcacacacccgtaacgctggacctgcct |

-continued

| Sequences |
|---|
| cccccgccgacacccagcagaaacctgtgctgccaggcccgaccgcgttgttgtaacccgtcctagccgcgcgtccctgcgccgc |
| gccgccagcggtccgcgatcgttgcggcccgtagccagtggcaactggcaaagcacactgaacagcatcgtgggtctgggggtgcaa |
| tccctgaagcgccgacgatgcttctgaatagctaacgtgtcgtatgtgtgtcatgtatgcgtccatgtcgccgccagaggagctgct |
| gagccgccgcgcgcccgctttccaagatggctaccccttcgatgatgccgcagtggtcttacatgcacatctcgggccaggacgcct |
| cggagtacctgagccccgggctggtgcagtttgcccgcgccaccgagacgtacttcagcctgaataacaagtttagaaaccccacgg |
| tggcgcctacgcacgacgtgaccacagaccggtcccagcgtttgacgctgcggttcatccctgtggaccgtgaggatactgcgtact |
| cgtacaaggcgcggttcaccctagctgtgggtgataaccgtgtgctggacatggcttccacgtactttgacatccgcggcgtgctgg |
| acaggggccctacttttaagccctactctggcactgcctacaacgccctggctcccaagggtgcccaaatccttgcgaatgggatg |
| aagctgctactgctcttgaaataaacctagaagaagaggacgatgacaacgaagacgaagtagacgagcaagctgagcagcaaaaa |
| ctcacgtatttgggcaggcgccttattctggtataaatattacaaaggagggtattcaaataggtgtcgaaggtcaaacacctaaat |
| atgccgataaaacatttcaacctgaacctcaaataggagaatctcagtggtacgaaactgaaattaatcatgcagctgggagagtcc |
| ttaaaaagactaccccaatgaaaccatgttacggttcatatgcaaaacccacaaatgaaaatggagggcaaggcattcttgtaaagc |
| aacaaaatggaaagctagaaagtcaagtggaaatgcaattttttctcaactggaagcggttctcgctacctggagcctggcccagtga |
| ctgccgctggttccggaagcagatacatggacggaacaatgtcccaggttgccggttctggctcccctaaagtggtattgtacagtg |
| aagatgtagatatagaaaccccagacactcatatttcttacatgcccactattaaggaaggtaactcacgagaactaatgggccaac |
| aatctatgcccaacaggcctaattacattgcttttagggacaattttattggtctaatgtattacaacagcacgggtaatatgggtg |
| ttctggcgggccaagcatcgcagttgaatgctgttgtagatttgcaagacagaaacacagagctttcataccagcttttgcttgatt |
| ccattggtgatagaaccaggtacttttctatgtggaatcaggctgttgacagctatgatccagatgttagaattattgaaaatcatg |
| gaactgaagatgaacttccaaattactgctttccactgggaggtgtgattaatacagagactcttaccaaggtaaaacctaaaacag |
| gtcaggaaatggatgggaaaaagatgctacagaattttcagataaaaatgaataagagttggaaataattttgccatggaaatca |
| atctaaatgccaacctgtggagaaatttcctgtactccaacatagcgctgtatttgcccgacaagctaaagtacagtccttccaacg |
| taaaaatttctgataacccaaacacctacgactacatgaacaagcgagtggtggctcccgggttagtggactgctacattaaccttg |
| gagcacgctggtcccttgactatatggacaacgtcaacccatttaaccaccaccgcaatgctggcctgcgctaccgctcaatgttgc |
| tgggcaatggtcgctatgtgcccttccacatccaggtgcctcagaagttctttgccattaaaaacctccttctcctgccgggctcat |
| acacctacgagtggaacttcaggaaggatgttaacatggttctgcagagctccctaggaaatgacctaagggttgacggagccagca |
| ttaagtttgatagcatttgcctttacgccaccttcttccccatggcccacaacaccgcctccacgcttgaggccatgcttagaaacg |
| acaccaacgaccagtccttaaacgactatctctccgccgccaacatgctctaccctatacccgccaacgctaccaacgtgcccatat |
| ccatcccctcccgcaactgggcggcttccgcggctgggccttcacgcgccttaagactaaggaaacccatcactgggctcgggct |
| acgaccctattacacctactctggctctataccctacctagatggaaccttttacctcaaccacacctttaagaaggctgccatta |
| cctttgactcttctgtcagctggcctggcaatgaccgctgcttaccccaacgagtttgaaattaagcgctcagttgacggggagg |
| gttacaacgttgcccagtgtaacatgaccaaagactggttcctggtacaaatgctagctaactataacattggctaccagggcttct |
| atatcccagagagctacaaggaccgcatgtactccttctttagaaacttccagcccatgagccgtcaggtggtggatgatactaaat |
| acaaggactaccaacaggtgggcatcctacaccaacacaacaactctggatttgttggctaccttgcccccaccatgcgcgaaggac |
| aggcctaccctgctaacttcccctatccgcttataggcaagaccgcagttgacagcattacccagaaaaagtttctttgcgatcgca |
| ccctttggcgcatcccattctccagtaactttatgtccatgggcgcactcacagacctgggcaaaacctcctctacgccaactccg |
| cccactccctagacatgacttttgaggtggatcccatggacgagcccaccttctttatgttttgtttgaagtcttttgacaaggtcc |
| gtgtgcaccagccgcaccgcggcgtcatcgaaaccgtgtacctgcgcacgcccttctcggccggcaacgccacaacataaagaagca |
| agcaacatcaacaacagctgccgccatgggctccagtgagcaggaactgaaagccattgtcaaagatcttggttgtgggccatattt |
| tttgggcacctatgacaagcgctttccaggctttgtttctccacacaagctcgcctgcgccatagtcaatacggccggtcgcgagac |

-continued

Sequences tgggggcgtacactggatggcctttgcctggaacccgcactcaaaaacatgctacctctttgagccctttggcttttctgaccagcg actcaagcaggtttaccagtttgagtacgagtcactcctgcgccgtagcgccattgcttcttccccgaccgctgtataacgctgga aaagtccacccaaagcgtacaggggcccaactcggccgcctgtggactattctgctgcatgtttctccacgcctttgccaactggcc ccaaactcccatggatcacaaccccaccatgaaccttattaccggggtacccaactccatgctcaacagtccccaggtacagcccac cctgcgtcgcaaccaggaacagctctacagcttcctggagcgccactcgccctacttccgcagccacagtgcgcagattaggagcgc cacttcttttttgtcacttgaaaaacatgtaaaaataatgtactagagacactttcaataaaggcaaatgcttttatttgtacactct cgggtgattatttacccccacccttgccgtctgcgccgtttaaaaatcaaaggggttctgccgcgcatcgctatgcgccactggcag ggacacgttgcgatactggtgtttagtgctccacttaaactcaggcacaaccatccgcggcagctcggtgaagttttcactccacag gctgcgcaccatcaccaacgcgtttagcaggtcgggcgccgatatcttgaagtcgcagttggggcctccgccctgcgcgcgcgagtt gcgatacacagggttgcagcactggaacactatcagcgccggtggtgcacgctggccagcacgctcttgtcggagatcagatccgc gtccaggtcctccgcgttgctcagggcgaacggagtcaactttggtagctgccttcccaaaaagggcgcgtgcccaggctttgagtt gcactcgcaccgtagtggcatcaaaaggtgaccgtgcccggtctgggcgttaggatacagcgcctgcataaaagccttgatctgctt aaaagccacctgagcctttgcgccttcagagaagaacatgccgcaagacttgccggaaaactgattggccggacaggccgcgtcgtg cacgcagcaccttgcgtcggtgttggagatctgcaccacatttcggccccaccggttcttcacgatcttggccttgctagactgctc cttcagcgcgcgctgcccgttttcgctcgtcacatccatttcaatcacgtgctccttatttatcataatgcttccgtgtagacactt aagctcgccttcgatctcagcgcagcggtgcagccacaacgcgcagcccgtgggctcgtgatgcttgtaggtcacctctgcaaacga ctgcaggtacgcctgcaggaatcgccccatcatcgtcacaaaggtcttgttgctggtgaaggtcagctgcaaccgcggtgctcctc gttcagccaggtcttgcatacggccgccagagcttccacttggtcaggcagtagtttgaagttcgcctttagatcgttatccacgtg gtacttgtccatcagcgcgcgcgcagcctccatgcccttctcccacgcagacacgatcggcacactcagcgggttcatcaccgtaat ttcactttccgcttcgctgggctcttcctcttcctcttgcgtccgcataccacgcgccactgggtcgtcttcattcagccgccgcac tgtgcgcttacctcctttgccatgcttgattagcaccggtggttgctgaaacccaccatttgtagcgccacatcttctctttcttc ctcgctgtccacgattacctctggtgatggcgggcgctcgggcttgggagaagggcgcttcttttttcttcttgggcgcaatggccaa atccgccgccgaggtcgatggccgcgggctgggtgtgcgcggcaccagcgcgtcttgtgatgagtcttcctcgtcctcggactcgat acgccgcctcatccgcttttttgggggcgcccggggaggcggcggcgacggggacggggacgacacgtcctccatggttgggggacg tcgcgccgcaccgcgtccgcgctcggggtggtttcgcgctgctcctcttcccgactggccatttccttctcctataggcagaaaaa gatcatggagtcagtcgagaagaaggacagcctaaccgcccctctgagttcgccaccaccgcctccaccgatgccgccaacgcgcc taccaccttccccgtcgaggcaccccgcttgaggaggaggaagtgattatcgagcaggacccaggttttgtaagcgaagacgacga ggaccgctcagtaccaacagaggataaaaagcaagaccaggacaacgcagaggcaaacgaggaacaagtcgggcgggggggacgaaag gcatggcgactacctagatgtgggagacgacgtgctgttgaagcatctgcagcgccagtgcgccattatctgcgacgcgttgcaaga gcgcagcgatgtgcccctcgccatagcggatgtcagccttgcctacgaacgccacctattctcaccgcgcgtaccccccaaacgcca agaaaacggcacatgcgagcccaacccgcgcctcaacttctaccccgtatttgccgtgccagaggtgcttgccacctatcacatctt tttccaaaactgcaagataccctatcctgccgtgccaaccgcagccgagcggacaagcagctggccttgcggcagggcgctgtcat acctgatatcgcctcgctcaacgaagtgccaaaaatctttgagggtcttggacgcgacgagaagcgcgcggcaaacgctctgcaaca ggaaaacagcgaaaatgaaagtcactctggagtgttggtggaactcgagggtgacaacgcgcgcctagccgtactaaaacgcagcat cgaggtcacccactttgcctacccggcacttaacctaccccccaaggtcatgagcacagtcatgagtgagctgatcgtgcgccgtgc gcagcccctggagagggatgcaaatttgcaagaacaaacagaggagggcctacccgcagttggcgacgagcagctagcgcgctggct tcaaacgcgcgagcctgccgacttggaggagcgacgcaaactaatgatggccgcagtgctcgttaccgtggagcttgagtgcatgca gcggttctttgctgacccggagatgcagcgcaagctagaggaaacattgcactacacctttcgacagggctacgtacgccaggcctg

| Sequences |
| --- |
| caagatctccaacgtggagctctgcaacctggtctcctaccttggaattttgcacgaaaaccgccttgggcaaaacgtgcttcattc |
| cacgctcaagggcgaggcgcgccgcgactacgtccgcgactgcgtttacttatttctatgctacacctggcagacggccatgggcgt |
| tggcagcagtgcttggaggagtgcaacctcaaggagctgcagaaactgctaaagcaaaacttgaaggacctatggacggccttcaa |
| cgagcgctccgtggccgcgcacctggcggacatcattttccccgaacgcctgcttaaaaccctgcaacagggtctgccagacttcac |
| cagtcaaagcatgttgcagaactttaggaactttatcctagagcgctcaggaatcttgcccgccacctgctgtgcacttcctagcga |
| ctttgtgcccattaagtaccgcgaatgccctccgccgctttggggccactgctaccttctgcagctagccaactaccttgcctacca |
| ctctgacataatggaagacgtgagcggtgacggtctactggagtgtcactgtcgctgcaacctatgcaccccgcaccgctccctggt |
| ttgcaattcgcagctgcttaacgaaagtcaaattatcggtacctttgagctgcagggtccctcgcctgacgaaaagtccgcggctcc |
| ggggttgaaactcactccggggctgtggacgtcggcttaccttcgcaaatttgtacctgaggactaccacgcccacgagattaggtt |
| ctacgaagaccaatcccgcccgccaaatgcggagcttaccgcctgcgtcattacccagggccacattcttggccaattgcaagccat |
| caacaaagcccgccaagagtttctgctacgaaagggacggggggtttacttggaccccagtccggcgaggagctcaacccaatccc |
| cccgccgccgcagccctatcagcagcagccgcgggcccttgcttcccaggatggcacccaaaaagaagctgcagctgccgccgccac |
| ccacggacgaggaggaatactgggacagtcaggcagaggaggttttggacgaggaggaggaggacatgatggaagactgggagagcc |
| tagacgaggaagcttccgaggtcgaagaggtgtcagacgaaaccgtcaccctcggtcgcattccctcgccggcgccccagaaat |
| cggcaaccggttccagcatggctacaacctccgctcctcaggcgccgccggcactgcccgttcgccgacccaaccgtagatgggaca |
| ccactggaaccagggccggtaagtccaagcagccgccgccgttagcccaagagcaacaacagcgccaaggctaccgctcatggcgcg |
| ggcacaagaacgccatagttgcttgcttgcaagactgtgggggcaacatctccttcgcccgccgctttcttctctaccatcacggcg |
| tggccttcccccgtaacatcctgcattactaccgtcatctctacagcccatactgcaccggcggcagcggcagcggcagcaacagca |
| gcggccacacagaagcaaaggcgaccggatagcaagactctgacaaagcccaagaaatccacagcggcggcagcagcaggaggagga |
| gcgctgcgtctggcgcccaacgaacccgtatcgaccccgcgagcttagaaacaggatttttcccactctgtatgctatatttcaacag |
| agcaggggccaagaacaagagctgaaaataaaaaacaggtctctgcgatccctcacccgcagctgcctgtatcacaaaagcgaagat |
| cagcttcggcgcacgctggaagacgcggaggctctcttcagtaaatactgcgcgctgactcttaaggactagtttcgcgcccttct |
| caaatttaagcgcgaaaactacgtcatctccagcggccacacccggcgccagcacctgtcgtcagcgccattatgagcaaggaaatt |
| cccacgccctacatgtggagttaccagccacaaatgggacttgcggctggagctgcccaagactactcaacccgaataaactacatg |
| agcgcgggaccccacatgatatcccgggtcaacggaatccgcgccaccgaaaccgaattctcttggaacaggcggctattaccacc |
| acacctcgtaataaccttaatccccgtagttggcccgctgccctggtgtaccaggaaagtcccgctcccaccactgtggtacttccc |
| agagacgcccaggccgaagttcagatgactaactcaggggcgcagcttgcgggcggctttcgtcacagggtgcggtcgcccgggcag |
| ggtataactcacctgacaatcagagggcgaggtattcagctcaacgacgagtcggtgagctcctcgcttggtctccgtccggacggg |
| acatttcagatcggcggcgccggccgtccttcattcacgcctcgtcaggcaatcctaactctgcagacctcgtcctctgagccgcgc |
| tctggaggcattggaactctgcaatttattgaggagtttgtgccatcggtctactttaacccttctcgggacctcccggccactat |
| ccggatcaatttattcctaactttgacgcggtaaaggactcggcggacggctacgactgaatgttaagtggagaggcagagcaactg |
| cgcctgaaacacctggtccactgtcgccgccacaagtgctttgcccgcgactccggtgagttttgctactttgaattgcccgaggat |
| catatcgagggcccggcgcacggcgtccggcttaccgcccagggagagcttgcccgtagcctgattcggagtttacccagcgcccc |
| ctgctagttgagcgggacaggggaccctgtgttctcactgtgatttgcaactgtcctaaccttggattacatcaagatctttgttgc |
| catctctgtgctgagtataataaatacagaaattaaaatatactggggctcctatcgccatcctgtaaacgccaccgtcttcacccg |
| cccaagcaaaccaaggcgaaccttacctggtacttttaacatctctccctctgtgatttacaacagtttcaacccagacggagtgag |
| tctacgagagaacctctccgagctcagctactccatcagaaaaacaccaccctccttacctgccgggaacgtacgagtgcgtcacc |
| ggccgctgcaccacacctaccgcctgaccgtaaaccagacttttccggacagacctcaataactctgtttaccagaacaggaggtg |
| agcttagaaaacccttagggtattaggccaaaggcgcagctactgtggggtttatgaacaattcaagcaactctacgggctattcta |

-continued

Sequences attcaggtttctctagaatcggggttggggttattctctgtcttgtgattctctttattcttatactaacgcttctctgcctaaggc tcgccgcctgctgtgtgcacatttgcatttattgtcagcttttaaacgctggggtcgccacccaagatgattaggtacataatcct aggtttactcacccttgcgtcagcccacggtaccaccccaaaaggtggattttaaggagccagcctgtaatgttacattcgcagctga agctaatgagtgcaccactcttataaaatgcaccacagaacatgaaaagctgcttattcgccacaaaaacaaaattggcaagtatgc tgtttatgctatttggcagccaggtgacactacagagtataatgttacagttttccagggtaaaagtcataaaacttttatgtatac ttttccattttatgaaatgtgcgacattaccatgtacatgagcaaacagtataagttgtggcccccacaaaattgtgtggaaaacac tggcactttctgctgcactgctatgctaattacagtgctcgctttggtctgtaccctactctatattaaatacaaaagcagacgcag ctttattgaggaaagaaaatgccttaatttactaagttacaaagctaatgtcaccactaactgctttactcgctgcttgcaaaaca aattcaaaaagttagcattataattagaataggatttaaaccccccggtcatttcctgctcaataccattcccctgaacaattgact ctatgtgggatatgctccagcgctacaaccttgaagtcaggcttcctggatgtcagcatctgactttggccagcacctgtcccgcgg atttgttccagtccaactacagcgacccaccctaacagagatgaccaacacaaccaacgcggccgccgctaccggacttacatctac cacaaatacaccccaagtttctgcctttgtcaataactgggataacttgggcatgtggtggttctccatagcgcttatgtttgtatg ccttattattatgtggctcatctgctgcctaaagcgcaaacgcgcccgaccacccatctatagtcccatcattgtgctacacccaaa caatgatggaatccatagattggacggactgaaacacatgttcttttctcttacagtatgattaaatgagacatgattcctcgagtt tttatattactgaccccttgttgcgcttttttgtgcgtgctccacattggctgcggtttctcacatcgaagtagactgcattccagcc ttcacagtctatttgctttacggatttgtcaccctcacgctcatctgcagcctcatcactgtggtcatcgcctttatccagtgcatt gactgggtctgtgtgcgctttgcatatctcagacaccatccccagtacagggacaggactatagctgagcttcttagaattcttaa ttatgaaatttactgtgacttttctgctgattatttgcaccctatctgcgtttgttccccgacctccaagcctcaaagacatatat catgcagattcactcgtatatggaatattccaagttgctacaatgaaaaaagcgatcttccgaagcctggttatatgcaatcatct ctgttatggtgttctgcagtaccatcttagccctagctatatatccctaccttgacattggctggaaacgaatagatgccatgaacc acccaactttccccgcgcccgctatgcttccactgcaacaagttgttgccggcggctttgtcccagccaatcagcctcgccccactt ctcccaccccactgaaatcagctactttaatctaacaggaggagatgactgacaccctagatctagaaatggacggaattattaca gagcagcgcctgctagaaagacgcagggcagcggccgagcaacagcgcatgaatcaagagctccaagacatggttaacttgcaccag tgcaaaagggggtatcttttgtctggtaaagcaggccaaagtcacctacgacagtaataccaccggacaccgccttagctacaagttg ccaaccaagcgtcagaaattggtggtcatggtgggagaaaagcccattaccataactcagcactcggtagaaaccgaaggctgcatt cactcaccttgtcaaggacctgaggatctctgcacccttattaagacctgtgcggtctcaaagatcttattcccttaactaataa aaaaaaataataaagcatcacttacttaaaatcagttagcaaatttctgtccagtttattcagcagcacctccttgccctcctccca gctctggtattgcagcttcctcctggctgcaaactttctccacaatctaaatggaatgtcagtttcctcctgttcctgtccatccgc acccactatcttcatgttgttgcagatgaagcgcgcaagaccgtctgaagataccttcaacccgtgtatccatatgacacggaaac cggtcctccaactgtgccttttcttactcctccctttgtatccccaatgggtttcaagagagtcccctgggtactctctttgcg cctatccgaacctctagttacctccaatggcatgcttgcgctcaaaatgggcaacggcctctctctggacgaggccggcaaccttac ctcccaaaatgtaaccactgtgagcccacctctccgaggagacaagtcaaacataaacctggaaatatctgcacccctcacagttac ctcagaagccctaactgtggctgccgccgcacctctaatggtcgcgggcaacacactcaccatgcaatcacaggccccgctaaccgt gcacgactccaaacttagcattgccacccaaggaccccctcacagtgtcagaaggaaagctagccctgcaaacatcaggcccctcac caccaccgatagcagtaccttactatcactgcctcacccctctaactactgccactggtagcttgggcattgacttgaaagagcc catttatacacaaaatggaaaactaggactaaagtacggggctcctttgcatgtaacagacgacctaaacactttgaccgtagcaac tggtccaggtgtgactattaataatacttccttgcaaactaaagttactggagccttgggttttgattcacaaggcaatatgcaact taatgtagcaggaggactaaggattgattctcaaaacagacgcctttacttgatgttagttatccgtttgatgctcaaaaccaact

| Sequences |
| --- |
| aaatctaagactaggacagggccctcttttttataaactcagcccacaacttggatattaactacaacaaaggcctttacttgtttac |
| agcttcaaacaattccaaaaagcttgaggttaacctaagcactgccaaggggttgatgtttgacgctacagccatagccattaatgc |
| aggagatgggcttgaatttggttcacctaatgcaccaaacacaaatcccctcaaaacaaaaattggccatggcctagaatttgattc |
| aaacaaggctatggttcctaaactaggaactggccttagttttgacagcacaggtgccattacagtaggaaacaaaaataatgataa |
| gctaactttgtggaccacaccagctccatctcctaactgtagactaaatgcagagaaagatgctaaactcactttggtcttaacaaa |
| atgtggcagtcaaatacttgctacagtttcagttttggctgttaaaggcagtttggctccaatatctggaacagttcaaagtgctca |
| tcttattataagatttgacgaaaatggagtgctactaaacaattccttcctggacccagaatattggaactttagaaatggagatct |
| tactgaaggcacagcctatacaaacgctgttggatttatgcctaacctatcagcttatccaaaatctcacggtaaaactgccaaaag |
| taacattgtcagtcaagtttacttaaacggagacaaaactaaacctgtaacactaaccattacactaaacggtacacaggaaacagg |
| agacacaactccaagtgcatactctatgtcattttcatgggactggtctggccacaactacattaatgaaatatttgccacatcctc |
| ttacacttttttcatacattgcccaagaataaagaatcgtttgtgttatgtttcaacgtgtttattttttcaattgcagaaaatttcaa |
| gtcattttcattcagtagtatagccccaccaccacatagcttatacagatcaccgtaccttaatcaaactcacagaaccctagtat |
| tcaacctgccacctccctcccaacacacagagtacacagtcctttctccccggctggccttaaaaagcatcatatcatgggtaacag |
| acatattcttaggtgttatattccacacggtttcctgtcgagccaaacgctcatcagtgatattaataaactcccccgggcagctcac |
| ttaagttcatgtcgctgtccagctgctgagccacaggctgctgtccaacttgcggttgcttaacgggcggcgaaggagaagtccacg |
| cctacatgggggtagagtcataatcgtgcatcaggataggcggtggtgctgcagcagcgcgcgaataaactgctgccgccgccgct |
| ccgtcctgcaggaatacaacatggcagtggtctcctcagcgatgattcgcaccgcccgcagcataaggcgccttgtcctccgggcac |
| agcagcgcaccctgatctcacttaaatcagcacagtaactgcagcacagcaccacaatattgttcaaaatcccacagtgcaaggcgc |
| tgtatccaaagctcatggcggggaccacagaacccacgtggccatcataccacaagcgcaggtagattaagtggcgacccctcataa |
| acacgctggacataaacattacctcttttggcatgttgtaattcaccacctcccggtaccatataaacctctgattaaacatggcgc |
| catccaccaccatcctaaaccagctggccaaaacctgcccgccggctatacactgcagggaaccgggactggaacaatgacagtgga |
| gagcccaggactcgtaaccatggatcatcatgctcgtcatgatatcaatgttggcacaacacaggcacacgtgcatacacttcctca |
| ggattacaagctcctcccgcgttagaaccatatcccagggaacaacccattcctgaatcagcgtaaatcccacactgcagggaagac |
| ctcgcacgtaactcacgttgtgcattgtcaaagtgttacattcgggcagcagcggatgatcctccagtatggtagcgcgggtttctg |
| tctcaaaaggaggtagacgatccctactgtacggagtgcgccgagacaaccgagatcgtgttggtcgtagtgtcatgccaaatggaa |
| cgccggacgtagtcatatttcctgaagcaaaaccaggtgcgggcgtgacaaacagatctgcgtctccggtctcgccgcttagatcgc |
| tctgtgtagtagttgtagtatatccactctctcaaagcatccaggcgcccctggcttcgggttctatgtaaactccttcatgcgcc |
| gctgccctgataacatccaccaccgcagaataagccacacccagccaacctacacattcgttctgcgagtcacacacgggaggagcg |
| ggaagagctggaagaaccatgtttttttttttattccaaaagattatccaaaacctcaaaatgaagatctattaagtgaacgcgctc |
| ccctccggtggcgtggtcaaactctacagccaaagaacagataatggcatttgtaagatgttgcacaatggcttccaaaaggcaaac |
| ggccctcacgtccaagtggacgtaaaggctaaacccttcagggtgaatctcctctataaacattccagcaccttcaaccatgcccaa |
| ataattctcatctcgccaccttctcaatatatctctaagcaaatcccgaatattaagtccggccattgtaaaaatctgctccagagc |
| gccctccaccttcagcctcaagcagcgaatcatgattgcaaaaattcaggttcctcacagacctgtataagattcaaaagcggaaca |
| ttaacaaaaataccgcgatcccgtaggtcccttcgcagggccagctgaacataatcgtgcaggtctgcacggaccagcgcggccact |
| tccccgccaggaaccatgacaaaagaacccacactgattatgacacgcatactcggagctatgctaaccagcgtagcccgatgtaa |
| gcttgttgcatgggcggcgatataaaatgcaaggtgctgctcaaaaaatcaggcaaagcctcgcgcaaaaaagaaagcacatcgtag |
| tcatgctcatgcagataaaggcaggtaagctccggaaccaccacagaaaaagacaccattttttctctcaaacatgtctgcgggtttc |
| tgcataaacacaaaataaaataacaaaaaaacatttaaacattagaagcctgtcttacaacaggaaaaacaacccttataagcataa |
| gacggactacggccatgccggcgtgaccgtaaaaaaaactggtcaccgtgattaaaaagcaccaccgacagctcctcggtcatgtccg |

| Sequences |
| --- |
| gagtcataatgtaagactcggtaaacacatcaggttgattcacatcggtcagtgctaaaaagcgaccgaaatagcccgggggaatac |
| atacccgcaggcgtagagacaacattacagcccccataggaggtataacaaaattaataggagagaaaaacacataaacacctgaaa |
| aaccctcctgcctaggcaaaatagcacccteccgctccagaacaacatacagcgcttccacagcggcagccataacagtcagcctta |
| ccagtaaaaagaaaacctattaaaaaaacaccactcgacacggcaccagctcaatcagtcacagtgtaaaaaagggccaagtgcag |
| agcgagtatatataggactaaaaaatgacgtaacggttaaagtccacaaaaaacacccagaaaaccgcacgcgaacctacgcccaga |
| aacgaaagccaaaaaacccacaacttcctcaaatcgtcacttccgttttcccacgttacgtcacttcccattttaagaaaactacaa |
| ttcccaacacatactagttactccgccctaaaacctacgtcacccgccccgttcccacgcccgcgccacgtcacaaactccacccc |
| ctcattatcatattggcttcaatccaaaataaggtatattattgatgatgt |

SEQ ID NO: 5 - ICOVIR15K-QD
catcatcaataatatacctta ttttggattgaagccaatatgataatgagggggtggagtttgtgacgtggcgcggggcgtgggaac
ggggcgggtgacgtagtagtgtggcggaagtgtgatgttgcaagtgtggcggaacacatgtaagcgacggatgtggcaaaagtgacg
ttttggtgtgcgccggtgtacacaggaagtgacaattttcgcgcggttttaggcggatgttgtagtaaatttgggcgtaaccgagt
aagatttggccattttcgcgggaaaactgaataagaggaagtgaaatctgaataattttgtgttactcatagcgcgtaatatttgtc
tagggccgcggggactttgaccgtttacgtggagactcgcccaggtgttttt ctcaggtgttttccgcgtacgtcggcggctcgtgg
ctctttcgcggcaaaaggatttggcgcgtaaaagtggttcgagtacgtcggcggctcgtggctctttcgcggcaaaaggatttgg
cgcgtaaaagtggttcgaagtacgtcgaccacaaaccccgcccagcgtcttgtcattggcgtcgacgctgtacggggtcaaagttgg
cgttttattattatagtcagctgacgtgtagtgtatttatacccggtgagttcctcaagaggccactcttgagtgccagcgagtaga
gttttctcctccgagccgctccgacaccgggactgaaaatgagacatattatctgccacggaggtgttattaccgaagaaatggccg
ccagtcttttggaccagctgatcgaagaggtactggctgataatcttccacctcctagccattttgaaccacctaccatcacgaact
gtatgatttagacgtgacggccccgaagatcccaacgaggaggcggtttcgcagattttt cccgactctgtaatgttggcggtgca
ggaagggattgacttactcacttttccgccggcgcccggttctccggagccgcctcacctttcccggcagcccgagcagccggagca
gagagccttgggtccggtttctatgccaaaccttgtaccggaggtgatcgatccacccagtgacgacgaggatgaagagggtgagga
gtttgtgttagattatgtggagcaccccgggcacggttgcaggtcttgtcattatcaccggaggaatacgggggacccagatattat
gtgttcgctttgctatatgaggacctgtggcatgtttgtctacagtaagtgaaaattatgggcagtgggtgatagagtggtgggttt
ggtgtggtaattttttttttaattttttacagttttgtggtttaaagaattttgtattgtgatttttttaaaaggtcctgtgtctgaa
cctgagcctgagcccgagccagaaccggagcctgcaagacctacccgccgtcctaaaatggcgcctgctatcctgagacgcccgaca
tcacctgtgtccagagaatgcaatagtagtacggatagctgtgactccggtccttctaacacacctcctgagatacacccggtggtc
ccgctgtgccccattaaaccagttgccgtgagagttggtgggcgtcgccaggctgtggaatgtatcgaggacttgataacgagcctg
ggcaacattggacttgagctgtaaacgccccaggccataaggtgtaaacctgtgattgcgtgtgtggttaacgcctttgtttgctga
atgagttgatgtaagtttaataaagggtgagataatgtttaacttgcatggcgtgttaaatggggcggggcttaaagggtatataat
gcgccgtgggctaatcttggttacatctgacctcatggaggcttgggagtgtttggaagattttt ctgctgtgcgtaacttgctgga
acagagctctaacagtacctcttggttttggaggtttctgtggggctcatcccaggcaaagttagtctgcagaattaaggaggatta
caagtgggaatttgaagagcttttgaaatcctgtggtgagctgtttgattctttgaatctgggtcaccaggcgcttttccaagagaa
ggtcatcaagactttggattttt ccacaccggggcgcgctgcggctgctgttgcttttttgagttttataaaggataaatggagcga
agaaacccatctgagcggggggtacctgctgattttctggccatgcatctgtggagagcggttgtgagacacaagaatcgcctgct
actgttgtcttccgtccgcccggcgataataccgacggaggagcagcagcagcagcaggaggaagccaggcggcggcggcaggagca
gagcccatggaacccgagagccggcctggaccctcgggaatgaatgttgtacaggtggctgaactgtatccagaactgagacgcatt
ttgacaattacagaggatgggcaggggctaaaggggg taaagaggggagcggggggcttgtgaggctacagaggaggctaggaatcta
gatttagataatgaccagacaccgtcctgagtgtattactttt caacagatcaaggataattgcgctaatgagcttgatctgctggc -continued

| Sequences |
|---|
| gcagaagtattccatagagcagctgaccacttactggctgcagccaggggatgattttgaggaggctattagggtatatgcaaggt |
| ggcacttaggccagattgcaagtacaagatcagcaaacttgtaaatatcaggaattgttgctacatttctgggaacggggccgaggt |
| ggagatagatacggaggatagggtggcctttagatgtagcatgataaatatgtggccggggtgcttggcatggacggggtggttat |
| tatgaatgtaaggtttactggccccaattttagcggtacggttttcctggccaataccaaccttatcctacacggtgtaagcttcta |
| tgggtttaacaatacctgtgtggaagcctggaccgatgtaagggttcggggctgtgccttttactgctgctggaaggggtggtgtg |
| tcgcccaaaagcagggcttcaattaagaaatgcctctttgaaaggtgtaccttgggtatcctgtctgagggtaactccagggtgcg |
| ccacaatgtggcctccgactgtggttgcttcatgctagtgaaaagcgtggctgtgattaagcataacatggtatgtggcaactgcga |
| ggacagggcctctcagatgctgacctgctcggacggcaactgtcacctgctgaagaccattcacgtagccagccactctcgcaaggc |
| ctggccagtgtttgagcataacatactgaccgctgttccttgcatttgggtaacaggaggggggtgttcctaccttaccaatgcaa |
| tttgagtcacactaagatattgatgagcccgagagcatgtccaaggtgaacctgaacggggtgtttgacatgaccatgaagatctgg |
| aaggtgctgaggtacgatgagacccgcaccaggtgcagaccctgcgagtgtggcggtaaacatattaggaaccagcctgtgatgctg |
| gatgtgaccgaggagctgaggcccgatcacttggtgctggcctgcacccgcgctgagtttggctctagcgatgaagatacagattga |
| ggtactgaaatgtgtgggcgtggcttaagggtgggaaagaatatataaggtgggggtcttatgtagttttgtatctgtttttgcagca |
| gccgccgccgccatgagcaccaactcgtttgatggaagcattgtgagctcatatttgacaacgcgcatgccccatgggccggggtg |
| cgtcagaatgtgatgggctccagcattgatggtcgccccgtcctgcccgcaaactctactaccttgacctacgagaccgtgtctgga |
| acgccgttggagactgcagcctccgccgccgcttcagccgctgcagccaccgcccgcgggattgtgactgactttgctttcctgagc |
| ccgcttgcaagcagtgcagcttcccgttcatccgcccgcgatgacaagttgacggctcttttggcacaattggattctttgacccgg |
| gaacttaatgtcgtttctcagcagctgttggatctgcgccagcaggtttctgccctgaaggcttcctcccctcccaatgcggtttaa |
| aacataaataaaaaaccagactctgtttggatttggatcaagcaagtgtcttgctgtctttatttagggtttttgcgcgcgcggtag |
| gcccgggaccagcggtctcggtcgttgagggtcctgtgtatttttccaggacgtggtaaaggtgactctggatgttcagatacatg |
| ggcataagcccgtctctggggtggaggtagcaccactgcagagcttcatgctgcggggtggtgttgtagatgatccagtcgtagcag |
| gagcgctgggcgtggtgcctaaaaatgtctttcagtagcaagctgattgccaggggcaggcccttggtgtaagtgtttacaaagcgg |
| ttaagctgggatgggtgcatacgtggggatatgagatgcatcttggactgtattttaggttggctatgttcccagccatatccctc |
| cggggattcatgttgtgcagaaccaccagcacagtgtatccggtgcacttgggaaatttgtcatgtagcttagaaggaaatgcgtgg |
| aagaacttggagacgcccttgtgacctccaagattttccatgcattcgtccataatgatggcaatgggcccacgggcggcggcctgg |
| gcgaagatatttctgggatcactaacgtcatagttgtgttccaggatgagatcgtcataggccatttttacaaagcgcgggcggagg |
| gtgccagactgcggtataatggttccatccggcccaggggcgtagttaccctcacagatttgcatttcccacgctttgagttcagat |
| gggggatcatgtctacctgcggggcgatgaagaaaacggtttccggggtaggggagatcagctgggaagaaagcaggttcctgagc |
| agctgcgacttaccgcagccggtgggcccgtaaatcacacctattaccgggtgcaactggtagttaagagagctgcagctgccgtca |
| tccctgagcagggggggccacttcgttaagcatgtccctgactcgcatgttttccctgaccaaatccgccagaaggcgctcgccgccc |
| agcgatagcagttcttgcaaggaagcaaagttttttcaacggtttgagaccgtccgccgtaggcatgcttttgagcgtttgaccaagc |
| agttccaggcggtcccacagctcggtcacctgctctacggcatctcgatccagcatatctcctcgtttcgcgggttggggcggcttt |
| cgctgtacggcagtagtcggtgctcgtccagacgggccagggtcatgtcttccacgggcgcagggtcctcgtcagcgtagtctggg |
| tcacggtgaaggggtgcgctccgggctgcgcgctggccagggtgcgcttgaggctggtcctgctggtgctgaagcgctgccggtctt |
| cgccctgcgcgtcggccaggtagcatttgaccatggtgtcatagtccagcccctccgcggcgtggcccttggcgcgcagcttgccct |
| tggaggaggcgccgcacgaggggcagtgcagacttttgagggcgtagagcttgggcgcgagaaataccgattccggggagtaggcat |
| ccgcgccgcaggccccgcagacggtctcgcattccacgagccaggtgagctctggccgttcggggtcaaaaaccaggtttcccccat |
| gcttttgatgcgtttcttacctctggttccatgagccggtgtccacgctcggtgacgaaaaggctgtccgtgtccccgtatacag |

| Sequences |
| --- |
| acttgagaggcctgtcctcgagcggtgttccgcggtcctcctcgtatagaaactcggaccactctgagacaaaggctcgcgtccagg |
| ccagcacgaaggaggctaagtgggaggggtagcggtcgttgtccactaggggtccactcgctccagggtgtgaagacacatgtcgc |
| cctcttcggcatcaaggaaggtgattggtttgtaggtgtaggccacgtgaccgggtgttcctgaaggggggctataaaaggggtgg |
| gggcgcgttcgtcctcactctcttccgcatcgctgtctgcgagggccagctgttggggtgagtactccctctgaaaagcgggcatga |
| cttctgcgctaagattgtcagtttccaaaaacgaggaggatttgatattcacctggcccgcggtgatgcctttgagggtggccgcat |
| ccatctggtcagaaaagacaatcttttttgttgtcaagcttggtggcaaacgacccgtagagggcgttggacagcaacttggcgatgg |
| agcgcagggtttggtttttgtcgcgatcggcgcgctccttggccgcgatgtttagctgcacgtattcgcgcgcaacgcaccgccatt |
| cgggaaagacggtggtgcgctcgtcggcaccaggtgcacgcgccaaccgcggttgtgcagggtgacaaggtcaacgctggtggcta |
| cctctccgcgtaggcgctcgttggtccagcagaggcggccgcccttgcgcgagcagaatggcggtaggggctctagctgcgtctcgt |
| ccgggggtctgcgtccacggtaaagaccccgggcagcaggcgcgcgtcgaagtagtctatcttgcatccttgcaagtctagcgcct |
| gctgccatgcgcggcggcaagcgcgcgctcgtatgggttgagtgggggaccccatggcatgggtgggtgagcgcggaggcgtaca |
| tgccgcaaatgtcgtaaacgtagagggcgtctctgagtattccaagatatgtagggtagcatcttccaccgcggatgctggcgcgca |
| cgtaatcgtatagttcgtgcgagggagcgaggaggtcgggaccgaggttgctacgggcgggctgctctgctcggaagactatctgcc |
| tgaagatggcatgtgagttggatgatatggttggacgctggaagacgttgaagctggcgtctgtgagacctaccgcgtcacgcacga |
| aggaggcgtaggagtcgcgcagcttgttgaccagctcggcggtgacctgcacgtctagggcgcagtagtccagggtttccttgatga |
| tgtcatacttatcctgtccctttttttccacagctcgcggttgaggacaaactcttcgcggtctttccagtactcttggatcggaa |
| acccgtcggcctccgaacggtaagagcctagcatgtagaactggttgacggcctggtaggcgcagcatcccttttctacgggtagcg |
| cgtatgcctgcgcggccttccggagcgaggtgtgggtgagcgcaaaggtgtccctgaccatgactttgaggtactggtatttgaagt |
| cagtgtcgtcgcatccgccctgctcccagagcaaaaagtccgtgcgcttttggaacgcggatttggcagggcgaaggtgacatcgt |
| tgaagagtatctttcccgcgcgaggcataaagttgcgtgtgatgcggaagggtcccggcacctcggaacggttgttaattacctggg |
| cggcgagcacgatctcgtcaaagccgttgatgttgtggcccacaatgtaaagttccaagaagcgcgggatgcccttgatggaaggca |
| atttttaagttcctcgtaggtgagctcttcaggggagctgagcccgtgctctgaaagggccagtctgcaagatgagggttggaag |
| cgacgaatgagctccacaggtcacgggccattagcatttgcaggtggtcgcgaaaggtcctaaactggcgacctatggccatttttt |
| ctgggtgatgcagtagaaggtaagcgggtcttgttcccagcggtcccatccaaggttcgcggctaggtctcgcgcggcagtcacta |
| gaggctcatctccgccgaacttcatgaccagcatgaagggcacgagctgcttcccaaaggcccccatccaagtataggtctctacat |
| cgtaggtgacaaagagacgctcggtgcgaggatgcgagccgatcgggaagaactggatctcccgccaccaattggaggagtggctat |
| tgatgtggtgaaagtagaagtccctgcgacgggccgaacactcgtgctggcttttgtaaaaacgtgcgcagtactggcagcggtgca |
| cgggctgtacatcctgcacgaggttgacctgacgaccgcgcacaaggaagcagagtgggaatttgagcccctcgcctggcgggtttg |
| gctggtggtcttctacttcggctgcttgtccttgaccgtctggctgctcgaggggagttacggtggatcggaccaccacgccgcgcg |
| agcccaaagtccagatgtccgcgcgcggcggtcggagcttgatgacaacatcgcgcagatggagctgtccatggtctggagctccc |
| gcggcgtcaggtcaggcgggagctcctgcaggtttacctcgcatagacgggtcagggcgcgggctagatccaggtgatacctaattt |
| ccaggggctggttggtggcggcgtcgatggcttgcaagaggccgcatccccgcggcgcgactacggtaccgcgcggcgggcggtggg |
| ccgcgggggtgtccttggatgatgcatctaaaagcggtgacgcgggcgagcccccggaggtaggggggctccggacccgccgggag |
| aggggcaggggcacgtcggcgccgcgcgcgggcaggagctggtgctgcgcgcgtaggttgctggcgaacgcgacgacgcggcggtt |
| gatctcctgaatctggcgcctctgcgtgaagacgacgggccggtgagcttgagcctgaaagagagttcgacagaatcaatttcggt |
| gtcgttgacggcggcctggcgcaaaatctcctgcacgtctcctgagttgtcttgataggcgatctcggccatgaactgctcgatctc |
| ttcctcctggagatctccgcgtccggctcgctccacggtggcggcgaggtcgttggaaatgcgggccatgagctgcgagaaggcgtt |
| gaggcctccctcgttccagacgcggctgtagaccacgcccccttcggcatcgcgggcgcgcatgaccacctgcgcgagattgagctc |
| cacgtgccgggcgaagacggcgtagtttcgcaggcgctgaaagaggtagttgagggtggtggcggtgtgttctgccacgaagaagta |

| Sequences |
| --- |
| cataacccagcgtcgcaacgtggattcgttgatatcccccaaggcctcaaggcgctccatggcctcgtagaagtccacggcgaagtt
gaaaaactgggagttgcgcgccgacacggttaactcctcctccagaagacggatgagctcggcgacagtgtcgcgcacctcgcgctc
aaaggctacaggggcctcttcttcttcttcaatctcctcttccataagggcctcccttcttcttcttctggcggcggtgggggagg
ggggacacggcggcgacgacggcgcaccgggaggcggtcgacaaagcgctcgatcatctccccgcggcgacggcgcatggtctcggt
gacggcgcggccgttctcgcggggggcgcagttggaagacgccgcccgtcatgtcccggttatgggttggcgggggctgccatgcgg
cagggatacggcgctaacgatgcatctcaacaattgttgtgtaggtactccgccgccagggacctgagcgagtccgcatcgaccgg
atcggaaaacctctcgagaaaggcgtctaaccagtcacagtcgcaaggtaggctgagcaccgtggcgggcggcagcgggcggcggtc
ggggttgtttctggcggaggtgctgctgatgatgtaattaaagtaggcggtcttgagacggcggatggtcgacagaagcaccatgtc
cttgggtccggcctgctgaatgcgcaggcggtcggccatgccccaggcttcgttttgacatcggcgcaggtctttgtagtagtcttg
catgagccttctaccggcacttcttcttctccttcctcttgtcctgcatctcttgcatctatcgctgcggcggcggcggagtttgg
ccgtaggtggcgccctcttcctcccatgcgtgtgaccccgaagcccctcatcggctgaagcagggctaggtcggcgacaacgcgctc
ggctaatatggcctgctgcacctgcgtgagggtagactggaagtcatccatgtccacaaagcggtggtatgcgcccgtgttgatggt
gtaagtgcagttggccataacggaccagttaacggtctggtgacccggctgcgagagctcggtgtacctgagacgcgagtaagccct
cgagtcaaatacgtagtcgttgcaagtccgcaccaggtactggtatcccaccaaaaagtgcggcggcggctggcggtagaggggcca
gcgtagggtggccggggctccgggggcgagatcttccaacataaggcgatgatatccgtagatgtacctggacatccaggtgatgcc
ggcggcggtggtggaggcgcgcggaaagtcgcggacgcggttccagatgttgcgcagcggcaaaaagtgctccatggtcgggacgct
ctggccggtcaggcgcgcgcaatcgttgacgctctagaccgtgcaaaaggagagcctgtaagcgggcactcttccgtggtctggtgg
ataaattcgcaagggtatcatggcggacgaccggggttcgagcccgtatccggccgtccgccgtgatccatgcggttaccgcccgc
gtgtcgaacccaggtgtgcgacgtcagacaacggggagtgctcctttggcttccttccaggcgcggcggctgctgcgctagctt
tttggccactggccgcgcgcagcgtaagcggttaggctggaaagcgaaagcattaagtggctcgctccctgtagccgagggttatt
ttccaagggttgagtcgcgggaccccggttcgagtctcggaccggccggactgcggcgaacggggggtttgcctccccgtcatgcaa
gaccccgcttgcaaattcctccggaaacagggacgagccccttttttgcttttcccagatgcatccggtgctgcggcagatgcgccc
ccctcctcagcagcggcaagagcaagagcagcggcagacatgcagggcaccctcccctcctcctaccgcgtcaggaggggcgacatc
cgcggttgacgcggcagcagatggtgattacgaaccccgcggcgccgggccccgcactacctggacttggaggagggcgagggcct
ggcgcggctaggagcgccctctcctgagcggtacccaagggtgcagctgaagcgtgatacgcgtgaggcgtacgtgccgcggcagaa
cctgtttcgcgaccgcgagggagaggagcccgaggagatgcgggatcgaaagttccacgcagggcgcgagctgcggcatggcctgaa
tcgcgagcggttgctgcgcgaggaggactttgagcccgacgcgcgaaccgggattagtcccgcgcgcgcacacgtggcggccgccga
cctggtaaccgcatacgagcagacggtgaaccaggagattaactttcaaaaaagctttaacaaccacgtgcgtacgcttgtggcgcg
cgaggaggtggctataggactgatgcatctgtgggactttgtaagcgcgctggagcaaaacccaaatagcaagccgctcatggcgca
gctgttccttatagtgcagcacagcagggacaacgaggcattcagggatgcgctgctaaacatagtagagcccgagggccgctggct
gctcgatttgataaacatcctgcagagcatagtggtgcaggagcgcagcttgagcctggctgacaaggtggccgccatcaactattc
catgcttagcctgggcaagttttacgcccgcaagatataccataccccttacgttcccatagacaaggaggtaaagatcgagggtt
ctacatgcgcatggcgctgaaggtgcttaccttgagcgacgacctgggcgtttatcgcaacgagcgcatccacaaggccgtgagcgt
gagccggcggcgcgagctcagcgaccgcgagctgatgcacagcctgcaaagggccctggctggcacgggcagcggcgatagagaggc
cgagtcctactttgacgcgggcgctgacctgcgctgggcccaagccgacgcgcctggaggcagctggggccgacctgggctggc
ggtggcacccgcgcgcgctggcaacgtcggcggcgtggaggaatatgacgaggacgatgagtacgagccagaggacggcgagtacta
agcggtgatgtttctgatcagatgatgcaagacgcaacgacccggcggtgcgggcggcgctgcagagccagccgtccgccttaac
tccacggacgactggcgccaggtcatggaccgcatcatgtcgctgactgcgcgcaatcctgacgcgttccggcagcagccgcaggcc |

-continued

| Sequences |
|---|
| aaccggctctccgcaattctggaagcggtggtcccggcgcgcgcaaaccccacgcacgagaaggtgctggcgatcgtaaacgcgctg |
| gccgaaaacagggccatccggcccgacgaggccggcctggtctacgacgcgctgcttcagcgcgtggctcgttacaacagcggcaac |
| gtgcagaccaacctggaccggctggtgggggatgtgcgcgaggccgtggcgcagcgtgagcgcgcgcagcagcagggcaacctgggc |
| tccatggttgcactaaacgccttcctgagtacacagcccgccaacgtgccgcggggacaggaggactacaccaactttgtgagcgca |
| ctgcggctaatggtgactgagacaccgcaaagtgaggtgtaccagtctgggccagactattttttccagaccagtagacaaggcctg |
| cagaccgtaaacctgagccaggctttcaaaaacttgcaggggctgtgggggggtgcgggctcccacaggcgaccgcgcgaccgtgtct |
| agcttgctgacgcccaactcgcgcctgttgctgctgctaatagcgcccttcacggacagtggcagcgtgtcccgggacataaccta |
| ggtcacttgctgacactgtaccgcgaggccataggtcaggcgcatgtggacgagcatactttccaggagattacaagtgtcagccgc |
| gcgctggggcaggaggacacgggcagcctggaggcaaccctaaactacctgctgaccaaccggcggcagaagatcccctcgttgcac |
| agtttaaacagcgaggaggagcgcattttgcgctacgtgcagcagagcgtgagccttaacctgatgcgcgacggggtaacgcccagc |
| gtggcgctggacatgaccgcgcgcaacatggaacgggcatgtatgcctcaaaccggccgtttatcaaccgcctaatggactacttg |
| catcgcgcggccgccgtgaaccccgagtatttcaccaatgccatcttgaacccgcactggctaccgcccccctggtttctacaccggg |
| ggattcgaggtgcccgagggtaacgatggattcctctgggacgacatagacgacagcgtgttttccccgcaaccgcagaccctgcta |
| gagttgcaacagcgcgagcaggcagaggcggcgctgcgaaaggaaaagcttccgcaggccaagcagcttgtccgatctaggcgctgcg |
| gccccgcggtcagatgctagtagcccatttccaagcttgatagggtctcttaccagcactcgcaccacccgcccgcgcctgctgggc |
| gaggaggagtacctaaacaactcgctgctgcagccgcagcgcgaaaaaaacctgcctccggcatttcccaacaacgggatagagagc |
| ctagtggacaagatgagtagatggaagacgtacgcgcaggagcacagggacgtgccaggcccgcgcccgcccacccgtcgtcaaagg |
| cacgaccgtcagcgggggtctggtgtgggaggacgatgactcggcagacgacagcagcgtcctggatttgggagggagtggcaacccg |
| tttgcgcaccttcgccccaggctggggagaatgttttaaaaaaaaaaagcatgatgcaaaataaaaaactcaccaaggccatggca |
| ccgagcgttggttttcttgtattcccttagtatgcggcgcgcggcgatgtatgaggaaggtcctcctccctcctacgagagtgtgg |
| tgagcgcggcgccagtggcggcggcgctgggttctcccttcgatgctcccctggacccgccgtttgtgcctccgcggtacctgcggc |
| ctaccggggggagaaacagcatccgttactctgagttggcaccccctattcgacaccaccgtgtgtacctggtggacaacaagtcaa |
| cggatgtggcatccctgaactaccagaacgaccacagcaactttctgaccacggtcattcaaaacaatgactacagcccgggggagg |
| caagcacacagaccatcaatcttgacgaccggtcgcactggggcggcgacctgaaaaccatcctgcataccaacatgccaaatgtga |
| acgagttcatgtttaccaataagtttaaggcgcgggtgatggtgtcgcgcttgcctactaaggacaatcaggtggagctgaaatacg |
| agtgggtggagttcacgctgcccgagggcaactactccgagaccatgaccatagaccttatgaacaacgcgatcgtggagcactact |
| gaaagtgggcagacagaacgggttctggaaagcgacatcggggtaaagtttgacacccgcaacttcagactggggtttgaccccg |
| tcactggtcttgtcatgcctggggtatatacaaacgaagccttccatccagacatcattttgctgccaggatgcggggtggacttca |
| cccacagccgcctgagcaacttgttgggcatccgcaagcggcaaccottccaggagggctttaggatcacctacgatgatctggagg |
| gtggtaacattcccgcactgttggatgtggacgcctaccaggcgagcttgaaagatgacaccgaacagggcggggtggcgcaggcg |
| gcagcaacagcagtggcagcggcgcggaagagaactccaacgcggcagccgcggcaatgcagccggtggaggacatgaacgatcatg |
| ccattcgcggcgacacctttgccacacgggctgaggagaagcgcgctgaggccgaagcagcggccgaagctgccgcccccgctgcgc |
| aacccgaggtcgagaagcctcagaagaaaccggtgatcaaaccctgacagaggacagcaagaaacgcagttacaacctaataagca |
| atgacagcaccttcacccagtaccgcagctggtaccttgcataccaactacggcgaccctcagaccggaatccgctcatggaccctgc |
| tttgcactcctgacgtaacctgcggctcggagcaggtctactggtcgttgccagacatgatgcaagaccccgtgaccttccgctcca |
| cgcgccagatcagcaactttccggtggtgggcgccgagctgttgccccgtgcactccaagagcttctacaacgaccaggccgtctact |
| cccaactcatccgccagtttacctctctgacccacgtgttcaatcgctttcccgagaaccagattttggcgcgcccgccagccccca |
| ccatcaccaccgtcagtgaaaacgttcctgctctcacagatcacgggacgctaccgctgcgcaacagcatcggaggagtccagcgag |
| tgaccattactgacgccagacgccgcacctgcccctacgtttacaaggccctgggcatagtctcgccgcgcgtcctatcgagccgca |

-continued

Sequences cttttttgagcaagcatgtccatccttatatcgcccagcaataacacaggctggggcctgcgcttcccaagcaagatgtttggcgggg ccaagaagcgctccgaccaacacccagtgcgcgtgcgcgggcactaccgcgcgccctggggcgcgcacaaacgcggccgcactgggc gcaccaccgtcgatgacgccatcgacgcggtggtggaggaggcgcgcaactacacgcccacgccgccaccagtgtccacagtggacg cggccattcagaccgtggtgcgcggagcccggcgctatgctaaaatgaagagacggcggaggcgcgtagcacgtcgccaccgccgcc gacccggcactgccgcccaacgcgcggcggcggccctgcttaaccgcgcacgtcgcaccggccgacgggcggccatgcgggccgctc gaaggctggccgcgggtattgtcactgtgcccccaggtccaggcgacgagcggccgccgcagcagccgcggccattagtgctatga ctcagggtcgcaggggcaacgtgtattgggtgcgcgactcggttagcggcctgcgcgtgcccgtgcgcaccgccccccgcgcaact agattgcaagaaaaaactacttagactcgtactgttgtatgtatccagcggcggcggcgcgcaacgaagctatgtccaagcgcaaaa tcaaagaagagatgctccaggtcatcgcgccggagatctatggccccccgaagaaggaagagcaggattacaagccccgaaagctaa agcgggtcaaaagaaaagaaagatgatgatgatgaacttgacgacgaggtggaactgctgcacgctaccgcgcccaggcgacggg tacagtggaaaggtcgacgcgtaaaacgtgttttgcgacccggcaccaccgtagtctttacgcccggtgagcgctccacccgcacct acaagcgcgtgtatgatgaggtgtacggcgacgaggacctgcttgagcaggccaacgagcgcctcggggagtttgcctacggaaagc ggcataaggacatgctggcgttgccgctggacgagggcaacccaacacctagcctaaagcccgtaacactgcagcaggtgctgcccg cgcttgcaccgtccgaagaaaagcgcggcctaaagcgcgagtctggtgacttggcacccaccgtgcagctgatggtacccaagcgcc agcgactggaagatgtcttggaaaaaatgaccgtggaacctgggctggagcccgaggtccgcgtgcggcaatcaagcaggtggcgc cgggactgggcgtgcagaccgtggacgttcagatacccactaccagtagcaccagtattgccaccgccacagagggcatggagacac aaacgtccccggttgcctcagcggtggcggatgccgcggtgcaggcggtcgctgcggccgcgtccaagacctctacggaggtgcaaa cggaccccgtggatgttttcgcgtttcagcccccggcgcccgcgcggttcgaggaagtacggcgccgccagcgcgctactgcccgaat atgccctacatccttccattgcgcctaccccccggctatcgtggctacacctaccgccccagaagacgagcaactacccgacgccgaa ccaccactggaacccgccgccgccgtcgccgtcgccagcccgtgctggcccccgatttccgtgcgcagggtggctcgcgaaggaggca ggaccctggtgctgccaacagcgcgctacacccccagcatcgtttaaaagcggtctttgtggttcttgcagatatggccctcacct gccgcctccgtttcccggtgccgggattccgaggaagaatgcaccgtaggaggggcatggccggccacggcctgacgggcggcatgc gtcgtgcgcaccaccgcggcggcgcgcgtcgcaccgtcgcatgcgcggcggtatcctgcccctccttattccactgatcgccgcgg cgattggcgccgtgcccggaattgcatccgtggccttgcaggcgcagagacactgattaaaaacaagttgcatgtggaaaaatcaaa ataaaaagtctggactctcacgctcgcttggtcctgtaactattttgtagaatggaagacatcaactttgcgtctctggccccgcga cacggctcgcgcccgttcatggaaactggcaagatatcggcaccagcaatatgagcggtggcgccttcagctggggctcgctgtgg agcggcattaaaaatttcggttccaccgttaagaactatggcagcaaggcctggaacagcagcacaggccagatgctgagggataag ttgaaagagcaaaatttccaacaaaggtggtagatggcctggcctctggcattagcggggtggtggacctggccaaccaggcagtg caaaataagattaacagtaagcttgatccccgccctcccgtagaggagcctccaccggccgtggagacagtgtctccagagggcgt ggcgaaaagcgtccgcgccccgacagggaagaaactctggtgacgcaaatagacgagcctccctcgtacgaggaggcactaaagcaa ggcctgcccaccacccgtcccatcgcgcccatggctaccggagtgctgggccagcacacacccgtaacgctggacctgcctcccccc gccgacacccagcagaaacctgtgctgccaggcccgaccgcgttgttgtaaccgtcctagccgcgcgtccctgccgcgcgccgcc agcggtccgcgatcgttgcggcccgtagccagtggcaactggcaaagcacactgaacagcatcgtgggtctgggggtgcaatccctg aagcgccgacgatgcttctgaatagctaacgtgtcgtatgtgtgtcatgtatgcgtccatgtcgccgccagaggagctgctgagccg ccgcgcgcccgctttccaagatggctacccttcgatgatgccgcagtggtcttacatgcacatctcgggccaggacgcctcggagt acctgagcccgggctggtgcagtttgcccgcgccaccgagacgtacttcagcctgaataacaagtttagaaaccccacggtggcgc ctacgcacgacgtgaccacagaccggtcccagcgtttgacgctgcggttcatccctgtggaccgtgaggatactgcgtactcgtaca aggcgcggttcacccctagctgtgggtgataaccgtgtgctggacatggcttccacgtactttgacatccgcggcgtgctggacaggg -continued

| Sequences |
|---|
| gccctacttttaagccctactctggcactgcctacaacgccctggctcccaagggtgccccaaatccttgcgaatgggatgaagctg |
| ctactgctcttgaaataaacctagaagaagaggacgatgacaacgaagacgaagtagacgagcaagctgagcagcaaaaaactcacg |
| tatttgggcaggcgccttattctggtataaatattacaaaggagggtattcaaataggtgtcgaaggtcaaacacctaaatatgccg |
| ataaaacatttcaacctgaacctcaaataggagaatctcagtggtacgaaactgaaattaatcatgcagctgggagagtccttaaaa |
| agactacccccaatgaaaccatgttacggttcatatgcaaaacccacaaatgaaatggagggcaaggcattcttgtaaagcaacaaa |
| atggaaagctagaaagtcaagtggaaatgcaattttttctcaactactgaggcgaccgcaggcaatggtgataacttgactcctaaag |
| tggtattgtacagtgaagatgtagatatagaaaccccagacactcatatttcttacatgcccactattaaggaaggtaactcacgag |
| aactaatgggccaacaatctatgcccaacaggcctaattacattgcttttagggacaattttattggtctaatgtattacaacagca |
| cgggtaatatgggtgttctggcgggccaagcatcgcagttgaatgctgttgtagatttgcaagacagaaacacagagctttcatacc |
| agcttttgcttgattccattggtgatagaaccaggtactttctatgtggaatcaggctgttgacagctatgatccagatgttagaa |
| ttattgaaaatcatggaactgaagatgaacttccaaattactgcttttccactgggaggtgtgattaatacagagactcttaccaagg |
| taaacctaaaacaggtcaggaaaatggatgggaaaaagatgctacagaattttcagataaaaatgaaataagagttggaaataatt |
| ttgccatggaaatcaatctaaatgccaacctgtggagaaatttcctgtactccaacatagcgctgtatttgcccgacaagctaaagt |
| acagtccttccaacgtaaaaatttctgataacccaaacacctacgactacatgaacaagcgagtggtggctcccgggttagtggact |
| gctacattaaccccggagcacgctggtcccttgactatatggacaacgtcaacccatttaaccaccaccgcaatgctggcctgcgct |
| accgctcaatgttgctgggcaatggtcgctatgtgcccttccacatccaggtgcctcagaagttctttgccattaaaaacctccttc |
| tcctgccgggctcatacacctacgagtggaacttcaggaaggatgttaacatggttctgcagagctccctaggaaatgacctaaggg |
| ttgacggagccagcattaagtttgatagcatttgcctttacgccaccttcttccccatgcccacaacaccgcctccacgcttgagg |
| ccatgcttagaaacgacaccaacgaccagtcctttaacgactatctctccgccgccaacatgctctaccctatacccgccaacgcta |
| ccaacgtgcccatatccatcccctcccgcaactgggcggctttccgcggctgggccttcacgcgccttaagactaaggaaaccccat |
| cactgggctcgggctacgacccttattacacctactctggctctatacccctacctagatggaaccttttacctcaaccacacctttta |
| agaaggctgccattacctttgactcttctgtcagctggcctggcaatgaccgcctgcttaccccccaacgagtttgaaattaagcgct |
| cagttgacggggagggttacaacgttgcccagtgtaacatgaccaaagactggttcctggtacaaatgctagctaactataacattg |
| gctaccagggcttctatatcccagagagctacaaggaccgcatgtactccttctttagaaacttccagcccatgagccgtcaggtgg |
| tggatgatactaaatacaaggactaccaacaggtgggcatcctacaccaacacaacaactctggatttgttggctaccttgccccca |
| ccatgcgcgaaggacaggcctaccctgctaacttcccctatccgcttataggcaagaccgcagttgacagcattacccagaaaaagt |
| ttctttgcgatcgcaccctttggcgcatccattctccagtaactttatgtccatgggcgcactcacagacctgggccaaaaccttc |
| tctacgccaactccgcccactccctagacatgacttttgaggtggatcccatggacgagcccaccccttctttatgtttgtttgaag |
| tctttgacaaggtccgtgtgcaccagccgcaccgcggcgtcatcgaaaccgtgtacctgcgcacgccttctcggccggcaacgcca |
| caacataaagaagcaagcaacatcaacaacagctgccgcatgggctccagtgagcaggaactgaaagccattgtcaaagatcttgg |
| ttgtgggccatattttttgggcacctatgacaagcgctttccaggctttgtttctccacacaagctcgcctgcgccatagtcaatac |
| ggccggtcgcgagactgggggcgtacactggatggcctttgcctggaacccgcactcaaaaacatgctacctcttttgagccctttgg |
| cttttctgaccagcgactcaagcaggtttaccagtttgagtacgagtcactcctgcgccgtagcgccattgcttcttcccccgaccg |
| ctgtataacgctggaaaagtccacccaaagcgtacaggggcccaactcggccgcctgtggactattctgctgcatgtttctccacgc |
| ctttgccaactggccccaaactcccatggatcacaacccaccatgaaccttattaccggggtacccaactccatgctcaacagtcc |
| ccaggtacagcccaccctgcgtcgcaaccaggaacagctctacagcttcctggagcgccactcgccctacttccgcagccacagtgc |
| gcagattaggagcgccacttctttttgtcacttgaaaaacatgtaaaaataatgtactagagacactttcaataaaggcaaatgctt |
| ttatttgtacactctcgggtgattatttaccccaccccttgccgtctgcgccgtttaaaaatcaaagggggttctgccgcgcatcgct |
| atgcgccactggcagggacacgttgcgatactggtgtttagtgctccactttaaactcaggcacaaccatccgcggcagctcggtgaa |

-continued

Sequences gttttcactccacaggctgcgcaccatcaccaacgcgtttagcaggtcgggcgccgatatcttgaagtcgcagttggggcctccgcc ctgcgcgcgcgagttgcgatacacaggggttgcagcactggaacactatcagcgccgggtggtgcacgctggccagcacgctcttgtc ggagatcagatccgcgtccaggtcctccgcgttgctcagggcgaacggagtcaactttggtagctgccttcccaaaaagggcgcgtg cccaggctttgagttgcactcgcaccgtagtggcatcaaaaggtgaccgtgcccggtctgggcgttaggatacagcgcctgcataaa agccttgatctgcttaaaagccacctgagcctttgcgccttcagagaagaacatgccgcaagacttgccggaaaactgattggccgg acaggccgcgtcgtgcacgcagcaccttgcgtcggtgttggagatctgcaccacatttcggccccaccggttcttcacgatcttggc cttgctagactgctccttcagcgcgcgctgcccgttttcgctcgtcacatccatttcaatcacgtgctccttatttatcataatgct tccgtgtagacacttaagctcgccttcgatctcagcgcagcggtgcagccacaacgcgcagcccgtgggctcgtgatgcttgtaggt cacctctgcaaacgactgcaggtacgcctgcaggaatcgcccatcatcgtcacaaaggtcttgttgctggtgaaggtcagctgcaa cccgcggtgctcctcgttcagccaggtcttgcatacggccgccagagcttccacttggtcaggcagtagtttgaagttcgcctttag atcgttatccacgtggtacttgtccatcagcgcgcgcgcagcctccatgcccttctcccacgcagacacgatcggcacactcagcgg gttcatcaccgtaatttcactttccgcttcgctgggctcttcctcttcctcttgcgtccgcataccacgcgccactgggtcgtcttc attcagccgccgcactgtgcgcttacctcctttgccatgcttgattagcaccggtggttgctgaaacccacctatttgtagcgccac atcttctctttcttcctcgctgtccacgattacctctggtgatggcgggcgctcgggcttgggagaagggcgcttcttttttcttctt gggcgcaatggccaaatccgccgccgaggtcgatggccgcgggctgggtgtgcgcggcaccagcgcgtcttgtgatgagtcttcctc gtcctcggactcgatacgccgcctcatccgcttttttgggggcgcccggggaggcggcggcgacggggacggggacgacgtcctc catggttggggacgtcgcgccgcaccgcgtccgcgctcgggggtggtttcgcgctgctcctcttcccgactggccatttccttctc ctataggcagaaaagatcatggagtcagtcgagaagaaggacagcctaaccgcccctctgagttcgccaccaccgcctccaccga tgccgccaacgcgcctaccaccttccccgtcgaggcaccccgcttgaggaggaggaagtgattatcgagcaggaccaggttttgt aagcgaagacgacgaggaccgctcagtaccaacagaggataaaaagcaagaccaggacaacgcagaggcaaacgaggaacaagtcgg gcgggggggacgaaaggcatggcgactacctagatgtgggagacgacgtgctgttgaagcatctgcagcgccagtgcgccattatctg cgacgcgttgcaagagcgcagcgatgtgcccctcgccatagcggatgtcagccttgcctacgaacgccacctattctcaccgcgcgt acccccaaacgccaagaaaacggcacatgcgagcccaacccgcgcctcaacttctaccccgtatttgccgtgccagaggtgcttgc cacctatcacatctttttccaaaactgcaagataccctatcctgccgtgccaaccgcagccgagcggacaagcagctggccttgcg gcagggcgctgtcatacctgatatcgcctcgctcaacgaagtgccaaaaatctttgagggtcttggacgcgacgagaagcgcgcggc aaacgctctgcaacaggaaaacagcgaaaatgaaagtcactctggagtgttggtggaactcgagggtgacaacgcgcgcctagccgt actaaaacgcagcatcgaggtcacccactttgcctacccggcacttaacctaccccccaaggtcatgagcacagtcatgagtgagct gatcgtgcgccgtgcgcagcccctggagagggatgcaaatttgcaagaacaaacagaggagggcctacccgcagttggcgacgagca gctagcgcgctggcttcaaacgcgcgagcctgccgacttggaggagcgacgcaaactaatgatggccgcagtgctcgttaccgtgga gcttgagtgcatgcagcggttctttgctgacccggagatgcagcgcaagctagaggaaacattgcactacacctttcgacagggcta cgtacgccaggcctgcaagatctccaacgtggagctctgcaacctggtctcctaccttggaattttgcacgaaaaccgccttgggca aaacgtgcttcattccacgctcaagggcgaggcgcgccgcgactacgtccgcgactgcgtttacttatttctatgctacacctggca gacggccatgggcgtttggcagcagtgcttggaggagtgcaacctcaaggagctgcagaaactgctaaagcaaaacttgaaggacct atggacggccttcaacgagcgctccgtggccgcgcacctggcggacatcattttccccgaacgcctgcttaaaaccctgcaacaggg tctgccagacttcaccagtcaaagcatgttgcagaactttaggaactttatcctagagcgctcaggaatcttgcccgccacctgctg tgcacttcctagcgactttgtgcccattaagtaccgcgaatgccctccgccgctttgggccactgctaccttctgcagctagccaa ctaccttgcctaccactctgacataatggaagacgtgagcggtgacggtctactggagtgtcactgtcgctgcaacctatgcacccc gcaccgctccctggtttgcaattcgcagctgcttaacgaaagtcaaattatcggtaccttgagctgcagggtccctcgcctgacga

| Sequences |
| --- |
| aaagtccgcggctccggggttgaaactcactccggggctgtggacgtcggcttaccttcgcaaatttgtacctgaggactaccacgc |
| ccacgagattaggttctacgaagaccaatcccgcccgccaaatgcggagcttaccgcctgcgtcattacccagggccacattcttgg |
| ccaattgcaagccatcaacaaagcccgccaagagtttctgctacgaaagggacgggggtttacttggaccccccagtccggcgagga |
| gctcaacccaatcccccgccgccgcagccctatcagcagcagccgcgggcccttgcttcccaggatggcacccaaaaagaagctgc |
| agctgccgccgccacccacggacgaggaggaatactgggacagtcaggcagaggaggttttggacgaggaggaggaggacatgatgg |
| aagactgggagagcctagacgaggaagcttccgaggtcgaagaggtgtcagacgaaacaccgtcaccctcggtcgcattcccctcgc |
| cggcgccccagaaatcggcaaccggttccagcatggctacaacctccgctcctcaggcgccgccggcactgcccgttcgccgaccca |
| accgtagatgggacaccactggaaccagggccggtaagtccaagcagccgccgccgttagcccaagagcaacaacagcgccaaggct |
| accgctcatggcgcgggcacaagaacgccatagttgcttgcttgcaagactgtggggcaacatctccttcgcccgccgctttcttc |
| tctaccatcacggcgtggccttcccccgtaacatcctgcattactaccgtcatctctacagcccatactgcaccggcggcagcggca |
| gcggcagcaacagcagcggccacacagaagcaaaggcgaccggatagcaagactctgacaaagcccaagaaatccacagcggcggca |
| gcagcaggaggaggagcgctgcgtctggcgcccaacgaacccgtatcgacccgcgagcttagaaacaggattttttcccactctgtat |
| gctatatttcaacagagcaggggccaagaacaagagctgaaaataaaaaacaggtctctgcgatccctcacccgcagctgcctgtat |
| cacaaaagcgaagatcagcttcggcgcacgctggaagacgcggaggctctcttcagtaaatactgcgcgctgactcttaaggactag |
| tttcgcgccctttctcaaatttaagcgcgaaaactacgtcatctccagcggccacacccggcgccagcacctgtcgtcagcgccatt |
| atgagcaaggaaattcccacgccctacatgtggagttaccagccacaaatgggacttgcggctggagctgcccaagactactcaacc |
| cgaataaactacatgagcgcgggaccccacatgatatcccgggtcaacggaatccgcgcccaccgaaaccgaattctcttggaacag |
| gcggctattaccaccacacctcgtaataaccttaatcccccgtagttggcccgctgccctggtgtaccaggaaagtcccgctcccacc |
| actgtggtacttcccagagacgcccaggccgaagttcagatgactaactcaggggcgcagcttgcgggcggctttcgtcacagggtg |
| cggtcgcccgggcagggtataactcacctgacaatcagagggcgaggtattcagctcaacgacgagtcggtgagctcctcgcttggt |
| ctccgtccggacgggacatttcagatcggcggcgccggccgtccttcattcacgcctcgtcaggcaatcctaactctgcagacctcg |
| tcctctgagccgcgctctggaggcattggaactctgcaatttattgaggagtttgtgccatcggtctactttaaccccttctcggga |
| cctcccggccactatccggatcaatttattcctaactttgacgcggtaaaggactcggcggacggctacgactgaatgttaagtgga |
| gaggcagagcaactgcgcctgaaacacctggtccactgtcgccgccacaagtgctttgcccgcgactccggtgagttttgctacttt |
| gaattgcccgaggatcatatcgagggcccggcgcacggcgtccggcttaccgcccagggagagcttgcccgtagcctgattcgggag |
| tttacccagcgcccctgctagttgagcgggacagggaccctgtgttctcactgtgatttgcaactgtcctaaccttggattacat |
| caagatctttgttgccatctctgtgctgagtataataaatacagaaattaaaatatactggggctcctatcgccatcctgtaaacgc |
| caccgtcttcacccgcccaagcaaaccaaggcgaaccttacctggtacttttaacatctctccctctgtgatttacaacagtttcaa |
| cccagacggagtgagtctacgagagaacctctccgagctcagctactccatcagaaaaaacaccaccctccttacctgccgggaacg |
| tacgagtgcgtcaccggccgctgcaccacacctaccgctgaccgtaaaccagacttttttccggacagacctcaataactctgttta |
| ccagaacaggaggtgagcttagaaaaccctttagggtattaggccaaaggcgcagctactgtggggtttatgaacaattcaagcaact |
| ctacgggctattctaattcaggtttctctagaatcgggggttgggggttattctctgtcttgtgattctctttattcttatactaacgc |
| ttctctgcctaaggctcgccgcctgctgtgtgcacatttgcatttattgtcagcttttaaacgctggggtcgccacccaagatgat |
| taggtacataatcctaggtttactcacccttgcgtcagcccacggtaccacccaaaaggtggattttaaggagccagcctgtaatgt |
| tacattcgcagctgaagctaatgagtgcaccactcttataaaatgcaccacagaacatgaaaagctgcttattcgccacaaaaacaa |
| aattggcaagtatgctgtttatgctatttggcagccaggtgacactacagagtataatgttacagttttccagggtaaaagtcataa |
| aacttttatgtatacttttccatttatgaaatgtgcgacattaccatgtacatgagcaaacagtataagttgtggcccccacaaaa |
| ttgtgtggaaaacactggcactttctgctgcactgctatgctaattacagtgctcgctttggtctgtaccctactctatattaaata |
| caaaagcagacgcagctttattgaggaaaagaaaatgccttaatttactaagttacaaagctaatgtcaccactaactgctttactc |

-continued

Sequences gctgcttgcaaaacaaattcaaaaagttagcattataattagaataggatttaaaccccccggtcatttcctgctcaataccattcc
cctgaacaattgactctatgtgggatatgctccagcgctacaaccttgaagtcaggcttcctggatgtcagcatctgactttggcca
gcacctgtcccgcggatttgttccagtccaactacagcgacccaccctaacagagatgaccaacacaaccaacgcggccgccgctac
cggacttacatctaccacaaatacaccccaagtttctgcctttgtcaataactgggataacttgggcatgtggtggttctccatagc
gcttatgtttgtatgccttattattatgtggctcatctgctgcctaaagcgcaaacgcgcccgaccacccatctatagtcccatcat
tgtgctacacccaaacaatgatggaatccatagattggacggactgaaacacatgttcttttctcttacagtatgattaaatgagac
atgattcctcgagttttt atattactgaccc ttgttgcgcttttttgtgcgtgctccacattggctgcggtttctcacatcgaagta
gactgcattccagccttcacagtctatttgctttacggatttgtcaccctcacgctcatctgcagcctcatcactgtggtcatcgcc
tttatccagtgcattgactgggtctgtgtgcgctttgcatatctcagacaccatcccagtacagggacaggactatagctgagctt
cttagaattctttaattatgaaatttactgtgacttttctgctgattatttgcaccctatctgcgtttgttccccgacctccaagc
ctcaaagacatatatcatgcagattcactcgtatatggaatattccaagttgctacaatgaaaaaagcgatcttccgaagcctggt
tatatgcaatcatctctgttatggtgttctgcagtaccatcttagccctagctatatatccctaccttgacattggctggaaacgaa
tagatgccatgaaccacccaacttt ccccgcgccgctatgcttccactgcaacaagttgttgccggcggctttgtcccagccaatc
agcctcgcccacttctcccaccccactgaaatcagctactttaatctaacaggaggagatgactgacaccctagatctagaaatg
gacggaattattacagagcagcgcctgctagaaagacgcagggcagcggccgagcaacagcgcatgaatcaagagctccaagacatg
gttaacttgcaccagtgcaaaaggggtatctttgtctggtaaagcaggccaaagtcacctacgacagtaataccaccggacaccgc
cttagctacaagttgccaaccaagcgtcagaaattggtggtcatggtgggagaaaagcccattaccataactcagcactcggtagaa
accgaaggctgcattcactcaccttgtcaaggacctgaggatctctgcacccttattaagaccctgtgcggtctcaaagatcttatt
ccctttaactaataaaaaaaataataaagcatcacttacttaaaatcagttagcaaatttctgtccagtttattcagcagcacctc
cttgccctcctcccagctctggtattgcagcttcctcctggctgcaaactttctccacaatctaaatggaatgtcagtttcctcctg
ttcctgtccatccgcacccactatcttcatgttgttgcagatgaagcgcgcaagaccgtctgaagataccttcaacccgtgtatcc
atatgacacggaaaccggtcctccaactgtgccttttcttactcctcccttt gtatcccccaatgggtttcaagagagtcccctgg
ggtactctctttgcgcctatccgaacctctagttacctccaatggcatgcttgcgctcaaaatgggcaacggcctctctctggacga
ggccggcaaccttacctcccaaaatgtaaccactgtgagcccacctctccgaggagacaagtcaaacataaacctggaaatatctgc
accccctcacagttacctcagaagccctaactgtggctgccgccgcacctctaatggtcgcgggcaacacactcaccatgcaatcaca
ggccccgctaaccgtgcacgactccaaacttagcattgccacccaaggaccccctcacagtgtcagaaggaaagctagccctgcaaac
atcaggcccctcaccaccaccgatagcagtacccttactatcactgcctcaccccctctaactactgccactggtagcttgggcat
tgacttgaaagagcccatttatacacaaaatggaaaactaggactaaagtacggggctccttt gcatgtaacagacgacctaaacac
tttgaccgtagcaactggtccaggtgtgactattaataatacttccttgcaaactaaagttactggagccttgggttttgattcaca
aggcaatatgcaacttaatgtagcaggaggactaaggattgattctcaaaacagacgcctt atacttgatgttagttatccgtttga
tgctcaaaaccaactaaatctaagactaggacagggccctctttttataaactcagcccacaacttggatattaactacaacaaagg
cctttacttgtttacagcttcaaacaattccaaaaagcttgaggttaacctaagcactgccaaggggttgatgtttgacgctacagc
catagccattaatgcaggagatgggcttgaatttggttcacctaatgcaccaaacacaaatcccctcaaaacaaaaattggccatgg
cctagaatttgattcaaacaaggctatggttcctaaactaggaactggcctt agttttgacagcacaggtgccattacagtaggaaa
caaaaataatgataagctaactttgtggaccacaccagctccatctcctaactgtagactaaatgcagagaaagatgctaaactcac
tttggtcttaacaaaatgtggcagtcaaatacttgctacagtttcagttttggctgttaaaggcagtttggctccaatatctggaac
agttcaaagtgctcatcttatt ataagatttgacgaaaatggagtgctactaaacaattccttcctggacccagaatattggaactt
tagaaatggagatcttactgaaggcacagcctatacaaacgctgttggatttatgcctaacctatcagcttatccaaaatctcacgg

| Sequences |
| --- |
| taaaactgccaaaagtaacattgtcagtcaagtttacttaaacggagacaaaactaaacctgtaacactaaccattacactaaacgg
tacacaggaaacaggagacacaactccaagtgcatactctatgtcattttcatgggactggtctggccacaactacattaatgaaat
atttgccacatcctcttacactttttcatacattgcccaagaataaagaatcgtttgtgttatgtttcaacgtgtttattttcaat
tgcagaaaatttcaagtcattttcattcagtagtatagccccaccaccacatagcttatacagatcaccgtaccttaatcaaactc
acagaaccctagtattcaacctgccacctccctcccaacacacagagtacacagtcctttctccccggctggccttaaaaagcatca
tatcatgggtaacagacatattcttaggtgttatattccacacggtttcctgtcgagccaaacgctcatcagtgatattaataaact
ccccgggcagctcacttaagttcatgtcgctgtccagctgctgagccacaggctgctgtccaacttgcggttgcttaacgggcggcg
aaggagaagtccacgcctacatgggggtagagtcataatcgtgcatcaggatagggcggtggtgctgcagcagcgcgcgaataaact
gctgccgccgctccgtcctgcaggaatacaacatggcagtggtctcctcagcgatgattcgcaccgcccgcagcataaggcgcc
ttgtcctccgggcacagcagcgcaccctgatctcacttaaatcagcacagtaactgcagcacagcaccacaatattgttcaaaatcc
cacagtgcaaggcgctgtatccaaagctcatggcggggaccacagaaccacgtggccatcataccacaagcgcaggtagattaagt
ggcgacccctcataaacacgctggacataaacattacctcttttggcatgttgtaattcaccacctcccggtaccatataaacctct
gattaaacatggcgccatccaccaccatcctaaaccagctggccaaaacctgcccgccggctatacactgcagggaaccgggactgg
aacaatgacagtggagagcccaggactcgtaaccatggatcatcatgctcgtcatgatatcaatgttggcacaacacaggcacacgt
gcatacacttcctcaggattacaagctcctcccgcgttagaaccatatcccagggaacaacccattcctgaatcagcgtaaatccca
cactgcaggaagacctcgcacgtaactcacgttgtgcattgtcaaagtgttacattcgggcagcagcggatgatcctccagtatgg
tagcgcgggtttctgtctcaaaaggaggtagacgatccctactgtacggagtgcgccgagacaaccgagatcgtgttggtcgtagtg
tcatgccaaatggaacgccggacgtagtcatatttcctgaagcaaaaccaggtgcgggcgtgacaaacagatctgcgtctccggtct
cgccgcttagatcgctctgtgtagtagttgtagtatatccactctctcaaagcatccaggcgcccctggcttcgggttctatgtaa
actccttcatgcgccgctgccctgataacatccaccaccgcagaataagccacacccagccaacctacacattcgttctgcgagtca
cacacgggaggagcgggaagagctggaagaaccatgttttttttttattccaaaagattatccaaaacctcaaaatgaagatctat
taagtgaacgcgctcccctccggtggcgtggtcaaactctacagccaaagaacagataatggcatttgtaagatgttgcacaatggc
ttccaaaaggcaaacggccctcacgtccaagtggacgtaaaggctaaacccttcagggtgaatctcctctataaacattccagcacc
ttcaaccatgcccaaataattctcatctcgccaccttctcaatatatctctaagcaaatcccgaatattaagtccggccattgtaaa
aatctgctccagagcgccctccaccttcagcctcaagcagcgaatcatgattgcaaaaattcaggttcctcacagacctgtataaga
ttcaaaagcggaacattaacaaaaataccgcgatcccgtaggtccatcgcagggccagctgaacataatcgtgcaggtctgcacgga
ccagcgcggccacttccccgccaggaaccatgacaaaagaacccacactgattatgacacgcatactcggagctatgctaaccagcg
tagcccgatgtaagcttgttgcatgggcggcgatataaaatgcaaggtgctgctcaaaaaatcaggcaaagcctcgcgcaaaaaag
aaagcacatcgtagtcatgctcatgcagataaaggcaggtaagctccggaaccaccacagaaaaagacaccattttctctcaaaca
tgtctgcgggtttctgcataaacacaaataaaataacaaaaaaacatttaaacattagaagcctgtcttacaacaggaaaaacaac
ccttataagcataagacggactacggccatgccggcgtgaccgtaaaaaaactggtcaccgtgattaaaaagcaccaccgacagctc
ctcggtcatgtccggagtcataatgtaagactcggtaaacacatcaggttgattcacatcggtcagtgctaaaaagcgaccgaaata
gcccggggaatacatacccgcaggcgtagagacaacattacagcccccataggaggtataacaaaattaataggagagaaaaacac
ataaacacctgaaaaaccctcctgcctaggcaaaatagcaccctcccgctccagaacaacatacagcgcttccacagcggcagccat
aacagtcagccttaccagtaaaaagaaaacctattaaaaaaacaccactcgacacggcaccagctcaatcagtcacagtgtaaaaa
agggccaagtgcagagcgagtatatataggactaaaaaatgacgtaacggttaaagtccacaaaaaacacccagaaaaccgcacgcg
aacctacgcccagaaacgaaagccaaaaaacccacaacttcctcaaatcgtcacttccgttttcccacgttacgtcacttcccatt
taagaaaactacaattcccaacacatactagttactccgccctaaaacctacgtcacccgccccgttcccacgccccgcgccacgtc
acaaactccaccccctcattatcatattggcttcaatccaaaataaggtatattattgatgatgt |

| Sequences |
|---|

SEQ ID NO: 6 - gp100-tyr insertion with linkers
ggaagcggttctcgctacctggagcctggcccagtgactgccgctggttccggaagcagatacatggacggaacaatgtcccaggtt gccggttctggctcc SEQ ID NO: 7 - gp100-tyr insertion with linkers
GSGSRYLEPGPVTAAGSGSRYMDGTMSQVAGSGS SEQ ID NO: 8 - wt Hexon
atggctacccctttcgatgatgccgcagtggtcttacatgcacatctcgggccaggacgcctcggagtacctgagccccgggctggtg cagtttgcccgcgccaccgagacgtacttcagcctgaataacaagtttagaaaccccacggtggcgcctacgcacgacgtgaccaca gaccggtcccagcgttttgacgctgcggttcatccctgtggaccgtgaggatactgcgtactcgtacaaggcgcggttcaccctagct gtgggtgataaccgtgtgctggacatggcttccacgtactttgacatccgcggcgtgctggacaggggccctacttttaagccctac tctggcactgcctacaacgccctggctcccaagggtgccccaaatccttgcgaatgggatgaagctgctactgctcttgaaataaac ctagaagaagaggacgatgacaacgaagacgaagtagacgagcaagctgagcagcaaaaaactcacgtatttgggcaggcgccttat tctggtataaatattacaaaggagggtattcaaataggtgtcgaaggtcaaacacctaaatatgccgataaaacatttcaacctgaa cctcaaataggagaatctcagtggtacgaaactgaaattaatcatgcagctgggagagtccttaaaagactaccccaatgaaacca tgttacggttcatatgcaaaacccacaaatgaaatggagggcaaggcattcttgtaaagcaacaaaatggaaagctagaaagtcaa gtggaaatgcaattttctcaactactgaggcgaccgcaggcaatggtgataacttgactcctaaagtggtattgtacagtgaagat gtagatatagaaaccccagacactcatatttatacatgcccactattaaggaaggtaactcacgagaactaatgggccaacaatcta tgcccaacaggcctaattacattgcttttagggacaattttattggtctaatgtattacaacagcacgggtaatatgggtgttctgg cgggccaagcatcgcagttgaatgctgttgtagatttgcaagacagaaacacagagattcataccagcttttgcttgattccattgg tgatagaaccaggtacttttctatgtggaatcaggctgttgacagctatgatccagatgttagaattattgaaaatcatggaactga agatgaacttccaaattactgctttccactgggaggtgtgattaatacagagactcttaccaaggtaaaacctaaaacaggtcagga aaatggatgggaaaaagatgctacagaattttcagataaaaatgaaataagagttggaaataattttgccatggaaatcaatctaaa tgccaacctgtggagaaatttcctgtactccaacatagcgctgtatttgcccgacaagctaaagtacagtccttccaacgtaaaaat ttctgataacccaaacacctacgactacatgaacaagcgagtggtggctcccgggttagtggactgctacattaaccttggagcacg ctggtcccttgactatatggacaacgtcaacccatttaaccaccaccgcaatgctggcctgcgctaccgctcaatgttgctgggcaa tggtcgctatgtgcccttccacatccaggtgcctcagaagttattgccattaaaaacctccttctcctgccgggctcatacacctac gagtggaacttcaggaaggatgttaacatggttctgcagagctccctaggaaatgacctaagggttgacggagccagcattaagttt gatagcatttgcctttacgccaccttcttccccatggcccacaacaccgcctccacgcttgaggccatgcttagaaacgacaccaac gaccagtcctttaacgactatctctccgcgccaacatgctctaccctataccgccaacgctaccaacgtgcccatatccatcccc tcccgcaactgggcggctttccgcggctgggccttcacgcgccttaagactaaggaaacccccatcactgggctcgggctacgaccct tattacacctactctggctctataccctacctagatggaaccttttacctcaaccacaccttttaagaaggtggccattacctttgac tcttctgtcagctggcctggcaatgaccgcctgcttaccccaacgagtttgaaattaagcgctcagttgacggggagggttacaac gttgcccagtgtaacatgaccaaagactggttcctggtacaaatgctagctaactacaacattggctaccagggcttctatatccca gagagctacaaggaccgcatgtactccttctttagaaacttccagcccatgagccgtcaggtggtggatgatactaaatacaaggac taccaacaggtgggcatcctacaccaacacaacaactctggatttgttggctaccttgcccccaccatgcgcgaaggacaggcctac cctgctaacttcccctatccgcttataggcaagaccgcagttgacagcattacccagaaaagtttctttgcgatcgcacccttgg cgcatcccattctccagtaactttatgtccatgggcgcactcacagacctgggccaaaaccttctctacgccaactccgcccacgcg ctagacatgactttgaggtggatccatggacgagcccaccttctttatgttttgtttgaagtctttgacgtggtccgtgtgcac cagccgcaccgcggcgtcatcgaaaccgtgtacctgcgcacgcccttctcggccggcaacgccacaacataa SEQ ID NO: 9 - wt Hexon -continued

| Sequences |
|---|
| MATPSMMPQWSYMHISGQDASEYLSPGLVQFARATETYFSLNNKFRNPTVAPTHDV |
| TTDRSQRLTLRFIPVDREDTAYSYKARFTLAVGDNRVLDMASTYFDIRGVLDRGPT |
| FKPYSGTAYNALAPKGAPNPCEWDEAATALEINLEEEDDDNEDEVDEQAEQQKTHV |
| FGQAPYSGINITKEGIQIGVEGQTPKYADKTFQPEPQIGESQWYETEINHAAGRVL |
| KKTTPMKPCYGSYAKPTNENGGQGILVKQQNGKLESQVEMQFFSTTEATAGNGDNL |
| TPKVVLYSEDVDIETPDTHISYMPTIKEGNSRELMGQQSMPNRPNYIAFRDNFIGL |
| MYYNSTGNMGVLAGQASQLNAVVDLQDRNTELSYQLLLDSIGDRTRYFSMWNQAVD |
| SYDPDVRIIENHGTEDELPNYCFPLGGVINTETLTKVKPKTGQENGWEKDATEFSD |
| KNEIRVGNNFAMEINLNANLWRNFLYSNIALYLPDKLKYSPSNVKISDNPNTYDYM |
| NKRVVAPGLVDCYINLGARWSLDYMDNVNPFNHHRNAGLRYRSMLLGNGRYVPFHI |
| QVPQKFFAIKNLLLLPGSYTYEWNFRKDVNMVLQSSLGNDLRVDGASIKFDSICLY |
| ATFFPMAHNTASTLEAMLRNDTNDQSFNDYLSAANMLYPIPANATNVPISIPSRNW |
| AAFRGWAFTRLKTKETPSLGSGYDPYYTYSGSIPYLDGTFYLNHTFKKVAITFDSS |
| VSWPGNDRLLTPNEFEIKRSVDGEGYNVAQCNMTKDWFLVQMLANYNIGYQGFYIP |
| ESYKDRMYSFFRNFQPMSRQVVDDTKYKDYQQVGILHQHNNSGFVGYLAPTMREGQ |
| AYPANFPYPLIGKTAVDSITQKKFLCDRTLWRIPFSSNFMSMGALTDLGQNLLYAN |
| SAHALDMTFEVDPMDEPTLLYVLFEVFDVVRVHQPHRGVIETVYLRTPFSAGNATT- |
| SEQ ID NO: 10 - Hex713 epitope<br>tacctcaaccacacctttaagaaggtg |
| SEQ ID NO: 11 - Hex713 epitope<br>YLNHTFKKV |
| SEQ ID NO: 12 - V721A epitope<br>tacctcaaccacacctttaagaaggct |
| SEQ ID NO: 13 - V721A epitope<br>YLNHTFKKA |
| SEQ ID NO: 14 - Hex892 epitope<br>cttctctacgccaactccgcccacgcg |
| SEQ ID NO: 15 - Hex892 epitope<br>LLYANSAHA |
| SEQ ID NO: 16 - A901S epitope<br>cttctctacgccaactccgcccactcc |
| SEQ ID NO: 17 - A901S epitope<br>LLYANSAHS |
| SEQ ID NO: 18 - Hex917 epitope<br>tatgttttgtttgaagtattgacgtg |
| SEQ ID NO: 19 - Hex917 epitope<br>YVLFEVFDV |
| SEQ ID NO: 20 - V925K epitope<br>tatgtttttttgtttgaagtattgacaag |
| SEQ ID NO: 21 - V925K epitope<br>YVLFEVFDK |
| SEQ ID NO: 22 - Hex512 epitope<br>gggttagtggactgctacattaacctt |
| SEQ ID NO: 23 - Hex512 epitope<br>GLVDCYINL |
| SEQ ID NO: 24 - L520P epitope |

-continued

| Sequences |
|---|
| gggttagtggactgctacattaaccccc |

SEQ ID NO: 25 - L520P epitope
GLVDCYINP

SEQ ID NO: 26 - heparin sulphate glycosaminoglycan (HSG)-binding site
KKTK

SEQ ID NO: 27 - integrin-binding motif
RGDK

SEQ ID NO: 28 - flexible linker
GSGSR

SEQ ID NO: 29 - flexible linker
AGSGSR

SEQ ID NO: 30 - flexible linker
AGSGS

SEQ ID NO: 31 - gp100-280 epitope
YLEPGPVTA

SEQ ID NO: 32 - Tyr369(3D) epitope
YMDGTMSQV

SEQ ID NO: 33 - E1A19 epitope
LLDQLIEEV

SEQ ID NO: 34 - Hex63 epitope
RLTLRFIPV

SEQ ID NO: 35 - Hex548 epitope
MLLGNGRYV

SEQ ID NO: 36 - Hex652 epitope
MLYPIPANA

SEQ ID NO: 37 - Hex914 epitope
TLLYVLFEV

SEQ ID NO: 38 - gp100-209 epitope
IMDQVPFSV

What is claimed is:

1. An oncolytic adenovirus comprising at least one functional deletion of an immunodominant T-cell epitope of an adenovirus hexon protein,
wherein the oncolytic adenovirus comprises at least one mutation selected from the group consisting of
a L520P mutation in the Hex512 epitope,
a V721A mutation in the Hex713 epitope,
an A900S mutation in the Hex892 epitope, and
a V925K mutation in the Hex917 epitope.

2. The oncolytic adenovirus of claim 1, wherein the adenovirus comprises the L520P mutation in the Hex512 epitope and the V925K mutation in the Hex917 epitope.

3. The oncolytic adenovirus of claim 1, wherein the adenovirus comprises the V721A mutation in the Hex713 epitope, the A900S mutation in the Hex892 epitope, and the V925K mutation in the Hex917 epitope.

4. The oncolytic adenovirus of claim 3, wherein the adenovirus comprises the L520P mutation in the Hex512 epitope, the V721A mutation in the Hex713 epitope, the A900S mutation in the Hex892 epitope, and the V925K mutation in the Hex917 epitope.

5. The oncolytic adenovirus of claim 1, further comprising one or more heterologous nucleic acid sequences, wherein each of the one or more heterologous nucleic acid sequence encode a tumor antigen or an epitope thereof.

6. The oncolytic adenovirus of claim 5, wherein the tumor antigen or the epitope is selected from the group consisting of: MAGE-1, MAGE-2, MAGE-3, CEA, Tyrosinase, midkine, BAGE, CASP-8, β-catenin, CA-125, CDK-1, ESO-1, gp75, gp100, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orf112, SART1, SART2, SART3, BRAP, RTN4, GLEA2, TNKS2, KIAA0376, ING4, HSPH1, C13orf24, RBPSUH, C6orf153, NKTR, NSEP1, U2AF1L, CYNL2, TPR, SOX2, GOLGA, BMI1, COX-2, EGFRvIII, EZH2, LICAM, Livin, MRP-3, Nestin, OLIG2, ART1, ART4, Bcyclin, Gli1, Cav-1, cathepsin B, CD74, E-cadherin, EphA2/Eck, Fra-1/Fosl1, GAGE-1, Ganglioside/GD2, GnT-V, β1, 6-N, Ki67, Ku70/80, PROX1, PSCA, SOX10, SOX11, Survivin, UPAR, Mesothelin, and WT-1, and an epitope thereof.

7. The oncolytic adenovirus of claim 5, wherein the tumor antigen or the epitope is flanked by flexible linkers wherein said flexible linkers comprise an amino acid sequence selected from the group consisting of: GSGSR (SEQ ID NO: 28), AGSGSR (SEQ ID NO: 29), and AGSGS (SEQ ID NO: 30).

8. The oncolytic adenovirus of claim 5, wherein said one or more heterologous nucleic acid sequences encode
a gp100 tumor antigen or an epitope thereof, or
a tyrosinase tumor antigen or an epitope thereof, or
wherein said one or more heterologous nucleic acid sequences comprise (a) a heterologous nucleic acid sequence encoding a gp100 antigen or an epitope thereof and (b) a heterologous nucleic acid sequence encoding a tyrosinase antigen or an epitope thereof.

9. The oncolytic adenovirus of claim 1, wherein the oncolytic adenovirus further comprises a tissue-specific or a tumor-specific promoter to achieve selective replication in tumors.

* * * * *